US012653900B2

(12) United States Patent
Cuevas Marchante et al.

(10) Patent No.: US 12,653,900 B2
(45) Date of Patent: Jun. 16, 2026

(54) ANTIBODY DRUG CONJUGATES COMPRISING ECTEINASCIDIN DERIVATIVES

(71) Applicant: PHARMA MAR, S.A., Colmenar Viejo (ES)

(72) Inventors: Maria del Carmen Cuevas Marchante, Colmenar Viejo (ES); Andrés M. Francesch Solloso, Colmenar Viejo (ES); Alfonso Latorre Lozano, Colmenar Viejo (ES); Valentin Martinez Barrasa, Colmenar Viejo (ES)

(73) Assignee: PHARMA MAR, S.A., Madrid (ES)

( * ) Notice: Subject to any disclaimer, the term of this patent is extended or adjusted under 35 U.S.C. 154(b) by 1404 days.

(21) Appl. No.: 17/288,567

(22) PCT Filed: Oct. 25, 2019

(86) PCT No.: PCT/EP2019/079188
§ 371 (c)(1),
(2) Date: Apr. 25, 2021

(87) PCT Pub. No.: WO2020/084115
PCT Pub. Date: Apr. 30, 2020

(65) Prior Publication Data

US 2023/0012681 A1 Jan. 19, 2023

(30) Foreign Application Priority Data

Oct. 25, 2018 (EP) .................................... 18382759

(51) Int. Cl.
*A61K 47/68* (2017.01)
*A61K 31/4995* (2006.01)
*A61P 35/00* (2006.01)

(52) U.S. Cl.
CPC ...... *A61K 47/6803* (2017.08); *A61K 31/4995* (2013.01); *A61K 47/6851* (2017.08); *A61P 35/00* (2018.01)

(58) Field of Classification Search
CPC ............ A61K 47/6803; A61K 47/6851; A61K 31/4995; A61P 35/00
See application file for complete search history.

(56) References Cited

U.S. PATENT DOCUMENTS

| | | | |
|---|---|---|---|
| 4,816,567 A | 3/1989 | Cabilly et al. | |
| 5,149,804 A | 9/1992 | Rinehart et al. | |
| 5,545,806 A | 8/1996 | Lonberg et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 7,662,387 B2 | 2/2010 | Law et al. | |
| 10,538,535 B2 | 1/2020 | del Carmen Cuevas Marchante et al. | |
| 2006/0106021 A1 | 5/2006 | Martinez et al. | |
| 2007/0093658 A1 | 4/2007 | Martinez | |
| 2018/0099055 A1* | 4/2018 | Van Berkel | A61K 45/06 |
| 2021/0070775 A1 | 3/2021 | Cuevas Marchante et al. | |
| 2021/0246146 A1 | 8/2021 | Cuevas Marchante et al. | |
| 2024/0131180 A1* | 4/2024 | Latorre Lozano | C07D 515/22 |

FOREIGN PATENT DOCUMENTS

| | | | | |
|---|---|---|---|---|
| EP | 1864682 A1 | | 12/2007 | |
| EP | 3395820 | | 5/2019 | |
| WO | WO 94/04690 | | 3/1994 | |
| WO | WO 97/34631 | | 9/1997 | |
| WO | 0069862 | | 11/2000 | |
| WO | WO 01/87895 | | 11/2001 | |
| WO | 03008423 | | 1/2003 | |
| WO | WO 03/014127 | | 2/2003 | |
| WO | WO-03014127 A1 | * | 2/2003 | C07D 515/22 |
| WO | WO 2004/010957 | | 2/2004 | |
| WO | 2005037992 A2 | | 4/2005 | |
| WO | 2006027711 A2 | | 3/2006 | |
| WO | WO 2006/060533 | | 6/2006 | |
| WO | WO 2007/024536 | | 3/2007 | |
| WO | 2007144423 A1 | | 12/2007 | |
| WO | 2009080761 A1 | | 7/2009 | |
| WO | 2009080769 A1 | | 7/2009 | |
| WO | 2009143313 A1 | | 11/2009 | |
| WO | 2010009124 A2 | | 1/2010 | |
| WO | 2010149688 A2 | | 12/2010 | |
| WO | 2011147828 | | 12/2011 | |
| WO | WO-2014191578 A1 | * | 12/2014 | A61P 35/00 |
| WO | WO 2018/1897663 | | 11/2018 | |

OTHER PUBLICATIONS

Dan et al., Pharmaceuticals 2018, 11(2), 32; https://doi.org/10.3390/ph11020032.*
Gupta, Molecules, Jul. 14, 2018; 23(7):1719 (Year: 2018).*
Blackadar, World Journal of Clinical Oncology, Feb. 10, 2016; 7(1): 54-86 (Year: 2016).*
The American Cancer Society, cancer.org, Can Acute Lymphocytic Leukemia Be Prevented?, https://web.archive.org/web/20241209175137/https://www.cancer.org/cancer/types/acute-lymphocytic-leukemia/causes-risks-prevention/prevention.html, Last updated Oct. 17, 2018 (Year: 2018).*

(Continued)

*Primary Examiner* — Andrew D Kosar
*Assistant Examiner* — Phillip Matthew Rzeczycki
(74) *Attorney, Agent, or Firm* — Ballard Spahr LLP

(57) ABSTRACT

Drug conjugates having formula $[D-(X)_b-(AA)_w-(T)_g-(L)-]_n$-Ab wherein: D is a drug moiety having the following formula (I) or a pharmaceutically acceptable salt, ester, solvate, tautomer or stereoisomer thereof, (I) wherein D is covalently attached via a hydroxy or amine group to $(X)_b$ if any, or $(AA)_w$ if any, or to $(T)_g$ if any, or (L); that are useful in the treatment of cancer.

39 Claims, 13 Drawing Sheets

Specification includes a Sequence Listing.

(56) References Cited

OTHER PUBLICATIONS

The American Cancer Society, cancer.org, Can Hodgkin Lymphoma be Prevented?, https://web.archive.org/web/20231211145704/https://www.cancer.org/cancer/types/hodgkin-lymphoma/causes-risks-prevention/prevention.html, Last updated May 1, 2018 (Year: 2018).*
Hassanpour, Journal of Cancer Research and Practice, 4, 2017, 127-129 (Year: 2017).*
Ecuadorian Notice of Opposition from Ecuadorian Application No. SENADI-2021-35414 dated Jul. 4, 2022.
First Office Action received for UAE Application No. P600656/2021, mailed between Nov. 2023-Jan. 2024.
Bowen, M.A. et al. "Functional effects of CD30 on a large granular lymphoma cell line, YT. Inhibition of cytotoxicity, regulation of CD28 and IL-2R, and induction of homotypic aggregation", J. Immunol. 1993, 151, 5896-5096.
Boyd. M.R. & Paull K.D. "Some practical considerations and applications of the National Cancer Institute in vitro anticancer drug discovery screen". Drug. Dev. Res. 1995, 34, 91-109.
Calvo, E. et. al. "Antitumor activity of lurbinectedin (PM01183) and doxorubicin in relapsed small-cell lung cancer: Results from a phase I study". Annals of Oncology 2017, 28(10), 2559-2566.
Carter, P. et. al. "High level *Escherichia coli* expression and production of a bivalent humanized antibody fragment". Biotechnology 1992, 10, 163-167.
Carter, P. et. al. "Toward the production of bispecific antibody fragments for clinical applications" J. of Hematotherapy, 1995, 4, 463-470.
Chari, R.V. Targeted cancer therapy: conferring specificity to cytotoxic drugs. Acc. Chem. Res. 2008, 41, 98-107.
Chari, R. V. J. et. al. "Immunoconjugates containing novel maytansinoids: Promising anticancer drugs", Cancer Research 1992, 52, 127-131.
Clackson et. al. "Making antibody fragments using phage display libraries". Nature 1991, 352, 624-628.
Cole et. al. "The EBV-hybrodoma technique and its application to human lung cancer" Monoclonal Antibodies and Cancer Therapy, Alan R. Liss, Inc 1985, pp. 77-96.
Cuevas, C. "MI180021: A novel ADC with a new marine DNA binder payload" World ADC Congress, Nov. 12-15, 2018. San Diego California [Oral Presentation].
Dan, N. et. al. "Antibody-Drug Conjugates for Cancer Therapy: Chemistry to Clinical Implications". Pharmaceutical 2018, 11(2), 32.
Drebin, J. A. et. al. "Monoclonal antibodies identify a cell-surface antigen associates with an activated cellular oncogene". Nature, 1984, 312, 545-548.
Francisco, J. A. et. al. "Agonistic properties and in vivo antitumor activity of the anti-CD40 antibody SGN-14". Cancer Res. 2000, 60, 3225-3231.
Frankel, A.E. et. al. "Cell Surface Receptor-Targeted Therapy of Acute Myeloid Leukemia: A review". Cancer Biother. Radiopharm. 2000, 15, 459-476.
Holliger. P.; Hudson, P.J., "Engineered antibody fragments and the rise of single domains". Nature Biotechnology 2005, 23(9), 1126-1136.
Kabat, E.A. "Origins of antibody complementarity and specificity-hypervariable regions and minigene hypothesis". J. of Immunology 1980, 125(3), 961-969.
Kohler G. and Milstein C. "Continuous cultures of fused cells secreting antibody of predefined specificity". Nature 1975, 256, 495-497.
Kozbor, D.; Roder, J. C. "The Production of monoclonal antibodies from human lymphocytes". Immunology Today, 1983, 4, 72-79.
Latorre, A. et. al. "MI180021, a novel ADC with a new marine DNA Binder Payload, shows outstanding activity against HER2 expressing tumors". MaNaPro. 16th International Symposium on Marine Natural products and 11th European Congress on Marine Natural Products (ECMNP), Sep. 1-5, 2019, Peniche, Portugal. [Abstracts and poster].
Latorre, A. et al. "MI180021, a novel ADC with a new marine DNA binder payload, shows outstanding activity". World ADC Congress, Nov. 12-15, 2018. San Diego, California. [Abstracts and poster].
Leal, J.F.M. et. al. "PM01183, a new DNA minor groove covalent binder with potent in vitro and in vivo anti-tumour activity", British Journal of Pharmacology 2010, 161(5), 1099-1110.
Liu, C. et. al. "Eradication of large colon tumor xenografts by targeted delivery of maytansinoids", Proc. Natl. Acad. Sci. USA 1996, 93, 8618-8623.
Lonberg, N. and Huszar, D., "Human antibodies from transgenic mice" Int. Rev. Immunol. 1995, 13, 65-93.
Marks, J. D. et. al. "By-passing immunization. Human antibodies from V-gene libraries displayed on phage". J. Mol. Biol. 1991, 222, 581-597.
Merchant, A. M. et. al. "An efficient route to human bispecific IgG". Nature Biotechnology 1998, 16, 677-681.
Meyer, D.L. & Senter, P.D Recent advances in antibody drug conjugates for cancer therapy. Annu. Rep. Med. Chem. 2003, 38, 229-237.
Mosmann, T. et. al. Rapid Colorimetric Assay for cellular Growth and survival: Application to proliferation and cytotoxicity assays. J. Immunol. Meth. 1983, 65, 55-63.
Murray, J. L. "Monoclonal antibody treatment of solid tumors: a coming of age". Semin. Oncol. 2000, 27, 64-70.
Podea, P.V. et al. "Chemoenzymatic preparation of enantiopure L-benzofuranyl- and L-benzo[b]thiophenyl alanines". Tetrahedron Asymmetry 2008, 19, 500-511.
Rodrigues, M. L. et. al. "Engineering Fab' fragments for efficient F(ab)2 formation in *Escherichia coli* and for improved in vivo stability". J. of Immunology 1993, 151, 6954-6961.
Schecter, A. L. et. al. The neu oncogene: and erb-B related gene encoding a 185,000-M, tumour antigen. Nature, 1984, 312, 513-516.
Skehan, P. et. al. "New colorimetric cytotoxicity assay for anticancer-drug screening". J. Natl. Cancer Inst. 1990, 82, 1107-1112.
Suresh, M.R. et. al. "Bispecific monoclonal antibodies from hybrid hybridomas". Methods in Enzymology, 1986, 121, 210-228.
Teicher, B.A. Antibody drug conjugate targets. Curr. Cancer Drug Targets 2009, 9(8), 982-1004.
Trail, P.A. et. al. "Cure of xenografted human carcinomas by BR96-doxorubicin immunoconjugates", Science, 1993, 261, 212-215.
Trail, P.A. et. al. "Effect of linker variation on the stability, potency and efficacy of carcinoma reactive BR64-Doxorubicin immunoconjugates" Cancer Research, 1997, 57, 100-105.
Vichai, V & Kirtikara, K. Sulforhodamine B colorimetric assay for cytotoxicity screening. Nature Protocols 2006, 1, 1112-1116.
Wahl, A. F. et. al. "The anti-CD30 monoclonal antibody SGN-30 promotes growth arrest and DNA fragmentation in vitro and affects antitumor activity in models of Hodgkin's disease". Cancer Res. 2002, 62(13), 3736-3742.
Office Action for Japanese Patent Application No. 2021-523064 mailed Dec. 11, 2023.
ADC Review, What Are Cytotoxic Agents, Mar. 23, 2019.
Annual report 2017, Published 2017.
Annual report 2018, Published 2018.
Annual report 2019, Published 2019.
Annual report 2020, Published 2020.
Annual report 2021, Published 2021.
Annual report 2022, Published 2022.
Aviles et al. entitled "MI130110, a new antibody-drug conjugate combining an anti-CD13 antibody and a payload [PM050489] of marine origin shows remarkable in vivo activity", European J. Cancer, 69(1):S130-S131, Dec. 2016 (Poster and Abstract).
Avilés, P., et al. (2018). MI130004, a novel antibody-drug conjugate combining trastuzumab with a molecule of marine origin, shows outstanding In Vivo activity against HER2-expressing tumors. Molecular cancer therapeutics, 17(4), 786-794.
Cebrian et al., Triggering of T Cell Proliferation Through Aim, and Activation Inducer Molcule Expressed on Activated Human Lymphocytes, J. Exp. Med., vol. 168, No. 5, pp. 1621-1637, Nov. 1988.
CNMV Submissions, Published 2017.

(56) References Cited

OTHER PUBLICATIONS

Dominguez et al., CD13 as a new tumor target for antibod-drug conjugates: validation with the conjugate MI130110, Journal of Hematology & Oncology, (2020) 13;32.
Dumontet, C, "Microtubule binding agents: a dynamic target for cancer therapeutics," Nature Reviews Drug Discovery, 9(10): 790-803 (2010).
Financial statements 2017, Published 2017.
Financial statements 2018, Published 2018.
Financial statements 2019, Published 2019.
Financial statements 2020, Published 2020.
Financial statements 2021, Published 2021.
Flygare et al., "Antibody-Drug Conjugates for the Treatment of Cancer," Chem. Biol. Drug Des., vol. 81, pp. 113-121, 2013.
Garranzo et al., "PharmaMar Payloads: the essential link for ADCs," PharmaMar, poster presented during the ADC World Congress, Frankfurt, Germany, Feb. 17-21, 2014.
Gromek S. & M.J. Balunas, "Natural Products as Exquisitely Potent Cytotoxic Payloads for Antibody-Drug Conjugates," Current Topics in Medicinal Chemistry, 14:2822-2834 (2014).
H1 Interim report (2018), Published Jul. 26, 2018.
Hernandez Baltazar, E. and Gonzalez Christian, J. Antibody-Drug Conjugates: The state of the art. Rev. mex. science. farm [online]. 2011, vol. 42, n.3 [cited Jul. 7, 2023], pp. 7-16. Available at: <http://www.scielo.org.mx/scielo.php?script=sci_arttext&pid=S1870-01952011000300002&Ing=es&nrm=iso>. ISSN 1870-0195. [English abstract].
Identifier 2021-000833-15 Clinical trial informantion, Published Jul. 22, 2021.
Jain, N., Smith, S. W., Ghone, S., & Tomczuk, B. (2015). Current ADC linker chemistry. Pharmaceutical research, 32(11), 3526-3540.
Tolcher, A. W. (2016). Antibody drug conjugates: lessons from 20 years of clinical experience. Annals of Oncology, 27(12), 2168-2172.
Kirtikara, K. and Vichai, V., Sulforhodamine B colorimetric assay for cytotoxicity screening, Nature Protocols, vol. 1, No. 3, pp. 1112-1116, Aug. 2006.
Kudo, N., et al. (1999). Leptomycin B inactivates CRM1/exportin 1 by covalent modification at a cysteine residue in the central conserved region. Proceedings of the National Academy of Sciences, 96(16), 9112-9117.
Lanotte et al., NB4, a maturation inducible cell line with t(15;17) marker isolated from a human acute promyelocytic leukemia (M3), Blood, vol. 77, No. 5, pp. 1080-1086, Mar. 1991.
Marcus Vinicius Nora De Souza, (+)-Discodermolide: A Marine Natural Product Against Cancer, The Scientific World Journal, vol. 4, pp. 415-436, 2004.
Sakai et al., Additional Antitumor Ecteinascidins from a Caribbean Tunicate: Crystal Structures and Activities In vivoProc. Natl. Acad. Sci. USA, vol. 89, 11456-11460, Published Dec. 1, 1992.
Nunez et al. Ecubectedin is a novel transcriptional inhibitor that displays potent antitumor effects in vitro and in vivo. (abstract) AACR American Association for Cancer Research. Annual Meeting. Apr. 14-19, 2023. Orlando, FL. Philadelphia (PA) Cancer Res. vol. 83(7 Supl) Abs N° 1622.
Pera, B., et al. (2013). New interfacial microtubule inhibitors of marine origin, PM050489/PM060184 with potent antitumor activity and a distinct mechanism. ACS chemical biology, 8(9), 2084-2094.
Pharma Mar S.A.U., Search Report under Section 17(5) for Application No. GB1309807.4, 5 pages, Dec. 2, 2013.
PharmaMar has published the results of its antibody conjugate active in breast, ovarian and gastric cancers that express HER2, Published Feb. 16, 2018.
PharmaMar leads the ONCOLIBERYX consortium together with four research centers to develop new marine-based oncology drug administration strategies, Published Dec. 2, 2022.
PharmaMar licences fully synthetic marine-derived payloads to Seattle Genetics for use in drug conjugates, Published Feb. 14, 2018.
PharmaMar presents a new Antibody Drug Conjugate at the World ADC Congress in San Diego, Published Nov. 12, 2018.
PharmaMar presents at MaNaPro & ECMNP its latest advances in the development of compounds of marine origin, Published Sep. 2, 2019.
Phase I clinical trials, Published Dec. 1, 2021.
Prota, A.E. et al "A new tubulin-binding site and phamacophore for microtubule-destabilizing anticaner drugs," PNAS, vol. 111(38), 13817-13821 (2014).
Q1 Interim report (2018), Published Apr. 26, 2018.
Q3 Interim report (2018), Published Oct. 30, 2018.
Q4 Report (2019), Published Feb. 28, 2019.
Q4 Report (2020), Published Feb. 26, 2020.
Rodriguez et al. PM14: A New Antitumor Compound in Clinical Studies in Patients with Solid Tumors (abstract). MaNaPro. 16th International Symposium on Marine Natural Products and 11th European Congress on Marine Natural Products. Sep. 1-5, 2019, Peniche, Portugal. Abs PC110 pp. 183.

* cited by examiner

DL 1

ADC 1

DL 1

ADC 4

SEQUENCE LISTING

<160> NUMBER OF SEQ ID NOS: 3

<210> SEQ ID NO 1
<211> LENGTH: 5
<212> TYPE: PRT
<213> ORGANISM: Homo sapiens

<400> SEQUENCE: 1

Ala Arg His Cys Leu
1 5

<210> SEQ ID NO 2
<211> LENGTH: 4
<212> TYPE: PRT
<213> ORGANISM: Homo sapiens

<400> SEQUENCE: 2

Gln Asn Gly Ser
1

<210> SEQ ID NO 3
<211> LENGTH: 11
<212> TYPE: PRT
<213> ORGANISM: Homo sapiens

<400> SEQUENCE: 3

Pro Pro Phe Cys Val Ala Arg Cys Pro Ser Gly
1 5 10

ANTIBODY DRUG CONJUGATES COMPRISING ECTEINASCIDIN DERIVATIVES

International patent application number PCT/EP2018/060868 is directed to novel ecteinascidin derivatives which demonstrate very promising anti-tumor activity. One of the compounds disclosed in such patent application is currently in Phase I clinical trials for the prevention and treatment of solid tumors.

FIELD OF THE INVENTION

The present invention relates to novel drug conjugates, drug linker compounds, to methods for their preparation, pharmaceutical compositions containing said drug conjugates and their use as antitumoral agents.

BACKGROUND TO THE INVENTION

The treatment of cancer has progressed significantly in recent years with the development of pharmaceutical entities that target and kill cancer cells more efficiently. Researchers have taken advantage of cell-surface receptors and antigens selectively expressed by target cells such as cancer cells to develop pharmaceutical entities based on antibodies that bind, in the example of tumors, the tumor-specific or tumor-associated antigens. In order to achieve this, cytotoxic molecules such as chemotherapeutic drugs, bacteria and plant toxins and radionuclides have been chemically linked to monoclonal antibodies that bind tumor-specific or tumor-associated cell surface antigens ADCs therefore represent a challenging area of development given the complex payload, linker and antibody structure but there remains a need for further ADCs to be developed.

SUMMARY OF THE INVENTION

There is a need for novel active drug conjugates. The present invention addresses this need. It further provides novel drug linker compounds for use in the preparation of drug conjugates of the present invention, processes for the preparation of the novel drug conjugates of the present invention, pharmaceutical compositions containing said drug conjugates and their use as antitumoral agents, as well as a kit comprising the drug conjugate of the present invention for use in the treatment of cancer.

In a first aspect of the present invention there is provided a drug conjugate comprising a drug moiety covalently attached to the rest of the drug conjugate, the drug conjugate having formula $[D-(X)_b-(AA)_w-(T)_g-(L)-]_n-Ab$ wherein:

D is a drug moiety having the following formula (I) or a pharmaceutically acceptable salt, ester, solvate, tautomer or stereoisomer thereof, (I)

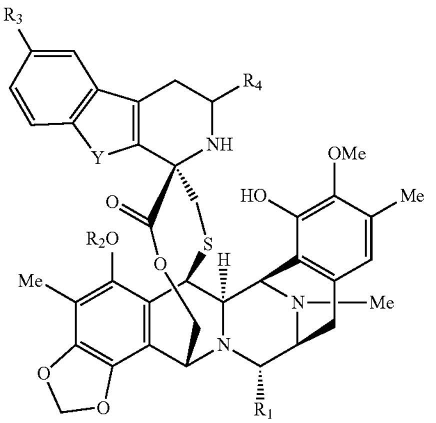

wherein:

D is covalently attached via a hydroxy or amine group to $(X)_b$ if any, or $(AA)_w$ if any, or to $(T)_g$ if any, or (L);

Y is —NH— or —O—;

$R_1$ is —OH or —CN;

$R_2$ is a —C(=O)$R_a$ group;

$R_3$ is hydrogen or a —O$R_b$ group;

$R_4$ is selected from hydrogen, —$CH_2OH$, —$CH_2OC$(=O)$R_c$, —$CH_2NH_2$, and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino, with the optional proviso that when $R_4$ is hydrogen then Y is —O—;

X and T are extending groups that may be the same or different;

each AA is independently an amino acid unit;

L is a linker group;

w is an integer ranging from 0 to 12;

b is an integer of 0 or 1;

g is an integer of 0 or 1;

Ab is a moiety comprising at least one antigen binding site; and n is the ratio of the group $[D-(X)_b-(AA)_w-(T)_g-(L)-]$ to the moiety comprising at least one antigen binding site and is in the range from 1 to 20.

In a further aspect of the present invention there is provided a drug conjugate comprising a drug moiety covalently attached to the rest of the drug conjugate, the compound having formula $[D-(X)_b-(AA)_w-(T)_g-(L)-]_n-Ab$ wherein:

D is a drug moiety having the following formula (IH) or a pharmaceutically acceptable salt, ester, solvate, tautomer or stereoisomer thereof, (IH)

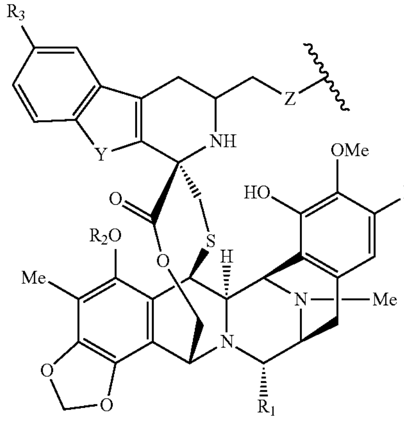

wherein:

the wavy line indicates the point of covalent attachment to $(X)_b$ if any, or $(AA)_w$ if any, or to $(T)_g$ if any, or to (L);

each of Y and Z is independently selected from —NH— and —O—;

$R_1$ is —OH or —CN;

$R_2$ is a —C(═O)$R_a$ group;

$R_3$ is hydrogen or a —O$R_b$ group;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $S(O)R_y$, $SO_2R_y$, $P(O)(R_y)OR_z$, $NR_yR_z$, $NR_yCOR_z$, $NR_yC(=O)NR_yR_z$, $NR_yC(=NR_y)NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC(=NR_y)NR_yR_z$, aralkyl groups comprising an alkyl group having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different;

each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl groups comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s);

X and T are extending groups that may be the same or different;

each AA is independently an amino acid unit;

L is a linker group;

w is an integer ranging from 0 to 12;

b is an integer of 0 or 1;

g is an integer of 0 or 1;

where b+g+w is optionally not 0;

Ab is a moiety comprising at least one antigen binding site; and n is the ratio of the group $[D-(X)_b-(AA)_w-(T)_g-(L)-]$ to the moiety comprising at least one antigen binding site and is in the range from 1 to 20.

In a further aspect of the present invention there is provided a drug conjugate comprising a drug moiety covalently attached to the rest of the drug conjugate, the drug conjugate having formula $[D-(X)_b-(AA)_w-(T)_g-(L)-]_n$-Ab wherein:

D is a drug moiety having the following formula (I) or a pharmaceutically acceptable salt, ester, solvate, tautomer or stereoisomer thereof, (I)

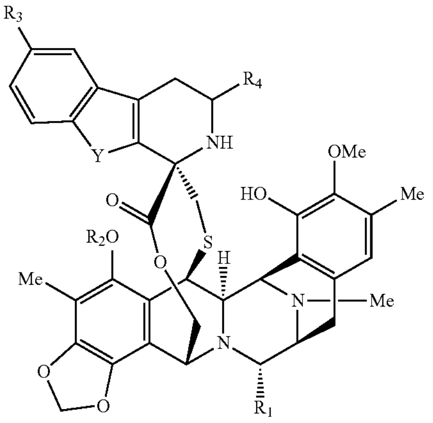

wherein:

D is covalently attached via a hydroxy or amine group to $(X)_b$ if any, or $(AA)_w$ if any, or to $(T)_g$ if any, or (L);

Y is —NH— or —O—;

$R_1$ is —OH or —CN;

$R_2$ is a —C(═O)$R_a$ group;

$R_3$ is hydrogen or a —O$R_b$ group;

$R_4$ is selected from hydrogen, —$CH_2OH$, —$CH_2OC$(═O)$R_c$, —$CH_2NH_2$, and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino, with the optional proviso that when $R_4$ is hydrogen then Y is —O—;

X and T are extending groups that may be the same or different;

each AA is independently an amino acid unit;

L is a linker group;

w is an integer ranging from 0 to 12;

b is 1;

g is an integer of 0 or 1;

Ab is a moiety comprising at least one antigen binding site; and n is the ratio of the group $[D-(X)_b-(AA)_w-(T)_g-(L)-]$ to the moiety comprising at least one antigen binding site and is in the range from 1 to 20.

In a further aspect of the present invention there is provided a drug conjugate comprising a drug moiety covalently attached to the rest of the drug conjugate, the drug conjugate having formula $[D-(X)_b-(AA)_w-(T)_g-(L)-]_n-Ab$ wherein:

D is a drug moiety having the following formula (I) or a pharmaceutically acceptable salt, ester, solvate, tautomer or stereoisomer thereof, (I)

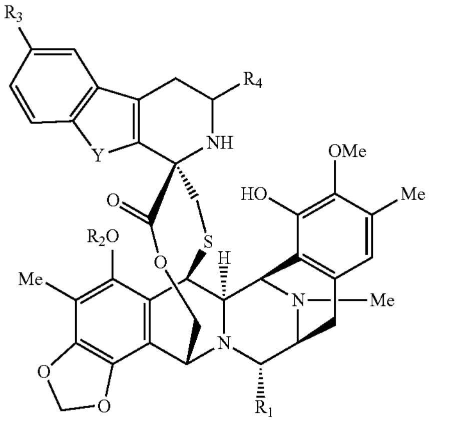

wherein:

D is covalently attached via a hydroxy or amine group to $(X)_b$ if any, or $(AA)_w$ if any, or to $(T)_g$ if any, or (L);

Y is —NH— or —O—;

$R_1$ is —OH or —CN;

$R_2$ is a —C(═O)$R_a$ group;

$R_3$ is hydrogen or a —O$R_b$ group;

$R_4$ is selected from hydrogen, —$CH_2OH$, —$CH_2OC$(═O)$R_c$, —$CH_2NH_2$, and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino, with the optional proviso that when $R_4$ is hydrogen then Y is —O—;

X and T are extending groups that may be the same or different;

each AA is independently an amino acid unit;

L is a linker group;

w is 2;

b is 1;

g is an integer of 0 or 1;

Ab is a moiety comprising at least one antigen binding site; and n is the ratio of the group $[D-(X)_b-(AA)_w-(T)_g-(L)-]$ to the moiety comprising at least one antigen binding site and is in the range from 1 to 20.

As we shall explain and exemplify in greater detail below, the drug conjugates of formula $[D-(X)_b-(AA)_w-(T)_g-(L)-]_n-Ab$ of the present invention represent a breakthrough in addressing the problems outlined above of requiring further drug conjugates in addition to those based on the three main families of cytotoxic drugs that have been used as payloads to date, that show excellent antitumor activity.

In preferred embodiments of the present invention, there is provided a drug conjugate as defined herein, or a pharmaceutically acceptable salt, ester, solvate, tautomer or stereoisomer thereof, wherein D is a drug moiety selected from formulas (IHa) and (IHb):

(IHa)

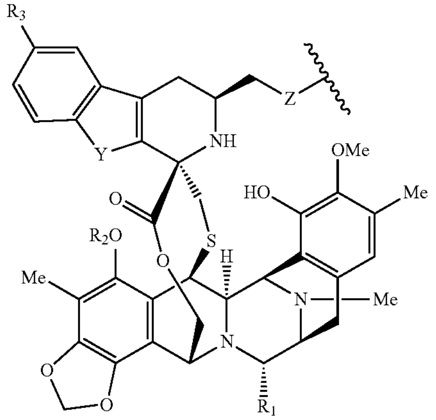

(IHb)

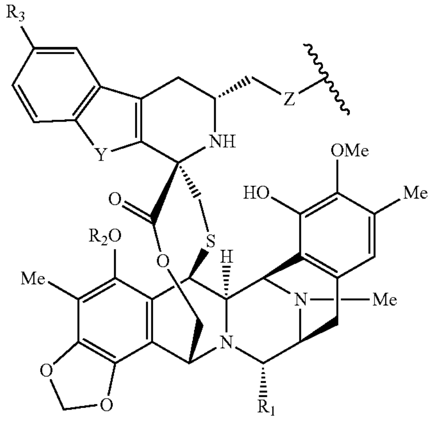

Where the wavy lines, $R_1$, $R_2$, $R_3$, Y, and Z are as defined for formula (IH).

In a further aspect of the present invention, there is provided a compound of formula $D-(X)_b-(AA)_w-(T)_g-L_1$ or of formula $D-(X)_b-(AA)_w-(T)_g-H$, wherein:

$L_1$ is a linker selected from the group of formulas consisting of:

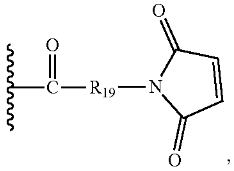

,

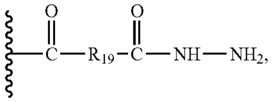

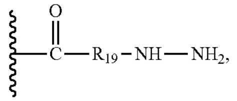

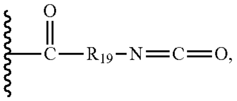

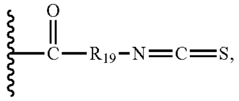

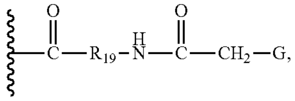

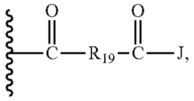

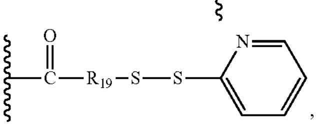

,

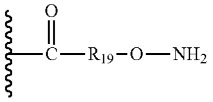

each of the the wavy lines indicates the point of covalent attachment to $(T)_g$ if any, or $(AA)_w$ if any, or to $(X)_b$ if any, or to D;

G is selected from halo, —O-mesyl and —O-tosyl;

J is selected from halo, hydroxy, —N-succinimidoxy, —O-(4-nitrophenyl), —O-pentafluorophenyl, —O-tetrafluorophenyl and —O—C(O)—$OR_{20}$;

$R_{19}$ is selected from —$C_1$-$C_{12}$ alkylene-, —$C_3$-$C_8$ carbocyclo, —O—($C_1$-$C_{12}$ alkylene), —$C_6$-$C_{18}$ arylene in one or more rings which may optionally be substituted with one or more substituents $R_x$, —$C_1$-$C_{12}$ alkylene-$C_6$-$C_{18}$ arylene- wherein the arylene group is in one or more rings which may optionally be substituted with one or more substituents $R_x$, —$C_6$-$C_{18}$ arylene-$C_1$-$C_{12}$ alkylene- wherein the arylene group is in one or more rings which may optionally be substituted with one or more substituents $R_x$, —$C_1$-$C_{12}$ alkylene-($C_3$-$C_8$ carbocyclo)-, —($C_3$-$C_8$ carbocyclo)-$C_1$-$C_{12}$ alkylene-, —$C_5$-$C_{14}$ heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, —$C_1$-$C_{12}$ alkylene-($C_5$-$C_{14}$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, —($C_5$-$C_{14}$ heterocyclo)-$C_1$-$C_{12}$ alkylene-, wherein said heterocyclo group may be a saturated or unsaturated group having one or more rings and comprising at least one oxygen, nitrogen or sulphur atom in said ring(s), said group optionally being substituted with one or more substituents $R_x$, —$(OCH_2CH_2)_r$ and —$CH_2$—$(OCH_2CH_2)_r$, wherein each of the above alkylene substituents whether alone or attached to another moiety the carbon chain may optionally be substituted by one or more substituents $R_x$;

$R_{20}$ is a $C_1$-$C_{12}$ alkyl or an aryl group having from 6 to 18 carbon atoms in one or more aromatic rings, said aryl groups optionally being substituted with one or more substituents $R_x$;

r is an integer ranging from 1-10;

g is an integer of 0 or 1;

b is an integer of 0 or 1;

w is an integer ranging from 0 to 12; and each of D, $R_x$, X, T, and AA is as defined in the first aspect of the invention.

In preferred embodiments of the present invention, b+g+w is not 0. In further embodiments, b+w is not 0. In yet further embodiments, when w is not 0, then b is 1. In a further embodiment, when w is 0 then b is 1.

In a further aspect of the present invention, there is provided a compound of formula D-$(X)_b$-$(AA)_w$-$(T)_g$-$L_1$ or of formula D-$(X)_b$-$(AA)_w$-$(T)_g$-H, or a pharmaceutically acceptable salt, ester, solvate, tautomer or stereoisomer thereof; wherein each of D, X, AA, T, Li, b, g and w are as defined herein; but further wherein if the compound is a compound of formula D-$(X)_b$-$(AA)_w$-$(T)_g$-H then $b+w+g \neq 0$.

In a preferred embodiment according to aspects of the present invention, n is the ratio of the group [D-$(X)_b$-$(AA)_w$-$(T)_g$-(L)-] to the moiety comprising at least one antigen binding site and is in the range from 1 to 20. In further embodiments n is in the range from 1-12, 1-8, 3-8, 3-6, 3-5 or is 1, 2, 3, 4, 5 or 6 preferably, 3, 4 or 5 or 4.

In a further aspect of the present invention, there is provided a drug moiety D for use in an antibody drug conjugate. In a further aspect of the present invention, there is provided a drug moiety D for use as a payload in an antibody drug conjugate. In a further aspect of the present invention, there is provided the use of a drug moiety D as described herein, in the manufacture of an antibody drug conjugate.

In a further aspect of the present invention, there is provided a drug conjugate according to the present invention, for use as a medicament.

In a further aspect of the present invention, there is provided a drug conjugate according to the present invention for use in the treatment of cancer, and more preferably a cancer selected from lung cancer, colorectal cancer, breast cancer, pancreas carcinoma, kidney cancer, leukaemia, multiple myeloma, lymphoma, gastric and ovarian cancer. Most preferred cancer is breast cancer.

In a further aspect of the present invention, there is provided a pharmaceutical composition comprising a drug conjugate according to the present invention and a pharmaceutically acceptable carrier.

In a further aspect of the present invention, there is provided a method for the prevention or treatment of cancer, comprising administering an effective amount of a drug conjugate according to the present invention to a patient in need thereof. Preferably, the cancer is selected from lung cancer, colorectal cancer, breast cancer, pancreas carcinoma, kidney cancer, leukaemia, multiple myeloma, lymphoma, gastric and ovarian cancer. Most preferred cancer is breast cancer.

In a further aspect of the present invention, there is provided the use of a drug conjugate according to the present invention in the preparation of a medicament for the treatment of cancer, and more preferably a cancer selected from lung cancer, colorectal cancer, breast cancer, pancreas carcinoma, kidney cancer, leukaemia, multiple myeloma, lymphoma, gastric and ovarian cancer. Most preferred cancer is breast cancer.

In a further aspect of of the present invention, there is provided a kit comprising a therapeutically effective amount of a drug conjugate according to the present invention and a pharmaceutically acceptable carrier. The kit is for use in the treatment of cancer, and more preferably a cancer selected from lung cancer, colorectal cancer, breast cancer, pancreas carcinoma, kidney cancer, leukaemia, multiple myeloma, lymphoma, gastric and ovarian cancer. Most preferred cancer is breast cancer. A kit according to the present invention may comprise a therapeutically effective amount of a drug conjugate according to the present invention and, optionally, instructions for use of the drug conjugate in the treatment of cancer, particularly a cancer selected from lung cancer, colorectal cancer, breast cancer, pancreas carcinoma, kidney cancer, leukaemia, multiple myeloma, lymphoma, gastric and ovarian cancer; most preferably for use of the drug conjugate in the treatment of breast cancer.

In a further aspect of the present invention there is provided a process for the preparation of a drug conjugate according to the present invention comprising conjugating a moiety Ab comprising at least one antigen binding site and a drug D, Ab and D being as defined herein.

DETAILED DESCRIPTION OF PREFERRED EMBODIMENTS

The following apply to all aspects of the present invention:

In the compounds of the present invention, the alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, n-propyl, isopropyl and butyl, including n-butyl, isobutyl, sec-butyl and tert-butyl are particularly preferred alkyl groups in the compounds of the present invention.

In the compounds of the present invention, the alkenyl groups may be branched or unbranched, have one or more double bonds and from 2 to about 12 carbon atoms. One more preferred class of alkenyl groups has from 2 to about 6 carbon atoms. Even more preferred are alkenyl groups having 2, 3 or 4 carbon atoms. Ethenyl, 1-propenyl, 2-propenyl, 1-methylethenyl, 1-butenyl, 2-butenyl, and 3-butenyl are particularly preferred alkenyl groups in the compounds of the present invention.

In the compounds of the present invention, the alkynyl groups may be branched or unbranched, have one or more triple bonds and from 2 to about 12 carbon atoms. One more preferred class of alkynyl groups has from 2 to about 6 carbon atoms. Even more preferred are alkynyl groups having 2, 3 or 4 carbon atoms.

Suitable aryl groups in the compounds of the present invention include single and multiple ring compounds, including multiple ring compounds that contain separate and/or fused aryl groups. Typical aryl groups contain from 1 to 3 separated and/or fused rings and from 6 to about 18 carbon ring atoms. Preferably aryl groups contain from 6 to about 10 carbon ring atoms. Specially preferred aryl groups included substituted or unsubstituted phenyl, substituted or unsubstituted naphthyl, substituted or unsubstituted biphenyl, substituted or unsubstituted phenanthryl and substituted or unsubstituted anthryl.

Suitable heterocyclic groups include heteroaromatic and heteroalicyclic groups containing from 1 to 3 separated and/or fused rings and from 5 to about 18 ring atoms. Preferably heteroaromatic and heteroalicyclic groups contain from 5 to about 10 ring atoms, most preferably 5, 6, or 7 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S and include, e.g., pyrrolidinyl, tetrahydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pirrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The groups above mentioned may be substituted at one or more available positions by one or more suitable groups such as OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, protected amino, protected SH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, where each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. In addition, where there are more than one R' groups on a substituent, each R' may be the same or different.

In the compounds for the present invention, the halogen substituents include F, Cl, Br, and I.

More particularly, in the compounds of the present invention, the alkyl groups in the definitions of $R_{20}$, Fla, Fib, $R_c$, Rx, $R_y$ and $R_z$ may be straight chain or branched alkyl chain groups having from 1 to 12 carbon atoms, and they are preferably an alkyl group having from 1 to 6 carbon atoms, more preferably a methyl group, an ethyl group or an i-propyl group, and most preferably a methyl group. In the definitions of M and Q, they may be straight chain or branched alkyl chain groups having from 1 to 6 carbon atoms. Methyl, ethyl, n-propyl, isopropyl and butyl, including n-butyl, isobutyl, sec-butyl and tert-butyl are particularly preferred alkyl groups in the compounds of the present invention.

In the compounds of the present invention, the alkenyl groups in the definitions of $R_a$, $R_b$, $R_c$ and $R_x$ are branched or unbranched, and may have one or more double bonds and from 2 to 12 carbon atoms. Preferably, they have from 2 to 6 carbon atoms, and more preferably they are branched or unbranched alkenyl groups having 2, 3 or 4 carbon atoms. Ethenyl, 1-propenyl, 2-propenyl, 1-methylethenyl, 1-butenyl, 2-butenyl, and 3-butenyl are particularly preferred alkenyl groups in the compounds of the present invention.

In the compounds of the present invention, the alkynyl group in the definitions of $R_a$, $R_b$, $R_c$ and $R_x$ are branched or unbranched, and may have one or more triple bonds and from 2 to 12 carbon atoms. Preferably, they have from 2 to 6 carbon atoms, and more preferably they are branched or unbranched alkynyl groups having 2, 3 or 4 carbon atoms.

In the compounds of the present invention, the halogen substituents in the definitions of $R_x$, $R_y$ and $R_z$ include F, Cl, Br and I, preferably Cl.

In the compounds of the present invention, the 5- to 14-membered saturated or unsaturated heterocyclic group in the definitions of $R_x$ is a heterocyclic group having one or more rings, comprising at least one oxygen, nitrogen or sulphur atom in said ring(s). The heterocyclic group is a group which may be a heteroaromatic group or a heteroalicyclic group, the latter of which may be partially unsaturated, both the aromatic and the alicyclic heterocyclic group containing from 1 to 3 separated or fused rings. Preferably the heteroaromatic and heteroalicyclic group contain from 5 to 10 ring atoms. Suitable heteroaromatic groups in the compounds of the present invention contain one, two or three heteroatoms selected from N, O and S atoms and include, for example, quinolyl including 8-quinolyl, isoquinolyl, coumarinyl including 8-coumarinyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O and S atoms and include, for example, pyrrolidinyl, tetrahydrofuranyl, dihydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

In the compounds of the present invention, the aryl group in the definition of $R_x$ and $R_{20}$ is a single or multiple ring compound that contain separate and/or fused aryl groups and has from 6 to 18 ring atoms and is optionally substituted. Typical aryl groups contain from 1 to 3 separated or fused rings. Preferably aryl groups contain from 6 to 12 carbon ring atoms. Particularly preferred aryl groups include substituted or unsubstituted phenyl, substituted or unsubstituted naphthyl, substituted or unsubstituted biphenyl, substituted or unsubstituted phenanthryl and substituted or unsubstituted anthryl, and most preferred substituted or unsubstituted phenyl, wherein the substituents are as indicated above.

In the compounds of the present invention, the aralkyl groups in the definitions of $R_x$, $R_y$ and $R_z$ comprise an alkyl group as defined and exemplified above which is substituted with one or more aryl groups as defined and exemplified above. Preferred examples include optionally substituted benzyl, optionally substituted phenylethyl and optionally substituted naphthylmethyl.

In the compounds of the present invention, the aralkyloxy groups in the definitions of $R_x$ comprise an alkoxy group having from 1 to 12 carbon atoms which is substituted with one or more aryl groups as defined and exemplified above. Preferably, the alkoxy moiety has from 1 to 6 carbon atoms and the aryl group contains from 6 to about 12 carbon ring atoms, and most preferably the aralkyloxy group is optionally substituted benzyloxy, optionally substituted phenylethoxy and optionally substituted naphthylmethoxy.

In the compounds of the present invention, the heterocycloalkyl groups in the definitions of $R_y$ and $R_z$ comprise an alkyl group as defined and exemplified above which is substituted with one or more heterocyclyl groups as defined and exemplified above. Preferably, the heterocycloalkyl groups comprise an alkyl group having from 1 to 6 carbon atoms which is substituted with a heterocyclyl group having from 5 to 10 ring atoms in 1 or 2 ring atoms and can be aromatic, partially saturated or fully saturated. More preferably, the heterocycloalkyl groups comprise a methyl or ethyl group which is substituted with a heterocyclyl group selected from the group consisting of pyrrolidinyl, imidazolidinyl, piperidinyl, piperazinyl, morpholinyl, tetrahydrofuranyl, oxanyl, thianyl, 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl and benzimidazole.

In the compounds of the present invention, the alkylene groups in the definition of $R_{19}$ are straight or branched alkylene groups having from 1 to 12 carbon atoms and the alkylene groups in the definitions of M, X, T, and $R_{30}$ are straight or branched alkylene groups having from 1 to 6 carbon atoms. Preferably, the alkylene groups in the definition of $R_{19}$ are straight or branched alkylene groups having from 1 to 8 carbon atoms, more preferably straight or branched alkylene groups having from 1 to 6 carbon atoms. For M, preferred are straight or branched alkylene groups having from 1 to 3 carbon atoms. In the definition of X, the alkylene groups in the definition of X are preferably straight or branched alkylene groups having from 2 to 4 carbon atoms. For T, preferred are straight or branched alkylene groups having from 2 to 4 carbon atoms. In the definition of $R_{30}$, preferred are straight or branched alkylene groups having from 2 to 4 carbon atoms, being most preferred a straight alkylene group having 3 carbon atoms. For the avoidance of doubt, the term "alkylene" is used to refer to alkanediyl groups.

In the compounds of the present invention, the carbocyclo groups in the definitions of $R_{19}$ and M are cycloalkyl groups having from 3 to 8 carbon atoms which have two covalent bonds at any position on the cycloalkyl ring connecting said cycloalkyl group to the remainder of the drug conjugate. Preferably, the carbocyclo groups in the definitions of $R_{19}$ and M are cycloalkyl groups having from 3 to 7 carbon atoms, and more preferably carbocyclo groups having from 5 to 7 carbon atoms.

In the compounds of the present invention, the arylene groups in the definition of $R_{19}$ are aryl groups having from 6 to 18 carbon atoms in one or more rings which have two covalent bonds at any position on the aromatic ring system connecting said arylene groups to the remainder of the drug conjugate. Preferably, the arylene groups in the definition of $R_{19}$ are aryl groups having from 6 to 12 carbon atoms in one or more rings which have two covalent bonds at any position on the aromatic ring system, and most preferably they are phenylene groups.

In the compounds of the present invention, the heterocyclo groups in the definition of $R_{19}$ are heterocyclyl groups containing from 1 to 3 separated or fused rings having from 5 to 14 ring atoms and comprising at least one oxygen, nitrogen or sulphur atom in said ring(s), wherein there are two covalent bonds at any position on the ring system of said heterocyclic groups. The heterocyclic groups are groups which may be heteroaromatic groups or heteroalicyclic groups (the latter may be partially unsaturated). Preferably, the heterocyclo groups in the definition of $R_{19}$ are heterocyclyl groups containing from 1 to 3 separated or fused rings having from 5 to 12 ring atoms and comprising at least one oxygen, nitrogen or sulphur atom in said ring(s), wherein there are two covalent bonds at any position on the ring system of said heterocyclic groups.

Where there are more than one optional substituents $R_x$, $R_y$ or $R_z$ on a substituent, each substituent $R_x$ may be the same or different, each substituent $R_y$ may be the same or different and each $R_z$ may be the same or different.

In an embodiment, D may be a compound of formula I or a pharmaceutically acceptable salt or ester thereof:

(I)

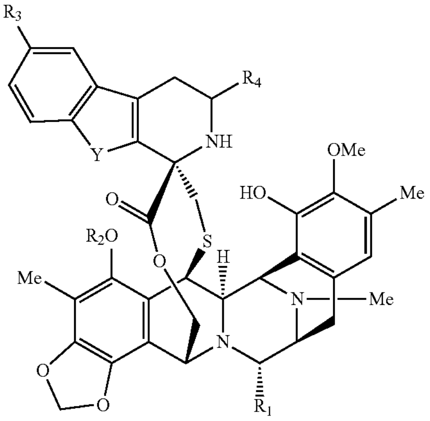

wherein:

Y is —NH— or —O—;

$R_1$ is —OH or —CN;

$R_2$ is a —C(=O)$R_a$ group;

$R_3$ is hydrogen or a —O$R_b$ group;

$R_4$ is selected from hydrogen, —$CH_2OH$, —$CH_2OC$(=O)$R_c$, —$CH_2NH_2$, and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino.

In an embodiment, the compound of formula I has the proviso that when $R_4$ is hydrogen then Y is —O—.

In a further embodiment, the compound of formula I may be a compound of formula IC, or a pharmaceutically acceptable salt or ester thereof:

IC

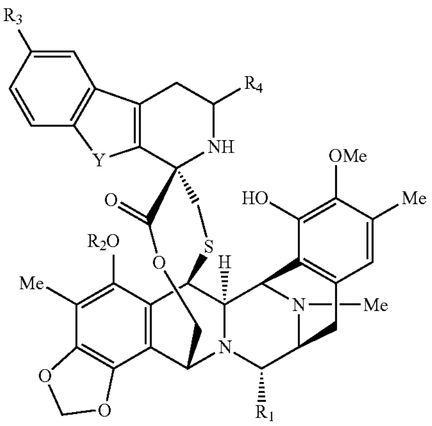

wherein:

Y is —NH—;

$R_1$ is —OH or —CN;

$R_2$ is a —C(=O)$R_a$ group;

$R_3$ is hydrogen or a —O$R_b$ group;

$R_4$ is selected from —$CH_2OH$, —$CH_2O$—(C=O)$R_c$, —$CH_2NH_2$ and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino.

In a yet further embodiment, the compound of formula I may be a compound of formula ID, or a pharmaceutically acceptable salt or ester thereof:

ID

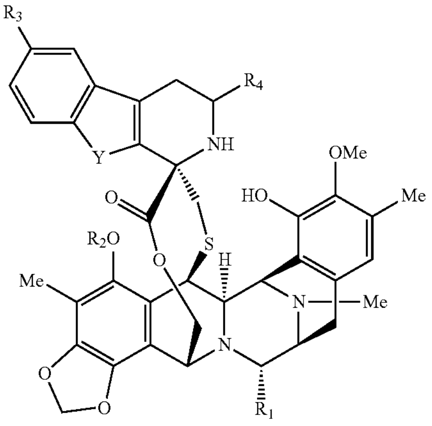

wherein:

Y is —O—;

$R_1$ is —OH or —CN;

$R_2$ is a —C(=O)$R_a$ group;

$R_3$ is hydrogen or a —O$R_b$ group;

$R_4$ is selected from hydrogen, —$CH_2OH$, —$CH_2O$—(C=O)$R_c$, —$CH_2NH_2$ and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino.

In a yet further embodiment, the compound of formula I may be a compound of formula IE, or a pharmaceutically acceptable salt or ester thereof:

IE

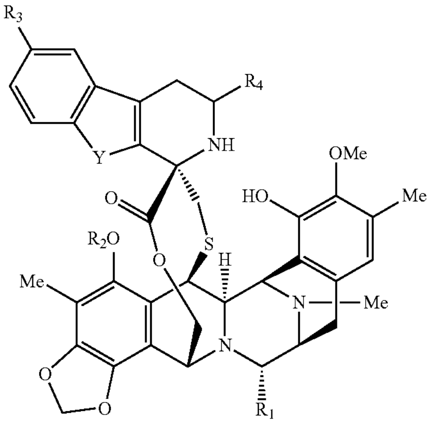

wherein:

Y is —NH— or —O—;

$R_1$ is —OH or —CN;

$R_2$ is a —C(=O)$R_a$ group;

$R_3$ is hydrogen or a —O$R_b$ group;

$R_4$ is selected from —$CH_2NH_2$ and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl; and $Prot^{NH}$ is a protecting group for amino.

In a yet further embodiment, the compound of formula I may be a compound of formula IA or a pharmaceutically acceptable salt or ester thereof:

IA

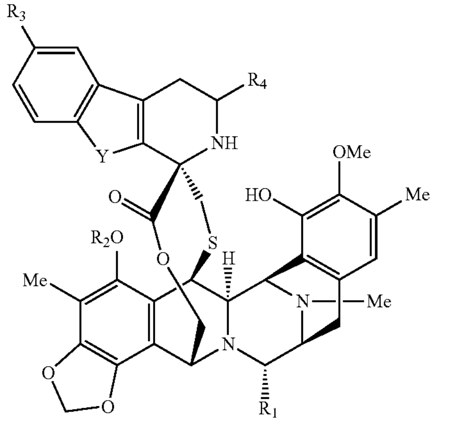

wherein:

Y is —NH— or —O—;

$R_1$ is —OH or —CN;

$R_2$ is a —C(=O)$R_a$ group;

$R_3$ is hydrogen;

$R_4$ is selected from hydrogen, —$CH_2OH$, —$CH_2O$—(C=O)$R_c$, —$CH_2NH_2$ and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino.

In an embodiment, the compound of formula IA has the proviso that when $R_4$ is hydrogen then Y is —O—.

In a yet further embodiment, the compound of formula I may be a compound of formula IB or a pharmaceutically acceptable salt or ester thereof:

IB

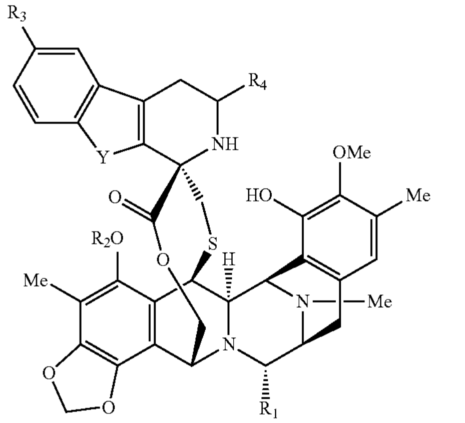

wherein:

Y is —NH— or —O—;

$R_1$ is —OH or —CN;

$R_2$ is a —C(=O)$R_a$ group;

$R_3$ is a —O$R_b$ group;

$R_4$ is selected from hydrogen, —$CH_2OH$, —$CH_2O$—(C=O)$R_c$, —$CH_2NH_2$ and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino.

In an embodiment, the compound of formula IB has the proviso that when $R_4$ is hydrogen then Y is —O—.

In a yet further embodiment, the compound of formula I may be a compound of formula IF or a pharmaceutically acceptable salt or ester thereof:

IF

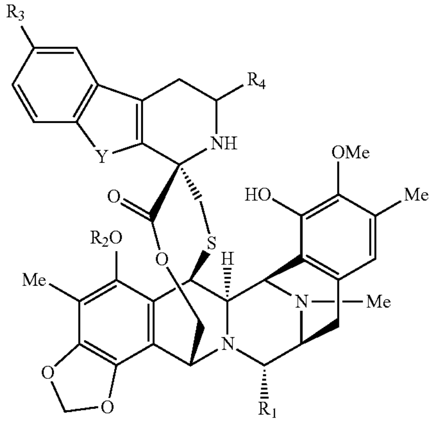

wherein:

Y is —NH— or —O—;

$R_1$ is —OH;

$R_2$ is a —C(═O)$R_a$ group;

$R_3$ is hydrogen or a —O$R_b$ group;

$R_4$ is selected from hydrogen, —$CH_2OH$, —$CH_2OC$(═O)$R_c$, —$CH_2NH_2$, and —$CH_2NHProt^{NH}$;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino.

In an embodiment, the compound of formula IF has the proviso that when $R_4$ is hydrogen then Y is —O—.

In a yet further embodiment, the compound of formula I may be a compound of formula IG or a pharmaceutically acceptable salt or ester thereof:

IG

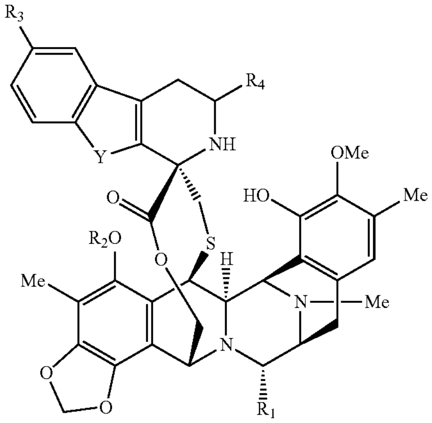

wherein:

Y is —NH— or —O—;

$R_1$ is —OH or —CN;

$R_2$ is acetyl;

$R_3$ is hydrogen or a —O$R_b$ group;

$R_4$ is selected from hydrogen, —$CH_2OH$, —$CH_2OC$(═O)$R_c$, —$CH_2NH_2$, and —$CH_2NHProt^{NH}$;

$R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $Prot^{NH}$ is a protecting group for amino In an embodiment, the compound of formula IG has the proviso that when FU is hydrogen then Y is —O—.

Preferred compounds of the compounds of formula I, IA, IB, IC, ID, IE, IF, or IG, are those having general formula a or b, or a pharmaceutically acceptable salt or ester thereof:

a

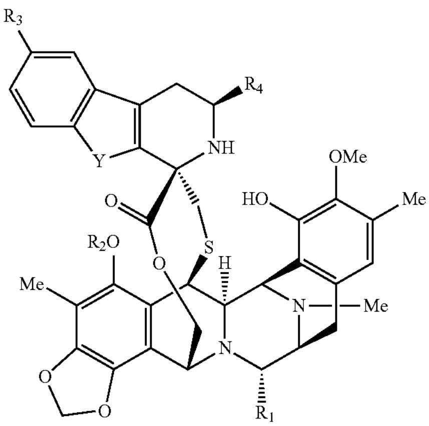

-continued b

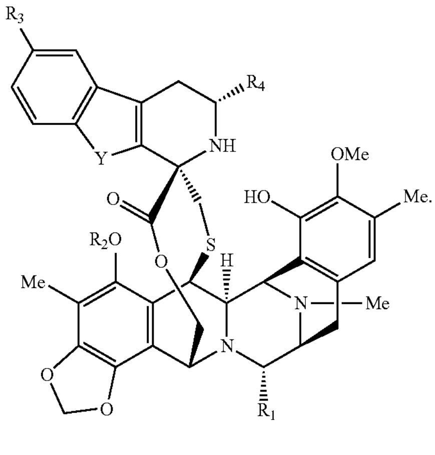

Note where the compounds have general formula a or b, $R_4$ may not be hydrogen.

Preferred compounds of the compounds of formula I, IA, IB, ID, IF, or IG may be those having formula c or a pharmaceutically acceptable salt or ester thereof:

c

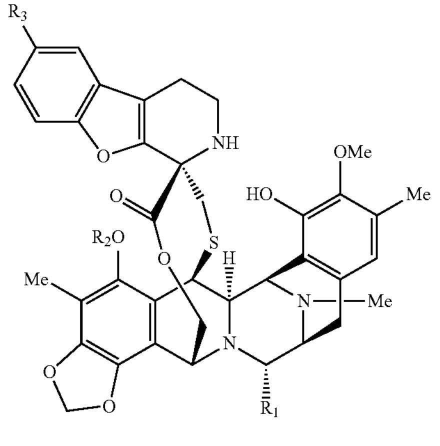

wherein:

$R_1$ is —OH or —CN;

$R_2$ is a —C(═O)$R_a$ group;

$R_3$ is hydrogen or a —$OR_b$ group;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

For the avoidance of doubt, the compounds above may be the drug moiety D and are covalently attached via a hydroxy or amine group to $(X)_b$ if any, or $(AA)_w$ if any, or to $(T)_g$ if any, or (L). Thus, when conjugated, a covalent bond replaces a proton on a hydroxy or amine group on the compound.

Preferred compounds include compounds of general formula I, IA, IB, IE, IF, IG, Ia, IAa, IBa, IEa, IFa, IGa, Ib, IAb, IBb, IEb, IFb, and IGb, wherein:

Y is —NH—;

and $R_1$; $R_2$; $R_3$; $R_4$; $R_a$; $R_b$; $R_c$; and $Prot^{NH}$ are as defined as above.

Preferred compounds include compounds of general formula I, IA, IB, IE, IF, IG, Ia, IAa, IBa, IEa, IFa, IGa, Ib, IAb, IBb, IEb, IFb, and IGb, wherein:

Y is —O—;

and $R_1$; $R_2$; $R_3$; $R_4$; $R_a$; $R_b$; $R_c$; and $Prot^{NH}$ are as defined as above.

Further preferred compounds include compounds of general formula I, IA, IB, IC, ID, IE, IG, Ia, IAa, IBa, ICa, IDa, IEa, IGa, Ib, IAb, IBb, ICb, IDb, IEb, and IGb, wherein:

$R_1$ is —OH;

and Y; $R_2$; $R_3$; $R_4$; $R_a$; $R_b$; $R_c$; and $Prot^{NH}$ are as defined as above.

Further preferred compounds include compounds of general formula I, IA, IB, IC, ID, IE, IF, Ia, IAa, IBa, ICa, IDa, IEa, IFa, Ib, IAb, IBb, ICb, IDb, IEb, and IFb, wherein:

$R_2$ is a —C(═O)$R_a$ group where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

and Y; $R_1$; $R_3$; $R_4$; $R_b$; $R_c$; and $Prot^{NH}$ are as defined as above.

Further preferred compounds include compounds of general formula I, IB, IC, ID, IE, IF, IG, Ia, IBa, ICa, IDa, IEa, IFa, IGa, Ib, IBb, ICb, IDb, IEb, IFb, and IGb, wherein:

$R_3$ is hydrogen or a —$OR_b$ group for compounds of formula I, IC, ID, IE, IF, IG, Ia, ICa, IDa, IEa, IFa, IGa, Ib, ICb, IDb, IEb, IFb, or IGb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and Y; $R_1$; $R_2$; $R_4$; $R_a$; $R_c$; and $Prot^{NH}$ are as defined as above.

Further preferred compounds include compounds of general formula I, IA, IB, IC, ID, IE, IF, IG, Ia, IAa, IBa, ICa, IDa, IEa, IFa, IGa, Ib, IAb, IBb, ICb, IDb, IEb, IFb, and IGb, wherein:

$R_4$ is selected from —$CH_2OH$, —$CH_2OC(═O)R_c$, —$CH_2NH_2$, and —$CH_2NHProt^{NH}$ for compounds of formula I, IA, IB, IC, ID, IF, IG, Ia, IAa, IBa, ICa, IDa, IFa, IGa, Ib, IAb, IBb, ICb, IDb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from —$CH_2OH$ and —$CH_2NH_2$. More preferably, $R_4$ may be —$CH_2NH_2$. Most preferred $R_4$ is —$CH_2OH$;

and Y; $R_1$; $R_2$; $R_3$; $R_a$; and $R_b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_1$ is —OH;

and $R_2$; $R_3$; $R_4$; $R_a$; $R_b$; $R_c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_2$ is a —C(═O)$R_a$ for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

and $R_1$; $R_3$; $R_4$; $R_b$; $R_c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_3$ is hydrogen or a —O$R_b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —O$R_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_1$; $R_2$; $R_4$; $R_a$; $R_c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_4$ is selected from —$CH_2OH$, —$CH_2OC(═O)R_c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, or substituted or unsubstituted tert-butyl. Most preferred $R_c$ is methyl. More preferred $R_4$ is selected from $CH_2OH$ and $CH_2NH_2$. More preferably, $R_4$ may be —$CH_2NH_2$. Most preferred $R_4$ is —$CH_2OH$;

and $R_1$; $R_2$; $R_3$; $R_a$; and $R_b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_1$ is —OH;

$R_2$ is a —C(═O)$R_a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

and $R_3$; $R_4$; $R_b$; $R_c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_1$ is —OH;

$R_3$ is hydrogen or a —O$R_b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —O$R_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_2$; $R_4$; $R_a$; $R_c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_1$ is —OH;

$R_4$ is selected from —$CH_2OH$, —$CH_2OC(═O)R_c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred FU is selected from $CH_2OH$ and $CH_2NH_2$. More preferably, FU may be —$CH_2NH_2$. Most preferred FU is —$CH_2OH$;

and $R_2$; $R_3$; $R_a$; and $R_b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_2$ is a —C(═O)$R_a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R_a$ is a substituted or unsubstituted $C_1$-$C_6$ alkyl. Particularly preferred FU is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —$OR_b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_1$; $R_4$; $R_c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_2$ is a —C(═O)$R_a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_4$ is selected from —$CH_2OH$, —$CH_2OC(═O)R_c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from $CH_2OH$ and $CH_2NH_2$. More preferably, $R_4$ may be —$CH_2NH_2$. Most preferred $R_4$ is —$CH_2OH$;

and $R_1$; $R_3$; and $R_b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_3$ is hydrogen or a —$OR_b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —$CH_2OH$, —$CH_2OC(═O)R_c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from $CH_2OH$ and $CH_2NH_2$. More preferably, $R_4$ may be —$CH_2NH_2$. Most preferred $R_4$ is —$CH_2OH$;

and $R_1$; $R_2$; and $R_a$; are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_1$ is —OH;

$R_2$ is a —C(═O)$R_a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —$OR_b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_4$; $R_c$; and $Prot^{NH}$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_1$ is —OH;

$R_2$ is a —C(═O)$R_a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_4$ is selected from —$CH_2OH$, —$CH_2OC(=O)R_c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from $CH_2OH$ and $CH_2NH_2$. More preferably, $R_4$ may be —$CH_2NH_2$. Most preferred $R_4$ is —$CH_2OH$;

and $R_3$; and $R_b$ are as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_2$ is a —$C(=O)R_a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —$OR_b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —$CH_2OH$, —$CH_2OC(=O)R_c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred FU is selected from $CH_2OH$ and $CH_2NH_2$. More preferably, FU may be —$CH_2NH_2$. Most preferred FU is —$CH_2OH$;

and $R_1$ is as defined as above.

Further preferred compounds include compounds of general formula I, IA, IB, IC, IE, IF, IG, Ia, IAa, IBa, ICa, IEa, IFa, IGa, Ib, IAb, IBb, ICb, IEb, IFb, and IGb, wherein:

Y is —NH—;

$R_1$ is —OH;

$R_2$ is a —$C(=O)R_a$ group for compounds of formula I, IA, IB, IC, IE, IF, Ia, IAa, IBa, ICa, IEa, IFa, Ib, IAb, IBb, ICb, IEb, or IFb; and $R_2$ is acetyl for compounds of formula IG, IGa or IGb; where $R_a$ is a substituted or unsubstituted $C_1$-$C_6$ alkyl. Particularly preferred FU is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —$OR_b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —$CH_2OH$, —$CH_2OC(=O)R_c$, —$CH_2NH_2$, and —$CH_2NHProt^{NH}$ for compounds of formula I, IA, IB, IC, IF, IG, Ia, IAa, IBa, ICa, IFa, IGa, Ib, IAb, IBb, ICb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from $CH_2OH$ and $CH_2NH_2$. More preferably, $R_4$ may be —$CH_2NH_2$. Most preferred $R_4$ is —$CH_2OH$.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_1$ is —OH;

and $R_2$; $R_3$; $R_4$; $R_a$; $R_b$; $R_c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_2$ is a —$C(=O)R_a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

and $R_1$; $R_3$; $R_4$; $R_b$; $R_c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_3$ is hydrogen or a —$OR_b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ is hydrogen and methoxy, being hydrogen the most preferred $R_3$ group;

and $R_1$; $R_2$; $R_4$; $R_a$; $R_c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_4$ is selected from —$CH_2OH$, —$CH_2OC({=}O)R_c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and FU is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from —$CH_2OH$ and $CH_2NH_2$. More preferably, $R_4$ may be —$CH_2NH_2$. Most preferred $R_4$ is —$CH_2OH$;

and $R_1$; $R_2$; $R_3$; $R_a$; and $R_b$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_1$ is —OH;

$R_2$ is a —$C({=}O)R_a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

and $R_3$; $R_4$; $R_b$; $R_c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_1$ is —OH;

$R_3$ is hydrogen or a —$OR_b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_2$; FU; $R_a$; $R_c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_1$ is —OH;

$R_4$ is selected from —$CH_2OH$, —$CH_2OC({=}O)R_c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from —$CH_2OH$ and $CH_2NH_2$. More preferably, $R_4$ may be —$CH_2NH_2$. Most preferred $R_4$ is —$CH_2OH$;

and $R_2$; $R_3$; $R_a$; and $R_b$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_2$ is a —$C({=}O)R_a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —$OR_b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group; and $R_1$; $R_4$; $R_c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_2$ is a —C(═O)$R_a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_4$ is selected from —$CH_2OH$, —$CH_2OC$(═O)$R_c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from —$CH_2OH$ and —$CH_2NH_2$. More preferably, $R_4$ may be —$CH_2NH_2$. Most preferred $R_4$ is —$CH_2OH$;

and $R_1$; $R_3$; and $R_b$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_3$ is hydrogen or a —$OR_b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —$CH_2OH$, —$CH_2OC$(═O)$R_c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from —$CH_2OH$ and —$CH_2NH_2$. More preferably, $R_4$ may be —$CH_2NH_2$. Most preferred $R_4$ is —$CH_2OH$;

and $R_1$; $R_2$; and $R_a$; are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_1$ is —OH;

$R_2$ is a —C(═O)$R_a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —$OR_b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and FU; $R_c$; and $Prot^{NH}$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_1$ is —OH;

$R_2$ is a —C(═O)$R_a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_4$ is selected from —$CH_2OH$, —$CH_2OC$(═O)$R_c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from —$CH_2OH$ and —$CH_2NH_2$. More preferably, $R_4$ may be —$CH_2NH_2$. Most preferred $R_4$ is —$CH_2OH$;

and $R_3$; and $R_b$ are as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_2$ is a —C(=O)$R_a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —$OR_b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —$CH_2OH$, —$CH_2OC(=O)R_c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from —$CH_2OH$ and —$CH_2NH_2$. More preferably, $R_4$ may be —$CH_2NH_2$. Most preferred $R_4$ is —$CH_2OH$;

and $R_1$ is as defined as above.

Further preferred compounds include compounds of general formula I, IA, IB, ID, IE, IF, IG, Ia, IAa, IBa, IDa, IEa, IFa, IGa, Ib, IAb, IBb, IDb, IEb, IFb, and IGb, wherein:

Y is —O—;

$R_1$ is —OH;

$R_2$ is a —C(=O)$R_a$ group for compounds of formula I, IA, IB, ID, IE, IF, Ia, IAa, IBa, IDa, IEa, IFa, Ib, IAb, IBb, IDb, IEb, or IFb; and $R_2$ is acetyl for compounds of formula IG, IGa or IGb; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —$OR_b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa, or IAb; and $R_3$ is a —$OR_b$ group for compounds of formula IB, IBa or IBb; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

$R_4$ is selected from —$CH_2OH$, —$CH_2OC(=O)R_c$, —$CH_2NH_2$, and —$CH_2NHProt^{NH}$ for compounds of formula I, IA, IB, ID, IF, IG, Ia, IAa, IBa, IDa, IFa, IGa, Ib, IAb, IBb, IDb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from —$CH_2OH$ and —$CH_2NH_2$. More preferably, $R_4$ may be —$CH_2NH_2$. Most preferred $R_4$ is —$CH_2OH$.

Further preferred compounds include compounds of general formula Ic, IAc, IBc, IDc, and IGc wherein:

$R_1$ is —OH;

and $R_2$; $R_3$; $R_a$ and $R_b$ are as defined as above.

Further preferred compounds include compounds of general formula Ic, IAc, IBc, IDc, IFc, and IGc, wherein:

$R_2$ is a —C(=O)$R_a$ group for compounds of formula Ic, IAc, IBc, IDc, or IFc; and $R_2$ is acetyl for compounds of formula IGc; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

and $R_1$; $R_3$; $R_b$ are as defined as above.

Further preferred compounds include compounds of general formula Ic, IAc, IBc, IDc, IFc, and IGc, wherein:

$R_3$ is hydrogen or a —$OR_b$ group for compounds of formula Ic, IDc, IFc, or IGc; $R_3$ is hydrogen for compounds of formula IAc; and $R_3$ is a —$OR_b$ group for compounds of formula IBc; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_1$; $R_2$; and $R_3$ are as defined as above.

Further preferred compounds include compounds of general formula Ic, IAc, IBc, IDc, IFc, and IGc, wherein:

$R_1$ is —OH;

$R_3$ is a —C(═O)$R_3$ group for compounds of formula Ic, IAc, IBc, IDc, or IFc; and $R_3$ is acetyl for compounds of formula IGc; where $R_3$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

and $R_3$; and $R_b$ are as defined as above.

Further preferred compounds include compounds of general formula Ic, IAc, IBc, IDc, IFc, and IGc, wherein:

$R_1$ is —OH;

$R_3$ is hydrogen or a —O$R_b$ group for compounds of formula Ic, IDc, IFc, or IGc; $R_3$ is hydrogen for compounds of formula IAc; and $R_3$ is a —O$R_b$ group for compounds of formula IBc; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_2$; and $R_a$ are as defined as above.

Further preferred compounds include compounds of general formula Ic, IAc, IBc, IDc, IFc, and IGc, wherein:

$R_2$ is a —C(═O)$R_a$ group for compounds of formula Ic, IAc, IBc, IDc, or IFc; and $R_2$ is acetyl for compounds of formula IGc; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —O$R_b$ group for compounds of formula Ic, IDc, IFc, or IGc; $R_3$ is hydrogen for compounds of formula IAc; and $R_3$ is a —O$R_b$ group for compounds of formula IBc; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group;

and $R_1$ is as defined as above.

Further preferred compounds include compounds of general formula Ic, IAc, IBc, IDc, IFc, and IGc, wherein:

$R_1$ is —OH;

$R_2$ is a —C(═O)$R_a$ group for compounds of formula Ic, IAc, IBc, IDc, or IFc; and $R_2$ is acetyl for compounds of formula IGc; where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl;

$R_3$ is hydrogen or a —O$R_b$ group for compounds of formula Ic, IDc, IFc, or IGc; $R_3$ is hydrogen for compounds of formula IAc; and $R_3$ is a —O$R_b$ group for compounds of formula IBc; where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group.

The following preferred substituents (where allowed by possible substituent groups) apply to compounds of formula I, IA, IB, IC, ID, IE, IF, IG, Ia, IAa, IBa, ICa, IDa, IEa, IFa, IGa, Ib, IAb, IBb, ICb, IDb, IEb, IFb, IGb, Ic, IAc, IBc, IDc, IFc, and IGc: In compounds of the present invention, particularly preferred $R_1$ is —OH.

In compounds of the present invention, particularly preferred $R_2$ is a —C(═O)$R_a$ group where $R_a$ is a substituted or unsubstituted $C_1$-$C_6$ alkyl. Particularly preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. Most preferred $R_2$ is acetyl.

In compounds of the present invention, particularly preferred $R_3$ is hydrogen or a —O$R_b$ group where $R_b$ is a substituted or unsubstituted $C_1$-$C_6$ alkyl. Particularly preferred $R_b$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl and substituted or unsubstituted tert-butyl. More preferred $R_3$ are hydrogen and methoxy, being hydrogen the most preferred $R_3$ group.

In compounds of the present invention, particularly preferred $R_4$ is selected from H, —$CH_2OH$, —$CH_2OC(=O)R_c$, —$CH_2NH_2$, and —$CH_2NHProt^{NH}$ where $R_c$ is a substituted or unsubstituted $C_1$-$C_6$ alkyl. Particularly preferred $R_c$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from H, $CH_2OH$ and $CH_2NH_2$. Most preferred $R_4$ is —$CH_2OH$.

In compounds of general formula I, IA, IB, IC, ID, IE, IF, IG, Ia, IAa, IBa, ICa, IDa, IEa, IFa, IGa, Ib, IAb, IBb, ICb, IDb, IEb, IFb, and IGb particularly preferred $R_4$ is selected from —$CH_2OH$, —$CH_2OC(=O)R_c$, —$CH_2NH_2$, and —$CH_2NHProt^{NH}$ for compounds of formula I, IA, IB, IC, ID, IF, IG, Ia, IAa, IBa, ICa, IDa, IFa, IGa, Ib, IAb, IBb, ICb, IDb, IFb, or IGb; and $R_4$ is selected from —$CH_2NH_2$, and —$CH_2NHProt^{NH}$ for compounds of formula IE, IEa or IEb; where $R_c$ is a substituted or unsubstituted $C_1$-$C_6$ alkyl. Particularly preferred $R_c$ is a substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, substituted or unsubstituted sec-butyl, and substituted or unsubstituted tert-butyl. Most preferred $R_c$ is methyl. More preferred $R_4$ is selected from $CH_2OH$ and $CH_2NH_2$. Most preferred $R_4$ is —$CH_2OH$.

Being particularly preferred compounds of formula Ia, IAa, IBa, ICa, IDa, IFa, IGa when $R_4$ is —$CH_2OH$ or —$CH_2OC(=O)R_c$ and compounds of formula Ib, IAb, IBb, ICb, IDb, IEb, IFb, IGb when $R_4$ is —$CH_2NH_2$ or —$CH_2NHProt^{NH}$.

In compounds of the present invention, particularly preferred Y is —NH—.

Alternatively, in compounds of the present invention, particularly preferred Y is —O—.

Preferred compounds according to the present invention include:

Compounds of formula I, IA, IB, IC, ID, IF, IG, Ia, IAa, IBa, ICa, IDa, IFa, IGa, Ib, IAb, IBb, ICb, IDb, IFb, and IGb wherein:

$R_4$ is selected from —$CH_2OH$ and —$CH_2OC(=O)R_c$;

Being particularly preferred compounds of formula Ia, IAa, IBa, ICa, IDa, IFa, and IGa and/or compounds where FU is —$CH_2OH$.

Compounds of formula I, IA, IB, IC, ID, IE IF, IG, Ia, IAa, IBa, ICa, IDa, IEa, IFa, IGa, Ib, IAb, IBb, ICb, IDb, IEb, IFb, and IGb wherein $R_4$ is selected from —$CH_2NH_2$ and —$CH_2NHProt^{NH}$; and $Prot^{NH}$ is a protecting group for amino.

Being particularly preferred compounds of formula Ib, IAb, IBb, ICb, IDb, IEb, IFb, and IGb and/or compounds where FU is —$CH_2NH_2$.

Compounds of formula Ic, IAc, IBc, IDc, IFc, IGc wherein $R_2$ is a —$C(=O)R_a$ group for compounds of formula Ic, IAc, IBc, IDc, or IFc; and $R_2$ is acetyl for compounds of formula IGc;

$R_3$ is hydrogen or a —$OR_b$ group for compounds of formula Ic, IDc, IFc, IGc; $R_3$ is hydrogen for compounds of formula IAc; or $R_3$ is a —$OR_b$ group for compounds of formula IBc;

$R_a$ is selected from hydrogen, and substituted or unsubstituted $C_1$-$C_6$ alkyl; and $R_b$ is substituted or unsubstituted $C_1$-$C_6$ alkyl.

Particularly preferred compounds according to the present invention include:

Compounds of formula I, IA, IB, IC, IF, IG, Ia, IAa, IBa, ICa, IFa, IGa, Ib, IAb, IBb, ICb, IFb, and IGb wherein Y is —NH—;

$R_4$ is selected from —$CH_2OH$, and —$CH_2OC(=O)R_c$; and $R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

Being more preferred compounds of formula Ia, IAa, IBa, ICa, IFa, IGa and/or compounds where $R_4$ is —$CH_2OH$.

Compounds of formula I, IA, IB, ID, IF, IG, Ia, IAa, IBa, IDa, IFa, IGa, Ib, IAb, IBb, IDb, IFb, and IGb wherein Y is —O—;

$R_4$ is selected from —$CH_2OH$ and —$CH_2OC(=O)R_c$; and $R_c$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

Being more preferred compounds of formula Ia, IAa, IBa, IDa, IFa, IGa and/or compounds where $R_4$ is —$CH_2OH$.

Compounds of formula I, IA, IB, IC, IE, IF, IG, Ia, IAa, IBa, ICa, IEa, IFa, IGa, Ib, IAb, IBb, ICb, IEb, IFb, and IGb wherein Y is —NH—;

$R_4$ is selected from —$CH_2NH_2$ and —$CH_2NHProt^{NH}$; and $Prot^{NH}$ is a protecting group for amino.

Being more preferred compounds of formula Ib, IAb, IBb, ICb, IEb, IFb, IGb and/or compounds where $R_4$ is —$CH_2NH_2$.

Compounds of formula I, IA, IB, ID, IE, IF, IG, Ia, IAa, IBa, IDa, IEa, IFa, IGa, Ib, IAb, IBb, IDb, IEb, IFb, and IGb wherein Y is —O—;

$R_4$ is selected from —$CH_2NH_2$ and —$CH_2NHProt^{NH}$; and $Prot^{NH}$ is a protecting group for amino.

Being more preferred compounds of formula Ib, IAb, IBb, IDb, IEb, IFb, IGb and/or compounds where FU is —$CH_2NH_2$.

Compounds of formula I, IA, IB, IC, ID, IF, IG, Ia, IAa, IBa, ICa, IDa, IFa, IGa, Ib, IAb, IBb, ICb, IDb, IFb, IGb wherein $R_2$ is a —$C(=O)R_a$ group for compounds of formula I, IA, IB, IC, ID, IF, Ia, IAa, IBa, ICa, IDa, IFa, Ib, IAb, IBb, ICb, IDb, or IFb; and $R_2$ is acetyl for compounds of formula IG, IGa or IGb;

$R_3$ is hydrogen or a —$OR_b$ group for compounds of formula I, IC, ID, IF, IG, Ia, ICa, IDa, IFa, IGa, Ib, ICb, IDb, IFb, or IGb; $R_3$ is hydrogen for compounds of formula IA, IAa or IAb; or $R_3$ is a —$OR_b$ group for compounds of formula IB, IBa or IBb;

$R_4$ is selected from —$CH_2OH$, and —$CH_2OC(=O)R_c$;

$R_a$ is selected from hydrogen, and substituted or unsubstituted $C_1$-$C_6$ alkyl;

$R_b$ is substituted or unsubstituted $C_1$-$C_6$ alkyl; and $R_c$ is substituted or unsubstituted $C_1$-$C_6$ alkyl.

Being more preferred compounds of formula Ia, IAa, IBa, ICa, IDa, IFa, IGa and/or compounds where $R_4$ is —$CH_2OH$.

Compounds of formula I, IA, IB, IC, ID, IE, IF, IG, Ia, IAa, IBa, ICa, IDa, IEa, IFa, IGa, Ib, IAb, IBb, ICb, IDb, IEb, IFb, and IGb wherein $R_2$ is a —$C(=O)R_a$ group for compounds of formula I, IA, IB, IC, ID, IF, Ia, IAa, IBa, ICa, IDa, IFa, Ib, IAb, IBb, ICb, IDb, or IFb; and $R_2$ is acetyl for compounds of formula IG, IGa or IGb;

$R_3$ is hydrogen or a —$OR_b$ group for compounds of formula I, IC, ID, IE, IF, IG, Ia, ICa, IDa, IEa, IFa, IGa, Ib, ICb, IDb, IEb, IFb, or IGb; $R_3$ is hydrogen for compounds of formula IA, IAa or IAb; or $R_3$ is a —$OR_b$ group for compounds of formula IB, IBa or IBb;

$R_4$ is selected from —$CH_2NH_2$ and —$CH_2NHProt^{NH}$;

$R_a$ is selected from hydrogen, and substituted or unsubstituted $C_1$-$C_6$ alkyl;

$R_b$ is substituted or unsubstituted $C_1$-$C_6$ alkyl; and $Prot^{NH}$ is a protecting group for amino.

Being more preferred compounds of formula Ib, IAb, IBb, ICb, IDb, IEb, IFb, IGb and/or compounds where FU is —$CH_2NH_2$.

Compounds of formula Ic, IAc, IBc, IDc, IFc, IGc wherein $R_2$ is a —C(═O)$R_a$ group for compounds of formula Ic, IAc, IBc, IDc, or IFc; and $R_2$ is acetyl for compounds of formula IGc;

$R_3$ is hydrogen or a —$OR_b$ group for compounds of formula Ic, IDc, IFc, IGc; $R_3$ is hydrogen for compounds of formula IAc; or $R_3$ is a —$OR_b$ group for compounds of formula IBc;

$R_a$ is substituted or unsubstituted $C_1$-$C_6$ alkyl; and $R_b$ is substituted or unsubstituted $C_1$-$C_6$ alkyl.

More preferred compounds according to the present invention include

Compounds of formula I, IA, IB, IC, IF, IG, Ia, IAa, IBa, ICa, IFa, IGa, Ib, IAb, IBb, ICb, IFb, and IGb wherein Y is —NH—;

$R_2$ is a —C(═O)$R_a$ group for compounds of formula I, IA, IB, IC, IF, Ia, IAa, IBa, ICa, IFa, Ib, IAb, IBb, ICb, or IFb; and $R_2$ is acetyl for compounds of formula IG, IGa or IGb;

$R_3$ is hydrogen or a —$OR_b$ group for compounds of formula I, IC, IF, IG, Ia, ICa, IFa, IGa, Ib, ICb, IFb, or IGb; $R_3$ is hydrogen for compounds of formula IA, IAa or IAb; or $R_3$ is a —$OR_b$ group for compounds of formula IB, IBa or IBb;

$R_4$ is —$CH_2OH$;

$R_a$ is selected from hydrogen and substituted or unsubstituted $C_1$-$C_6$ alkyl; and $R_b$ is substituted or unsubstituted $C_1$-$C_6$ alkyl.

Being particularly more preferred compounds of formula Ia, IAa, or IBa, ICa, IFa, IGa.

Compounds of formula I, IA, IB, ID, IF, IG, Ia, IAa, IBa, IDa, IFa, IGa, Ib, IAb, IBb, IDb, IFb, and IGb wherein Y is —O—;

$R_2$ is a —C(═O)$R_a$ group for compounds of formula I, IA, IB, ID, IF, Ia, IAa, IBa, IDa, IFa, Ib, IAb, IBb, IDb, or IFb; and $R_2$ is acetyl for compounds of formula IG, IGa or IGb;

$R_3$ is hydrogen or a —$OR_b$ group for compounds of formula I, ID, IF, IG, Ia, IDa, IFa, IGa, Ib, IDb, IFb, or IGb; $R_3$ is hydrogen for compounds of formula IA, IAa or IAb; or $R_3$ is a —$OR_b$ group for compounds of formula IB, IBa or IBb;

$R_4$ is —$CH_2OH$;

$R_a$ is selected from hydrogen and substituted or unsubstituted $C_1$-$C_6$ alkyl; and $R_b$ is substituted or unsubstituted $C_1$-$C_6$ alkyl.

Being particularly more preferred compounds of formula Ia, IAa, IBa, IDa, IFa, or IGa.

Compounds of formula I, IA, IB, IC, IE, IF, IG, Ia, IAa, IBa, ICa, IEa, IFa, IGa, Ib, IAb, IBb, ICb, IEb, IFb, and IGb wherein Y is —NH—;

$R_2$ is a —C(═O)$R_a$ group for compounds of formula I, IA, IB, IC, IE, IF, Ia, IAa, IBa, ICa, IEa, IFa, Ib, IAb, IBb, ICb, IEb or IFb; and $R_2$ is acetyl for compounds of formula IG, IGa or IGb;

$R_3$ is hydrogen or a —$OR_b$ group for compounds of formula I, IC, IE, IF, IG, Ia, ICa, IEa, IFa, IGa, Ib, ICb, IEb, IFb, or IGb; $R_3$ is hydrogen for compounds of formula IA, IAa or IAb; or $R_3$ is a —$OR_b$ group for compounds of formula IB, IBa or IBb;

$R_4$ is selected from —$CH_2NH_2$ and —$CH_2NHProt^{NH}$;

$R_a$ is selected from hydrogen and substituted or unsubstituted $C_1$-$C_6$ alkyl;

$R_b$ is substituted or unsubstituted $C_1$-$C_6$ alkyl; and $Prot^{NH}$ is a protecting group for amino.

Being particularly more preferred compounds of formula Ib, IAb, IBb, ICb, IEb, IFb, IGb and/or compounds where $R_4$ is —$CH_2NH_2$.

Compounds of formula I, IA, IB, ID, IE, IF, IG, Ia, IAa, IBa, IDa, IEa, IFa, IGa, Ib, IAb, IBb, IDb, IEb, IFb, and IGb wherein Y is —O—;

$R_2$ is a —C(═O)$R_a$ group for compounds of formula I, IA, IB, ID, IE, IF, Ia, IAa, IBa, IDa, IEa, IFa, Ib, IAb, IBb, IDb, IEb or IFb; and $R_2$ is acetyl for compounds of formula IG, IGa or IGb;

$R_3$ is hydrogen or a —$OR_b$ group for compounds of formula I, ID, IE, IF, IG, Ia, IDa, IEa, IFa, IGa, Ib, IDb, IEb, IFb, or IGb; $R_3$ is hydrogen for compounds of formula IA, IAa or IAb; or $R_3$ is a —$OR_b$ group for compounds of formula IB, IBa or IBb;

$R_4$ is selected from —$CH_2NH_2$ and —$CH_2NHProt^{NH}$;

$R_a$ is selected from hydrogen and substituted or unsubstituted $C_1$-$C_6$ alkyl;

$R_b$ is substituted or unsubstituted $C_1$-$C_6$ alkyl; and $Prot^{NH}$ is a protecting group for amino.

Being particularly more preferred compounds of formula Ib, IAb, IBb, IDb, IEb, IFb, IGb and/or compounds where $R_4$ is $CH_2NH_2$.

Compounds of formula I, IA, IB, IC, ID, IF, IG, Ia, IAa, IBa, ICa, IDa, IFa, IGa, Ib, IAb, IBb, ICb, IDb, IFb, and IGb wherein $R_2$ is a —C(═O)$R_a$ group for compounds of formula I, IA, IB, IC, ID, IF, Ia, IAa, IBa, ICa, IDa, IFa, Ib, IAb, IBb, ICb, IDb or IFb; and $R_2$ is acetyl for compounds of formula IG, IGa or IGb;

$R_3$ is hydrogen or a —$OR_b$ group for compounds of formula I, IC, ID, IF, IG, Ia, ICa, IDa, IFa, IGa, Ib, ICb, IDb, IFb, or IGb; $R_3$ is hydrogen for compounds of formula IA, IAa or IAb; or $R_3$ is a —$OR_b$ group for compounds of formula IB, IBa or IBb;

$R_4$ is —$CH_2OH$;

$R_a$ is substituted or unsubstituted $C_1$-$C_6$ alkyl; and $R_b$ is substituted or unsubstituted $C_1$-$C_6$ alkyl.

Being particularly more preferred compounds of formula Ia, IAa, IBa, ICa, IDa, IFa, or IGa.

Compounds of formula I, IA, IB, IC, ID, IE, IF, IG, Ia, IAa, IBa, ICa, IDa, IEa, IFa, IGa, Ib, IAb, IBb, ICb, IDb, IEb, IFb, and IGb wherein $R_2$ is a —C(═O)$R_a$ group for compounds of formula I, IA, IB, IC, ID, IE, IF, Ia, IAa, IBa, ICa, IDa, IEa, IFa, Ib, IAb, IBb, ICb, IDb, IEb or IFb; and $R_2$ is acetyl for compounds of formula IG, IGa or IGb;

$R_3$ is hydrogen or a —$OR_b$ group for compounds of formula I, IC, ID, IE, IF, IG, Ia, ICa, IDa, IEa, IFa, IGa, Ib, ICb, IDb, IEb, IFb, or IGb; $R_3$ is hydrogen for compounds of formula IA, IAa or IAb; or $R_3$ is a —$OR_b$ group for compounds of formula IB, IBa or IBb;

$R_4$ is selected from —$CH_2NH_2$ and —$CH_2NHProt^{NH}$;

$R_a$ is substituted or unsubstituted $C_1$-$C_6$ alkyl;

$R_b$ is substituted or unsubstituted $C_1$-$C_6$ alkyl; and $Prot^{NH}$ is a protecting group for amino.

Being particularly more preferred compounds of formula Ib, IAb, IBb, ICb, IDb, IEb, IFb, IGb and/or compounds where $R_4$ is —$CH_2NH_2$.

Compounds of formula I, IA, IB, IC, IF, IG, Ia, IAa, IBa, ICa, IFa, IGa, Ib, IAb, IBb, ICb, IFb, and IGb wherein Y is —NH—;

$R_2$ is a —C(=O)$R_a$ group for compounds of formula I, IA, IB, IC, IF, Ia, IAa, IBa, ICa, IFa, Ib, IAb, IBb, ICb, or IFb; and $R_2$ is acetyl for compounds of formula IG, IGa or IGb;

$R_3$ is hydrogen or a —$OR_b$ group for compounds of formula I, IC, IF, IG, Ia, ICa, IFa, IGa, Ib, ICb, IFb, or IGb; $R_3$ is hydrogen for compounds of formula IA, IAa or IAb; or $R_3$ is a —$OR_b$ group for compounds of formula IB, IBa or IBb;

$R_4$ is —$CH_2OC$(=O)RC;

$R_a$ is selected from hydrogen and substituted or unsubstituted $C_1$-$C_6$ alkyl;

$R_b$ is substituted or unsubstituted $C_1$-$C_6$ alkyl; and $R_c$ is a substituted or unsubstituted $C_1$-$C_6$ alkyl.

Being more preferred compounds of formula Ia, IAa, IBa, ICa, IFa, or IGa.

Compounds of formula Ic, IAc, IBc, IDc, IFc, and IGc wherein $R_2$ is a —C(=O)$R_a$ group for compounds of formula Ic, IAc, IBc, IDc, or IFc; and $R_2$ is acetyl for compounds of formula IGc;

$R_3$ is hydrogen or methoxy for compounds of formula Ic, IDc, IFc, or IGc; $R_3$ is hydrogen for compounds of formula IAc; or $R_3$ is methoxy for compounds of formula IBc; and $R_a$ is substituted or unsubstituted $C_1$-$C_6$ alkyl.

Particularly more preferred compounds according to the present invention include:

Compounds of formula I, IA, IB, IC, IF, IG, Ia, IAa, IBa, ICa, IFa, IGa, Ib, IAb, IBb, ICb, IFb, and IGb wherein Y is —NH—;

$R_2$ is a —C(=O)$R_a$ group for compounds of formula I, IA, IB, IC, IF, Ia, IAa, IBa, ICa, IFa, Ib, IAb, IBb, ICb, or IFb; and $R_2$ is acetyl for compounds of formula IG, IGa or IGb;

$R_3$ is hydrogen or methoxy for compounds of formula I, IC, IF, IG, Ia, ICa, IFa, IGa, Ib, ICb, IFb, or IGb; $R_3$ is hydrogen for compounds of formula IA, IAa or IAb; and $R_3$ is methoxy for compounds of formula IB, IBa or IBb;

$R_4$ is —$CH_2OH$; and $R_a$ is substituted or unsubstituted $C_1$-$C_6$ alkyl.

Being even more preferred compounds of formula Ia, IAa, IBa, ICa, IFa, IGa.

Compounds of formula I, IA, IB, ID, IF, IG, Ia, IAa, IBa, IDa, IFa, IGa, Ib, IAb, IBb, IDb, IFb, and IGb wherein Y is —O—;

$R_2$ is a —C(=O)$R_a$ group for compounds of formula I, IA, IB, ID, IF, Ia, IAa, IBa, IDa, IFa, Ib, IAb, IBb, IDb, or IFb; and $R_2$ is acetyl for compounds of formula IG, IGa or IGb;

$R_3$ is hydrogen or methoxy for compounds of formula I, ID, IF, IG, Ia, IDa, IFa, IGa, Ib, IDb, IFb, or IGb; $R_3$ is hydrogen for compounds of formula IA, IAa or IAb; or $R_3$ is methoxy for compounds of formula IB, IBa or IBb;

$R_4$ is —$CH_2OH$; and $R_a$ is substituted or unsubstituted $C_1$-$C_6$ alkyl.

Being even more preferred compounds of formula Ia, IAa, IBa, IDa, IEa, IFa, IGa.

Compounds of formula I, IA, IB, IC, IE, IF, IG, Ia, IAa, IBa, ICa, IEa, IFa, IGa, Ib, IAb, IBb, ICb, IEb, IFb, and IGb wherein Y is —NH—;

$R_2$ is a —C(=O)$R_a$ group for compounds of formula I, IA, IB, IC, IE, IF, Ia, IAa, IBa, ICa, IEa, IFa, Ib, IAb, IBb, ICb, IEb or IFb; and $R_2$ is acetyl for compounds of formula IG, IGa or IGb;

$R_3$ is hydrogen or methoxy for compounds of formula I, IC, IE, IF, IG, Ia, ICa, IEa, IFa, IGa, Ib, ICb, IEb, IFb, or IGb; $R_3$ is hydrogen for compounds of formula IA, IAa or IAb; or $R_3$ is methoxy for compounds of formula IB, IBa or IBb;

$R_4$ is selected from —$CH_2NH_2$ and —$CH_2NHProt^{NH}$;

$R_a$ is substituted or unsubstituted $C_1$-$C_6$ alkyl; and $Prot^{NH}$ is a protecting group for amino.

Being even more preferred compounds of formula Ib, IAb, IBb, ICb, IEb, IFb, IGb and/or compounds where $R_4$ is —$CH_2NH_2$.

Compounds of formula I, IA, IB, ID, IE, IF, IG, Ia, IAa, IBa, IDa, IEa, IFa, IGa, Ib, IAb, IBb, IDb, IEb, IFb, and IGb wherein Y is —O—;

$R_2$ is a —C(=O)$R_a$ group for compounds of formula I, IA, IB, ID, IE, IF, Ia, IAa, IBa, IDa, IEa, IFa, Ib, IAb, IBb, IDb, IEb or IFb; and $R_2$ is acetyl for compounds of formula IG, IGa or IGb;

$R_3$ is hydrogen or methoxy for compounds of formula I, ID, IE, IF, IG, Ia, IDa, IEa, IFa, IGa, Ib, IDb, IEb, IFb, or IGb; $R_3$ is hydrogen for compounds of formula IA, IAa or IAb; or $R_3$ is methoxy for compounds of formula IB, IBa or IBb;

$R_4$ is selected from —$CH_2NH_2$ and —$CH_2NHProt^{NH}$;

$R_a$ is substituted or unsubstituted $C_1$-$C_6$ alkyl; and $Prot^{NH}$ is a protecting group for amino.

Being even more preferred compounds of formula Ib, IAb, IBb, IDb, IEb, IFb, IGb and/or compounds where $R_4$ is —$CH_2NH_2$.

Compounds of formula I, IA, IB, IC, ID, IF, IG, Ia, IAa, IBa, ICa, IDa, IFa, IGa, Ib, IAb, IBb, ICb, IDb, IFb, and IGb wherein $R_2$ is a —C(=O)$R_a$ group for compounds of formula I, IA, IB, IC, ID, IF, Ia, IAa, IBa, ICa, IDa, IFa, Ib, IAb, IBb, ICb, IDb, or IFb; and $R_2$ is acetyl for compounds of formula IG, IGa or IGb;

$R_3$ is hydrogen or methoxy for compounds of formula I, IC, ID, IF, IG, Ia, ICa, IDa, IFa, IGa, Ib, ICb, IDb, IFb, and IGb; $R_3$ is hydrogen for compounds of formula IA, IAa or IAb; or $R_3$ is methoxy for compounds of formula IB, IBa or IBb;

$R_4$ is —$CH_2OH$; and $R_a$ is selected from methyl, ethyl, n-propyl, isopropyl and butyl, including n-butyl, sec-butyl, isobutyl and tert-butyl.

Being even more preferred compounds of formula Ia, IAa, IBa, ICa, IDa, IEa, IFa, or IGa.

Compounds of formula I, IA, IB, IC, ID, IE, IF, IG, Ia, IAa, IBa, ICa, IDa, IEa, IFa, IGa, Ib, IAb, IBb, ICb, IDb, IEb, IFb, and IGb wherein $R_2$ is a —C(=O)$R_a$ group for compounds of formula I, IA, IB, IC, ID, IE, IF, Ia, IAa, IBa, ICa, IDa, IEa, IFa, Ib, IAb, IBb, ICb, IDb, IEb or IFb; and $R_2$ is acetyl for compounds of formula IG, IGa or IGb;

$R_3$ is hydrogen or a methoxy for compounds of formula I, IC, ID, IE, IF, IG, Ia, ICa, IDa, IEa, IFa, IGa, Ib, ICb, IDb, IEb, IFb, and IGb; $R_3$ is hydrogen for compounds of formula IA, IAa or IAb; or $R_3$ is methoxy for compounds of formula IB, IBa or IBb;

$R_4$ is selected from —$CH_2NH_2$ and —$CH_2NHProt^{NH}$;

$R_a$ is selected from methyl, ethyl, n-propyl, isopropyl and butyl, including n-butyl, sec-butyl, isobutyl and tert-butyl; and $Prot^{NH}$ is a protecting group for amino.

Being even more preferred compounds of formula Ib, IAb, IBb, ICb, IDb, IEb, IFb, IGb and/or compounds where $R_4$ is —$CH_2NH_2$.

Compounds of formula Ic or IAc, IDc, IFc, and IGc wherein $R_2$ is a —C(═O)$R_a$ group for compounds of formula Ic, IAc, IDc, or IFc; and $R_2$ is acetyl for compounds of formula IGc;

$R_3$ is hydrogen; and $R_a$ is selected from methyl, ethyl, n-propyl, isopropyl and butyl, including n-butyl, sec-butyl, isobutyl and tert-butyl.

Compounds of formula Ic, IBc, IDc, IFc, and IGc wherein $R_2$ is a —C(═O)$R_a$ group for compounds of formula Ic, IBc, IDc, or IFc; and $R_2$ is acetyl for compounds of formula IGc;

$R_3$ is methoxy; and $R_a$ is selected from methyl, ethyl, n-propyl, isopropyl and butyl, including n-butyl, sec-butyl, isobutyl and tert-butyl.

Even more preferred compounds according to the present invention include:

Compounds of formula I, IA, IC, IF, IG, Ia, IAa, ICa, IFa, IGa, Ib, IAb, ICb, IFb, and IGb wherein Y is —NH—;

$R_2$ is acetyl;

$R_3$ is hydrogen; and $R_4$ is —$CH_2OH$.

Being most preferred compounds of formula Ia, IAa, ICa, IFa, or IGa.

Compounds of formula I, IA, ID, IF, IG, Ia, IAa, IDa, IFa, IGa, Ib, IAb, IDb, IFb, and IGb wherein Y is —O—;

$R_2$ is acetyl;

$R_3$ is hydrogen; and $R_4$ is —$CH_2OH$.

Being most preferred compounds of formula Ia, IAa, IDa, IFa, or IGa

Compounds of formula I, IA, IC, IE, IF, IG, Ia, IAa, ICa, IEa, IFa, IGa, Ib, IAb, ICb, IEb, IFb, and IGb wherein Y is —NH—;

$R_2$ is acetyl;

$R_3$ is hydrogen; and $R_4$ is —$CH_2NH_2$.

Being most preferred compounds of formula Ib, IAb, ICb, IEb, IFb, or IGb.

Compounds of formula I, IA, ID, IE, IF, IG, Ia, IAa, IDa, IEa, IFa, IGa, Ib, IAb, IDb, IEb, IFb, and IGb wherein Y is —O—;

$R_2$ is acetyl;

$R_3$ is hydrogen; and $R_4$ is —$CH_2NH_2$.

Being most preferred compounds of formula Ib, IAb, IDb, IEb, IFb, or IGb.

Compounds of formula I, IA, IC, ID, IF, IG, Ia, IAa, ICa, IDa, IFa, IGa, Ib, IAb, ICb, IDb, IFb, and IGb wherein $R_2$ is acetyl;

$R_3$ is hydrogen; and $R_4$ is —$CH_2OH$.

Being most preferred compounds of formula Ia, IAa, ICa, IDa, IFa or IGa.

Compounds of formula I, IA, IC, ID, IF, IG, Ia, IAa, ICa, IDa, IFa, IGa, Ib, IAb, ICb, IDb, IFb, and IGb wherein $R_1$ is —OH;

$R_2$ is acetyl;

$R_3$ is hydrogen; and $R_4$ is —$CH_2OH$.

Being most preferred compounds of formula Ia, IAa, ICa, IDa, IFa or IGa.

Compounds of formula I, IA, IC, ID, IE, IF, IG, Ia, IAa, ICa, IDa, IEa, IFa, IGa, Ib, IAb, ICb, IDb, IEb, IFb, and IGb wherein $R_2$ is acetyl;

$R_3$ is hydrogen; and $R_4$ is —$CH_2NH_2$.

Being most preferred compounds of formula Ib, IAb, ICb, IDb, IEb, IFb, or IGb.

Compounds of formula Ic or IAc, IDc, IFc, IGc wherein $R_2$ is acetyl; and $R_3$ is hydrogen.

Compounds of formula Ic or IBc, IDc, IFc, IGc wherein $R_2$ is acetyl; and $R_3$ is methoxy.

A compound according to the present invention of formula:

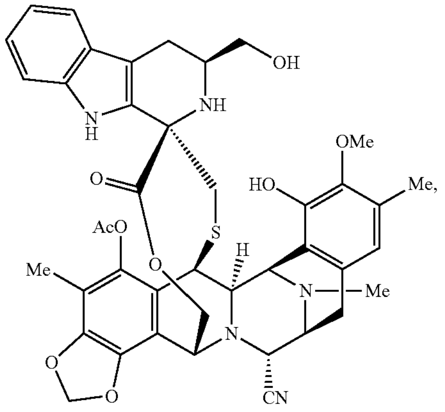

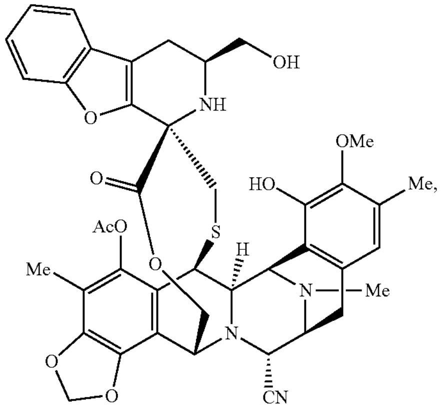

-continued
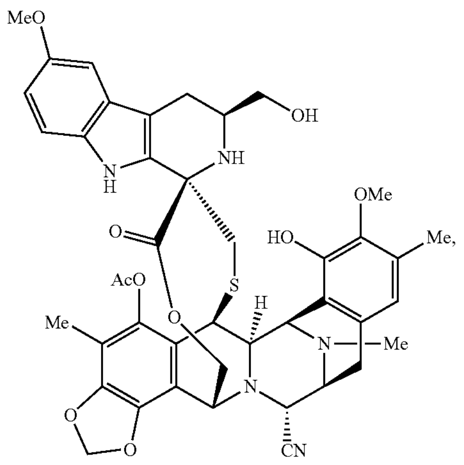
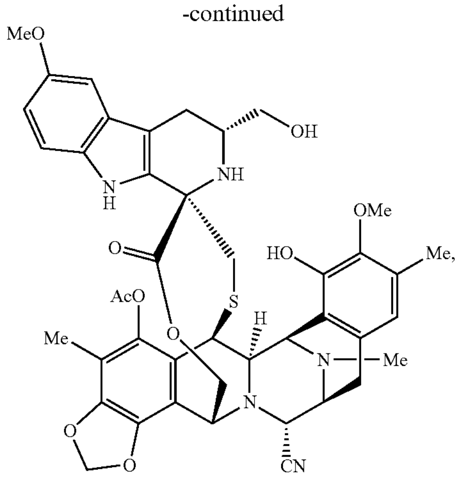
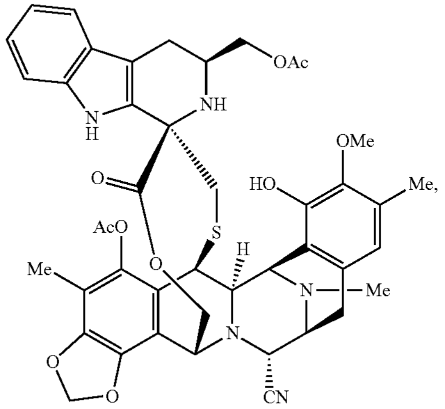
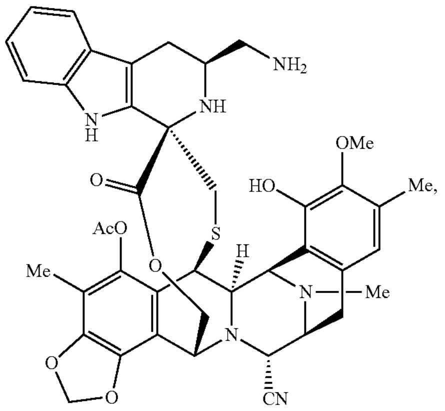
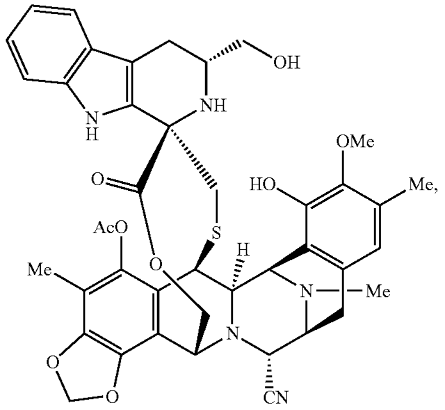
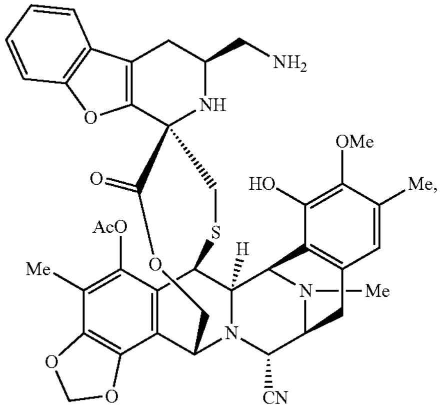
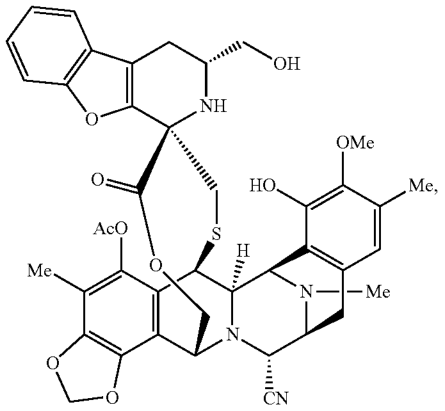
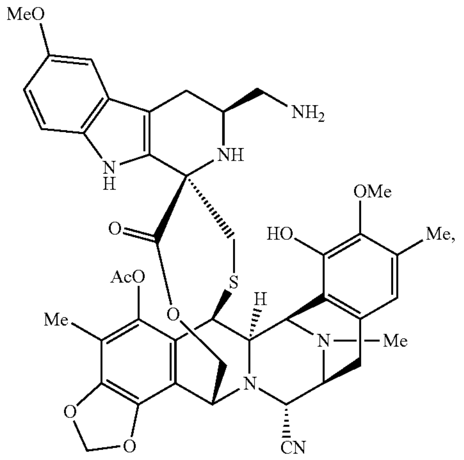

-continued
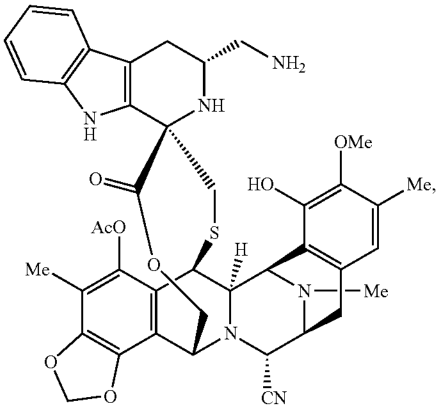
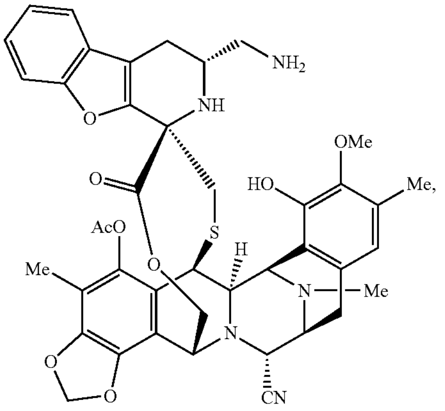
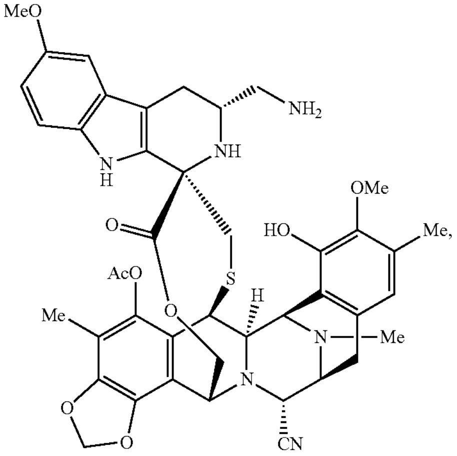
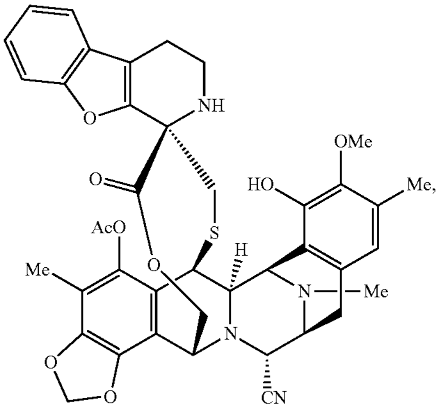
-continued
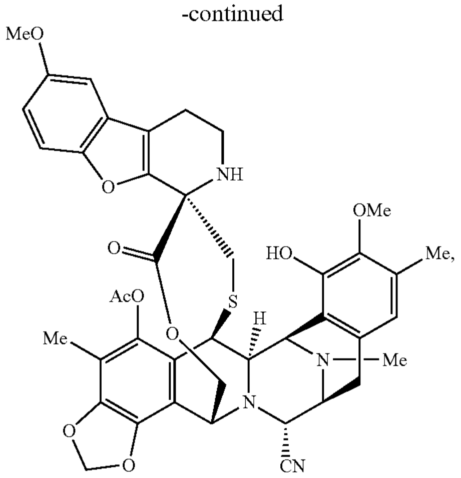
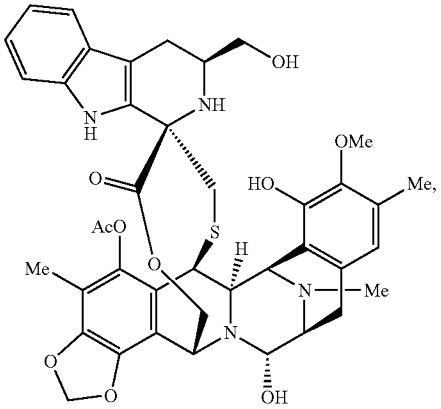
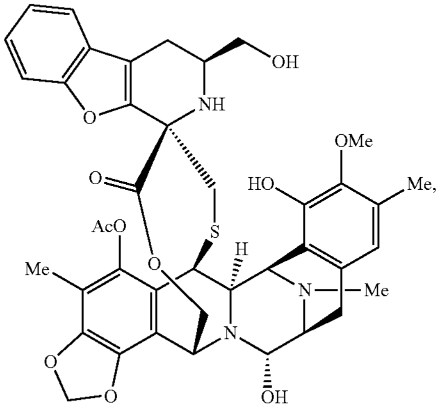
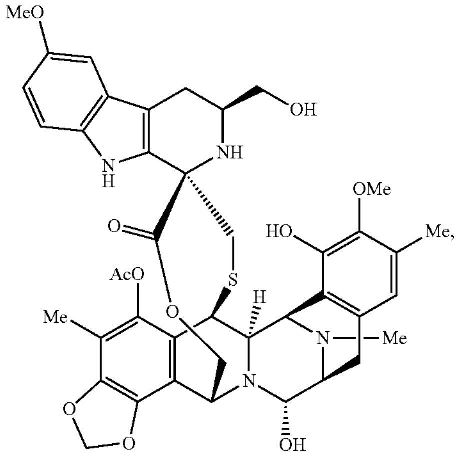

-continued
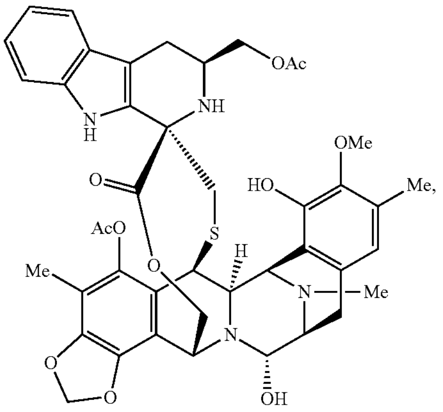
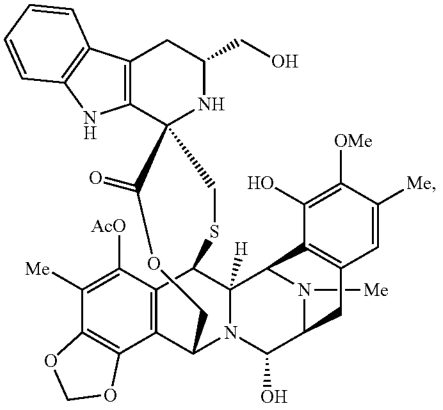
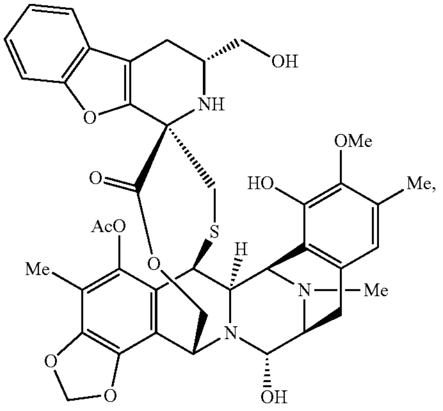
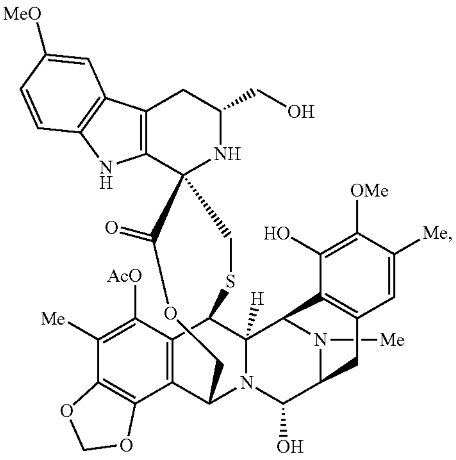
-continued
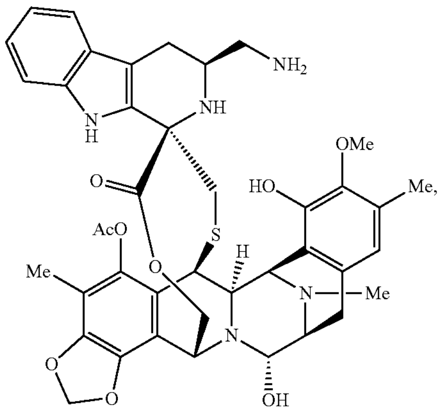
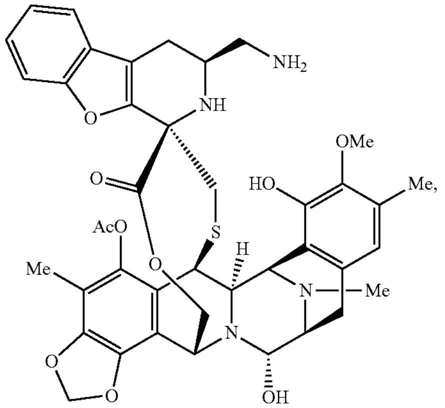
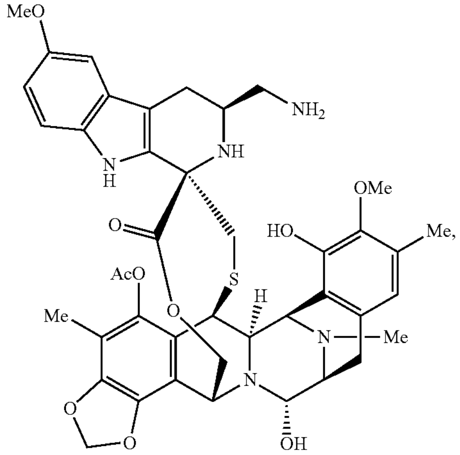
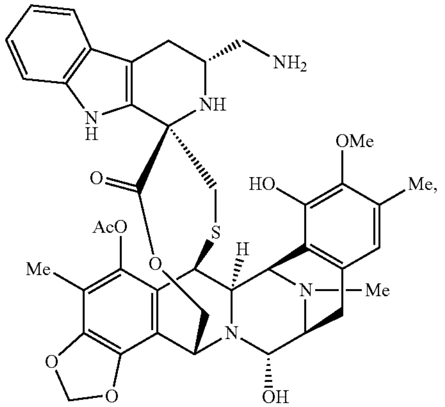

-continued
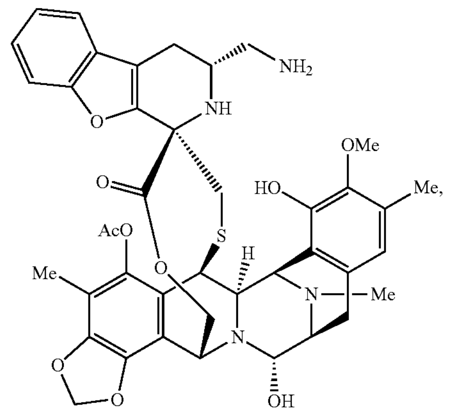
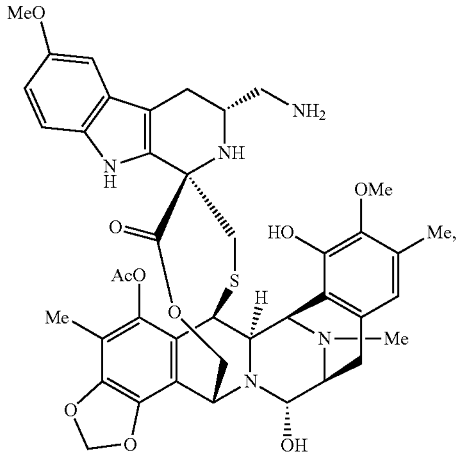
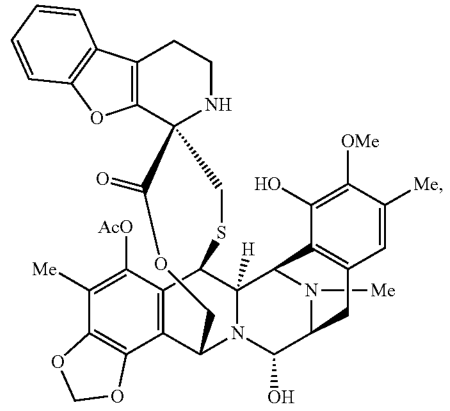
-continued
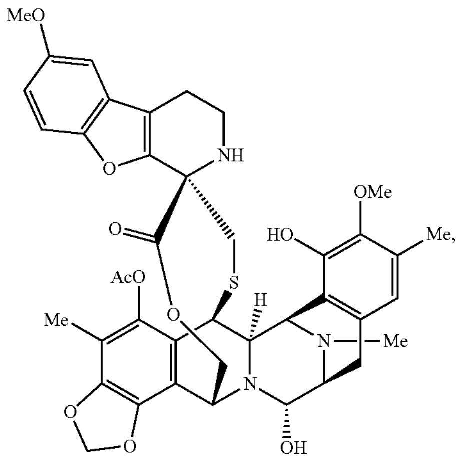
or a pharmaceutically acceptable salt or ester thereof. Being particularly preferred a compound of formula:
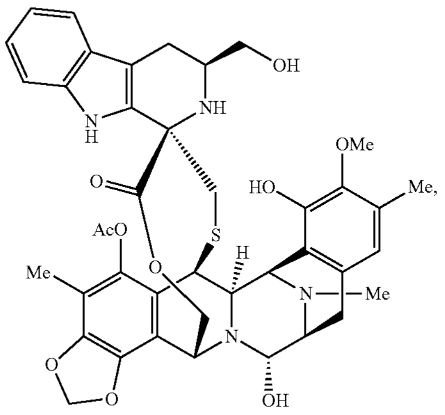
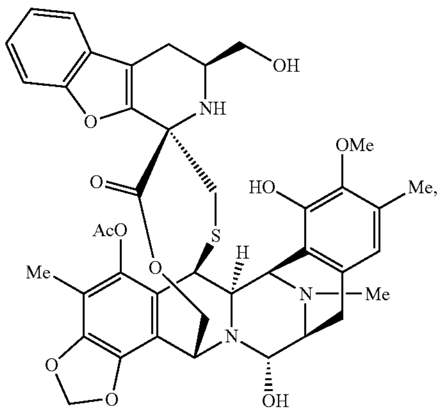

-continued
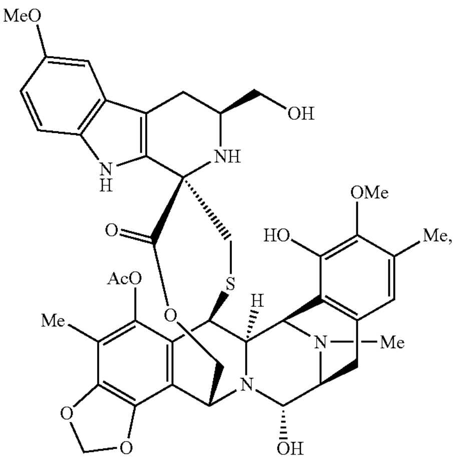
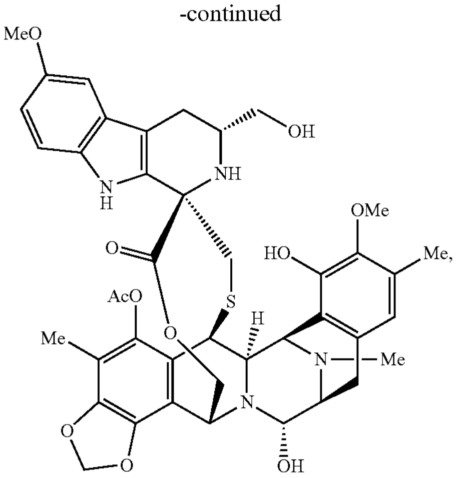
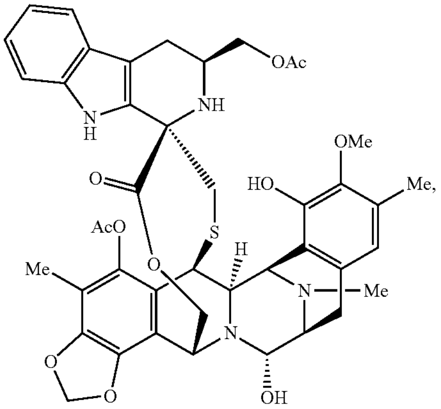
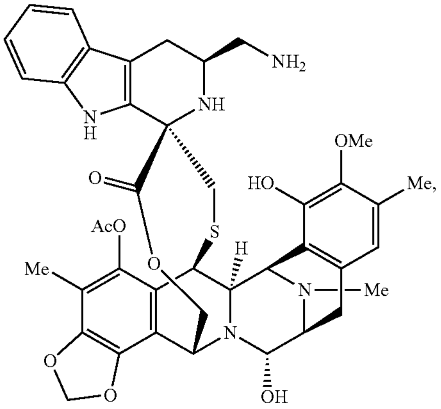
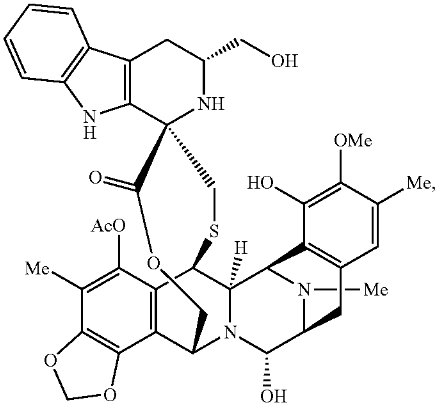
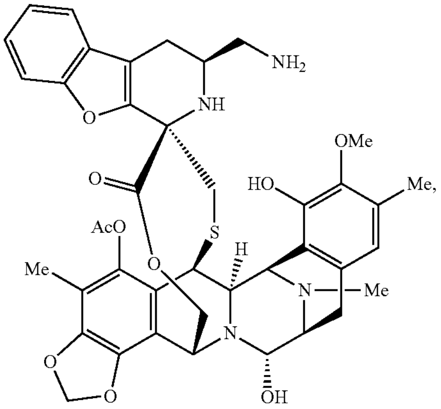
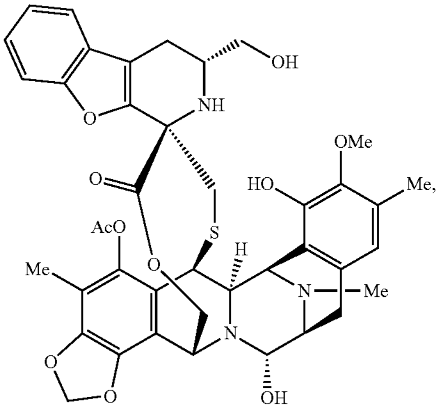
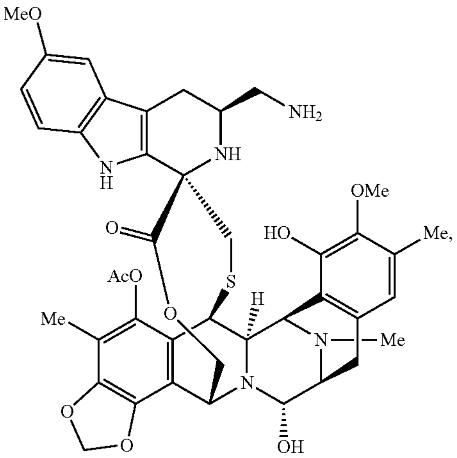

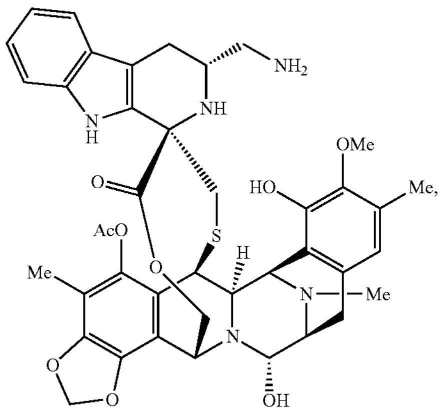
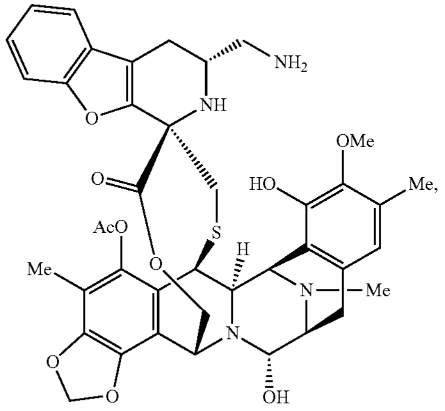
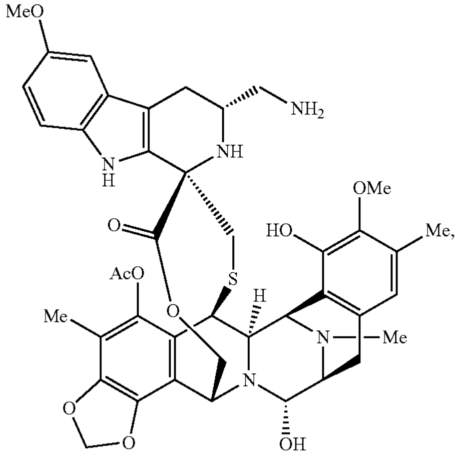
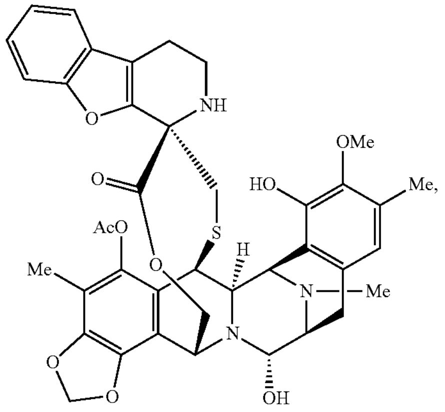
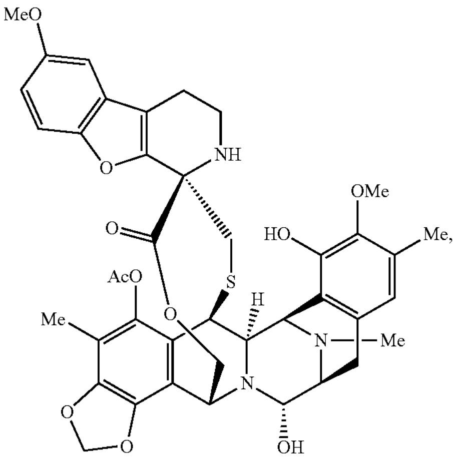
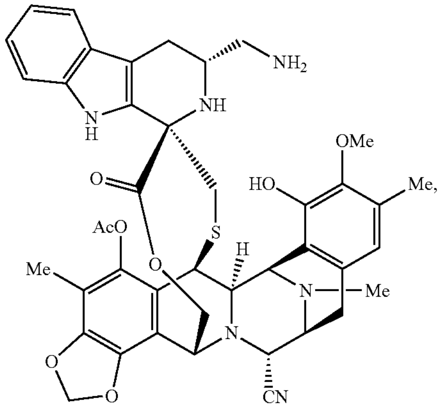
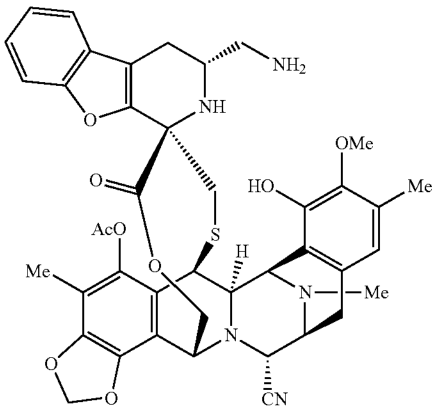
or a pharmaceutically acceptable salt or ester thereof.

A compound according to the present invention of formula:
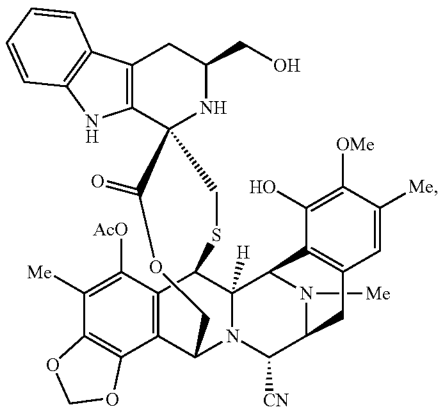
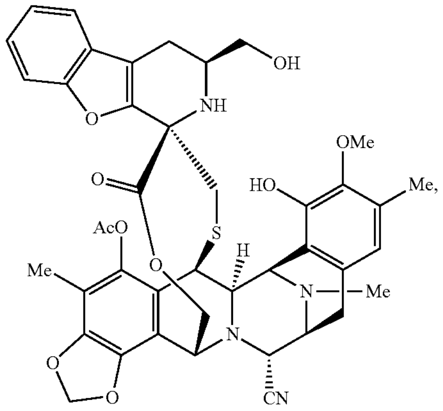
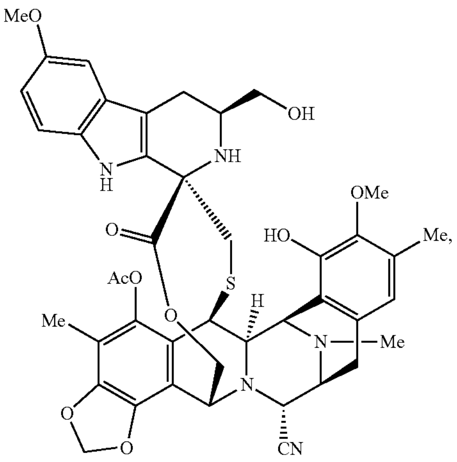
-continued
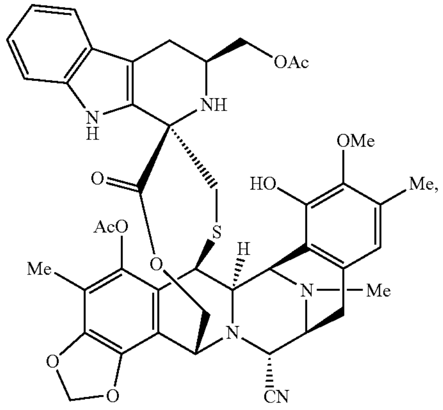
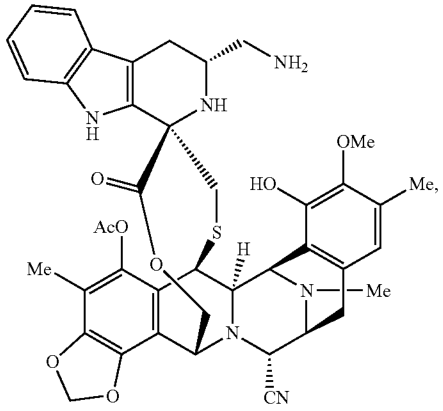
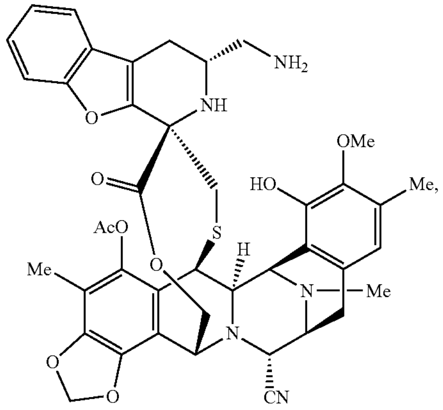
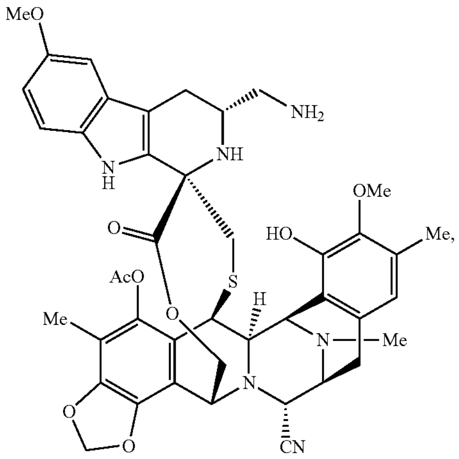

-continued
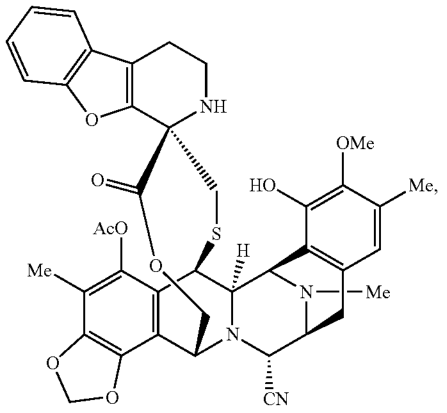
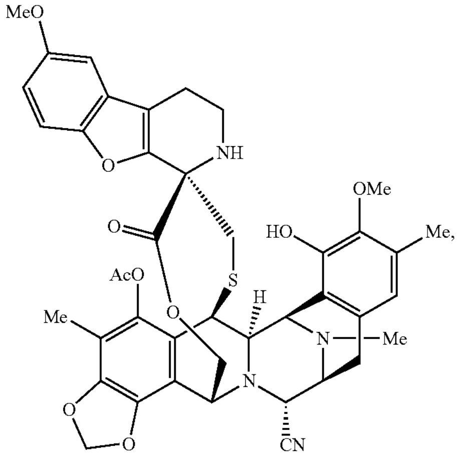
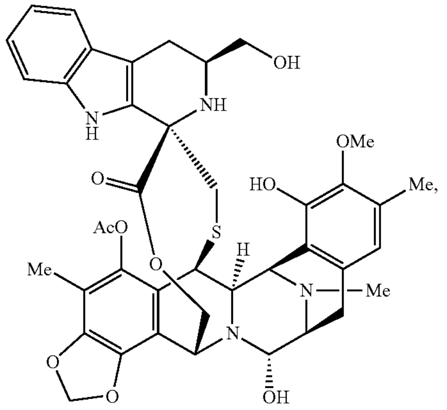
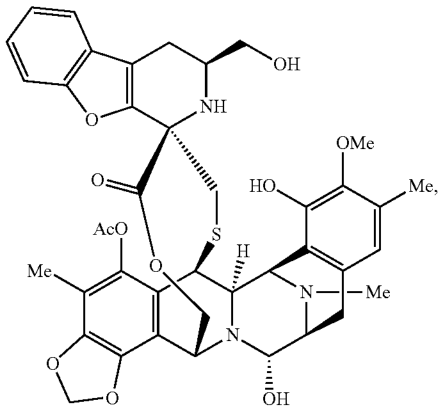
-continued
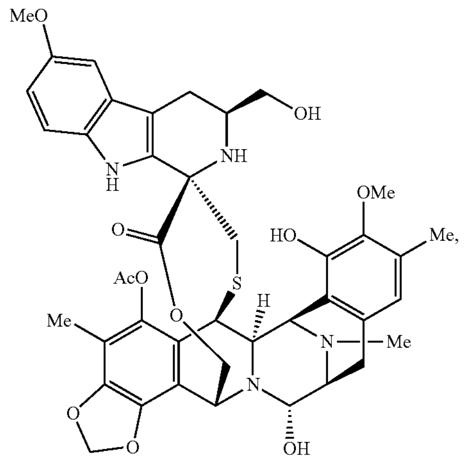
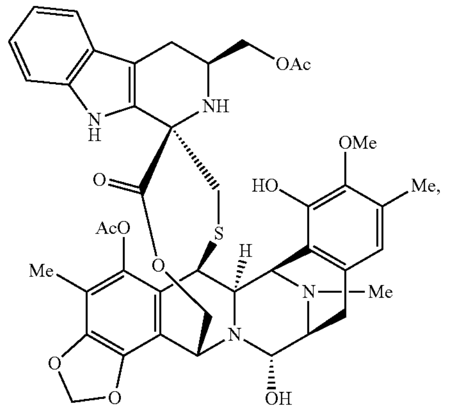
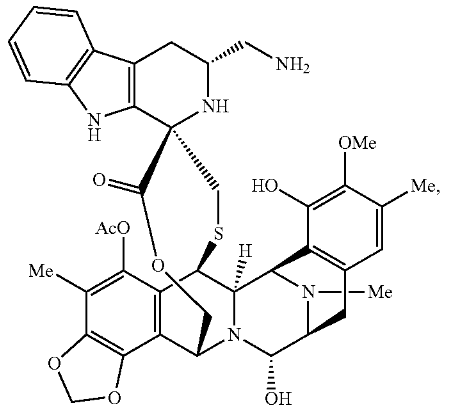
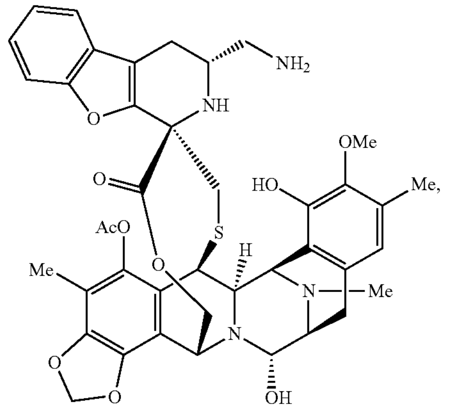

-continued
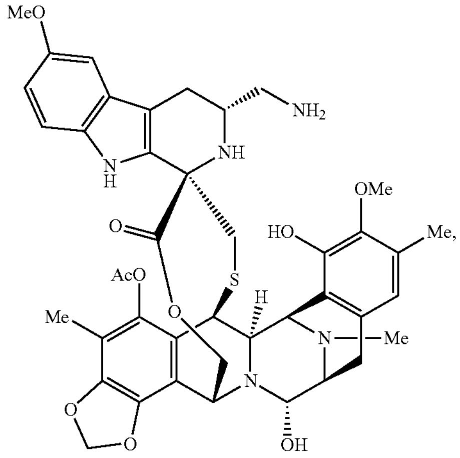
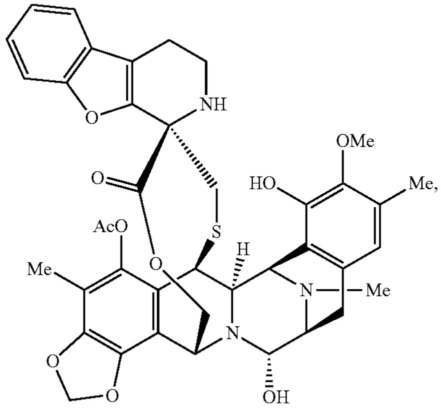
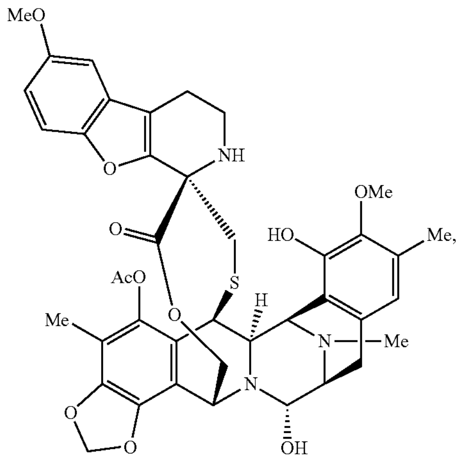
or a pharmaceutically acceptable salt or ester thereof.
Being particularly preferred a compound of formula:
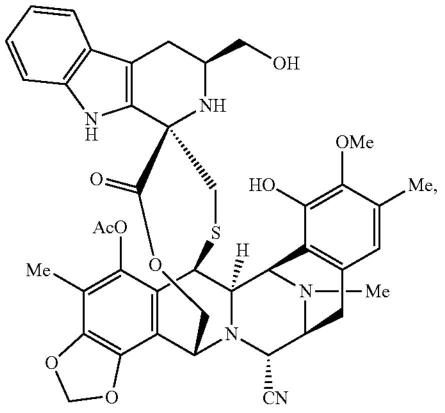
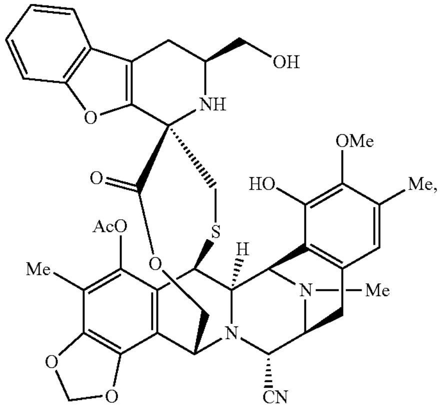
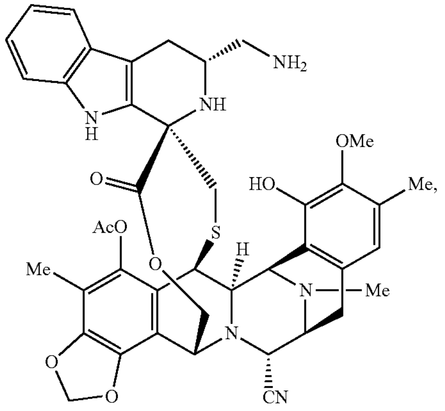
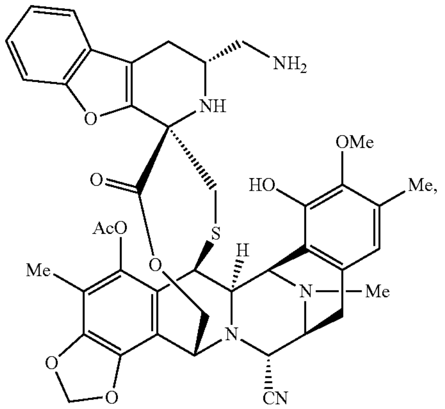

-continued
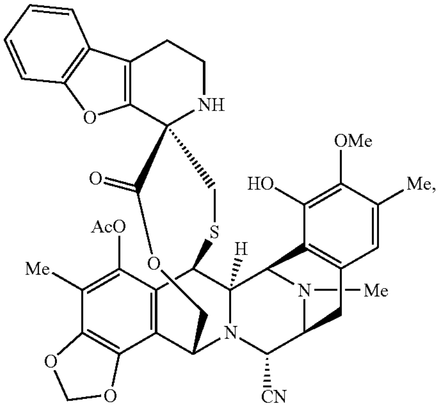
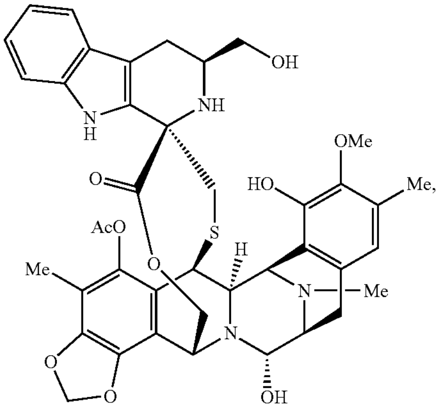
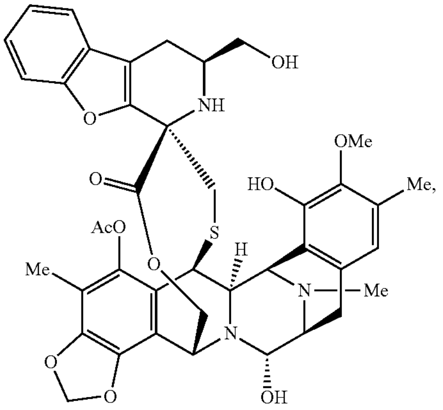
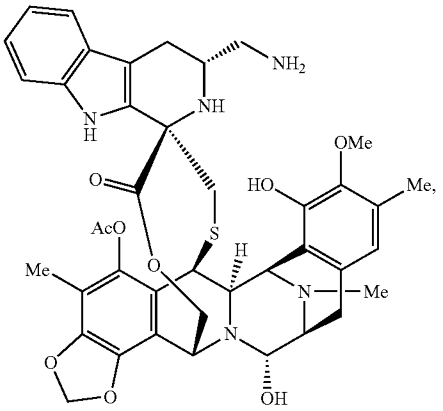
-continued
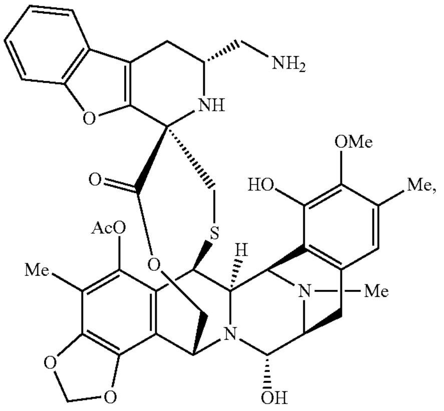
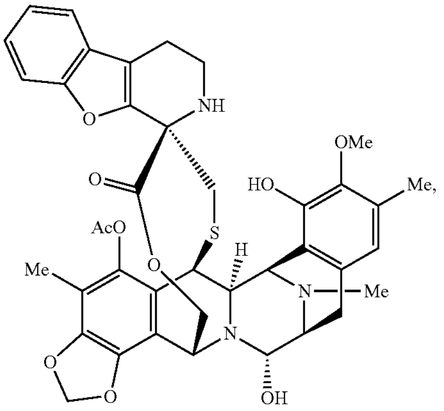
or a pharmaceutically acceptable salt or ester thereof. Being more preferred a compound of formula:
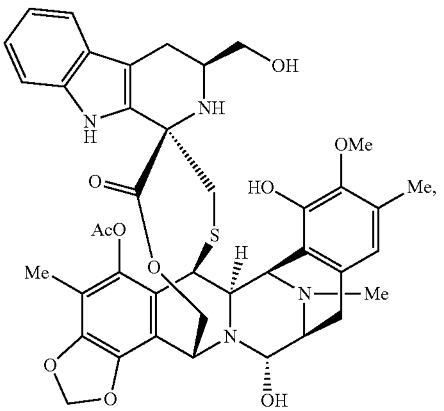

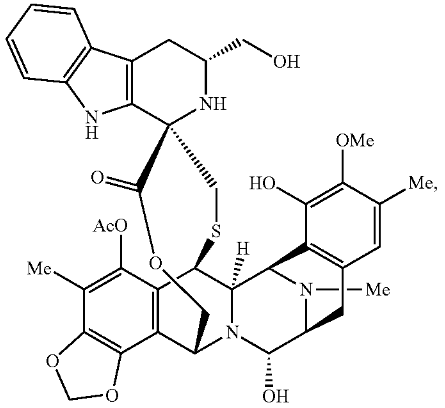
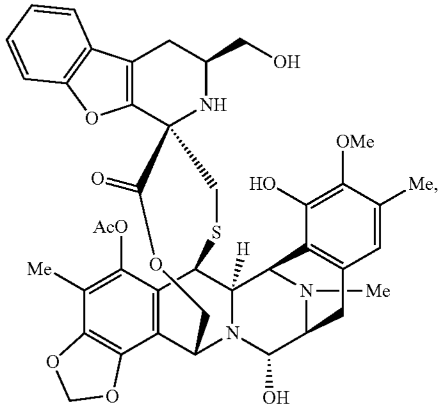
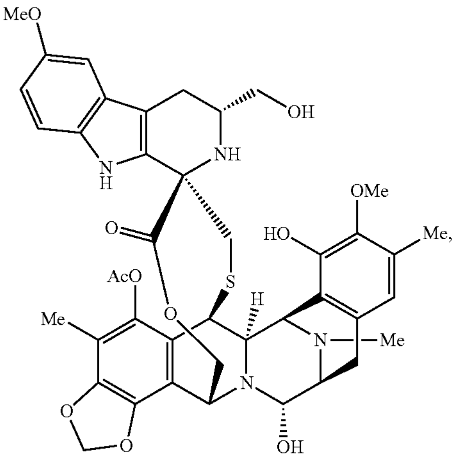
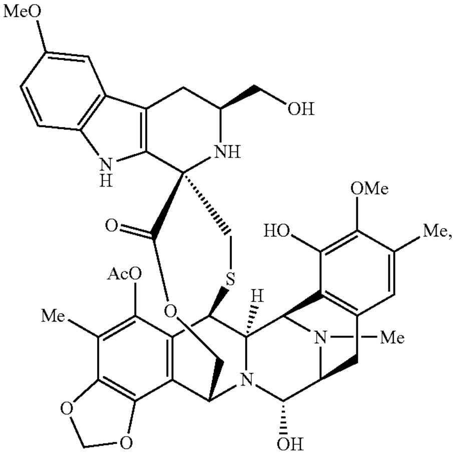
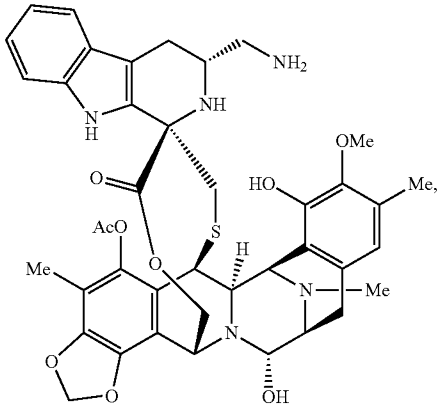
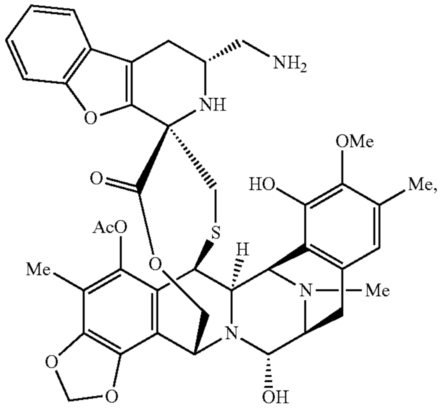
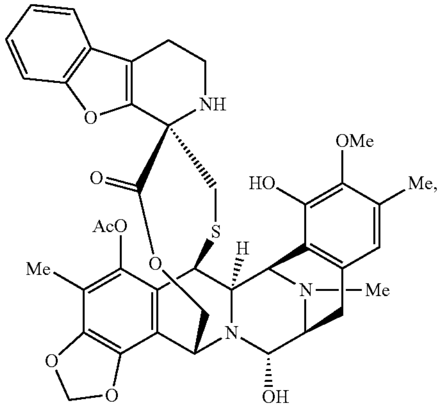
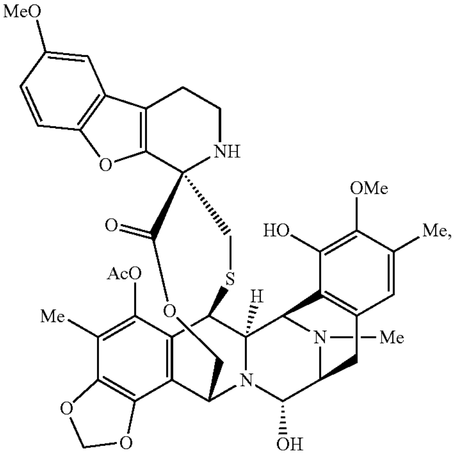

-continued
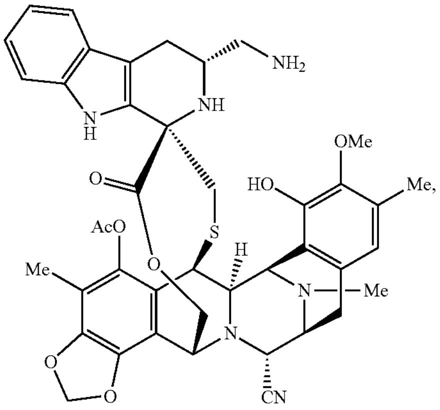
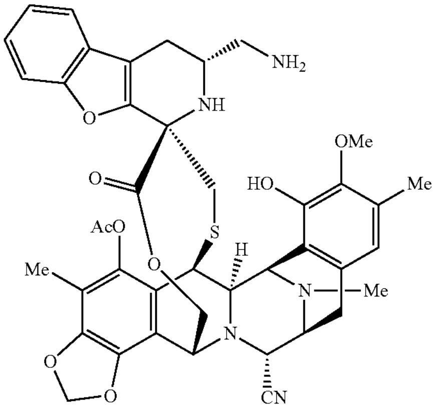
or a pharmaceutically acceptable salt or ester thereof.
Being even more preferred compounds according to the present invention are compounds of formula:
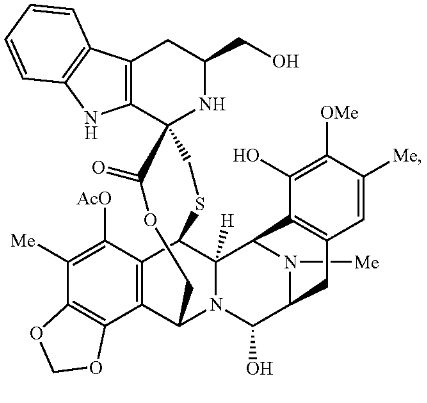
-continued
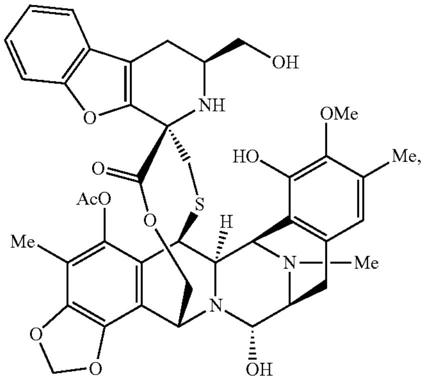
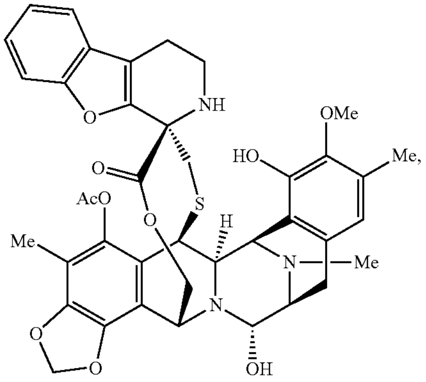
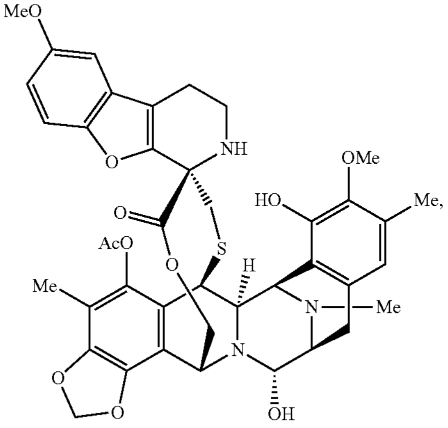
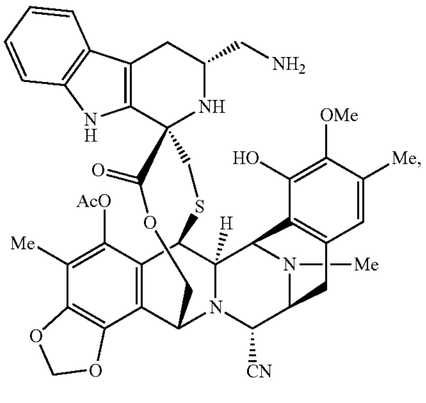

-continued
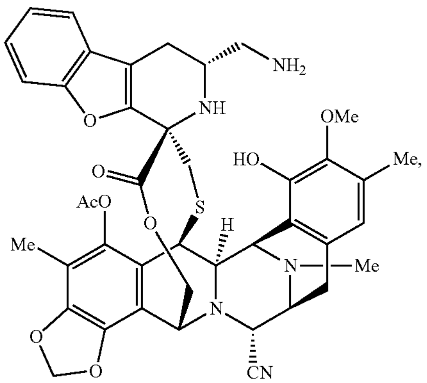
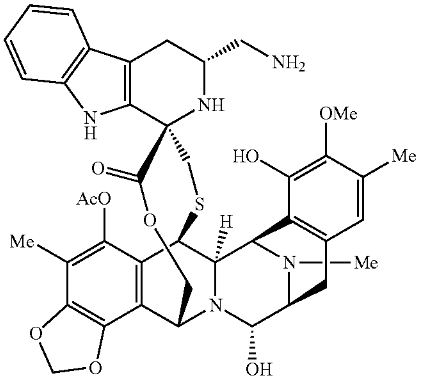
or a pharmaceutically acceptable salt or ester thereof.
Further preferred compounds according to the present invention are compounds of formula:
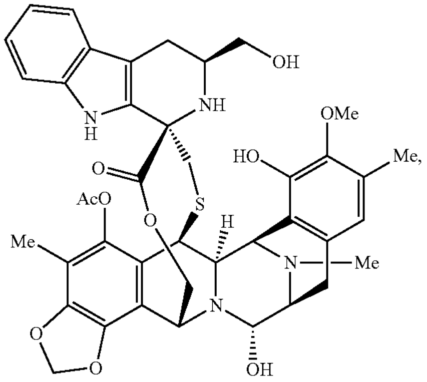
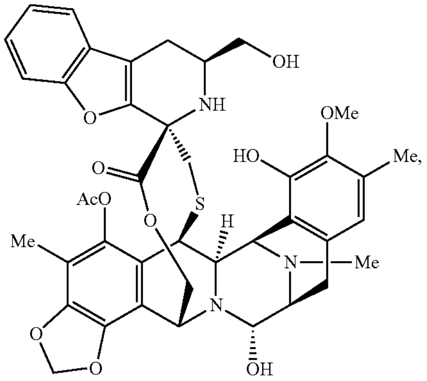
-continued
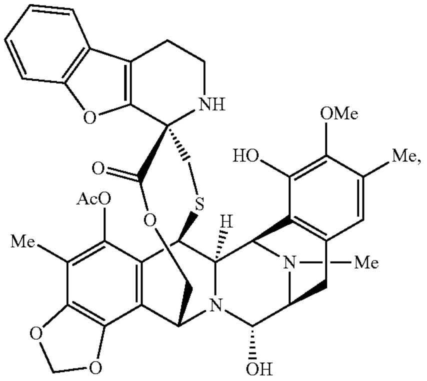
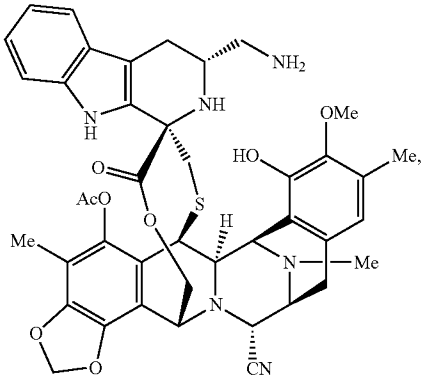
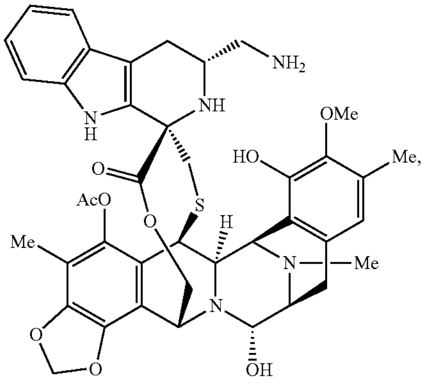
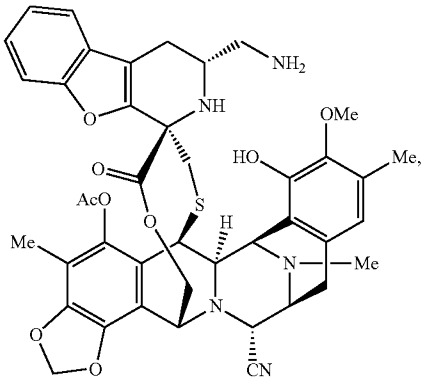
or a pharmaceutically acceptable salt or ester thereof.

In a further embodiment, according to the present invention preferred compounds are compounds of formula:
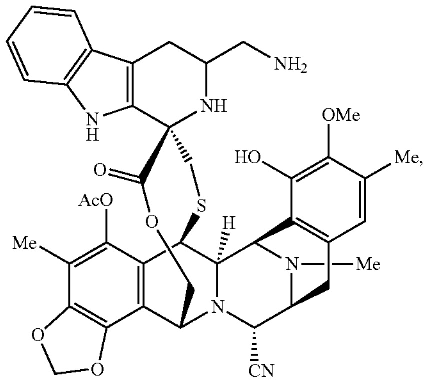
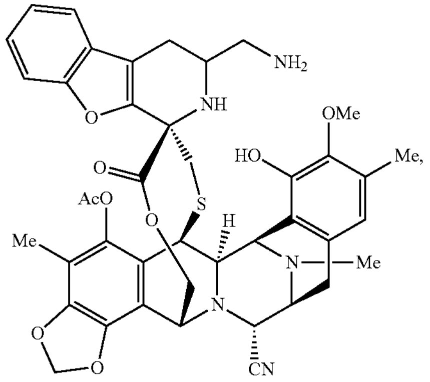
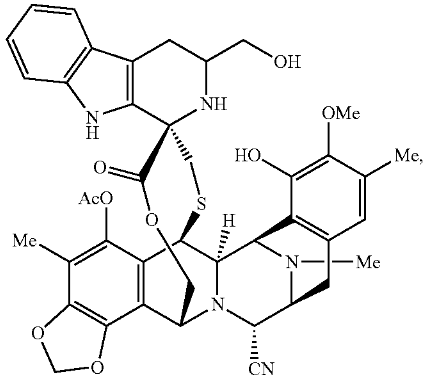
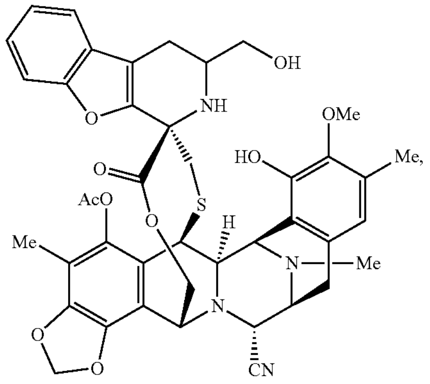
-continued
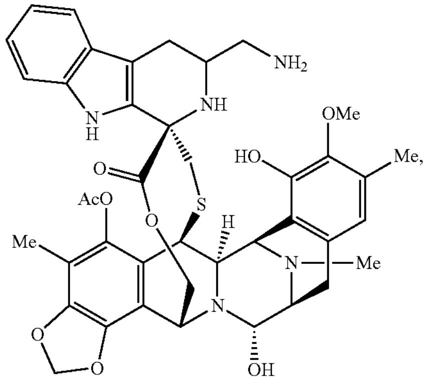
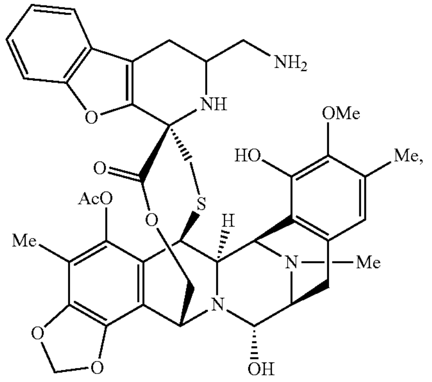
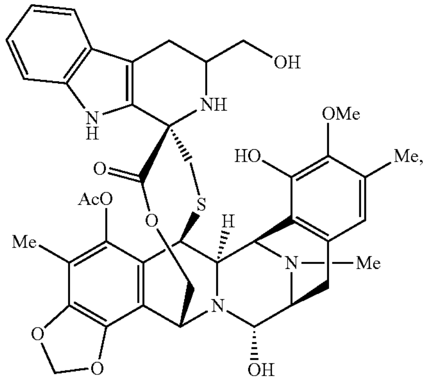
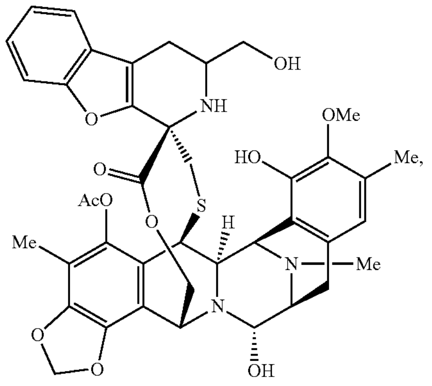
or a pharmaceutically acceptable salt or ester thereof.

Further preferred compounds include a compound of formula:
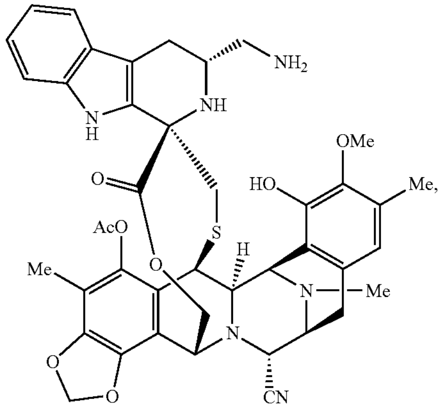
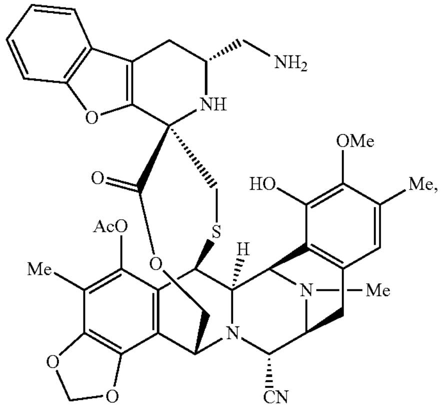
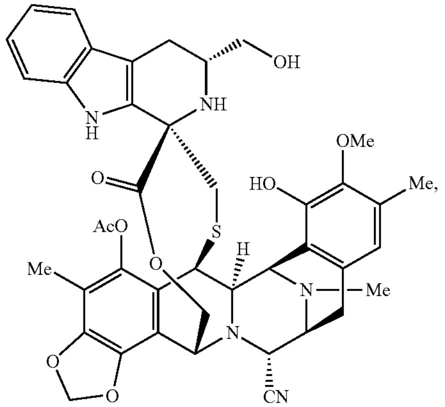
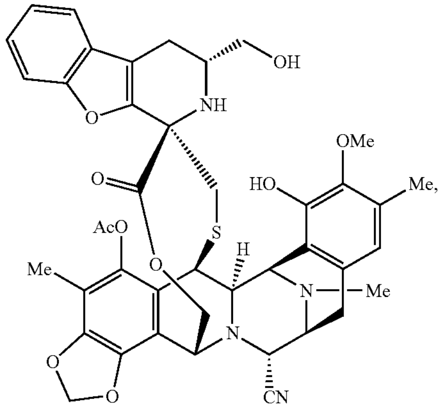
-continued
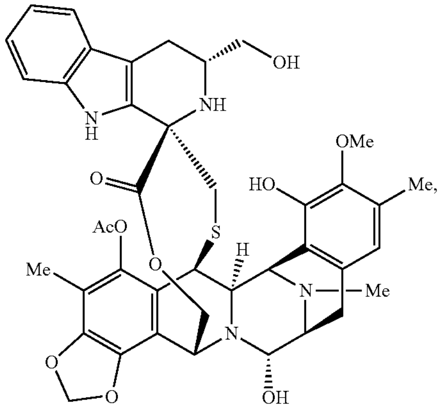
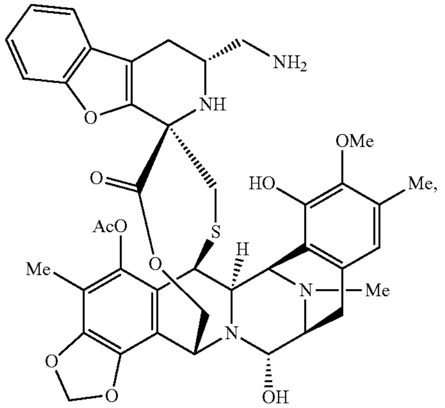
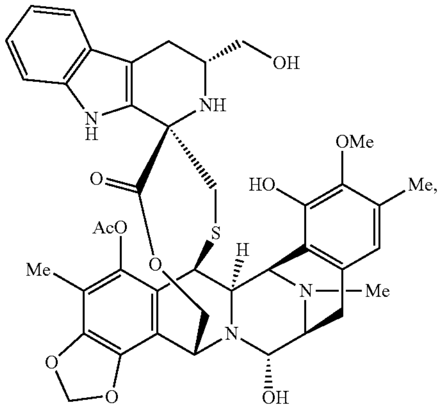
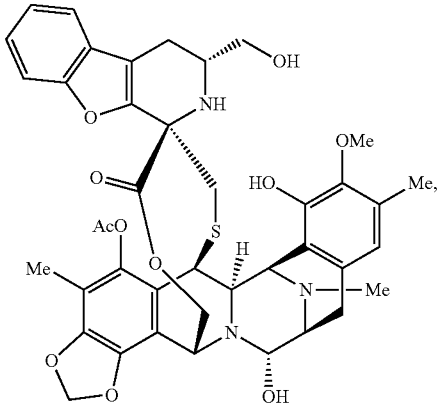

-continued
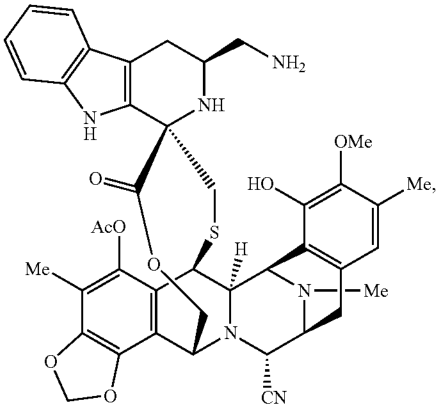
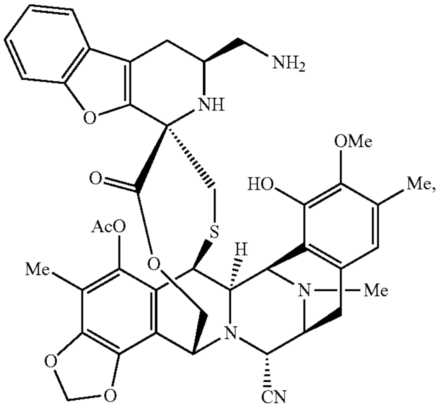
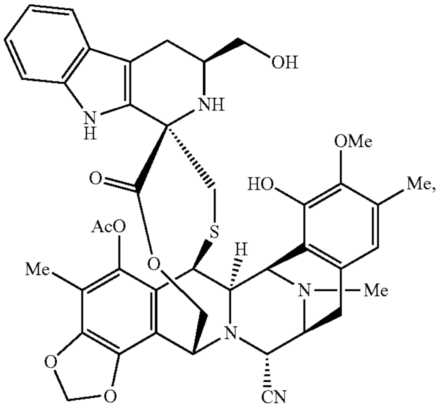
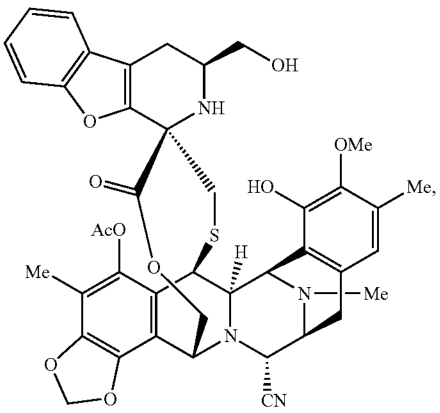
-continued
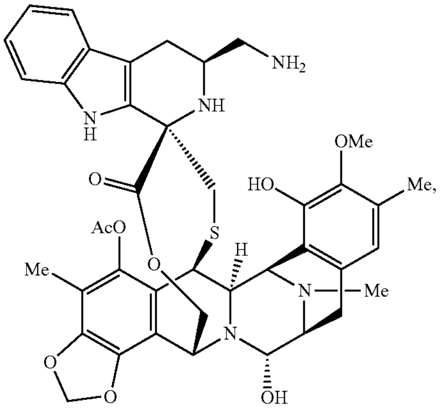
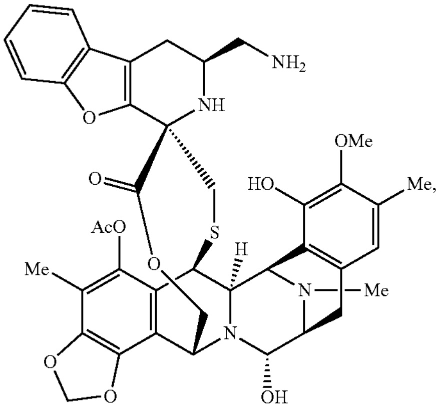
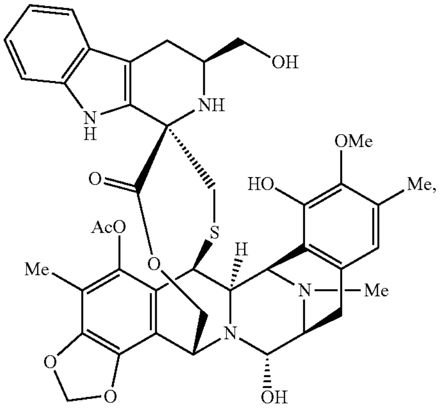
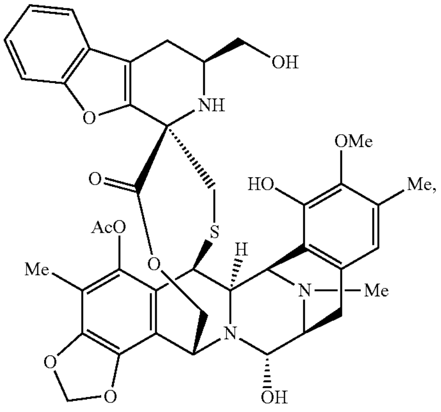
or a pharmaceutically acceptable salt or ester thereof.

Further preferred compounds include a compound of formula:

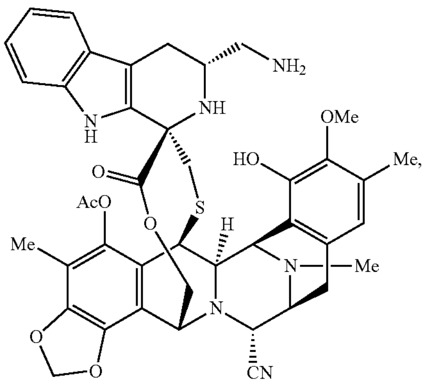

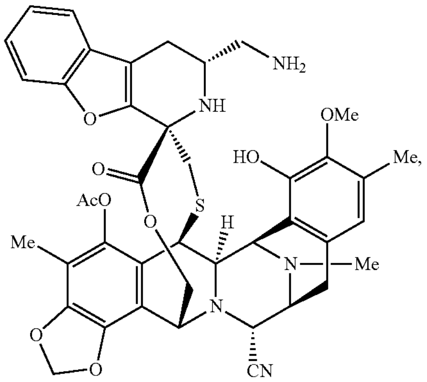

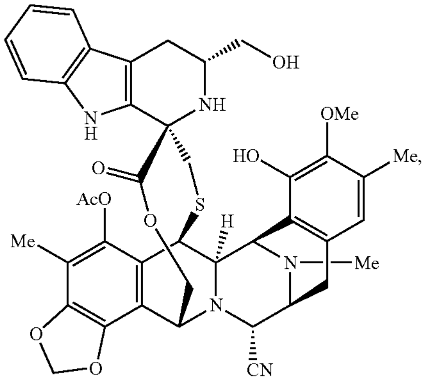

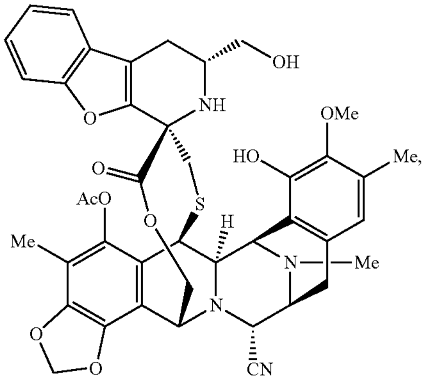

-continued

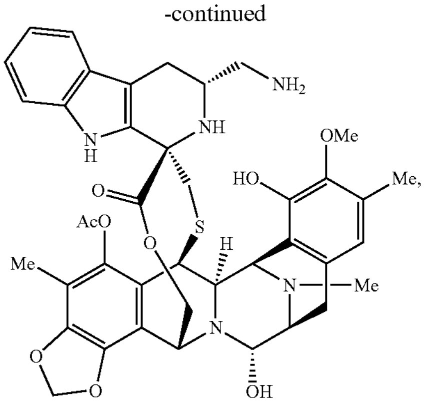

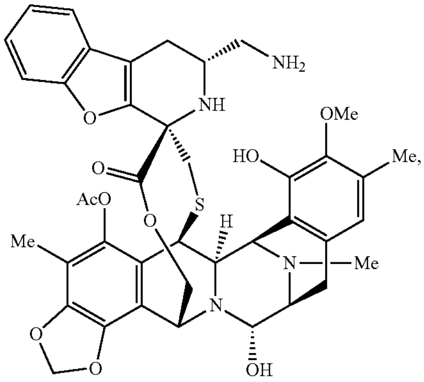

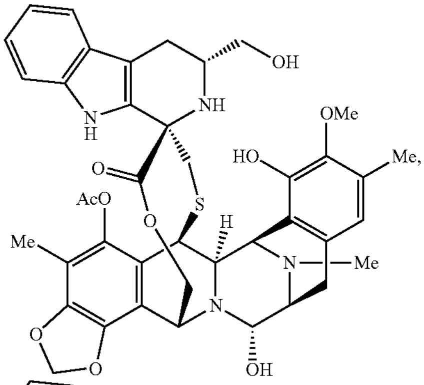

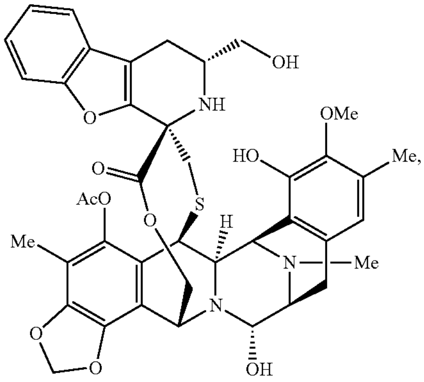

or a pharmaceutically acceptable salt or ester thereof.

In additional preferred embodiments, the preferences described above for the different substituents are combined. The present invention is also directed to such combinations of preferred substitutions (where allowed by possible substituent groups) in compounds of formula I, IA, IB, IC, ID, IE, IF, IG, Ia, IAa, IBa, ICa, IDa, IEa, IFa, IGa, Ib, IAb, IBb, ICb, IDb, IEb, IFb, IGb, Ic, IAc, IBc, IDc, IFc or IGc according to the present invention.

For the avoidance of doubt, the compounds above may be the drug moiety D and are covalently attached via a hydroxy or amine group to $(X)_b$ if any, or $(AA)_w$ if any, or to $(T)_g$ if any, or (L). Thus, when conjugated, a covalent bond replaces a proton on a hydroxy or amine group on the compound.

Preferred drug conjugates according to the the present invention are given below. The preferred definitions of $(X)_b$, $(AA)_w$, $(T)_g$, and (L) as set out below are applicable to all of the drug moiety D compounds described above. Preferred drug conjugates according to the the present invention include:

a drug conjugate of formula $[D-(X)_b-(AA)_w-(T)_g-(L)-]_n$-Ab according to the present invention wherein L is a linker group selected from the group consisting of:

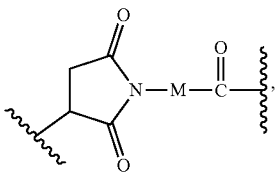,
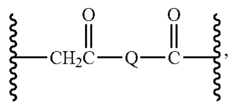,
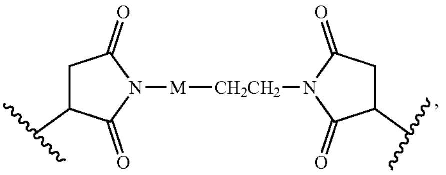,
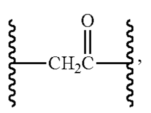,
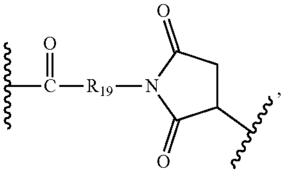,
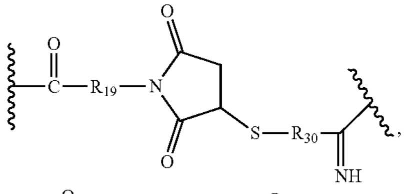,
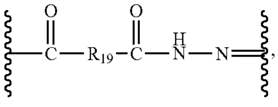,
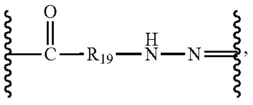,
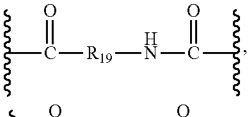,
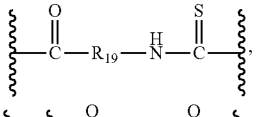,
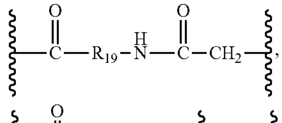,
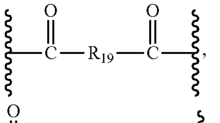,
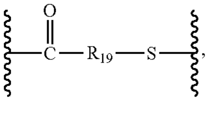,
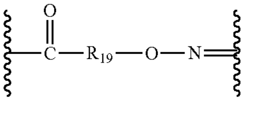

wherein the wavy lines indicate the point of covalent attachments to an Ab (the wavy line to the right) and to $(T)_g$ if any, or $(AA)_w$ if any, or to $(X)_b$ if any, or to D (the wavy line to the left);

$R_{19}$ is selected from $-C_1-C_{12}$ alkylene-, $-C_3-C_8$ carbocyclo, $-O-(C_1-C_{12}$ alkylene), $-C_6-C_{18}$ arylene in one or more rings which may optionally be substituted with one or more substituents $R_x$, $-C_1-C_{12}$ alkylene-$C_6-C_{18}$ arylene- wherein the arylene group is in one or more rings which may optionally be substituted with one or more substituents $R_x$, $-C_6-C_{18}$ arylene-$C_1-C_{12}$ alkylene- wherein the arylene group is in one or more rings which may optionally be substituted with one or more substituents $R_x$, $-C_1-C_{12}$ alkylene-($C_3-C_8$ carbocyclo)-, $-(C_3-C_8$ carbocyclo)-$C_1-C_{12}$ alkylene-, $-C_5-C_{14}$ heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, $-C_1-C_{12}$ alkylene-($C_5-C_{14}$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, $-(C_5-C_{14}$ heterocyclo)-$C_1-C_{12}$ alkylene- wherein said heterocyclo group may be a saturated or unsaturated group having one or more rings and comprising at least one oxygen, nitrogen or sulphur atom in said ring(s), said group optionally being substituted with one or more substituents $R_x$, $-(OCH_2CH_2)_r-$, and $-CH_2-(OCH_2CH_2)_r-$, wherein each of the above alkylene substituents whether alone or attached to another moiety the carbon chain may optionally be substituted by one or more substituents $R_x$;

$R_{30}$ is a $-C_1-C_6$ alkylene- group;

M is selected from the group consisting of $-C_1-C_6$ alkylene-, $-C_1-C_6$ alkylene-($C_3-C_8$ carbocyclo)-, $-(CH_2CH_2O)_s-$, $-C_1-C_6$ alkylene-($C_3-C_8$ carbocyclo)-CON(H or $C_1-C_6$ alkyl)-$C_1-C_6$ alkylene-, phenylene which may optionally be substituted with one or more substituents $R_x$, phenylene-$C_1-C_6$ alkylene- wherein the phenylene moiety may optionally be substituted with one or more substituents $R_x$ and $-C_1-C_6$ alkylene-CON(H or $C_1-C_6$alkyl)$C_1-C_6$ alkylene-;

Q is selected from the group consisting of $-N$(H or $C_1-C_6$ alkyl)phenylene- and $-N$(H or $C_1-C_6$alkyl)-$(CH_2)_s$;

r is an integer ranging from 1 to 10; and s is an integer ranging from 1 to 10.

a drug conjugate of formula $[D-(X)_b-(AA)_w-(T)_g-(L)-]_n$-Ab according to the present invention wherein L is selected from the group consisting of:

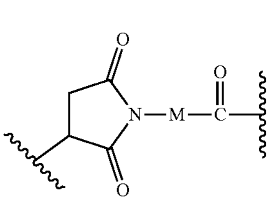,
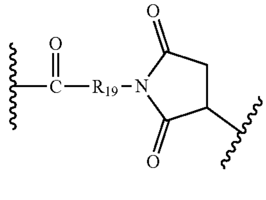

and

-continued

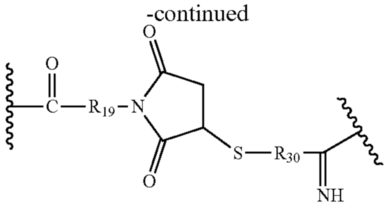

wherein:

the wavy lines indicate the point of covalent attachments to an Ab (the wavy line to the right) and to $(T)_g$ if any, or $(AA)_w$ if any, or to $(X)_b$ if any, or to D (the wavy line to the left);

$R_{19}$ is selected from —$C_1$-$C_{12}$ alkylene-, —O—($C_1$-$C_{12}$ alkylene), —$C_6$-$C_{12}$ arylene in one or more rings which may optionally be substituted with one or more substituents $R_x$, —$C_1$-$C_{12}$ alkylene-$C_6$-$C_{12}$ arylene- wherein the arylene group is in one or more rings which may optionally be substituted with one or more substituents $R_x$, —$C_6$-$C_{12}$ arylene-$C_1$-$C_{12}$ alkylene- wherein the arylene group is in one or more rings which may optionally be substituted with one or more substituents $R_x$, —$C_5$-$C_{12}$ heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, —$C_1$-$C_{12}$ alkylene-($C_5$-$C_{12}$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, —($C_5$-$C_{12}$ heterocyclo)-$C_1$-$C_{12}$ alkylene- wherein said heterocyclo group may be a saturated or unsaturated group having one or more rings and comprising at least one oxygen, nitrogen or sulphur atom in said ring(s), said group optionally being substituted with one or more substituents $R_x$, —$(OCH_2CH_2)_r$—, and —$CH_2$—$(OCH_2CH_2)_r$— wherein each of the above alkylene substituents whether alone or attached to another moiety the carbon chain may optionally be substituted by one or more substituents $R_x$;

$R_{30}$ is a —$C_1$-$C_6$ alkylene- group;

M is selected from the group consisting of —$C_1$-$C_6$ alkylene-, —$C_1$-$C_6$ alkylene-($C_3$-$C_8$ carbocyclo)- and phenylene which may optionally be substituted with one or more substituents $R_x$; and r is an integer ranging from 1-6.

a drug conjugate of formula $[D-(X)_b-(AA)_w-(T)_g-(L)-]_n$-Ab according to the present invention selected from formulas (IV), (V) and (VI):

(IV)

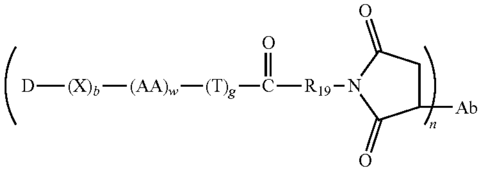

-continued (V)

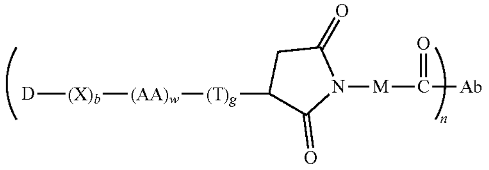

(VI)

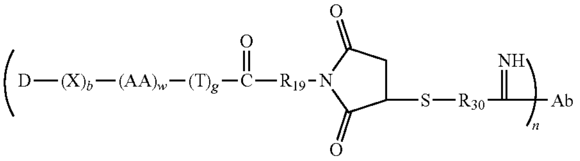

wherein:

X and T are extending groups as defined herein;

each AA is independently an amino acid unit as defined herein;

w is an integer ranging from 0 to 12;

b is an integer of 0 or 1;

g is an integer of 0 or 1;

where b+g+w is optionally not 0;

D is a drug moiety; Ab is a moiety comprising at least one antigen binding site;

n is the ratio of the group $[D-(X)_b-(AA)_w-(T)_g-(L)-]$ wherein L is as defined in formula (IV), (V) or (VI) to the moiety comprising at least one antigen binding site and is in the range from 1 to 20;

$R_{19}$ is selected from —$C_1$-$C_8$ alkylene-, —O—($C_1$-$C_8$ alkylene), —$C_1$-$C_8$ alkylene-$C_6$-$C_{12}$ arylene- wherein the arylene group is in one or more rings which may optionally be substituted with one or more substituents $R_x$, and —$C_6$-$C_{12}$ arylene-$C_1$-$C_8$ alkylene- wherein the arylene group is in one or more rings which may optionally be substituted with one or more substituents $R_x$, wherein each of the above alkylene substituents whether alone or attached to another moiety the carbon chain may optionally be substituted by one or more substituents $R_x$;

$R_{30}$ is a —$C_2$-$C_4$ alkylene- group; and

M is selected from the group consisting of —$C_1$-$C_3$ alkylene- and —$C_1$-$C_3$ alkylene-($C_5$-$C_7$ carbocyclo)-.

a drug conjugate of formula $[D-(X)_b-(AA)_w-(T)_g-(L)-]_n$-Ab according to the present invention, selected from formulas (IV), (V) and (VI):

(IV)

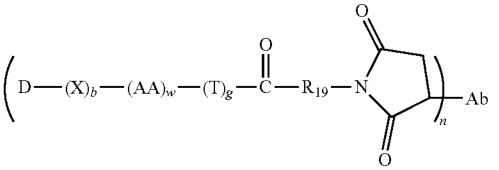

(V)

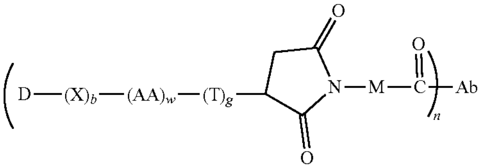

-continued (VI)

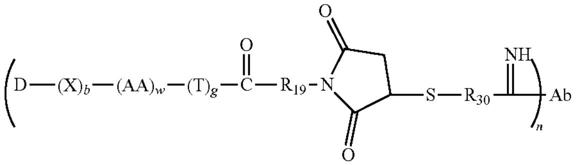

wherein:

X and T are extending groups that may be the same or different;

each AA is independently an amino acid unit;

w is an integer ranging from 0 to 12;

b is an integer of 0 or 1;

g is an integer of 0 or 1;

where b+g+w is optionally not 0;

D is a drug moiety;

Ab is a moiety comprising at least one antigen binding site;

n is the ratio of the group $[D-(X)_b-(AA)_w-(T)_g-(L)-]$ wherein L is as defined in formulas (IV), (V) or (VI) to the moiety comprising at least one antigen binding site and is in the range from 1 to 20;

$R_{19}$ is selected from $-C_1-C_6$ alkylene-, phenylene-$C_1$-$C_6$ alkylene- wherein the phenylene group may optionally be substituted with one or more substituents $R_x$ selected from the group consisting of alkyl groups having from 1 to 6 carbon atoms, alkoxy groups having from 1 to 6 carbon atoms, halogen atoms, nitro groups and cyano groups, wherein each of the above alkylene substituents whether alone or attached to another moiety in the carbon chain may optionally be substituted by one or more substituents $R_x$ selected from the group consisting of alkyl groups having from 1 to 6 carbon atoms, alkoxy groups having from 1 to 6 carbon atoms, aryl groups having from 6 to 12 carbon atoms, halogen atoms, nitro groups and cyano groups, and preferably $R_{19}$ is a $-C_1-C_6$ alkylene group;

$R_{30}$ is a $-C_2-C_4$ alkylene- group; and

M is $-C_1-C_3$ alkylene-($C_5$-$C_7$carbocyclo)-.

It is preferred that in the definition of the drug conjugate of formula $[D-(X)_b-(AA)_w-(T)_g-(L)-]_n-Ab$, L is as defined in the preferred definitions for said group above and $(AA)_w$ is of formula (II):

(II)

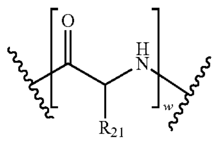

wherein the wavy lines indicate the point of covalent attachments to $(X)_b$ if any, or to the drug moiety (the wavy line to the left) and to $(T)_g$ if any, or to the linker (the wavy line to the right); and $R_{21}$ is, at each occurrence, selected from the group consisting of hydrogen, methyl, isopropyl, isobutyl, sec-butyl, benzyl, p-hydroxybenzyl, $-CH_2OH$, $-CH(OH)CH_3$, $-CH_2CH_2SCH_3$, $-CH_2CONH_2$, $-CH_2COOH$, $-CH_2CH_2CONH_2$, $-CH_2CH_2COOH$, $-(CH_2)_3NHC(=NH)NH_2$, $-(CH_2)_3NH_2$, $-(CH_2)_3NHCOCH_3$, $-(CH_2)_3NHCHO$, $-(CH_2)_4NHC(=NH)NH_2$, $-(CH_2)_4NH_2$, $-(CH_2)_4NHCOCH_3$, $-(CH_2)_4NHCHO$, $-(CH_2)_3NHCONH_2$, $-(CH_2)_4NHCONH_2$, $-CH_2CH_2CH(OH)CH_2NH_2$, 2-pyridylmethyl-, 3-pyridylmethyl-, 4-pyridylmethyl-, phenyl, cyclohexyl,

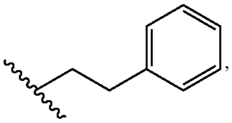, 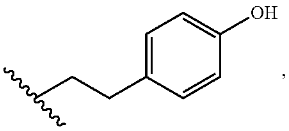,

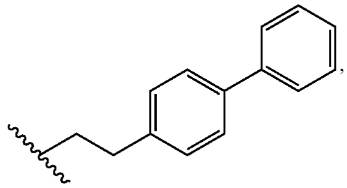,

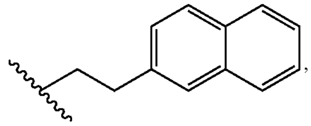, 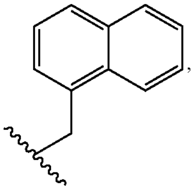,

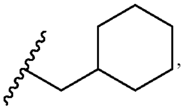, 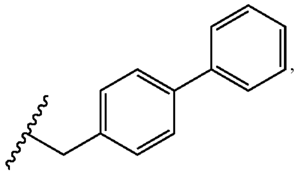,

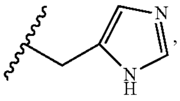, and 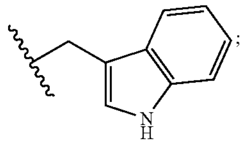;

and w is an integer ranging from 0 to 12.

a drug conjugate of formula $[D-(X)_b-(AA)_w-(T)_g-(L)-]_n-Ab$ according to the first aspect of the present invention, wherein L is as defined in the preferred definitions for said group above and $(AA)_w$ is of formula (II) wherein:

$R_{21}$ is selected, at each occurrence, from the group consisting of hydrogen, methyl, isopropyl, sec-butyl, benzyl, indolylmethyl, $-(CH_2)_3NHCONH_2$, $-(CH_2)_4NH_2$, $-(CH_2)_3NHC(=NH)NH_2$ and $-(CH_2)_4NHC(=NH)NH_2$; and w is an integer ranging from 0 to 6.

a drug conjugate of formula $[D-(X)_b-(AA)_w-(T)_g-(L)-]_n-Ab$ according to the first aspect of the present invention, wherein L is as defined in the preferred definitions for said group above, wherein w is 0 or 2, and when w is 2, then $(AA)_w$ is of formula (III) wherein:

(III)

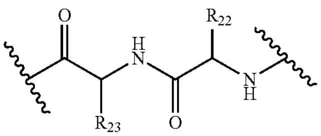

the wavy lines indicate the point of covalent attachments to $(X)_b$ if any, or to the drug moiety (the wavy line to the left) and to $(T)_g$ if any, or to the linker (the wavy line to the right);

$R_{22}$ is selected from methyl, benzyl, isopropyl, sec-butyl and indolylmethyl; and $R_{23}$ is selected from methyl, $-(CH_2)_4NH_2$, $-(CH_2)_3NHCONH_2$ and $-(CH_2)_3NHC(=NH)NH_2$.

In embodiments of the present invention b+g+w is not 0. In further embodiments, b+w is not 0. In yet further embodiments, when w is not 0, then b is 1. Further, it is preferred that in the definition of the drug conjugate of formula $[D-(X)_b-(AA)_w-(T)_g-(L)-]_n-Ab$, L and $(AA)_w$ are as defined in the preferred definitions for said groups above and X is an extending group selected from:

where D is conjugated via an amine group (for example where Z is —NH—):

—COO—($C_1$-$C_6$ alkylene)NH—;

—COO—$CH_2$-(phenylene which may optionally be substituted with one or more substituents $R_x$)—NH—;

—COO—($C_1$-$C_6$ alkylene)NH—COO—$CH_2$-(phenylene which may optionally be substituted with one or more substituents $R_x$)—NH—;

—$COCH_2NH$—$COCH_2$—NH—;

—$COCH_2NH$—;

—COO—($C_1$-$C_6$ alkylene)S—;

—COO—($C_1$-$C_6$ alkylene)NHCO($C_1$-$C_6$ alkylene)S—; or where D is conjugated via an hydroxy group (for example where Z is —O—):

—CONH—($C_1$-$C_6$ alkylene)NH—;

—COO—$CH_2$-(phenylene which may optionally be substituted with one or more substituents $R_x$)—NH—;

—CONH—($C_1$-$C_6$ alkylene)NH—COO—$CH_2$-(phenylene which may optionally be substituted with one or more substituents $R_x$)—NH—;

—$COCH_2NH$—$COCH_2$—NH—;

—$COCH_2NH$—;

—CONH—($C_1$-$C_6$ alkylene)S—;

—CONH—($C_1$-$C_6$ alkylene)NHCO($C_1$-$C_6$ alkylene)S—; and b is 0 or 1, preferably 1.

a drug conjugate of formula $[D-(X)_b-(AA)_w-(T)_g-(L)-]_n-Ab$ according to the present invention, wherein L and $(AA)_w$ are as defined in the preferred definitions for said groups above and X is an extending group selected from the group consisting of:

where D is conjugated via an amine group (for example where Z is —NH—):

—COO—($C_2$-$C_4$ alkylene)NH—;

—COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups;

—COO—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—;

—$COCH_2NH$—$COCH_2$—NH—;

—COO—($C_2$-$C_4$ alkylene)S—;

—COO—($C_2$-$C_4$ alkylene)NHCO($C_1$-$C_3$ alkylene)S—; or where D is conjugated via an hydroxy group (for example where Z is —O—):

—CONH—($C_2$-$C_4$ alkylene)NH—;

—COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups;

—CONH—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—;

—$COCH_2NH$—$COCH_2$—NH—;

—CONH—($C_2$-$C_4$ alkylene)S—;

—CONH—($C_2$-$C_4$ alkylene)NHCO($C_1$-$C_3$ alkylene)S—; and b is 0 or 1, preferably 1.

a drug conjugate of formula $[D-(X)_b-(AA)_w-(T)_g-(L)-]_n-Ab$ according to the present invention, wherein L and $(AA)_w$ are as defined in the preferred definitions for said groups above and X is an extending group selected from the group consisting of:

where D is conjugated via an amine group (for example where Z is —NH—):

—COO—$CH_2$-phenylene-NH—

—COO$(CH_2)_3$NHCOO$CH_2$-phenylene-NH—;

—COO$(CH_2)_3$NH—;

—COO$(CH_2)_3$—S—;

—COO$(CH_2)_3$NHCO$(CH_2)_2$—; or where D is conjugated via an hydroxy group (for example where Z is —O—):

—COO—$CH_2$-phenylene-NH—

—CONH$(CH_2)_3$NHCOO$CH_2$-phenylene-NH—;

—CONH$(CH_2)_3$NH—;

—CONH$(CH_2)_3$—S—;

—CONH$(CH_2)_3$NHCO$(CH_2)_2$—; and b is 0 or 1, preferably 1.

a drug conjugate of formula $[D-(X)_b-(AA)_w-(T)_g-(L)-]_n-Ab$ according to the present invention, wherein L, $(AA)_w$, and $(X)_b$ are as defined in the preferred definitions for said groups above and T is an extending group selected from the group consisting of:

—CO—($C_1$-$C_6$ alkylene)-NH—;

—CO—($C_1$-$C_6$ alkylene)-[O—($C_2$-$C_6$ alkylene)$]_j$—NH—;

—COO—($C_1$-$C_6$ alkylene)-[O—($C_2$-$C_6$ alkylene)$]_j$—NH—;

where j is an integer from 1 to 25, and g is 0 or 1.

A drug conjugate of formula $[D-(X)_b-(AA)_w-(T)_g-(L)-]_n-Ab$ according to the present invention, wherein L, $(AA)_w$, and $(X)_b$ are as defined in the preferred definitions for said groups above and T is an extending group selected from the group consisting of:

—CO—($C_1$-$C_4$ alkylene)NH—

—CO—($C_1$-$C_4$ alkylene)-[O—($C_2$-$C_4$ alkylene)]j-NH—;

—COO—($C_1$-$C_4$ alkylene)-[O—($C_2$-$C_4$ alkylene)]j-NH—;

where j is an integer from 1 to 10; and g is 0 or 1.

A drug conjugate of formula [D-$(X)_b$-$(AA)_w$-$(T)_g$-(L)-$]_n$-Ab according to the present invention, wherein L, $(AA)_w$, and $(X)_b$ are as defined in the preferred definitions for said groups above and T is an extending group selected from the group consisting of:

—CO—($C_1$-$C_4$ alkylene)NH—

—CO—($C_1$-$C_4$ alkylene)-[O—($C_2$-$C_4$ alkylene)$]_j$-NH—;

—COO—($C_1$-$C_4$ alkylene)-[O—($C_2$-$C_4$ alkylene)$]_j$-NH—;

where j is an integer from 1 to 5; and g is 0 or 1.

A preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is a compound of formula I, IA, IB, IC, ID, IE, IF, IG, Ia, IAa, IBa, ICa, IDa, IEa, IFa, IGa, Ib, IAb, IBb, ICb, IDb, IEb, IFb, IGb, (IH), (IHa) or (IHb), or a pharmaceutically acceptable salt, ester, solvate, tautomer or stereoisomer thereof, wherein $R_1$ is CN or OH in compounds of formula I, IA, IB, IC, ID, IE, IG, Ia, IAa, IBa, ICa, IDa, IEa, IGa, Ib, IAb, IBb, ICb, IDb, IEb, IGb, (IH), (IHa) or (IHb); $R_1$ is OH in compounds of formula IF, IFa and IFb, and more preferably $R_1$ is CN.

Another preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is a compound of formula I, IA, IB, IC, ID, IE, IF, Ia, IAa, IBa, ICa, IDa, IEa, IFa, Ib, IAb, IBb, ICb, IDb, IEb, IFb, (IH), (IHa) or (IHb), or a pharmaceutically acceptable salt, ester, solvate, tautomer or stereoisomer thereof, wherein $R_2$ is C(═O)$R_a$, wherein $R_a$ is selected from hydrogen and substituted or unsubstituted $C_1$-$C_6$ alkyl, wherein the optional substituents are one or more substituents $R_x$, and more preferably $R_2$ is acetyl.

Another preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is a compound of formula I, IA, IB, IC, ID, IE, IF, IG, Ia, IAa, IBa, ICa, IDa, IEa, IFa, IGa, Ib, IAb, IBb, ICb, IDb, IEb, IFb, IGb, (IH), (IHa) or (IHb), or a pharmaceutically acceptable salt, ester, solvate, tautomer or stereoisomer thereof, wherein $R_3$ is hydrogen or a —$OR_b$ group in compounds of formula I, IC, ID, IE, IF, IG, la, ICa, IDa, IEa, IFa, IGa, Ib, ICb, IDb, IEb, IFb, IGb, (IH), (IHa) or (IHb); $R_3$ is hydrogen in compounds of formula IA, IAa, or IAb; $R_3$ is a —$OR_b$ group in compounds of formula IB, IBa, or IBb, wherein $R_b$ is a substituted or unsubstituted $C_1$-$C_6$ alkyl group, wherein the optional substituents are one or more substituents $R_x$, and more preferably $R_3$ is hydrogen or methoxy. Most preferably $R_3$ is hydrogen.

Another preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is a compound of formula (IH), (IHa) or (IHb), or a pharmaceutically acceptable salt, ester, solvate, tautomer or stereoisomer thereof, wherein Y is —NH— or —O—.

Another preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is a compound of formula (IH), (IHa) or (IHb), or a pharmaceutically acceptable salt, ester, solvate, tautomer or stereoisomer thereof, wherein Z is —NH— or —O—, and more preferably Z is —NH—.

A further preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is a compound of formula (IHa) or (IHb), or a pharmaceutically acceptable salt, ester, solvate, tautomer or stereoisomer thereof, wherein:

$R_1$ is —CN or —OH;

$R_2$ is —C(═O)$R_a$, wherein $R_a$ is selected from hydrogen and substituted or unsubstituted $C_1$-$C_6$ alkyl, wherein the optional substituents are one or more substituents $R_x$;

$R_3$ is hydrogen or a —$OR_b$ group wherein $R_b$ is a substituted or unsubstituted $C_1$-$C_6$ alkyl group, wherein the optional substituents are one or more substituents $R_x$, Y is —NH— or —O—; and Z is —NH— or —O—.

A further preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is a compound of formula (IHa) or (IHb), or a pharmaceutically acceptable salt, ester, solvate, tautomer or stereoisomer thereof, wherein:

$R_1$ is —CN or —OH;

$R_2$ is acetyl;

$R_3$ is hydrogen or methoxy, more preferably hydrogen;

Y is —NH— or —O—; and

Z is —NH— or —O—.

A further preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is a compound of formula (IHa) or (IHb), or a pharmaceutically acceptable salt, ester, solvate, tautomer or stereoisomer thereof, wherein:

$R_1$ is —CN;

$R_2$ is acetyl:

$R_3$ is hydrogen;

Y is —NH— or —O—; and

Z is —NH—.

A further preferred drug conjugate of formula [D-$(X)_b$-$(AA)_w$-$(T)_g$-(L)-$]_n$-Ab according to the present invention is one wherein L, $(AA)_w$, $(X)_b$, and $(T)_g$ are as defined above and wherein D is selected from:

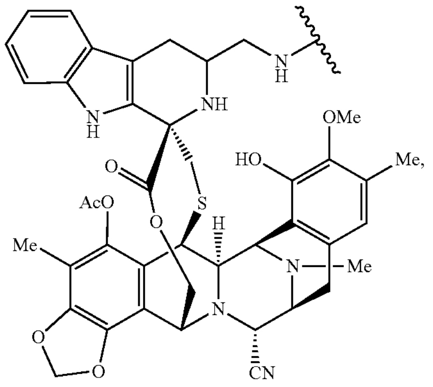

,

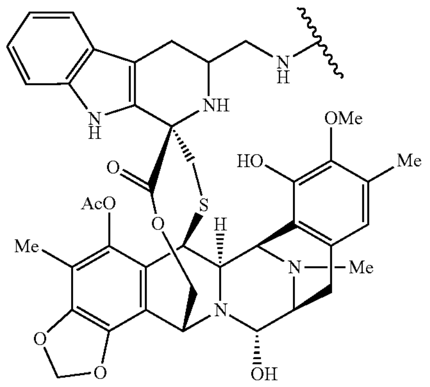

and

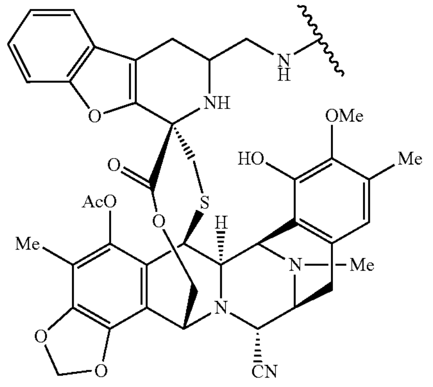

or a pharmaceutically acceptable salt, ester, solvate, tautomer or stereoisomer thereof; wherein the wavy lines indicate the point of covalent attachment to $(X)_b$ if any, or $(AA)_w$ if any, or to $(T)_g$ if any or to (L).

A further preferred drug conjugate of formula $[D-(X)_b-(AA)_w-(T)_g-(L)-]_n-Ab$ according to the present invention is one wherein L, $(AA)_w$, $(X)_b$, and $(T)_g$ are as defined above and wherein D is selected from:

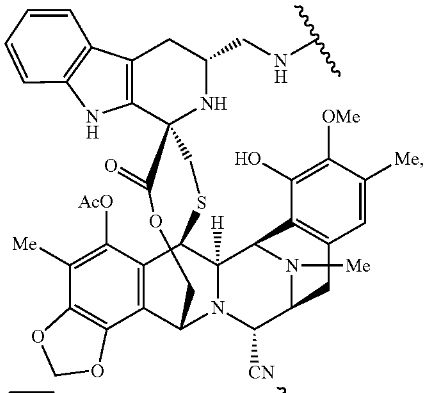

,

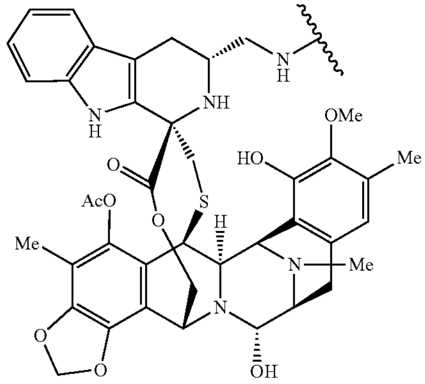

and

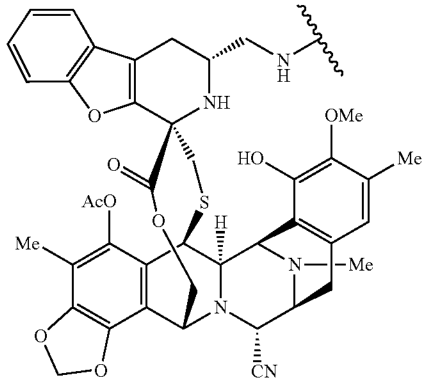

or a pharmaceutically acceptable salt, ester, solvate, tautomer or stereoisomer thereof; wherein the wavy lines indicate the point of covalent attachment to $(X)_b$ if any, or $(AA)_w$ if any, or to $(T)_g$ if any or to (L).

A further preferred drug conjugate of formula $[D-(X)_b-(AA)_w-(T)_g-(L)-]_n-Ab$ according to the present invention is one wherein L, $(AA)_w$, $(X)_b$, $(T)_g$ and D are as defined above and wherein the moiety Ab comprising at least one antigen binding site is an antigen-binding peptide.

A further preferred drug conjugate of formula $[D-(X)_b-(AA)_w-(T)_g-(L)-]_n-Ab$ according to the present invention is one wherein L, $(AA)_w$, $(X)_b$, $(T)_g$ and D are as defined above and the moiety Ab comprising at least one antigen binding site is an antibody, a single domain antibody or an antigen-binding fragment thereof.

A further preferred drug conjugate of formula $[D-(X)_b-(AA)_w-(T)_g-(L)-]_n-Ab$ according to the present invention is one wherein L, $(AA)_w$, $(X)_b$, $(T)_g$ and D are as defined above and the moiety Ab comprising at least one antigen binding site is a monoclonal, polyclonal antibody or bispecific antibody and wherein the antibody or antigen-binding fragment thereof is derived from any species, preferably a human, mouse or rabbit.

A further preferred drug conjugate of formula $[D-(X)_b-(AA)_w-(T)_g-(L)-]_n$-Ab according to the present invention is one wherein L, $(AA)_w$, $(X)_b$, $(T)_g$ and D are as defined above and the moiety Ab comprising at least one antigen binding site is an antibody or antigen-binding fragment thereof which is selected from the group consisting of a human antibody, an antigen-binding fragment of a human antibody, a humanized antibody, an antigen-binding fragment of a humanized antibody, a chimeric antibody, an antigen-binding fragment of a chimeric antibody, a glycosylated antibody and a glycosylated antigen binding fragment.

A further preferred drug conjugate of formula $[D-(X)_b-(AA)_w-(T)_g-(L)-]_n$-Ab according to the present invention is one wherein L, $(AA)_w$, $(X)_b$, $(T)_g$ and D are as defined above and the moiety Ab comprising at least one antigen binding site is an antibody or antigen-binding fragment thereof, wherein the antibody or antigen-binding fragment thereof is an antigen-binding fragment selected from the group consisting of an Fab fragment, an Fab' fragment, an $F(ab')_2$ fragment and an Fv fragment.

A further preferred drug conjugate of formula $[D-(X)_b-(AA)_w-(T)_g-(L)-]_n$-Ab according to the present invention is one wherein L, $(AA)_w$, $(X)_b$, $(T)_g$ and D are as defined above and the moiety Ab comprising at least one antigen binding site is an antibody or antigen-binding fragment thereof, wherein the antibody or antigen-binding fragment thereof is a monoclonal antibody which immunospecifically binds to cancer cell antigens, viral antigens, antigens of cells that produce autoimmune antibodies associated with autoimmune disease, microbial antigens, and preferably a monoclonal antibody which immunospecifically binds to cancer cell antigens.

A further preferred drug conjugate of formula $[D-(X)_b-(AA)_w-(T)_g-(L)-]_n$-Ab according to the the present invention is one wherein L, $(AA)_w$, $(X)_b$, $(T)_g$ and D are as defined herein and the moiety Ab comprising at least one antigen binding site is an antibody selected from the group consisting of Abciximab, Alemtuzumab, Anetumab, Atezolizumab, Avelumab, Basiliximab, Bevacizumab, Blinatomumab, Brentuximab, Catumaxomab, Cetuximab, Coltuximab, Daclizumab, Daratumumab, Denintuzumab, Denosumab, Depatuxizumab, Dinutuximab, Durvalumab, Elotuzumab, Enfortumab, Glembatumumab, Gemtuzumab, Ibritumomab, Indatuximab, Indusatumab, Inotuzumab, Ipilimumab, Labetuzumab, Ladiratuzumab, Laprituximab, Lifastuzumab, Lorvotuzumab, Milatuzumab, Mirvetuximab, Naratuximab, Necitumumab, Nimotuzumab, Nivolumab, Obinutuzumab, Ofatumumab, Olaratumab, Omalizumab, Palivizumab, Panitumumab, Pembrolizumab, Pertuzumab, Pinatuzumab, Polatuzumab, Ramucirumab, Rovalpituzumab, Sacituzumab, Siltuximab, Sirtratumab, Sofituzumab, Vadastuximab, Vorsetuzumab, Trastuzumab, an anti-CD4 antibody, an anti-CD5 antibody, an anti-CD13 antibody and an anti-CD 30 antibody, or an antigen-binding fragment or an immunologicallly active portion thereof, wherein preferably the antibody is selected from Abciximab, Alemtuzumab, Anetumab, Atezolizumab, Avelumab, Basiliximab, Bevacizumab, Blinatomumab, Brentuximab, Catumaxomab, Cetuximab, Daclizumab, Daratumumab, Denintuzumab, Denosumab, Depatuxizumab, Dinutuximab, Durvalumab, Elotuzumab, Enfortumab, Glembatumumab, Gemtuzumab, Ibritumomab, Indatuximab, Indusatumab, Inotuzumab, Ipilimumab, Labetuzumab, Ladiratuzumab, Laprituximab, Mirvetuximab, Naratuximab, Necitumumab, Nimotuzumab, Nivolumab, Obinutuzumab, Ofatumumab, Olaratumab, Omalizumab, Palivizumab, Panitumumab, Pembrolizumab, Pertuzumab, Polatuzumab, Ramucirumab, Rovalpituzumab, Sacituzumab, Siltuximab, Sirtratumab, Vadastuximab, Vorsetuzumab, Trastuzumab, an anti-CD4 antibody, an anti-CD5 antibody, an anti-CD13 antibody and an anti-CD antibody, or an antigen-binding fragment or an immunologicallly active portion thereof, and yet more preferably Abciximab, Alemtuzumab, Atezolizumab, Avelumab, Basiliximab, Bevacizumab, Blinatomumab, Brentuximab, Catumaxomab, Cetuximab, Daclizumab, Daratumumab, Denosumab, Dinutuximab, Durvalumab, Elotuzumab, Gemtuzumab, Ibritumomab, Inotuzumab, Ipilimumab, Labetuzumab, Necitumumab, Nimotuzumab, Nivolumab, Obinutuzumab, Ofatumumab, Olaratumab, Omalizumab, Palivizumab, Panitumumab, Pembrolizumab, Pertuzumab, Ramucirumab, Rovalpituzumab, Siltuximab, Trastuzumab, an anti-CD4 antibody, an anti-CD5 antibody, an anti-CD13 antibody and an anti-CD 30 antibody, or an antigen-binding fragment or an immunologically active portion thereof. Of these, particularly preferred are Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologicallly active portion thereof; or the antibody is selected from Trastuzumab and anti-CD13 antibody or an antigen-binding fragment or an immunologically active portion thereof, particularly Trastuzumab or an antigen-binding fragment or an immunologicallly active portion thereof.

Particularly preferred drug conjugates of formula $[D-(X)_b-(AA)_w-(T)_g-(L)-]_n$-Ab according to the present invention include the following:

(a) a drug conjugate according to the present invention wherein:

L is selected from the group consisting of:

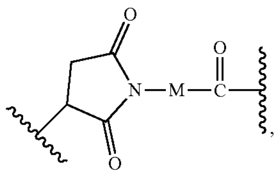
,

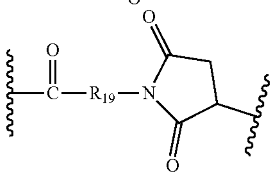
and

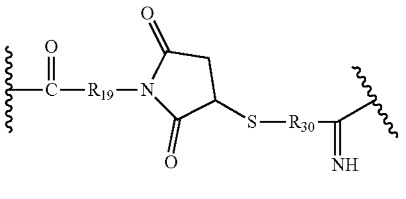

wherein:

the wavy lines indicate the point of covalent attachments to an Ab (the wavy line to the right) and to $(T)_g$ if any, or $(AA)_w$ if any, or to $(X)_b$ if any, or to (D) (the wavy line to the left);

$R_{19}$ is selected from —$C_1$-$C_{12}$ alkylene-, —O—($C_1$-$C_{12}$ alkylene), —$C_6$-$C_{12}$ arylene in one or more rings which may optionally be substituted with one or more substituents $R_x$, —$C_1$-$C_{12}$ alkylene-$C_6$—$C_{12}$ arylene-wherein the arylene group is in one or more rings which may optionally be substituted with one or more substituents $R_x$, —$C_6$-$C_{12}$ arylene-$C_1$-$C_{12}$ alkylene-wherein the arylene group is in one or more rings which may optionally be substituted with one or more substituents $R_x$, —$C_5$-$C_{12}$ heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, —$C_1$-$C_{12}$ alkylene-($C_5$-$C_{12}$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, —($C_5$-$C_{12}$ heterocyclo)-$C_1$-$C_{12}$ alkylene- wherein said heterocyclo group may be a saturated or unsaturated group having one or more rings and comprising at least one oxygen, nitrogen or sulphur atom in said ring(s), said group optionally being substituted with one or more substituents $R_x$, —$(OCH_2CH_2)_r$— and —$CH_2$—$(OCH_2CH_2)_r$—, wherein each of the above alkylene substituents whether alone or attached to another moiety the carbon chain may optionally be substituted by one or more substituents $R_x$;

$R_{30}$ is a —$C_1$-$C_6$ alkylene- group;

M is selected from the group consisting of —$C_1$-$C_6$ alkylene-, —$C_1$-$C_6$ alkylene-($C_3$-$C_8$ carbocyclo)- and phenylene which may optionally be substituted with one or more substituents $R_x$;

r is an integer ranging from 1-6;

$(AA)_w$ is of formula (II):

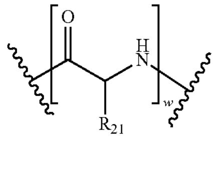

(II)

wherein the wavy lines indicate the point of covalent attachments to $(X)_b$ if any, or to the drug moiety (the wavy line to the left) and to $(T)_g$ if any, or to the linker (the wavy line to the right);

$R_{21}$ is, at each occurrence, selected from the group consisting of hydrogen, methyl, isopropyl, isobutyl, sec-butyl, benzyl, p-hydroxybenzyl, —$CH_2OH$, —CH(OH)$CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, $CH_2CH_2CH(OH)CH_2NH_2$, 2-pyridylmethyl-, 3-pyridylmethyl-, 4-pyridylmethyl-, phenyl, cyclohexyl,

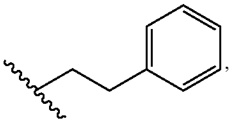, 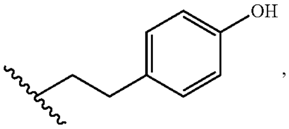,

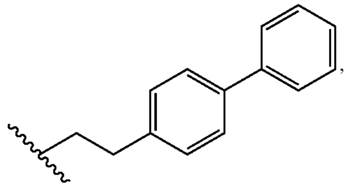,

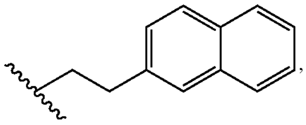, 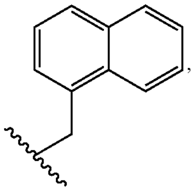,

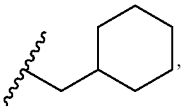, 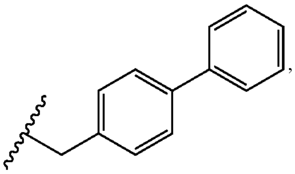,

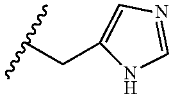, and 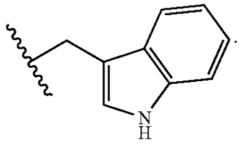.

w is an integer ranging from 0 to 12;

wherein X is an extending group selected from where D is conjugated via an amine group (for example where Z is —NH—): —COO—($C_1$-$C_6$ alkylene)NH—, —COO—$CH_2$-(phenylene which may optionally be substituted with one or more substituents $R_x$)—NH—, —COO—($C_1$-$C_6$ alkylene)NH—COO—$CH_2$-(phenylene which may optionally be substituted with one or more substituents $R_x$)—NH—, —$COCH_2NH$—$COCH_2$—NH—, —$COCH_2$—NH—, —COO—($C_1$-$C_6$ alkylene)S—, —COO—($C_1$-$C_6$ alkylene)NHCO($C_1$-$C_6$ alkylene)S—; or where D is conjugated via an hydroxy group (for example where Z is —O—): —CONH—($C_1$-$C_6$ alkylene)NH—, —COO—$CH_2$-(phenylene which may optionally be substituted with one or more substituents $R_x$)—NH—, —CONH—($C_1$-$C_6$ alkylene)NH—COO—$CH_2$-(phenylene which may optionally be substituted with one or more substituents $R_x$)—NH—, —$COCH_2NH$—$COCH_2$—NH—, —$COCH_2NH$—, —CONH—($C_1$-$C_6$ alkylene)S—, and —CONH—($C_1$-$C_6$ alkylene)NHCO($C_1$-$C_6$ alkylene)S—;

b is 0 or 1, preferably 1;

wherein T is an extending group selected from —CO—($C_1$-$C_6$ alkylene)-NH—, —CO—($C_1$-$C_6$ alkylene)-$[O—(C_2\text{-}C_6\ alkylene)]_j$-NH—, and —COO—($C_1$-$C_6$ alkylene)-$[O—(C_2\text{-}C_6\ alkylene)]_j$-NH—, where j is an integer from 1 to 25;

g is 0 or 1;

D is a drug moiety of formula I, IA, IB, IC, ID, IE, IF, IG, IH, la, IAa, IBa, ICa, IDa, IEa, IFa, IGa, Ib, IAb, IBb, ICb, IDb, IEb, IFb, IGb, (IHa) or (IHb), or a pharmaceutically acceptable salt, ester, solvate, tautomer or stereoisomer thereof wherein:

$R_2$ is $C(=O)R_a$, in compounds of formula I, IA, IB, IC, ID, IE, IF, Ia, IAa, IBa, ICa, IDa, IEa, IFa, Ib, IAb, IBb, ICb, IDb, IEb, IFb, (IH), (IHa) or (IHb); $R_2$ is acetyl in compounds of formula IG, IGa or IGb, wherein $R_a$ is selected from hydrogen and substituted or unsubstituted $C_1$-$C_6$ alkyl, wherein the optional substituents are one or more substituents $R_x$;

$R_3$ is hydrogen or a —$OR_b$ group in compounds of formula I, IC, ID, IE, IF, IG, Ia, ICa, IDa, IEa, IFa, IGa, Ib, ICb, IDb, IEb, IFb, IGb, (IH), (IHa) or (IHb); $R_3$ is hydrogen in compounds of formula IA, IAa, or IAb; $R_3$ is a —$OR_b$ group in compounds of formula IB, IBa, or IBb, wherein $R_b$ is a substituted or unsubstituted $C_1$-$C_6$ alkyl group, wherein the optional substituents are one or more substituents $R_x$;

the moiety Ab comprising at least one antigen binding site is an antibody or an antigen-binding fragment thereof and it is selected from the group consisting of a human antibody, an antigen-binding fragment of a human antibody, a humanized antibody, an antigen-binding fragment of a humanized antibody, a chimeric antibody, an antigen-binding fragment of a chimeric antibody, a glycosylated antibody and a glycosylated antigen binding fragment; and n is the ratio of the group $[D-(X)_b-(AA)_w-(T)_g-(L)-]$ to the moiety Ab comprising at least one antigen binding site and is in the range from 1 to 12.

(b) a drug conjugate according to the present invention selected from the formulas (IV), (V) and (VI):

(IV)

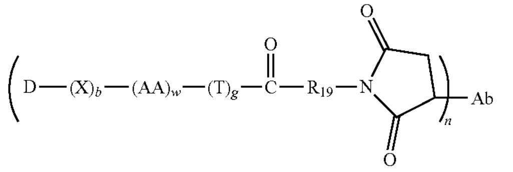

(V)

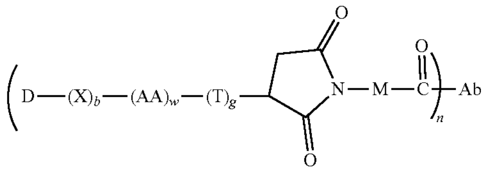

(VI)

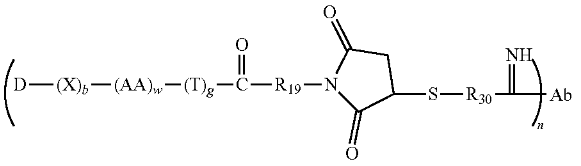

wherein:

$R_{19}$ is selected from —$C_1$-$C_8$ alkylene-, —O—($C_1$-$C_8$ alkylene), —$C_1$-$C_8$ alkylene-$C_6$-$C_{12}$ arylene- wherein the arylene group is in one or more rings which may optionally be substituted with one or more substituents $R_x$ and —$C_6$-$C_{12}$ arylene-$C_1$-$C_8$ alkylene- wherein the arylene group is in one or more rings which may optionally be substituted with one or more substituents $R_x$, wherein each of the above alkylene substituents whether alone or attached to another moiety the carbon chain may optionally be substituted by one or more substituents $R_x$;

$R_{30}$ is a —$C_2$-$C_4$ alkylene- group;

M is selected from the group consisting of —$C_1$-$C_3$ alkylene- and —$C_1$-$C_3$ alkylene-($C_5$-$C_7$ carbocyclo)-;

$(AA)_w$ is of formula (II)

(II)

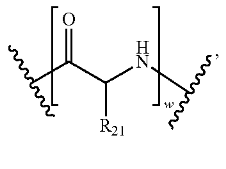

wherein:

the wavy lines indicate the point of covalent attachments to $(X)_b$ if any, or to the drug moiety (the wavy line to the left) and to $(T)_g$ if any, or to the linker (the wavy line to the right);

$R_{21}$ is, at each occurrence, selected from the group consisting of hydrogen, methyl, isopropyl, sec-butyl, benzyl, indolylmethyl, —$(CH_2)_3NHCONH_2$, —$(CH_2)_4NH_2$, —$(CH_2)_3NHC(=NH)NH_2$ and —$(CH_2)_4NHC(=NH)NH_2$;

w is an integer from 0 to 6;

X is an extending group selected from the group consisting of where D is conjugated via an amine group (for example where Z is —NH—): —COO—($C_2$-$C_4$ alkylene)NH—, —COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —COO—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —$COCH_2NH$—$COCH_2$—NH—, —COO—($C_2$-$C_4$ alkylene)S—, and —COO—($C_2$-$C_4$ alkylene)NHCO($C_1$-$C_3$ alkylene)S—; or where D is conjugated via an hydroxy group (for example where Z is —O—): —CONH—($C_2$-$C_4$ alkylene)NH—, —COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —CONH—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —$COCH_2NH$—$COCH_2$—NH—, —CONH—($C_2$-$C_4$ alkylene)S—, and —CONH—($C_2$-$C_4$ alkylene)NHCO ($C_1$-$C_3$ alkylene)S—;

b is 0 or 1, preferably 1;

wherein T is an extending group selected from —CO—($C_1$-$C_4$ alkylene)-NH—, —CO—($C_1$-$C_4$ alkylene)-[O—($C_2$-$C_4$ alkylene)]$_j$-NH—, and —COO—($C_1$-$C_4$ alkylene)-[O—($C_2$-$C_4$ alkylene)]$_j$-NH—, where j is an integer from 1 to 10;

g is 0 or 1;

D is a drug moiety of formula I, IA, IB, IC, ID, IE, IF, IG, IH, la, IAa, IBa, ICa, IDa, IEa, IFa, IGa, Ib, IAb, IBb, ICb, IDb, IEb, IFb, IGb, (IHa) or (IHb), or a pharmaceutically acceptable salt, ester, solvate, tautomer or stereoisomer thereof wherein:

$R_2$ is acetyl;

$R_3$ is hydrogen or methoxy in compounds of formula I, IC, ID, IE, IF, IG, Ia, ICa, IDa, IEa, IFa, IGa, Ib, ICb, IDb, IEb, IFb, IGb, (IH), (IHa) or (IHb); $R_3$ is hydrogen in compounds of formula IA, IAa, or IAb; $R_3$ is a methoxy group in compounds of formula IB, IBa, or IBb, preferably $R_3$ is hydrogen;

the moiety Ab comprising at least one antigen binding site is an antibody or an antigen-binding fragment thereof, wherein the antibody or antigen-binding fragment is a monoclonal antibody which immunospecifically binds to cancer cell antigens, viral antigens, antigens of cells that produce autoimmune antibodies associated with autoimmune disease, microbial antigens, and preferably a monoclonal antibody which immunospecifically binds to cancer cell antigens; and n is the ratio of the group [D-$(X)_b$-$(AA)_w$-$(T)_g$-(L)-] wherein L is as defined in formulas (IV), (V) or (VI) to the moiety Ab comprising at least one antigen binding site and is in the range from 3 to 8.

(c) a drug conjugate according to the present invention selected from the formulas (IV), (V) and (VI):

(IV)

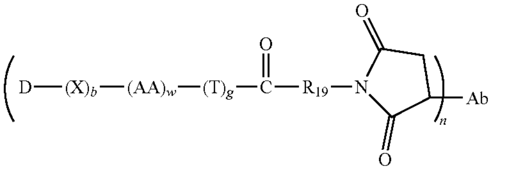

(V)

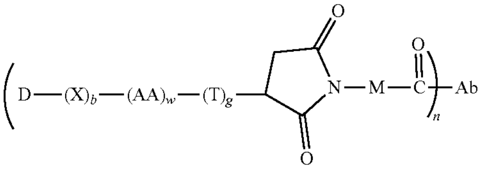

(VI)

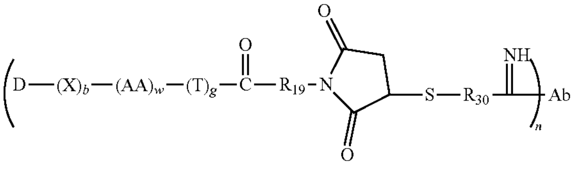

wherein:

$R_{19}$ is selected from —$C_1$-$C_6$ alkylene-, -phenylene-$C_1$-$C_6$ alkylene- wherein the phenylene group may optionally be substituted with one or more substituents $R_x$ selected from the group consisting of alkyl groups having from 1 to 6 carbon atoms, alkoxy groups having from 1 to 6 carbon atoms, halogen atoms, nitro groups and cyano groups, wherein each of the above alkylene substituents whether alone or attached to another moiety in the carbon chain may optionally be substituted by one or more substituents $R_x$ selected from the group consisting of alkyl groups having from 1 to 6 carbon atoms, alkoxy groups having from 1 to 6 carbon atoms, aryl groups having from 6 to 12 carbon atoms, halogen atoms, nitro groups and cyano groups, and preferably $R_{19}$ is a $C_1$-$C_6$ alkylene group;

$R_{30}$ is a —$C_2$-$C_4$ alkylene- group;

M is —$C_1$-$C_3$ alkylene-($C_5$-$C_7$carbocyclo)-;

w is 0 or 2, and where w is 2, then $(AA)_w$ is of formula (III):

(III)

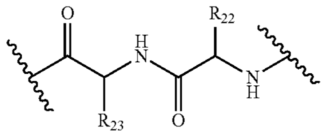

wherein the wavy lines indicate the point of covalent attachments to $(X)_b$ if any, or to the drug moiety (the wavy line to the left) and to $(T)_g$ if any, or to the linker (the wavy line to the right);

$R_{22}$ is selected from methyl, benzyl, isopropyl, sec-butyl and indolylmethyl;

$R_{23}$ is selected from methyl, —$(CH_2)_4NH_2$, —$(CH_2)_3NHCONH_2$ and —$(CH_2)_3NHC({=}NH)NH_2$;

X is an extending group selected from the group consisting of —COO—($C_2$-$C_4$ alkylene)NH—, —COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —COO—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups or cyano groups)-NH—, —$COCH_2NH$—$COCH_2$—NH—, —COO—($C_2$-$C_4$ alkylene)S—, and —COO—($C_2$-$C_4$ alkylene)NHCO($C_1$-$C_3$ alkylene) S—;

b is 0 or 1, preferably 1;

wherein T is an extending group selected from —CO—($C_1$-$C_4$ alkylene)-NH—, —CO—($C_1$-$C_4$ alkylene)-[O—($C_2$-$C_4$ alkylene)]$_j$-NH—, and —COO—($C_1$-$C_4$ alkylene)-[O—($C_2$-$C_4$ alkylene)]$_j$-NH—, where j is an integer from 1 to 5;

g is 0 or 1;

D is a drug moiety of formula I, IA, IC, ID, IE, IG, IH, la, IAa, ICa, IDa, IEa, IGa, Ib, IAb, ICb, IDb, IEb, IGb, (IHa) or (IHb), or a pharmaceutically acceptable salt, ester, solvate, tautomer or stereoisomer thereof wherein:

$R_1$ is CN;

$R_2$ is acetyl:

$R_3$ is hydrogen;

Y is —NH— or —O—;

Z is —NH—;

the moiety Ab comprising at least one antigen binding site is a monoclonal antibody selected from the group consisting of Abciximab, Alemtuzumab, Anetumab, Atezolizumab, Avelumab, Basiliximab, Bevacizumab, Blinatomumab, Brentuximab, Catumaxomab, Cetuximab, Coltuximab, Daclizumab, Daratumumab, Denintuzumab, Denosumab, Depatuxizumab, Dinutuximab, Durvalumab, Elotuzumab, Enfortumab, Glembatumumab, Gemtuzumab, Ibritumomab, Indatuximab, Indusatumab, Inotuzumab, Ipilimumab, Labetuzumab, Ladiratuzumab, Laprituximab, Lifastuzumab, Lorvotuzumab, Milatuzumab, Mirvetuximab, Naratuximab, Necitumumab, Nimotuzumab, Nivolumab, Obinutuzumab, Ofatumumab, Olaratumab, Omalizumab, Palivizumab, Panitumumab, Pembrolizumab, Pertuzumab, Pinatuzumab, Polatuzumab, Ramucirumab, Rovalpituzumab, Sacituzumab, Siltuximab, Sirtratumab, Sofituzumab, Vadastuximab, Vorsetuzumab, Trastuzumab, an anti-CD4 antibody, an anti-CD5 antibody, an anti-CD13 antibody and an anti-CD 30 antibody, or an antigen-binding fragment or an immunologicallly active portion thereof, wherein preferably the antibody is selected from Abciximab, Alemtuzumab, Anetumab, Atezolizumab, Avelumab, Basiliximab, Bevacizumab, Blinatomumab, Brentuximab, Catumaxomab, Cetuximab, Daclizumab, Daratumumab, Denintuzumab, Denosumab, Depatuxizumab, Dinutuximab, Durvalumab, Elotuzumab, Enfortumab, Glembatumumab, Gemtuzumab, Ibritumomab, Indatuximab, Indusatumab, Inotuzumab, Ipilimumab, Labetuzumab, Ladiratuzumab, Laprituximab, Mirvetuximab, Naratuximab, Necitumumab, Nimotuzumab, Nivolumab, Obinutuzumab, Ofatumumab, Olaratumab, Omalizumab, Palivizumab, Panitumumab, Pembrolizumab, Pertuzumab, Polatuzumab, Ramucirumab, Rovalpituzumab, Sacituzumab, Siltuximab, Sirtratumab, Vadastuximab, Vorsetuzumab, Trastuzumab, an anti-CD4 antibody, an anti-CD5 antibody, an anti-CD13 antibody and an anti-CD antibody, or an antigen-binding fragment or an immunologicallly active portion thereof, and yet more preferably Abciximab, Alemtuzumab, Atezolizumab, Avelumab, Basiliximab, Bevacizumab, Blinatomumab, Brentuximab, Catumaxomab, Cetuximab, Daclizumab, Daratumumab, Denosumab, Dinutuximab, Durvalumab, Elotuzumab, Gemtuzumab, Ibritumomab, Inotuzumab, Ipilimumab, Labetuzumab, Necitumumab, Nimotuzumab, Nivolumab, Obinutuzumab, Ofatumumab, Olaratumab, Omalizumab, Palivizumab, Panitumumab, Pembrolizumab, Pertuzumab, Ramucirumab, Rovalpituzumab, Siltuximab, Trastuzumab, an anti-CD4 antibody, an anti-CD5 antibody, an anti-CD13 antibody and an anti-CD 30 antibody, or an antigen-binding fragment or an immunologically active portion thereof. Of these, particularly preferred are Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologicallly active portion thereof; or the antibody is selected from Trastuzumab and anti-CD13 antibody or an antigen-binding fragment or an immunologically active portion thereof, particularly Trastuzumab or an antigen-binding fragment or an immunologicallly active portion thereof; and n is the ratio of the group [D-$(X)_b$-$(AA)_w$-$(T)_g$-(L)-] wherein L is as defined in formulas (IV), (V) or (VI) to the moiety Ab comprising at least one antigen binding site and is in the range from 3 to 5.

(d) A drug conjugate according to the present invention selected from the formulas (IV), (V) and (VI):

(IV)

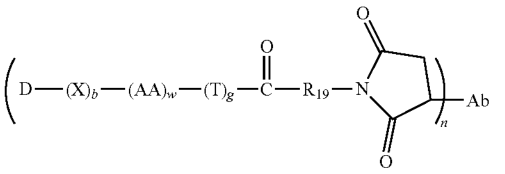

(V)

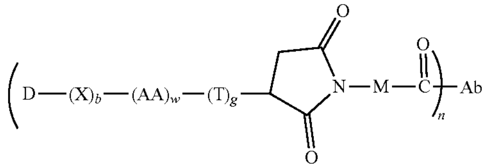

(VI)

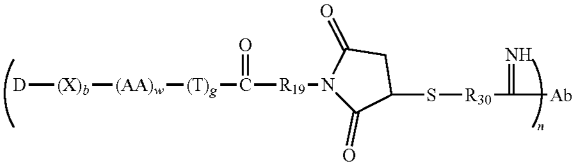

wherein:

$R_{19}$ is —$C_2$-$C_6$ alkylene-;

$R_{30}$ is a —$C_2$-$C_4$ alkylene-;

M is —$C_1$-$C_3$ alkylene-($C_5$-$C_7$carbocyclo)-;

w is 0 or 2, and where w is 2, then $(AA)_w$ is of formula (III):

(III)

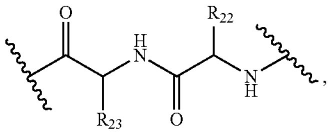

wherein $R_{22}$ is isopropyl, $R_{23}$ is selected from methyl and —$(CH_2)_3NHCONH_2$, wherein the wavy lines indicate the point of covalent attachments to $(X)_b$ if any, or to the drug moiety (the wavy line to the left) and to $(T)_g$ if any, or to the linker (the wavy line to the right);

X is an extending group selected from the group consisting of —COO—($C_2$-$C_4$ alkylene)NH—, —COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —COO—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —$COCH_2NH$—$COCH_2$—NH—, —COO—($C_2$-$C_4$ alkylene)S—, and —COO—($C_2$-$C_4$ alkylene)NHCO($C_1$-$C_3$ alkylene) S—;

b is 0 or 1, preferably 1; wherein T is an extending group selected from —CO—($C_1$-$C_4$ alkylene)-NH—, —CO—($C_1$-$C_4$ alkylene)-[O—($C_2$-$C_4$ alkylene)]$_j$-NH—, and —COO—($C_1$-$C_4$ alkylene)-[O—($C_2$-$C_4$ alkylene)]$_j$-NH—, where j is an integer from 1 to 5;

g is 0 or 1;

D is a drug moiety selected from:

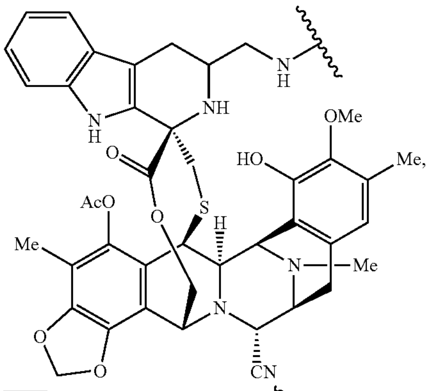

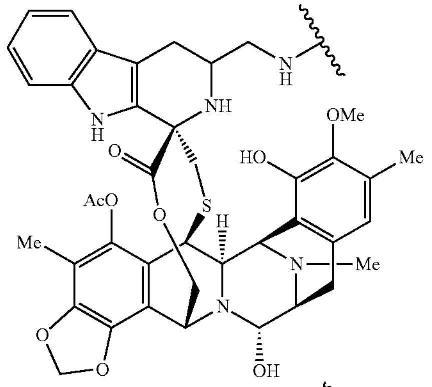

and

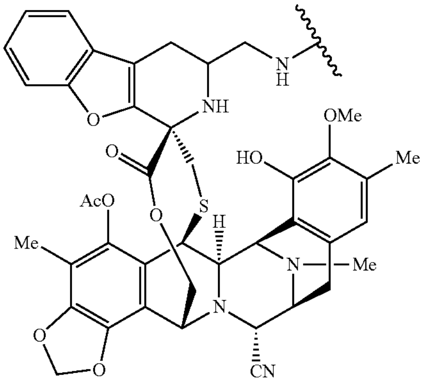

or a pharmaceutically acceptable salt, ester, solvate, tautomer or stereoisomer thereof; wherein the wavy line indicates the point of covalent attachment to $(X)_b$ if any, or $(AA)_w$ if any, or to $(T)_g$ if any, or to (L);

the moiety Ab comprising at least one antigen binding site is selected from Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologicallly active portion thereof, and more preferably its is selected from Trastuzumab and anti-CD13 antibody or an antigen-binding fragment or an immunologically active portion thereof, particularly Trastuzumab or an antigen-binding fragment or an immunologicallly active portion thereof; and n is the ratio of the group [D-$(X)_b$-$(AA)_w$-$(T)_g$-(L)-] wherein L is as defined in formulas (IV), (V) or (VI) to the moiety Ab comprising at least one antigen binding site and is in the range from 3 to 5.

(e) A drug conjugate according to the present invention selected from the formulas (IV), (V), and (VI):

(IV)

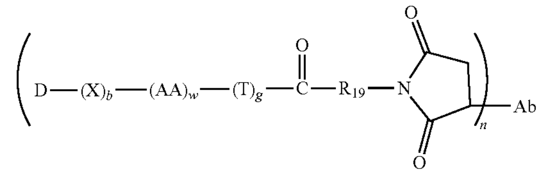

(V)

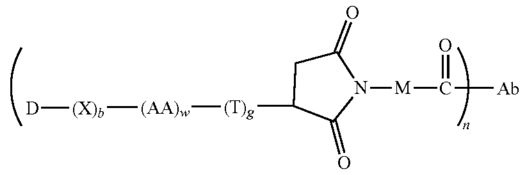

(VI)

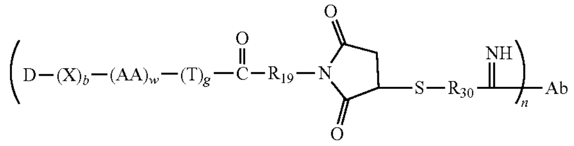

wherein:

$R_{19}$ is —$C_2$-$C_6$ alkylene-;

$R_{30}$ is —$C_2$-$C_4$ alkylene-;

M is —$C_1$-$C_3$ alkylene-($C_5$-$C_7$carbocyclo)-;

w is 0 or 2, and where w is 2, then $(AA)_w$ is of formula (III):

(III)

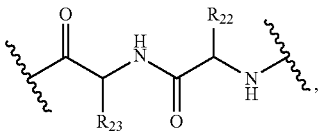

wherein $R_{22}$ is isopropyl, $R_{23}$ is selected from methyl and —$(CH_2)_3NHCONH_2$, and the wavy lines indicate the point of covalent attachments to $(X)_b$ if any, or to the drug moiety (the wavy line to the left) and to $(T)_g$ if any, or to the linker (the wavy line to the right);

X is an extending group selected from the group consisting of —COO—($C_2$-$C_4$ alkylene)NH—, —COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —COO—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —$COCH_2NH$—$COCH_2$—NH—, —COO—($C_2$-$C_4$ alkylene)S—, and —COO—($C_2$-$C_4$ alkylene)NHCO($C_1$-$C_3$ alkylene) S—;

b is 0 or 1, preferably 1;

wherein T is an extending group selected from —CO—($C_1$-$C_4$ alkylene)-NH—, —CO—($C_1$-$C_4$ alkylene)-[O—($C_2$-$C_4$ alkylene)]$_j$-NH—, and —COO—($C_1$-$C_4$ alkylene)-[O—($C_2$-$C_4$ alkylene)]$_j$-NH—, where j is an integer from 1 to 5;

g is 0 or 1;

D is a drug moiety selected from:

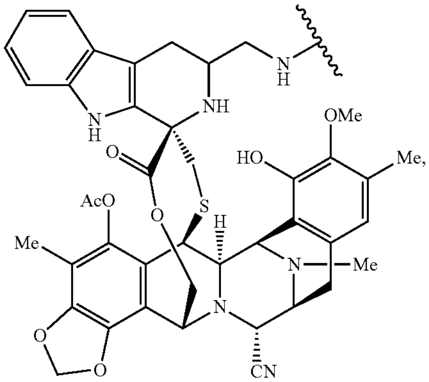

,

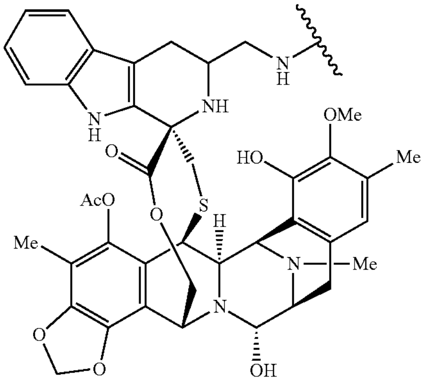

and

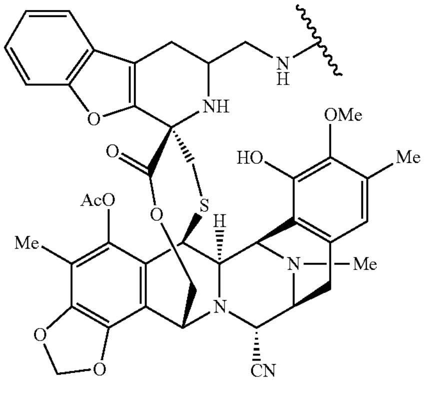

or a pharmaceutically acceptable salt, ester, solvate, tautomer or stereoisomer thereof; wherein the wavy line indicates the point of covalent attachment to $(X)_b$ if any, or $(AA)_w$ if any, or to $(T)_g$ if any, or to (L);

the moiety Ab comprising at least one antigen binding site is selected from Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologicallly active portion thereof, and more preferably its is selected from Trastuzumab and anti-CD13 antibody or an antigen-binding fragment or an immunologically active portion thereof, particularly Trastuzumab or an antigen-binding fragment or an immunologicallly active portion thereof; and n is the ratio of the group [D-$(X)_b$-$(AA)_w$-$(T)_g$-(L)-] wherein L is as defined in formulas (IV), (V) or (VI) to the moiety comprising at least one antigen binding site and is in the range from 3 to 5.

(f) A drug conjugate according to the present invention of formula (IV):

(IV)

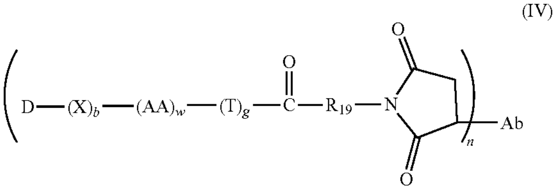

wherein:

$R_{19}$ is $C_2$-$C_5$ alkylene-;

w is 0 or 2, and where w is 2, then $(AA)_w$ is of formula (III):

(III)

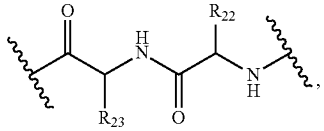

wherein $R_{22}$ is isopropyl, $R_{23}$ is selected from methyl and —$(CH_2)_3NHCONH_2$, and the wavy lines indicate the point of covalent attachments to $(X)_b$ (the wavy line to the left) and to $(T)_g$ if any, or to the linker (the wavy line to the right); and X is a —$COOCH_2$-phenylene-NH group;

b is 1;

T is an extending group of formula —CO—($C_1$-$C_4$ alkylene)-[O—($C_2$-$C_4$ alkylene)]$_4$—NH—;

g is 0 or 1;

or of formula (V)

(V)

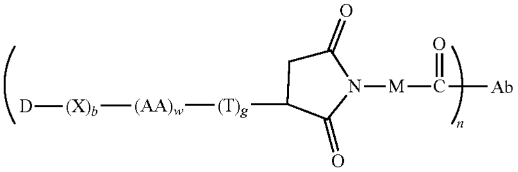

wherein M is -methyl-cyclohexylene-;

b is 1;

w is 0;

X is an extending group selected from $—(CH_2)_3S—$ and $—(CH_2)_3NHCO(CH_2)_2S—$ g is 0;

or of formula (VI)

(VI)

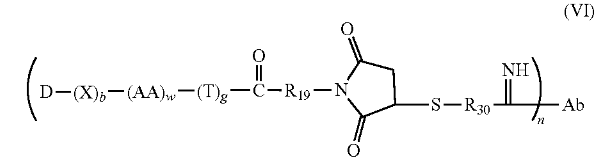

wherein $R_{19}$ is $—C_2$-$C_5$ alkylene-;

$R_{30}$ is $—C_3$ alkylene-;

w is 0 or 2, and where w is 2, then $(AA)_w$ is of formula (III):

(III)

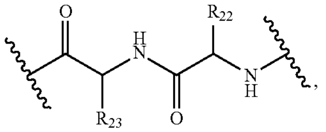

wherein $R_{22}$ is isopropyl, $R_{23}$ is selected from methyl and $—(CH_2)_3NHCONH_2$, and the wavy lines indicate the point of covalent attachments to $(X)_b$ (the wavy line to the left) and to $(T)_g$ if any, or to the linker (the wavy line to the right); and X is a $—COOCH_2$-phenylene-NH group;

b is 1;

T is an extending group of formula $—CO—(C_1$-$C_4$ alkylene)-$[O—(C_2$-$C_4$ alkylene)$]_4—NH—$;

g is 0 or 1;

D is a drug moiety selected from:

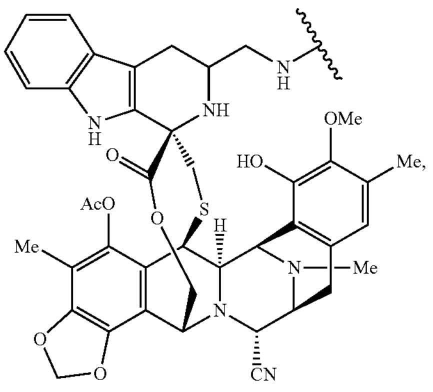

-continued

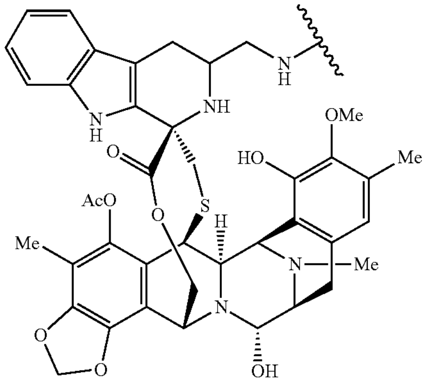

and

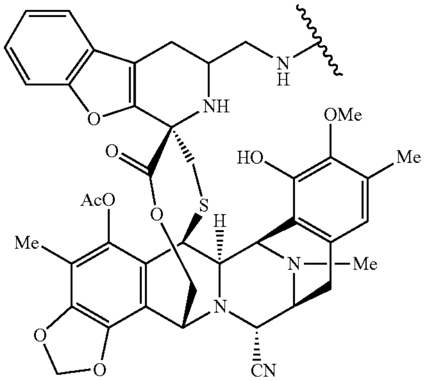

or a pharmaceutically acceptable salt, ester, solvate, tautomer or stereoisomer thereof; wherein the wavy line indicates the point of covalent attachment to $(X)_b$;

the moiety Ab comprising at least one antigen binding site is Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologicallly active portion thereof, and more preferably its is selected from Trastuzumab and anti-CD13 antibody or an antigen-binding fragment or an immunologically active portion thereof, particularly Trastuzumab or an antigen-binding fragment or an immunologicallly active portion thereof; and n is the ratio of the group $[D-(X)_b-(AA)_w-(T)_g-(L)-]$ wherein L is as defined in formula (IV) to the moiety Ab comprising at least one antigen binding site and is in the range from 3 to 5, and preferably 4.

g) an antibody drug conjugate according according to the present invention, selected from the group consisting of:
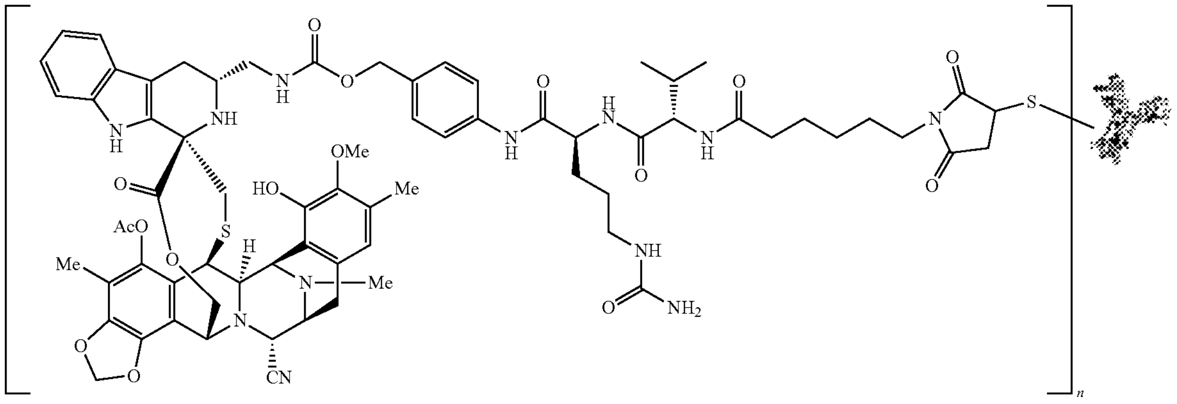
,
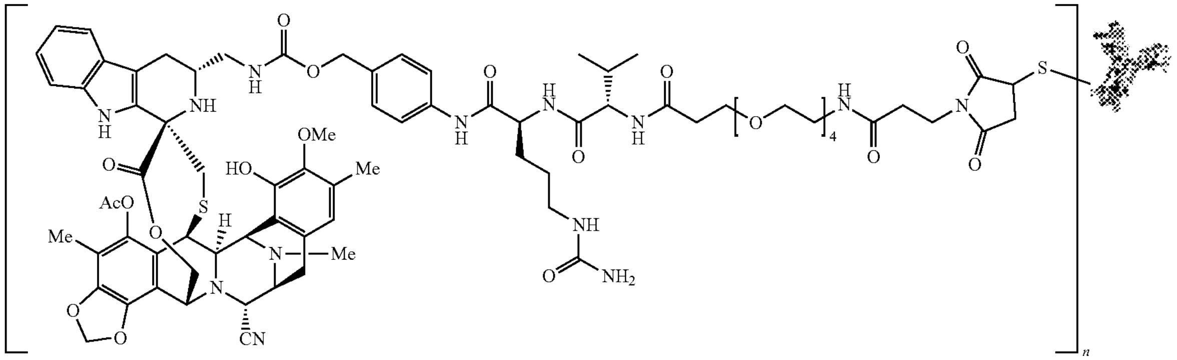
,
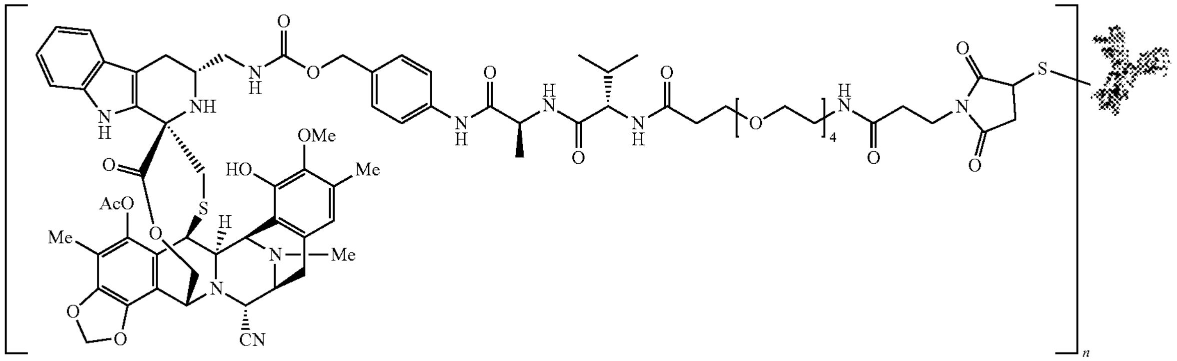
,
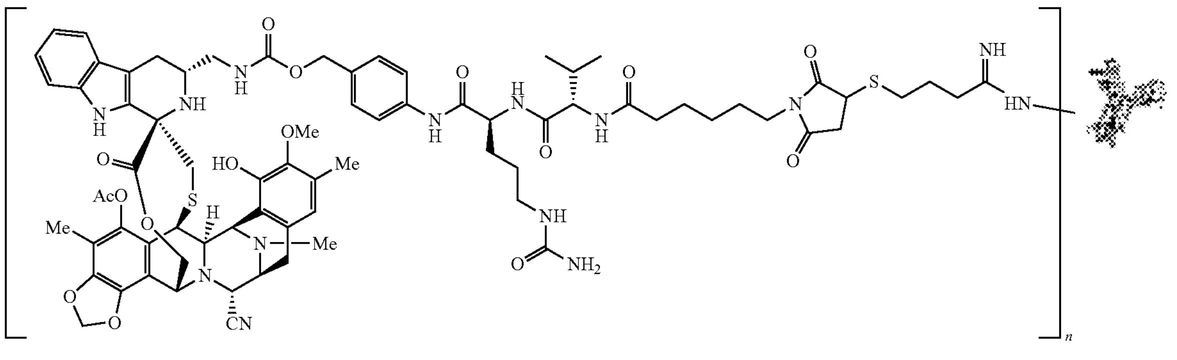
, -continued

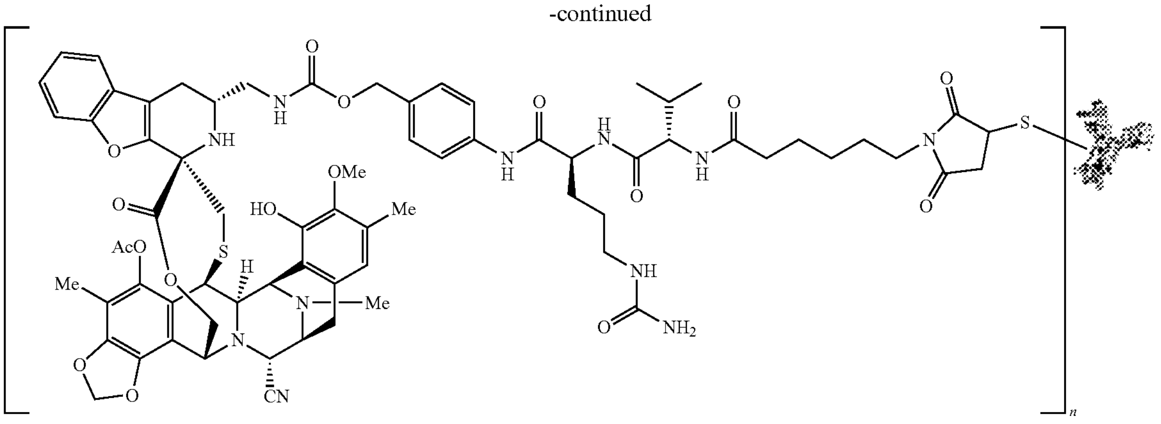

,

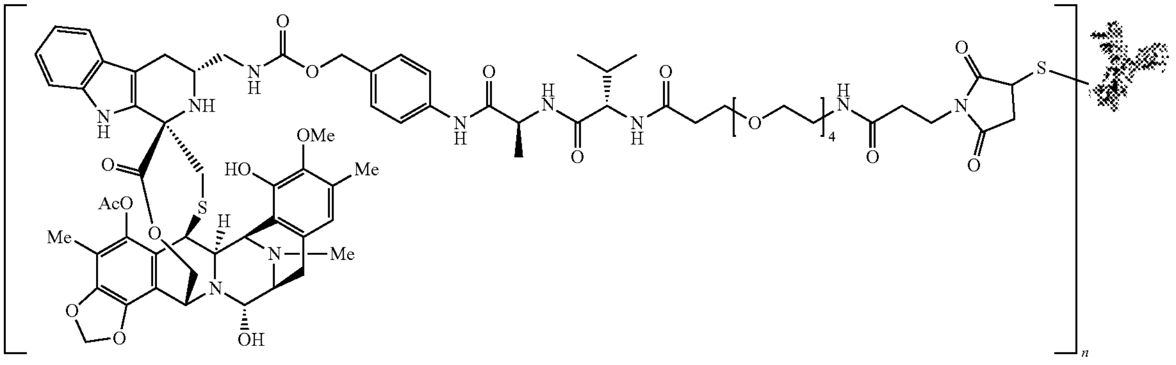

, wherein n is from 2 to 6, more preferably 3, 4, or 5 and each and is independently selected from Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologically active portion thereof, and more preferably its is selected from Trastuzumab and anti-CD13 antibody or an antigen-binding fragment or an immunologically active portion thereof, particularly Trastuzumab or an antigen-binding fragment or an immunologically active portion thereof.

In an embodiment, antibody drug conjugates according to the present invention excludes:

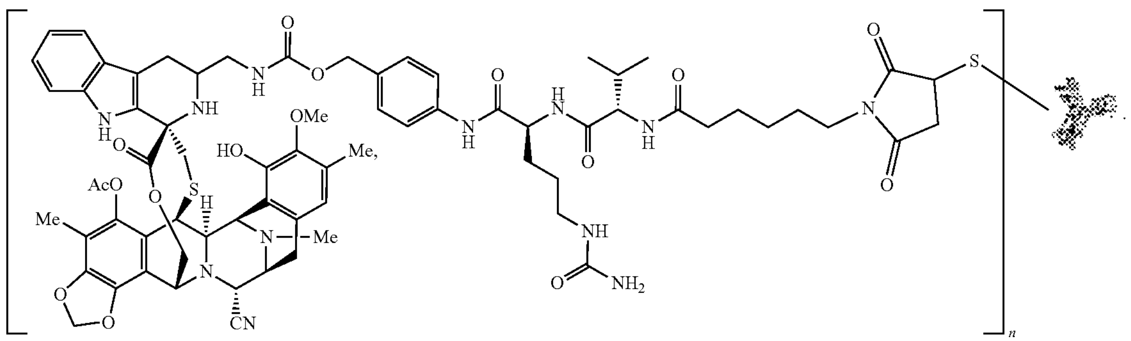

More preferably the antibody drug conjugate is selected from the group consisting of:

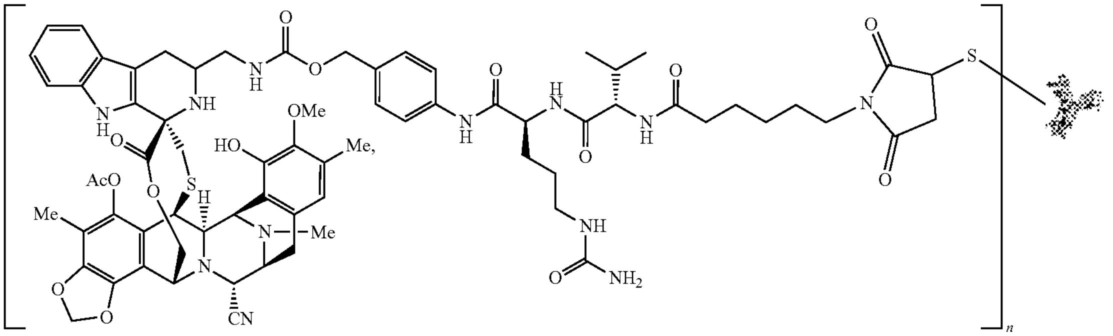

wherein n is from 2 to 6, more preferably 3, 4, or 5 and is selected from Trastuzumab and an anti-CD13 antibody or an antigen-binding fragment or an immunologically active portion thereof, more preferably is Trastuzumab or an antigen binding fragment or an immunologically active portion thereof,

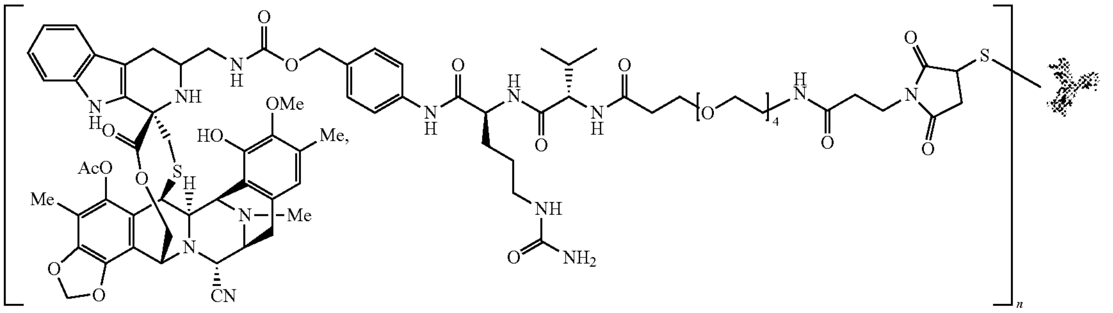

wherein n is from 2 to 6, more preferably 3, 4, or 5 and is Trastuzumab or an antigen-binding fragment or an immunologically active portion thereof,

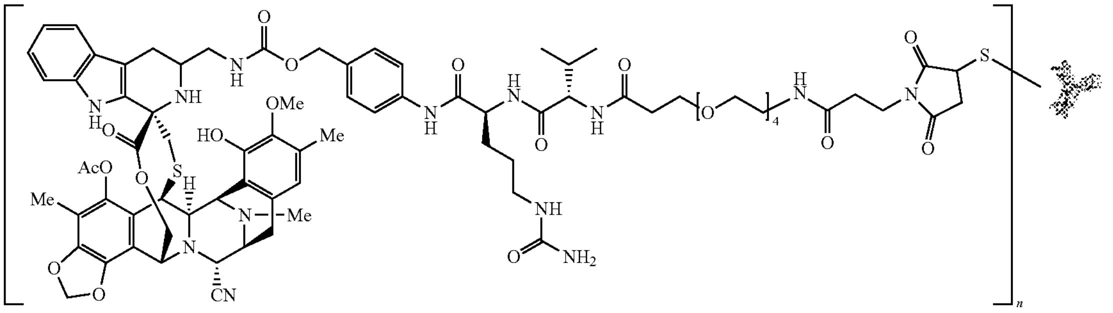

wherein n is from 2 to 6, more preferably 3, 4, or 5 and is selected from Trastuzumab and an anti-CD13 antibody or an antigen-binding fragment or an immunologically active portion thereof, more preferably is Trastuzumab or an antigen-binding fragment or an immunologically active portion thereof,

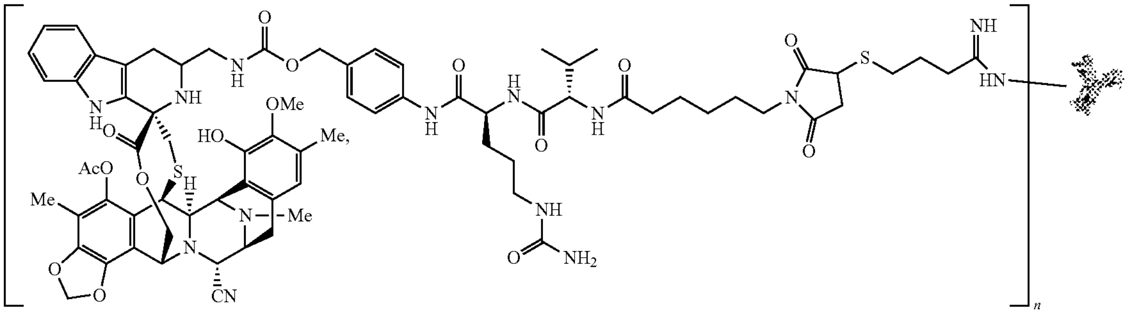

wherein n is from 2 to 6, more preferably 3, 4, or 5 and is Trastuzumab or an antigen-binding fragment or an immunologically active portion thereof,

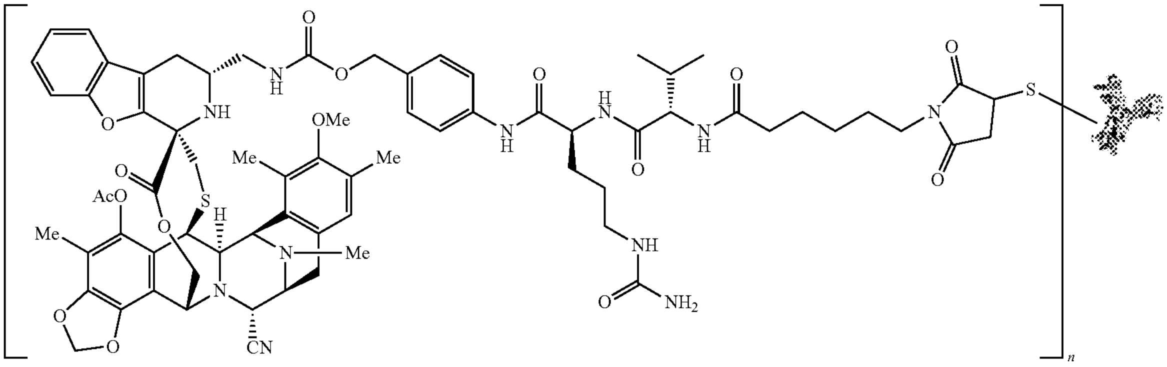

wherein n is from 2 to 6, more preferably 3, 4, or 5 and is Trastuzumab or an antigen-binding fragment or an immunologically active portion thereof, and

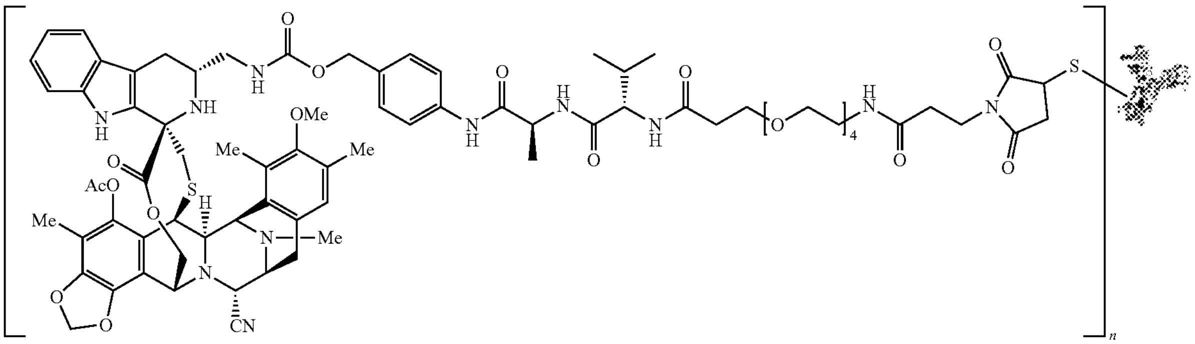

wherein n is from 2 to 6, more preferably 3, 4, or 5 and is selected from Trastuzumab and an anti-CD13 antibody or an antigen-binding fragment or an immunologically active portion thereof, more preferably is Trastuzumab or an antigen-binding fragment or an immunologically active portion thereof.

h) an antibody drug conjugate according to the present invention, selected from the group consisting of:

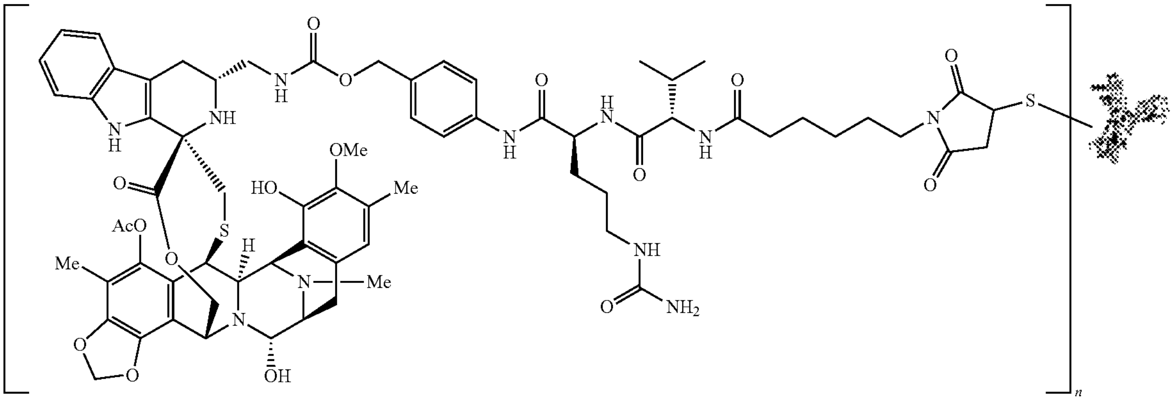

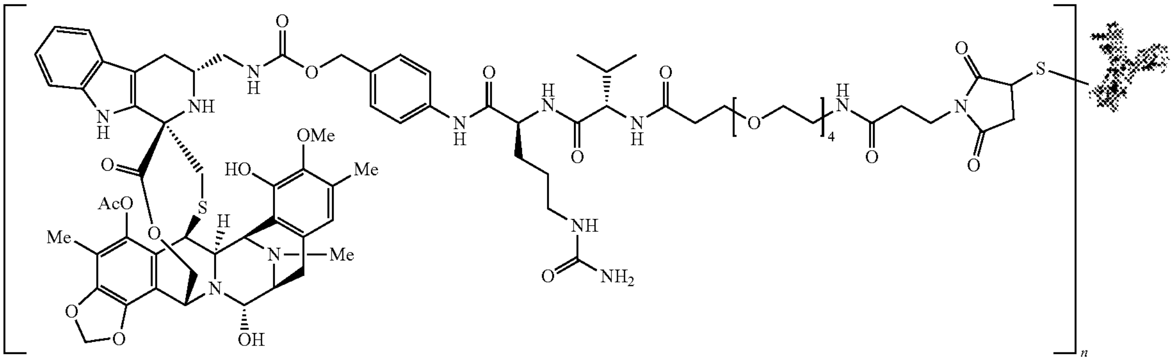

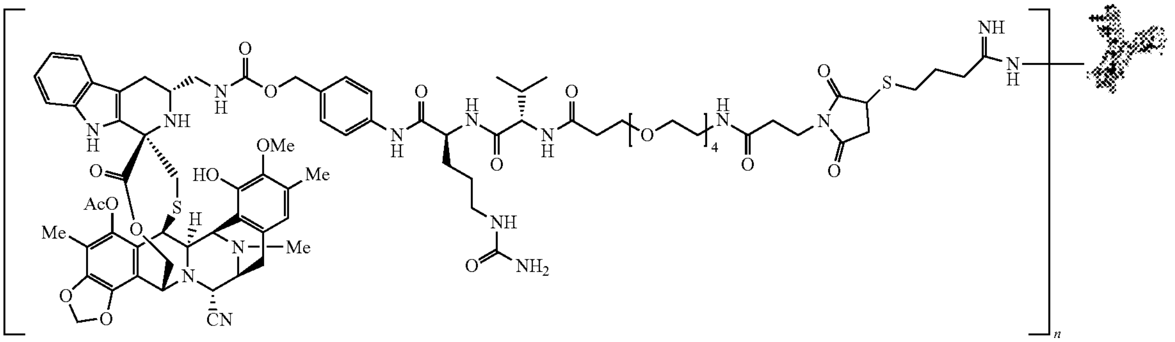

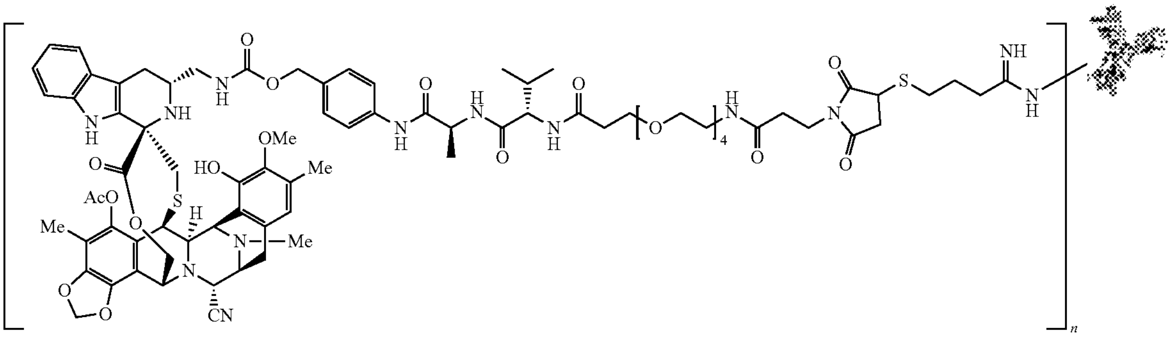

-continued
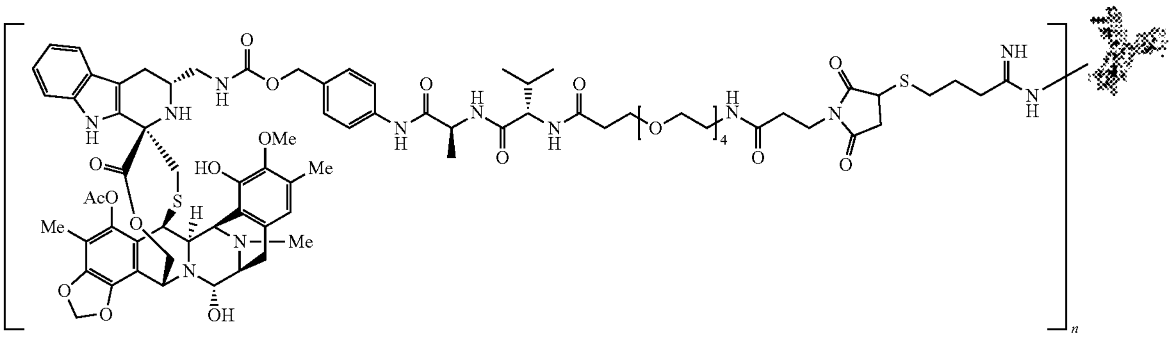
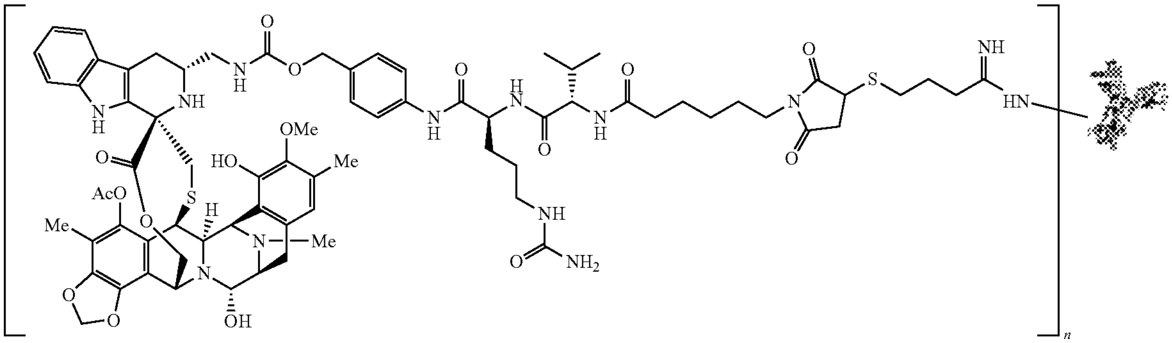
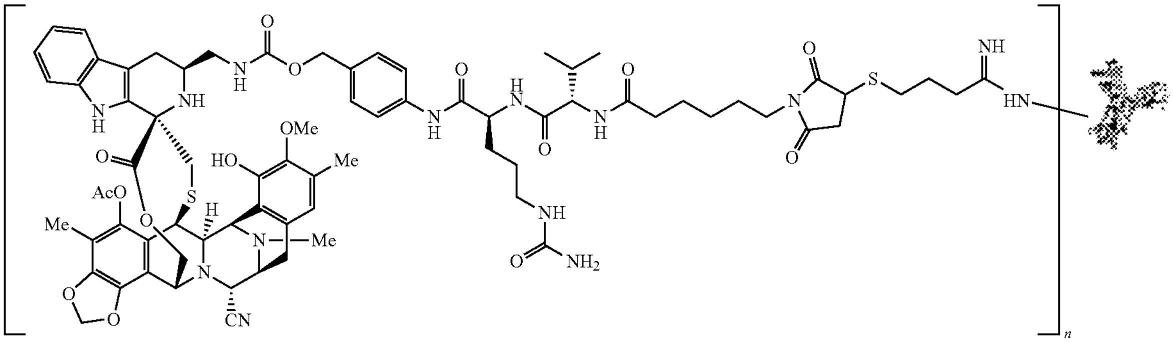
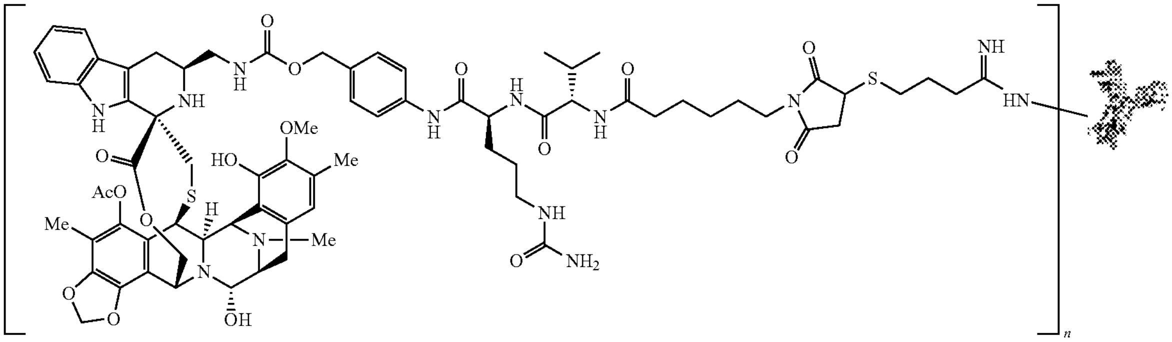
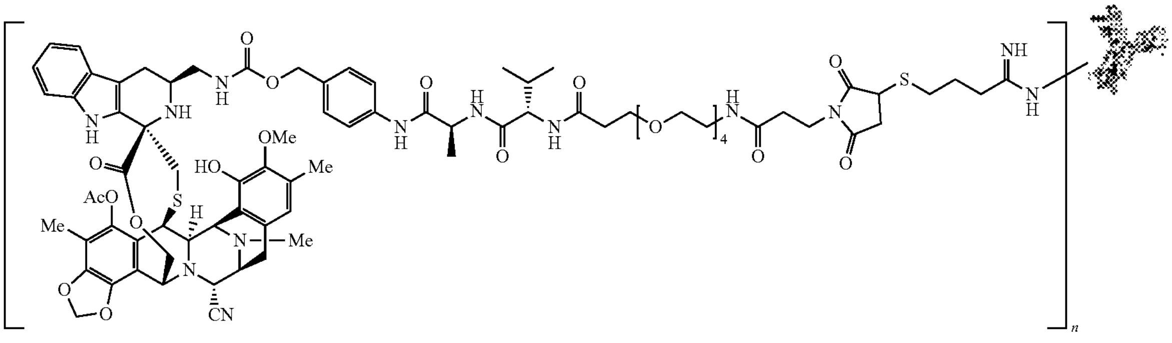

-continued

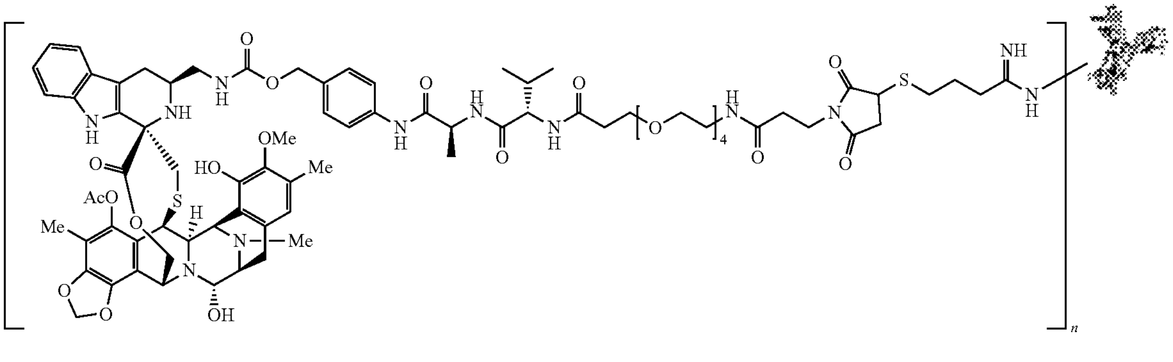

wherein n is from 2 to 6, more preferably 3, 4, or 5 and each and is independently selected from Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologically active portion thereof, and more preferably its is selected from Trastuzumab and anti-CD13 antibody or an antigen-binding fragment or an immunologically active portion thereof, particularly Trastuzumab or an antigen-binding fragment or an immunologically active portion thereof; or

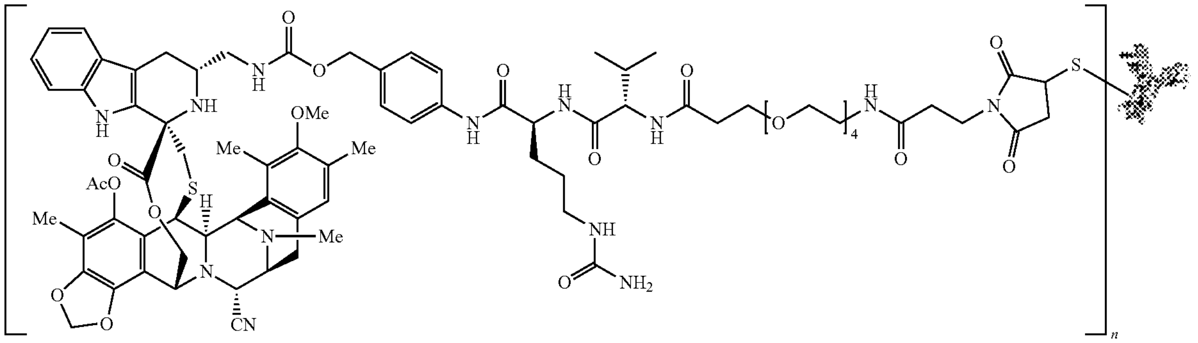

wherein n is from 2 to 6, more preferably 3, 4, or 5 and is an anti-CD13 antibody or an antigen-binding fragment or an immunologically active portion thereof. More preferably the antibody drug conjugate is selected from the group consisting of:

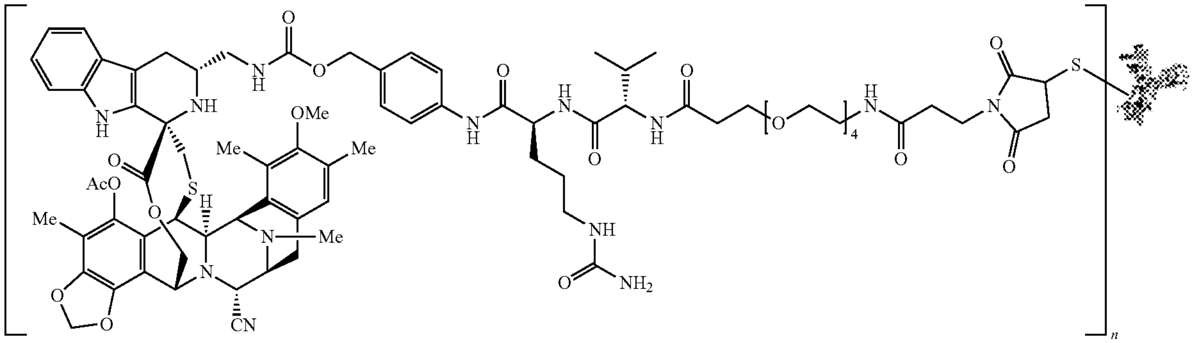

wherein n is from 2 to 6, more preferably 3, 4, or 5 and ⅄ is an anti-CD13 antibody or an antigen-binding fragment or an immunologically active portion thereof.

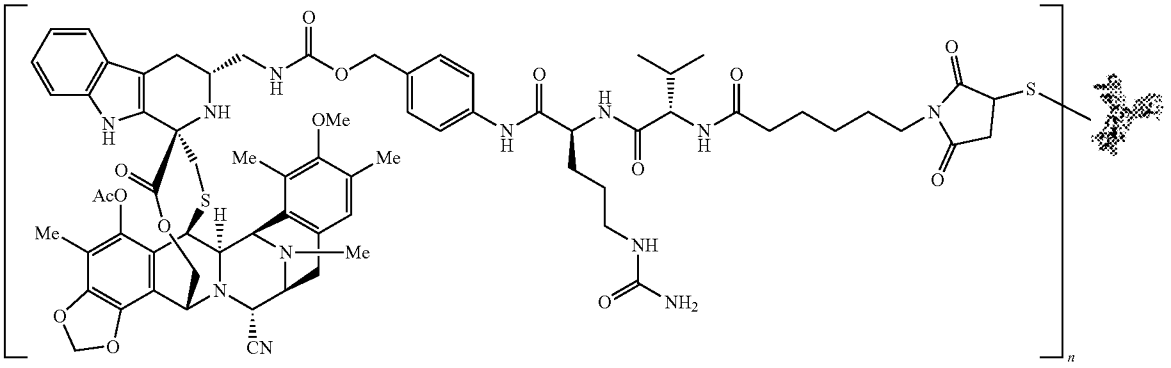

wherein n is from 2 to 6, more preferably 3, 4, or 5 and ⅄ is Trastuzumab or an antigen-binding fragment or an immunologically active portion thereof,

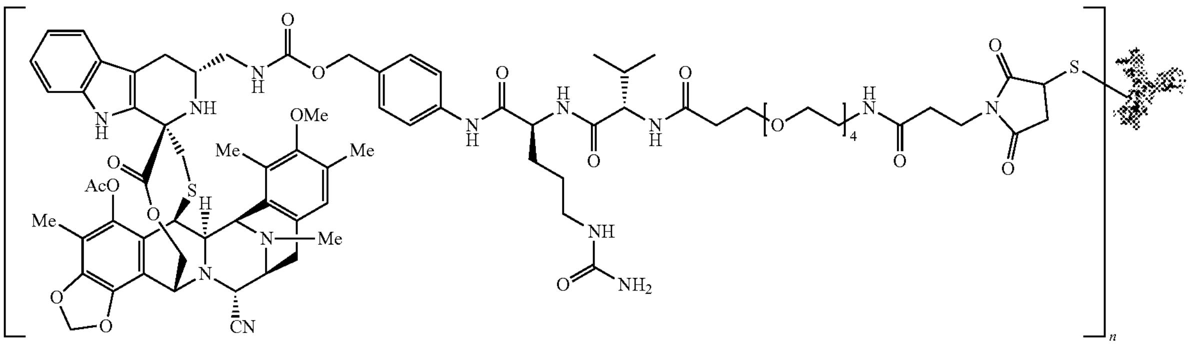

wherein n is form 2 to 6, more preferably 3, 4, or 5 and and ⅄ is Trastuzumab or an antigen-binding fragment or an immunologically active portion thereof,

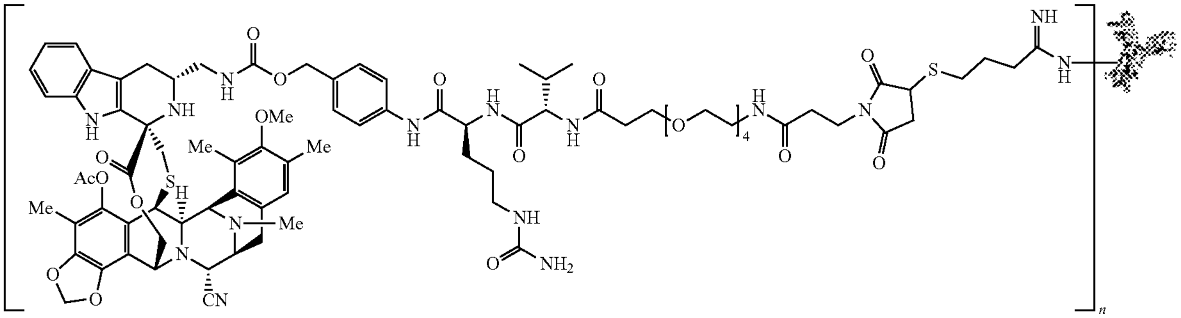

wherein n is form 2 to 6, more preferably 3, 4, or 5 and and is Trastuzumab or an antigen-binding fragment or an immunologically active portion thereof,

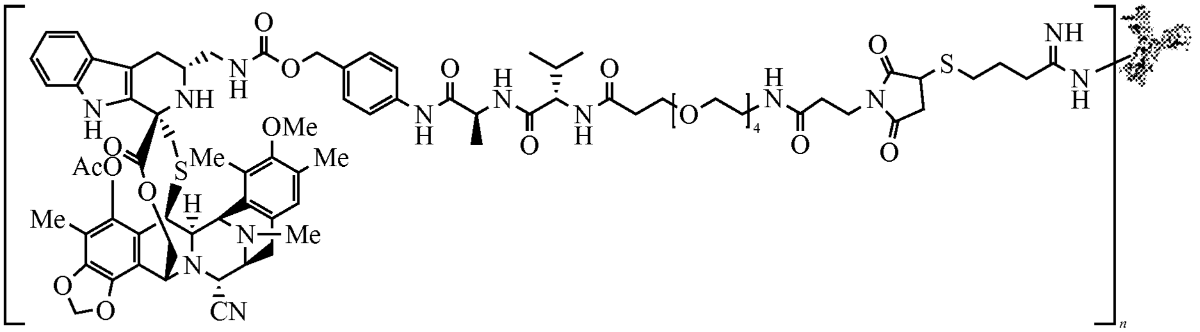

wherein n is form 2 to 6, more preferably 3, 4, or 5 and and is Trastuzumab or an antigen-binding fragment or an immunologically active portion thereof,

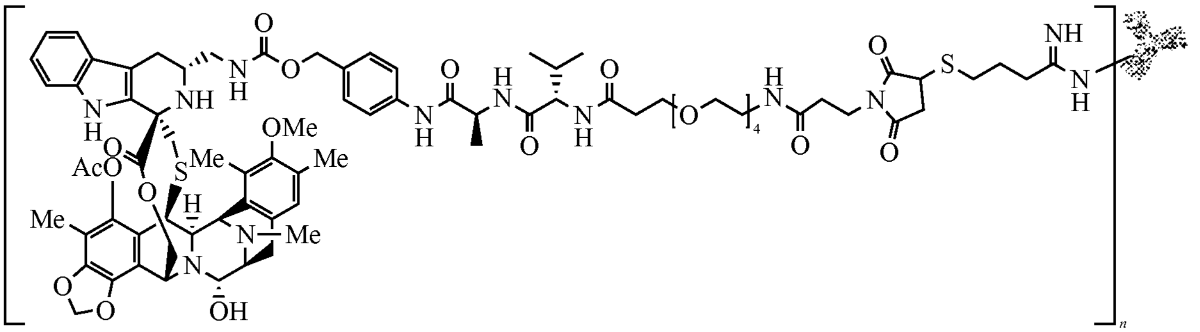

wherein n is form 2 to 6, more preferably 3, 4, or 5 and and is Trastuzumab or an antigen-binding fragment or an immunologically active portion thereof,

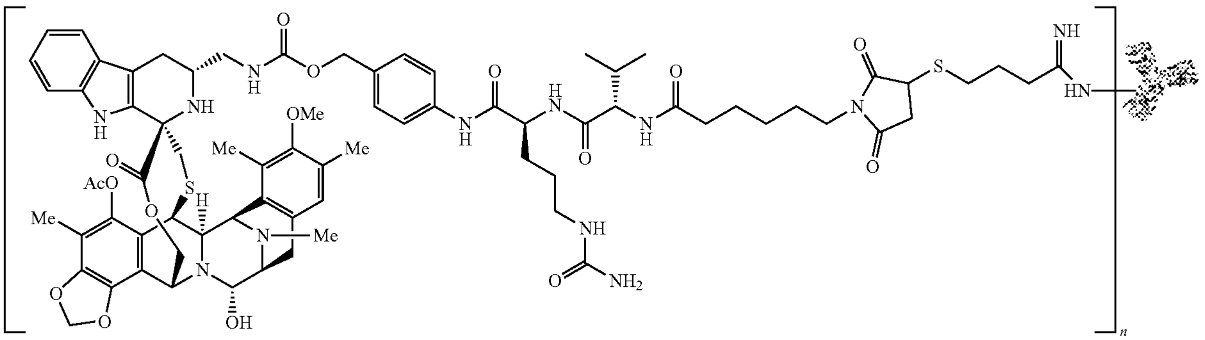

wherein n is form 2 to 6, more preferably 3, 4, or 5 and and is Trastuzumab or an antigen-binding fragment or an immunologically active portion thereof,

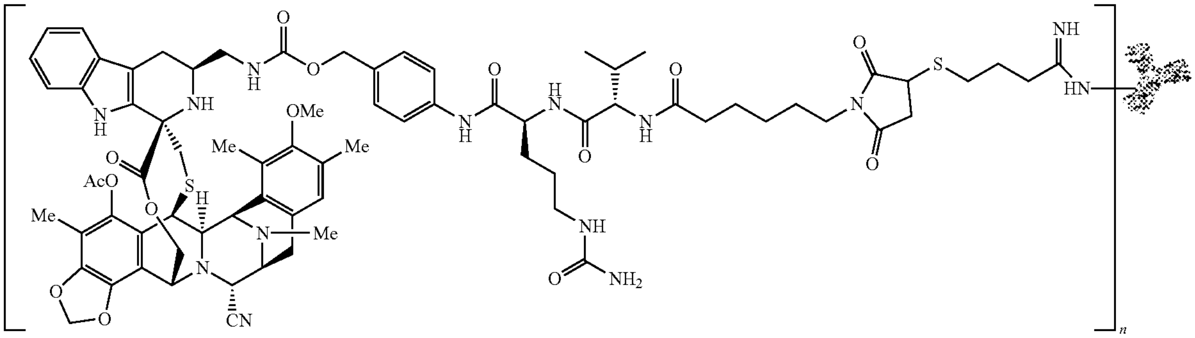

wherein n is form 2 to 6, more preferably 3, 4, or 5 and and is Trastuzumab or an antigen-binding fragment or an immunologically active portion thereof,

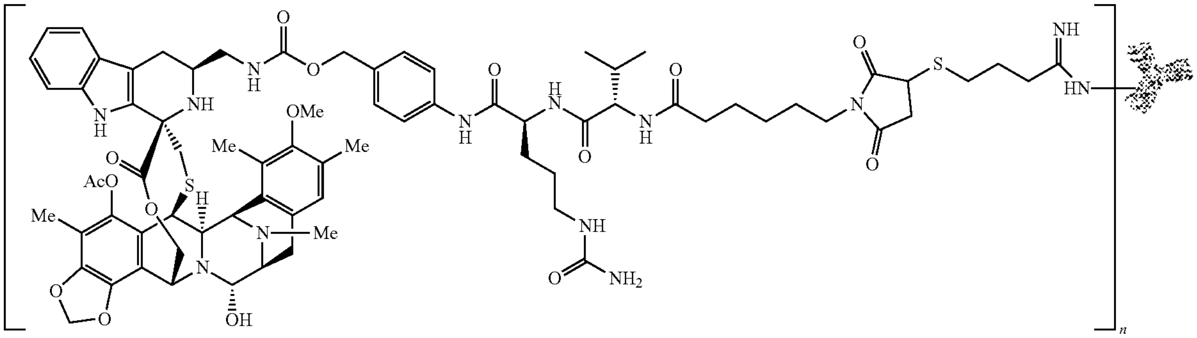

wherein n is form 2 to 6, more preferably 3, 4, or 5 and and is Trastuzumab or an antigen-binding fragment or an immunologically active portion thereof,

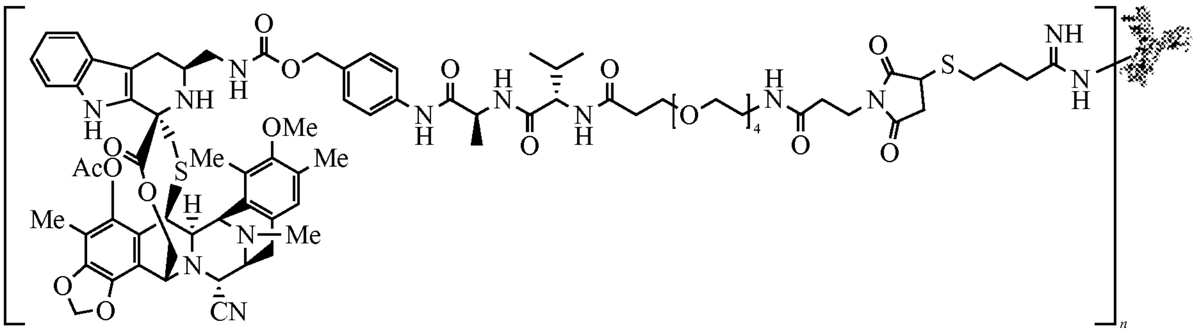

wherein n is form 2 to 6, more preferably 3, 4, or 5 and and  is Trastuzumab or an antigen-binding fragment or an immunologically active portion thereof, clo)- wherein said heterocyclo group may be a saturated or unsaturated group having one or more rings and comprising at least one oxygen, nitrogen or sulphur

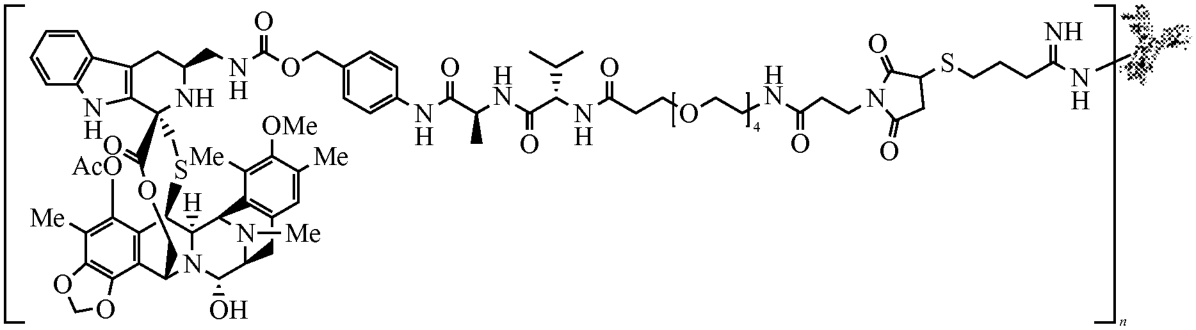

wherein n is form 2 to 6, more preferably 3, 4, or 5 and and 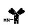 is Trastuzumab or an antigen-binding fragment or an immunologically active portion thereof, Particularly preferably, the antibody drug conjugates according to the present invention should be in isolated or purified form.

Preferred compounds of formula $D-(X)_b-(AA)_w-(T)_g-L_1$ or of formula $D-(X)_b-(AA)_w-(T)_g-H$ according to the present invention include:

a compound of formula $D-(X)_b-(AA)_w-(T)_g-L_1$ or of formula $D-(X)_b-(AA)_w-(T)_g-H$ wherein each of D, X, AA, T, Li, b, g and w are as defined herein in the present invention; but further wherein if the compound is a compound of formula $D-(X)_b-(AA)_w-(T)_g-H$ then $b+w+g\neq 0$.

a compound of formula $D-(X)_b-(AA)_w-(T)_g-L_1$ or of formula $D-(X)_b-(AA)_w-(T)_g-H$ according to the present invention wherein:

$L_1$ is a linker of formula:

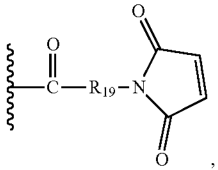

, wherein:

the wavy line indicates the point of covalent attachment to $(T)_g$ if any, or $(AA)_w$ if any, or to $(X)_b$ if any, or to D;

$R_{19}$ is selected from —$C_1$-$C_{12}$ alkylene-, —O—($C_1$-$C_{12}$ alkylene), —$C_6$-$C_{12}$ arylene in one or more rings which may optionally be substituted with one or more substituents $R_x$, —$C_1$-$C_{12}$ alkylene-$C_6$-$C_{12}$ arylene- wherein the arylene group is in one or more rings which may optionally be substituted with one or more substituents $R_x$, —$C_6$-$C_{12}$ arylene-$C_1$-$C_{12}$ alkylene- wherein the arylene group is in one or more rings which may optionally be substituted with one or more substituents $R_x$, —$C_5$-$C_{12}$ heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, —$C_1$-$C_{12}$ alkylene-($C_5$-$C_{12}$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, —($C_5$-$C_{12}$ heterocyclo)-$C_1$-$C_{12}$ alkylene- wherein said heterocyclo group may be a saturated or unsaturated group having one or more rings and comprising at least one oxygen, nitrogen or sulphur atom in said ring(s), said group optionally being substituted with one or more substituents $R_x$, —$(OCH_2CH_2)_r$ and —$CH_2$—$(OCH_2CH_2)_r$, wherein each of the above alkylene substituents whether alone or attached to another moiety the carbon chain may optionally be substituted by one or more substituents $R_x$;

r is an integer ranging from 1-6; and each of D, $R_x$, X, AA, T, b, g and w is as defined in the present invention; but wherein if the compound is a compound of formula $D-(X)_b-(AA)_w-(T)_g-H$ then $b+w+g\neq 0$.

a compound of formula $D-(X)_b-(AA)_w-(T)_g-L_1$ or of formula $D-(X)_b-(AA)_w-(T)_g-H$ according to the present invention wherein:

$L_1$ is linker of formula:

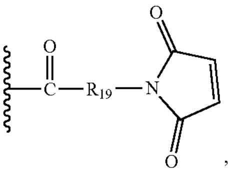

, wherein:

the wavy line indicates the point of covalent attachment to $(T)_g$ if any, or $(AA)_w$ if any, or to $(X)_b$ if any, or to D;

$R_{19}$ is selected from —$C_1$-$C_8$ alkylene-, —O—($C_1$-$C_8$ alkylene), —$C_1$-$C_8$ alkylene-$C_6$-$C_{12}$ arylene- wherein the arylene group is in one or more rings which may optionally be substituted with one or more substituents $R_x$, and —$C_6$-$C_{12}$ arylene-$C_1$-$C_8$ alkylene- wherein the arylene group is in one or more rings which may optionally be substituted with one or more substituents $R_x$, wherein each of the above alkylene substituents whether alone or attached to another moiety the carbon chain may optionally be substituted by one or more substituents $R_x$;

$(AA)_w$ is of formula (II):

(II)

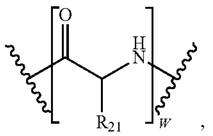

wherein the wavy lines indicate the point of covalent attachments to $(X)_b$, if any, or to D (the wavy line to the left) and to $(T)_g$ if any, or $L_1$ or to a hydrogen atom (the wavy line to the right);

wherein $R_{21}$ is selected, at each occurrence, from the group consisting of hydrogen, methyl, isopropyl, sec-butyl, benzyl, indolylmethyl, $-(CH_2)_3NHCONH_2$, $-(CH_2)_4NH_2$, $(CH_2)_3NHC(=NH)NH_2$ and $-(CH_2)_4NHC-(=NH)NH_2$, and w is an integer from 0 to 6;

X is an extending group selected from the group consisting of where D is conjugated via an amine group (for example where Z is —NH—): —COO—($C_2$-$C_4$ alkylene)NH—, —COO—$CH_2$-phenylene-NH, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —COO—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —$COCH_2NH$—$COCH_2$—NH—, —COO—($C_2$-$C_4$ alkylene)S—, and —COO—($C_2$-$C_4$ alkylene)-NHCO($C_1$-$C_3$ alkylene)S— or where D is conjugated via an hydroxy group (for example where Z is —O—): —CONH—($C_2$-$C_4$ alkylene)NH—, —COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups, —CONH—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—, —$COCH_2NH$—$COCH_2$—NH—, —CONH—($C_2$-$C_4$ alkylene)S—, and —CONH—($C_2$-$C_4$ alkylene)NHCO($C_1$-$C_3$ alkylene)S—;

T is an extending group selected from —CO—($C_1$-$C_4$ alkylene)-NH—; —CO—($C_1$-$C_4$ alkylene)-[O—($C_2$-$C_4$ alkylene)]$_j$-NH— and —COO—($C_1$-$C_4$ alkylene)-[O—($C_2$-$C_4$ alkylene)]$_j$-NH—, where j is an integer from 1 to 10;

b is 0 or 1;

g is 0 or 1;

wherein if the compound is a compound of formula D-$(X)_b$-$(AA)_w$-$(T)_g$-H then b+w+g≠0; and D is a drug moiety of formula I, IA, IB, IC, ID, IE, IF, IG, Ia, IAa, IBa, ICa, IDa, IEa, IFa, IGa, Ib, IAb, IBb, ICb, IDb, IEb, IFb, and IGb; and is covalently attached via a hydroxy or amine group; or is a drug moiety of formula (IHa) or a formula (IHb), or a pharmaceutically acceptable salt, ester, solvate, tautomer or stereoisomer thereof wherein:

(IHa)

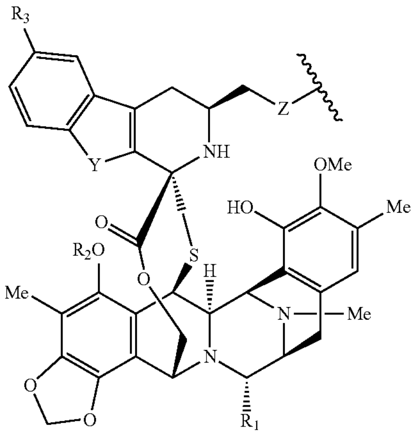

(IHb)

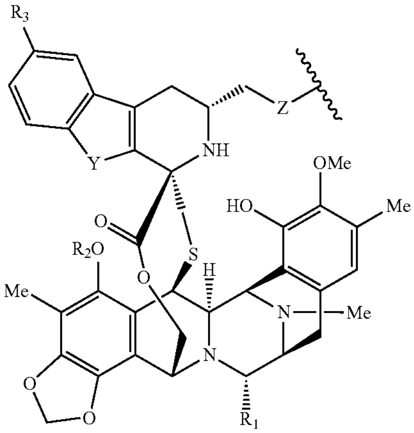

wherein the wavy lines of (IHa) and (IHb) indicate the point of covalent attachment to $(X)_b$ if any, or $(AA)_w$ if any, or to $(T)_g$ if any, or to Li;

$R_1$ is —OH or —CN;

$R_2$ is a —C(=O)$R_a$ group, wherein $R_a$ is selected from hydrogen and substituted or unsubstituted $C_1$-$C_6$ alkyl, wherein the optional substituents are one or more substituents $R_x$;

$R_3$ is hydrogen or a —$OR_b$ group wherein $R_b$ is a substituted or unsubstituted $C_1$-$C_6$ alkyl group, wherein the optional substituents are one or more substituents $R_x$.

Y is —NH— or —O—; and

Z is —NH— or —O—.

a compound of formula D-$(X)_b$-$(AA)_w$-$(T)_g$-$L_1$ or of formula D-$(X)_b$-$(AA)_w$-$(T)_g$-H according to the present invention wherein:

$L_1$ is a group of formula:

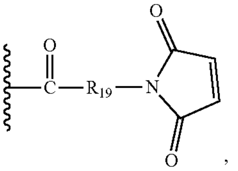
, wherein:

the wavy line indicates the point of covalent attachment to $(T)_g$ if any, or $(AA)_w$ if any, or to $(X)_b$ if any, or to D;

$R_{19}$ is selected from —$C_1$-$C_6$ alkylene-, phenylene-$C_1$-$C_6$ alkylene- wherein the phenylene group may optionally be substituted with one or more substituents $R_x$ selected from the group consisting of alkyl groups having from 1 to 6 carbon atoms, alkoxy groups having from 1 to 6 carbon atoms, halogen atoms, nitro groups and cyano groups, wherein each of the above alkylene substituents whether alone or attached to another moiety in the carbon chain may optionally be substituted by one or more substituents $R_x$ selected from the group consisting of alkyl groups having from 1 to 6 carbon atoms, alkoxy groups having from 1 to 6 carbon atoms, aryl groups having from 6 to 12 carbon atoms, halogen atoms, nitro groups and cyano groups, and preferably $R_{19}$ is a $C_1$-$C_6$ alkylene group;

w is 0 or 2, and where w is 2, then $(AA)_w$ is of formula (III):

(III)

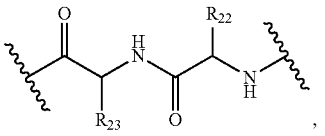

, wherein the wavy lines indicate the point of covalent attachments to X (the wavy line to the left) and to $(T)_g$ if any, or $L_1$ or to a hydrogen atom (the wavy line to the right);

$R_{22}$ is selected from methyl, benzyl, isopropyl, sec-butyl and indolylmethyl;

$R_{23}$ is selected from methyl, —$(CH_2)_4NH_2$, —$(CH_2)_3NHCONH_2$ and —$(CH_2)_3NHC(=NH)NH_2$;

X is an extending group selected from where D is conjugated via an amine group (for example where Z is —NH—): —COO—$CH_2$-phenylene-NH—, —$COO(CH_2)_3NHCOO$—$CH_2$-phenylene-NH, —COO—$(CH_2)_3)NH$—, —$COO(CH_2)_3$—S—, and —COO—$(CH_2)_3NHCO$—$(CH_2)_2S$—, or where D is conjugated via an hydroxy group (for example where Z is —O—): —COO—$CH_2$-phenylene-NH—, —$CONH(CH_2)_3NHCOOCH_2$-phenylene-NH—, —$CONH(CH_2)_3NH$—, —$CONH(CH_2)_3$—S—, and —$CONH(CH_2)_3NHCO(CH_2)_2S$—.

wherein T is an extending group selected from —CO—($C_1$-$C_4$ alkylene)-NH—, —CO—($C_1$-$C_4$ alkylene)-[O—($C_2$-$C_4$ alkylene)$]_j$-NH—, and —COO—($C_1$-$C_4$ alkylene)-[O—($C_2$-$C_4$ alkylene)$]_j$-NH—, where j is an integer from 1 to 5;

b is 0 or 1;

g is 0 or 1;

wherein if the compound is a compound of formula D-$(X)_b$-$(AA)_w$-$(T)_g$-H then b+w+g≠0; and D is a drug moiety of formula I, IA, IB, IC, ID, IE, IF, IG, Ia, IAa, IBa, ICa, IDa, IEa, IFa, IGa, Ib, IAb, IBb, ICb, IDb, IEb, IFb, and IGb; and is covalently attached via a hydroxy or amine group; or is a drug moiety of formula (IHa) or a formula (IHb), or a pharmaceutically acceptable salt, ester, solvate, tautomer or stereoisomer thereof:

(IHa)

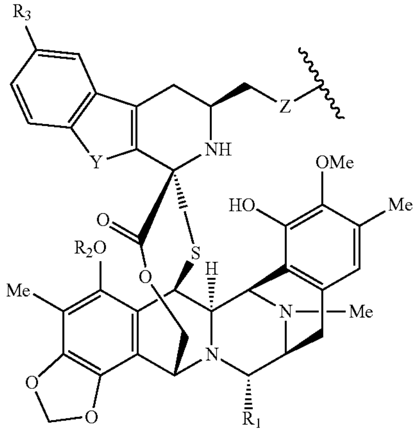

(IHb)

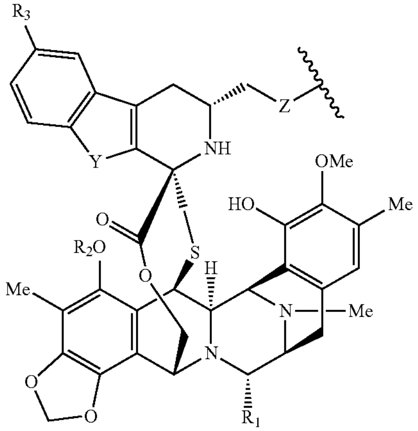

wherein the wavy lines of (IHa) and (IHb) indicate the point of covalent attachment;

$R_1$ is —CN or —OH;

$R_2$ is acetyl;

$R_3$ is hydrogen or methoxy, preferably hydrogen;

Y is —NH— or —O—. and

Z is —NH— or —O—.

a compound of formula D-$(X)_b$-$(AA)_w$-$(T)_g$-$L_1$ or of formula D-$(X)_b$-$(AA)_w$-$(T)_g$-H according to the present invention wherein:

$L_1$ is a linker of formula:

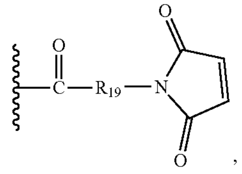

, wherein:

the wavy line indicates the point of covalent attachment to $(T)_g$ if any, or $(AA)_w$ if any, or to $(X)_b$ if any, or to D;

$R_{19}$ is —$C_2$-$C_6$ alkylene-;

w is 0 or 2, and where w is 2, then $(AA)_w$ is of formula (III):

(III)

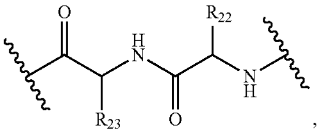

, $R_{22}$ is isopropyl, $R_{23}$ is selected from methyl and $—(CH_2)_3NHCONH_2$, wherein the wavy lines indicate the point of covalent attachments to X (the wavy line to the left) and to $(T)_g$ if any, or $L_1$ or to a hydrogen atom (the wavy line to the right);

X is an extending group selected from $—COO—CH_2$-phenylene-NH—, $—COO(CH_2)_3NHCOO—CH_2$-phenylene-NH, $—COO—(CH_2)_3)NH—$, $—COO(CH_2)_3—S—$, and $—COO—(CH_2)_3NHCO—(CH_2)_2—$;

wherein T is an extending group selected from —CO—($C_1$-$C_4$ alkylene)-NH—, —CO—($C_1$-$C_4$ alkylene)-[O—($C_2$-$C_4$ alkylene)$]_j$-NH—, and —COO—($C_1$-$C_4$ alkylene)-[O—($C_2$-$C_4$ alkylene)$]_j$-NH—, where j is an integer from 1 to 5;

b is 0 or 1;

g is 0 or 1;

wherein if the compound is a compound of formula D-$(X)_b$-$(AA)_w$-$(T)_g$-H then b+w+g≠0; and D is a drug moiety selected from:

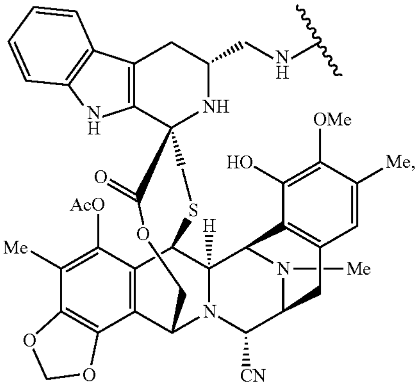

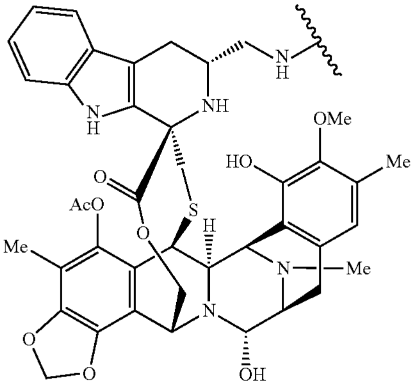

and

-continued

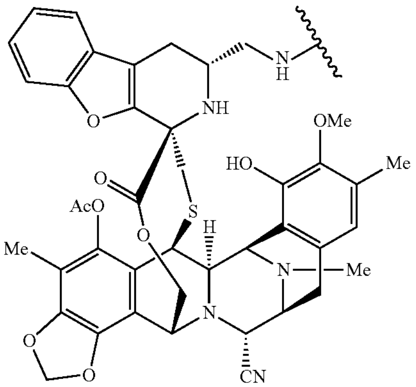

or a pharmaceutically acceptable salt, ester, solvate, tautomer or stereoisomer thereof; wherein the wavy line indicates the point of covalent attachment.

a compound of formula D-$(X)_b$-$(AA)_w$-$(T)_g$-$L_1$ or of formula D-$(X)_b$-$(AA)_w$-$(T)_g$-H according to the present invention wherein:

$L_1$ is a group of formula:

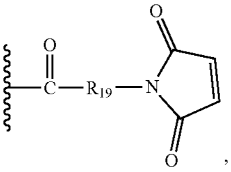

, wherein:

the wavy line indicates the point of covalent attachment to $(T)_g$ if any, or $(AA)_w$ if any, or to $(X)_b$, if any or to D;

$R_{19}$ is a —$C_2$-$C_5$ alkylene-;

w is 0 or 2, and where w is 2, then $(AA)_w$ is of formula (III):

(III)

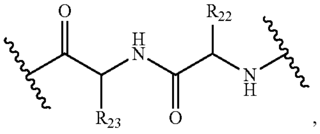

, wherein $R_{22}$ is isopropyl, $R_{23}$ is selected from methyl and $—(CH_2)_3NHCONH_2$, wherein the wavy lines indicate the point of covalent attachments to X (the wavy line to the left) and to $(T)_g$ if any, or $L_1$ or to a hydrogen atom (the wavy line to the right);

X is a $—COO—CH_2$-phenylene-NH— group;

T is a $—CO—(CH_2)_2—[O—(CH_2)_2]_4—NH—$ group;

b is 0 or 1;

g is 0 or 1;

wherein if the compound is a compound of formula D-$(X)_b$-$(AA)_w$-$(T)_g$-H then b+w+g≠0; and D is a drug moiety selected from:
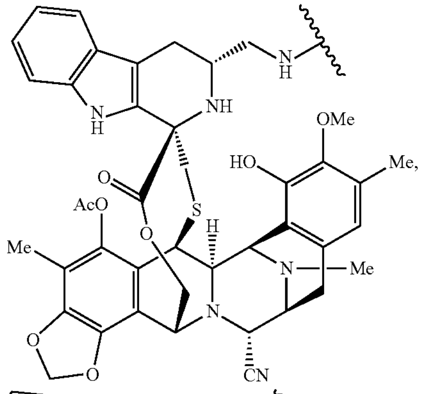
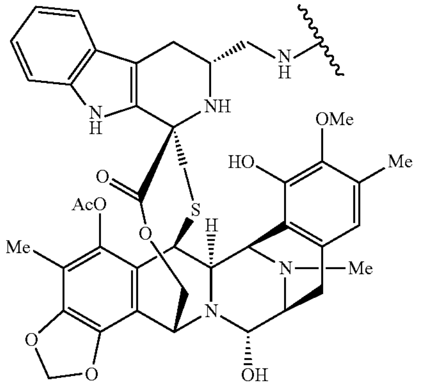
and
-continued
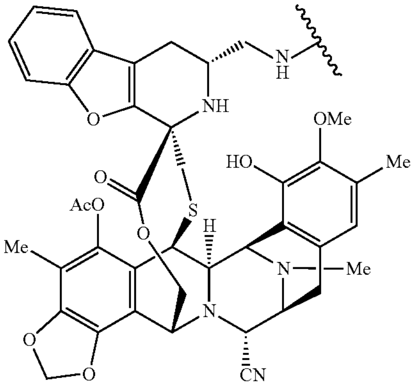
or a pharmaceutically acceptable salt, ester, solvate, tautomer or stereoisomer thereof; wherein the wavy line indicates the point of covalent attachment.
a compound of formula D-X-$(AA)_w$-$(T)_g$-$L_1$ selected from:
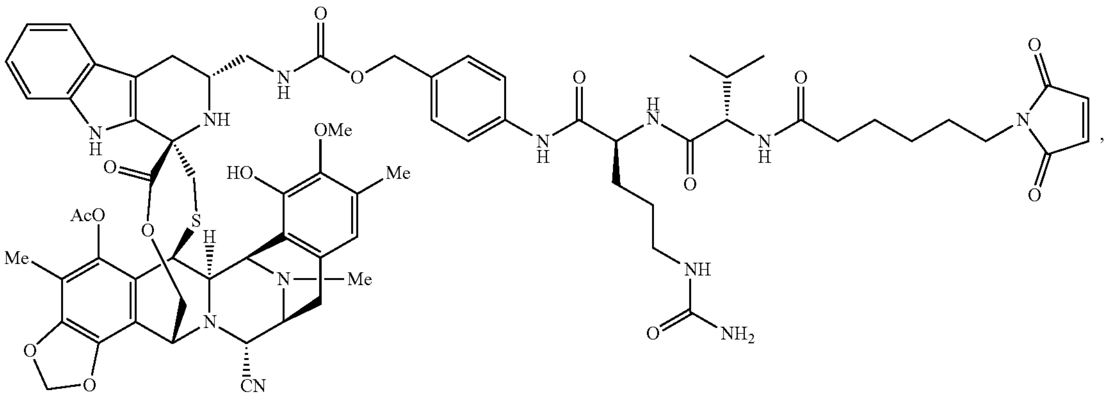
,
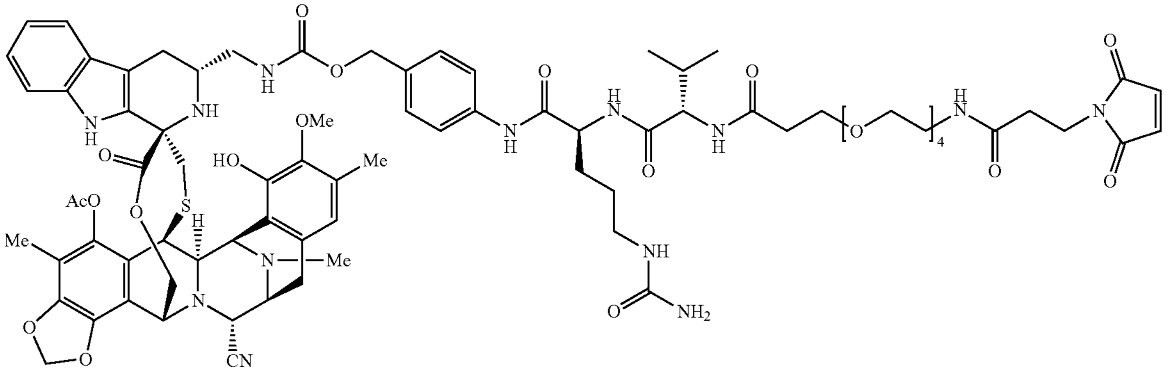
, -continued
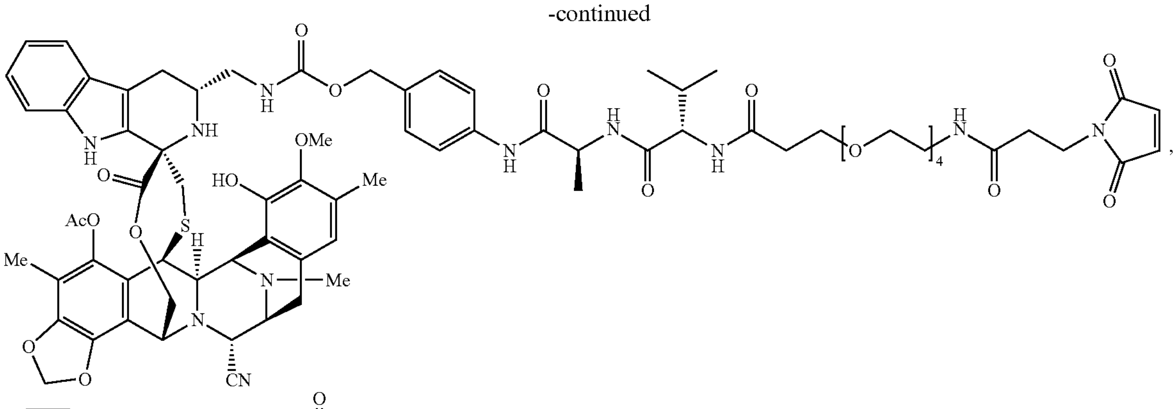
,
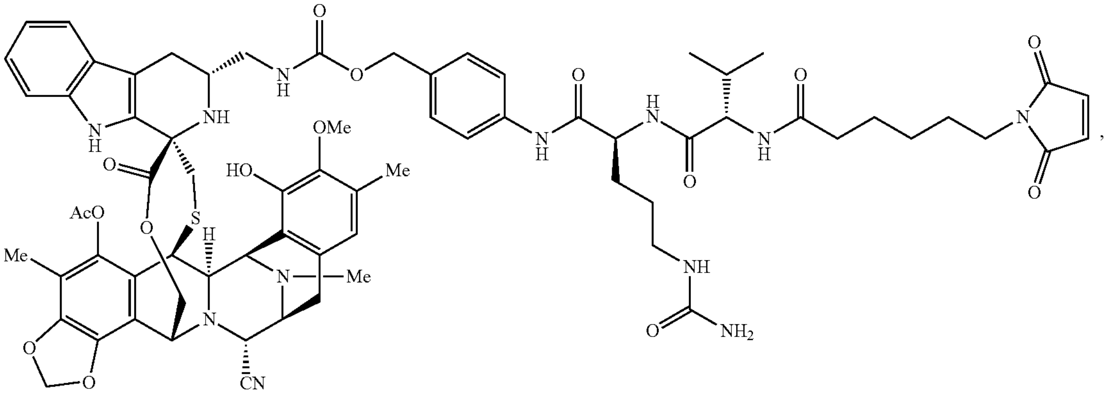
, and
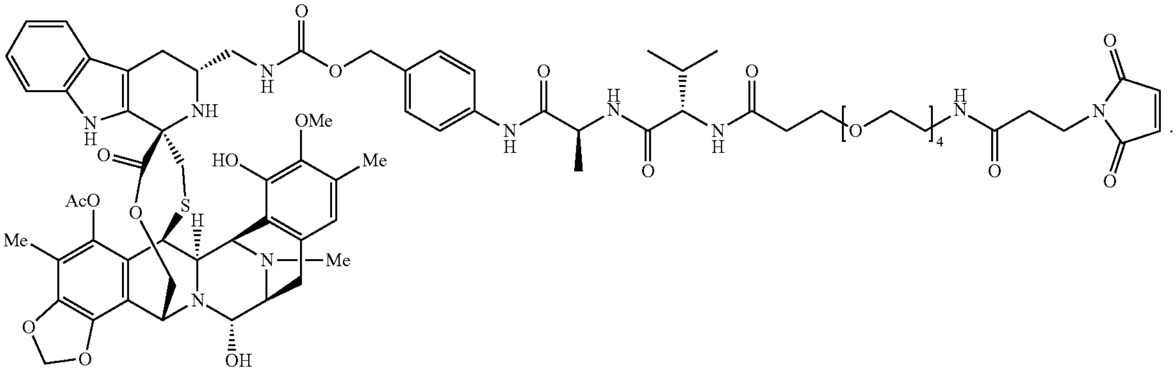
.
a compound of formula D-X-$(AA)_w$-$(T)_g$-$L_1$ selected from:
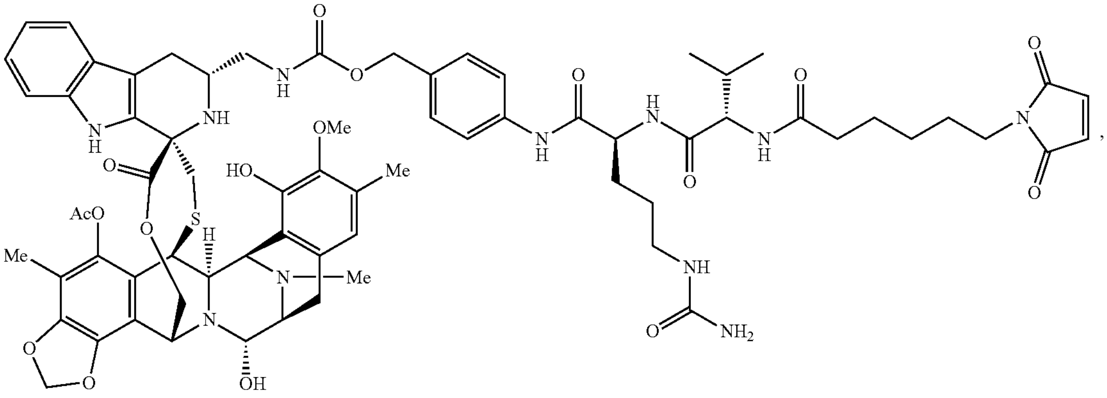
, -continued
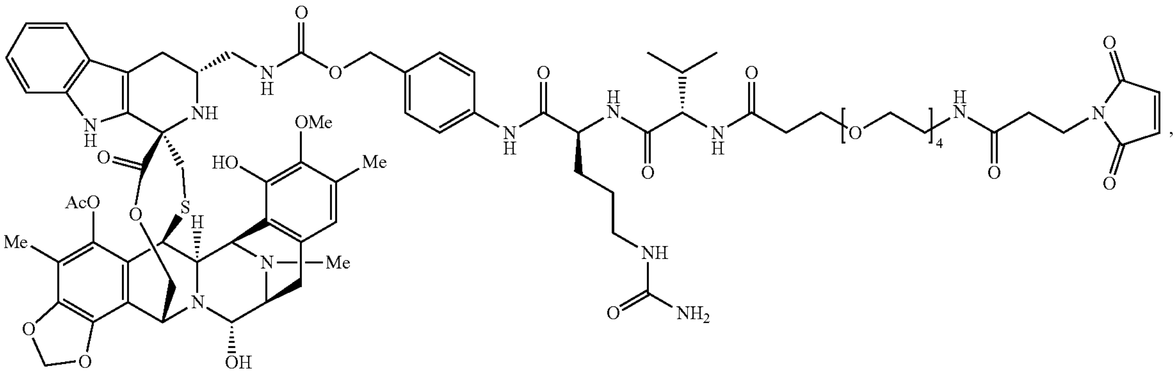
,
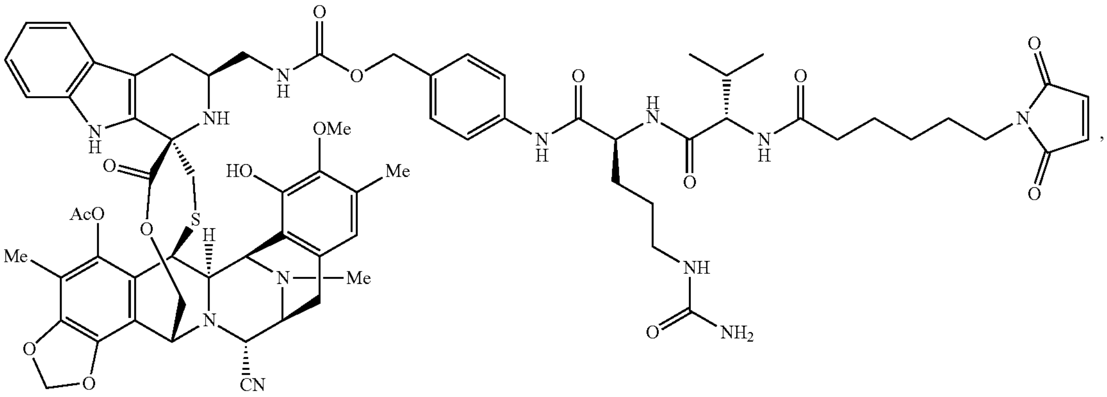
,
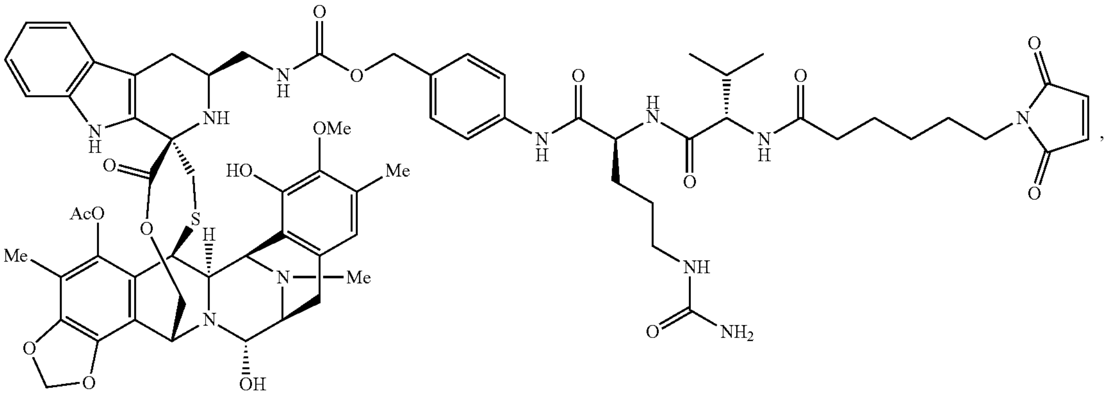
,
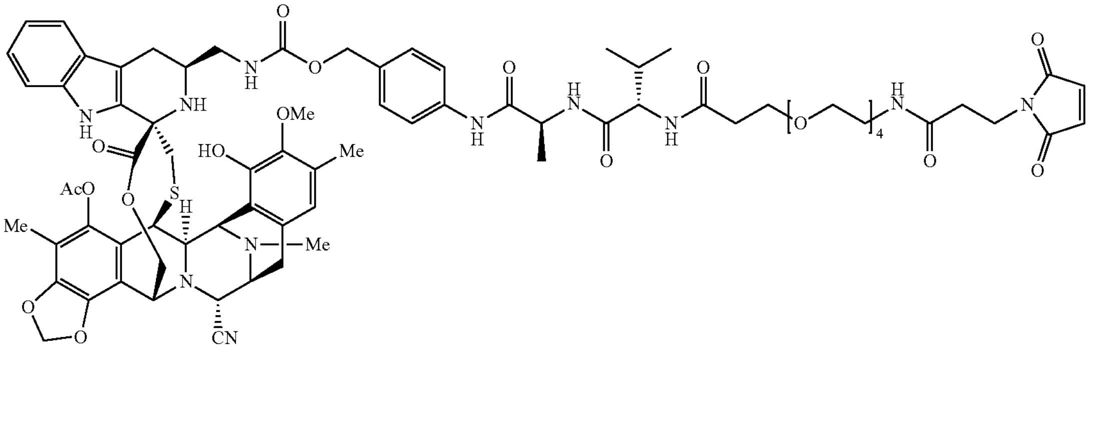
and -continued

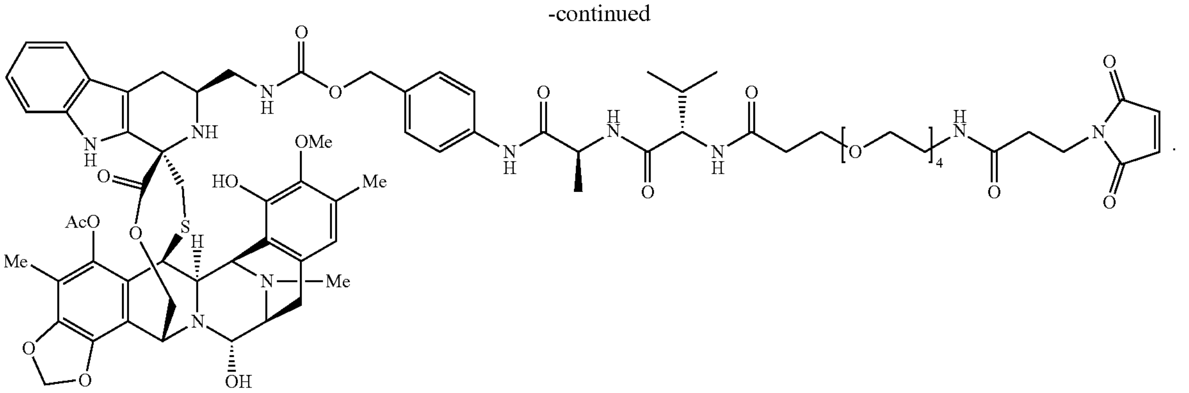

The term "pharmaceutically acceptable salts, esters, solvates, tautomers or stereoisomers" in the drug conjugates of the present invention refers to any pharmaceutically acceptable salt, ester, solvate, hydrate or stereosiomeric form or any other compound which, upon administration to the patient is capable of providing a compound as described herein, whether directly or indirectly. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The drug conjugates of the present invention may be in crystalline form either as free compounds or as solvates (e.g. hydrates) and it is intended that both forms are within the scope of the present invention. Methods of solvation are generally known within the art.

Any compound that is a prodrug of the drug conjugate of the present invention is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative. Many suitable prodrugs are well-known to the person in the art and can be found, for example, in Burger "Medicinal Chemistry and Drug Discovery $6^{th}$ ed. (Donald J. Abraham ed., 2001, Wiley) and "Design and Applications of Prodrugs" (H. Bundgaard ed., 1985, Harwood Academic Publishers), the contents of which are incorporated herein by reference.

In relations to the compounds of the present invention, the pharmacologically acceptable esters are not particularly restricted, and can be selected by a person with an ordinary skill in the art. In the case of said esters, it is preferable that such esters can be cleaved by a biological process such as hydrolysis in vivo. The group constituting the said esters (the group shown as R when the esters thereof are expressed as —COOR) can be, for example, a $C_1$-$C_4$ alkoxy $C_1$-$C_4$ alkyl group such as methoxyethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, propoxymethyl, isopropoxymethyl, butoxymethyl or t-butoxymethyl; a $C_1$-$C_4$ alkoxylated $C_1$-$C_4$ alkoxy $C_1$-$C_4$ alkyl group such as 2-methoxyethoxymethyl; a $C_6$-$C_{10}$ aryloxy $C_1$-$C_4$ alkyl group such as phenoxymethyl; a halogenated $C_1$-$C_4$ alkoxy $C_1$-$C_4$ alkyl group such as 2,2,2-trichloroethoxymethyl or bis(2-chloroethoxy)methyl; a $C_1$-$C_4$ alkoxycarbonyl $C_1$-$C_4$ alkyl group such as methoxycarbonylmethyl; a cyano $C_1$-$C_4$ alkyl group such as cyanomethyl or 2-cyanoethyl; a $C_1$-$C_4$ alkylthiomethyl group such as methylthiomethyl or ethylthiomethyl; a $C_6$-$C_{10}$ arylthiomethyl group such as phenylthiomethyl or naphthylthiomethyl; a $C_1$-$C_4$ alkylsulfonyl $C_1$-$C_4$ lower alkyl group, which may be optionally substituted with a halogen atom(s) such as 2-methanesulfonylethyl or 2-trifluoromethanesulfonylethyl; a $C_6$-$C_{10}$ arylsulfonyl $C_1$-$C_4$ alkyl group such as 2-benzenesulfonylethyl or 2-toluenesulfonylethyl; a $C_1$-$C_7$ aliphatic acyloxy $C_1$-$C_4$ alkyl group such as formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl; a $C_5$-$C_6$ cycloalkylcarbonyloxy $C_1$-$C_4$ alkyl group such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl or 1-cyclohexylcarbonyloxybutyl; a $C_6$-$C_{10}$ arylcarbonyloxy $C_1$-$C_4$ alkyl group such as benzoyloxymethyl; a $C_1$-$C_6$ alkoxycarbonyloxy $C_1$-$C_4$ alkyl group such as methoxycarbonyloxymethyl, 1-(methoxycarbonyloxy)ethyl, 1-(methoxycarbonyloxy)propyl, 1-(methoxycarbonyloxy) butyl, 1-(methoxycarbonyloxy)pentyl, 1-(methoxycarbonyloxy)hexyl, ethoxycarbonyloxymethyl, 1-(ethoxycarbonyloxy)ethyl, 1-(ethoxycarbonyloxy)propyl, 1-(ethoxycarbonyloxy)butyl, 1-(ethoxycarbonyloxy)pentyl, 1-(ethoxycarbonyloxy)hexyl, propoxycarbonyloxymethyl, 1-(propoxycarbonyloxy)ethyl, 1-(propoxycarbonyloxy)propyl, 1-(propoxycarbonyloxy)butyl, isopropoxycarbonyloxymethyl, 1-(isopropoxycarbonyloxy)ethyl, 1-(isopropoxycarbonyloxy)butyl, butoxycarbonyloxymethyl, 1-(butoxycarbonyloxy)ethyl, 1-(butoxycarbonyloxy)propyl, 1-(butoxycarbonyloxy)butyl, isobutoxycarbonyloxymethyl, 1-(isobutoxycarbonyloxy)ethyl, 1-(isobutoxycarbonyloxy) propyl, 1-(isobutoxycarbonyloxy)butyl, t-butoxycarbonyloxymethyl, 1-(t-butoxycarbonyloxy)ethyl, pentyloxycarbonyloxymethyl, 1-(pentyloxycarbonyloxy)ethyl, 1-(pentyloxycarbonyloxy)propyl, hexyloxycarbonyloxymethyl, 1-(hexyloxycarbonyloxy)ethyl or 1-(hexyloxycarbonyloxy)propyl; a $C_5$-$C_6$ cycloalkyloxycarbonyloxy $C_1$-$C_4$ alkyl group such as cyclopentyloxycarbonyloxymethyl, 1-(cyclopentyloxycarbonyloxy)ethyl, 1-(cyclopentyloxycarbonyloxy)propyl, 1-(cyclopentyloxycarbonyloxy)butyl, cyclohexyloxycarbonyloxymethyl, 1-(cyclohexyloxycarbonyloxy)ethyl, 1-(cyclohexyloxycarbonyloxy)propyl or 1-(cyclohexyloxycarbonyloxy)butyl; a [5-($C_1$-$C_4$ alkyl)-2-oxo-1,3-dioxolen-4-yl]methyl group such as (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl or (5-butyl-2-oxo-1,3-dioxolen-4-yl)methy; a [5-(phenyl, which may be optionally substituted with a $C_1$-$C_4$ alkyl, $C_1$-$C_4$ alkoxy or halogen atom(s))-2-oxo-1,3-dioxolen-4-yl]methyl group such as (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl or [5-(4-chlorophenyl)-2-oxo-1,3-dioxolen-4-yl]methyl; or a phthalidyl group, which may be optionally substituted with a $C_1$-$C_4$ alkyl or $C_1$-$C_4$ alkoxy group(s), such as phthalidyl, dimethylphthalidyl or dimethoxyphthalidyl, and is preferably a pivaloyloxymethyl group, phthalidyl group or (5-methyl-2-oxo-1,3-dioxolen-4-yl)methyl group, and more preferably a (5-methyl-2-oxo-1,3-dioxolen-4-yl)methyl group.

Any compound referred to herein is intended to represent such specific compound as well as certain variations or forms. In particular, compounds referred to herein may have asymmetric centres and therefore exist in different enantiomeric forms. All optical isomers and stereoisomers of the compounds referred to herein, and mixtures thereof, are considered within the scope of the present invention. Thus any given compound referred to herein is intended to represent any one of a racemate, one or more enantiomeric forms, one or more diastereomeric forms, one or more atropisomeric forms, and mixtures thereof. Particularly, the drug conjugates of formula $[D-(X)_b-(AA)_w-(T)_g-(L)]_n$-Ab and compounds of formula D-X-$(AA)_w$-$(T)_g$-$L_1$ or D-X-$(AA)_w$-$(T)_g$-H may include enantiomers depending on their asymmetry or diastereoisomers. Stereoisomerism about the double bond is also possible, therefore in some cases the molecule could exist as (E)-isomer or (Z)-isomer. If the molecule contains several double bonds, each double bond will have its own stereoisomerism, that could be the same or different than the stereoisomerism of the other double bonds of the molecule. The single isomers and mixtures of isomers fall within the scope of the present invention.

Furthermore, compounds referred to herein may exist as geometric isomers (i.e., cis and trans isomers), as tautomers, or as atropisomers. Specifically, the term tautomer refers to one of two or more structural isomers of a compound that exist in equilibrium and are readily converted from one isomeric form to another. Common tautomeric pairs are amine-imine, amide-imide, keto-enol, lactam-lactim, etc. Additionally, any compound referred to herein is intended to represent hydrates, solvates, and polymorphs, and mixtures thereof when such forms exist in the medium. In addition, compounds referred to herein may exist in isotopically-labelled forms. All geometric isomers, tautomers, atropisomers, hydrates, solvates, polymorphs, and isotopically labelled forms of the compounds referred to herein, and mixtures thereof, are considered within the scope of the present invention.

Protected forms of the compounds disclosed herein are considered within the scope of the present invention. Suitable protecting groups are well known for the skilled person in the art. A general review of protecting groups in organic chemistry is provided by Wuts, PGM and Greene T W in Protecting Groups in Organic Synthesis, $4^{th}$ Ed. Wiley-Interscience, and by Kocienski P J in Protecting Groups, $3^{rd}$ Ed. Georg Thieme Verlag. These references provide sections on protecting groups for OH, amino and SH groups. All these references are incorporated by reference in their entirety.

Within the scope of the present invention an OH protecting group is defined to be the O-bonded moiety resulting from the protection of the OH through the formation of a suitable protected OH group. Examples of such protected OH groups include ethers, silyl ethers, esters, sulfonates, sulfenates and sulfinates, carbonates, and carbamates. In the case of ethers the protecting group for the OH can be selected from methyl, methoxymethyl, methylthiomethyl, (phenyldimethylsilyl)methoxymethyl, benzyloxymethyl, p-methoxybenzyloxymethyl, [(3,4-dimethoxybenzyl)oxy] methyl, p-nitrobenzyloxymethyl, o-nitrobenzyloxymethyl, [(R)-1-(2-nitrophenyl)ethoxy]methyl, (4-methoxyphenoxy) methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, 0-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxy-tetrahydrothiopyranyl, 4-methoxytetrahydrothiopyranyl S,S-dioxide, 1-[(2-chloro-4-methyl)-phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-(phenylselenyl)ethyl, t-butyl, cyclohexyl, 1-methyl-T-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2-picolyl, 4-picolyl, 3-methyl-2-picolyl N-oxide, 2-quinolinylmethyl, 6-methoxy-2-(4-methylphenyl)-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl) methyl, a-naphthyldiphenylmethyl, p-methoxyphenyldiphenylmethyl, di(p-methoxyphenyl)phenyl-methyl, tri(p-methoxyphenyl)methyl, 4-(4'-bromophenacyloxy) phenyldiphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i] fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, 4,5-bis (ethoxycarbonyl)-[1,3]-dioxolan-2-yl, benzisothiazolyl S,S-dioxide. In the case of silyl ethers the protecting group for the OH can be selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(f-butyl)-1-pyrenylmethoxysilyl, tris (trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy) ethoxy]disiloxane-1-yl, and fluorous silyl. In the case of esters the protecting group for the OH together with the oxygen atom of the unprotected OH to which it is attached form an ester that can be selected from formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)pentanoate, 5[3-bis(4-methoxyphenyl)hydro-xymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azido-butyrate, (2-azidomethyl)phenylacetate, 2-{[(tritylthio)oxy]methyl}benzoate, 2-{[(4-methoxytritylthio) oxy]methyl}benzoate, 2-{[methyl(tritylthio)amino] methyl}benzoate, 2-{{[(4-methoxytrityl)thio] methylamino}methyl}benzoate, 2-(allyloxy)phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxy-butyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthio-methoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenyl-acetate, isobutyrate, monosuccinoate, (E)-2-methyl-2-butenoate, o-(methoxycarbonyl)benzoate, a-naphthoate, nitrate, alkyl N,N,N',N'-tetramethylphosphorodiamidate, and 2-chlorobenzoate. In the case of sulfonates, sulfenates and sulfinates the protecting group for the OH together with the oxygen atom of the unprotected OH to which it is attached form a sulfonate, sulfenate or sulfinates that can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, and dimethylphosphinothioyl. In the case of carbonates the protecting group for the OH together with the oxygen atom of the unprotected OH to which it is attached form a carbonate that can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl) ethyl carbonate, 2-(triphenylphosphonio)ethyl carbonate, c/s-[4-[[(methoxytrityl)sulfenyl]oxy]tetrahydrofuran-3-yl] oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, 2-(3,4-methylenedioxy-6-nitrophenyl)propyl carbonate, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for OH together with the oxygen atom of the unprotected OH to which it is attached forms a carbamate that can be selected from dimethyl thiocarbamate, N-phenyl carbamate, and N-methyl-N-(o-nitrophenyl) carbamate.

Within the scope of the present invention an amino protecting group is defined to be the N-bonded moiety resulting from the protection of the amino group through the formation of a suitable protected amino group. Examples of protected amino groups include carbamates, ureas, amides, heterocyclic systems, N-alkyl amines, N-alkenyl amines, N-alkynyl amines, N-aryl amines, imines, enamines, N-metal derivatives, N—N derivatives, N—P derivatives, N—Si derivatives, and N—S derivatives. In the case of carbamates the protecting group for the amino group together with the amino group to which it is attached form a carbamate that can be selected from methyl carbamate, ethyl carbamate, 9-fluorenylmethyl carbamate, 2,6-di-t-butyl-9-fluorenylmethyl carbamate, 2,7-bis(trimethylsilyl) fluorenylmethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate, 2-chloro-3-indenylmethyl carbamate, benz[f]inden-3-ylmethyl carbamate, 1,1-dioxobenzo[b]-thiophene-2-ylmethyl carbamate, 2-methylsulfonyl-3-phenyl-1-prop-2-enyl carbamate, 2,7-di-t-butyl-[9,(10,10-dioxo-10,10,10,10-tetrahydrothioxanthyl)]methyl carbamate, 2,2,2-trichloroethyl carbamate, 2-trimethylsilylethyl carbamate, (2-phenyl-2-trimethylsilyl)ethyl carbamate, 2-phenylethyl carbamate, 2-chloroethyl carbamate, 1,1-dimethyl-2-haloethyl carbamate, 1,1-dimethyl-2,2-dibromoethyl carbamate, 1,1-dimethyl-2,2,2-trichloroethyl carbamate, 2-(2'-pyridyl)ethyl carbamate, 2-(4'-pyridyl)ethyl carbamate, 2,2-bis(4'-nitrophenyl)ethyl carbamate, 2-[(2-nitrophenyl)dithio]-1-phenylethyl carbamate, 2-(N,N-dicyclohexylcarboxamido) ethyl carbamate, t-butyl carbamate, fluorous BOC carbamate, 1-adamantyl carbamate, 2-adamantyl carbamate, 1-(1-adamantyl)-1-methylethyl carbamate, 1-methyl-1-(4-byphenylyl)ethyl carbamate, 1-(3,5-di-t-butylphenyl)-1-methylethyl carbamate, triisopropylsilyloxy carbamate, vinyl carbamate, allyl carbamate, prenyl carbamate, 1-isopropylallyl carbamate, cinnamyl carbamate, 4-nitrocinnamyl carbamate, 3-(3'-pyridyl)prop-2-enyl carbamate, hexadienyl carbamate, propargyl carbamate, 1,4-but-2-ynyl biscarbamate, 8-quinolyl carbamate, N-hydroxypiperidinyl carbamate, alkyl dithiocarbamate, benzyl carbamate, 3,5-di-t-butylbenzyl carbamate, p-methoxybenzyl carbamate, p-nitrobenzyl carbamate, p-bromobenzyl carbamate, p-chlorobenzyl carbamate, 2,4-dichlorobenzyl carbamate, 4-methylsulfinylbenzyl carbamate, 4-trifluoromethylbenzyl carbamate, fluorous benzyl carbamate, 2-naphthylmethyl carbamate, 9-anthrylmethyl carbamate, diphenylmethyl carbamate, 4-phenylacetoxybenzyl carbamate, 4-azidobenzyl carbamate, 4-azido-methoxybenzyl carbamate, m-chloro-p-acyloxybenzyl carbamate, p-(dihydroxyboryl)-benzyl carbamate, 5-benzisoxazolylmethyl carbamate, 2-(trifluoromethyl)-6-chromonylmethyl carbamate, 2-methylthioethyl carbamate, 2-methylsulfonylethyl carbamate, 2-(p-toluenesulfonyl)ethyl carbamate, 2-(4-nitrophenylsulfonyl)ethyl carbamate, 2-(2,4-dinitrophenylsulfonyl)ethyl carbamate, 2-(4-trifluoromethylphenylsulfonyl)ethyl carbamate, [2-(1,3-dithianyl)]methyl carbamate, 2-phosphonioethyl carbamate, 2-[phenyl(methyl)sulfonio]ethyl carbamate, 1-methyl-1-(triphenylphosphonio)ethyl carbamate, 1,1-dimethyl-2-cyanoethyl carbamate, 2-dansylethyl carbamate, 2-(4-nitrophenyl)ethyl carbamate, 4-methylthiophenyl carbamate, 2,4-dimethylthiophenyl carbamate, m-nitrophenyl carbamate, 3,5-dimethoxybenzyl carbamate, 1-methyl-1-(3,5-dimethoxyphenyl)ethyl carbamate, a-methylnitropiperonyl carbamate, o-nitrobenzyl carbamate, 3,4-dimethoxy-6-nitrobenzyl carbamate, phenyl(o-nitrophenyl)methyl carbamate, 2-nitrophenylethyl carbamate, 6-nitroveratryl carbamate, 4-methoxyphenacyl carbamate, 3',5'-dimethoxybenzoin carbamate, 9-xanthenylmethyl carbamate, N-methyl-N-(o-nitrophenyl) carbamate, t-amyl carbamate, 1-methylcyclobutyl carbamate, 1-methylcyclohexyl carbamate, 1-methyl-1-cyclopropylmethyl carbamate, cyclobutyl carbamate, cyclopentyl carbamate, cyclohexyl carbamate, isobutyl carbamate, isobornyl carbamate, cyclopropylmethyl carbamate, p-decyloxybenzyl carbamate, diisopropylmethyl carbamate, 2,2-dimethoxy-carbonylvinyl carbamate, o-(N,N-dimethylcarboxamido)benzyl carbamate, 1,1-dimethyl-3-(N,N-dimethyl-carboxamido)propyl carbamate, butynyl carbamate, 1,1-dimethylpropynyl carbamate, 2-iodoethyl carbamate, 1-methyl-1-(4'-pyridyl) ethyl carbamate, 1-methyl-1-(p-phenylazophenyl)ethyl carbamate, p-(p'-methoxyphenylazo)benzyl carbamate, p-(phenylazo)benzyl carbamate, 2,4,6-trimethylbenzyl carbamate, isonicotinyl carbamate, 4-(trimethyl-ammonium) benzyl carbamate, p-cyanobenzyl carbamate, di(2-pyridyl) methyl carbamate, 2-furanylmethyl carbamate, phenyl carbamate, 2,4,6-tri-t-butylphenyl carbamate, 1-methyl-1-phenylethyl carbamate, and S-benzyl thiocarbamate. In the case of ureas the protecting groups for the amino group can be selected from phenothiazinyl-(10)-carbonyl, N'-p-toluenesulfonylaminocarbonyl, N'-phenylaminothiocarbonyl, 4-hydroxyphenylaminocarbonyl, 3-hydroxytryptaminocarbonyl, and N'-phenylaminothiocarbonyl. In the case of amides the protecting group for the amino together with the amino group to which it is attached form an amide that can be selected from formamide, acetamide, chloroacetamide, trichloroacetamide, trifluoroacetamide, phenylacetamide, 3-phenylpropanamide, pent-4-enamide, picolinamide, 3-pyridylcarboxamide, N-benzoylphenylalanyl amide, benzamide, p-phenylbenzamide, o-nitrophenylacetamide, 2,2-dimethyl-2-(o-nitrophenyl)acetamide, o-nitrophenoxyacetamide, 3-(o-nitrophenyl)propanamide, 2-methyl-2-(o-nitrophenoxy)propanamide, 3-methyl-3-nitrobutanamide, o-nitrocinnamide, o-nitrobenzamide, 3-(4-t-butyl-2,6-dinitrophenyl)-2,2-dimethylpropanamide, o-(benzoyloxymethyl)benzamide, 2-(acetoxymethyl)benzamide, 2-[(f-butyldiphenylsiloxy)methyl]benzamide, 3-(3',6'-dioxo-2',4',5'-trimethylcyclohexa-1',4'-diene)-3,3-dimethylpropionamide, o-hydroxy-frans-cinnamide, 2-methyl-2-(o-phenylazophenoxy)propanamide, 4-chlorobutanamide, aceto-acetamide, 3-(p-hydroxyphenyl)propanamide, (N'-dithiobenzyloxycarbonylamino)acetamide, and N-acetylmethionine amide. In the case of heterocyclic systems the protecting group for the amino group together with the amino group to which it is attached form a heterocyclic system that can be selected from 4,5-diphenyl-3-oxazolin-2-one, N-phthalimide, N-dichlorophthalimide, N-tetrachlorophthalimide, N-4-nitrophthalimide, N-thiodiglycoloyl, N-dithiasuccinimide, N-2,3-diphenylmaleimide, N-2,3-dimethylmaleimide, N-2,5-dimethylpyrrole, N-2,5-bis(triisopropylsiloxy)pyrrole, N-1,1,4,4-tetramethyldisilylazacyclopentane adduct, N-1,1,3,3-tetramethyl-1,3-disilaisoindoline, N-diphenylsilyldiethylene, N-5-substituted-1,3-dimethyl-1,3,5-triazacyclohexan-2-one, N-5-substituted-1,3-benzyl-1,3,5-triazacyclohexan-2-one, 1-substituted 3,5-dinitro-4-pyridone, and 1,3,5-dioxazine. In the case of N-alkyl, N-alkenyl, N-alkynyl or N-aryl amines the protecting group for the amino group can be selected from N-methyl, N-t-butyl, N-allyl, N-prenyl, N-cinnamyl, N-phenylallyl, N-propargyl, N-methoxymethyl, N-[2-(trimethylsilyl) ethoxy]methyl, N-3-acetoxypropyl, N-cyanomethyl, N-2-azanorbornenes, N-benzyl, N-4-methoxybenzyl, N-2,4-dimethoxybenzyl, N-2-hydroxybenzyl, N-ferrocenylmethyl, N-2,4-dinitrophenyl, o-methoxyphenyl, p-methoxyphenyl, N-9-phenylfluorenyl, N-fluorenyl, N-2-picolylamine N'-oxide, N-7-methoxycoumar-4-ylmethyl, N-diphenylmethyl, N-bis(4-methoxyphenyl)methyl, N-5-dibenzosuberyl, N-triphenylmethyl, N-(4-methylphenyl)diphenylmethyl, and N-(4-methoxyphenyl)diphenylmethyl. In the case of imines the protecting group for the amino group can be selected from N-1,1-dimethylthiomethylene, N-benzylidene, N-p-methoxybenzylidene, N-diphenylmethylene, N-[2-pyridyl) mesityl]methylene, N—(N',N'-dimethylaminomethylene), N—(N,N-dibenzylaminomethylene), N—(N'-t-butylaminome-thylene), N,N-isopropylidene, N-p-nitrobenzylidene, N-salicylidene, N-5-chlorosalicylidene, N-(5-chloro-2-hydroxyphenyl)phenylmethylene, N-cyclohexylidene, and N-t-butylidene. In the case of enamines the protecting group for the amino group can be selected from N-(5,5-dimethyl-3-oxo-1-cyclohexenyl), N-2,7-dichloro-9-fluorenylmethylene, N-1-(4,4-dimethyl-2,6-dioxocyclohexylidene)ethyl, N-(1,3-dimethyl-2,4,6-(1H,3H,5H)-trioxopyrimidine-5-ylidene)-methyl, N-4,4,4-trifluoro-3-oxo-1-butenyl, and N-(1-isopropyl-4-nitro-2-oxo-3-pyrrolin-3-yl). In the case of N-metal derivatives the protecting group for the amino group can be selected from N-borane, N-diphenylborinic ester, N-diethylborinic ester, N-9-borabicyclononane, N-difluoroborinic ester, and 3,5-bis(trifluoromethyl)phenylboronic acid; and also including N-phenyl(pentacarbonylchromium)carbenyl, N-phenyl(pentacarbonyl-tungsten) carbenyl, N-methyl(pentacarbonylchromium)carbenyl, N-methyl(pentacarbonyltungsten)carbenyl, N-copper chelate, N-zinc chelate, and a 18-crown-6-derivative. In the case of N—N derivatives the protecting group for the amino group together with the amino group to which it is attached form a N—N derivative that can be selected from N-nitroamino, N-nitrosoamino, amine N-oxide, azide, triazene derivative, and N-trimethylsilylmethyl-N-benzylhydrazine. In the case of N—P derivatives the protected group for the amino group together with the amino group to which it is attached form a N—P derivative that can be selected from diphenylphosphinamide, dimethylthiophosphinamide, diphenylthiophosphinamide, dialkyl phosphoramidate, dibenzyl phosphoramidate, diphenyl phosphoramidate, and iminotriphenylphosphorane. In the case of N—Si derivatives the protecting group for the $NH_2$ can be selected from t-butyldiphenylsilyl and triphenylsilyl. In the case of N—S derivatives the protected amino group can be selected from N-sulfenyl or N-sulfonyl derivatives. The N-sulfenyl derivatives can be selected from benzenesulfenamide, 2-nitrobenzenesulfenamide, 2,4-dinitrobenzenesulfenamide, pentachlorobenzenesulfenamide, 2-nitro-4-methoxybenzenesulfenamide, triphenylmethylsulfe-namide, 1-(2,2,2-trifluoro-1,1-diphenyl)ethylsulfenamide, and N-3-nitro-2-pyridinesulfenamide. The N-sulfonyl derivatives can be selected from methanesulfonamide, trifluoromethanesulfonamide, t-butylsulfonamide, benzylsulfonamide, 2-(trimethylsilyl) ethanesulfonamide, p-toluenesulfonamide, benzenesulfonamide, o-anisylsulfonamide, 2-nitrobenzenesulfonamide, 4-nitrobenzenesulfonamide, 2,4-dinitrobenzenesulfonamide, 2-naphthalenesulfonamide, 4-(4',8'-dimethoxynaphthylmethyl)benzenesulfonamide, 2-(4-methylphenyl)-6-methoxy-4-methylsulfonamide, 9-anthracenesulfonamide, pyridine-2-sulfonamide, benzothiazole-2-sulfonamide, phenacylsulfonamide, 2,3,6-trimethyl-4-methoxybenzenesulfonamide, 2,4,6-trimethoxybenzenesulfonamide, 2,6-dimethyl-4-methoxybenzenesulfonamide, pentamethylbenzenesulfonamide, 2,3,5,6-tetramethyl-4-methoxyben-zenesulfonamide, 4-methoxybenzenesulfonamide, 2,4,6-trimethylbenzenesulfonamide, 2,6-dimethoxy-4-methylbenzenesulfonamide, 3-methoxy-4-t-butylbenzenesulfonamide, and 2,2,5,7,8-pentamethylchroman-6-sulfonamide.

Within the scope of the present invention a protecting group for SH is defined to be the S-bonded moiety resulting from the protection of the SH group through the formation of a suitable a protected SH group. Examples of such protected SH groups include thioethers, disulfides, silyl thioethers, thioesters, thiocarbonates, and thiocarbamates. In the case of thioethers the protecting group for the SH can be selected from S-alkyl, S-benzyl, S-p-methoxybenzyl, S-o-hydroxybenzyl, S-p-hydroxybenzyl, S-o-acetoxybenzyl, S-p-acetoxybenzyl, S-p-nitrobenzyl, S-o-nitrobenzyl, S-2,4,6-trimethylbenzyl, S-2,4,6-trimethoxybenzyl, S-4-picolyl, S-2-picolyl-N-oxide, S-2-quinolinylmethyl, S-9-anthrylmethyl, S-9-fluorenylmethyl, S-xanthenyl, S-ferrocenylmethyl, S-diphenylmethyl, S-bis(4-methoxyphenyl)methyl, S-5-dibenzosuberyl, S-triphenylmethyl, 4-methoxytrityl, S-diphenyl-4-pyridylmethyl, S-phenyl, S-2,4-dinitrophenyl, S-2-quinolyl, S-t-butyl, S-1-adamantyl, S-methoxymethyl, S-isobutoxymethyl, S-benzyloxymethyl, S-1-ethoxyethyl, S-2-tetrahydropyranyl, S-benzylthiomethyl, S-phenylthiomethyl, S-acetamidomethyl (Acm), S-trimethylacetamidomethyl, S-benzamidomethyl, S-allyloxycarbonylaminomethyl, S—N-[2,3,5,6-tetrafluoro-4-(N'-piperidino)-phenyl-N-allyloxycarbonylaminomethyl, S-phthalimidomethyl, S-phenylacetamidomethyl, S-acetylmethyl, S-carboxymethyl, S-cyanomethyl, S-(2-nitro-1-phenyl)ethyl, S-2-(2,4-dinitrophenyl)ethyl, S-2-(4'-pyridyl)ethyl, S-2-cyanoethyl, S-2-(trimethylsilyl)ethyl, S-2,2-bis(carboethoxy)ethyl, S-(1-m-nitrophenyl-2-benzoyl)ethyl, S-2-phenylsulfonylethyl, S-1-(4-methylphenylsulfonyl)-2-methylprop-2-yl, and S-p-hydroxyphenacyl. In the case of disulfides the protected SH group can be selected from S-ethyl disulfide, S-t-butyl disulfide, S-2-nitrophenyl disulfide, S-2,4-dinitrophenyl disulfide, S-2-phenylazophenyl disulfide, S-2-carboxyphenyl disulfide, and S-3-nitro-2-pyridyl disulfide. In the case of silyl thioethers the protecting group for the SH can be selected from the list of groups that was listed above for the protection of OH with silyl ethers. In the case of thioesters the protecting group for the SH can be selected from S-acetyl, S-benzoyl, S-2-methoxyisobutyryl, S-trifluoroacetyl, S—N-[[p-biphenylyl)-isopropyloxy]carbonyl]-N-methyl-y-aminothiobutyrate, and S—N-(t-butoxycarbonyl)-N-methyl-y-aminothiobutyrate. In the case of thiocarbonate protecting group for the SH can be selected from S-2,2,2-trichloroethoxycarbonyl, S-t-butoxycarbonyl, S-benzyloxycarbonyl, S-p-methoxybenzyloxycarbonyl, and S-fluorenylmethylcarbonyl. In the case of thiocarbamate the protected SH group can be selected from S—(N-ethylcarbamate) and S—(N-methoxymethylcarbamate).

The mention of these groups should not be interpreted as a limitation of the scope of the invention, since they have been mentioned as a mere illustration of protecting groups for OH, amino and SH groups, but further groups having said function may be known by the skilled person in the art, and they are to be understood to be also encompassed by the present invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

"Antibody-drug-conjugates (ADCs)" represent a targeted strategy to deliver a cytotoxic molecule to a cancer cell (see, for example, International Patent Applications WO-A-2004/010957, WO-A-2006/060533 and WO-A-2007/024536). Such compounds are typically referred to as drug, toxin and radionuclide "conjugates". Tumor cell killing occurs upon binding of the drug conjugate to a tumor cell and release and/or activation of the cytotoxic activity of the drug moiety. The selectivity afforded by drug conjugates minimizes toxicity to normal cells, thereby enhancing tolerability of the drug in the patient. Three examples of drug antibody conjugates of this type that have received marketing approval are: Gemtuzumab ozogamicin for acute myelogenous leukemia, Brentuximab vedotin for relapsed and refractory Hodgkin lymphoma and anaplastic large cell lymphoma, and ado-Trastuzumab emtansine for breast cancer, especially HER2+.

The effectiveness of drugs for cancer chemotherapy generally relies on differences in growth rates, biochemical pathways, and physiological characteristics between cancer and normal tissues. Consequently, most standard chemotherapeutics are relatively nonspecific and exhibit dose-limiting toxicities that contribute to suboptimal therapeutic effects. One approach to selectively target malignant cells and not healthy tissues is to use specific monoclonal antibodies (mAbs) that recognize tumor-associated antigens expressed on the surface of tumor cells [Meyer, D. L. & Senter, P. D. (2003) Recent advances in antibody drug conjugates for cancer therapy. Annu. Rep. Med. Chem., 38, 229-237; Chari, R. V. (2008) Targeted cancer therapy: conferring specificity to cytotoxic drugs. Acc. Chem. Res. 41, 98-107]. More than 30 G-type immunoglobulins (IgG) and related agents have been approved over the past 25 years mainly for cancers and inflammatory diseases.

An alternative strategy is to look to chemically conjugate small anti-neoplastic molecules to mAbs, used both as carriers (increased half-life) and as targeting agents (selectivity). Considerable effort has been directed toward the use of monoclonal antibodies (mAbs) for targeted drug delivery due to their high selectivities for tumor-associated antigens, favorable pharmacokinetics, and relatively low intrinsic toxicities. The mAb-drug conjugates (ADCs) are formed by covalently linking anticancer drugs to mAbs, usually through a conditionally stable linker system. Upon binding to cell surface antigens, mAbs used for most ADCs are actively transported to lysosomes or other intracellular compartments, where enzymes, low pH, or reducing agents facilitate drug release. There are, however, currently limited ADCs in development.

Antigens must have high tumor cell selectivity to limit toxicity and off-target effects. A plethora of tumor-associated antigens have been investigated in pre-clinical models and in clinical trials including antigens over-expressed in B-cells (e.g., CD20, CD22, CD40, CD79), T-cells (CD25, CD30), carcinoma cells (HER2, EGFR, EpCAM, EphB2, PSMA), endothelial (endoglin), or stroma cells (fibroblast activated protein), to name a few [Teicher B A. Antibody-drug conjugate targets. Curr Cancer Drug Targets 9(8):982-1004, 2009]. An important property for ADC targets is their ability to be internalized; this can be an intrinsic feature of the antigen by itself, or it can be induced by the binding of the antibody to its antigen. Indeed, ADC internalization is crucial to reduce toxicity associated with an extracellular delivery of the drug payload.

Regarding the conjugated small molecules and in contrast to the vast variety of putative antigen targets, a limited number of families of cytotoxic drugs used as payloads in ADCs are currently actively investigated in clinical trials: calicheamycin (Pfizer), duocarmycins (Synthon), pyrrolobenzodiazepines (Spirogen), irinotecan (Immunomedics), maytansinoids (DM1 and DM4; ImmunoGen+ Genentech/Roche, Sanofi-Aventis, Biogen Idec, Centocor/Johnson & Johnson, Millennium/Takeda), and auristatins (MMAE and MMAF; Seattle Genetics+Genentech/Roche, MedImmune/AstraZeneca, Bayer-Schering, Celldex, Progenics, Genmab). Calicheamycin, duocarmycins and pyrrolobenzodiazepines are DNA minor groove binders, irinotecan is a topoisomerase I inhibitor, whereas maytansinoids and auristatins are tubulin depolymerization agents.

Interestingly, a representative of three of these cytotoxic-derived ADCs has reached late stage clinical trials. Trastuzumab emtansine (T-DM1), trastuzumab linked to a maytansinoid hemi-synthetic drug by a stable linker (FDA approval on Feb. 22, 2013 for advanced HER2 positive breast cancer); Inotuzumab ozogamicin (CMC-544), a humanized anti-CD22 mAb (G5/44, IgG4) conjugated to calicheamycin with an acid labile linker (acetylphenoxy-butanoic) (B-cell non-Hodgkin's lymphoma); Brentuximab vedotin, a humanized anti-CD30 mAb linked to monomethyl auristatin E (MMAE), via a maleimidecaproyl-valyl-citrullinyl-p-aminobenzylcarbamate linker (FDA approval on Aug. 19, 2011 for anaplastic large cell lymphoma and Hodking's lymphoma).

Linkers represent the key component of ADC structures. Several classes of second generation linkers have been investigated, including acid-labile hydrazone linkers (lysosomes) (e.g. gemtuzumab and inotuzumab ozogamicin); disulfide-based linkers (reductive intracellular environment); non-cleavable thioether linkers (catabolic degradation in lysosomes) (e.g., trastuzumab emtansine); peptide linkers (e.g. citruline-valine) (lysosomal proteases like cathepsin-B) (e.g. brentuximab vedotin): see, for example, WO-A-2004/010957, WO-A-2006/060533 and WO-A-2007/024536. Purification of antibody-drug conjugates by size exclusion chromatography (SEC) has also been described [see, e.g., Liu et al., Proc. Natl. Acad. Sci. USA, 93: 8618-8623 (1996), and Chari et al., Cancer Research, 52: 127-131 (1992)].

Trastuzumab (Herceptin) is a monoclonal antibody that interferes with the HER2/neu receptor. Its main use is to treat certain breast cancers. The HER receptors are proteins that are embedded in the cell membrane and communicate molecular signals from outside the cell (molecules called EGFs) to inside the cell, and turn genes on and off. The HER proteins stimulate cell proliferation. In some cancers, notably certain types of breast cancer, HER2 is over-expressed, and causes cancer cells to reproduce uncontrollably.

The HER2 gene is amplified in 20-30% of early-stage breast cancers, which makes it overexpress epidermal growth factor (EGF) receptors in the cell membrane. In some types of cancer, HER2 may send signals without growth factors arriving and binding to the receptor, making its effect in the cell constitutive; however, trastuzumab is not effective in this case.

The HER2 pathway promotes cell growth and division when it is functioning normally; however when it is over-expressed, cell growth accelerates beyond its normal limits. In some types of cancer the pathway is exploited to promote rapid cell growth and proliferation and hence tumor formation. In cancer cells the HER2 protein can be expressed up to 100 times more than in normal cells (2 million versus 20,000 per cell). This overexpression leads to strong and constant proliferative signaling and hence tumor formation. Overexpression of HER2 also causes deactivation of checkpoints, allowing for even greater increases in proliferation.

In the compounds of the present invention, Ab is a moiety comprising at least one antigen binding site. In an alternative embodiment, Ab can be any suitable agent that is capable of binding to a target cell, preferably an animal cell and more preferably, a human cell. Examples of such agents include lymphokines, hormones, growth factors and nutrient-transport molecules (e.g. transferrin). In another example, Ab may be an aptamer, and may include a nucleic acid or a peptide aptamer.

Where Ab is a moiety comprising at least one antigen binding site, the moiety is preferably an antigen-binding peptide or polypeptide. In a preferred embodiment, the moiety is an antibody or an antigen-binding fragment thereof.

The term 'antibody' in the drug conjugates of the present invention refers to any immunolglobulin, preferably a full-length immunoglobulin. Preferably, the term covers monoclonal antibodies, polyclonal antibodies, multispecific antibodies, such as bispecific antibodies, and antibody fragments thereof, so long as they exhibit the desired biological activity. Antibodies may be derived from any species, but preferably are of rodent, for examples rat or mouse, human or rabbit origin. Alternatively, the antibodies, preferably monoclonal antibodies, may be humanised, chimeric or antibody fragments thereof. The term 'chimeric antibodies' may also include "primatised" antibodies comprising variable domain antigen-binding sequences derived from a non-human primate (e.g., Old World Monkey, Ape etc) and human constant region sequences. The immunoglobulins can also be of any type (e.g. IgG, IgE, IgM, IgD, and IgA), class (e.g., IgGI, IgG2, IgG3, IgG4, IgAI and IgA2) or subclass of immunoglobulin molecule.

The term 'monoclonal antibody' refers to a substantially homogenous population of antibody molecules (i.e. the individual antibodies comprising the population are identical except for possible naturally occurring mutations that may be present in minor amounts), produced by a single clone of B lineage cells, often a hybridoma. Importantly, each monoclonal has the same antigenic specificity—i.e. it is directed against a single determinant on the antigen.

The production of monoclonal antibodies can be carried out by methods known in the art. However, as an example, the monoclonal antibodies can be made by the hybridoma method (Kohler et al (1975) Nature 256:495), the human B cell hybridoma technique (Kozbor et al., 1983, Immunology Today 4: 72), or the EBV-hybridoma technique (Cole et al., 1985, Monoclonal Antibodies and Cancer Therapy, Alan R. Liss, Inc., pp. 77-96). Alternatively, the monoclonal antibody can be produced using recombinant DNA methods (see, U.S. Pat. No. 4,816,567) or isolated from phage antibody libraries using the techniques described in Clackson et al (1991) Nature, 352:624-628; Marks et al (1991) J. Mol. Biol., 222:581-597.

Polyclonal antibodies are antibodies directed against different determinants (epitopes). This heterogenous population of antibody can be derived from the sera of immunised animals using various procedures well known in the art.

The term 'bispecific antibody' refers to an artificial antibody composed of two different monoclonal antibodies. They can be designed to bind either to two adjacent epitopes on a single antigen, thereby increasing both avidity and specificity, or bind two different antigens for numerous applications, but particularly for recruitment of cytotoxic T- and natural killer (NK) cells or retargeting of toxins, radionuclides or cytotoxic drugs for cancer treatment (Holliger & Hudson, Nature Biotechnology, 2005, 23(9), 1126-1136). The bispecific antibody may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al., Methods in Enzymology, 1986, 121:210; Rodrigues et al., 1993, J. of Immunology 151:6954-6961; Carter et al., 1992, Bio/Technology 10:163-167; Carter et al., 1995, J. of Hematotherapy 4:463-470; Merchant et al., 1998, Nature Biotechnology 16:677-681.

Methods to prepare hybrid or bispecific antibodies are known in the art. In one method, bispecific antibodies can be produced by fusion of two hybridomas into a single 'quadroma' by chemical cross-linking or genetic fusion of two different Fab or scFv modules (Holliger & Hudson, Nature Biotechnology, 2005, 23(9), 1126-1136).

The term 'chimeric' antibody refers to an antibody in which different portions are derived from different animal species. For example, a chimeric antibody may derive the variable region from a mouse and the constant region from a human. In contrast, a 'humanised antibody' comes predominantly from a human, even though it contains non-human portions. Specifically, humaised antibodies are human immunoglobulins (recipient antibody) in which residues from a hypervariable region of the recipient are replaced by residues from hypervariable regions of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanised antibodies may comprise residues that are not found in the recipient antibody or in the donor antibody. These modifications are made to further refine antibody performance. In general, the humanised antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanised antibody optionally also will comprise at least a portion of an immunoglobulin constant region (Fc), typically that of a human immunoglobulin.

Recombinant antibodies such as chimeric and humanised monoclonal antibodies can be produced by recombinant DNA techniques known in the art. Completely human antibodies can be produced using transgenic mice that are incapable of expressing endogenous immunoglobulin heavy and light chains genes, but which can express human heavy and light chain genes. The transgenic mice are immunized in the normal fashion with a selected antigen. Monoclonal antibodies directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93).

For a detailed discussion of this technology for producing human antibodies and human monoclonal antibodies and protocols for producing such antibodies, see, for example, U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (Freemont, CA) and Genpharm (San Jose, CA).

The term 'antigen-binding fragment' in the drug conjugates of the present invention refers to a portion of a full length antibody where such antigen-binding fragments of antibodies retain the antigen-binding function of a corresponding full-length antibody. The antigen-binding fragment may comprise a portion of a variable region of an antibody, said portion comprising at least one, two, preferably three CDRs selected from CDR1, CDR2 and CDR3. The antigen-binding fragment may also comprise a portion of an immunoglobulin light and heavy chain. Examples of antibody fragments include Fab, Fab', $F(ab')_2$, scFv, di-scFv, sdAb, and BiTE (Bi-specific T-cell engagers), Fv fragments including nanobodies, diabodies, diabody-Fc fusions, triabodies and, tetrabodies; minibodies; linear antibodies; fragments produced by a Fab expression library, anti-idiotypic (anti-Id) antibodies, CDR (complementary determining region), and epitope-binding fragments of any of the above that immunospecifically bind to a target antigen such as a cancer cell antigens, viral antigens or microbial antigens, single-chain or single-domain antibody molecules including heavy chain only antibodies, for example, camelid VHH domains and shark V-NAR; and multispecific antibodies formed from antibody fragments. For comparison, a full length antibody, termed 'antibody' is one comprising a VL and VH domains, as well as complete light and heavy chain constant domains.

The antibody may also have one or more effector functions, which refer to the biological activities attributable to the Fc region (a native sequence Fc region or amino acid sequence variant Fc region engineered according to methods in the art to alter receptor binding) of an antibody. Examples of antibody effector functions include Clq binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

The antibody can also be a functionally active fragment (also referred to herein as an immunologically active portion), derivative or analog of an antibody that immunospecifically binds to a target antigen such as a cancer cell antigen, viral antigen, or microbial antigen or other antibodies bound to tumour cells. In this regard, functionally active means that the fragment, derivative or analog is able to elicit anti-idiotype antibodies that recognise the same antigen that the antibody from which the fragment, derivative or analog is derived recognised.

Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay), see, for example, Kabat et al., 1991, Sequences of Proteins of Immunological Interest, Fifth Edition, National Institute of Health, Bethesda, Md; Kabat E et al., 1980, J. of Immunology 125(3):961-969).

The term 'antibody' may also include a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Furthermore, the antibody or antigen-binding fragments of the present invention may include analogs and derivatives of antibodies or antigen-binding fragments thereof that are either modified, such as by the covalent attachment of any type of molecule as long as such covalent attachment permits the antibody to retain its antigen binding immunospecificity. Examples of modifications include glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies or antigen-binding fragments of the present invention may also have modifications (e.g., substitutions, deletions or additions) in the Fc domain of the antibody. Specifically, the modifications may be in the Fc-hinge region and result in an increased binding for the FcRn receptor (WO 97/34631).

In one embodiment, the antibody in the drug conjugate of the present invention may be any antibody or antigen-binding fragment thereof, preferably a monoclonal antibody that is useful in the treatment of a disease, preferably cancer. The cancer may be breast cancer, colorectal cancer, endometrial cancer, kidney cancer melanoma, leukaemias, lung cancer, multiple myeloma, lymphomas (e.g. Hodgkin's disease and non-Hodgkin's Lymphoma), solid tumors such as sarcoma and carcinomas, melanoma, mesothelioma, osteosarcoma, ovarian cancer and renal cancer. In a preferred embodiment the cancer is lung cancer, colorectal cancer, breast cancer, pancreas carcinoma, kidney cancer, leukaemia, multiple myeloma, lymphoma, gastric and ovarian cancer. In a more preferred embodiment the cancer is colorectal cancer, breast cancer, leukaemia, lymphoma, and ovarian cancer Antibodies that may be useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas) for example EGF receptor 2 protein (breast cancer), MAGE-I (carcinomas), MAGE-2 (carcinomas), MAGE-3 (carcinomas), MAGE-4 (carcinomas), anti-transferrin receptor (carcinomas), p97 (melanoma), MUCl-KLH (breast cancer), CEA (colorectal), gplOO (melanoma), MARTI (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., et al Science (1993) 261, 212-215), BR64 (Trail, P A, et al Cancer Research (1997) 57, 100-105, mAbs against the CD40 antigen, such as S2C6 mAb (Francisco, J. A., et al Cancer Res. (2000) 60:3225-3231), mAbs against the CD70 antigen, such as 1F6 mAb, and mAbs against the CD30 antigen, such as ACIO (Bowen, M. A., et al (1993) J. Immunol., 151:5896-5906; Wahl et al., 2002 Cancer Res. 62(13):3736-3742). Many other internalizing antibodies that bind to tumor associated antigens can be used and have been reviewed (Franke, A. E., et al Cancer Biother Radiopharm. (2000) 15:459-476; Murray, J. L., (2000) Semin Oncol, 27:64-70; Breitling, F., and Dubel, S., Recombinant Antibodies, John Wiley, and Sons, New York, 1998).

The present invention encompasses treating cancers associated with these antibodies.

Other tumour-associated antigens include, but are not limited to, BMPR1B, E16, STEAPI, STEAP2, 0772P. MPF, Napi3b, Sema5b, PSCA hlg, ETBR, MSG783, TrpM4, CRIPTO, CD21, CD79b, FcRH2, HER2, NCA, MDP, IL20Ra, Brevican, EphB2R, ASLG659, PSCA, GEDA, BAFF-R, CD79A, CXCR5, HLA-DOB, P2X5, CD72, LY64, FCRH1, IRTA2 and TENB2.

In an alternative embodiment, the antibody in the drug conjugate of the present invention may be an antibody or antigen-binding fragment thereof, preferably a monoclonal antibody, that immunospecifically binds to a viral antigen, microbial antigen or an antigen of a cell that produces autoimmune antibodies associated with autoimmune disease.

The viral antigen may include, but is not limited to, any viral peptide, polypeptide or protein such as HIV gpl20, HIV nef, RSV F glycoprotein, influenza virus neuraminidase, influenza virus hemagglutinin, HTLV tax, herpes simplex virus glycoprotein (e.g., Gb, Gc, Gd, and Ge) and hepatitis B surface antigen that is capable of eliciting an immune response.

The microbial antigen may include, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide) that is capable of eliciting an immune response.

In a further embodiment, the antibody or antigen-binding fragment binds to an epitope that is present on a cell, such as a tumour cell. Preferably, where the cell is a tumour cell, the tumour cell epitope is not present on non-tumour cells, or is present at a lower concentration or in a different steric configuration than in tumour cells.

In one embodiment, the antibody or antigen-binding fragment binds to an epitope present in the context of one of the following antigens: CA125, CA15-3, CA19-9 L6, Lewis Y, Lewis X, alpha fetoprotein, CA 242, placental alkaline phosphatase, prostate specific antigen, prostatic acid phosphatase, epidermal growth factor for example EGF receptor 2 protein, MAGE-1, MAGE-2, MAGE-3, MAGE-4, anti-transferrin receptor, p97, MUCl-KLH, CEA, gplOO, MARTI, PSA, IL-2 receptor, CD20, CD52, CD33, CD22, human chorionic gonadotropin, CD38, CD40, mucin, P21, MPG, Neu oncogene product, BMPR1B, E16, STEAPI, STEAP2, 0772P. MPF, Napi3b, Sema5b, PSCA hlg, ETBR, MSG783, TrpM4, CRIPTO, CD21, CD79b, FcRH2, HER2, NCA, MDP, IL20Ra, Brevican, EphB2R, ASLG659, PSCA, GEDA, BAFF-R, CD79A, CXCR5, HLA-DOB, P2X5, CD72, LY64, FCRH1, IRTA2, TENB2, a viral antigen (such as any viral peptide, polypeptide or protein such as HIV gp120, HIV nef, RSV F glycoprotein, influenza virus neuraminidase, influenza virus hemagglutinin, HTLV tax, herpes simplex virus glycoprotein (e.g., Gb, Gc, Gd, and Ge) and hepatitis B surface antigen) that is capable of eliciting an immune response), microbial antigen (any microbial peptide, polypeptide, protein, saccharide, polysaccharide, or lipid molecule (e.g., a bacterial, fungi, pathogenic protozoa, or yeast polypeptide including, e.g., LPS and capsular polysaccharide) that is capable of eliciting an immune response) or an antigen of a cell that produces autoimmune antibodies associated with autoimmune disease.

In one embodiment, where the antigen is ErBB2 (also known as ERBB2, CD340 or HER2; such terms may be used interchangeably), the antibody or antigen-binding fragment may bind to one or more of the following epitopes: ARHC L (SEQ ID NO: 1), QNGS (SEQ ID NO: 2) and PPFCVARC PSG (SEQ ID NO: 3). These epitopes correspond to positions 557-561, 570-573 and 593-603 respectively of the human HER2 polypetide sequence (Accession: NM_004448, Version: NM_004448.3).

In another embodiment, the antibody may be any antibody known for the treatment or prevention of viral or microbial infection—i.e. an infectious disease. Examples of such antibodies include, but are not limited to, PR0542 (Progenies) which is a CD4 fusion antibody useful for the treatment of HIV infection; OsTAVIR (Protein Design Labs, Inc., CA) which is a human antibody useful for the treatment of hepatitis B virus; PROTOVIR. (Protein Design Labs, Inc., CA) which is a humanised IgG1 antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococcus aureus, Vibrio colerae, Escherichia coli, Pseudomonas aeruginosa, Campylobacter* (*Vibrio*) fetus, *Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohernorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp.); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium* malaria); or *Helminiths* (*Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms).

Other antibodies useful for the treatment of viral disease include, but are not limited to, antibodies against antigens of pathogenic viruses, including as examples and not by limitation: Poxviridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

In an alternative embodiment, the antibody of the drug conjugate of the present invention may also be any antibody known for the treatment of prevention of autoimmune disorders, such as, but not limited to, Th2-lymphocyte related disorders (e.g. atopic dermatitis, atopic asthma, rhinoconjunctivitis, allergic rhinitis, Omenn's syndrome, systemic sclerosis, and graft versus host disease); Th1 lymphocyte-related disorders (e.g. rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g. systemic lupus erythematosus, Goodpasture's syndrome, rheumatoid arthritis, and type I diabetes); and Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dresser's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibritis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthahnia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia and Wegener's Granulomatosis.

Antibodies immunospecific for an antigen of a cell that is responsible for producing autoimmune antibodies can be obtained by any method known to one of skill in the art such as, e.g., chemical synthesis or recombinant expression techniques. Examples of autoimmune antibodies include, but are not limited to, Anti-Nuclear Antibody; Anti ds DNA; Anti ss DNA, Anti Cardiolipin Antibody IgM, IgG; Anti Phospholipid Antibody IgM, IgG; Anti SM Antibody; Anti Mitochondrial Antibody; Thyroid Antibody; Microsomal Antibody; Thyroglobulin Antibody; Anti SCL-70; Anti-Jo; Anti-U1RNP; Anti-La/SSB; Anti SSA; Anti SSB; Anti Perital Cells Antibody; Anti Histones; Anti-RNP; C-ANCA; P-ANCA; Anti centromere; Anti-Fibrillarin, and Anti-GBM Antibody.

In another embodiment, the antibody of the drug conjugate of the present invention can be one that binds to both a receptor or a receptor complex expressed on an activated lymphocyte, such as one associated with an autoimmune disease. The receptor or receptor complex can comprise an immunoglobulin gene superfamily member, a TNF receptor superfamily member, an integrin, an interleukin, a cytokine receptor, a chemokine receptor, a major histocompatibility protein, a lectin, or a complement control protein. Non-limiting examples of suitable immunoglobulin superfamily members are CD2, CD3, CD4, CD5, CD8, CD13, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-RI, TNFR-2, RANK, TACI, BCMA, osteoprotegerin, Apo2/TRAEL-RI, TRAIL-R2, TRAIL-R3, TRABL-R4, and APO-3. Non-limiting examples of suitable integrins are CDI la, CDIIb, CDIIc, CD18, CD29, CD41, CD49a, CD49b, CD49c, CD49d, CD49e, CD49f, CD103, and CD104. Non-limiting examples of suitable lectins are C-type, S-type, and I-type lectin.

An antibody that binds a molecular target or an antigen of interest, e.g., ErbB2 antigen, is one capable of binding that antigen with sufficient affinity such that the antibody is useful in targeting a cell expressing the antigen. Where the antibody is one which binds ErbB2, it will usually preferentially bind ErbB2 as opposed to other ErbB receptors, and may be one which does not significantly cross-react with other proteins such as EGFR, ErbB 3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al., Nature 312: 513-516 (1984) and Drebin et al., Nature 312:545-548 (1984).

In another embodiment, the antibody of the drug conjugate or target of the present invention may be selected from an antibody or target in the below table. Such antibodies are immunospecific for a target antigen and can be obtained commercially or produced by any method known in the art such as, e.g., recombinant expression techniques.

TABLE 1

Therapeutic monoclonal antibodies

| Name | Trade name | Target |
|---|---|---|
| 3F8 | | GD2 ganglioside |
| 8H9 | | B7-H3 |
| Abagovomab | | CA-125 (imitation) |
| Abciximab | ReoPro | CD41 7E3 |
| Abituzumab | | CD51 |
| Abrilumab | | Integrin $\alpha 4\beta 7$ |
| Actoxumab | | *Clostridium difficile* |
| Adalimumab | Humira | TNF-$\alpha$ |
| Adecatumumab | | EpCAM |

TABLE 1-continued

Therapeutic monoclonal antibodies

| Name | Trade name | Target |
|---|---|---|
| Atidortoxumab | | *Staphylococcus aureus* alpha toxin |
| Aducanumab | | Beta-amyloid |
| Afasevikumab | | IL17A and IL17F |
| Afutuzumab | | CD20 |
| Alemtuzumab | Campath, Lemtrada | CD52 |
| Alirocumab | Praluent | PCSK9 |
| Altumomab | Hybri-ceaker | CEA |
| Amatuximab | | Mesothelin |
| Andecaliximab | | gelatinase B |
| Anetumab | | MSLN |
| Anifrolumab | | interferon α/β receptor |
| Anrukinzumab | | IL-13 |
| Apolizumab | | HLA-DR β-chain |
| Aprutumab | | FGFR2 |
| Ascrinvacumab | | Activin receptor-like kinase 1 |
| Aselizumab | | L-selectin (CD62L) |
| Atezolizumab | Tecentriq | PD-L1 |
| Atidortoxumab | | *Staphylococcus aureus* alpha toxin |
| Atinumab | | RTN4 |
| Atorolimumab | | Rhesus factor |
| Avelumab | Bavencio | PD-L1 |
| Azintuxizumab | | CD319 |
| Bapineuzumab | | beta amyloid |
| Basiliximab | Simulect | CD25 (α chain of IL-2 receptor) |
| Bavituximab | | phosphatidylserine |
| BCD-100 | | PD-1 |
| Bectumomab | LymphoScan | CD22 |
| Begelomab | | DPP4 |
| Belantamab | | BCMA |
| Belimumab | Benlysta | BAFF |
| Bemarituzumab | | FGFR2 |
| Benralizumab | Fasenra | CD125 |
| Berlimatoxumab | | *Staphylococcus aureus* bi-component leukocidin |
| Bersanlimab | | ICAM-1 |
| Bertilimumab | | CCL11 (eotaxin-1) |
| Besilesomab | Scintimun | CEA-related antigen |
| Bevacizumab | Avastin | VEGF-A |
| Bezlotoxumab | Zinplava | *Clostridium difficile* |
| Blinatomumab | Blincyto | CD19, CD3 |
| Bimagrumab | | ACVR2B |
| Bimekizumab | | IL 17A and IL17F |
| Birtamimab | | Serum amyloid A protein |
| Bivatuzumab | | CD44 v6 |
| BIVV009 | | C1s |
| Bleselumab | | CD40 |
| Blontuvetmab | Biontress | CD20 |
| Blosozumab | | SOST |
| Bococizumab | | Neural apoptosis-regulated proteinase 1 |
| Brazikumab | | IL23 |
| Brentuximab | Adcentris | CD30 (TNFRSF8) |
| Briakinumab | | IL-12, IL-23 |
| Brodalumab | Siliz | IL-17 |
| Brontictuzumab | | Notch 1 |
| Burosumab | Crysvita | FGF23 |
| Cabiralizumab | | CSF1R |
| Camidanlumab | | CD25 |
| Camrelizumab | | Programmed cell death 1 |
| Canakinumab | Haris | IL-1 |
| Cantuzumab | | MUC-1 |
| Capromab | Prostascint | prostatic carcinoma cells |
| Carlumab | | MCP-1 |
| Carotuximab | | endoglin |
| Catumaxomab | Removab | EpCAM, CD3 |
| CC49 | | TAG-72 |
| CBR96 | | Lewis-Y antigen |
| Cedelizumab | | CD4 |
| Cemiplimab | | PCDC1 |
| Cergutuzumab | | IL2 |
| Cetrelimab | | Programmed cell death 1 |
| Cetuximab | Erbitux | EGFR |
| Cibisatamab | | CEACAM5 |
| Cixutumumab | | IGF-1 receptor (CD221) |
| Clazakizumab | | IL6 |
| Clenoliximab | | CD4 |
| Clivatuzumab | hPAM4-Cide | MUC1 |

TABLE 1-continued

| Therapeutic monoclonal antibodies | | |
|---|---|---|
| Name | Trade name | Target |
| Codrituzumab | | glypican 3 |
| Cofetuzumab | | PTK7 |
| Coltuximab | | CD19 |
| Conatumumab | | TRAIL-R2 |
| Concizumab | | TFPI |
| Cosfroviximab | ZMapp | Ebolavirus glycoprotein |
| CR6261 | | Influenza A hemagglutinin |
| Crenezumab | | 1-40-β-amyloid |
| Crizanlizumab | | Selectin P |
| Crotedumab | | GCGR |
| Cusatuzumab | | CD70 |
| Dacetuzumab | | CD40 |
| Daclizumab | Zenapax | CD25 (α chain of IL-2 receptor) |
| Dalotuzumab | | IGF-1 receptor (CD221) |
| Dapirolizumab pegol | | CD154 (CD40L) |
| Daratumumab | Darzalex | CD38 |
| Dectrekumab | | IL-13 |
| Demcizumab | | DLL4 |
| Denintuzumab | | CD19 |
| Denosumab | Prolia | RANKL |
| Depatuxizumab | | EGFR |
| Derlotuximab | | Histone complex |
| Detumomab | | B-lymphoma cell |
| Dezamizumab | | Serum amyloid P component |
| Dinutuximab | Unituxin | GD2 ganglioside |
| Diridavumab | | hemagglutinin |
| Domagrozumab | | GDF-8 |
| Drozitumab | | DR5 |
| Duligotuzumab | | ERBB3 (HER3) |
| Dupilumab | Dupixent | IL4 |
| Durvalumab | Imfinzi | PD-L1 |
| Dusigitumab | | ILGF2 |
| Ecromeximab | | GD3 ganglioside |
| Eculizumab | Soliris | C5 |
| Edobacomab | | endotoxin |
| Edrecolomab | Panorex | EpCAM |
| Efalizumab | Raptiva | LFA-1 (CD11a) |
| Eldelumab | | interferon gamma-induced protein |
| Elezanumab | | RGMA |
| Elgemtumab | | ERBB3 (HER3) |
| Elotuzumab | Empliciti | SLAMF7 |
| Elsilimomab | | IL-6 |
| Emactuzumab | | CSF1R |
| Emapalumab | Gamifant | Interferon gamma |
| Emibetuzumab | | HHGFR |
| Emicizumab | Hemlibra | Activated F9, F10 |
| Enapotamab | | AXL |
| Enavatuzumab | | TWEAK receptor |
| Enfortumab | | nectin-4 |
| Enlimomab pegol | | ICAM-1 (CD54) |
| Enoblituzumab | | CD276 |
| Enokizumab | | IL9 |
| Enoticumab | | DLL4 |
| Ensituximab | | 5AC |
| Epitumomab | | episialin |
| Epratuzumab | | CD22 |
| Eptinezumab | | Calcitonin gene-related peptide |
| Erenumab | Aimovig | CGRP |
| Ertumaxomab | Rexomun | HER2/neu, CD3 |
| Etaracizumab | Abegrin | integrin $\alpha_v\beta_3$ |
| Etigilimab | | TIGIT |
| Etrolizumab | | integrin $\beta_7$ |
| Evinacumab | | Angiopoietin 3 |
| Evolocumab | Repatha | PCSK9 |
| Exbivirumab | | hepatitis B surface antigen |
| Fanolesomab | NeutroSpec | CD15 |
| Faralimomab | | interferon receptor |
| Faricimab | | VEGF-A and Ang-2 |
| Farletuzumab | | folate receptor 1 |
| Fasinumab | | HNGF |
| FBTA05 | Lymphomun | CD20 |
| Felvizumab | | respiratory syncytial virus |
| Fezakinumab | | IL-22 |
| Fibatuzumab | | Ephrin receptor A3 |
| Ficlatuzumab | | HGF |

TABLE 1-continued

Therapeutic monoclonal antibodies

| Name | Trade name | Target |
|---|---|---|
| Figitumumab | | IGF-1 receptor (CD221) |
| Firivumab | | Influenza A virus hemagglutinin |
| Flanvotumab | | TYRP1 (glycoprotein 75) |
| Fletikumab | | IL-20 |
| Fontolizumab | HuZAF | IFN-γ |
| Foralumab | | CD3 epsilon |
| Foravirumab | | rabies virus glycoprotein |
| Fremanezumab | | Calcitonin gene-related peptide alpha |
| Fresolimumab | | TGF-β |
| Frunevetmab | | NGF |
| Fulranumab | | NGF |
| Futuximab | | EGFR |
| Galcanezumab | | calcitonin |
| Galiximab | | CD80 |
| Ganitumab | | 1 receptor (CD221) |
| Gantenerumab | | beta amyloid |
| Gatipotuzumab | | MUC1 |
| Gavilimomab | | CD147 (basigin) |
| Gedivumab | | Hemagglutinin HA |
| Gemtuzumab | Mylotarg | CD33 |
| Gevokizumab | | IL-1β |
| Gilvetmab | | PCDC1 |
| Gimsilumab | | CSF2 |
| Girentuximab | Rencarex | carbonic anhydrase 9 (CA-IX) |
| Glembatumumab | | GPNMB |
| Golimumab | Simponi | TNF-α |
| Gomiliximab | | CD23 (IgE receptor) |
| Gosuranemab | | tau protein |
| Guselkumab | Tremfya | IL23 |
| Ianalumab | | BAFF-R |
| Ibalizumab | Trogarzo | CD4 |
| Ibritumomab | Zevalin | CD20 |
| Icrucumab | | VEGFR-1 |
| Idarucizumab | Praxbind | dabigatran |
| Ifabotuzumab | | EPHA3 |
| Iladatuzumab | | CD97B |
| IMAB362 | | CLDN18.2 |
| Imalumab | | MIF |
| Imaprelimab | | MCAM |
| Imciromab | Myoscint | cardiac myosin |
| Imgatuzumab | | EGFR |
| Inclacumab | | selectin P |
| Indatuximab | | SDC1 |
| indusatumab | | GUCY2C |
| inebilizumab | | CD19 |
| Infliximab | Remicade | TNF-α |
| Inolimomab | | CD25 (α chain of IL-2 receptor) |
| Inotuzumab | Besponsa | CD22 |
| Intetumumab | | CD51 |
| Ipilimumab | Yervoy | CD152 |
| Iomab-B | | CD45 |
| Iratumumab | | CD30 (TNFRSF8) |
| Isatuximab | | CD38 |
| Iscalimab | | CD40 |
| Istiratumab | | IGF1R, CD221 |
| Itolizumab | Alzumab | CD6 |
| Ixekizumab | Taltz | IL-17A |
| Keliximab | | CD4 |
| Labetuzumab | CEA-Cide | CEA |
| Lacnotuzumab | | CSF1, MCSF |
| Ladiratuzumab | | LIV-1 |
| Lanadelumab | | kallikrein |
| Landogrozumab | | GDF-8 |
| Laprituximab | | EGFR |
| Larcaviximab | | Ebolavirus glycoprotein |
| Lebrikizumab | | IL-13 |
| Lemalesomab | | NCA-90 (granulocyte antigen) |
| Lendalizumab | | C5 |
| Lenvervimab | | Hepatitis B surface antigen |
| Lenzilumab | | CSF2 |
| Lerdelimumab | | TGF beta 2 |
| Leronlimab | | CCR5 |
| Lesofavumab | | Hemagglutinin HA |
| Lexatumumab | | TRAIL-R2 |
| Libivirumab | | hepatitis B surface antigen |
| Lifastuzumab | | Phosphate-sodium co-transporter |

TABLE 1-continued

| Therapeutic monoclonal antibodies | | |
|---|---|---|
| Name | Trade name | Target |
| Ligelizumab | | IGHE |
| Lilotomab | | CD37 |
| Lintuzumab | | CD33 |
| Lirilumab | | KIR2D |
| Lodelcizumab | | PCSK9 |
| Lokivetmab | Cytopoint | *Canis lupus familiaris* IL31 |
| Loncastuximab | | CD19 |
| Losatuxizumab | | EGFR, ERBB1 HER1 |
| Lorvotuzumab | | CD56 |
| Lucatumumab | | CD40 |
| Lulizumab pegol | | CD28 |
| Lumiliximab | | CD23 (IgE receptor) |
| Lumretuzumab | | ERBB3 (HER3) |
| Lupartumab | | LYPD3 |
| Lutikizumab | | Interleukin 1 alpha |
| MABp1 | Xilonix | IL1A |
| Mapatumumab | | TRAIL-R1 |
| Margetuximab | | HER2 |
| Marstacimab | | TFPI |
| Maslimomab | | T-cell receptor |
| Mavrilimumab | | GMCSF receptor α-chain |
| Matuzumab | | EGFR |
| Mepolizumab | Bosatria | IL-5 |
| Metelimumab | | TGF beta 1 |
| Milatuzumab | | CD74 |
| Minretumomab | | TAG-72 |
| Mirikizumab | | IL23A |
| Mirvetuximab | | Folate receptor alpha |
| Mitumomab | | GD3 ganglioside |
| Modotuximab | | EGFR extracellular domain III |
| Mogamulizumab | Poteligeo | CCR4 |
| Monalizumab | | NKG2A |
| Morolimumab | | Rhesus factor |
| Mosunetuzumab | | CD3E, MS4A1, CD20 |
| Motavizumab | Numax | respiratory syncytial virus |
| Moxetumomab | | CD22 |
| Muromonab-CD3 | Orthoclone OKT3 | CD3 |
| Namilumab | | CSF2 |
| Naratuximab | | CD37 |
| Narnatumab | | RON |
| Natalizumab | Tysabri | integrin $\alpha_4$ |
| Navicixizumab | | DLL4 |
| Navivumab | | Influenza A virus hemagglutinin HA |
| Naxitamab | | C-Met |
| Nebacumab | | endotoxin |
| Necitumumab | Portrazza | EGFR |
| Nemolizumab | | IL31RA |
| Nerelimomab | | TNF-α |
| Nesvacumab | | angiopoietin 2 |
| Netakimab | | Interleukin 17A |
| Nimotuzumab | Theracim, Theraloc | EGFR |
| Nirsevimab | | RSVFR |
| Nivolumab | Opdivo | PD-1 |
| Obiltoxaximab | Anthim | *Bacillus anthracis* anthrax |
| Obinutuzumab | Gazyva | CD20 |
| Ocaratuzumab | | CD20 |
| Ocrelizumab | Ocrevus | CD20 |
| Odulimomab | | LFA-1 (CD11a) |
| Ofatumumab | Arzerra | CD20 |
| Olaratumab | Lartruvo | PDGF-R α |
| Oleclumab | | 5'-nucleotidase |
| Olendalizumab | | Complement C5a |
| Olokizumab | | IL6 |
| Omalizumab | Xolair | IgE Fc region |
| OMS721 | | MASP-2 |
| Onartuzumab | | human scatter factor receptor kinase |
| Ontuxizumab | | TEM1 |
| Onvatilimab | | VSIR |
| Opicinumab | | LINGO-1 |
| Oregovomab | OvaRex | CA-125 |
| Orticumab | | oxLDL |
| Otelixizumab | | CD3 |
| Otilimab | | GMCSF |
| Otlertuzumab | | CD37 |
| Oxelumab | | OX-40 |
| Ozanezumab | | NOGO-A |

TABLE 1-continued

| Therapeutic monoclonal antibodies | | |
|---|---|---|
| Name | Trade name | Target |
| Ozoralizumab | | TNF-α |
| Pagibaximab | | lipoteichoic acid |
| Palivizumab | Synagis, Abbosynagis | F protein of respiratory syncytial virus |
| Pamrevlumab | | CTGF |
| Panitumumab | Vectibix | EGFR |
| Pankomab | | Tumor specific glycosylation of MUC1 |
| Panobacumab | | *Pseudomonas aeruginosa* |
| Parsatuzumab | | EGFL7 |
| Pascolizumab | | IL-4 |
| Pasotuxizumab | | Folate hydrolase |
| Pateclizumab | | LTA |
| Patritumab | | ERBB3 (HER3) |
| Pembrolizumab | Keytruda | PD1 |
| Pemtumomab | Theragyn | MUC1 |
| Perakizumab | | IL17A |
| Pertuzumab | Omnitarg | HER2/neu |
| Pidilizumab | | PD-1 |
| Pinatuzumab | | CD22 |
| Pintumomab | | adenocarcinoma antigen |
| Placulumab | | human TNF |
| Plozalizumab | | CCR2 |
| Pogalizumab | | TNFR superfamily member 4 |
| Polatuzumab | | CD79B |
| Ponezumab | | human beta-amyloid |
| Porgaviximab | | Zaire evolavirus glycoprotein |
| Prasinezumab | | NACP |
| Prezalizumab | | ICOSL |
| Priliximab | | CD4 |
| Pritoxaximab | | *E. coli* shiga toxin type-1 |
| Pritumumab | | vimentin |
| PRO 140 | | CCR5 |
| Quilizumab | | IGHE |
| Racotumomab | Vaxira | NGNA ganglioside |
| Radretumab | | fibronectin extra domain-B |
| Rafivirumab | | rabies virus glycoprotein |
| Ralpancizumab | | Neural apoptosis-regulated proteinase 1 |
| Ramucirumab | Cyramza | VEGFR2 |
| Ranevetmab | | NGF |
| Ravagalimab | | CD40 |
| Ravulizumab | | C5 |
| Raxibacumab | | anthrax toxin, protective antigen |
| Refanezumab | | Myelin-associated glycoprotein |
| Regavirumab | | cytomegalovirus glycoprotein B |
| Relatlimab | | LAG3 |
| Remtolumab | | Interleukin 17 alpha, TNF |
| Reslizumab | Cinqair | IL-5 |
| Rilotumumab | | HGF |
| Rinucumab | | Platelet-derived growth factor receptor beta. |
| Risankizumab | | IL23A |
| Rituximab | MabThera, Rituxan | CD20 |
| Rivabazumab pegol | | *Pseudomonas aeruginosa* type III secretion system |
| Robatumumab | | IGF-1 receptor (CD221) |
| Rmab | RabiShield | Rabies virus G glycoprotein |
| Roledumab | | RHD |
| Romilkimab | | Interleukin 13 |
| Romosozumab | Evenity | sclerostin |
| Rontalizumab | | IFN-α |
| Rosmantuzumab | | Root plate-specific spondin 3 |
| Rovalpituzumab | | DLL3 |
| Rovelizumab | LeukArrest | CD11, CD18 |
| Rozanolixizumab | | FCGRT |
| Ruplizumab | Antova | CD154 (CD40L) |
| SA237 | | IL-6R |
| Sacituzumab | | TROP-2 |
| Samalizumab | | CD200 |
| Samrotamab | | LRRC15 |
| Sapelizumab | | IL6R |
| Sarilumab | Kevzara | IL6 |
| Satralizumab | | IL6 receptor |
| Satumomab | | TAG-72 |
| Secukinumab | Cosentyx | IL-17A |
| Selicrelumab | | CD40 |
| Seribantumab | | ERBB3 (HER3) |
| Setoxaximab | | *E. coli* shiga toxin type-2 |

TABLE 1-continued

Therapeutic monoclonal antibodies

| Name | Trade name | Target |
|---|---|---|
| Setrusumab | | SOST |
| Sevirumab | | cytomegalovirus |
| Sibrotuzumab | | FAP |
| SGN-CD19A | | CD19 |
| SHP647 | | Mucosal addressin cell adhesion molecule |
| Sifalimumab | | IFN-α |
| Siltuximab | Sylvant | IL-6 |
| Simtuzumab | | LOXL2 |
| Sintilimab | | PD-1 |
| Siplizumab | | CD2 |
| Sirtratumab | | SLITRK6 |
| Sirukumab | | IL-6 |
| Sofituzumab | | CA-125 |
| Solanezumab | | beta amyloid |
| Sonepcizumab | | sphingosine-1-phosphate |
| Sontuzumab | | episialin |
| Spartalizumab | | PDCD1, CD279 |
| Stamulumab | | myostatin |
| Suptavumab | | RSVFR |
| Sutimlimab | | C1S |
| Suvizumab | | HIV-1 |
| Suvratoxumab | | *Staphylococcus aureus* alpha toxin |
| Tabalumab | | BAFF |
| Tacatuzumab | AFP-Cide | alpha-fetoprotein |
| Talacotuzumab | | CD123 |
| Talizumab | | IgE |
| Tamtuvetmab | Tactress | CD52 |
| Tanezumab | | NGF |
| Taplitumomab | | CD19 |
| Tarextumab | | Notch receptor |
| Tavolimab | | CD134 |
| Tefibazumab | Aurexis | clumping factor A |
| Telisotuzumab | | HGFR |
| Tenatumomab | | tenascin C |
| Teneliximab | | CD40 |
| Teplizumab | | CD3 |
| Tepoditamab | | Dendritic cell-associated lectin 2 |
| Teprotumumab | | IGF-1 receptor (CD221) |
| Tesidolumab | | C5 |
| Tetulomab | | CD37 |
| Tezepelumab | | TSLP |
| Tibulizumab | | BAFF |
| Tildrakizumab | Ilumya | IL23 |
| Tigatuzumab | | TRAIL-R2 |
| Timigutuzumab | | HER2 |
| Timolumab | | AOC3 |
| Tiragotumab | | TIGIT |
| Tislelizumab | | PCDC1, CD279 |
| Tisotumab | | Coagulation factor III |
| Tocilizumab | Actemra, RoActemra | IL-6 receptor |
| Tomuzotuximab | | EGFR, HER1 |
| Toralizumab | | CD154 (CD40L) |
| Tosatoxumab | | *Staphylococcus aureus* |
| Tositumomab | Bexxar | CD20 |
| Tovetumab | | CD140a |
| Tralokinumab | | IL-13 |
| Trastuzumab | Herceptin | HER2/neu |
| TRBS07 | Ektomab | GD2 ganglioside |
| Tregalizumab | | CD4 |
| Tremelimumab | | CTLA-4 |
| Trevogrumab | | Growth differentiation factor 8 |
| Tucotuzumab | | EpCAM |
| Tuvirumab | | hepatitis B virus |
| Ublituximab | | MS4A1 |
| Ulocuplumab | | CXCR4 (CD184) |
| Urelumab | | 4-1BB (CD137) |
| Urtoxazumab | | *Escherichia coli* |
| Ustekinumab | Stelara | IL-12, IL-23 |
| Utomilumab | | 4-1BB (CD137) |
| Vadastuximab | | CD33 |
| Vanalimab | | CD40 |
| Vandortuzumab | | STEAP1 |
| Vantictumab | | Frizzled receptor |
| Vanucizumab | | angiopoietin 2 |
| Vapaliximab | | AOC3 (VAP-1) |
| Varisacumab | | VEGF-A |

TABLE 1-continued

| Therapeutic monoclonal antibodies | | |
|---|---|---|
| Name | Trade name | Target |
| Varlilumab | | CD27 |
| Vatelizumab | | ITGA2 (CD49b) |
| Vedolizumab | Entyvio | integrin $\alpha_4\beta_7$ |
| Veltuzumab | | CD20 |
| Vepalimomab | | AOC3 (VAP-1) |
| Vesencumab | | NRP1 |
| Visilizumab | Nuvion | CD3 |
| Volociximab | | integrin $\alpha_5\beta_1$ |
| Vonlerolizumab | | CD134 |
| Vopratelimab | | ICOS |
| Vorsetuzumab | | CD70 |
| Votumumab | HumaSPECT | tumor antigen CTAA16.88 |
| Vunakizumab | | Interleukin 17 alpha |
| Xentuzumab | | IGF1, IGF2 |
| XMAB-5574 | | CD19 |
| Zalutumumab | HuMax-EGFr | EGFR |
| Zanolimumab | HuMax-CD4 | CD4 |
| Zatuximab | | HER1 |
| Zenocutuzumab | | ERBB3, HER3 |
| Ziralimumab | | CD147 (basigin) |
| Zolbetuximab | | CLDN18 |
| Zolimomab | | CD5 |

In addition to the above, the antibody of the drug antibody conjugate of the present invention may be Vitaxin which is a humanised antibody for the treatment of sarcoma; Smart IDIO which is a humanised anti-HLA-DR antibody for the treatment of non-Hodgkin's lymphoma; Oncolym which is a radiolabeled murine anti-HLA-DrIO antibody for the treatment of non-Hodgkin's lymphoma; and Allomune which is a humanised anti-RD2 mAb for the treatment of Hodgkin's Disease or non-Hodgkin's lymphoma.

The antibody of the drug conjugate of the present invention may also be any antibody-fragment known for the treatment of any disease, preferably cancer. Again, such antibody fragments are immunospecific for a target antigen and can be obtained commercially or produced by any method known in the art such as, e.g., recombinant expression techniques. Examples of such antibodies available include any from the below table.

TABLE 2

| Therapeutic monoclonal antibody fragments | | | |
|---|---|---|---|
| Fragment type/format | Name | Trade name | Target |
| Fab/chimeric | abciximab | ReoPro | CD41 (integrin alpha-IIb) |
| Fab/humanised | abrezekimab | | Interleukin 13 |
| $F(ab')_2$/mouse | Afelimomab | | TNF-$\alpha$ |
| $F(ab')_2$/humanised | Alacizumab pegol | | VEGFR2 |
| Fab/mouse | Anatumomab | | TAG-72 |
| Fab/ovine | | CroFab | Snake venom |
| Fab/ovine | | DigiFab | Digoxin |
| Fab/ovine | | Digibind | Digoxin |
| Fab'/mouse | arcitumomab | CEA-scan | CEA |
| Fab'/mouse | bectumomab | LymphoScan | CD22 |
| Fab'/mouse | biciromab | FibriScint | fibrin II, beta chain |
| BiTE/mouse | Blinatumomab | Blincyto | CD19 |
| scFv/humanised | brolucizumab | | VEGFA |
| sdAb/humanised | caplacizumab | Cablivi | VWF |
| Fab'/PEGylated humanised | certolizumab pegol | Cimzia | TNF-$\alpha$ |
| Fab/humanised | citatuzumab | | EpCAM |
| $F(ab')_2$/mouse | dorlimomab | | unknown |
| scFv/chimeric humanised | duvortuxizumab | | CD19, CD3E |
| scFv/human | efungumab | Mycograb | Hsp90 |
| $F(ab')_2$/humanised | erlizumab | | ITGB2 (CD18) |
| Di-scFy | flotetuzumab | | IL-3 receptor |
| scFv/human | gancotamab | | unknown |
| $F(ab')_2$/mouse | igovomab | Indimacis-125 | CA-125 |
| Fab/humanised | lampalizumab | | CFD |
| scFv/humanised | letolizumab | | TRAP |
| Fab/mouse | nacolomab | | C242 antigen |
| Fab/mouse | naptumomab | | 5T4 |
| Fab/mouse | nofetumomab | | unknown |

TABLE 2-continued

| Therapeutic monoclonal antibody fragments | | | |
|---|---|---|---|
| Fragment type/format | Name | Trade name | Target |
| scFv/humanised | oportuzumab | Vicinium | EpCAM |
| Fab/humanised | ranibizumab | Lucentis | VEGF-A |
| BiTE/mouse | Solitomab | | EpCAM |
| Fab'/mouse | sulesomab | LeukoScan | NCA-90 (granulocyte antigen) |
| Fab | Tadocizumab | | integrin $\alpha_{IIb}\beta_3$ |
| Fab/mouse | Telimomab | | unknown |
| scFv/humanised | Vobarilizumab | | IL6R |
| Fab/humanised | | Thromboview | D-dimer |
| Fab/PEGylated humanised | CDP791 | | VEGF |
| Fab/bispecific humanised | MDX-H210 | | Her2/Neu & CD64 (γFcR1) |
| scFv/humanised | Pexelizumab | | Complement C5 |
| $(ScFv)_4$ fused to streptavidin mouse | CC49 | | TAG-72 Pancarcinoma antigen |
| ScFv fused to β-lactamase human | SGN-17 | | P97 antigen |
| ScFv fused to PEG human | F5 scFv-PEG Immunoliposome | | Her2 |
| Diabody $(V_H-V_L)2$ human | C6.5K-A | | Her2/Neu |
| Diabody $(V_H-V_L)2$ human | L19 L19-yIFN | | EDB domain of fibronectin |
| Diabody $(V_L-V_H)2$ human | T84.66 | | CEA |
| Minibody $(scF_v-C_H3)_2$ murine-human chimera (minibody) | T84.66 | | CEA |
| Minibody murine-human chimera (minibody) | 10H8 | | Her2 |
| $S_cF_v$ dimer Fc $(S_cFv)_2$-FC murine-human chimera (minibody) | T84.66 | | CEA |
| Bispecific scFv $(V_L-V_H-V_H-V_L)$ mouse | r28M | | CD28 and MAP |
| Bispecific scFv $(V_L-V_H-V_H-V_L)$ origin unknown | BiTE MT103 | | CD19 and CD3 |
| Bispecific scFv $(V_L-V_H-V_H-V_L)$ origin unknown | BiTE | | Ep-CAM and CD3 |
| Bispecific tandem diabody (VH-VL- VH -VL) (mouse) | Tandab | | CD19 & CD3 |
| VhH-β-lactamase fusion camelid | Nanobody | | CEA |
| Dab/human | Anti-TNFα dAb | | TNFα |
| VhH/camelid | Nanobody | | TNFα |
| VhH/camelid | Nanobody | | Von Willebrand factor |

Fab fragment, antigen-binding (one arm)
F(ab')2 fragment, antigen-binding, including hinge region (both arms)
Fab'fragment, antigen-binding, including hinge region (one arm)
scFv single-chain variable fragment
di-scFv dimeric, single-chain variable fragment (Holliger & Hudson, Nature Biotechnology, 2005, 23(9), 1126-1136).

In a preferred embodiment, the antibody in the drug conjugates of the present invention targets a cell surface antigen.

In preferred embodiments, the antibody in the drug conjugates of the present invention may bind to a receptor encoded by the ErbB gene. The antibody may bind specifically to an ErbB receptor selected from EGFR, HER2, HER3 and HER4. Preferably, the antibody in the drug conjugate may specifically bind to the extracellular domain of the HER2 receptor and inhibit the growth of tumour cells which overexpress the HER2 receptor. The antibody of the drug conjugate may be a monoclonal antibody, e.g. a murine monoclonal antibody, a chimeric antibody, or a humanised antibody. Preferably, the humanised antibody may be huMAb4D5-1, huMAb4D5-2, huMAb4D5-3, huMAb4D5-4, huMAb4D5-5, huMAb4D5-6, huMAb4D5-7 or huMAb4D5-8 (Trastuzumab), particularly preferably Trastuzumab. The antibody may also be an antibody fragment, e.g. a Fab fragment.

Other preferred antibodies include:

(i) anti-CD4 antibodies. The antibody of the drug conjugate may be a monoclonal antibody, e.g. a murine monoclonal antibody, a chimeric antibody, or a humanised antibody;

(ii) anti-CD5 antibodies. The antibody of the drug conjugate may be a monoclonal antibody, e.g. a murine monoclonal antibody, a chimeric antibody, or a humanised antibody;

(iii) anti-CD13 antibodies. The antibody of the drug conjugate may be a monoclonal antibody, e.g. a murine monoclonal antibody, a chimeric antibody, or a humanised antibody;

(iv) anti-CD20 antibodies. The antibody of the drug conjugate may be a monoclonal antibody, e.g. a murine monoclonal antibody, a chimeric antibody, or a humanised antibody. Preferably, the humanised antibody is Rituximab or an antibody fragment thereof, e.g. a Fab fragment; and (v) anti-CD30 antibodies. The antibody of the drug conjugate may be a monoclonal antibody, e.g. a murine monoclonal antibody, a chimeric antibody, or a humanised antibody. Preferably the humanised antibody is Brentuximab vedotin or an antibody fragment thereof.

In one embodiment of the invention, the drug antibody conjugate may demonstrate one or more of the following: (i) increased cytotoxicity (or a decrease in cell survival), (ii) increased cytostatic activity (cytostasis), (iii) increased binding affinity to the target antigen or epitope, (iv) increased internalisation of the conjugate, (v) reduction of patient side effects, and/or (vi) improved toxicity profile. Such increase may be relative to a known drug antibody conjugate in the art that binds the same or a different epitope or antigen.

Processes For The Preparation Of The Drug Antibody Conjugates

The drug antibody conjugates of the present invention can be prepared according to techniques that are well known in the art. Processes for conjugating moieties comprising at least one antigen binding site antibodies such as antibodies to a number of different drugs using different processes have been described and exemplified previously in, for example, WO-A-2004/010957, WO-A-2006/060533 and WO-A-2007/024536, the contents of which are incorporated herein by reference thereto. These involve use of a linker group that derivatises the drug, toxin or radionuclide in such a way that it can then be attached to the moiety such as an antibody. Attachment to the moiety such as an antibody is typically by one of three routes: via free thiol groups in cysteines after partial reduction of disulfide groups in the antibody; via free amino groups in lysines in the antibody; and via free hydroxyl groups in serines and/or threonines in the antibody. The attachment method varies depending upon the site of attachment on the moiety such as an antibody. Purification of antibody-drug conjugates by size exclusion chromatography (SEC) has also been described [see, e.g., Liu et al., Proc. Natl. Acad. Set (USA), 93: 8618-8623 (1996), and Chari et al., Cancer Research, 52: 127-131 (1992)].

As previously noted, the drug payloads of the drug conjugates of the present invention are ecteinascidin derivatives disclosed in, or fall within the scope of, International patent application no. PCT/EP2018/060868, the contents of which are incorporated herein by reference thereto. These compounds are synthesised according to the processes described in the present application.

As noted earlier, there is provided a process for the preparation of a drug conjugate according to the present invention comprising conjugating a moiety Ab comprising at least one antigen binding site and a drug D of formula (IH), (IHa) or (IHb), Ab and D being as defined herein.

One example of a process for the preparation of a drug conjugate of the present invention involves the preparation of drug antibody conjugates of formula (G) or (G') of the present invention as follows:

(G)

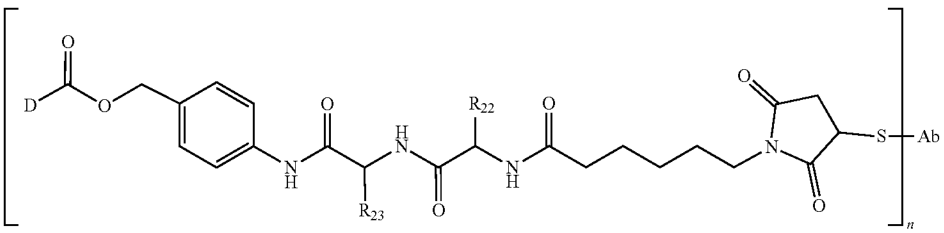

(G)

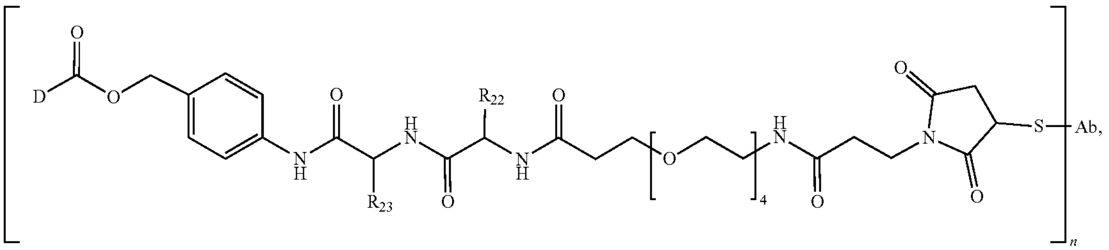

said process comprising the following steps:
(i) reacting a drug (D-H) of formula (IH)-H:
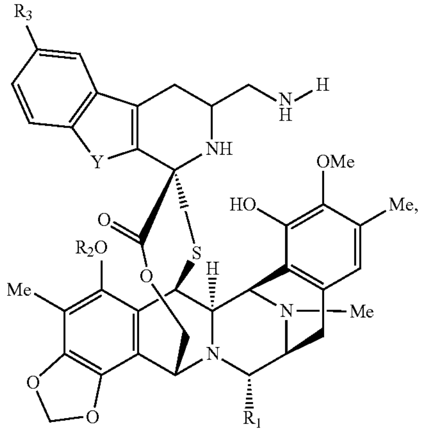
wherein the substituents in the definitions of (IH)-H are as defined above for formula (IH), with a compound of formula (D') or (E):
(D)
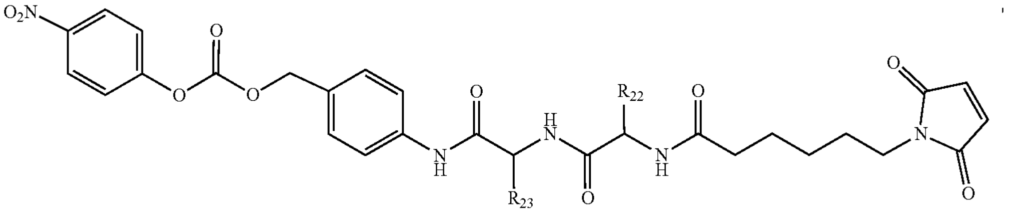
(E)
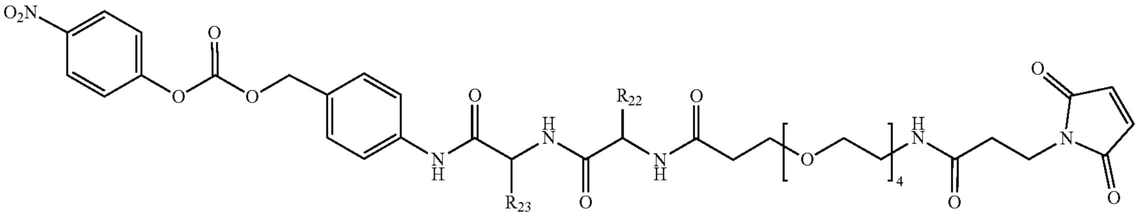
to give a compound of formula (F) or (F'), respectively:
(F)
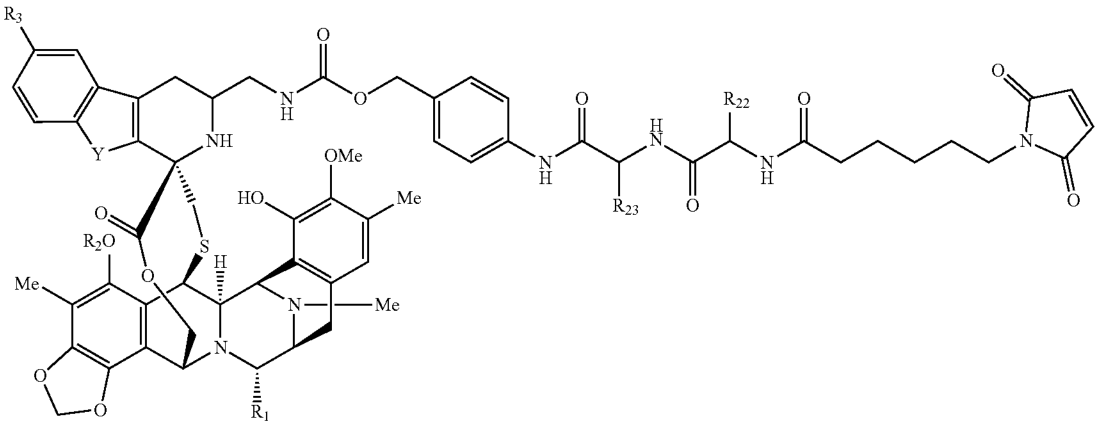

-continued (F')

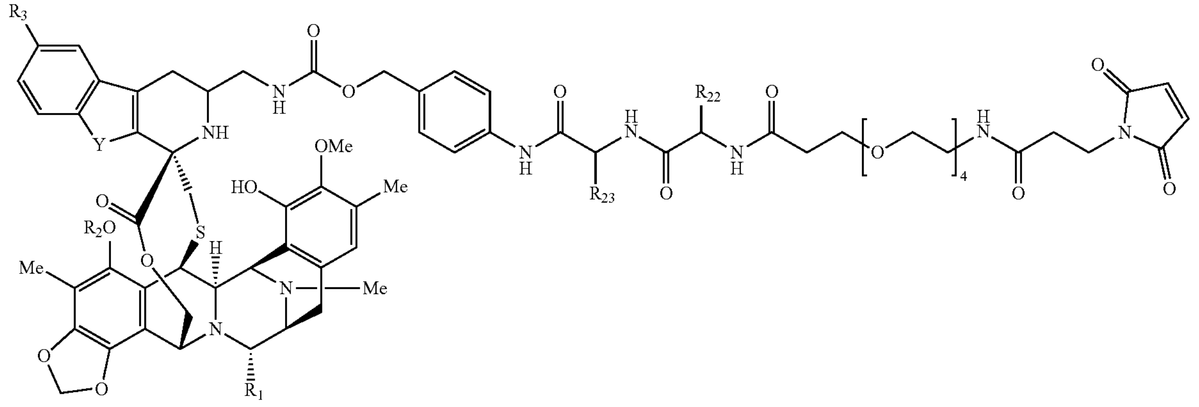

(ii) partial reduction of one or more disulfide bonds in the antibody to be conjugated to give a reduced antibody Ab-SH having free thiol groups:

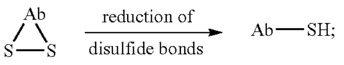

and (iii) reaction of the partially reduced antibody Ab-SH having free thiol groups with the compound of formula (F) or (F') produced in step (i) to give the desired drug antibody conjugate of formula (G) or (G') respectively:

(G)

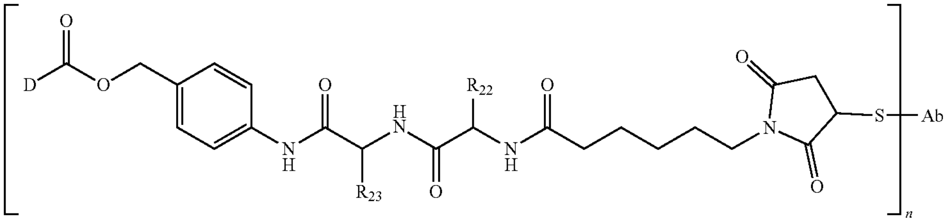

(G')

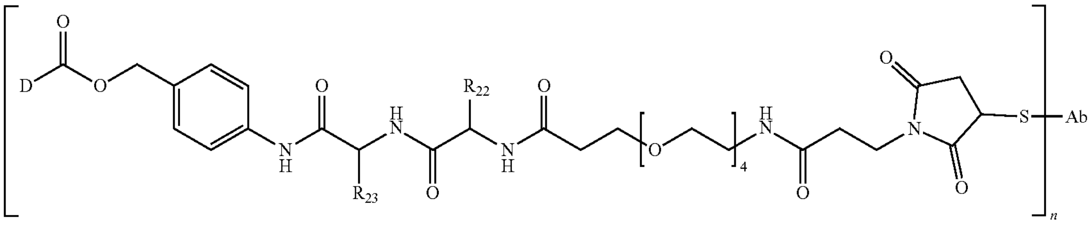

In another preferred embodiment of this process, the antibody is selected from Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologically active portion thereof, or it is selected from Trastuzumab and anti-CD13 antibody or an antigen-binding fragment or an immunologically active portion thereof, and most preferably it is Trastuzumab or an antigen-binding fragment or an immunologically active portion thereof. Furthermore, the partial reduction of this monoclonal antibody is performed using tris[2-carboxyethyl]phosphine hydrochloride (TCEP).

Another example of a process for the preparation of a drug conjugate of the present invention involves the preparation of drug antibody conjugates of formula (W) or (W') of the present invention as follows:

(W)
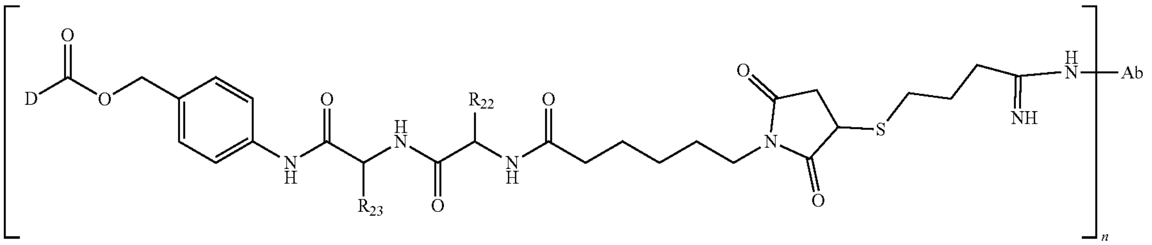
(W')
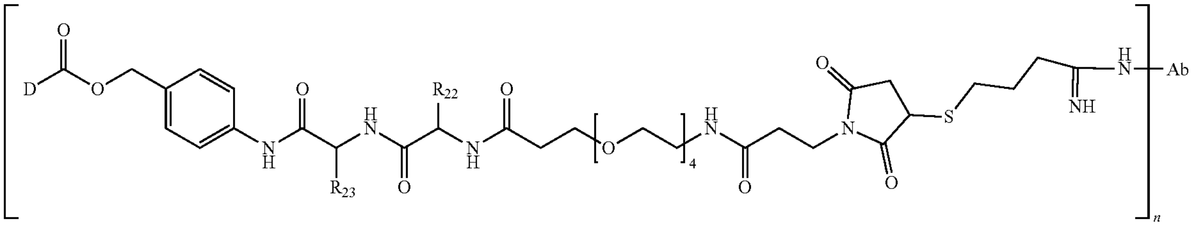
said process comprising the following steps:
(i) reacting the antibody with 2-iminothiolane hydrochloride (Traut's reagent) to give a thiol-activated antibody:
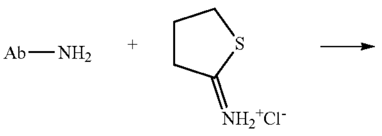
-continued
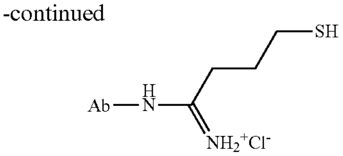
(ii) reacting the thiol-activated antibody with the compound of formula (F) or (F'), to give the desired drug antibody conjugate of formula (W) or (W'), respectively.
(W)
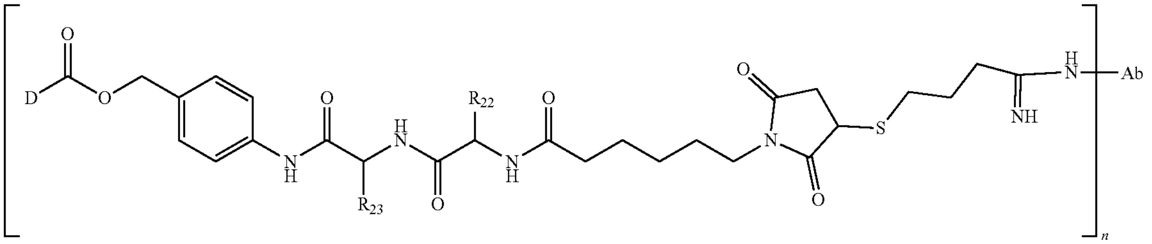
(W')
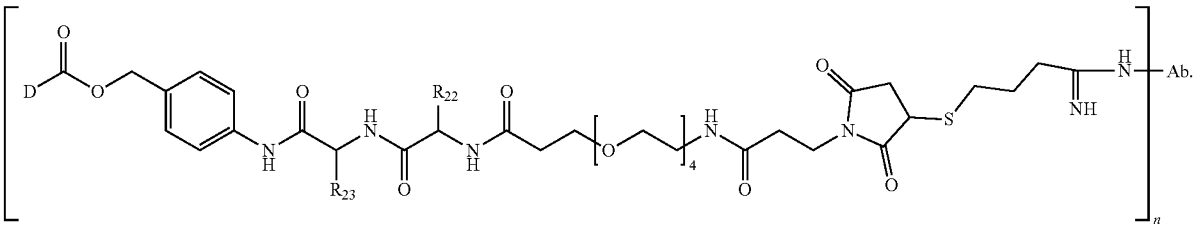

In another preferred embodiment of this process, the antibody is selected from Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologically active portion thereof, or it is selected from Trastuzumab and anti-CD13 antibody or an antigen-binding fragment or an immunologically active portion thereof, and most preferably it is Trastuzumab or an antigen-binding fragment or an immunologically active portion thereof.

Another example of a process for the preparation of a drug antibody conjugate of the present invention, involves the preparation of drug antibody conjugates of formula (O) or (P) as follows:

(O)

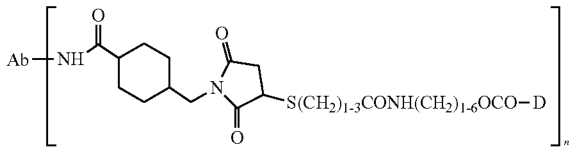

(P)

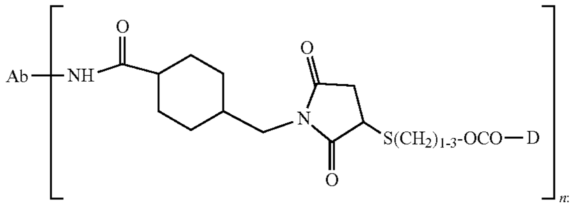

said process comprising the following steps:

(i) either:

(a) reacting a drug (D-H) of formula (IH)-H:

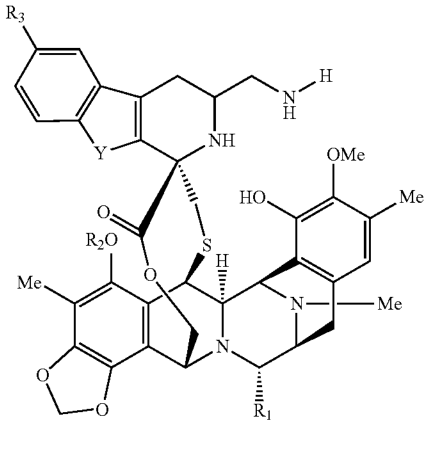

wherein the substituents in the definitions of (IH)-H are as defined above, with a compound of formula $X_2$—C(O)—$X_1$ wherein X1 and X2 are leaving groups to give a compound of formula (B):

(B)

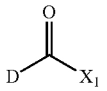

and the point of attachment of the —(C═O)$X_1$ moiety is the free —$NH_2$ group of the compound of formula D-H, or (b) reacting said drug (D-H) of formula (IH)-H as defined above with 4-nitro-phenylchloroformate to give a compound of formula (J):

(J)

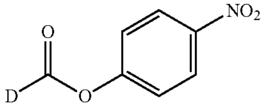

and the point of attachment of the (4-nitrophenyl)-O—CO— group is the same as that for the $X_1$(CO) moiety in (a) above;

(ii) either:

(c) reacting the compound of formula (B) produced in step (i) with a hydroxy compound of formula HO—$(CH_2)_{1-6}$NHProt$^{NH}$ and removing the Prot$^{NH}$ group from the coupled compound to give a compound of formula (C):

(C)

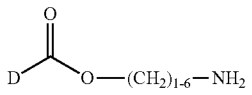

and then reacting the resulting compound of formula (C) with a compound of formula Me-S—S—$(CH_2)_{1-3}$—$CO_2H$ to give a compound of formula (K):

(K)

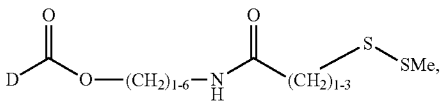

(d) reacting the compound (J) produced in step (i) with a compound of formula HO—$(CH_2)_{1-3}$SProt$^{SH}$ and removing the Prot$^{SH}$ group from the coupled compound to give a compound of formula (L):

(L)

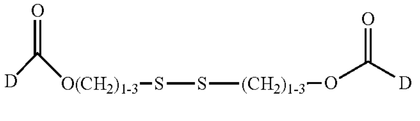

(iii) reacting (K) or (L) produced in step (ii) with dithiothreitol under disulfide reducing conditions to give compounds of formula (M) and (N) respectively:

(M)

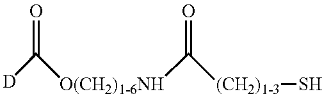

(N)

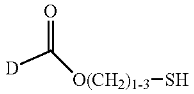

(iv) reacting the antibody to be conjugated with succininimidyl-4-(N-maleimidomethyl)cyclohexane-1-carboxylate to derivatise said antibody at one or more lysine groups with a succininimidyl-4-(N-maleimidomethyl)cyclohexane-1-carbonyl group:

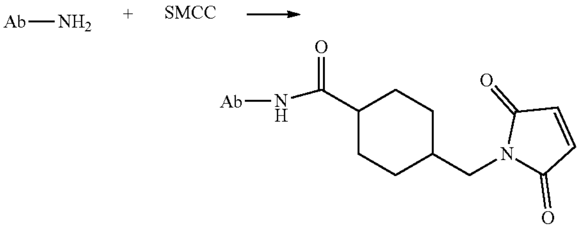

(v) reacting the derivatised antibody produced in step (iv) with either (M) or (N) produced in step (iii) to give the desired drug antibody conjugate of formula (O) or (P):

(O)

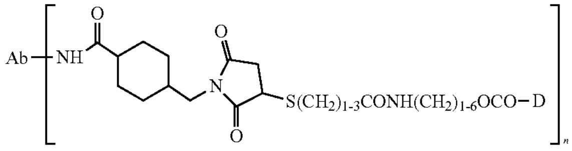

(P)

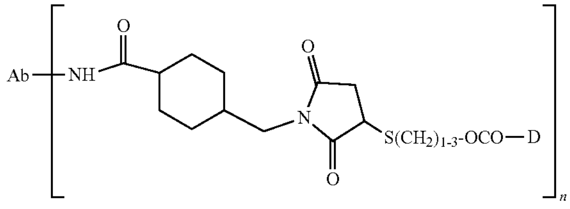

The compound of formula $X_2$—C(O)—$X_1$ is preferably 1,1'-carbonyldiimidazole. Similarly, the hydroxy compound reacted with the compound of formula (B) is preferably HO—$(CH_2)_{2\text{-}4}$-NHProtNH, and more preferably HO—$(CH_2)_3$-$NHProt^{NH}$.

In one preferred embodiment of this invention, the compound reacted with the compound of formula (C) to give the compound of formula (K) is 3-(methyldisulfanyl)propanoic acid.

In another preferred embodiment, the compound HO—$(CH_2)_{1\text{-}3}SProt^{SH}$ that is reacted with a compound of formula (J) to give a compound of formula (L) is HO—$(CH_2)_3SProt^{SH}$.

Where attachment to the drug linker moiety is via free thiol groups in cysteines after partial reduction of disulfide groups in the moiety comprising at least one antigen binding site such as a monoclonal antibody, the partial reduction is typically conducted by first diluting to a suitable concentration and buffering the solution before partial reduction of the disulfide bonds by means of the addition of a suitable reducing agent such as tris[2-carboxyethyl]phosphine hydrochloride (TCEP) or dithiothreitol (DTT). By choosing appropriate ratios of the moiety to be reduced such as a monoclonal antibody and the reducing agent, the reaction conditions and the time of the reduction it is possible to obtain a desired free thiol to moiety ratio, e.g. four free thiol groups per monoclonal antibody.

The partially reduced moiety such as the partially reduced monoclonal antibody having the free thiol groups, prepared as described above, is then reacted with drug-linker compounds of the invention of formula D-$(X)_b$-$(AA)_w$-$(T)_g$-L1 (wherein the group $L_1$ in such compound is a maleimide group which is free to react with the thiol groups). The resulting drug antibody conjugates are purified by any suitable means known in the art, e.g. by size exclusion chromatography (SEC) [see, e.g., Liu et al., Proc. Natl. Acad. Sci. USA, 93: 8618-8623 (1996), and Chari et al., Cancer Research, 52: 127-131 (1992)].

In one preferred embodiment of this invention, the partially reduced monoclonal antibody is Trastuzumab or an anti-CD13 antibody or an antigen-binding fragment or an immunologically active portion thereof, preferably Trastuzumab or an antigen-binding fragment or an immunologically active portion thereof; or preferably an anti-CD13 antibody or an antigen-binding fragment or an immunologically active portion thereof.

In an alternative embodiment of the invention, lysines in the moiety comprising at least one antigen binding site such as a monoclonal antibody can first be reacted with succinimidyl-4-(N-maleimidomethyl)cyclohexane-1-carboxylate. A free amine group on an antibody can react with the N-hydroxysuccinimide ester to give a maleimide-activated antibody:

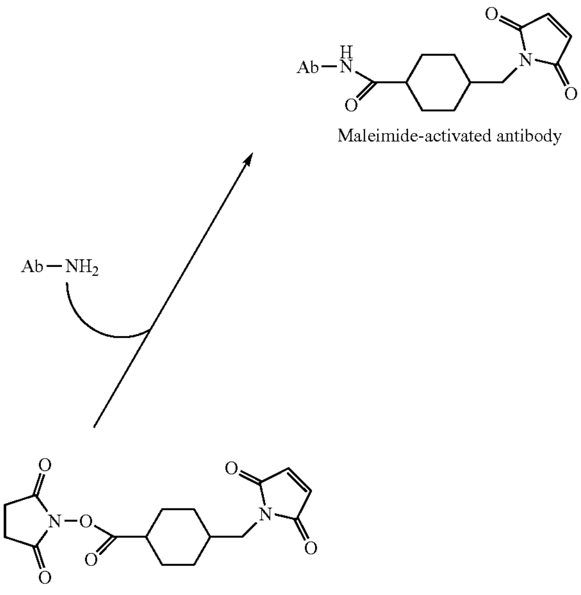

The maleimide-activated antibody can then be reacted with a compound of formula D-$(X)_b$-$(AA)_w$-$(T)_g$-H having a reactive thiol moiety.

In an alternative embodiment of the invention, lysines in the moiety comprising at least one antigen binding site such as a monoclonal antibody can first be reacted with 2-iminothiolane hydrochloride (Traut's reagent). A free amine group on an antibody can react with the imidic thiolactone to give a thiol-activated antibody.

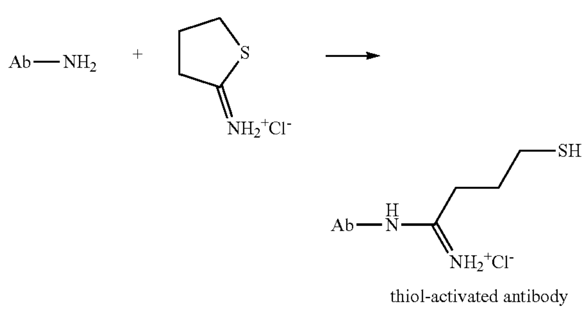

One specific example of processes for the preparation of drug antibody conjugates of formula $[D-(X)_b-(AA)_w-(T)_g-(L)-]n-Ab$ of the present invention by conjugation via free thiol groups in cysteines after partial reduction of disulfide groups in the antibody is shown in FIG. 1.

Another specific example of processes for the preparation of drug antibody conjugates of formula $[D-(X)_b-(AA)_w-(T)_g-(L)-]n-Ab$ of the present invention by conjugation with free amino groups in lysines after reaction of the antibody with Traut's reagent is shown in FIG. 2.

Compositions Comprising the Drug Antibody Conjugate of the Invention and Uses Thereof There is also provided a pharmaceutical composition comprising a drug conjugate according to the present invention and a pharmaceutically acceptable carrier. Examples of the administration form of a drug conjugate having the general formula $[D-(X)_b-(AA)_w-(T)_g-(L)-]n-Ab$ of the present invention include without limitation oral, topical, parenteral, sublingual, rectal, vaginal, ocular, and intranasal. Parenteral administration includes subcutaneous injections, intravenous, intramuscular, intrasternal injection or infusion techniques. Preferably, the compositions are administered parenterally. Pharmaceutical compositions of the invention can be formulated so as to allow a drug conjugate of the present invention to be bioavailable upon administration of the composition to an animal, preferably human. Compositions can take the form of one or more dosage units, where for example, a tablet can be a single dosage unit, and a container of a drug antibody conjugate of the present invention in aerosol form can hold a plurality of dosage units.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, for example, inhalatory administration. The term "carrier" refers to a diluent, adjuvant or excipient, with which a drug antibody conjugate of the present invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the drug antibody conjugates of the present invention or compositions and pharmaceutically acceptable carriers are sterile. Water is a preferred carrier when the drug antibody conjugates of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When the composition is in the form of a capsule (e.g. a gelatin capsule), it can contain, in addition to materials of the above type, a liquid carrier such as polyethylene glycol, cyclodextrin or a fatty oil.

The composition can be in the form of a liquid, e.g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, the present drug antibody conjugates of the present invention are administered intravenously.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant.

The amount of the drug conjugate of the present invention that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a drug conjugate of the present invention such that a suitable dosage will be obtained. The correct dosage of the compounds will vary according to the particular formulation, the mode of application, and its particular site, host and the disease being treated, e.g. cancer and, if so, what type of tumor. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The drug conjugate of the present invention or compositions can be administered by any convenient route, for example by infusion or bolus injection, by absorption through epithelial or mucocutaneous linings.

In specific embodiments, it can be desirable to administer one or more drug conjugates of the present invention or compositions locally to the area in need of treatment. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

Pulmonary administration can also be employed, e.g. by use of an inhaler or nebulizer, and formulation with an aerosolizing agent, or via perfusion in a fluorocarbon or synthetic pulmonary surfactant. In certain embodiments, the drug antibody conjugate of the present invention or compositions can be formulated as a suppository, with traditional binders and carriers such as triglycerides.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

The pharmaceutical compositions can be prepared using methodology well known in the pharmaceutical art. For example, a composition intended to be administered by injection can be prepared by combining a drug conjugate of the present invention with water so as to form a solution. A surfactant can be added to facilitate the formation of a homogeneous solution or suspension.

We have found that the drug conjugates and compositions of the present invention are particularly effective in the treatment of cancer.

Thus, as described earlier, the present invention provides a method of treating a patient in need thereof, notably a human, affected by cancer which comprises administering to the affected individual a therapeutically effective amount of a drug conjugate or a composition of the present invention.

The present invention provides a drug conjugate according to the present invention for use in the treatment of cancer, and more preferably a cancer selected from lung cancer, colorectal cancer, breast cancer, pancreas carcinoma, kidney cancer, leukaemia, multiple myeloma, lymphoma, gastric and ovarian cancer. Most preferred cancer is breast cancer.

The drug conjugates and compositions of the present invention are useful for inhibiting the multiplication of a tumor cell or cancer cell, or for treating cancer in an animal. The drug conjugates and compositions of the present invention can be used accordingly in a variety of settings for the treatment of animal cancers. The conjugates of the invention comprising Drug-Linker-Moiety comprising at least one antigen binding site can be used to deliver a Drug or Drug unit to a tumor cell or cancer cell. Without being bound by theory, in one embodiment, the Moiety comprising at least one antigen binding site of a drug conjugate of the present invention binds to or associates with a cancer-cell or a tumor-cell-associated antigen, and the drug conjugate of the present invention can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific sequences within the Linker unit are hydrolytically cleaved by one or more tumor-cell or cancer-cell-associated proteases or hydrolases, resulting in release of a Drug or a Drug-Linker Compound. The released Drug or Drug-Linker Compound is then free to migrate in the cell and induce cytotoxic activities. In an alternative embodiment, the Drug or Drug unit is cleaved from the drug conjugate of the present invention outside the tumor cell or cancer cell, and the Drug or Drug-Linker Compound subsequently penetrates the cell.

In one embodiment, the Moiety comprising at least one antigen binding site binds to the tumor cell or cancer cell. In another embodiment, the Moiety comprising at least one antigen binding site binds to a tumor cell or cancer cell antigen which is on the surface of the tumor cell or cancer cell. In yet another embodiment, the Moiety comprising at least one antigen binding site binds to a tumor cell or cancer cell antigen which is an extracellular matrix protein associated with the tumor cell or cancer cell.

The specificity of the Moiety comprising at least one antigen binding site for a particular tumor cell or cancer cell can be important for determining those tumors or cancers that are most effectively treated. For example, drug conjugates of the present invention having a Trastuzumab unit can be useful for treating antigen positive carcinomas including leukaemias, lung cancer, colon cancer, lymphomas (e.g. Hodgkin's disease, non-Hodgkin's Lymphoma), solid tumors such as, sarcoma and carcinomas, Multiple myeloma, kidney cancer and melanoma. The cancer may preferably be lung cancer, colorectal cancer, breast cancer, pancreas carcinoma, kidney cancer, leukaemia, multiple myeloma, lymphoma or ovarian cancer. For example, drug conjugates of the present invention having a Rituximab unit can be useful for treating CD-20 expressing tumors such as haematological cancers including leukemias and lymphomas. For example, drug conjugates of the present invention having an anti-CD4 antibody unit can be useful for treating CD-4 expressing tumors such as haematological cancers including lymphomas. For example, drug conjugates of the present invention having an anti-CD5 antibody unit can be useful for treating CD-5 expressing tumors such as haematological cancers including leukemias and lymphomas. For example, drug conjugates of the present invention having an anti-CD13 antibody unit can be useful for treating CD-13 expressing tumors such as haematological cancers including leukemias and lymphomas.

Other particular types of cancers that can be treated with drug conjugates of the present invention include, but are not limited to: blood-borne cancers including all forms of leukemia; lymphomas, such as Hodgkin's disease, non-Hodgkin's Lymphoma and Multiple myeloma.

In particular, the drug conjugates and compositions of the present invention show excellent activity in the treatment of breast cancer.

Drug conjugates and compositions of the present invention provide conjugation specific tumor or cancer targeting, thus reducing general toxicity of these conjugates. The Linker units stabilize the drug antibody conjugates in blood, yet are cleavable by tumor-specific proteases and hydrolases within the cell, liberating a Drug.

The drug conjugates and compositions of the present invention can be administered to an animal that has also undergone surgery as treatment for the cancer. In one embodiment of the present invention, the additional method of treatment is radiation therapy.

In a specific embodiment of the present invention, the drug conjugate or composition of the present invention may be administered with radiotherapy. Radiotherapy may be administered at the same time, prior to or after treatment with the drug conjugate or composition of the present invention. In an embodiment, the drug conjugate or composition of the present invention is administered concurrently with radiation therapy. In another specific embodiment, the radiation therapy is administered prior or subsequent to administration of a drug conjugate or composition of the present invention, preferably at least an hour, five hours, 12 hours, a day, a week, a month, more preferably several months (e.g. up to three months), prior or subsequent to administration of a drug antibody conjugate or composition of the present invention.

With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

In the present invention, there is provided a kit comprising a therapeutically effective amount of a drug conjugate according to the present invention and a pharmaceutically acceptable carrier. In an embodiment, there is provided a kit comprising a composition according to the present invention and, optionally, instructions for use in the treatment of cancer, and more preferably a cancer selected from lung cancer, colorectal cancer, breast cancer, pancreas carcinoma, kidney cancer, leukaemia, multiple myeloma, lymphoma, gastric and ovarian cancer.

In one embodiment, the kit according to this aspect is for use in the treatment of cancer, and more preferably a cancer selected from lung cancer, colorectal cancer, breast cancer, pancreas carcinoma, kidney cancer, leukaemia, multiple myeloma, lymphoma, gastric and ovarian cancer. Most preferred kit is for use in the treatment of breast cancer.

BRIEF DESCRIPTION OF THE DRAWINGS

The invention is diagrammatically illustrated, by way of example, in the accompanying drawings in which.

EXAMPLES

Figure 1:
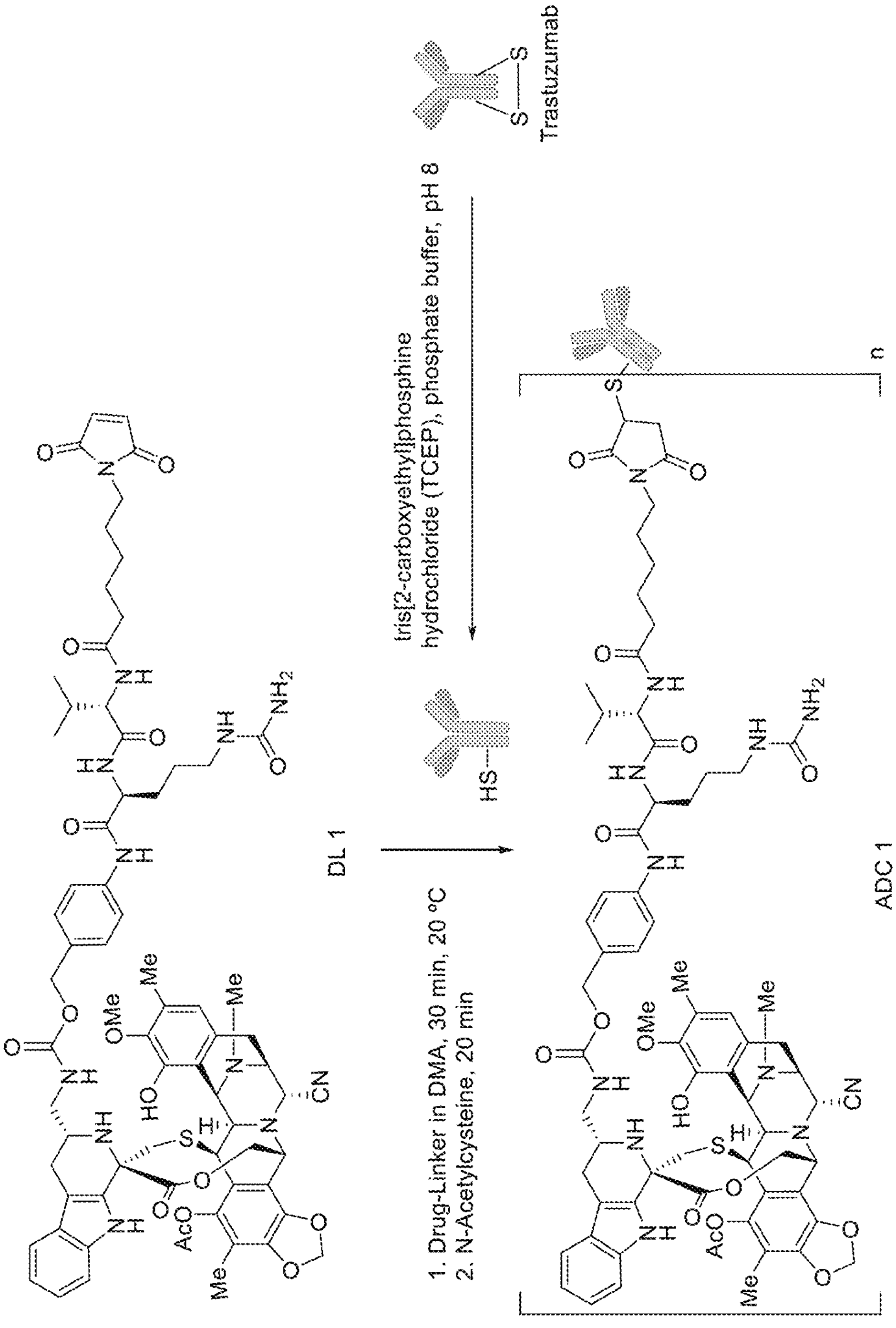
FIG. 1 is a schematic illustration of one process according to the present invention wherein conjugation to the antibody is via free thiol groups.
Figure 2:
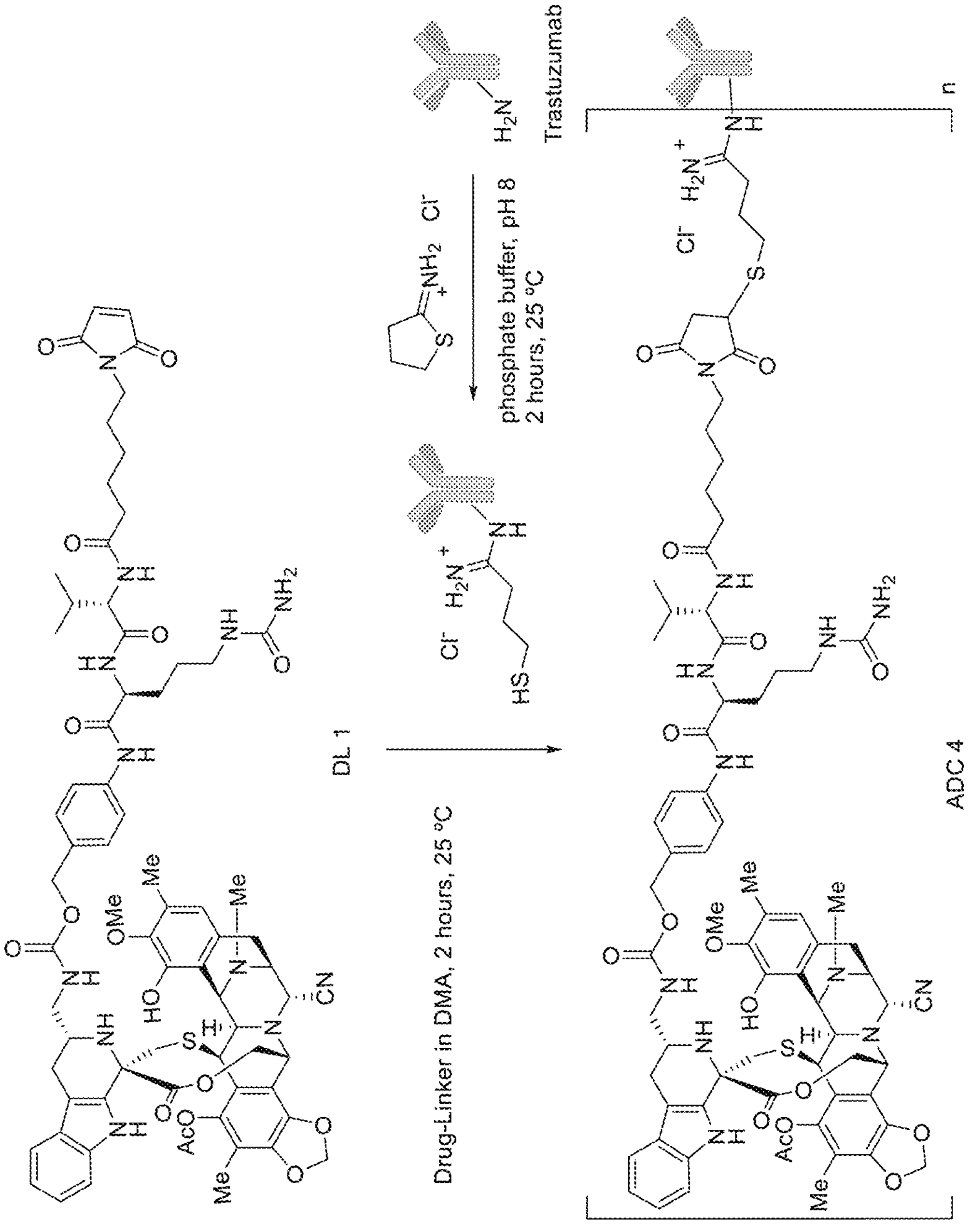
FIG. 2 is a schematic illustration of one process according to the present invention wherein conjugation to the antibody is via free amino groups.

The present invention is further illustrated by way of the following, non-limiting examples. In the examples, the following abbreviations are used:

CDI, 1,1'-Carbonyldiimidazole
DIPEA, N,N-Diisopropylethylamine
Hex, Hexane
EtOAc, Ethyl acetate
DCM, Dichloromethane
NMP, N-Methyl-2-pyrrolidone
DMF, Dimethylformamide
EDC, N-(3-Dimethylaminopropyl)-N'-ethylcarbodiimide hydrochloride
EDTA, Ethylenediaminetetraacetic acid
MeOH, Methanol
DTT, Dithiothreitol
Py, Pyridine
THF, Tetrahydrofuran
TCEP, Tris[2-carboxyethyl]phosphine hydrochloride
MC, 6-Maleimidocaproyl
Fmoc, 9-Fluorenylmethoxycarbonyl
Cit, Citrulline
Val, Valine
DMSO, Dimethylsulfoxide
Trt, Triphenylmethyl
HOBt, 1-Hydroxybenzotriazole
DIPCDI, N,N'-Diisopropylcarbodiimide
TFA, Trifluoroacetic acid
PABOH, 4-Aminobenzyl alcohol
bis-PNP, bis(4-Nitrophenyl) carbonate
NAC, N-Acetylcysteine
SEC, Size-Exclusion Chromatography
HPLC, High Performance Liquid Chromatography
ADC, Antibody Drug Conjugate
ATCC, American Type Culture Collection
DMEM, Dulbecco's Modified Eagle's Medium
RPMI, Rosmell Park Memorial Institute Medium
ITS, Insulin-transferrin-sodium selenite media supplement
FCS, Fetal Calf Serum
SRB, Sulforhodamine B
PBS, Phosphate Buffered Saline
DR, Dose-Response
UV, Ultraviolet
SMCC, Succinimidyl-4-(N-maleimidomethyl)cyclohexane-1-carboxylate
LAR, Linker to Antibody Ratio

Synthesis of Compounds

Compound 1 was prepared as described in Example 20 of WO 01/87895.

Example 0-1

A)

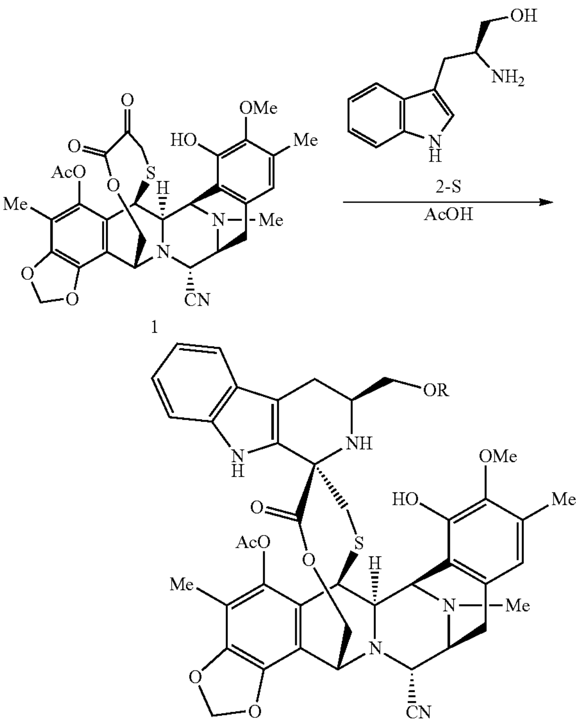

1

3-S R = H + 3a-S R = Ac

To a solution of 1 (0.5 g, 0.80 mmol) in acetic acid (20 mL, 0.04 M) was added L-tryptophanol (2-S) (533 mg, 3.0 mmol, Sigma-Aldrich). The reaction mixture was stirred at 23° C. for 16 h and then acetic acid was evaporated. An aqueous saturated solution of $NaHCO_3$ was added and the mixture was extracted with $CH_2Cl_2$. The combined organic layers were dried over anhydrous $Na_2SO_4$, filtered and concentrated under vacuum. Flash chromatography (Hexane:EtOAc, 1:1) gave compounds 3-S (616 mg, 97%) and 3a-S (12 mg, 2%).

3-S $R_f$=0.50 (Hexane:EtOAc, 1:1).

$^1H$ NMR (300 MHz, $CDCl_3$): δ 7.71 (s, 1H), 7.36 (dd, J=7.9, 1.0 Hz, 1H), 7.27 (dd, J=8.2, 0.9 Hz, 1H), 7.13 (ddd, J=8.3, 7.0, 1.2 Hz, 1H), 7.03 (ddd, J=8.0, 7.0, 1.0 Hz, 1H), 6.62 (s, 1H), 6.26 (d, J=1.4 Hz, 1H), 6.04 (d, J=1.3 Hz, 1H), 5.75 (s, 1H), 5.14 (dd, J=11.7, 1.2 Hz, 1H), 4.60 (s, 1H), 4.41 (s, 1H), 4.36-4.24 (m, 2H), 4.21 (d, J=2.7 Hz, 1H), 3.82 (s, 3H), 3.52 (s, 1H), 3.50-3.47 (m, 1H), 3.45 (dq, J=8.4, 2.2 Hz, 1H), 3.35 (t, J=10.1 Hz, 1H), 3.01-2.78 (m, 5H), 2.62 (dd, J=15.3, 4.7 Hz, 1H), 2.41 (s, 1H), 2.38 (s, 3H), 2.37-2.31 (m, 1H), 2.28 (s, 3H), 2.17 (s, 3H), 2.06 (s, 3H).

ESI-MS m/z: 794.2 $(M+H)^+$.

3a-S $R_f$=0.70 (Hexane:EtOAc, 1:1).

$^1H$ NMR (500 MHz, $CDCl_3$): δ 7.83 (s, 1H), 7.38 (dt, J=7.9, 0.9 Hz, 1H), 7.25 (dt, J=8.3, 0.9 Hz, 1H), 7.11 (ddd, J=8.2, 7.1, 1.2 Hz, 1H), 7.02 (ddd, J=8.0, 7.0, 1.0 Hz, 1H), 6.62 (s, 1H), 6.24 (d, J=1.4 Hz, 1H), 6.03 (d, J=1.3 Hz, 1H), 5.79 (s, 1H), 5.13 (d, J=11.7 Hz, 1H), 4.60 (s, 1H), 4.39 (s, 1H), 4.36-4.22 (m, 3H), 4.17-4.09 (m, 1H), 3.91 (dd, J=10.5, 8.6 Hz, 1H), 3.83 (s, 3H), 3.51-3.41 (m, 2H), 3.04-2.92 (m, 3H), 2.72 (dd, J=15.1, 4.0 Hz, 1H), 2.54-2.41 (m, 2H), 2.38 (s, 3H), 2.35-2.30 (m, 1H), 2.29 (s, 3H), 2.21-2.16 (m, 1H), 2.18 (s, 3H), 2.12 (s, 3H); 2.05 (s, 3H).

$^{13}C$ NMR (101 MHz, $CDCl_3$): δ 171.2, 170.7, 168.6, 147.5, 145.8, 143.0, 141.1, 140.4, 135.6, 130.1, 129.5, 126.7, 122.2, 121.2, 120.9, 119.4, 118.4, 118.2, 118.2, 113.6, 113.5, 110.9, 110.0, 109.1, 102.1, 91.4, 67.2, 63.4, 61.3, 60.4, 59.7, 59.1, 54.8, 54.6, 47.7, 42.0, 41.6, 31.6, 24.0, 22.6, 21.0, 15.9, 14.2, 9.7.

ESI-MS m/z: 836.2 $(M+H)^+$.

B)

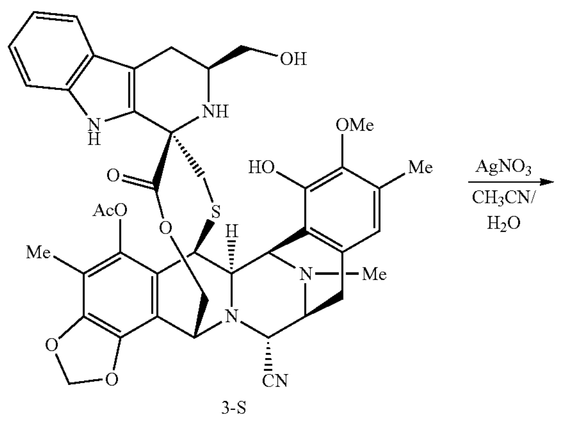

3-S

-continued

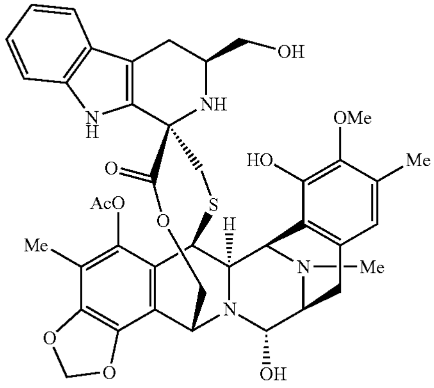

4-S

To a solution of 3-S (616 mg, 0.77 mmol) in $CH_3CN:H_2O$ (1.39:1, 51 mL, 0.015 M) was added $AgNO_3$ (3.40 g, 23.3 mmol). After 3 h at 23° C., the reaction mixture was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to give 4-S (471 mg, 78%).

$R_f$=0.50 ($CH_2Cl_2:CH_3OH$, 9:1).

$^1H$ NMR (500 MHz, $CDCl_3$): δ 7.71 (s, 1H), 7.36 (dd, J=7.8, 1.1 Hz, 1H), 7.26 (dd, J=7.8, 1.1 Hz, 1H), 7.12 (ddd, J=8.2, 7.0, 1.2 Hz, 1H), 7.03 (ddd, J=8.0, 7.1, 1.0 Hz, 1H), 6.64 (s, 1H), 6.23 (d, J=1.3 Hz, 1H), 6.01 (d, J=1.4 Hz, 1H), 5.75 (s, 1H), 5.25 (d, J=11.4 Hz, 1H), 4.92 (s, 1H), 4.52 (br s, 3H), 4.22 (dd, J=11.4, 2.2 Hz, 1H), 4.19 (s, 1H), 3.83 (s, 3H), 3.54 (br s, 2H), 3.35 (t, J=10.2 Hz, 1H), 3.26 (s, 1H), 3.01-2.93 (m, 3H), 2.88 (br s, 3H), 2.63 (dd, J=15.2, 4.8 Hz, 1H), 2.38 (s, 3H), 2.36-2.31 (m, 2H), 2.28 (s, 3H), 2.05 (s, 3H).

$^{13}C$ NMR (126 MHz, $CDCl_3$): δ 171.9, 168.6, 147.5, 145.4, 142.9, 141.2, 140.7, 135.5, 130.4, 126.8, 122.3, 122.0, 121.3, 119.4, 118.4, 115.2, 112.8, 111.0, 110.0, 109.6, 101.8, 81.9, 76.8, 65.2, 62.8, 62.5, 60.4, 58.1, 57.9, 55.9, 55.1, 53.4, 51.6, 41.8, 41.3, 39.6, 24.1, 23.8, 20.5, 15.8, 9.7.

ESI-MS m/z: 767.3 $(M-H_2O+H)^+$.

(+)-HR-ESI-TOF-MS m/z 767.2788 $[M-H_2O+H]^+$ (Calcd. for $C_{41}H_{43}N_4O_9S$: 767.2745).

B')

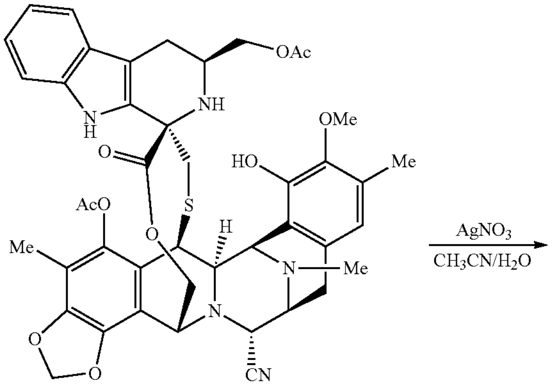

3a-S

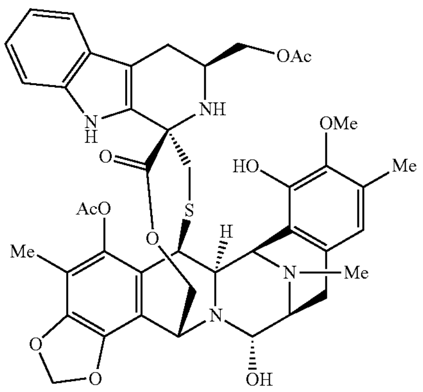

4a-S

To a solution of 3a-S (30 mg, 0.035 mmol) in $CH_3CN$:$H_2O$ (1.39:1, 2.4 mL, 0.015 M) was added $AgNO_3$ (180 mg, 1.07 mmol). After 3 h at 23° C., the reaction mixture was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give 4a-S (24 mg, 83%).

$R_f$=0.60 ($CH_2Cl_2$:$CH_3OH$, 9:1).

$^1$H NMR (400 MHz, $CDCl_3$): δ 7.81 (s, 1H), 7.37 (d, J=7.8 Hz, 1H), 7.30-7.21 (m, 1H), 7.06 (dddt, J=34.7, 8.0, 7.1, 1.1 Hz, 2H), 6.63 (s, 1H), 6.22 (d, J=1.3 Hz, 1H), 6.02 (dd, J=12.9, 1.4 Hz, 1H), 5.74 (s, 1H), 5.25-5.21 (m, 1H), 4.89 (d, J=8.7 Hz, 1H), 4.55-4.45 (m, 2H), 4.30-4.18 (m, 1H), 4.14 (dd, J=10.5, 4.2 Hz, 1H), 4.00-3.88 (m, 2H), 3.82 (s, 3H), 3.56-3.44 (m, 2H), 3.23 (d, J=9.0 Hz, 1H), 2.95 (d, J=15.7 Hz, 2H), 2.87-2.78 (m, 2H), 2.71 (dd, J=15.0, 3.9 Hz, 1H), 2.48 (dd, J=15.1, 9.6 Hz, 1H), 2.37 (s, 3H), 2.35-2.29 (m, 1H), 2.28 (s, 3H), 2.22-2.16 (m, 1H), 2.15 (s, 3H), 2.12 (s, 3H), 2.03 (s, 3H).

ESI-MS m/z: 809.2 $(M-H_2O+H)^+$.

Example 0-2

A)

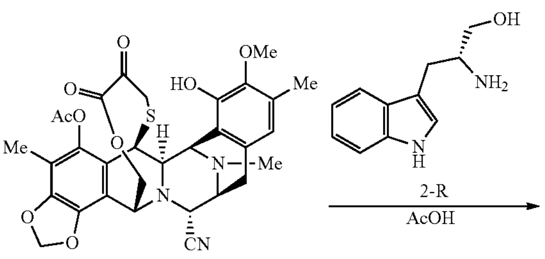

1

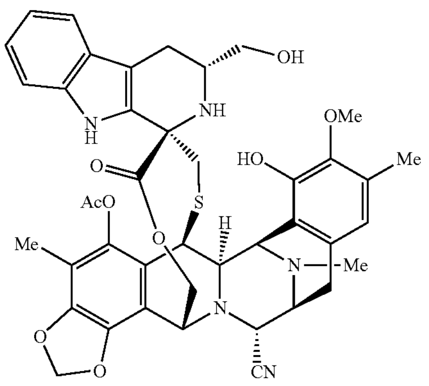

3-R

To a solution of 1 (0.5 g, 0.80 mmol) in acetic acid (20 mL, 0.04 M) was added D-tryptophanol (2-R) (533 mg, 3.0 mmol, Sigma-Aldrich). The reaction mixture was stirred at 23° C. for 16 h and then acetic acid was evaporated. An aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, 1:1) gave compound 3-R (479 mg, 75%).

$R_f$=0.44 (Hexane:EtOAc, 1:1).

$^1$H NMR (400 MHz, $CDCl_3$): δ 7.61 (s, 1H), 7.39 (d, J=7.8 Hz, 1H), 7.29 (d, J=9.6 Hz, 1H), 7.12 (t, J=7.3 Hz, 1H), 7.03 (t, J=7.3 Hz, 1H), 6.60 (s, 1H), 6.25 (s, 1H), 6.03 (s, 1H), 5.75 (s, 1H), 5.04 (d, J=11.7 Hz, 1H), 4.62 (s, 1H), 4.37 (s, 1H), 4.32-4.25 (m, 1H), 4.22 (d, J=2.7 Hz, 1H), 4.19-4.09 (m, 1H), 3.82 (s, 3H), 3.77 (s, 1H), 3.64 (d, J=9.0 Hz, 1H), 3.49-3.41 (m, 2H), 3.02-2.90 (m, 2H), 2.60-2.52 (m, 2H), 2.45 (d, J=14.7 Hz, 2H), 2.40 (s, 3H), 2.28 (s, 3H), 2.22-2.14 (m, 2H), 2.18 (s, 3H), 2.10 (m, 3H).

ESI-MS m/z: 794.3 $(M+H)^+$.

B)

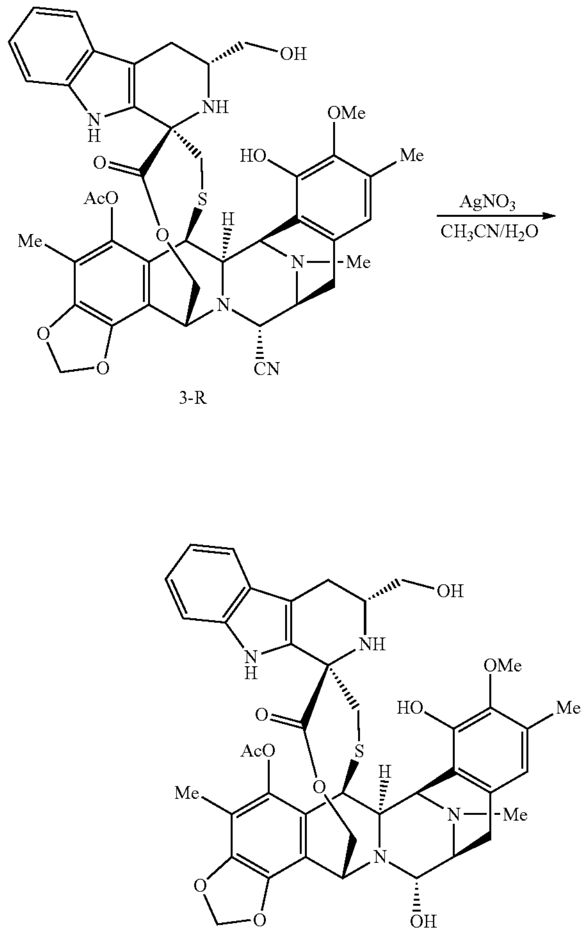

3-R

4-R

To a solution of 3-R (479 mg, 0.60 mmol) in $CH_3CN:H_2O$ (1.39:1, 40 mL, 0.015 M) was added $AgNO_3$ (3.03 g, 18.1 mmol). After 3 h at 23° C., the reaction mixture was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to afford 4-R (428 mg, 91%).

$R_f$=0.45 ($CH_2Cl_2:CH_3OH$, 9:1).

$^1H$ NMR (400 MHz, $CDCl_3$): δ 7.62 (s, 1H), 7.39 (d, J=8.1 Hz, 1H), 7.28 (d, J=8.1 Hz, 1H), 7.11 (ddd, J=8.2, 7.0, 1.2 Hz, 1H), 7.02 (ddd, J=7.9, 7.1, 1.0 Hz, 1H), 6.61 (s, 1H), 6.22 (d, J=1.3 Hz, 1H), 5.99 (d, J=1.3 Hz, 1H), 5.73 (s, 1H), 5.17 (dd, J=11.5, 1.2 Hz, 1H), 4.86 (s, 1H), 4.56-4.47 (m, 2H), 4.17 (dd, J=5.1, 1.6 Hz, 1H), 4.08 (dd, J=11.5, 2.1 Hz, 1H), 3.81 (s, 3H), 3.78 (d, J=3.8 Hz, 1H), 3.64 (dd, J=10.8, 3.8 Hz, 2H), 3.51 (d, J=5.1 Hz, 1H), 3.48-3.43 (m, 2H), 3.24 (d, J=8.6 Hz, 1H), 3.00-2.80 (m, 2H), 2.57 (s, 1H), 2.55-2.43 (m, 1H), 2.40 (s, 3H), 2.27 (s, 3H), 2.19-2.12 (m, 1H), 2.16 (s, 3H), 2.08 (s, 3H).

$^{13}C$ NMR (101 MHz, $CDCl_3$): δ 171.8, 168.6, 147.6, 145.4, 143.0, 141.3, 140.7, 136.0, 131.1, 130.0, 129.6, 126.6, 122.1, 121.6, 121.2, 119.4, 118.4, 115.6, 112.9, 111.1, 110.6, 101.8, 81.7, 65.8, 62.7, 61.8, 60.4, 60.3, 57.9, 57.8, 56.1, 55.0, 52.1, 42.2, 41.3, 41.1, 23.8, 23.4, 20.5, 15.7, 9.8.

ESI-MS m/z: 767.6 $(M-H_2O+H)^+$.

(+)-HR-ESI-TOF-MS m/z: 767.2799 $[M-H_2O+H]^+$ (Calcd. for $C_{41}H_{43}N_4O_9S$: 767.2745).

Example 0-3. Synthesis of allyl N—[(R)-(2-amino-3-(1H-indol-3-yl)propyl)]carbamate (9-R)

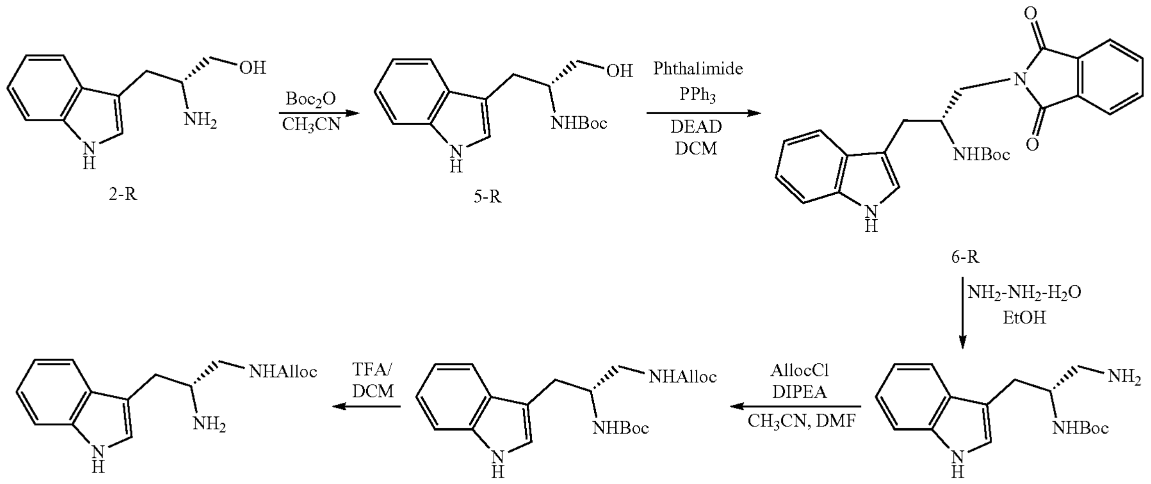

2-R

5-R

6-R

7-R

8-R

9-R

A)

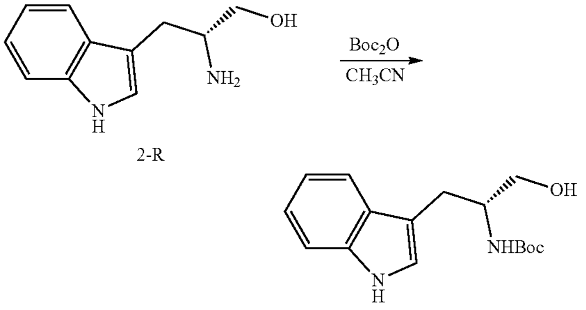

2-R

5-R

To a solution of D-tryptophanol (2-R) (2.0 g, 10.4 mmol) in $CH_3CN$ (42 mL, 4 mL/mmol) was added di-tert-butyl dicarbonate (4.6 g, 20.8 mmol). The reaction mixture was stirred at 23° C. for 3 h and concentrated under vacuum. Flash chromatography ($CH_2Cl_2$:$CH_3OH$ from 99:1 to 85:15) to afford 5-R (2.2 g, 73%).

$R_f$=0.5 ($CH_2Cl_2$:$CH_3OH$, 9:1).

$^1H$ NMR (400 MHz, $CDCl_3$): δ 8.13 (s, 1H), 7.67 (dd, J=7.8, 1.1 Hz, 1H), 7.38 (dd, J=8.1, 1.3 Hz, 1H), 7.29-7.10 (m, 2H), 7.06 (s, 1H), 4.82 (s, 1H), 4.00 (s, 1H), 3.71 (dd, J=11.0, 3.8 Hz, 1H), 3.62 (dd, J=11.0, 5.5 Hz, 1H), 3.01 (d, J=6.7 Hz, 2H), 2.14 (s, 1H), 1.44 (s, 9H).

B)

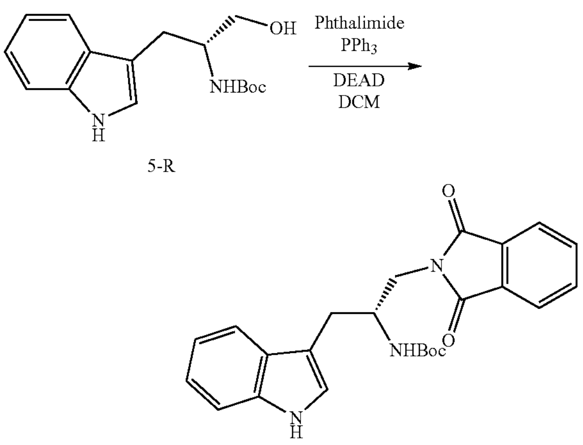

5-R

6-R

To a solution of 5-R (2.4 g, 8.2 mmol) in $CH_2Cl_2$ (50 mL, 6 mL/mmol) was added phthalimide (2.7 g, 18.2 mmol), triphenylphosphine (4.8 g, 18.2 mmol) and the mixture was cooled at 0° C. A solution of diethyl azodicarboxylate (DEAD) solution in $CH_2Cl_2$ (25 mL, 3 mL/mmol) was added for 15 min. The reaction was stirred at 23° C. for 16 h, concentrated under vacuum. The residue obtained was purified by flash chromatography ($CH_2Cl_2$:$CH_3OH$, from 99:1 to 85:15) to afford 6-R (3.3 g, 96%).

$R_f$=0.7 ($CH_2Cl_2$:$CH_3OH$, 9:1).

$^1H$ NMR (400 MHz, $CDCl_3$): δ 8.50 (s, 1H), 7.81 (dd, J=5.5, 3.1 Hz, 2H), 7.66 (dd, J=5.6, 3.2 Hz, 2H), 7.60 (d, J=7.8 Hz, 1H), 7.35 (d, J=8.0 Hz, 1H), 7.19-7.04 (m, 3H), 4.81 (s, 1H), 4.40 (s, 1H), 3.83 (dd, J=13.9, 3.7 Hz, 1H), 3.72 (dd, J=13.9, 9.9 Hz, 1H), 3.08-3.01 (m, 2H), 1.23 (s, 9H).

C)

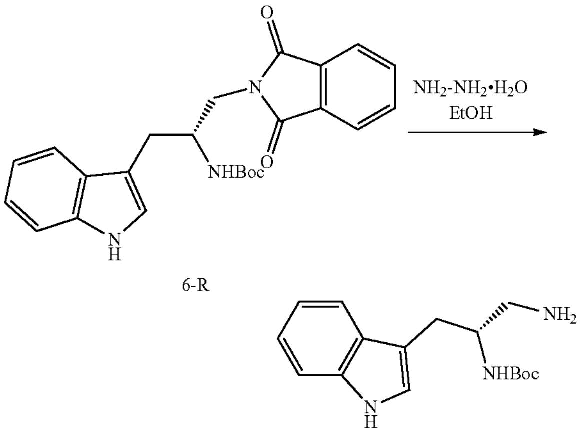

6-R

7-R

To a solution of 6-R (3.25 g, 7.74 mmol) in ethanol (231 mL, 30 mL/mmol) was added hydrazine monohydrate (37 mL, 774 mmol). The reaction mixture was stirred at 80° C. in sealed tube for 2.25 h, concentrated under vacuum. Flash chromatography (EtOAc:$CH_3OH$, from 100:1 to 50:50) afforded 7-R (2.15 g, 96%).

$R_f$=0.2 (EtOAc:$CH_3OH$, 6:4).

$^1H$ NMR (400 MHz, $CD_3OD$): δ 7.60 (d, J=7.9 Hz, 1H), 7.33 (d, J=8.1 Hz, 1H), 7.13-7.04 (m, 2H), 7.05-6.96 (m, 1H), 4.02-3.94 (m, 1H), 2.99-2.87 (m, 3H), 2.78 (dd, J=13.1, 9.7 Hz, 1H), 1.39 (s, 9H).

ESI-MS m/z: 290.2 $(M+H)^+$.

D)

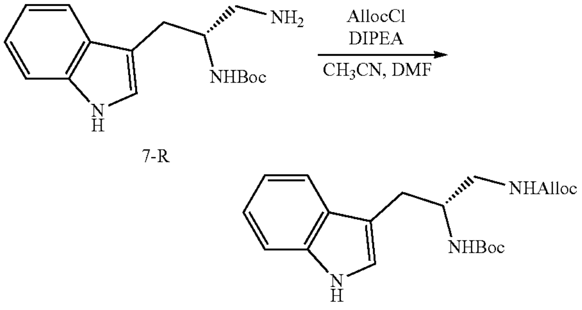

7-R

8-R

To a solution of 7-R (2.15 g, 7.4 mmol) in $CH_3CN$ (74 mL, 10 mL/mmol) and DMF (7.4 mL, 1 mL/mmol) was added N,N-diisopropylethylamine (1.06 mL, 5.9 mmol) and allyl chloroformate (7.9 mL, 74 mmol). The reaction was stirred at 23° C. for 16 h. The mixture was diluted with EtOAc, $NH_4Cl$ was added and the mixture was extracted with EtOAc. The combined organic layers were dried over anhydrous $Na_2SO_4$, filtered, and concentrated under vacuum. The residue obtained was purified by flash chromatography (Hexane:EtOAc, from 100:1 to 1:100) to afford 8-R (1.69 g, 61%).

$R_f$=0.4 (Hexane:EtOAc, 1:1).

$^1$H NMR (400 MHz, $CDCl_3$): δ 8.25 (s, 1H), 7.62 (d, J=7.8 Hz, 1H), 7.35 (dd, J=8.1, 0.9 Hz, 1H), 7.16 (dddd, J=27.8, 8.0, 7.0, 1.1 Hz, 2H), 7.04 (d, J=2.4 Hz, 1H), 5.90 (ddt, J=17.3, 10.7, 5.6 Hz, 1H), 5.34-5.22 (m, 1H), 5.20 (dt, J=10.5, 1.4 Hz, 1H), 5.12 (s, 1H), 4.82 (s, 1H), 4.55 (dq, J=7.5 Hz, 1H), 7.03 (t, J=7.5 Hz, 1H), 5.87 (ddt, J=16.4, 10.8, 5.6 Hz, 1H), 5.34-5.13 (m, 2H), 4.50 (d, J=5.5 Hz, 2H), 3.62 (bs, 1H), 3.42 (dd, J=14.9, 3.9 Hz, 1H), 3.36-3.20 (m, 1H), 3.11-3.00 (m, 2H).

ESI-MS m/z: 274.3 $(M+H)^+$.

Example 0-4. Synthesis of allyl N—[(S)-(2-amino-3-(1H-indol-3-yl)propyl)]carbamate (9-S)

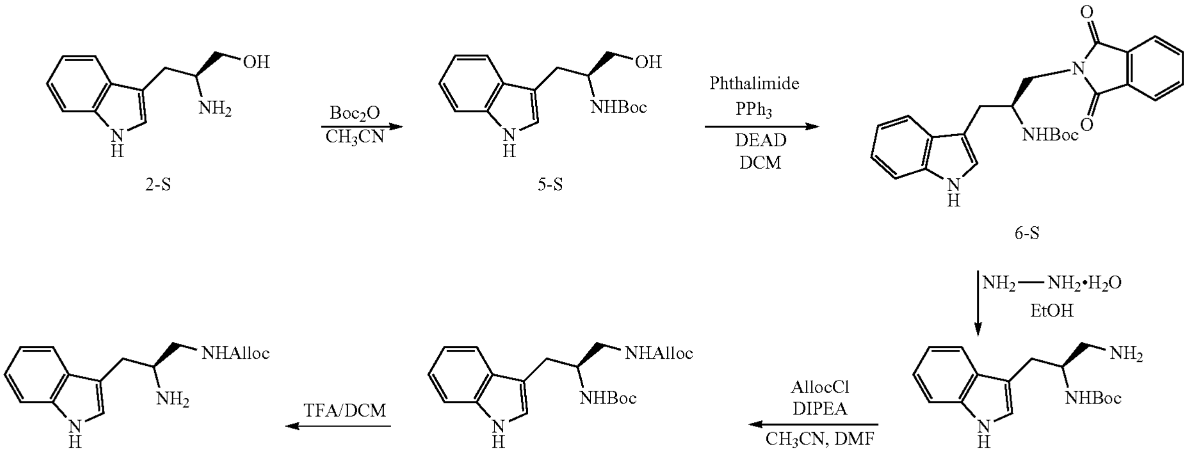

9-S 8-S 7-S

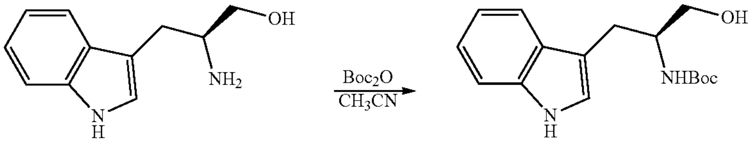

2-S 5-S

J=5.4, 1.7 Hz, 2H), 4.02 (s, 1H), 3.35 (dt, J=10.0, 4.7 Hz, 1H), 3.21 (s, 1H), 2.95 (ddd, J=21.6, 15.4, 9.1 Hz, 2H), 1.42 (s, 9H).

ESI-MS m/z: 274.3 $(M-Boc+H)^+$.

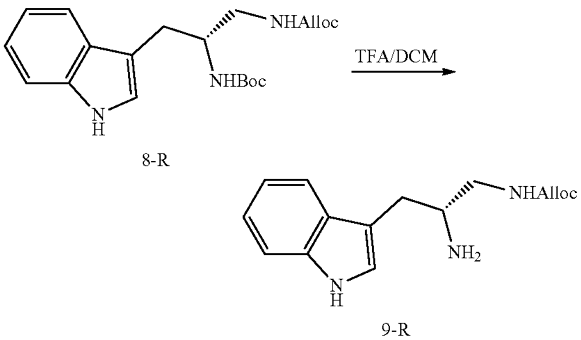

9-R

To a solution of 8-R (1.30 g, 3.50 mmol) in $CH_2Cl_2$ (58 mL, 16.6 mL/mmol) was added trifluoroacetic acid (30 mL, 8.3 mL/mmol). The reaction mixture was stirred at 23° C. for 1.5 h, concentrated under vacuum to give crude 9-R which was used in the next steps without further purification.

$R_f$=0.2 ($CH_2Cl_2$:$CH_3OH$, 9:1).

$^1$H NMR (400 MHz, $CDCl_3$): δ 7.95 (s, 1H), 7.53 (d, J=7.8 Hz, 1H), 7.36 (d, J=8.1 Hz, 1H), 7.17 (s, 1H), 7.09 (t,

A)

To a solution of L-tryptophanol (2-S) (2.0 g, 10.4 mmol) in $CH_3CN$ (42 mL, 4 mL/mmol) was added Di-tert-butyl dicarbonate (4.6 g, 20.8 mmol). The reaction mixture was stirred at 23° C. for 3 h, concentrated under vacuum. Flash chromatography ($CH_2Cl_2$:$CH_3OH$, from 99:1 to 85:15) to afford 5-S (2.24 g, 73%).

$R_f$=0.5 ($CH_2Cl_2$:$CH_3OH$, 9:1).

$^1$H NMR (400 MHz, $CDCl_3$): δ 8.10 (s, 1H), 7.65 (dd, J=7.8, 1.1 Hz, 1H), 7.37 (dd, J=8.1, 1.3 Hz, 1H), 7.23-7.11 (m, 2H), 7.06 (s, 1H), 4.81 (s, 1H), 3.99 (s, 1H), 3.70 (dd, J=11.0, 3.8 Hz, 1H), 3.61 (dd, J=11.0, 5.5 Hz, 1H), 3.00 (d, J=6.7 Hz, 2H), 2.01 (s, 1H), 1.42 (s, 9H).

B)

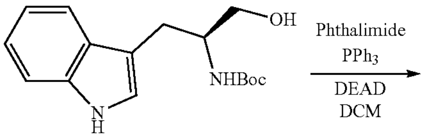

5-S

-continued

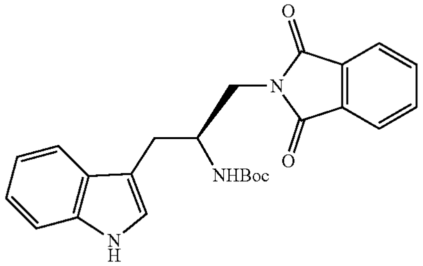

6-S

To a solution of 5-S (1.2 g, 4.13 mmol) in $CH_2Cl_2$ (24.8 mL, 6 mL/mmol) was added phthalimide (1.33 g, 9.1 mmol), triphenylphosphine (2.4 g, 9.1 mmol) and the mixture was cooled at 0° C. A solution of diethyl azodicarboxylate (DEAD) solution (3 mL, 10.32 mmol) in $CH_2Cl_2$ (12.4 mL, 3 mL/mmol) was added for 15 min. The reaction was stirred at 23° C. for 16 h, concentrated under vacuum. The residue obtained was purified by flash chromatography ($CH_2Cl_2$:$CH_3OH$, from 99:1 to 85:15) to afford 6-S (2.8 g, >100%).

$R_f$=0.7 ($CH_2Cl_2$:$CH_3OH$, 9:1).

$^1$H NMR (400 MHz, $CDCl_3$): δ 8.49 (s, 1H), 7.80 (dd, J=5.4, 3.1 Hz, 2H), 7.66 (dd, J=5.6, 3.2 Hz, 2H), 7.60 (d, J=7.8 Hz, 1H), 7.34 (d, J=8.0 Hz, 1H), 7.21-7.04 (m, 3H), 4.74 (s, 1H), 4.42 (s, 1H), 3.83 (dd, J=13.9, 3.7 Hz, 1H), 3.72 (dd, J=13.9, 9.9 Hz, 1H), 3.10-3.01 (m, 2H), 1.23 (s, 9H).

C)

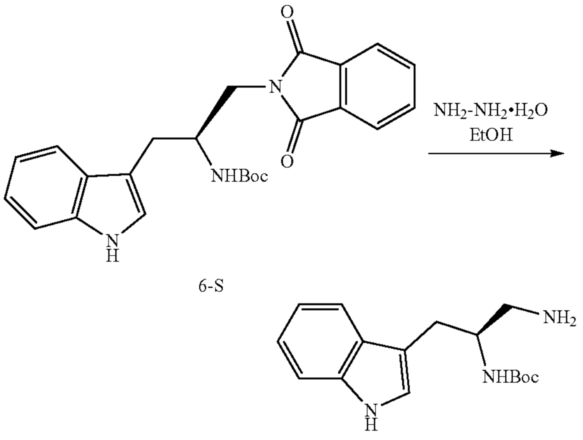

6-S

7-S

To a solution of 6-S (0.86 g, 2.07 mmol) in ethanol (72 mL, 36 mL/mmol) was added hydrazine monohydrate (10 mL, 207 mmol). The reaction mixture was stirred at 80° C. in sealed tube for 2.25 h, concentrated under vacuum. Flash chromatography (EtOAc:$CH_3OH$, from 100:1 to 50:50) to afford 7-S (1.0 g, 84%).

$R_f$=0.2 (EtOAc:$CH_3OH$, 6:4).

$^1$H NMR (400 MHz, $CD_3OD$): δ 7.61 (d, J=7.9 Hz, 1H), 7.35 (d, J=8.1 Hz, 1H), 7.13-6.97 (m, 2H), 7.09 (s, 1H), 4.06-3.96 (m, 1H), 3.01-2.76 (m, 4H), 1.38 (s, 9H).

ESI-MS m/z: 290.3 $(M+H)^+$.

D)

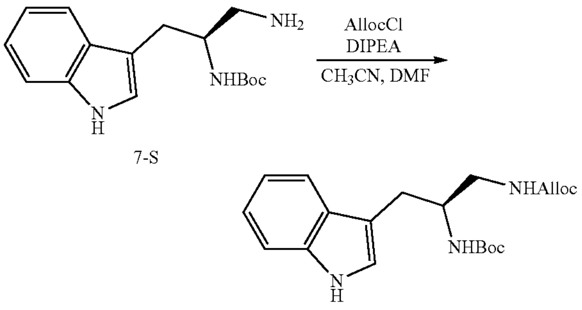

7-S

8-S

To a solution of 7-S (0.95 g, 3.3 mmol) in $CH_3CN$ (33 mL, 10 mL/mmol) and DMF (3.3 mL, 1 mL/mmol) was added N,N-diisopropylethylamine (0.5 mL, 2.6 mmol) and allyl chloroformate (3.5 mL, 33 mmol). The reaction was stirred at 23° C. for 20 h. The mixture was diluted with EtOAc, $NH_4Cl$ was added and the mixture was extracted with EtOAc. The combined organic layers were dried over anhydrous $Na_2SO_4$, filtered, and concentrated under vacuum. The residue obtained was purified by flash chromatography (Hexane:EtOAc, from 100:1 to 1:100) to afford 8-S (0.88 g, 73%).

$R_f$=0.5 (Hexane:EtOAc, 1:1).

$^1$H NMR (400 MHz, $CDCl_3$): δ 8.17 (s, 1H), 7.63 (d, J=7.8 Hz, 1H), 7.20 (dd, J=8.1, 0.9 Hz, 1H), 7.13 (dddd, J=27.8, 8.0, 7.0, 1.1 Hz, 2H), 7.06 (d, J=2.4 Hz, 1H), 5.90 (ddt, J=17.3, 10.7, 5.6 Hz, 1H), 5.31-5.18 (m, 2H), 5.09 (s, 1H), 4.80 (s, 1H), 4.59-4.52 (m, 2H), 4.03 (s, 1H), 3.37 (dt, J=10.0, 4.7 Hz, 1H), 3.21 (s, 1H), 3.05-2.87 (m, 2H), 1.42 (s, 9H).

ESI-MS m/z: 274.3 $(M-Boc+H)^+$.

E)

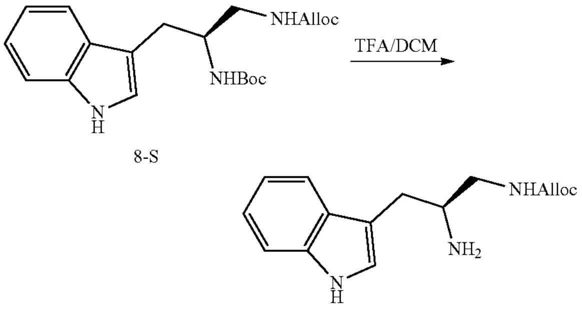

8-S

9-S

To a solution of 8-S (0.875 g, 2.3 mmol) in $CH_2Cl_2$ (38 mL, 16.6 mL/mmol) was added trifluoroacetic acid (19 mL, 8.3 mL/mmol). The reaction mixture was stirred at 23° C. for 2 h, concentrated under vacuum to give crude 9-S which was used in the next steps without further purification.

$R_f$=0.2 ($CH_2Cl_2$:$CH_3OH$, 9:1).

$^1$H NMR (400 MHz, $CD_3OD$): δ 7.56 (d, J=7.8 Hz, 1H), 7.37 (d, J=8.1 Hz, 1H), 7.21 (s, 1H), 7.13 (t, J=7.5 Hz, 1H), 7.05 (t, J=7.5 Hz, 1H), 5.94 (ddt, J=16.4, 10.8, 5.6 Hz, 1H), 5.34-5.16 (m, 2H), 4.56 (d, J=5.5 Hz, 2H), 3.60 (bs, 1H), 3.43 (dd, J=14.9, 3.9 Hz, 1H), 3.37-3.31 (m, 1H), 3.14-2.99 (m, 2H).

ESI-MS m/z: 274.3 $(M+H)^+$.

Example 0-5

A)

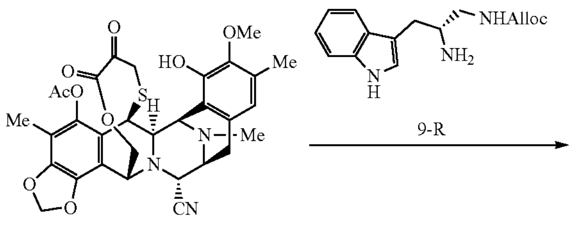

1

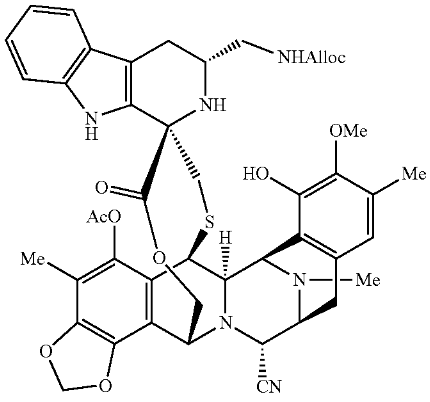

10-R

To a solution of 1 (1.45 g, 2.33 mmol) in acetic acid (58 mL, 0.08 M) was added 9-R (0.95 g, 3.50 mmol). The reaction mixture was stirred a 50° C. for 18 h and then acetic acid was evaporated. An aqueous saturated solution of $NaHCO_3$ was added and the mixture was extracted with $CH_2Cl_2$. The combined organic layers were dried over anhydrous $Na_2SO_4$. Flash chromatography (Hexane:EtOAc, 1:1) gives compound 10-R (1.3 g, 64%).

$R_f$=0.5 (Hexane:EtOAc, 1:1).

$^1H$ NMR (400 MHz, $CDCl_3$): δ 7.66 (s, 1H), 7.36 (d, J=7.9 Hz, 1H), 7.27 (d, J=7.9 Hz, 1H), 7.10 (ddd, J=8.3, 7.0, 1.3 Hz, 1H), 7.01 (td, J=7.5, 7.0, 1.0 Hz, 1H), 6.62 (s, 1H), 6.23 (d, J=1.4 Hz, 1H), 6.01 (d, J=1.4 Hz, 1H), 5.99-5.89 (m, 1H), 5.79 (s, 1H), 5.44-5.21 (m, 2H), 5.14-4.99 (m, 2H), 4.63 (ddd, J=7.3, 4.4, 1.5 Hz, 2H), 4.36 (s, 1H), 4.33-4.24 (m, 1H), 4.29-4.26 (m, 1H), 4.21 (d, J=2.7 Hz, 1H), 4.19-4.13 (m, 3H), 3.80 (s, 3H), 3.56 (s, 1H), 3.48-3.43 (m, 3H), 3.27 (dt, J=13.2, 4.0 Hz, 1H), 3.04-2.88 (m, 2H), 2.56 (dd, J=15.2, 3.8 Hz, 1H), 2.49-2.35 (m, 2H), 2.31 (s, 3H), 2.28 (s, 3H), 2.17 (s, 3H), 2.07 (s, 3H).

ESI-MS m/z: 877.3 $(M+H)^+$.

B)

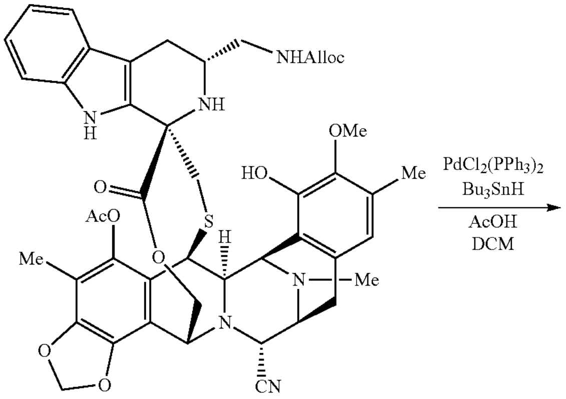

10-R

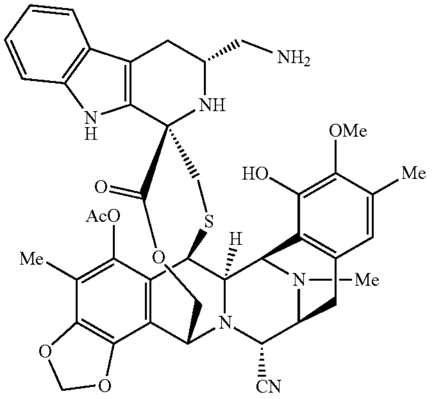

11-R

To a solution of 10-R (600 mg, 0.68 mmol) in $CH_2Cl_2$ (12 mL, 18 mL/mmol) was added bis(triphenylphosphine)palladium(II) dichloride (77 mg, 0.1 mmol) and acetic acid (0.4 mL, 6.8 mmol). Tributyltin hydride (1.1 mL, 4.08 mmol) was added at 0° C., the reaction mixture was stirred at 0° C. for 0.5 h and concentrated under vacuum. The crude obtained was diluted with EtOAc, saturated aqueous solution of $NH_4Cl$ was added, and the mixture was extracted with EtOAc. The combined organic layers were dried over anhydrous $Na_2SO_4$, filtered, and concentrated under vacuum. Flash chromatography (Hexane:EtOAc, from 100:1 to 1:100 and EtOAc:$CH_3OH$, from 100:1 to 1:100) to afford 11-R (440 mg, 82%).

$R_f$=0.5 ($CH_2Cl_2$:$CH_3OH$, 1:1).

$^1H$ NMR (400 MHz, $CDCl_3$): δ 7.64 (s, 1H), 7.38 (d, J=7.9 Hz, 1H), 7.29 (d, J=8.1 Hz, 1H), 7.11 (ddt, J=8.3, 7.0, 1.4 Hz, 1H), 7.03 (ddt, J=8.3, 7.0, 1.4 Hz, 1H), 6.58 (s, 1H), 6.24 (d, J=1.5 Hz, 1H), 6.02 (d, J=1.5 Hz, 1H), 5.02 (d, J=11.8 Hz, 1H), 4.63 (s, 1H), 4.36 (s, 1H), 4.28 (d, J=5.1 Hz, 1H), 4.21 (d, J=2.2 Hz, 1H), 4.16 (s, 1H), 3.80 (s, 3H), 3.51-3.39 (m, 4H), 3.32-3.13 (m, 3H), 2.95 (d, J=8.9 Hz, 2H), 2.89-2.76 (m, 2H), 2.73-2.57 (m, 1H), 2.42 (d, J=14.8 Hz, 1H), 2.36 (s, 3H), 2.25 (s, 3H), 2.16 (s, 3H), 2.09 (s, 3H).

ESI-MS m/z: 793.2 $(M+H)^+$.

C)

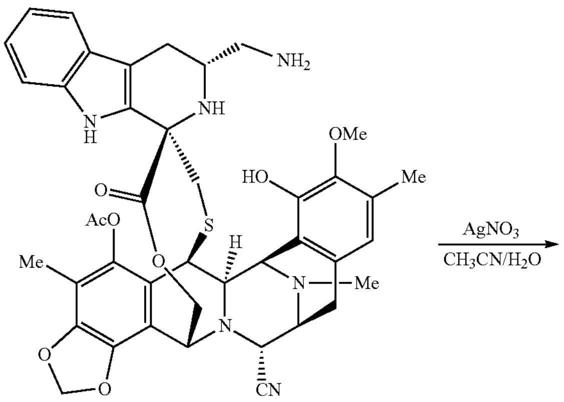

11-R

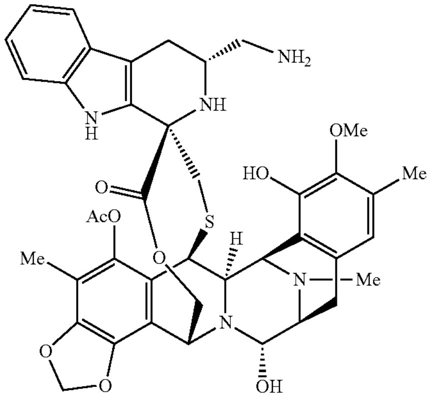

12-R

To a solution of 11-R (850 mg, 1.07 mmol) in $CH_3CN$:$H_2O$ (1.39:1, 70 mL, 0.015 M) was added $AgNO_3$ (3.64 g, 21.4 mmol). After 17 h at 23° C., the reaction was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give 12-R (553 mg, 66%).

$R_f$=0.3 ($CH_2Cl_2$:$CH_3OH$, 9:1).

$^1H$ NMR (500 MHz, $CDCl_3$): δ 7.60 (s, 1H), 7.38 (d, J=7.9 Hz, 1H), 7.28 (d, J=7.9 Hz, 1H), 7.11 (ddt, J=8.3, 7.1, 1.2 Hz, 1H), 7.02 (ddt, J=8.3, 7.1, 1.2 Hz, 1H), 6.58 (s, 1H), 6.22 (s, 1H), 6.00 (s, 1H), 5.16 (d, J=11.5 Hz, 1H), 4.87 (s, 1H), 4.54 (s, 1H), 4.51 (d, J=3.3 Hz, 1H), 4.17 (d, J=5.4 Hz, 1H), 4.07 (dd, J=11.3, 2.2 Hz, 1H), 3.81 (s, 3H), 3.52 (d, J=5.1 Hz, 1H), 3.24 (d, J=8.8 Hz, 2H), 2.99-2.78 (m, 4H), 2.66 (dd, J=14.9, 3.5 Hz, 1H), 2.49-2.39 (m, 2H), 2.38 (s, 3H), 2.28 (m, 2H), 2.25 (s, 3H), 2.21-2.16 (m, 2H), 2.15 (s, 3H), 2.08 (s, 3H).

$^{13}C$ NMR (101 MHz, $CD_3OD$): δ 171.7, 169.4, 148.7, 145.9, 143.7, 141.4, 140.9, 136.9, 130.8, 130.0, 129.7, 126.0, 121.4, 121.0, 119.7, 119.1, 118.4, 117.5, 114.9, 110.8, 107.5, 106.4, 102.1, 91.3, 63.2, 60.0, 59.0, 58.6, 55.3, 54.6, 52.7, 52.4, 48.4, 45.8, 42.5, 40.2, 24.5, 23.2, 19.2, 15.0, 8.2.

ESI-MS m/z: 766.2 $(M-H_2O+H)^+$.

(+)-HR-ESI-TOF-MS m/z: 766.2972 $[M-H_2O+H]^+$ (Calcd. for $C_{41}H_{44}N_5O_8S$+: 766.2905).

C')

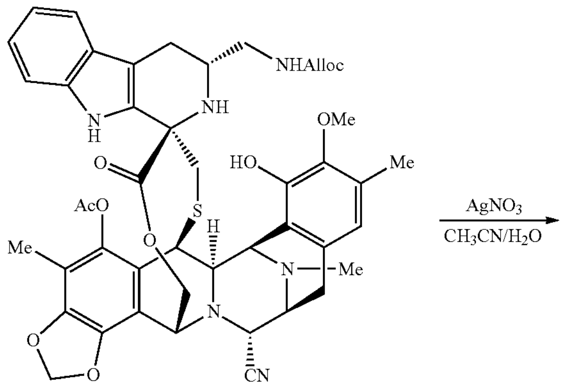

10-R

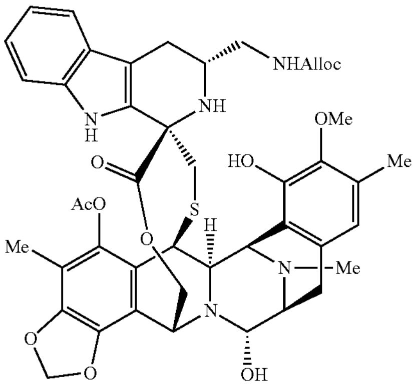

13-R

To a solution of 10-R (700 mg, 0.8 mmol) in $CH_3CN$:$H_2O$ (1.39:1, 52.5 mL, 0.015 M) was added $AgNO_3$ (2.66 g, 16 mmol). After 20 h at 23° C., the reaction mixture was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give 13-R (438 mg, 63%).

$R_f$=0.40 ($CH_2Cl_2$:$CH_3OH$, 9:1).

$^1H$ NMR (400 MHz, $CDCl_3$): δ 7.64 (s, 1H), 7.37 (d, J=7.9 Hz, 1H), 7.32-7.20 (m, 1H), 7.11 (t, J=7.7 Hz, 1H), 7.01 (t, J=7.4 Hz, 1H), 6.62 (s, 1H), 6.21 (s, 1H), 6.05-5.90 (m, 1H), 5.99 (s, 1H), 5.75 (d, J=6.0 Hz, 1H), 5.40-5.07 (m, 4H), 4.88 (d, J=14.7 Hz, 1H), 4.68-4.50 (m, 3H), 4.28-4.13 (m, 1H), 4.08 (dt, J=11.4, 2.4 Hz, 1H), 3.83 (s, 3H), 3.68-3.40 (m, 4H), 3.37-3.19 (m, 2H), 2.98-2.79 (m, 2H), 2.59-2.36 (m, 3H), 2.29 (s, 3H), 2.27 (s, 3H), 2.14 (s, 3H), 2.10-2.16 (m, 1H), 2.08 (s, 3H).

ESI-MS m/z: 850.3 $(M-H_2O+H)^+$.

Example 0-6

A)

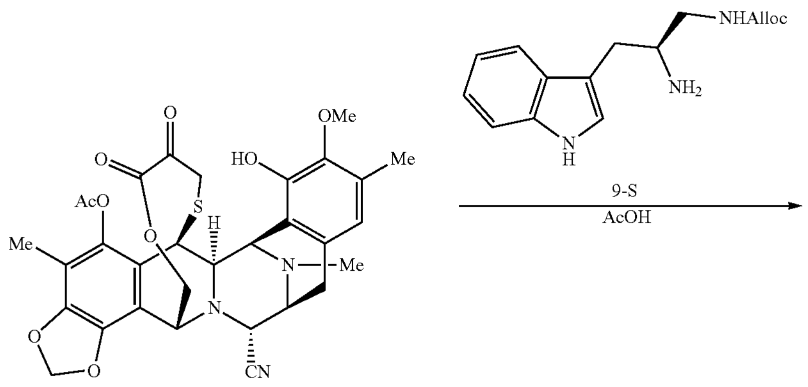

1

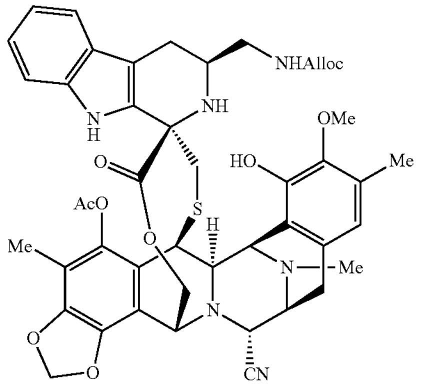

10-S

To a solution of 1 (955 mg, 1.5 mmol) in acetic acid (37.5 mL, 0.08 M) was added 9-S (627 mg, 2.29 mmol). The reaction mixture was stirred a 50° C. for 18 h and then acetic acid was evaporated. An aqueous saturated solution of $NaHCO_3$ was added and the mixture was extracted with $CH_2Cl_2$. The combined organic layers were dried over anhydrous $Na_2SO_4$. Flash chromatography (Hexane:EtOAc, 1:1) gives compound 10-S (756 mg, 58%).

$R_f$=0.4 (Hexane:EtOAc, 1:1).

$^1H$ NMR (400 MHz, $CDCl_3$): δ 7.78 (s, 1H), 7.36 (d, J=7.9 Hz, 1H), 7.24 (d, J=7.9 Hz, 1H), 7.10 (ddd, J=8.3, 7.0, 1.3 Hz, 1H), 7.01 (td, J=7.5, 7.0, 1.0 Hz, 1H), 6.68 (s, 1H), 6.23 (d, J=1.4 Hz, 1H), 6.01 (d, J=1.4 Hz, 1H), 6.07-5.93 (m, 1H), 5.82 (s, 1H), 5.41-5.19 (m, 2H), 5.1 (d, J=11.7 Hz, 1H), 4.66 (dt, J=5.9, 1.3 Hz, 1H), 4.57 (s, 1H), 4.37 (s, 1H), 4.33-4.20 (m, 3H), 3.81 (s, 3H), 3.46 (d, J=4.2 Hz, 2H), 3.22-3.13 (m, 1H), 3.11-2.88 (m, 4H), 2.66 (dd, J=15.2, 4.2 Hz, 1H), 2.51 (dd, J=15.3, 6.0 Hz, 1H), 2.43-2.32 (m, 2H), 2.31 (s, 3H), 2.26 (s, 3H), 2.19 (s, 3H), 2.04 (s, 3H).

ESI-MS m/z: 877.3 $(M+H)^+$.

B)

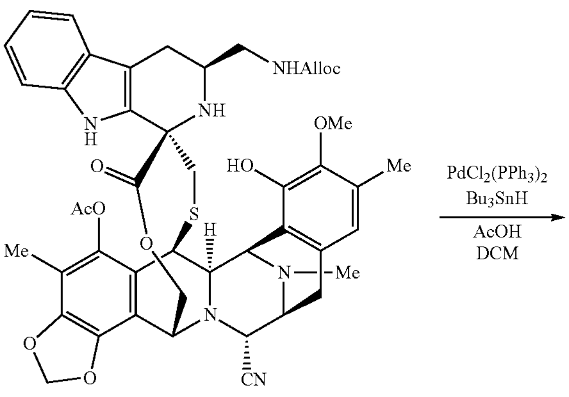

10-S

-continued

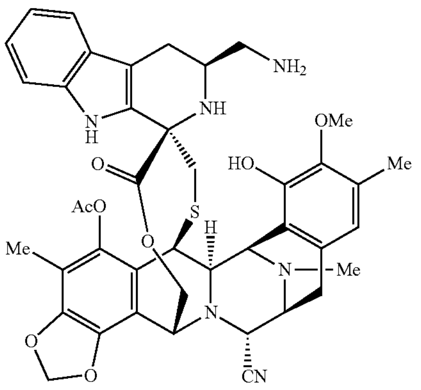

11-S

To a solution of 10-S (650 mg, 0.72 mmol) in $CH_2Cl_2$ (13.3 mL, 18 mL/mmol) was added bis(triphenylphosphine) palladium(II) dichloride (83 mg, 0.11 mmol) and acetic acid (0.42 mL, 7.4 mmol). Tributyltin hydride (1.2 mL, 4.4 mmol) was added at 0° C., the reaction mixture was stirred at 23° C. for 0.5 h, and concentrated under vacuum. Flash chromatography (Hexane:EtOAc, from 100:1 to 1:100 and EtOAc:$CH_3OH$, from 100:1 to 1:100) to afford 11-S (445 mg, 78%).

$R_f$=0.5 ($CH_2Cl_2$:$CH_3OH$, 1:1).

$^1H$ NMR (400 MHz, $CDCl_3$): δ 7.74 (s, 1H), 7.36 (d, J=7.9 Hz, 1H), 7.26 (d, J=8.1 Hz, 1H), 7.12 (ddt, J=8.3, 7.0, 1.4 Hz, 1H), 7.02 (ddt, J=8.3, 7.0, 1.4 Hz, 1H), 6.62 (s, 1H), 6.26 (d, J=1.5 Hz, 1H), 6.04 (d, J=1.5 Hz, 1H), 5.12 (d, J=11.8 Hz, 1H), 4.59 (s, 1H), 4.42 (s, 1H), 4.36-4.17 (m, 3H), 3.81 (s, 3H), 3.51-3.39 (m, 3H), 2.98-2.75 (m, 4H), 2.69-2.60 (m, 2H), 2.47 (d, J=16.1 Hz, 1H), 2.38 (s, 3H), 2.35-2.17 (m, 2H), 2.28 (s, 3H), 2.13 (s, 3H), 2.04 (s, 3H).

ESI-MS m/z: 793.3 $(M+H)^+$.

C)

-continued

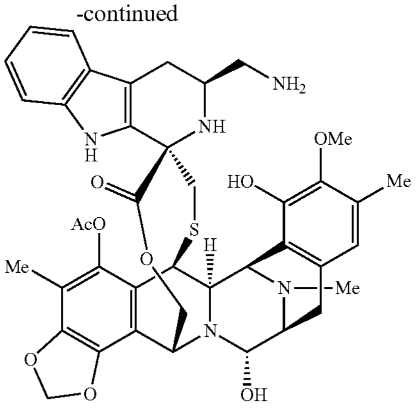

12-S

To a solution of 11-S (435 mg, 0.55 mmol) in $CH_3CN$:$H_2O$ (1.39:1, 38.5 mL, 0.015 M) was added $AgNO_3$ (1.84 g, 11 mmol). After 24 h at 23° C., the reaction was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give 12-S (152 mg, 35%).

$R_f$=0.2 ($CH_2Cl_2$:$CH_3OH$, 9:1).

$^1H$ NMR (500 MHz, $CD_3OD$): δ 7.34 (dd, J=7.7, 1.5 Hz, 1H), 7.28 (dd, J=7.7, 1.5 Hz, 1H), 7.04 (ddt, J=8.2, 7.0, 1.1 Hz, 1H), 6.95 (ddt, J=8.2, 7.0, 1.2 Hz, 1H), 6.55 (s, 1H), 6.31-6.25 (m, 1H), 6.15-6.05 (m, 1H), 5.31 (d, J=11.4 Hz, 1H), 4.91 (s, 1H), 4.64 (s, 1H), 4.40-4.19 (m, 3H), 3.76 (s, 3H), 3.64 (d, J=5.2 Hz, 1H), 3.44 (d, J=9.0 Hz, 1H), 3.03-2.85 (m, 4H), 2.85-2.65 (m, 2H), 2.59 (d, J=15.6 Hz, 1H), 2.52-2.39 (m, 2H), 2.37 (s, 3H), 2.27 (s, 3H), 2.09 (s, 3H), 2.00 (s, 3H).

$^{13}C$ NMR (126 MHz, $CD_3OD$): δ 171.4, 169.3, 148.6, 145.8, 143.5, 141.2, 140.8, 136.5, 131.2, 130.3, 129.5, 126.3, 121.6, 121.2, 119.8, 119.4, 118.6, 117.5, 114.9, 111.0, 107.5, 107.4, 102.2, 91.1, 63.5, 60.5, 59.2, 58.5, 55.3, 54.7, 53.4, 52.7, 48.6, 44.7, 42.7, 39.9, 24.3, 23.4, 19.2, 15.1, 8.2.

ESI-MS m/z: 766.2 $(M-H_2O+H)^+$.

(+)-HR-ESI-TOF-MS m/z: 766.2958 $[M-H_2O+H]^+$ (Calcd. for $C_{41}H_{44}N_5O_8S$: 766.2905).

C')

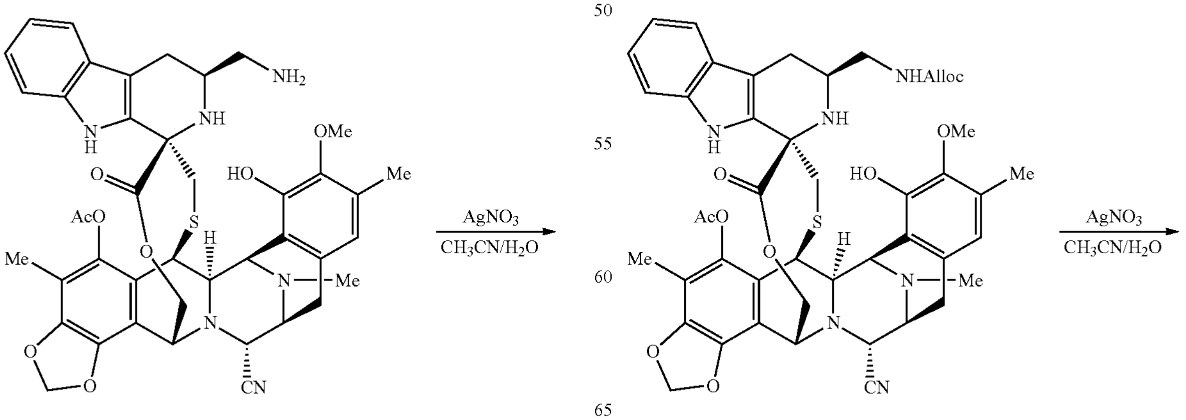

11-S

10-S

-continued

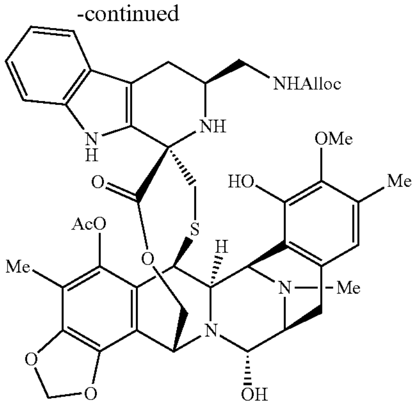

13-S

To a solution of 10-S (5 mg, 0.006 mmol) in $CH_3CN$:$H_2O$ (1.39:1, 0.5 mL, 0.015 M) was added $AgNO_3$ (29 mg, 0.17 mmol). After 20 h at 23° C., the reaction mixture was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give 13-S (5 mg, 100%).

$R_f$=0.40 ($CH_2Cl_2$:$CH_3OH$, 9:1).

$^1H$ NMR (400 MHz, $CDCl_3$): δ 7.75 (s, 1H), 7.37 (d, J=7.9 Hz, 1H), 7.32-7.20 (m, 1H), 7.12 (t, J=7.7 Hz, 1H), 7.02 (t, J=7.4 Hz, 1H), 6.84 (s, 1H), 6.24 (s, 1H), 6.08-5.97 (m, 1H), 6.01 (s, 1H), 5.87 (s, 1H), 5.42-5.19 (m, 4H), 4.88 (s, 1H), 4.69-4.65 (m, 2H), 4.58 (s, 1H), 4.28-4.13 (m, 2H), 3.84 (s, 3H), 3.68-3.40 (m, 2H), 3.24-3.15 (m, 2H), 3.08-2.90 (m, 2H), 2.73-2.57 (m, 2H), 2.53-2.37 (m, 3H), 2.34 (s, 3H), 2.25 (s, 3H), 2.14 (s, 3H), 2.10-2.16 (m, 1H), 2.03 (s, 3H).

ESI-MS m/z: 850.3 $(M-H_2O+H)^+$.

Example 0-7

A) Synthesis of (S)-5-methoxy-tryptophanol (17-S)

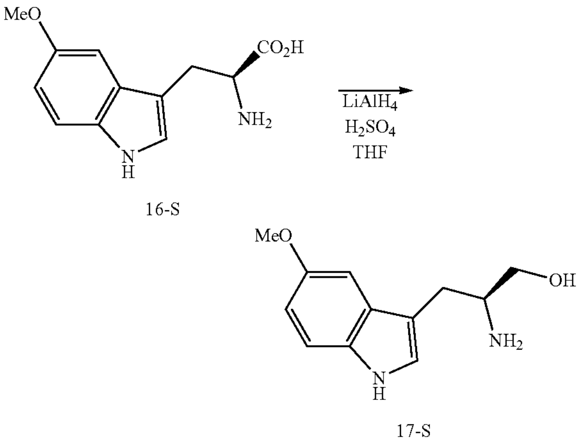

16-S

17-S

To a solution of $LiAlH_4$ (23.4 mL, 1.0 M in THF, 23.4 mmol) at −40° C. was added carefully $H_2SO_4$ (0.31 mL, 5.57 mmol) and a suspension of 5-methoxy-L-tryptophan (16-S) (1.0 g, 4.26 mmol, Chem-Impex) in THF (13.4 mL, 0.3 M). The reaction mixture was left evolution at 23° C., heated for 3 h at 80° C. and 18 h at 23° C. Cool at −21° C. the reaction mixture was quenched carefully with NaOH 2N until basic pH. EtOAc was added and the mixture filtered through Celite® and washed with $CH_3OH$. The crude was concentrated under vacuum to give 17-S as a crude which was used in the next step without further purification.

$R_f$=0.2 ($CH_2Cl_2$:$CH_3OH$, 4:1).

$^1H$ NMR (400 MHz, $CDCl_3$): δ 7.19 (dt, J=8.8, 0.7 Hz, 1H), 7.06-7.00 (m, 2H), 6.72 (dd, J=8.8, 2.4 Hz, 1H), 3.77 (s, 3H), 3.63-3.48 (m, 1H), 3.42-3.33 (m, 1H), 3.17-3.06 (m, 1H), 2.86 (ddt, J=14.3, 6.1, 0.8 Hz, 1H), 2.66 (dd, J=14.3, 7.5 Hz, 1H).

ESI-MS m/z: 221.4 $(M+H)^+$.

B) Synthesis of (R)-5-methoxy-tryptophanol (17-R)

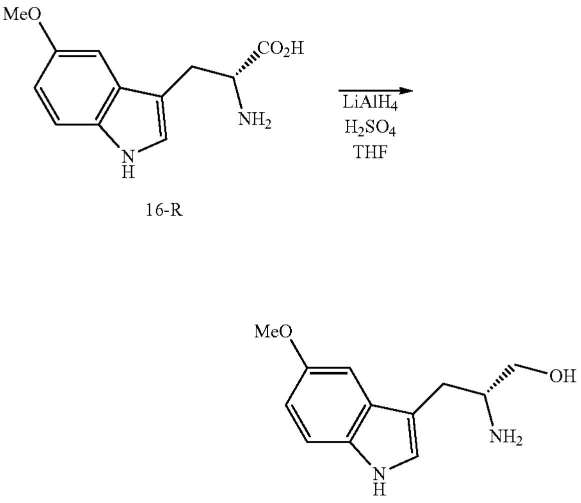

16-R

17-R

To a solution of $LiAlH_4$ (11.7 mL, 1.0 M in THF, 11.7 mmol) at −40° C. was added carefully $H_2SO_4$ (0.31 mL, 5.75 mmol) and a suspension of 5-methoxy-D-tryptophan (16-R) (0.5 g, 2.13 mmol, Aldrich) in THF (6.7 mL, 0.3 M). The reaction mixture was left evolution at 23° C., heated for 3.5 h at 80° C. and 18 h at 23° C. Cool at −21° C. the reaction mixture was quenched carefully with NaOH 2N until basic pH. EtOAc was added and the mixture filtered through Celite® and washed with $CH_3OH$. The crude was concentrated under vacuum to give 17-R as a crude which was used in the next step without further purification.

$R_f$=0.2 ($CH_2Cl_2$:$CH_3OH$, 4:1).

$^1H$ NMR (400 MHz, $CD_3OD$): δ 7.20 (d, J=8.9 Hz, 1H), 7.06-6.96 (m, 2H), 6.71 (dd, J=8.8, 2.5 Hz, 1H), 3.75 (s, 3H), 3.62-3.52 (m, 1H), 3.37 (dd, J=10.8, 7.0 Hz, 1H), 3.09 (br s, 1H), 2.82 (dd, J=14.3, 5.9 Hz, 1H), 2.62 (dd, J=14.4, 7.6 Hz, 1H).

ESI-MS m/z: 221.6 $(M+H)^+$.

Example 0-8

A)

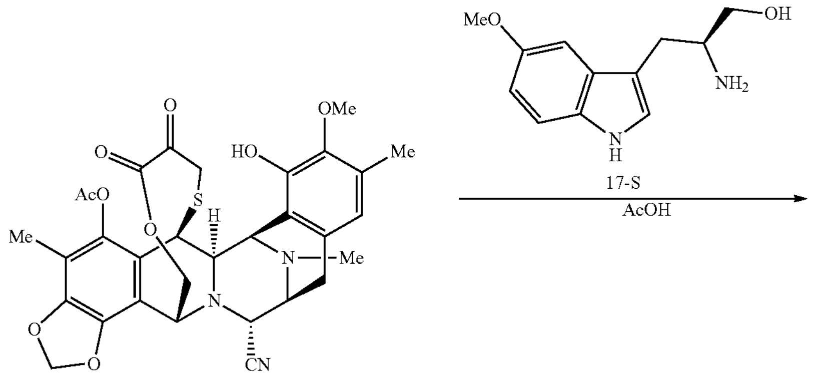

1

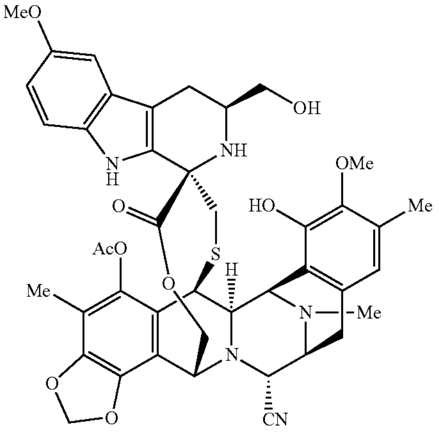

18-S

To a solution of 1 (530 mg, 0.85 mmol) in acetic acid (10.6 mL, 0.08 M) was added 17-S (469 mg, 2.13 mmol). The reaction mixture was stirred at 50° C. for 18 h and then acetic acid was evaporated. An aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, 1:1) gave compound 18-S (420 mg, 60%).

$R_f$=0.3 (Hexane:EtOAc, 1:1).

$^1$H NMR (400 MHz, $CD_3OD$): δ 7.13 (d, J=8.8 Hz, 1H), 6.80 (d, J=2.4 Hz, 1H), 6.66 (dd, J=8.8, 2.5 Hz, 1H), 6.51 (s, 1H), 6.27 (s, 1H), 6.11 (s, 1H), 5.21 (d, J=11.7 Hz, 1H), 4.67 (s, 1H), 4.49-4.29 (m, 4H), 3.75 (s, 3H), 3.73 (s, 3H), 3.47 (t, J=5.8 Hz, 3H), 3.37 (d, J=5.1 Hz, 1H), 3.01-2.81 (m, 2H), 2.75 (d, J=7.4 Hz, 1H), 2.66 (dd, J=15.1, 4.1 Hz, 1H), 2.55-2.35 (m, 4H), 2.34 (s, 3H), 2.28 (s, 3H), 2.11 (s, 3H), 1.99 (s, 3H).

ESI-MS m/z: 824.3 $(M+H)^+$.

B)

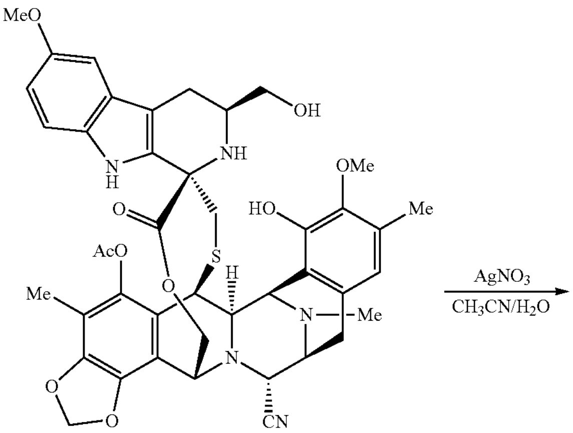

18-S

-continued

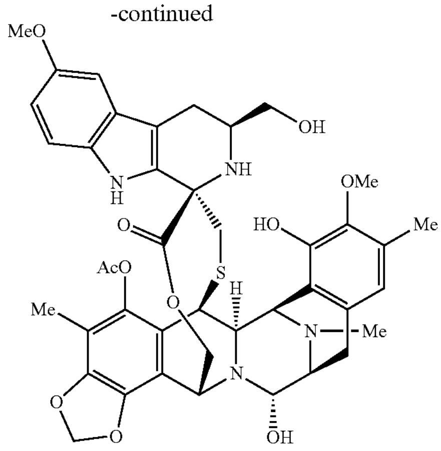

19-S

To a solution of 18-S (420 mg, 0.519 mmol) in $CH_3CN$:$H_2O$ (1.39:1, 36 mL, 0.015 M) was added $AgNO_3$ (2.60 g, 15.3 mmol). After 3 h at 23° C., the reaction mixture was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to obtain 19-S (250 mg, 60%).

$R_f$=0.45 ($CH_2Cl_2$:$CH_3OH$, 9:1).

$^1H$ NMR (500 MHz, $CD_3OD$): δ 7.15 (dd, J=8.9, 0.6 Hz, 1H), 6.82 (dd, J=2.4, 0.6 Hz, 1H), 6.68 (dd, J=8.8, 2.5 Hz, 1H), 6.54 (s, 1H), 6.27 (d, J=1.3 Hz, 1H), 6.08 (d, J=1.3 Hz, 1H), 5.30 (d, J=11.5 Hz, 1H), 4.62 (s, 1H), 4.34 (dd, J=11.4, 2.0 Hz, 1H), 4.31-4.27 (m, 2H), 3.76 (s, 3H), 3.75 (s, 3H), 3.66-3.58 (m, 1H), 3.55-3.45 (m, 2H), 3.42 (d, J=7.8 Hz, 1H), 2.93-2.73 (m, 3H), 2.68 (dd, J=15.1, 4.2 Hz, 1H), 2.54 (d, J=15.4 Hz, 1H), 2.42 (dd, J=15.1, 10.1 Hz, 2H), 2.35 (s, 3H), 2.29 (s, 3H), 2.09 (s, 3H), 2.00 (s, 3H).

$^{13}C$ NMR (126 MHz, $CD_3OD$): δ 172.7, 170.8, 155.1, 149.9, 147.2, 145.0, 142.6, 142.2, 133.1, 132.4, 132.1, 131.3, 128.1, 122.5, 121.6, 120.3, 116.4, 113.0, 112.9, 111.4, 109.0, 103.6, 100.8, 92.5, 66.6, 65.0, 61.7, 60.4, 59.9, 56.7, 56.1, 54.8, 54.1, 51.7, 44.1, 41.3, 30.7, 25.4, 24.7, 20.6, 16.3, 9.5.

ESI-MS m/z: 798.1 $(M-H_2O+H)^+$.

(+)-HR-ESI-TOF-MS m/z: 797.2899 $[M-H_2O+H]^+$ (Calcd. for $C_{42}H_{45}N_4O_{10}S$ 797.2851).

Example 0-9

A)

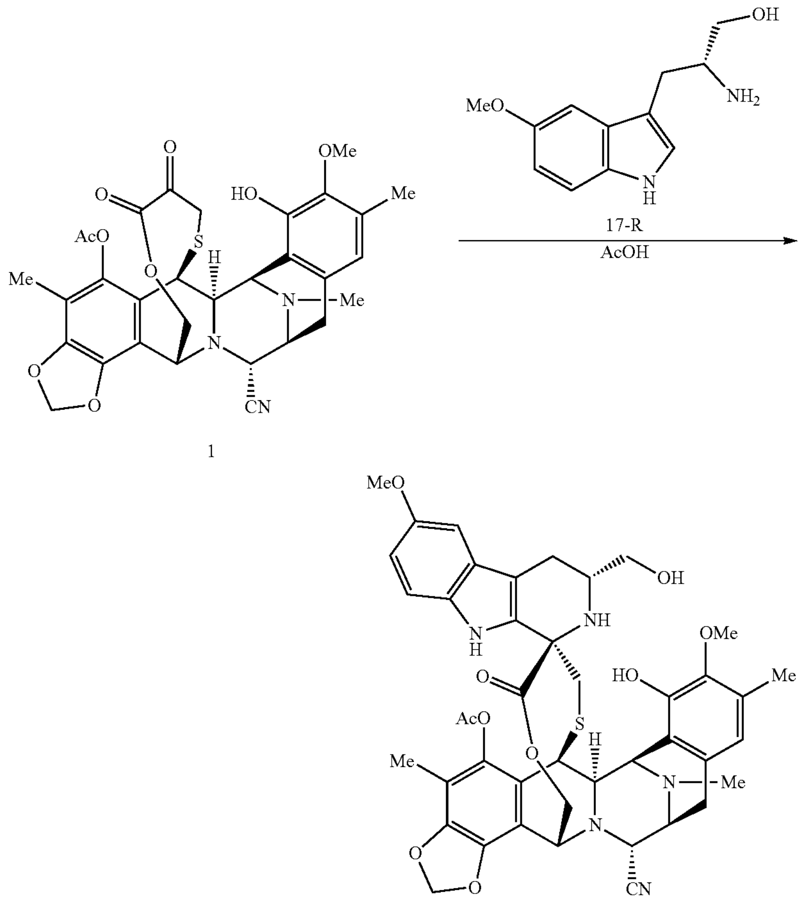

1

18-R

To a solution of 1 (311 mg, 0.50 mmol) in acetic acid (6.25 mL, 0.08 M) was added 17-R (220 mg, 1.0 mmol). The reaction mixture was stirred at 50° C. for 18 h and then acetic acid was evaporated. An aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, 1:1) gave compound 18-R (280 mg, 68%).

$R_f$=0.3 (Hexane:EtOAc, 1:1).

$^1$H NMR (400 MHz, $CDCl_3$): δ 7.53 (s, 1H), 7.18 (d, J=8.7 Hz, 1H), 6.82 (d, J=2.4 Hz, 1H), 6.78 (dd, J=8.6, 2.3 Hz, 1H), 6.60 (s, 1H), 6.23 (s, 1H), 6.02 (s, 1H), 5.76 (s, 1H), 5.04 (d, J=11.7 Hz, 1H), 4.62 (s, 1H), 4.36 (s, 1H), 4.28 (d, J=5.0 Hz, 1H), 4.24-4.09 (m, 3H), 3.81 (s, 3H), 3.79 (s, 3H), 3.64 (s, 1H), 3.47-3.40 (m, 3H), 3.01-2.90 (m, 2H), 2.53 (d, J=6.9 Hz, 2H), 2.45-2.41 (m, 1H), 2.40 (s, 3H), 2.27 (s, 3H), 2.22-2.14 (m, 1H), 2.18 (s, 3H), 2.06 (s, 3H).

ESI-MS m/z: 824.3 $(M+H)^+$.

B)

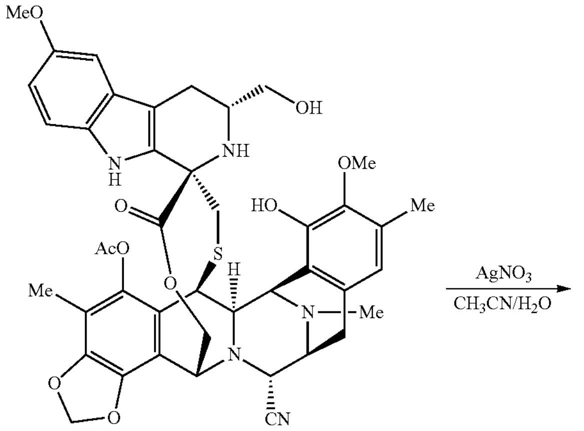

18-R

-continued

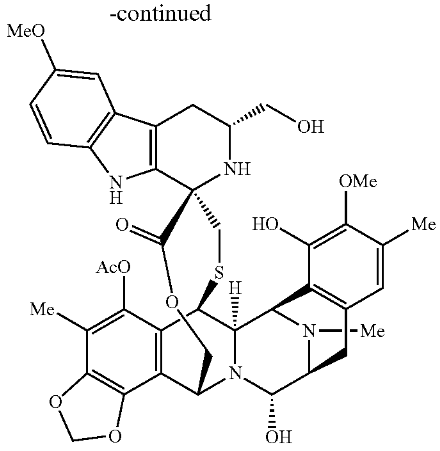

19-S

To a solution of 18-R (330 mg, 0.40 mmol) in $CH_3CN$:$H_2O$ (1.39:1, 28 mL, 0.015 M) was added $AgNO_3$ (2.04 g, 12.0 mmol). After 3 h at 23° C., the reaction was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to obtain 19-R (224 mg, 69%).

$R_f$=0.44 ($CH_2Cl_2$:$CH_3OH$, 9:1).

$^1$H NMR (500 MHz, $CD_3OD$): δ 7.14 (dd, J=8.8, 0.5 Hz, 1H), 6.83 (d, J=2.5 Hz, 1H), 6.68 (dd, J=8.8, 2.5 Hz, 1H), 6.59 (s, 1H), 6.26 (d, J=1.4 Hz, 1H), 6.07 (d, J=1.4 Hz, 1H), 5.21 (d, J=11.5 Hz, 1H), 4.68-4.55 (m, 1H), 4.32-4.25 (m, 2H), 4.12 (dd, J=11.5, 2.1 Hz, 1H), 3.75 (s, 3H), 3.74 (s, 3H), 3.60 (d, J=5.2 Hz, 1H), 3.57-3.45 (m, 3H), 3.41 (d, J=8.8 Hz, 1H), 2.97-2.83 (m, 3H), 2.73 (dd, J=15.0, 3.4 Hz, 1H), 2.69 (d, J=14.9 Hz, 1H), 2.34 (s, 3H), 2.30 (s, 3H), 2.20 (dd, J=15.1, 10.4 Hz, 1H), 2.12 (s, 3H), 2.11-2.08 (m, 1H), 2.05 (s, 3H).

$^{13}$C NMR (126 MHz, $CD_3OD$): δ 173.0, 170.8, 155.0, 149.8, 147.3, 145.0, 142.8, 142.3, 133.5, 133.1, 132.2, 132.1, 131.1, 130.5, 127.8, 122.5, 121.7, 120.0, 116.4, 113.5, 112.9, 111.4, 110.2, 103.5, 100.9, 92.6, 66.8, 64.5, 61.3, 60.4, 60.0, 56.8, 56.1, 55.9, 54.1, 44.1, 41.3, 25.6, 24.5, 20.6, 16.2, 9.6.

ESI-MS m/z: 797.4 $(M-H_2O+H)^+$.

(+)-HR-ESI-TOF-MS m/z: 797.2896 $[M-H_2O+H]^+$ (Calcd. for $C_{42}H_{45}N_4O_{10}S$ 797.2851).

Example 0-10. Synthesis of allyl N—[(S)-2-amino-3-(5-methoxy-1H-indol-3-yl)propyl)]carbamate (24-S)

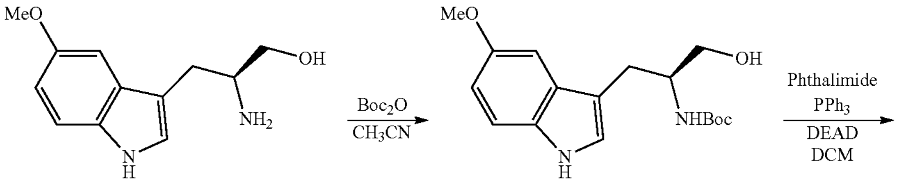

17-S

20-S

-continued

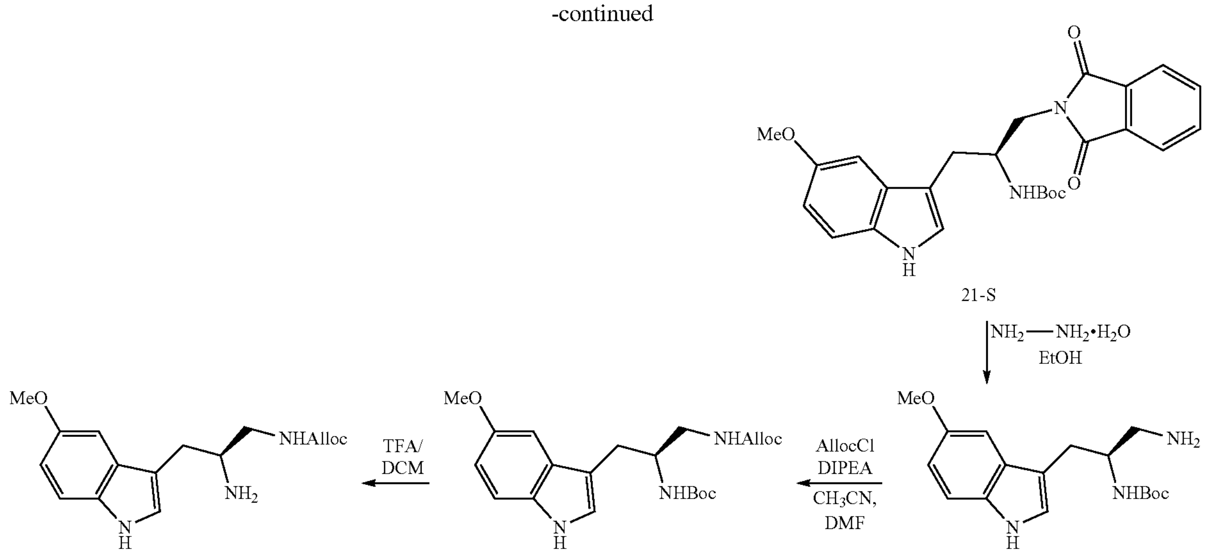

21-S

24-S 23-S 22-S

A) B)

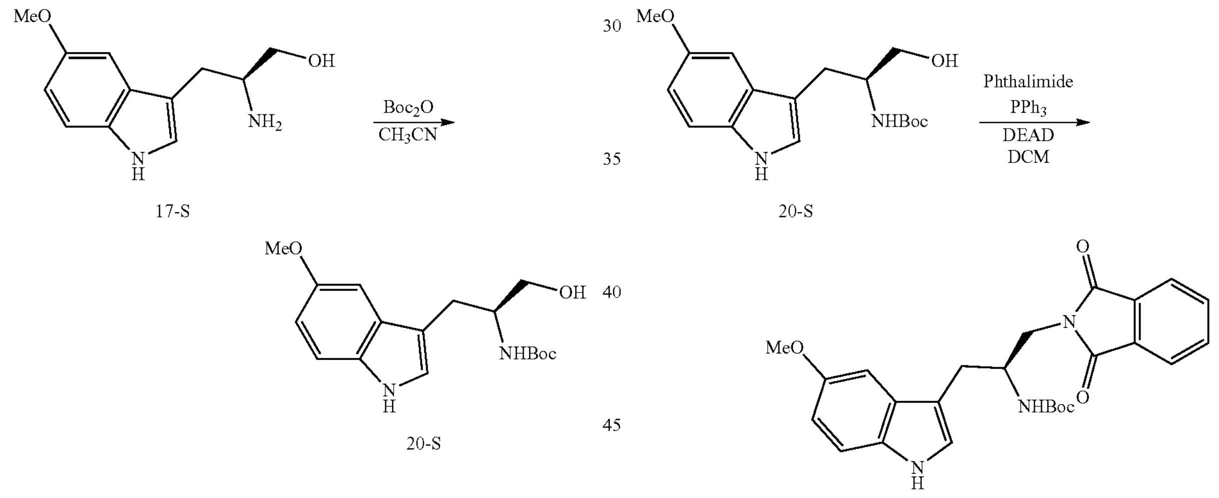

17-S 20-S

20-S 21-S

To a solution of 17-S (6.9 g, 31.4 mmol) in $CH_3CN$ (126 mL, 4 mL/mmol) was added di-tert-butyl dicarbonate (13.7 g, 62.8 mmol). The reaction mixture was stirred at 23° C. for 5.5 h, concentrated under vacuum. Flash chromatography ($CH_2Cl_2$:$CH_3OH$, from 99:1 to 85:15) gives 20-S (4.5 g, 45%).

$R_f$=0.6 ($CH_2Cl_2$:$CH_3OH$, 9:1).

$^1H$ NMR (400 MHz, $CDCl_3$): δ 8.04 (s, 1H), 7.25 (d, J=8.4 Hz, 1H), 7.10 (d, J=2.4 Hz, 1H), 7.03 (s, 1H), 6.87 (dd, J=8.8, 2.5 Hz, 1H), 4.83 (s, 1H), 3.98 (s, 1H), 3.87 (s, 3H), 3.73-3.58 (m, 2H), 2.96 (d, J=6.6 Hz, 2H), 1.42 (s, 9H).

To a solution of 20-S (4.5 g, 14 mmol) in $CH_2Cl_2$ (84 mL, 6 mL/mmol) was added phthalimide (4.5 g, 30.9 mmol), triphenylphosphine (8.1 g, 30.9 mmol) and the mixture was cooled at 0° C. A solution of 40% of diethyl azodicarboxylate (DEAD) in $CH_2Cl_2$ (10.4 mL, 35 mmol) was added for 15 min. The reaction was stirred at 23° C. for 18 h, concentrated under vacuum. The residue obtained was purified by flash chromatography (Hexane:EtOAc, from 99:1 to 85:15) to yield 21-S (5.8 g, 92%).

$R_f$=0.55 (Hexane:EtOAc, 1:1).

$^1H$ NMR (400 MHz, $CDCl_3$): δ 8.48 (s, 1H), 7.78 (dd, J=5.5, 3.1 Hz, 2H), 7.69-7.61 (m, 2H), 7.21 (d, J=8.8 Hz, 1H), 7.06 (dd, J=18.5, 2.4 Hz, 2H), 6.81 (dd, J=8.8, 2.4 Hz, 1H), 4.87 (s, 1H); 4.39 (s, 1H), 3.87 (s, 3H), 3.83-3.66 (m, 2H), 2.98 (d, J=6.1 Hz, 2H), 1.20 (s, 9H).

C)

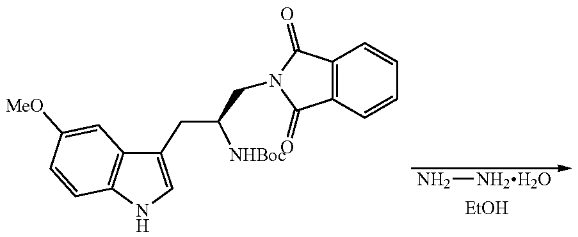

21-S

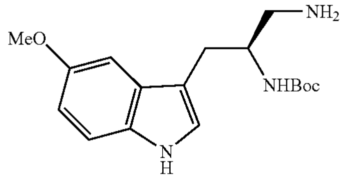

22-S

To a solution of 21-S (6.29 g, 14 mmol) in ethanol (420 mL, 30 mL/mmol) was added hydrazine monohydrate (61.1 mL, 1260 mmol). The reaction mixture was stirred at 80° C. in sealed tube for 2 h, concentrated under vacuum. Flash chromatography ($CH_2Cl_2$:$CH_3OH$, from 100:1 to 50:50) affords 22-S (4.2 g, 95%).

$R_f$=0.1 ($CH_2Cl_2$:$CH_3OH$, 8:2).

$^1H$ NMR (400 MHz, $CDCl_3$): δ 7.22 (d, J=8.8 Hz, 1H), 7.12 (d, J=2.4 Hz, 1H), 7.06 (s, 1H), 6.76 (dd, J=8.8, 2.4 Hz, 1H), 4.06-3.97 (m, 1H), 3.82 (s, 3H), 3.06-2.82 (m, 4H), 1.37 (s, 9H).

D)

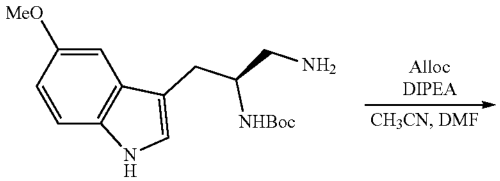

22-S

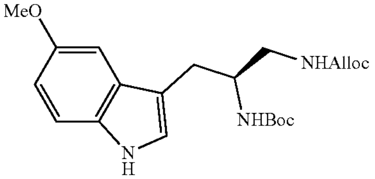

23-S

To a solution of 22-S (4.0 g, 12.52 mmol) in $CH_3CN$ (125 mL, 10 mL/mmol) and DMF (12 mL, 1 mL/mmol) was added N,N-diisopropylethylamine (1.8 mL, 10 mmol) and allyl chloroformate (13.3 mL, 125 mmol). The reaction was stirred at 23° C. for 5 h. The mixture was diluted with EtOAc and $NH_4Cl$ was added and the mixture was extracted with EtOAc. The combined organic layers were dried over anhydrous $Na_2SO_4$, filtered, and concentrated under vacuum. The residue obtained was purified by flash chromatography (Hexane:EtOAc, from 100:1 to 1:100) to obtain 23-S (2.65 g, 52%).

$R_f$=0.5 (Hexane:EtOAc, 1:1).

$^1H$ NMR (400 MHz, $CDCl_3$): δ 8.11 (s, 1H), 7.28-7.20 (m, 1H), 7.04 (d, J=13.1 Hz, 2H), 6.85 (dd, J=8.9, 2.4 Hz, 1H), 5.97-5.82 (m, 1H), 5.33-5.24 (m, 1H), 5.19 (dt, J=10.4, 1.3 Hz, 1H), 5.11 (s, 1H), 4.82 (s, 1H), 4.55 (d, J=5.6 Hz, 2H), 4.01 (s, 1H), 3.86 (s, 3H), 3.37 (d, J=13.7 Hz, 1H), 3.21 (s, 1H), 2.89 (dd, J=14.5, 7.0 Hz, 1H), 1.41 (s, 9H).

E)

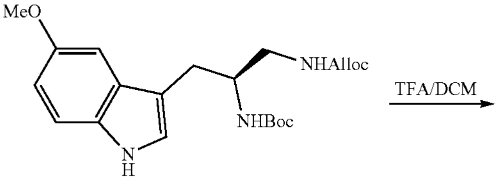

23-S

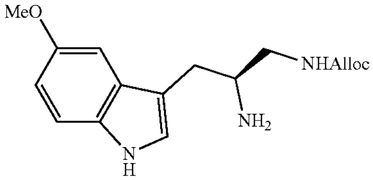

24-S

To a solution of 23-S (2.60 g, 6.44 mmol) in $CH_2Cl_2$ (106 mL, 16.6 mL/mmol) was added trifluoroacetic acid (54 mL, 8.3 mL/mmol). The reaction mixture was stirred at 23° C. for 1.5 h, concentrated under vacuum to afford 24-S (3.9 g, 100%).

$R_f$=0.1 ($CH_2Cl_2$:$CH_3OH$, 9:1).

$^1H$ NMR (400 MHz, $CD_3OD$): δ 8.27 (s, 1H), 7.25 (dd, J=9.0, 2.4 Hz, 1H), 7.10 (s, 1H), 6.96 (d, J=2.3 Hz, 1H), 6.87 (dd, J=9.0, 2.4 Hz, 1H), 5.81 (ddt, J=16.3, 10.9, 5.7 Hz, 1H), 5.23 (dd, J=19.3, 13.6 Hz, 2H), 4.49 (d, J=5.9 Hz, 2H), 3.82 (s, 3H), 3.81-3.55 (m, 1H), 3.62-3.39 (m, 2H), 3.08 (qd, J=15.1, 7.3 Hz, 2H).

Example 0-11

A)

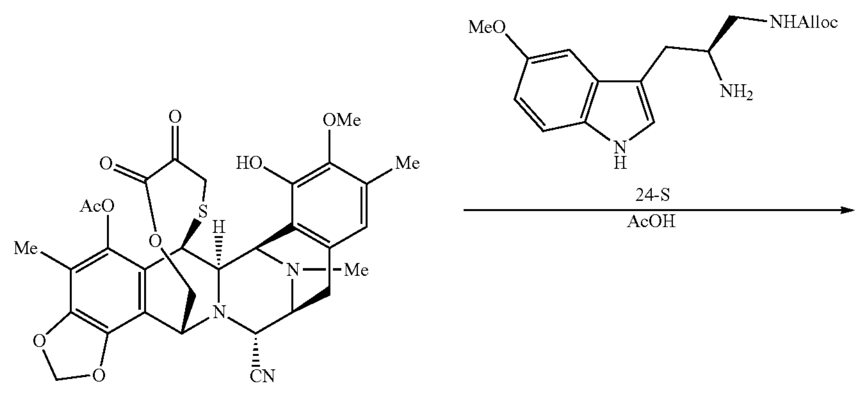

1

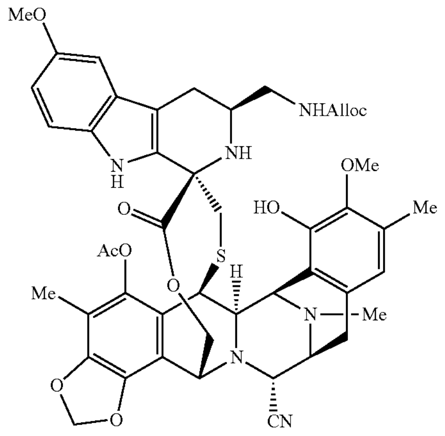

25-S

To a solution of 1 (120 mg, 0.19 mmol) in acetic acid (6 mL, 0.08 M) was added 24-S (117 mg, 0.35 mmol). The reaction mixture was stirred at 23° C. for 18 h and then acetic acid was evaporated. An aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, 1:1) gives compound 25-S (95 mg, 54%).

$R_f$=0.4 (Hexane:EtOAc, 1:1).

$^1$H NMR (400 MHz, $CDCl_3$): δ 7.64 (s, 1H), 7.14 (d, J=8.8 Hz, 1H), 6.80 (s, 1H), 6.77 (d, J=8.8 Hz, 1H), 6.68 (s, 1H), 6.24 (s, 1H), 6.03 (s, 1H), 6.02-5.93 (m, 1H), 5.76 (s, 1H), 5.38 (d, J=10.5 Hz, 1H), 5.26 (d, J=10.5 Hz, 1H), 5.11 (d, J=11.7 Hz, 1H), 4.66 (d, J=5.6 Hz, 2H), 4.57 (s, 1H), 4.37 (s, 1H), 4.33-4.19 (m, 3H), 3.82 (s, 3H), 3.79 (s, 3H), 3.46 (s, 2H), 3.17 (s, 1H), 3.10-2.90 (m, 3H), 2.68-2.45 (m, 2H), 2.38-2.33 (m, 1H), 2.32 (s, 3H), 2.27 (s, 3H), 2.16 (s, 3H), 2.04 (s, 2H).

ESI-MS m/z: 907.1 $(M+H)^+$.

B)

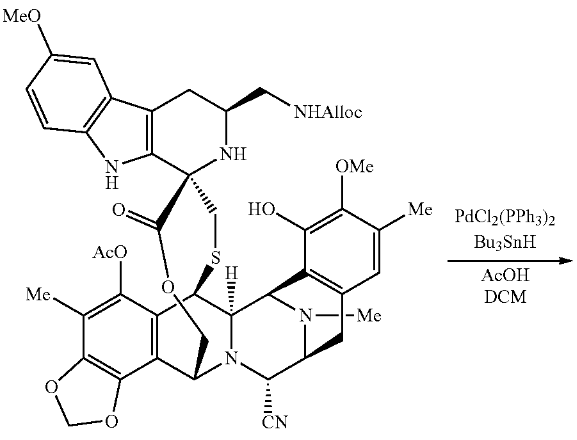

25-S

-continued

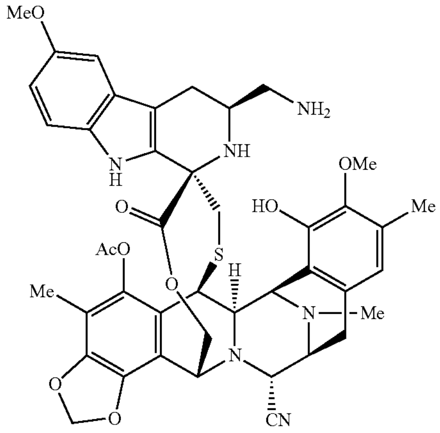

26-S

To a solution of 25-S (90 mg, 0.1 mmol) in $CH_2Cl_2$ (2 mL, 18 mL/mmol) was added bis(triphenylphosphine)palladium (II)dichloride (12 mg, 0.1 mmol) and acetic acid (0.056 mL, 0.99 mmol). Tributyltin hydride (0.16 mL, 0.60 mmol) was added at 0° C., the reaction mixture was stirred at 0° C. for 0.5 h, and concentrated under vacuum. Flash chromatography (Hexane:EtOAc, from 100:1 to 1:100 and EtOAc: $CH_3OH$, from 100:1 to 1:100) to afford 26-S (75 mg, 92%).

$R_f$=0.25 ($CH_2Cl_2$:$CH_3OH$, 1:1).

$^1H$ NMR (400 MHz, $CDCl_3$): δ 7.62 (s, 1H), 7.15 (d, J=9.3 Hz, 1H), 6.81-6.76 (m, 2H), 6.72 (s, 1H), 6.25 (d, J=1.2 Hz, 1H), 6.03 (d, J=1.2 Hz, 1H), 5.12 (d, J=11.7 Hz, 1H), 4.57 (s, 1H), 4.41 (s, 1H), 4.36-4.24 (m, 2H), 4.20 (d, J=11.7 Hz, 1H), 3.82 (s, 3H), 3.79 (s, 3H), 3.44 (dd, J=22.0, 7.1 Hz, 2H), 3.08-2.78 (m, 4H), 2.73-2.64 (m, 2H), 2.41-2.22 (m, 3H), 2.28 (s, 3H), 2.25-2.15 (m, 1H), 2.14 (s, 3H), 2.08 (s, 3H), 2.04 (s, 3H).

ESI-MS m/z: 823.3 $(M+H)^+$.

C)

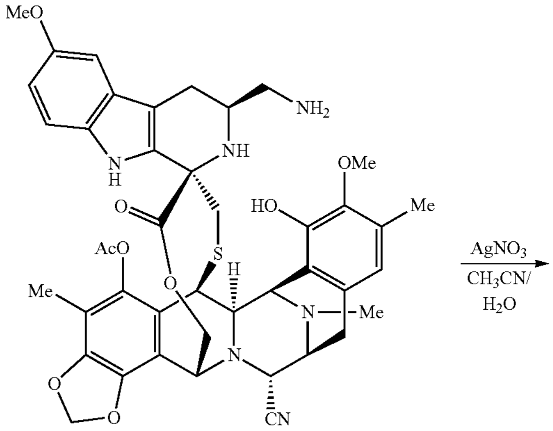

26-S

-continued

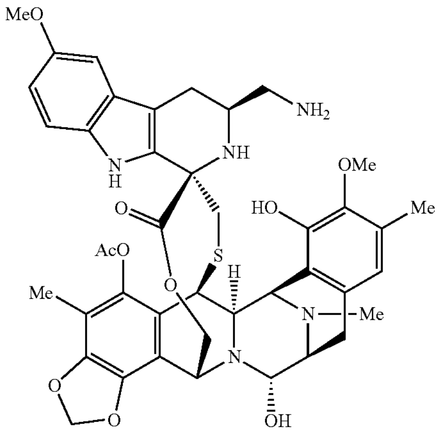

27-S

To a solution of 26-S (70 mg, 0.085 mmol) in $CH_3CN$: $H_2O$ (1.39:1, 6 mL, 0.015 M) was added $AgNO_3$ (335 mg, 1.7 mmol). After 18 h at 23° C., the reaction was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give 27-S (23 mg, 33%).

$R_f$=0.2 ($CH_2Cl_2$:$CH_3OH$, 9:1).

$^1H$ NMR (400 MHz, $CDCl_3$): δ 7.62 (s, 1H), 7.15 (d, J=7.8 Hz, 1H), 6.78 (s, 1H), 6.75 (d, J=7.8 Hz, 1H), 6.21 (d, J=1.5 Hz, 1H), 6.01 (d, J=1.5 Hz, 1H), 5.78 (s, 1H), 5.22 (d, J=11.5 Hz, 1H), 4.90 (s, 1H), 4.58-4.42 (m, 3H), 4.29-4.10 (m, 2H), 3.84-3.80 (m, 1H), 3.83 (s, 3H), 3.79 (s, 3H), 3.53-3.48 (m, 2H), 3.22 (d, J=8.7 Hz, 1H), 3.12 (s, 1H), 3.02 (d, J=12.8 Hz, 1H), 2.89-2.64 (m, 3H), 2.46 (s, 3H), 2.42-2.34 (m, 2H), 2.27 (s, 3H), 2.12 (s, 3H), 2.03 (s, 3H).

$^{13}C$ NMR (126 MHz, $CDCl_3$): δ 172.1, 168.7, 154.0, 147.6, 145.6, 143.0, 141.2, 140.8, 131.6, 130.6, 129.6, 127.1, 121.8, 120.9, 118.4, 115.2, 112.5, 111.8, 101.8, 100.2, 81.5, 62.6, 60.6, 58.0, 57.8, 56.0, 55.8, 55.0, 42.3, 41.4, 31.9, 29.7, 27.8, 26.9, 25.6, 24.0, 22.7, 20.5, 16.0, 14.1, 13.6, 9.7.

ESI-MS m/z: 796.3 $(M-H_2O+H)^+$.

(+)-HR-ESI-TOF-MS m/z: 796.3062 $[M-H_2O+H]^+$ (Calcd. for $C_{42}H_{46}N_5O_9S$ 796.3011).

Example 0-12. Synthesis of allyl N—[(R)-2-amino-3-(5-methoxy-1H-indol-3-yl)propyl)]carbamate (24-R)

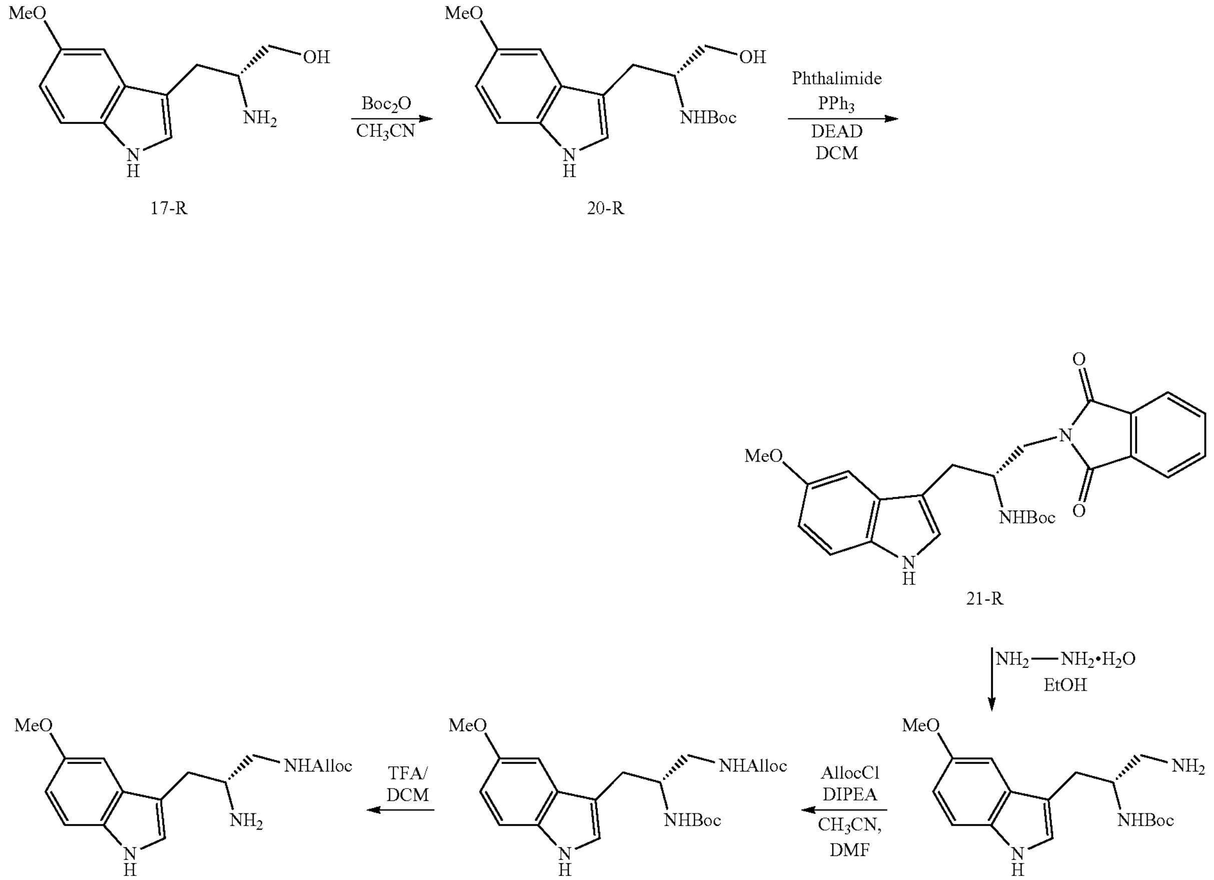

17-R 20-R 21-R 24-R 23-R 22-R

A)

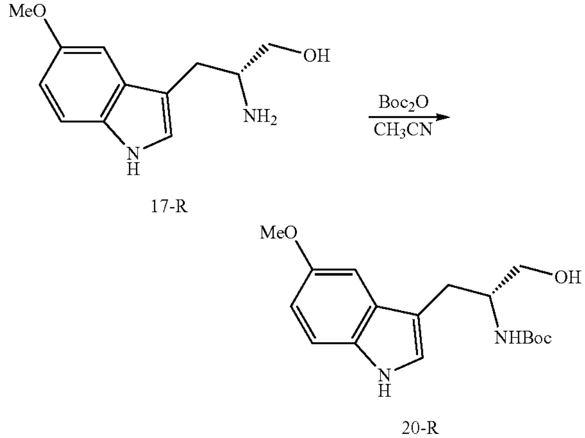

17-R

20-R

To a solution of 17-R (2.35 g, 10.7 mmol) in $CH_3CN$ (43 mL, 4 mL/mmol) was added di-tert-butyl dicarbonate (4.67 g, 21.4 mmol). The reaction mixture was stirred at 23° C. for 2.5 h, concentrated under vacuum. Flash chromatography ($CH_2Cl_2$:$CH_3OH$, from 99:1 to 85:15) afforded 20-R (1.7 g, 50%).

$R_f$=0.6 ($CH_2Cl_2$:$CH_3OH$, 9:1).

$^1H$ NMR (400 MHz, $CDCl_3$): δ 8.05 (s, 1H), 7.25 (d, J=8.9 Hz, 1H), 7.09 (d, J=2.4 Hz, 1H), 7.02 (d, J=2.4 Hz, 1H), 6.86 (dd, J=8.8, 2.4 Hz, 1H), 4.83 (s, 1H), 3.98 (s, 1H), 3.87 (s, 3H), 3.69 (td, J=9.2, 7.5, 5.3 Hz, 1H), 3.61 (dd, J=10.9, 5.6 Hz, 1H), 2.95 (d, J=6.8 Hz, 2H), 1.42 (s, 9H).

B)

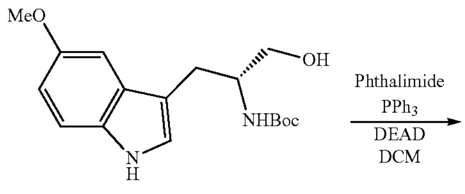

20-R

-continued

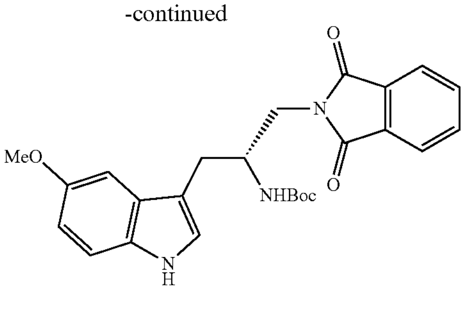

21-R

To a solution of 20-R (1.7 g, 5.3 mmol) in $CH_2Cl_2$ (32 mL, 6 mL/mmol) was added phthalimide (1.72 g, 11.7 mmol), triphenylphosphine (3.06 g, 11.7 mmol) and the mixture was cooled at 0° C. A solution of 40% of diethyl azodicarboxylate (DEAD) in $CH_2Cl_2$ (4.0 mL, 13.2 mmol) was added for 15 min. The reaction was stirred at 23° C. for 16 h, concentrated under vacuum. The residue obtained was purified by flash chromatography (Hexane:EtOAc, from 99:1 to 85:15) to afford 21-R (2.0 g, 84%).

$R_f$=0.45 (Hexane:EtOAc, 1:1).

$^1H$ NMR (400 MHz, $CDCl_3$): δ 8.31 (s, 1H), 7.80 (dd, J=5.4, 3.0 Hz, 2H), 7.67 (dd, J=5.4, 3.0 Hz, 2H), 7.30-7.12 (m, 2H), 7.08 (dd, J=15.2, 2.4 Hz, 1H), 6.84 (dd, J=8.8, 2.4 Hz, 1H), 4.85 (d, J=9.2 Hz, 1H), 4.43 (q, J=5.3 Hz, 1H), 3.86 (s, 3H), 3.83-3.68 (m, 2H), 3.01 (d, J=5.4 Hz, 2H), 1.22 (s, 9H).

C)

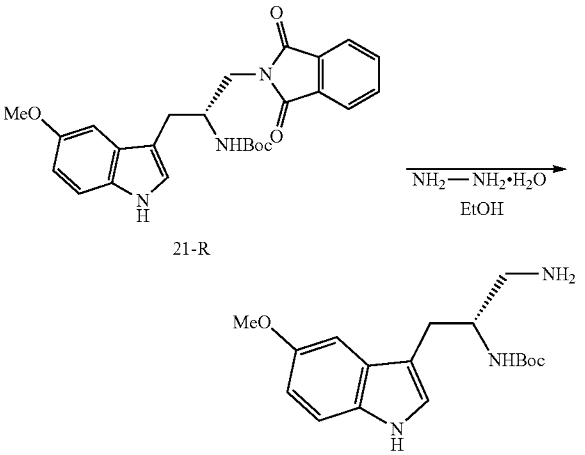

21-R

22-R

To a solution of 21-R (2.0 g, 4.45 mmol) in ethanol (133 mL, 30 mL/mmol) was added hydrazine monohydrate (21.6 mL, 445 mmol). The reaction mixture was stirred at 80° C. in sealed tube for 2 h, concentrated under vacuum. Flash chromatography ($CH_2Cl_2$:$CH_3OH$, from 100:1 to 50:50) to afford 22-R (1.15 g, 81%).

$R_f$=0.1 ($CH_2Cl_2$:$CH_3OH$, 8:2).

$^1H$ NMR (400 MHz, $CDCl_3$): δ 7.21 (d, J=8.8 Hz, 1H), 7.12 (s, 1H), 7.05 (s, 1H), 6.75 (dd, J=8.8, 2.4 Hz, 1H), 3.95 (ddd, J=10.7, 8.7, 5.4 Hz, 1H), 3.82 (s, 3H), 2.98-2.79 (m, 3H), 2.75 (dd, J=13.1, 9.4 Hz, 1H), 1.37 (s, 9H).

D)

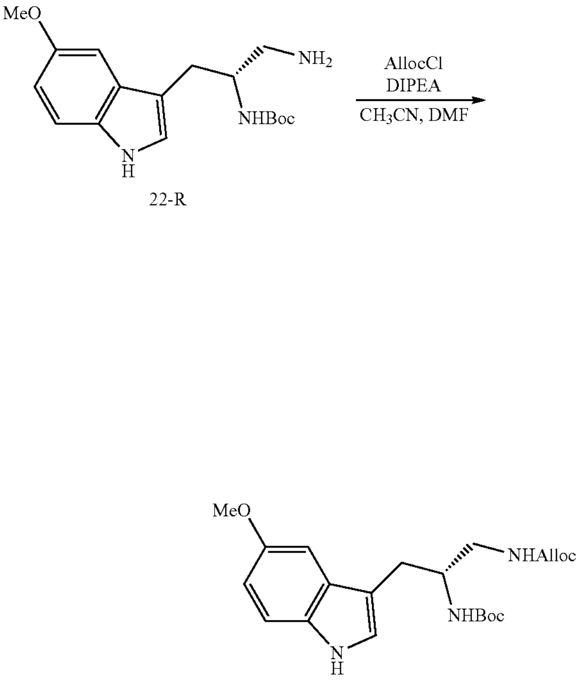

22-R

23-R

To a solution of 22-R (1.1 g, 3.4 mmol) in $CH_3CN$ (34 mL, 10 mL/mmol) and DMF (3.4 mL, 1 mL/mmol) was added N,N-diisopropylethylamine (0.5 mL, 2.7 mmol) and allyl chloroformate (3.7 mL, 34 mmol). The reaction was stirred at 23° C. for 19 h. The mixture was diluted with EtOAc and $NH_4Cl$ was added and the mixture was extracted with EtOAc. The combined organic layers were dried over anhydrous $Na_2SO_4$, filtered, and concentrated under vacuum. The residue obtained was purified by flash chromatography (Hexane:EtOAc, from 100:1 to 1:100) to afford 23-R (0.95 g, 69%).

$R_f$=0.5 (Hexane:EtOAc, 1:1).

$^1H$ NMR (400 MHz, $CDCl_3$): δ 8.55 (s, 1H), 7.20 (d, J=8.8 Hz, 1H), 7.05 (s, 1H), 6.98-6.87 (m, 1H), 6.82 (dt, J=8.8, 1.8 Hz, 1H), 5.96-5.81 (m, 1H), 5.37-5.22 (m, 2H), 5.22-5.14 (m, 1H), 5.02-4.97 (m, 1H), 4.60-4.47 (m, 2H), 4.00 (s, 1H), 3.84 (s, 3H), 3.31 (s, 1H), 3.19 (s, 1H), 2.88 (td, J=14.5, 13.3, 5.9 Hz, 2H), 1.40 (s, 9H).

E)

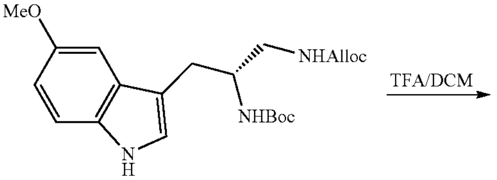

23-R

-continued

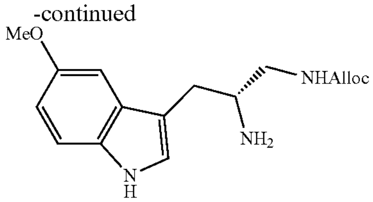

24-R

To a solution of 23-R (0.94 g, 2.3 mmol) in $CH_2Cl_2$ (39 mL, 16.6 mL/mmol) was added trifluoroacetic acid (19 mL, 8.3 mL/mmol). The reaction mixture was stirred at 23° C. for 1.5 h, concentrated under vacuum to afford 24-R (0.72 g, 100%).

$R_f$=0.1 ($CH_2Cl_2$:$CH_3OH$, 9:1).

$^1$H NMR (400 MHz, $CD_3OD$): δ 7.27 (d, J=8.8, 1H), 7.18 (s, 1H), 7.04 (d, J=2.4 Hz, 1H), 6.80 (ddd, J=8.8, 2.4, 0.9 Hz, 1H), 5.95 (ddt, J=16.4, 10.8, 5.5 Hz, 1H), 5.32 (d, J=17.1 Hz, 1H), 5.20 (d, J=10.5 Hz, 1H), 4.60-4.53 (m, 2H), 3.83 (s, 3H), 3.59 (dt, J=11.4, 5.5 Hz, 1H), 3.47-3.30 (m, 2H), 3.13-2.94 (m, 2H).

Example 0-13

A)

To a solution of 1 (0.71 g, 1.14 mmol) in acetic acid (45 mL, 0.08 M) was added 24-R (0.54 mg, 1.8 mmol). The reaction mixture was stirred at 23° C. for 7 h and then acetic acid was evaporated. An aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, 1:1) gives compound 25-R (670 mg, 65%).

$R_f$=0.4 (Hexane:EtOAc, 1:1).

$^1$H NMR (400 MHz, $CDCl_3$): δ 7.52 (s, 1H), 7.17 (d, J=8.8 Hz, 1H), 6.83-6.73 (m, 2H), 6.61 (s, 1H), 6.23 (d, J=1.0 Hz, 1H), 6.02 (d, J=1.0 Hz, 1H), 6.05-5.89 (m, 1H), 5.75 (s, 1H), 5.44-5.30 (m, 1H), 5.25 (d, J=10.4 Hz, 1H), 5.13-4.99 (m, 2H), 4.71-4.59 (m, 2H), 4.36 (s, 1H), 4.30-4.07 (m, 3H), 3.80 (s, 3H), 3.79 (s, 3H), 3.61-3.53 (m, 1H); 3.48-3.41 (m, 3H), 3.26 (dt, J=13.3, 3.8 Hz, 1H), 3.04-2.88 (m, 2H), 2.52 (dd, J=14.9, 3.7 Hz, 1H), 2.46-2.35 (m, 2H), 2.31 (s, 3H), 2.29 (s, 3H), 2.16 (s, 3H), 2.12-2.02 (m, 1H), 2.09 (s, 3H).

ESI-MS m/z: 907.3 (M+H)$^+$.

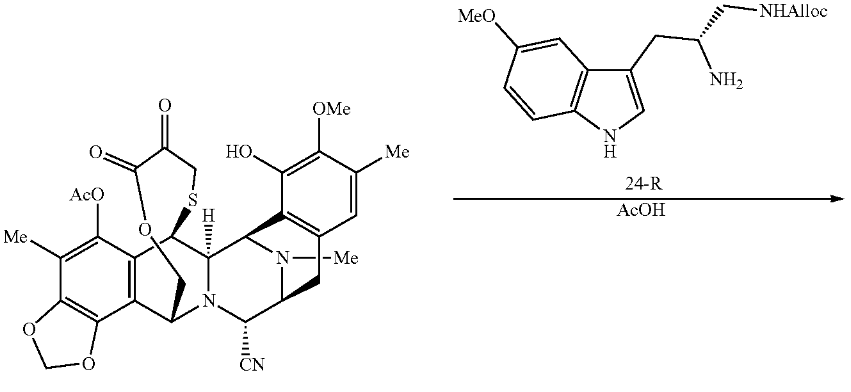

1

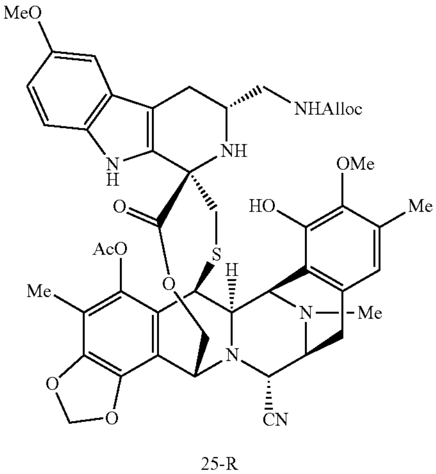

25-R

B)

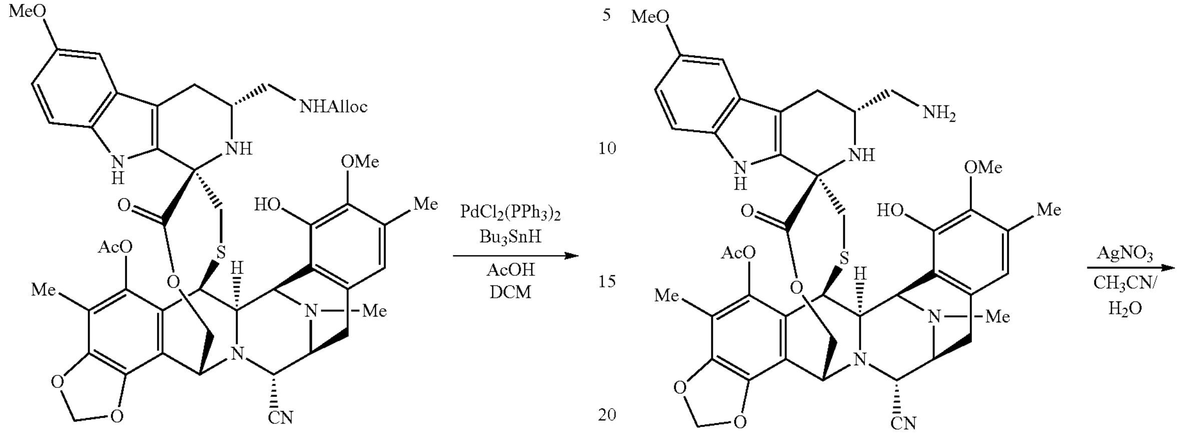

25-R

26-R

To a solution of 25-R (745 mg, 0.82 mmol) in $CH_2Cl_2$ (15 mL, 18 mL/mmol) was added bis(triphenylphosphine)palladium(II) dichloride (92 mg, 0.1 mmol) and acetic acid (0.47 mL, 8.2 mmol). Tributyltin hydride (1.33 mL, 4.9 mmol) was added at 0° C., the reaction mixture was stirred at 0° C. for 0.75 h and concentrated under vacuum. Flash chromatography (Hexane:EtOAc, from 100:1 to 1:100 and EtOAc:$CH_3OH$, from 100:1 to 1:100) to afford 26-R (680 mg, >100%).

$R_f$=0.25 ($CH_2Cl_2$:$CH_3OH$, 1:1).

$^1$H NMR (400 MHz, $CDCl_3$): δ 7.57 (s, 1H), 7.16 (d, J=8.8 Hz, 1H), 6.85-6.72 (m, 2H), 6.57 (s, 1H), 6.21 (d, J=1.4 Hz, 1H), 6.00 (d, J=1.3 Hz, 1H), 5.05-4.97 (m, 1H), 4.63 (s, 1H), 4.35 (s, 1H), 4.31-4.09 (m, 4H), 3.80 (s, 3H), 3.78 (s, 3H), 3.50-3.40 (m, 3H), 3.24 (dq, J=9.9, 5.3 Hz, 1H), 2.95 (s, 1H), 2.91-2.75 (m, 2H), 2.62 (dd, J=14.8, 3.6 Hz, 1H), 2.43-2.28 (m, 2H), 2.36 (s, 3H), 2.25 (s, 3H), 2.22-2.14 (m, 1H), 2.15 (s, 3H), 2.08 (s, 3H).

ESI-MS m/z: 823.3 $(M+H)^+$.

C)

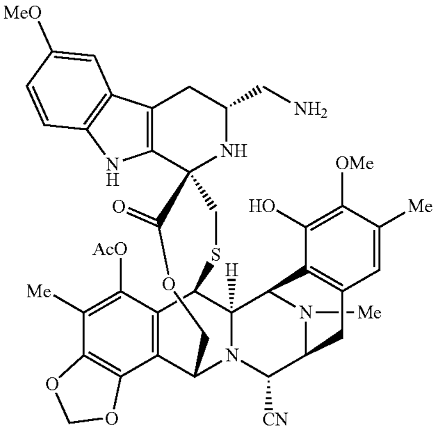

26-R

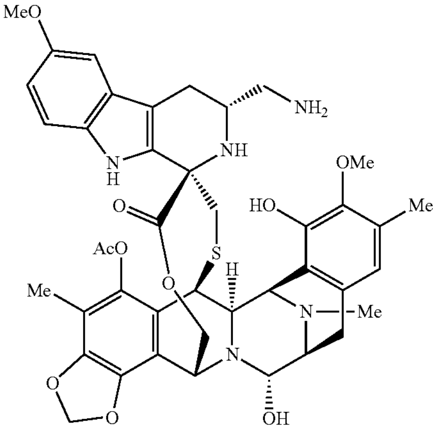

27-R

To a solution of 26-R (660 mg, 0.80 mmol) in $CH_3CN$:$H_2O$ (1.39:1, 56 mL, 0.015 M) was added $AgNO_3$ (2.70 g, 16.0 mmol). After 16.5 h at 23° C., the reaction was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give 27-R (271 mg, 42%).

$R_f$=0.1 ($CH_2Cl_2$:$CH_3OH$, 9:1).

$^1$H NMR (400 MHz, $CDCl_3$): δ 7.46 (s, 1H), 7.16 (d, J=8.9 Hz, 1H), 6.83 (s, 1H), 6.72 (d, J=8.9 Hz, 1H), 6.58 (s, 1H), 6.20 (d, J=1.8 Hz, 1H), 5.99 (d, J=1.8 Hz, 1H), 5.76 (s, 1H), 5.15 (d, J=11.4 Hz, 1H), 4.86 (s, 1H), 4.52 (m, 2H), 4.17 (d, J=5.3 Hz, 1H), 4.07 (d, J=11.4 Hz, 1H), 3.80 (s, 3H), 3.78 (s, 3H), 3.55-3.43 (m, 2H), 3.32-3.20 (m, 2H), 3.01-2.82 (m, 4H), 2.68-2.59 (m, 1H), 2.44-2.31 (m, 1H), 2.38 (s, 3H), 2.30-2.19 (m, 1H), 2.26 (s, 3H), 2.15 (s, 3H), 2.07 (s, 3H).

$^{13}C$ NMR (101 MHz, $CD_3OD$): δ 171.7, 171.3, 153.8, 153.3, 148.0, 147.6, 145.4, 145.4, 143.1, 141.3, 140.7, 131.6, 131.4, 131.2, 129.3, 126.8, 121.6, 120.9, 118.3, 115.6, 112.2, 111.8, 101.8, 100.2, 81.7, 63.5, 63.1, 61.7, 58.0, 57.8, 56.1, 55.8, 55.0, 42.2, 42.1, 41.4, 41.0, 25.1, 23.8, 20.5, 16.0, 9.7.

ESI-MS m/z: 796.3 $(M-H_2O+H)^+$.

(+)-HR-ESI-TOF-MS m/z: 796.3045 $[M-H_2O+H]^+$ (Calcd. for $C_{42}H_{46}N_5O_9S$ 796.3011).

Example 0-14

A)

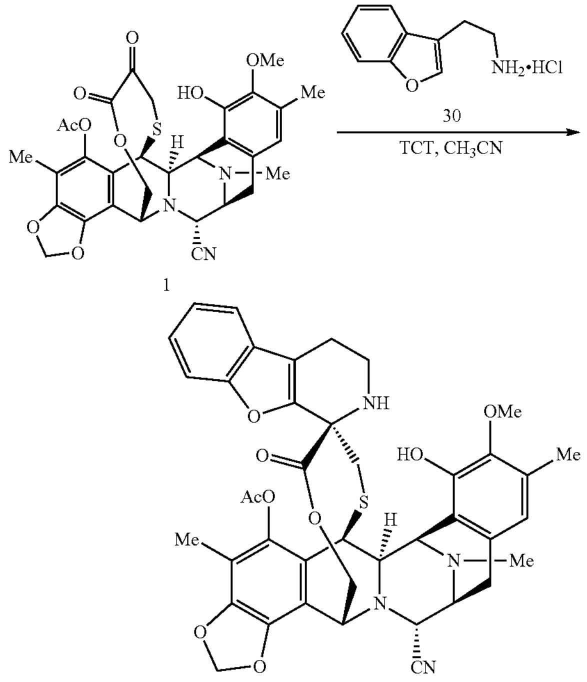

1

30

31

To a solution of compound 1 (2.0 g, 3.21 mmol) in acetonitrile (200 mL, 0.01 M) was added 2-benzofuran-3-yl-ethylamine hydrochloride (30) (1.90 g, 9.65 mmol, Sigma Aldrich) and cyanuric chloride (TCT) (200 mg, 10%). The reaction mixture was stirred at 85° C. for 24 h and then aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, from 9:1 to 1:9) gives compound 31 (1.95 g, 79%).

$R_f$=0.5 (Hexane:EtOAc, 1:1).

$^1H$ NMR (400 MHz, $CDCl_3$): δ 7.38-7.36 (m, 2H), 7.19-7.10 (m, 2H), 6.64 (s, 1H), 6.20 (d, J=1.5 Hz, 1H), 6.05 (d, J=1.5 Hz, 1H), 5.76 (s, 1H), 5.05 (d, J=11.7 Hz, 1H), 4.54 (s, 1H), 4.33-4.24 (m, 2H), 4.23-4.16 (m, 2H), 3.81 (s, 3H), 3.49-3.38 (m, 2H), 3.28-3.21 (m, 1H), 3.06-2.78 (m, 5H), 2.57-2.50 (m, 2H), 2.37 (s, 3H), 2.27 (s, 3H), 2.21 (m, 3H), 2.08 (s, 3H).

ESI-MS m/z: 765.3 $(M+H)^+$.

B)

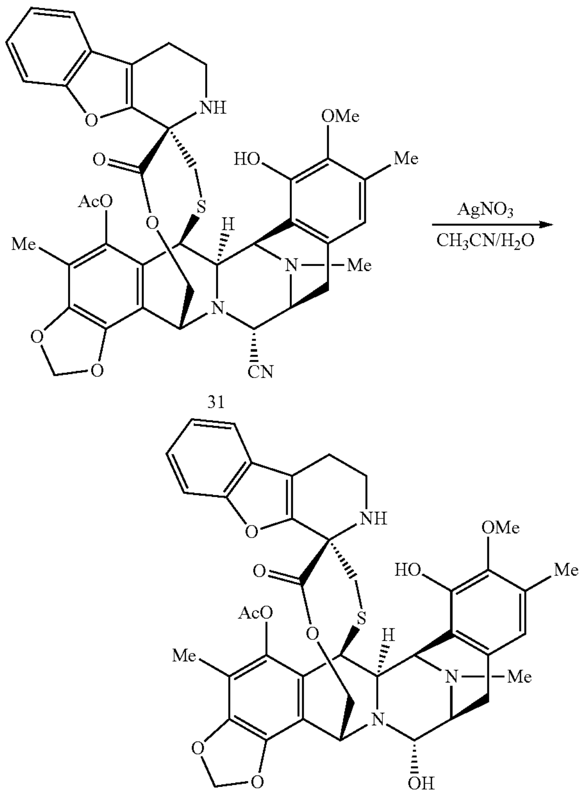

31

32

To a solution of compound 31 (380 mg, 0.49 mmol) in $CH_3CN:H_2O$ (1.39:1, 25 mL, 0.015 M) was added $AgNO_3$ (1.30 g, 7.45 mmol). After 5 h at 23° C., a mixture 1:1 of saturated aqueous solutions of NaCl and $NaHCO_3$ was added, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to afford compound 32 (175 mg, 47%).

$R_f$=0.40 ($CH_2Cl_2:CH_3OH$, 9:1).

$^1H$ NMR (400 MHz, $CDCl_3$): δ 7.35 (ddd, J=10.7, 7.6, 1.1 Hz, 2H), 7.14 (dtd, J=19.7, 7.3, 1.3 Hz, 2H), 6.65 (s, 1H), 6.16 (d, J=1.5 Hz, 1H), 6.01 (d, J=1.5 Hz, 1H), 5.75 (s, 1H), 5.15 (dd, J=11.5, 1.2 Hz, 1H), 4.80 (s, 1H), 4.48 (d, J=3.2 Hz, 1H), 4.44 (s, 1H), 4.20-4.06 (m, 2H), 3.81 (s, 1H), 3.50 (d, J=18.8 Hz, 1H), 3.30 (ddd, J=12.6, 7.9, 5.1 Hz, 1H), 3.22 (d, J=9.1 Hz, 1H), 2.99 (d, J=17.9 Hz, 1H), 2.84 (dd, J=19.2, 12.0 Hz, 3H), 2.59-2.49 (m, 2H), 2.36 (s, 3H), 2.27 (s, 3H), 2.21-2.14 (m, 1H), 2.18 (s, 3H), 2.06 (s, 3H).

$^{13}C$ NMR (101 MHz, $CDCl_3$): δ 171.2, 168.7, 154.4, 150.0, 147.9, 145.5, 142.9, 140.9, 140.8, 131.3, 129.0, 127.7, 123.7, 122.2, 121.2, 120.8, 118.9, 118.3, 115.5, 113.5, 111.7, 101.7, 82.1, 62.7, 61.7, 60.3, 57.8, 57.4, 55.9, 55.0, 42.2, 41.3, 39.7, 38.2, 29.7, 23.7, 21.3, 20.6, 15.9, 9.7.

ESI-MS m/z: 738.6 $(M-H_2O+H)^+$.

(+)-HR-ESI-TOF-MS m/z: 756.2654 $[M+H]^+$ (Calcd. for $C_{40}H_{42}N_3O_{10}S$ 756.2585).

Example 0-15

A)

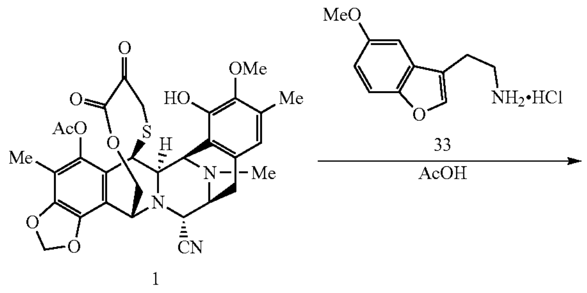

1

33

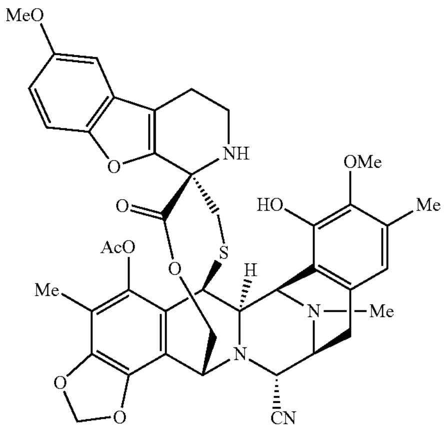

34

To a solution of 1 (500 mg, 0.80 mmol) in acetic acid (10 mL, 0.08 M) was added 2-(5-methoxybenzofuran-3-yl)-ethylamine hydrochloride (33) (Diverchim, ref: DW04590) (444 mg, 1.60 mmol). The reaction mixture was stirred at 50° C. for 6 days and then acetic acid was evaporated. An aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, 1:1) affords 34 (270 mg, 43%).

$R_f$=0.3 (Hexane:EtOAc, 1:1).

$^1$H NMR (400 MHz, $CDCl_3$): δ 7.25 (d, J=9.1 Hz, 1H), 6.80-6.73 (m, 2H), 6.63 (s, 1H), 6.18 (d, J=1.4 Hz, 1H), 6.03 (d, J=1.4 Hz, 1H), 5.78 (s, 1H), 5.03 (dd, J=11.5, 1.3 Hz, 1H), 4.52 (s, 1H), 4.29 (s, 1H), 4.26 (dd, J=4.7, 1.5 Hz, 1H), 4.23-4.16 (m, 2H), 3.80 (s, 3H), 3.78 (s, 3H), 3.46-3.43 (m, 1H), 3.43-3.37 (m, 1H), 3.24 (s, 1H), 3.03 (d, J=18.0 Hz, 1H), 2.91 (dd, J=17.9, 9.2 Hz, 1H), 2.87-2.72 (m, 2H), 2.53-2.47 (m, 2H), 2.36 (s, 3H), 2.27 (s, 3H), 2.20 (s, 3H), 2.06 (s, 3H).

ESI-MS m/z: 795.8 $(M+H)^+$.

B)

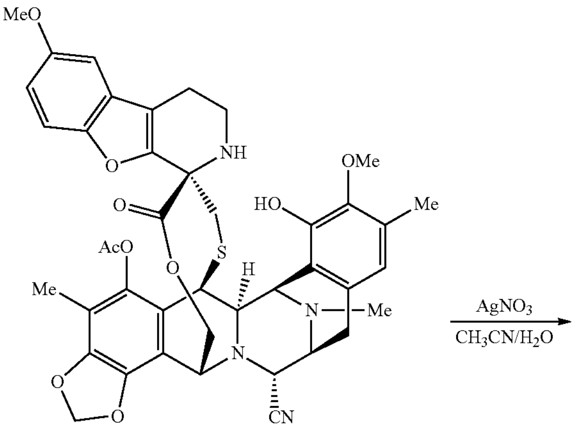

34

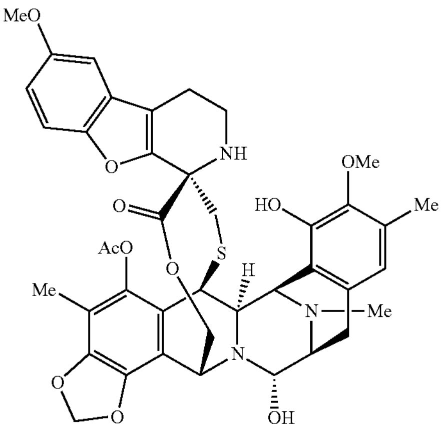

35

To a solution of 34 (345 mg, 0.43 mmol) in $CH_3CN:H_2O$ (1.39:1, 30 mL, 0.015 M) was added $AgNO_3$ (2.20 g, 13.0 mmol). After 3 h at 23° C., a mixture 1:1 of saturated aqueous solutions of NaCl and $NaHCO_3$ was added, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to obtain 35 (175 mg, 51%).

$R_f$=0.35 ($CH_2Cl_2:CH_3OH$, 9:1).

$^1$H NMR (500 MHz, $CD_3OD$): δ 7.27 (d, J=9.0 Hz, 1H), 6.90 (d, J=2.6 Hz, 1H), 6.80 (dd, J=9.0, 2.6 Hz, 1H), 6.57 (s, 1H), 6.23 (d, J=1.2 Hz, 1H), 6.05 (d, J=1.2 Hz, 1H), 5.23 (d, J=11.5 Hz, 1H), 4.27-4.08 (m, 4H), 3.77 (s, 3H), 3.75 (s, 3H), 3.63 (d, J=14.1 Hz, 2H), 3.40-3.34 (m, 2H), 2.93-2.87 (m, 5H), 2.80 (d, J=15.5 Hz, 1H), 2.57-2.54 (m, 2H), 2.34 (s, 3H), 2.30 (s, 3H), 2.14 (s, 3H), 2.05 (s, 3H).

$^{13}$C NMR (126 MHz, $CD_3OD$): δ 171.9, 170.6, 157.5, 147.0, 145.0, 142.3, 141.0, 132.2, 131.1, 129.1, 122.2, 120.9, 120.2, 116.3, 115.1, 114.0, 112.7, 111.4, 103.5, 102.7, 92.9, 62.0, 60.3, 59.8, 59.4, 56.5, 56.2, 56.0, 54.0, 43.8, 41.2, 40.7, 30.8, 30.3, 28.7, 24.5, 21.6, 20.6, 16.2, 9.6.

ESI-MS m/z: 768.6 $(M-H_2O+H)^+$.

(+)-HR-ESI-TOF-MS m/z: 768.2630 $[M-H_2O+H]^+$ (Calcd. for $C_{41}H_{42}N_3O_{10}S$ 768.2585).

Example 0-16

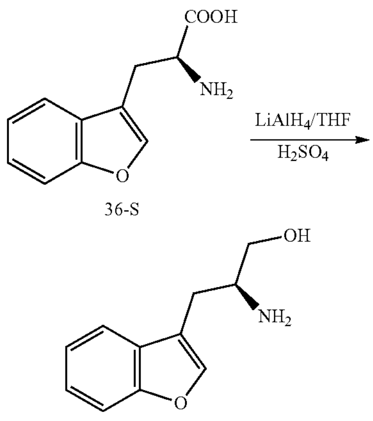

36-S

37-S

To a solution of $LiAlH_4$ (148 mL, 1.0 M in THF, 148 mmol) at −40° C. was added carefully $H_2SO_4$ (7.14 mL, 72.9 mmol) and a suspension of (S)-2-amino-3-(benzofuran-3-yl)propanoic acid (36-S) (prepared as described in Tetrahedron Asymmetry 2008, 19, 500-511) (5.54 g, 26.9 mmol) in THE (85 mL, 0.003 M). The reaction mixture was left evolution at 23° C., heated at 80° C. for 3 h and 18 h at 23° C. Cool at −21° C. the reaction mixture was quenched carefully with NaOH 2N until basic pH. EtOAc was added and the mixture filtered through Celite® and washed with $CH_3OH$. The crude was concentrated under vacuum to afford compound 37-S (3.93 g, >100%).

$R_f$=0.1 ($CH_2Cl_2$:$CH_3OH$, 4:1).

$^1H$ NMR (400 MHz, $CD_3OD$): δ 7.67-7.62 (m, 1H), 7.61 (s, 1H), 7.51-7.41 (m, 1H), 7.34-7.18 (m, 2H), 3.69-3.48 (m, 1H), 3.44 (dd, J=10.8, 6.6 Hz, 1H), 3.18 (dtd, J=7.4, 6.4, 4.6 Hz, 1H), 2.88 (ddd, J=14.4, 6.1, 1.0 Hz, 1H), 2.68 (ddd, J=14.4, 7.5, 0.9 Hz, 1H).

Example 0-17

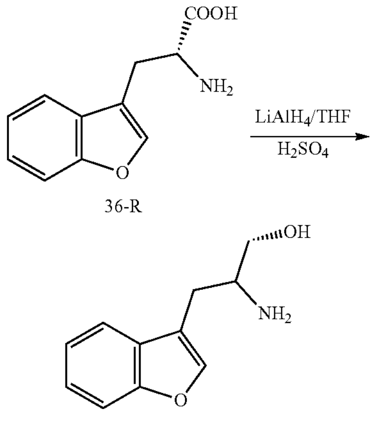

36-R

37-R

To a solution of $LiAlH_4$ (118 mL, 1.0 M in THF, 118 mmol) at −40° C. was added carefully $H_2SO_4$ (3.1 mL, 57.8 mmol) and a suspension of (R)-2-amino-3-(benzofuran-3-yl)propanoic acid (36-R) (prepared as described in Tetrahedron Asymmetry 2008, 19, 500-511) (4.4 g, 21.4 mmol) in THE (67.4 mL, 0.003 M). The reaction mixture was left evolution at 23° C., heated at 80° C. for 3 h and 18 h at 23° C. Cool at −21° C. the reaction mixture was quenched carefully with NaOH 2N until basic pH. EtOAc was added and the mixture filtered through Celite® and washed with $CH_3OH$. The crude was concentrated under vacuum. Flash chromatography ($CH_2Cl_2$:$CH_3OH$, from 99:1 to 85:15, Silice amine) to afford compound 37-R (2.77 g, 68%).

$R_f$=0.1 ($CH_2Cl_2$:$CH_3OH$, 4:1).

$^1H$ NMR (400 MHz, $CD_3OD$): δ 7.63-7.52 (m, 1H), 7.56 (s, 1H), 7.46-7.33 (m, 1H), 7.21 (dtd, J=19.9, 7.3, 1.3 Hz, 2H), 3.57 (dd, J=10.7, 4.6 Hz, 1H), 3.42 (dd, J=10.8, 6.6 Hz, 1H), 3.15 (dtd, J=7.6, 6.3, 4.6 Hz, 1H), 2.84 (ddd, J=14.4, 6.0, 1.0 Hz, 1H), 2.64 (ddd, J=14.4, 7.5, 0.9 Hz, 1H).

Example 0-18

A)

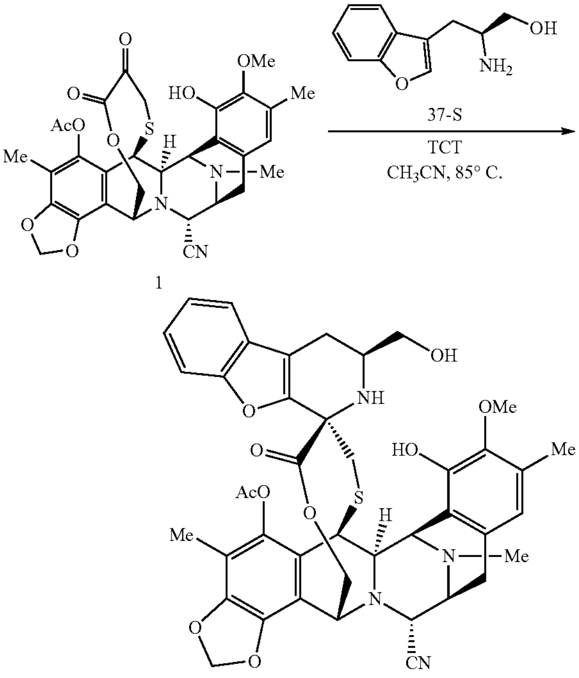

1

38-S

To a solution of compound 1 (850 mg, 1.36 mmol) in $CH_3CN$ (136 mL, 0.01 M) was added (S)-2-amino-3-(benzofuran-3-yl)propan-1-ol (37-S) (1.30 g, 6.83 mmol and cyanuric chloride (TCT) (170 mg, 20%). The reaction mixture was stirred at 85° C. for 24 h and then aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, from 9:1 to 1:9) gives compound 38-S (750 mg, 69%).

$R_f$=0.25 (Hexane:EtOAc, 1:1).

$^1H$ NMR (400 MHz, $CDCl_3$): δ 7.39-7.33 (m, 1H), 7.33-7.29 (m, 1H), 7.20 (ddd, J=8.3, 7.2, 1.4 Hz, 1H), 7.14 (td, J=7.4, 1.0 Hz, 1H), 6.61 (s, 1H), 6.21 (d, J=1.4 Hz, 1H), 6.06 (d, J=1.4 Hz, 1H), 5.74 (s, 1H), 5.08 (d, J=11.2 Hz, 1H), 4.58 (s, 1H), 4.37 (s, 1H), 4.32-4.23 (m, 2H), 4.19 (d, J=2.7

Hz, 1H), 3.81 (s, 3H), 3.52-3.41 (m, 3H), 3.36-3.29 (m, 1H), 3.13 (d, J=9.8 Hz, 1H), 3.00-2.81 (m, 3H), 2.57 (dd, J=15.7, 4.9 Hz, 1H), 2.50 (d, J=15.2 Hz, 1H), 2.37 (s, 3H), 2.31-2.25 (m, 1H), 2.29 (s, 3H), 2.16 (s, 3H), 2.10 (d, J=7.2 Hz, 1H), 2.05 (s, 3H).

ESI-MS m/z: 795.2 $(M)^+$.

B)

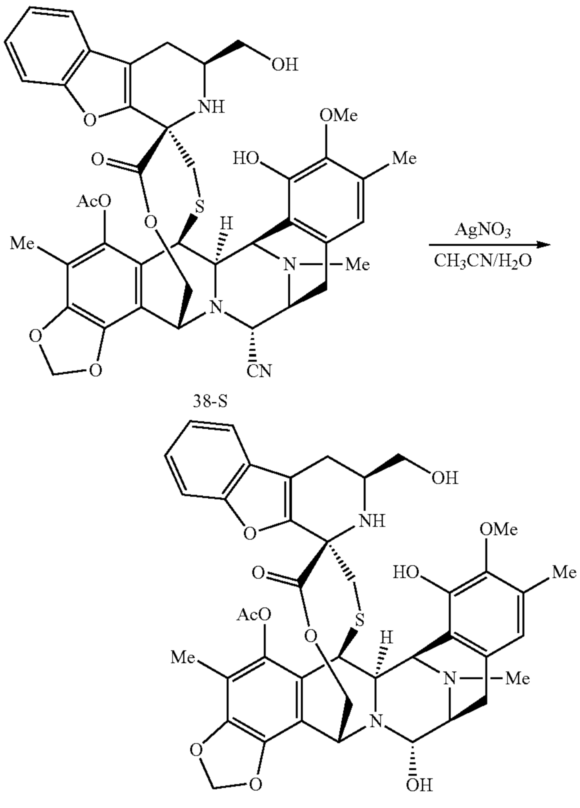

38-S

39-S

To a solution of compound 38-S (890 mg, 1.12 mmol) in $CH_3CN:H_2O$ (1.39:1, 75 mL, 0.015 M) was added $AgNO_3$ (4.70 g, 28.0 mmol). After 18 h at 23° C., a mixture 1:1 of saturated aqueous solutions of NaCl and $NaHCO_3$ was added, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to afford compound 39-S (500 mg, 57%).

$R_f$=0.30 ($CH_2Cl_2:CH_3OH$, 9:1).

$^1H$ NMR (400 MHz, $CDCl_3$): δ 7.38-7.33 (m, 1H), 7.33-7.28 (m, 1H), 7.23-7.16 (m, 1H), 7.16-7.09 (m, 1H), 6.62 (s, 1H), 6.18 (d, J=1.4 Hz, 1H), 6.03 (d, J=1.4 Hz, 1H), 5.71 (s, 1H), 5.19 (d, J=11.2 Hz, 1H), 4.85 (s, 1H), 4.49 (s, 2H), 4.24-4.10 (m, 3H), 3.81 (s, 3H), 3.54 (d, J=4.9 Hz, 1H), 3.49 (d, J=2.3 Hz, 3H), 3.33 (t, J=10.1 Hz, 2H), 3.22 (s, 1H), 2.98 (s, 1H), 2.84 (d, J=7.6 Hz, 2H), 2.62-2.53 (m, 2H), 2.37 (s, 3H), 2.30-2.24 (m, 1H), 2.28 (s, 3H), 2.14 (s, 3H), 2.04 (s, 3H).

$^{13}C$ NMR (126 MHz, $CDCl_3$): δ 172.0, 170.7, 156.1, 150.6, 149.9, 147.1, 145.0, 142.4, 142.2, 132.0, 131.4, 128.7, 125.5, 123.8, 122.6, 121.6, 120.1, 116.5, 114.4, 112.3, 103.5, 92.6, 66.0, 65.1, 62.2, 60.4, 59.7, 56.6, 56.1, 54.8, 54.1, 51.6, 44.0, 41.3, 38.3, 30.8, 24.8, 20.6, 16.3, 9.6.

ESI-MS m/z: 768.2 $(M-H_2O+H)^+$.

(+)-HR-ESI-TOF-MS m/z: 768.2652 $[M-H_2O+H]^+$ (Calcd. for $C_{41}H_{42}N_3O_{10}S$ 768.2585)

Example 0-19

A)

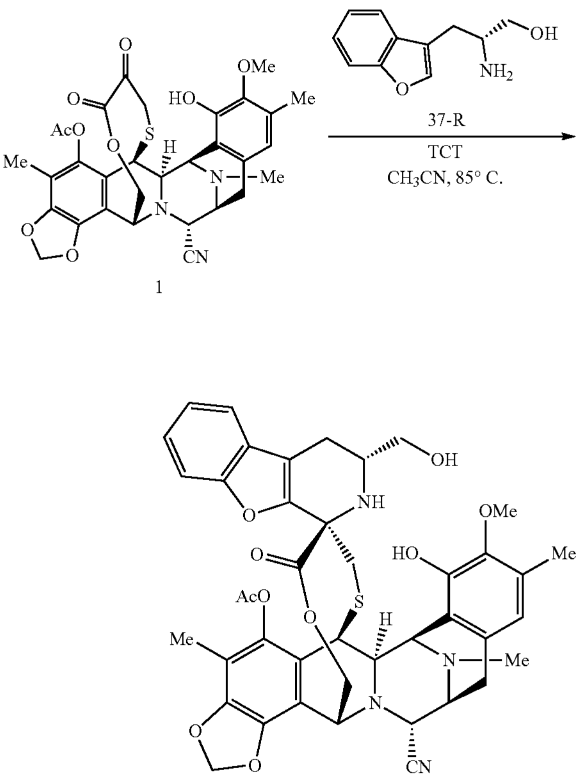

38-R

To a solution of compound 1 (100 mg, 0.16 mmol) in $CH_3CN$ (16 mL, 0.01 M) was added (R)-2-amino-3-(benzofuran-3-yl)propan-1-ol (37-R) (307 mg, 1.6 mmol) and cyanuric chloride (TCT) (40 mg, 40%). The reaction mixture was stirred at 85° C. for 44 h and then aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, from 9:1 to 1:9) gives compound 38-R (95 mg, 75%).

$R_f$=0.3 (Hexane:EtOAc, 1:1).

$^1H$ NMR (400 MHz, $CDCl_3$): δ 7.42-7.27 (m, 2H), 7.28-7.09 (m, 2H), 6.58 (s, 1H), 6.20 (d, J=1.4 Hz, 1H), 6.05 (d, J=1.4 Hz, 1H), 5.79 (s, 1H), 5.00 (d, J=11.4 Hz, 1H), 4.59 (s, 1H), 4.34 (s, 1H), 4.31-4.16 (m, 4H), 3.80 (s, 3H), 3.79-3.76 (m, 1H), 3.63 (s, 1H), 3.54-3.40 (m, 4H), 2.99-2.87 (m, 2H), 2.68 (d, J=15.0 Hz, 1H), 2.56-2.47 (m, 1H), 2.38 (s, 3H), 2.27 (s, 3H), 2.17 (s, 3H), 2.07 (s, 3H).

ESI-MS m/z: 795.2 $(M+H)^+$.

B)

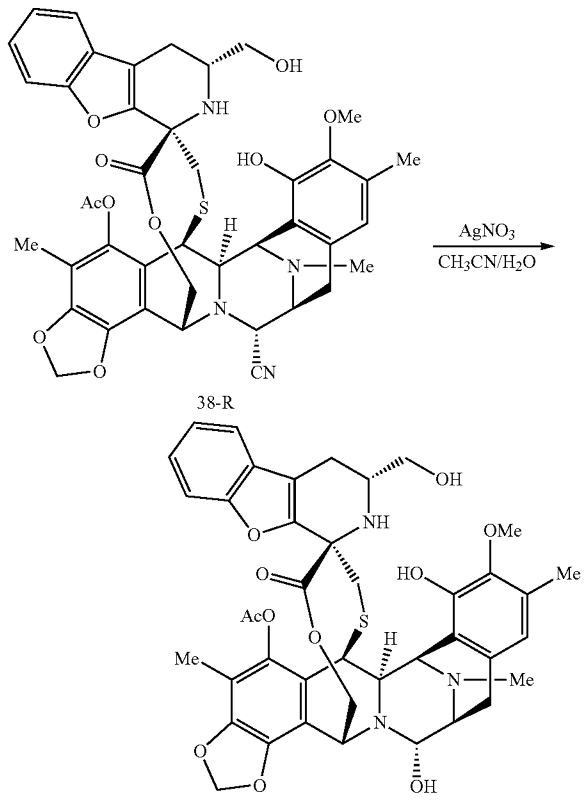

38-R

39-R

To a solution of compound 38-R (95 mg, 0.11 mmol) in $CH_3CN:H_2O$ (1.39:1, 11 mL, 0.015 M) was added $AgNO_3$ (601 mg, 3.58 mmol). After 18 h at 23° C., a mixture 1:1 of saturated aqueous solutions of NaCl and $NaHCO_3$ was added, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2:CH_3OH$, from 99:1 to 85:15) to afford compound 39-R (66 mg, 70%).

$R_f$=0.3 ($CH_2Cl_2:CH_3OH$, 9:1).

$^1H$ NMR (400 MHz, $CDCl_3$): δ 7.39-7.31 (m, 2H), 7.23-7.07 (m, 2H), 6.59 (s, 1H), 6.17 (d, J=1.4 Hz, 1H), 6.01 (d, J=1.4 Hz, 1H), 5.75 (s, 1H), 5.12 (dd, J=11.3, 1.2 Hz, 1H), 4.84 (s, 1H), 4.56-4.43 (m, 2H), 4.19-4.07 (m, 3H), 3.79 (s, 3H), 3.83-3.74 (m, 1H), 3.66-3.51 (m, 3H), 3.24 (s, 1H), 2.99-2.79 (m, 2H), 2.75-2.64 (m, 1H), 2.59-2.43 (m, 2H), 2.38 (s, 3H), 2.27 (s, 3H), 2.16 (s, 3H), 2.07 (s, 3H).

$^{13}C$ NMR (101 MHz, $CD_3OD$): δ 170.5, 169.1, 154.9, 148.9, 148.5, 145.7, 143.6, 141.1, 140.8, 130.6, 129.9, 127.1, 124.1, 122.4, 122.4, 121.2, 120.3, 118.7, 118.2, 115.1, 113.6, 110.9, 102.1, 91.1, 65.0, 63.3, 60.2, 59.0, 58.4, 55.4, 54.5, 52.7, 52.3, 42.5, 38.7, 29.4, 23.5, 23.2, 19.1, 14.8, 8.3.

ESI-MS m/z: 768.2 $(M-H_2O+H)^+$.

(+)-HR-ESI-TOF-MS m/z: 767.2628 $[M-H_2O+H]^+$ (Calcd. for $C_{41}H_{42}N_3O_{10}S$ 768.2585).

Example 0-20. Synthesis of allyl —N—[(S)-2-amino-3-(benzofuran-3-yl)propyl]carbamate (44-S)

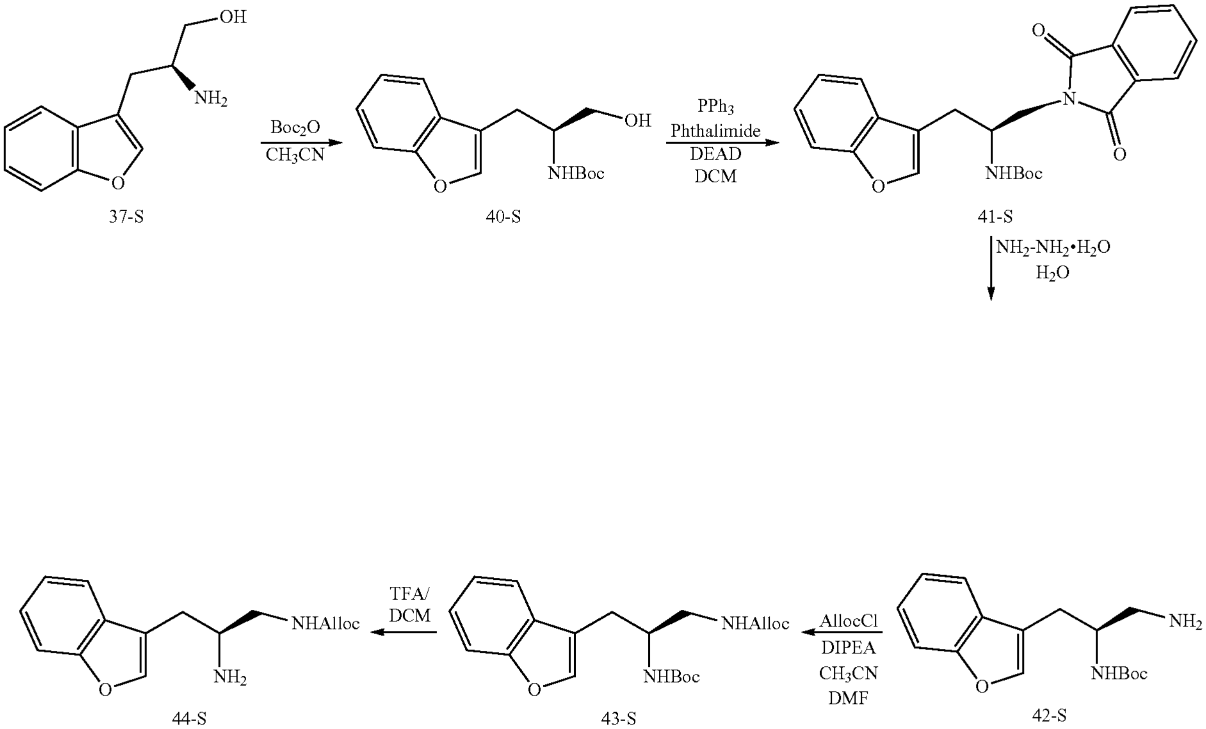

37-S 40-S 41-S 42-S 43-S 44-S

A)

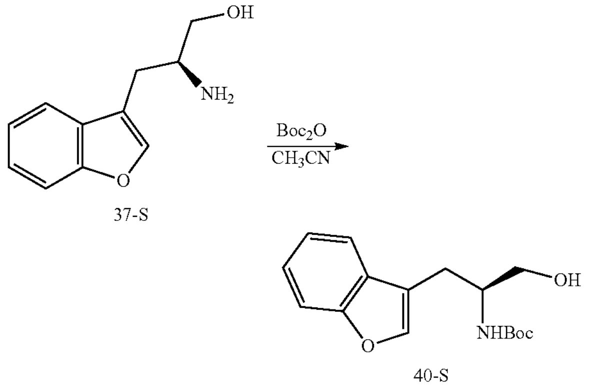

37-S
40-S

To a solution of compound 37-S (1.0 g, 5.22 mmol) in $CH_3CN$ (21 mL, 4 mL/mmol) was added di-tert-butyl dicarbonate (2.28 g, 10.4 mmol). The reaction mixture was stirred at 23° C. for 2 h, concentrated under vacuum. Flash chromatography ($CH_2Cl_2$:$CH_3OH$, from 99:1 to 85:15) to afford compound 40-S (0.5 g, 33%).

$R_f$=0.7 ($CH_2Cl_2$:$CH_3OH$, 9:1).

$^1$H NMR (400 MHz, $CDCl_3$): δ 7.64 (d, J=7.6 Hz, 1H), 7.49 (s, 1H), 7.46 (d, J=7.6 Hz, 1H), 7.36-7.19 (m, 2H), 4.94 (s, 1H), 3.98 (s, 1H), 3.71-3.56 (m, 2H), 2.93 (d, J=6.9 Hz, 2H), 1.41 (s, 9H).

B)

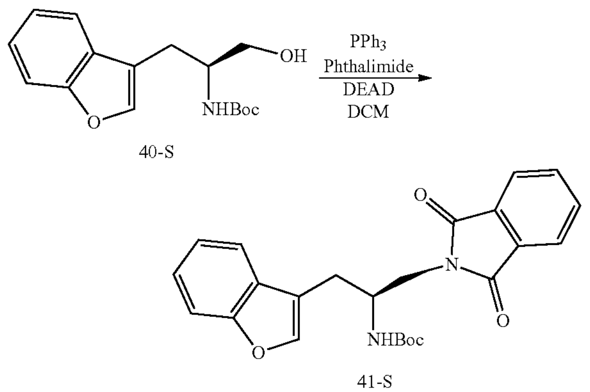

40-S
41-S

To a solution of compound 40-S (0.5 g, 1.71 mmol) in $CH_2Cl_2$ (11 mL, 6 mL/mmol) was added phthalimide (0.55 g, 3.77 mmol), triphenylphosphine (0.99 g, 3.77 mmol) and the mixture was cooled at 0° C. A solution of 40% of diethyl azodicarboxylate (DEAD) in $CH_2Cl_2$ (1.26 mL, 4.29 mmol) was added for 15 min. The reaction was stirred at 23° C. for 18 h, concentrated under vacuum. The residue obtained was purified by flash chromatography (Hexane:EtOAc, from 99:1 to 40:60) to afford compound 41-S (0.68 g, 94%).

$R_f$=0.8 ($CH_2Cl_2$:$CH_3OH$, 9:1).

$^1$H NMR (400 MHz, $CDCl_3$): δ 7.89-7.79 (m, 2H), 7.83-7.62 (m, 2H), 7.65-7.55 (m, 2H), 7.49-7.42 (m, 1H), 7.33-7.20 (m, 2H), 4.83 (d, J=9.0 Hz, 1H), 4.39 (ddt, J=12.1, 6.3, 2.9 Hz, 1H), 3.88-3.70 (m, 2H), 2.96 (d, J=6.4 Hz, 2H), 1.24 (s, 9H).

C)

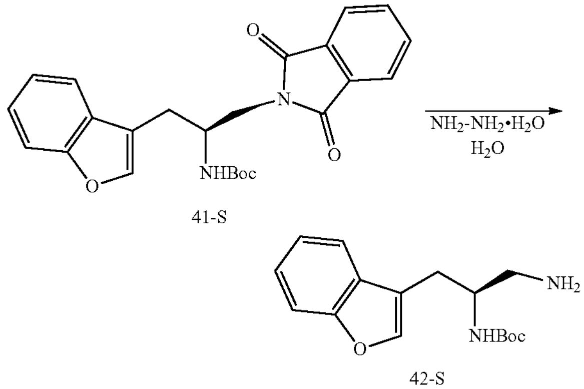

41-S
42-S

To a solution of compound 41-S (345 mg, 0.82 mmol) in ethanol (25 mL, 30 mL/mmol) was added hydrazine monohydrate (3.6 mL, 73.8 mmol). The reaction mixture was stirred at 80° C. in sealed tube for 2 h, concentrated under vacuum. Flash chromatography ($CH_2Cl_2$:$CH_3OH$, from 100:1 to 50:50) to afford compound 42-S (233 mg, 98%).

$R_f$=0.1 ($CH_2Cl_2$:$CH_3OH$, 8:2).

$^1$H NMR (400 MHz, $CDCl_3$): δ 7.62 (d, J=7.5 Hz, 1H), 7.49-7.42 (m, 2H), 7.33-7.18 (m, 2H), 4.85 (d, J=8.8 Hz, 1H), 3.91 (s, 1H), 2.91-2.76 (m, 3H), 2.67 (dd, J=13.1, 6.8 Hz, 1H), 1.25 (s, 9H).

D)

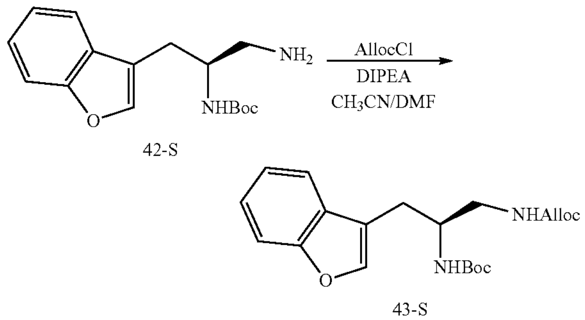

42-S
43-S

To a solution of compound 42-S (280 mg, 0.96 mmol) in $CH_3CN$ (10 mL, 10 mL/mmol) and DMF (16 mL, 1 mL/mmol) was added N,N-diisopropylethylamine (0.14 mL, 0.77 mmol) and allyl chloroformate (1.02 mL, 9.64 mmol). The reaction was stirred at 23° C. for 2 h. The mixture was diluted with EtOAc and $NH_4Cl$ was added and the mixture was extracted with EtOAc. The combined organic layers were dried over anhydrous $Na_2SO_4$, filtered, and concentrated under vacuum. The residue obtained was purified by flash chromatography (Hexane:EtOAc, from 100:1 to 1:100) to afford compound 43-S (445 mg, >100%).

$R_f$=0.5 (Hexane:EtOAc, 1:1).

$^1$H NMR (400 MHz, $CDCl_3$): δ 7.60 (d, J=7.6 Hz, 1H), 7.52-7.43 (m, 2H), 7.34-7.20 (m, 2H), 5.90 (ddt, J=16.4, 10.8, 5.6 Hz, 1H), 5.32-5.17 (m, 2H), 4.93-4.86 (m, 1H), 4.56 (d, J=5.6 Hz, 2H), 4.08-3.98 (m, 1H), 3.40-3.21 (m, 2H), 2.88 (m, 2H), 1.25 (s, 9H).

E)

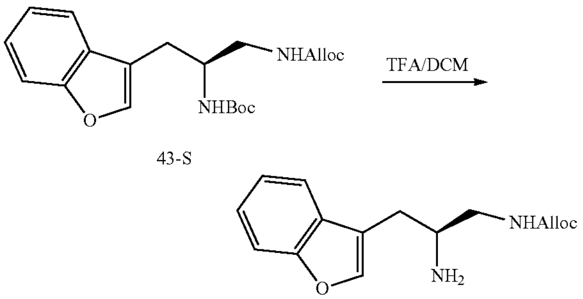

43-S

44-S

To a solution of compound 43-S (160 mg, 0.43 mmol) in $CH_2Cl_2$ (8 mL, 16.6 mL/mmol) was added trifluoroacetic acid (4 mL, 8.3 mL/mmol). The reaction mixture was stirred at 23° C. for 1.5 h, concentrated under vacuum. Flash chromatography ($CH_2Cl_2$:$CH_3OH$, from 100:1 to 50:50) to afford compound 44-S (175 mg, >100%).

$R_f$=0.2 ($CH_2Cl_2$:$CH_3OH$, 9:1).

$^1H$ NMR (400 MHz, $CD_3OD$): δ 7.72 (s, 1H), 7.64 (dt, J=8.4, 0.9 Hz, 1H), 7.49 (dt, J=8.4, 0.9 Hz, 1H), 7.37-7.22 (m, 2H), 5.94 (ddt, J=16.3, 10.7, 5.5 Hz, 1H), 5.32 (dq, J=17.3, 1.7 Hz, 1H), 5.19 (dq, J=10.6, 1.5 Hz, 1H), 4.56 (dt, J=5.7, 1.5 Hz, 2H), 3.56 (qd, J=7.0, 4.4 Hz, 1H), 3.46-3.32 (m, 1H), 3.32-3.24 (m, 1H), 3.03 (dd, J=14.8, 6.9 Hz, 1H), 2.91 (ddd, J=14.8, 7.1, 0.9 Hz, 1H).

Example 0-21. Synthesis of allyl —N—[(R)-2-amino-3-(benzofuran-3-yl)propyl]carbamate (44-R)

A)

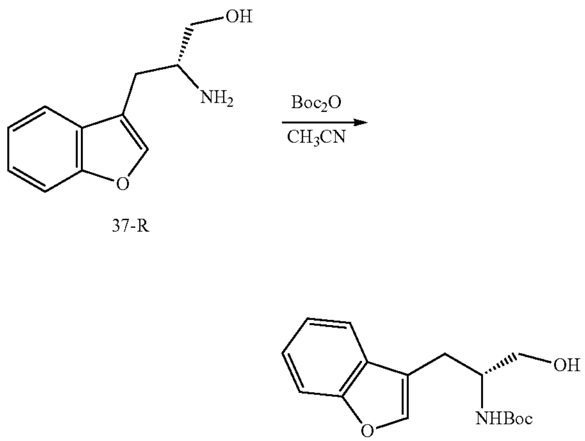

37-R

40-R

To a solution of compound 37-R (2.75 g, 14.4 mmol) in $CH_3CN$ (58 mL, 4 mL/mmol) was added di-tert-butyl dicarbonate (6.27 g, 28.76 mmol). The reaction mixture was stirred at 23° C. for 2.5 h, concentrated under vacuum. Flash chromatography ($CH_2Cl_2$:$CH_3OH$, from 99:1 to 85:15) to afford compound 40-R (3.7 g, 88%).

$R_f$=0.6 ($CH_2Cl_2$:$CH_3OH$, 9:1).

$^1H$ NMR (400 MHz, $CDCl_3$): δ 7.64 (d, J=7.6 Hz, 1H), 7.52-7.43 (m, 2H), 7.35-7.20 (m, 2H), 4.85 (d, J=8.2 Hz, 1H), 4.00 (bs, 1H), 3.69 (dd, J=11.0, 4.0 Hz, 1H), 3.62 (dd, J=10.9, 5.1 Hz, 1H), 2.94 (d, J=6.9 Hz, 2H), 1.42 (s, 9H).

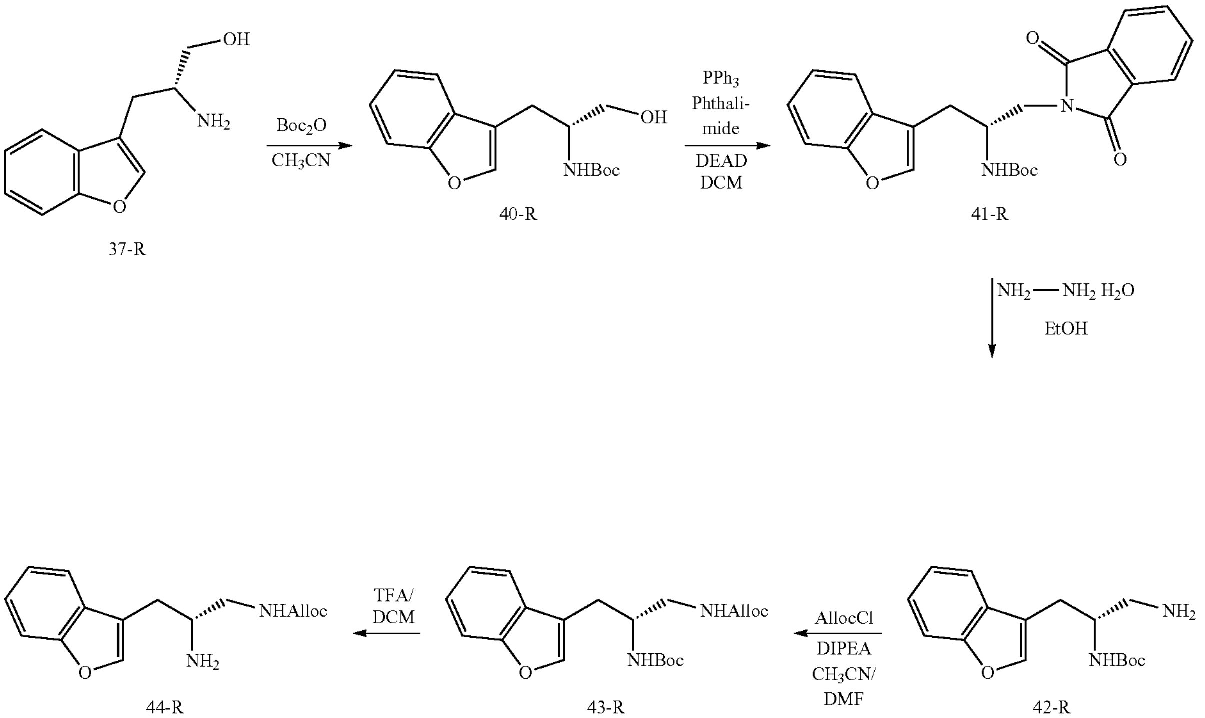

37-R 40-R 41-R 44-R 43-R 42-R

B)

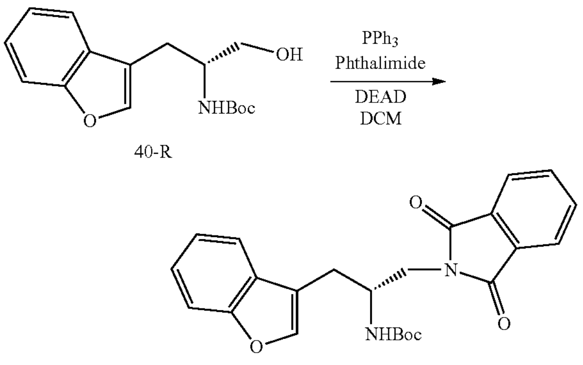

40-R

41-R

To a solution of compound 40-R (3.7 g, 12.7 mmol) in $CH_2Cl_2$ (76 mL, 6 mL/mmol) was added phthalimide (4.1 g, 28 mmol), triphenylphosphine (7.3 g, 28 mmol) and the mixture was cooled at 0° C. A solution of 40% of diethyl azodicarboxylate (DEAD) in $CH_2Cl_2$ (9.4 mL, 31.7 mmol) was added for 15 min. The reaction was stirred at 23° C. for 16 h, concentrated under vacuum. The residue obtained was purified by flash chromatography ($CH_2Cl_2$:$CH_3OH$, from 99:1 to 85:15) to afford compound 41-R (4.05 g, 76%).

$R_f$=0.8 ($CH_2Cl_2$:$CH_3OH$, 9:1).

$^1H$ NMR (400 MHz, $CDCl_3$): δ 7.67-7.68 (m, 4H), 7.61 (d, J=7.5 Hz, 1H), 7.58 (s, 1H), 7.46 (d, J=7.5 Hz, 1H), 7.27 (dtd, J=17.2, 7.3, 1.4 Hz, 2H), 4.84 (d, J=9.0 Hz, 1H), 4.46-4.30 (m, 1H), 3.89-3.66 (m, 2H), 2.97 (d, J=6.4 Hz, 2H), 1.24 (s, 9H).

C)

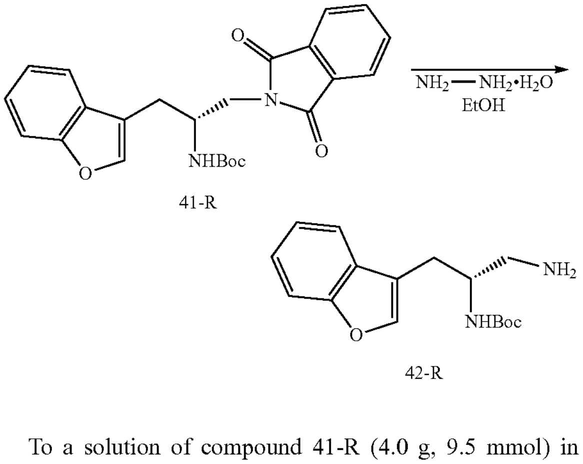

41-R

42-R

To a solution of compound 41-R (4.0 g, 9.5 mmol) in ethanol (285 mL, 30 mL/mmol) was added hydrazine monohydrate (41.5 mL, 856 mmol). The reaction mixture was stirred at 80° C. in sealed tube for 2 h, concentrated under vacuum. Flash chromatography ($CH_2Cl_2$:$CH_3OH$, from 100:1 to 50:50) to afford compound 42-R (2.2 g, 80%).

$R_f$=0.1 ($CH_2Cl_2$:$CH_3OH$, 8:2).

$^1H$ NMR (400 MHz, $CDCl_3$): δ 7.60 (d, J=7.5 Hz, 1H), 7.45 (s, 1H), 7.44 (d, J=7.1 Hz, 1H), 7.25 (dtd, J=18.8, 7.3, 1.3 Hz, 2H), 4.94 (d, J=8.8 Hz, 1H), 3.98-3.78 (m, 1H), 2.90-2.77 (m, 2H), 2.65 (dd, J=13.1, 7.0 Hz, 1H), 1.40 (s, 9H).

D)

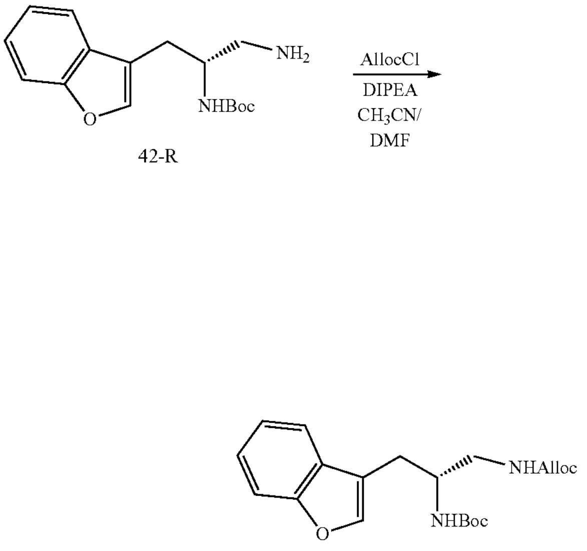

42-R

43-R

To a solution of compound 42-R (2.2 g, 7.6 mmol) in $CH_3CN$ (76 mL, 10 mL/mmol) and DMF (7.6 mL, 1 mL/mmol) was added N,N-diisopropylethylamine (1.1 mL, 6.08 mmol) and allyl chloroformate (8.05 mL, 76 mmol). The reaction was stirred at 23° C. for 7 h. The mixture was diluted with EtOAc and $NH_4Cl$ was added and the mixture was extracted with EtOAc. The combined organic layers were dried over anhydrous $Na_2SO_4$, filtered, and concentrated under vacuum. The residue obtained was purified by flash chromatography (Hexane:EtOAc, from 100:1 to 1:100) to afford compound 43-R (2.3 g, 81%).

$R_f$=0.7 (Hexane:EtOAc, 1:1).

$^1H$ NMR (400 MHz, $CDCl_3$): δ 7.60 (d, J=7.5 Hz, 1H), 7.52-7.43 (m, 2H), 7.34-7.20 (m, 2H), 5.90 (ddt, J=17.3, 10.8, 5.6 Hz, 1H), 5.29 (d, J=17.2, 1H), 5.20 (d, J=10.4, 1H), 5.10 (t, J=6.2 Hz, 1H), 4.86 (d, J=8.4 Hz, 1H), 4.56 (d, J=5.4, 2H), 4.08-3.97 (m, 1H), 3.36 (dt, J=10.7, 4.7 Hz, 1H), 3.30-3.23 (m, 1H), 2.87 (td, J=14.8, 6.5 Hz, 2H), 1.41 (s, 9H).

E)

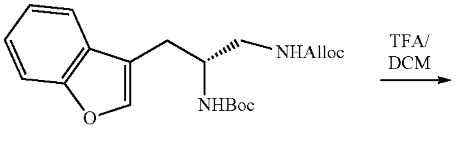

43-R

-continued

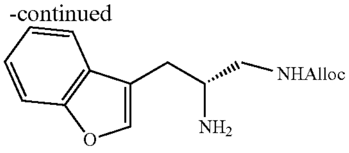

44-R

To a solution of compound 43-R (1.32 g, 3.52 mmol) in $CH_2Cl_2$ (60 mL, 16.6 mL/mmol) was added Trifluoroacetic acid (30 mL, 8.3 mL/mmol). The reaction mixture was stirred at 23° C. for 1.5 h, concentrated under vacuum. Flash chromatography ($CH_2Cl_2$:$CH_3OH$, from 100:1 to 50:50) to afford compound 44-R (0.90 g, 94%).

$R_f$=0.2 ($CH_2Cl_2$:$CH_3OH$, 9:1).

$^1$H NMR (400 MHz, $CDCl_3$): δ 7.75 (s, 1H), 7.69-7.61 (m, 1H), 7.54-7.46 (m, 1H), 7.39-7.24 (m, 2H), 5.95 (ddt, J=16.3, 10.8, 5.5 Hz, 1H), 5.32 (dd, J=17.3, 1.8 Hz, 1H), 5.24-5.16 (m, 1H), 4.57 (dt, J=5.7, 1.5 Hz, 2H), 3.68 (qd, J=7.1, 4.2 Hz, 1H), 3.48 (dd, J=14.8, 4.2 Hz, 1H), 3.42-3.30 (m, 1H), 3.14-2.95 (m, 2H).

Example 0-22

A)

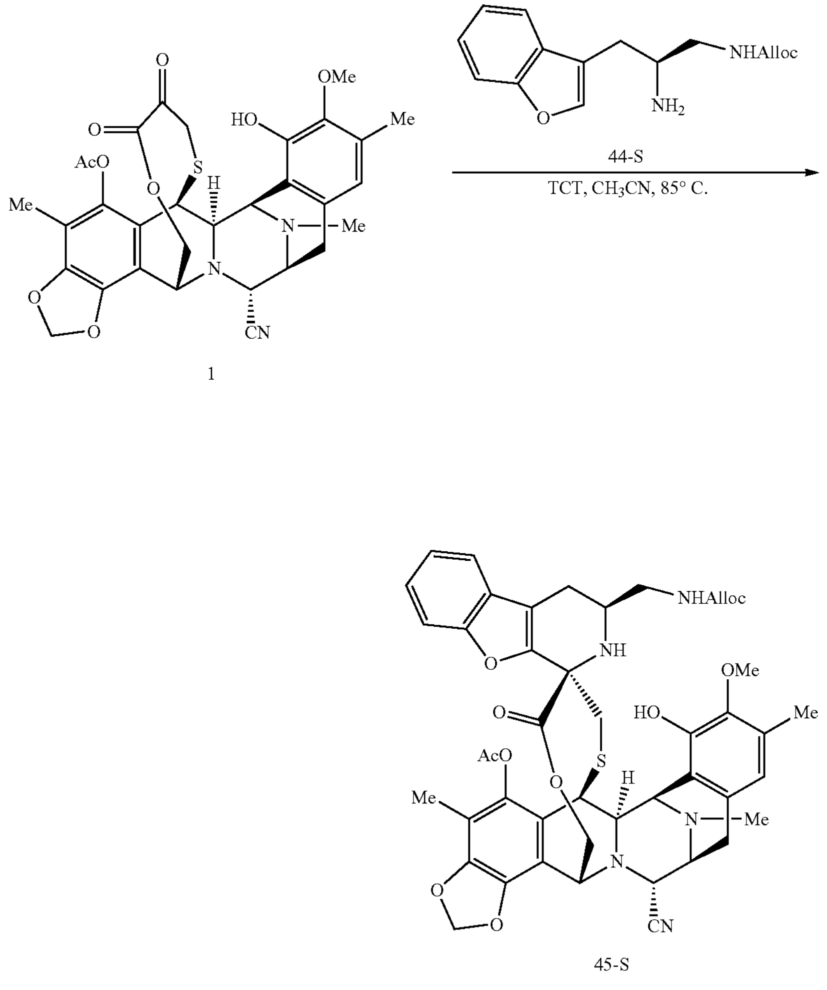

1

45-S

To a solution of compound 1 (750 mg, 1.2 mmol) in $CH_3CN$ (120 mL, 0.01 M) was added compound 44-S (1370 mg, 6 mmol) and cyanuric chloride (TCT) (184 mg, 20%). The reaction mixture was stirred at 85° C. for 23 h and then aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, from 9:1 to 1:9) gives compound 45-S (755 mg, 72%).

$R_f$=0.36 (Hexane:EtOAc, 1:1).

$^1$H NMR (400 MHz, $CDCl_3$): δ 7.38-7.28 (m, 2H), 7.23-7.08 (m, 2H), 6.67 (s, 1H), 6.19 (d, J=1.4 Hz, 1H), 6.09-5.95 (m, 1H), 6.04 (d, J=1.4 Hz, 1H), 5.92 (s, 1H), 5.80 (s, 1H), 5.44-5.34 (m, 1H), 5.26 (dq, J=10.4, 1.3 Hz, 1H), 5.08 (dd, J=11.4, 1.1 Hz, 1H), 4.70-4.63 (m, 2H), 4.56 (s, 1H), 4.34 (s, 1H), 4.31-4.18 (m, 3H), 3.80 (s, 3H), 3.50-3.39 (m, 2H), 3.24-3.15 (m, 1H), 3.00 (dt, J=12.2, 6.0 Hz, 2H), 2.95 (d, J=5.2 Hz, 2H), 2.60 (dd, J=15.4, 4.5 Hz, 2H), 2.44 (dd, J=15.6, 5.2 Hz, 1H), 2.29 (s, 3H), 2.27 (s, 3H), 2.25-2.20 (m, 1H), 2.18 (s, 3H), 2.12 (s, 1H), 2.04 (s, 3H).

ESI-MS m/z: 878.2 $(M+H)^+$.

B)

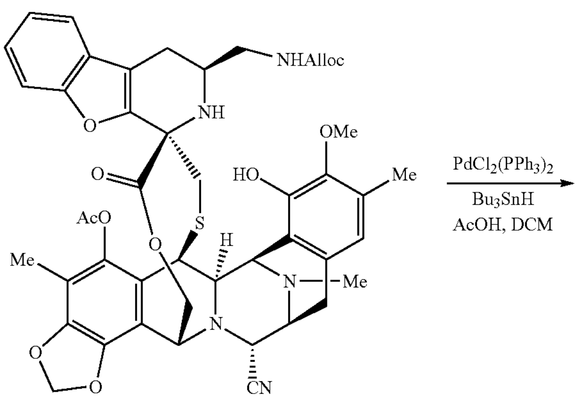

45-S

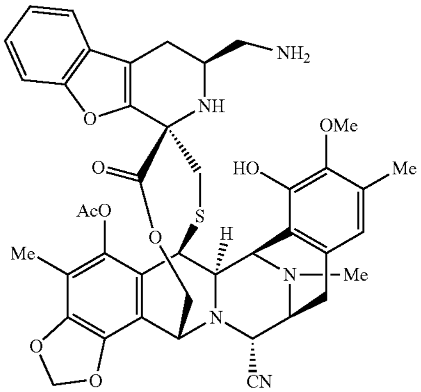

46-S

To a solution of compound 45-S (750 mg, 0.85 mmol) in $CH_2Cl_2$ (15.3 mL, 18 mL/mmol) was added bis(triphenylphosphine)palladium(II) dichloride (96 mg, 0.14 mmol) and acetic acid (0.5 mL, 8.5 mmol). Tributyltin hydride (1.4 mL, 5.1 mmol) was added at 0° C., and the reaction mixture was stirred at 0° C. for 30 minutes, and was concentrated under vacuum. Flash chromatography (Hexane:EtOAc, from 100:1 to 1:100 and $CH_2Cl_2$:$CH_3OH$, from 100:1 to 1:100) to afford compound 46-S (430 mg, 64%).

$R_f$=0.3 ($CH_2Cl_2$:$CH_3OH$, 1:1).

$^1$H NMR (400 MHz, $CDCl_3$): δ 7.37-7.29 (m, 2H), 7.22-7.11 (m, 2H), 6.57 (s, 1H), 6.21 (d, J=1.5 Hz, 1H), 6.06 (d, J=1.5 Hz, 1H), 5.07 (d, J=11.5 Hz, 1H), 4.57 (s, 1H), 4.37 (s, 1H), 4.29-4.23 (m, 2H), 4.14 (s, 1H), 3.79 (s, 3H), 3.50-3.47 (m, 2H), 3.38 (d, J=8.7 Hz, 1H), 2.95-2.71 (m, 4H), 2.68-2.52 (m, 2H), 2.51-2.38 (m, 1H), 2.35 (s, 3H), 2.33-2.26 (m, 1H), 2.29 (s, 3H), 2.17-2.08 (m, 1H), 2.10 (s, 3H), 2.04 (s, 3H).

ESI-MS m/z: 794.3 $(M+H)^+$.

C)

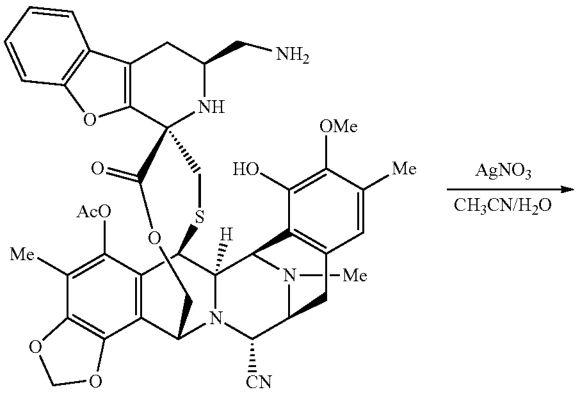

46-S

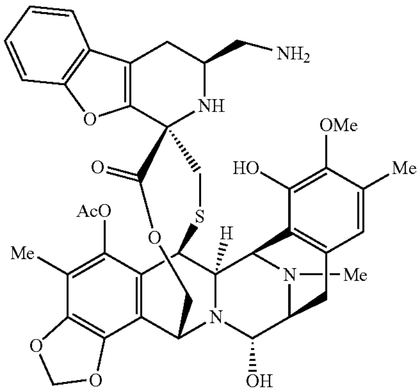

47-S

To a solution of compound 46-S (550 mg, 0.7 mmol) in $CH_3CN$:$H_2O$ (1.39:1, 49 mL, 0.015 M) was added $AgNO_3$ (2.4 g, 14 mmol). After 16 h at 23° C., the reaction was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give compound 47-S (53 mg, 10%).

$R_f$=0.1 ($CH_2Cl_2$:$CH_3OH$, 9:1).

$^1$H NMR (500 MHz, $CDCl_3$): δ 7.36 (d, 7.9 Hz, 1H), 7.33 (d, 7.4 Hz, 1H), 7.23 (t, J=7.4 Hz, 1H), 7.16 (t, J=7.4 Hz, 1H), 6.77 (s, 1H), 6.20 (s, 1H), 6.04 (s, 1H), 5.92 (s, 1H), 5.20 (d, J=11.1 Hz, 1H), 4.90 (s, 1H), 4.50 (s, 1H), 4.46-4.39 (m, 1H), 4.25 (d, J=11.1 Hz, 1H), 4.20 (s, 1H), 3.84 (s, 3H), 3.81 (d, J=4.2 Hz, 1H), 3.58 (s, 1H), 3.40-3.14 (m, 3H), 2.90 (t, J=13.0 Hz, 1H), 2.76 (m, 3H), 2.50 (s, 3H), 2.46-2.37 (m, 1H), 2.32-2.26 (m, 2H), 2.30 (s, 3H), 2.15 (s, 3H), 2.04 (s, 3H).

$^{13}$C NMR (126 MHz, $CD_3OD$): δ 170.5, 169.2, 154.6, 149.1, 148.7, 145.7, 143.5, 141.0, 140.9, 131.2, 129.6, 126.9, 124.4, 122.5, 121.4, 119.7, 118.7, 115.0, 112.7, 111.0, 110.7, 102.1, 91.2, 63.5, 61.2, 59.2, 58.5, 55.3, 54.7, 53.4, 52.7, 43.3, 42.5, 39.9, 36.9, 29.3, 24.1, 23.6, 19.1, 15.0, 8.2.

ESI-MS m/z: 767.2 $(M-H_2O+H)^+$.

(+)-HR-ESI-TOF-MS m/z: 767.2794 $[M-H_2O+H]^+$ (Calcd. for $C_{41}H_{43}N_4O_9S$ 767.2745).

Example 0-23

A)

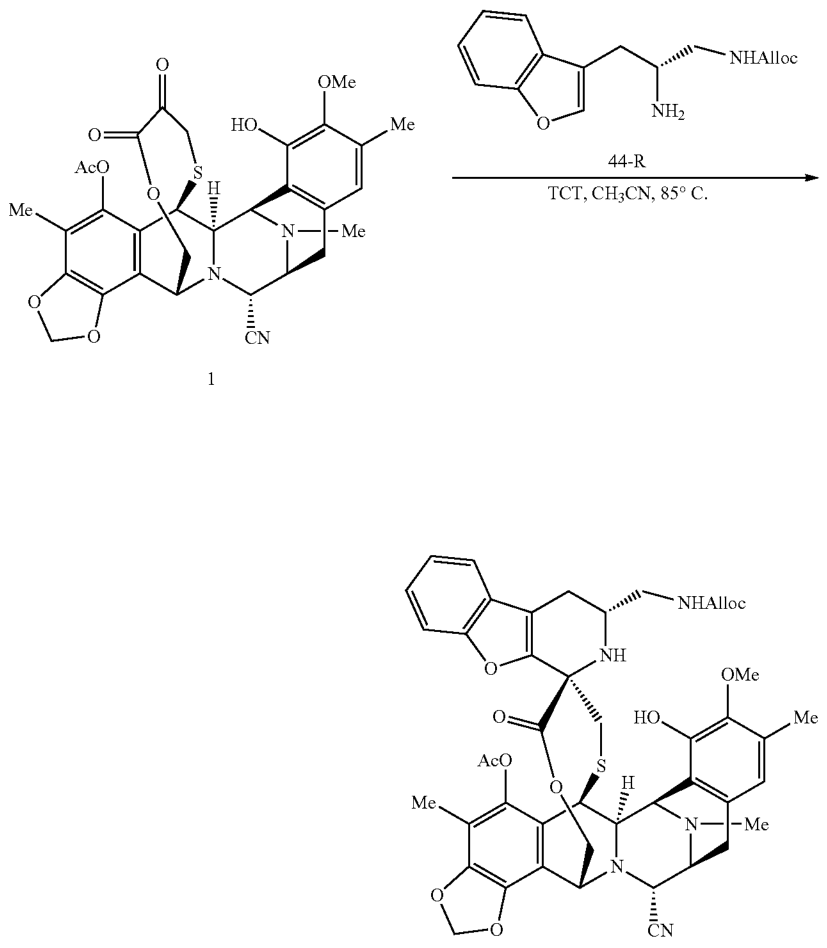

1

44-R

45-R

To a solution of compound 1 (621 mg, 1 mmol) in $CH_3CN$ (100 mL, 0.01 M) was added compound 44-R (825 mg, 3 mmol) and cyanuric chloride (TCT) (248 mg, 40%). The reaction mixture was stirred at 85° C. for 66 h and then aqueous saturated solution of $NaHCO_3$ was added and the mixture was extracted with $CH_2Cl_2$. The combined organic layers were dried over anhydrous $Na_2SO_4$, filtered, and concentrated under vacuum. Flash chromatography (Hexane:EtOAc, from 9:1 to 1:9) gives compound 45-R (530 mg, 58%).

$R_f$=0.4 (Hexane:EtOAc, 1:1).

$^1H$ NMR (400 MHz, $CDCl_3$): δ 7.42-7.28 (m, 2H), 7.23-7.08 (m, 2H), 6.60 (s, 1H), 6.20 (d, J=1.4 Hz, 1H), 6.04 (d, J=1.4 Hz, 1H), 6.01-5.92 (m, 1H), 5.77 (s, 1H), 5.44-5.20 (m, 2H), 5.09 (s, 1H), 5.04-4.96 (m, 1H), 4.71-4.55 (m, 2H), 4.34 (s, 1H), 4.30-4.18 (m, 3H), 3.79 (s, 3H), 3.53 (dd, J=10.2, 4.4 Hz, 1H), 3.46 (m, 2H), 3.50-3.40 (m, 1H), 3.03-2.87 (m, 2H), 2.67 (d, J=15.0 Hz, 1H), 2.47 (dd, J=15.6, 3.7 Hz, 1H), 2.40-2.32 (m, 2H), 2.30 (s, 3H), 2.29 (s, 3H), 2.19-2.12 (m, 2H), 2.16 (s, 3H), 2.09 (s, 3H).

ESI-MS m/z: 878.3 $(M+H)^+$.

B)

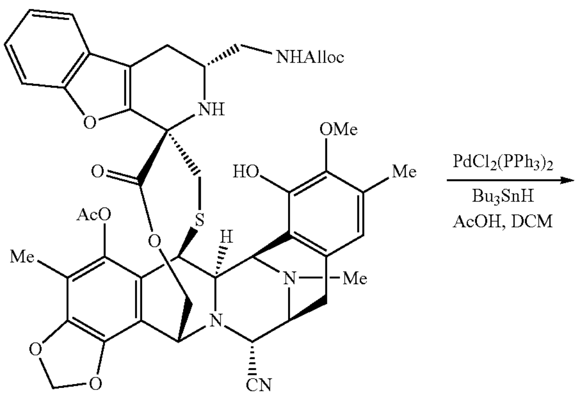

45-R

-continued

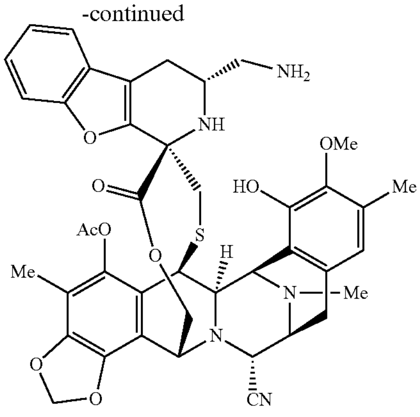

46-R

-continued

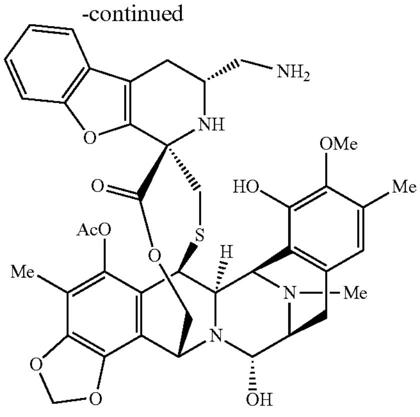

47-R

To a solution of compound 45-R (552 mg, 0.63 mmol) in $CH_2Cl_2$ (11.3 mL, 18 mL/mmol) was added bis(triphenylphosphine)palladium(II) dichloride (70.7 mg, 0.1 mmol) and acetic acid (0.36 mL, 6.3 mmol). Tributyltin hydride (1.02 mL, 3.8 mmol) was added at 0° C. and the reaction mixture was stirred at 0° C. for 0.5 h, and concentrated under vacuum The crude obtained was diluted with EtOAc, saturated aqueous solution of $NH_4Cl$ was added and the mixture was extracted with EtOAc. The combined organic layers were dried over anhydrous $Na_2SO_4$, filtered, and concentrated under vacuum. Flash chromatography (Hexane:EtOAc, from 100:1 to 1:100 and EtOAc:$CH_3OH$, from 100:1 to 1:100) to afford compound 46-R (423 mg, 85%).

$R_f$=0.3 ($CH_2Cl_2$:$CH_3OH$, 1:1).

$^1$H NMR (400 MHz, $CDCl_3$): δ 7.45-7.28 (m, 2H), 7.23-7.08 (m, 2H), 6.56 (s, 1H), 6.19 (d, J=1.4 Hz, 1H), 6.05 (d, J=1.4 Hz, 1H), 4.98 (d, J=11.5 Hz, 1H), 4.59 (s, 1H), 4.34 (s, 1H), 4.27 (dd, J=5.1, 1.7 Hz, 1H), 4.22-4.16 (m, 2H), 3.80 (s, 3H), 3.49-3.39 (m, 2H), 3.31 (dq, J=9.8, 5.5, 4.5 Hz, 2H), 2.95 (s, 1H), 2.83 (d, J=5.6 Hz, 2H), 2.74-2.51 (m, 3H), 2.35 (s, 3H), 2.32-2.21 (m, 2H), 2.26 (s, 3H); 2.16 (s, 3H), 2.06 (s, 3H).

ESI-MS m/z: 794.3 $(M+H)^+$.

C)

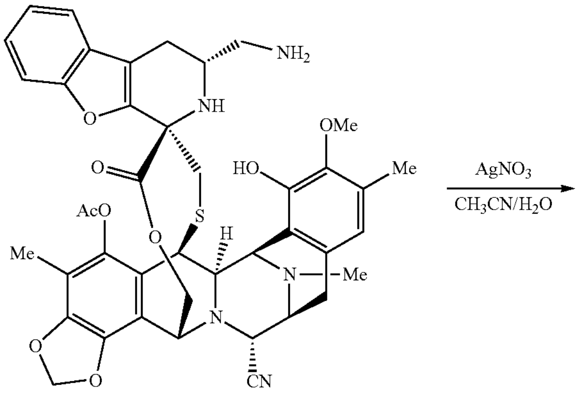

46-R

To a solution of compound 46-R (412 mg, 0.52 mmol) in $CH_3CN$:$H_2O$ (1.39:1, 36 mL, 0.015 M) was added $AgNO_3$ (1.76 g, 10.4 mmol). After 22 h at 23° C., the reaction was quenched with a mixture 1:1 of saturated aqueous solutions of NaCl and $NaHCO_3$, stirred for 15 min, diluted with $CH_2Cl_2$, stirred for 5 min, and extracted with $CH_2Cl_2$. The combined organic layers were dried over anhydrous $Na_2SO_4$, filtered, and concentrated under vacuum. The residue obtained was purified by flash chromatography ($CH_2Cl_2$:$CH_3OH$, from 99:1 to 85:15) to give compound 47-R (175 mg, 43%).

$R_f$=0.1 ($CH_2Cl_2$:$CH_3OH$, 9:1).

$^1$H NMR (500 MHz, $CDCl_3$): δ 7.34 (dd, J=11.1, 7.9 Hz, 2H), 7.22-7.07 (m, 2H), 6.57 (s, 1H), 6.17 (d, J=1.2 Hz, 1H), 6.01 (d, J=1.2 Hz, 1H), 5.11 (d, J=11.2 Hz, 1H), 4.84 (s, 1H), 4.53-4.47 (m, 2H), 4.21-4.07 (m, 2H), 3.80 (s, 3H), 3.56 (d, J=5.1 Hz, 1H), 3.43 (s, 1H), 3.24 (d, J=9.1 Hz, 1H), 2.98-2.78 (m, 4H), 2.72-2.58 (m, 2H), 2.38 (s, 3H), 2.35-2.27 (m, 2H), 2.28 (s, 3H), 2.14 (s, 3H), 2.08 (s, 3H).

$^{13}$C NMR (101 MHz, $CD_3OD$): δ 170.6, 169.1, 155.0, 148.8, 145.6, 143.7, 141.1, 140.8, 130.9, 129.7, 126.9, 124.2, 122.4, 121.1, 119.6, 118.9, 118.7, 115.0, 113.2, 112.5, 111.0, 102.1, 91.3, 63.3, 60.4, 59.0, 58.4, 55.3, 54.6, 52.6, 51.1, 44.9, 42.4, 39.8, 38.7, 29.4, 24.0, 23.2, 19.1, 15.0, 8.3.

ESI-MS m/z: 767.2 $(M-H_2O+H)^+$.

(+)-HR-ESI-TOF-MS m/z: 767.2806 $[M-H_2O+H]^+$ (Calcd. for $C_{41}H_{43}N_4O_9S$ 767.2745).

Bioactivity Example of the Payloads

The aim of this assay is to evaluate the in vitro cytostatic (ability to delay or arrest tumor cell growth) or cytotoxic (ability to kill tumor cells) activity of the samples being tested.

Cell Lines

| Name | No ATCC | Species | Tissue | Characteristics |
|---|---|---|---|---|
| A549 | CCL-185 | human | Lung | lung carcinoma (NSCLC) |
| HT29 | HTB-38 | human | Colon | colorectal adenocarcinoma |
| MDA-MB-231 | HTB-26 | human | Breast | breast adenocarcinoma |
| PSN1 | CRM-CRL-3211 | human | Pancreas | pancreas adenocarcinoma |
| PC-3 | CRL-1435 | human | Prostate | prostate adenocarcinoma |
| 22Rv1 | CRL-2505 | human | Prostate | prostate carcinoma |

Evaluation of Cytotoxic Activity Using the SRB and the MTT Colorimetric Assays

A colorimetric assay, using Sulforhodamine B (SRB) reaction has been adapted to provide a quantitative measurement of cell growth and viability (following the technique described by Skehan et al. *J. Natl. Cancer Inst.* 1990, 82, 1107-1112). Another colorimetric assay based on 3-(4, 5-Dimethylthiazol-2-yl)-2,5-diphenyltetrazolium bromide (MTT) reduction to a purple formazan has been also used to assess the antiproliferative activity (following the technique described by Mosmann et al. *J. Immunol. Meth.* 1983, 65, 55-63).

These forms of assays employ 96-well cell culture microplates following the standards of the American National Standards Institute and the Society for Laboratory Automation and Screening (ANSI SLAS January 2004 (R2012) Oct. 12, 2011. All the cell lines used in this study were obtained from the American Type Culture Collection (ATCC) and derive from different types of human cancer.

A549, HT29, MDA-MB-231 and PSN1 cells were maintained in Dulbecco's Modified Eagle Medium (DMEM) while PC-3 and 22Rv1 cells were maintained in Roswell Park Memorial Institute Medium (RPMI). All cell lines were supplemented with 10% Fetal Bovine Serum (FBS), 2 mM L-glutamine, 100 U/mL penicillin, and 100 U/mL streptomycin at 37° C., 5% $CO_2$ and 98% humidity. For the experiments, cells were harvested from subconfluent cultures using trypsinization and resuspended in fresh medium before counting and plating.

A549, HT29, MDA-MB-231 and PSN1 cells were seeded in 96 well microtiter plates, at 5000 cells per well in aliquots of 150 µL, and allowed to attach to the plate surface for 18 hours (overnight) in drug free medium. After that, one control (untreated) plate of each cell line was fixed (as described below) and used for time zero reference value. Culture plates were then treated with test compounds (50 µL aliquots of 4× stock solutions in complete culture medium plus 4% DMSO) using ten 2/5 serial dilutions (concentrations ranging from 10 to 0.003 µg/mL) and triplicate cultures (1% final concentration in DMSO). After 72 hours treatment, the antitumor effect was measured by using the SRB methodology: Briefly, cells were washed twice with PBS, fixed for 15 min in 1% glutaraldehyde solution at room temperature, rinsed twice in PBS, and stained in 0.4% SRB solution for 30 min at room temperature. Cells were then rinsed several times with 1% acetic acid solution and air-dried at room temperature. SRB was then extracted in 10 mM trizma base solution and the absorbance measured in an automated spectrophotometric plate reader at 490 nm.

An appropriate number of PC-3 and 22Rv1 cells, to reach a final cell density in the assay ranging from 5,000 to 15,000 cells per well depending on the cell line, were seeded in 96-well plates and allowed to stand in culture medium for 24 h at 37° C. under 5% CO2 and 98% humidity. Then, compounds or DMSO in culture medium were added to reach a final volume of 200 µL and the intended compound concentration in a range covering ten serial 2/5 dilutions starting from 0.1 µg/mL in 1% (v/v) DMSO. At this point a set of "time zero control plates" treated with 1% (v/v) DMSO were processed with MTT as described below. The rest of the plates were incubated during 72 h under the aforementioned environmental conditions. Afterwards 50 µL of a 1 mg/mL MTT solution in culture medium were added to the wells and incubated for 6-8 hours at 37° C. to allow formazan crystals generation. Culture medium was then removed and 100 µL of neat DMSO added to each well to dissolve the formazan product into a coloured solution whose absorbance at 540 nm was finally measured in a PolarStar Omega microplate multilabel reader (BMG Labtech, Ortenberg, Germany).

Effects on cell growth and survival were estimated by applying the NCl algorithm (Boyd M R and Paull K D. Drug Dev. Res. 1995, 34, 91-104). The values obtained in triplicate cultures were fitted by nonlinear regression to a four-parameters logistic curve by nonlinear regression analysis. Three reference parameters were calculated (according to the aforementioned NCl algorithm) by automatic interpolation of the curves obtained by such fitting: $GI_{50}$=compound concentration that produces 50% cell growth inhibition, as compared to control cultures; TGI=total cell growth inhibition (cytostatic effect), as compared to control cultures, and $LC_{50}$=compound concentration that produces 50% net cell killing cytotoxic effect).

Tables 3-9 illustrate data on the biological activity of compounds of the present invention.

TABLE 3

Biological activity (Molar)

Compound

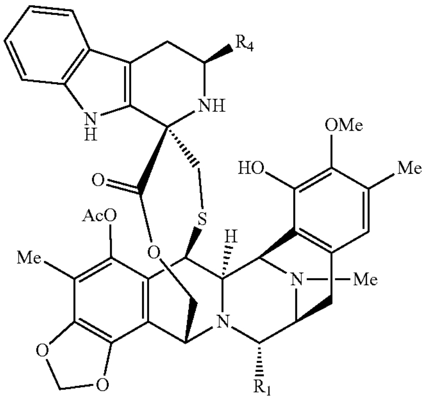

3-S $R_1$ = CN, $R_4$ = —$CH_2OH$

3a-S $R_1$ = CN, $R_4$ = —$CH_2OAc$

10-S $R_1$ = ON, $R_4$ = —$CH_2NHAlloc$

TABLE 3-continued

11-S $R_1$ = CN, $R_4$ = —$CH_2NH_2$
4-S $R_1$ = OH, $R_4$ = —$CH_2OH$
4a-S $R_1$ = OH, $R_4$ = —$CH_2OAc$
12-S $R_1$ = OH, $R_4$ = —$CH_2NH_2$
13-S $R_1$ = OH, $R_1$ = —$CH_2NHAlloc$

| | | A549 | HT29 | MDA-MB-231 | PSN1 | PC-3 | 22Rv1 |
|---|---|---|---|---|---|---|---|
| $GI_{50}$ | 3-S | 4.03E-10 | 2.77E-10 | 4.91E-10 | 9.95E-10 | | |
| TGI | | 6.17E-10 | >1.26E-07 | 5.29E-10 | 1.64E-09 | | |
| $LC_{50}$ | | >1.26E-07 | >1.26E-07 | 6.17E-10 | >1.26E-07 | | |
| $GI_{50}$ | 3a-S | 3.11E-09 | 2.99E-09 | 2.87E-09 | 2.15E-09 | | |
| TGI | | 3.23E-09 | 3.23E-09 | 3.59E-09 | 3.59E-09 | | |
| $LC_{50}$ | | >1.20E-07 | >1.20E-07 | 4.90E-09 | 1.20E-08 | | |
| GI50 | 10-S | 2.05E-08 | 1.14E-08 | 4.79E-09 | 7.64E-09 | | |
| TGI | | 3.08E-08 | 1.25E-08 | 8.44E-09 | 1.25·E-08 | | |
| $LC_{50}$ | | 7.53E-08 | >1.14E-06 | 1.60E-08 | 2.39E-08 | | |
| $GI_{50}$ | 11-S | 8.45E-09 | 3.41E-09 | 2.27E-09 | 3.28E-09 | | |
| TGI | | 2.65E-08 | >1.26E-07 | 3.41E-09 | 4.54E-09 | | |
| $LC_{50}$ | | >1.26E-07 | >1.26E-07 | 6.43E-09 | 8.07E-09 | | |
| $GI_{50}$ | 4-S | 1.27E-09 | 1.27E-09 | 1.22E-09 | 1.78E-09 | 8.08E-10 | 3.58E-10 |
| TGI | | 1.40E-09 | 1.40E-09 | 2.55E-09 | 2.29E-09 | | |
| $LC_{50}$ | | >1.27E-07 | >1.27E-07 | 6.50E-09 | 3.44E-09 | | |
| $GI_{50}$ | 4a-S | 3.99E-09 | 3.14E-09 | 3.39E-09 | 3.02E-09 | | |
| TGI | | 6.17E-09 | 3.39E-09 | 5.44E-09 | 3.27E-09 | | |
| $LC_{50}$ | | >1.21E-07 | >1.21E-07 | 1.00E-08 | 3.51E-09 | | |
| $GI_{50}$ | 12-S | 2.04E-08 | 4.85E-09 | 5.23E-09 | 3.44E-09 | | |
| TGI | | 5.61E-08 | 8.42E-09 | 8.42E-09 | 5.49E-09 | | |
| $LC_{50}$ | | >1.28E-07 | >1.28E-07 | 1.53E-08 | 1.21E-08 | | |
| $GI_{50}$ | 13-S | 1.15E-08 | 1.15E-08 | 1.15E-08 | 1.96E-08 | | |
| TGI | | 1.61E-08 | 1.27E-08 | 1.27E-08 | 2.88E-08 | | |
| $LC_{50}$ | | 2.42E-08 | >1.15E-06 | 1.38E-08 | 4.61E-08 | | |

TABLE 4

Biological activity (Molar)
Compound

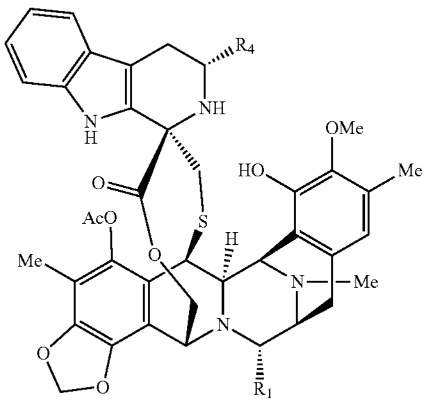

3-R $R_1$ = CN, $R_4$ = —$CH_2OH$
10-R $R_1$ = CN, $R_4$ = —$CH_2NHAlloc$
11-R $R_1$ = CN, $R_4$ = —$CH_2NH_2$
4-R $R_1$ = OH, $R_4$ = —$CH_2OH$
12-R $R_1$ = OH, $R_4$ = —$CH_2NH_2$
13-R $R_1$ = OH, $R_4$ = —$CH_2NHAlloc$ TABLE 4-continued

| | | A549 | HT29 | MDA-MB-231 | PSN1 |
|---|---|---|---|---|---|
| $GI_{50}$ | 3-R | 4.03E-10 | 2.77E-10 | 2.77E-10 | 3.90E-10 |
| TGI | | 5.79E-10 | >1.26E-07 | 5.04E-10 | 6.05E-10 |
| $LC_{50}$ | | >1.26E-07 | >1.26E-07 | 1.25E-09 | >1.26E-07 |
| $GI_{50}$ | 10-R | 3.76E-09 | 3.08E-09 | 2.85E-09 | 2.62E-09 |
| TGI | | 5.93E-09 | >1.14E-07 | 4.33E-09 | 3.88E-09 |
| $LC_{50}$ | | >1.14E-07 | >1.14E-07 | 7.18E-09 | 6.61E-09 |
| $GI_{50}$ | 11-R | 1.77E-09 | 1.39E-09 | 1.01E-09 | 1.39 E-09 |
| TGI | | 4.54E-09 | >1.26E-07 | 1.51E-09 | 1.89E-09 |
| $LC_{50}$ | | >1.26E-07 | >1.26E-07 | 2.65E-09 | >1.26E-07 |
| $GI_{50}$ | 4-R | 1.27E-09 | 1.26E-09 | 1.27E-09 | 4.59E-10 |
| TGI | | 1.40E-09 | 1.40E-09 | 1.40E-09 | 8.54E-10 |
| $LC_{50}$ | | >1.27E-07 | >1.27E-07 | 1.53E-09 | 2.55E-09 |
| $GI_{50}$ | 12-R | 1.40E-09 | 5.74E-10 | 3.19E-10 | 4.98E-10 |
| TGI | | 2.93E-09 | 1.10E-09 | 6.76E-10 | 1.22E-09 |
| $LC_{50}$ | | 1.22E-08 | 2.93E-09 | 1.40E-09 | >1.28E-07 |
| $GI_{50}$ | 13-R | 7.26E-09 | 6.91E-09 | 4.95E-09 | 2.88E-09 |
| TGI | | 7.72E-09 | 7.60E-09 | 7.95E-09 | 3.11E-09 |
| $LC_{50}$ | | >1.15E-07 | >1.15E-07 | 1.38E-08 | 3.46E-09 |

TABLE 5

Biological activity (Molar)
Compound

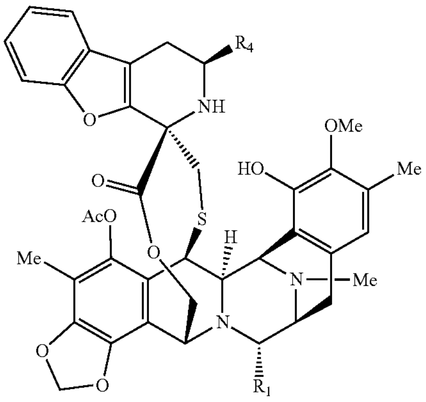

38-S $R_1$ = CN, $R_4$ = —$CH_2OH$
45-S $R_1$ = CN, $R_4$ = —$CH_2NHAlloc$
46-S $R_1$ = CN, $R_4$ = —$CH_2NH_2$
39-S $R_1$ = OH, $R_4$ = —$CH_2OH$
47-S $R_1$ = OH, $R_4$ = —$CH_2NH_2$

| | | A549 | HT29 | MDA-MB-231 | PSN1 | PC-3 | 22Rv1 |
|---|---|---|---|---|---|---|---|
| $GI_{50}$ | 38-S | 8.05E-09 | 4.53E-09 | 2.52E-09 | 5.03E-09 | | |
| TGI | | 8.55E-09 | 7.05E-09 | 4.28E-09 | 8.18E-09 | | |
| $LC_{50}$ | | 9.44E-09 | >1.26E-07 | 7.80E-09 | 1.51E-08 | | |
| $GI_{50}$ | 45-S | 1.82E-08 | 1.82E-08 | 1.71E-08 | 1.94E-08 | | |
| TGI | | 1.94E-08 | 1.94E-08 | 2.16E-08 | 2.62E-08 | | |
| $LC_{50}$ | | 2.16E-08 | >1.14E-07 | 2.96E-08 | 3.64E-08 | | |
| $GI_{50}$ | 46-S | 8.19E-09 | 2.77E-09 | 3.65E-09 | 3.15E-09 | | |
| TGI | | 2.14E-08 | 6.17E-09 | 6.80E-09 | 4.79E-09 | | |
| $LC_{50}$ | | >1.26E-07 | >1.26E-07 | 1.26E-08 | 9.20E-09 | | |
| $GI_{50}$ | 39-S | 4.84E-09 | 3.94E-09 | 3.44E-09 | 8.02E-09 | 2.78E-09 | 4.81E-10 |
| TGI | | 8.27E-09 | 6.74E-09 | 7.13E-09 | 1.02E-08 | | |
| $LC_{50}$ | | 1.65E-08 | >1.27E-07 | 1.78E-08 | 1.27E-08 | | |
| $GI_{50}$ | 47-S | 1.40E-08 | 4.33E-09 | 6.24E-09 | 5.99E-09 | | |
| TGI | | 2.80E-08 | 6.75E-09 | 9.68E-09 | 8.54E-09 | | |
| $LC_{50}$ | | >1.27E-07 | >1.27E-07 | 1.66E-08 | 1.27E-08 | | |

TABLE 6

Biological (Molar) activity
Compound

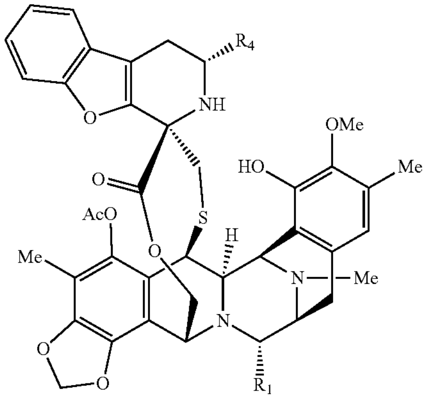

38-R $R_1$ = CN, $R_4$ = —$CH_2OH$
45-R $R_1$ = CN, $R_4$ = —$CH_2NHAlloc$

TABLE 6-continued

46-R $R_1$ = CN, $R_4$ = —$CH_2NH_2$
39-R $R_1$ = OH, $R_4$ = —$CH_2OH$
47-R $R_1$ = OH, $R_4$ = —$CH_2NH_2$

| | | A549 | HT29 | MDA-MB-231 | PSN1 |
|---|---|---|---|---|---|
| $GI_{50}$ | 38-R | 6.54E-10 | 5.41E-10 | 4.53E-10 | 6.54E-10 |
| TGI | | 1.04E-09 | 5.91E-10 | 8.43E-10 | 9.94E-10 |
| $LC_{50}$ | | >1.26E-07 | >1.26E-07 | 2.01E-09 | 1.76E-09 |
| $GI_{50}$ | 45-R | 1.82E-08 | 1.25E-08 | 9.57E-09 | 1.06E-08 |
| TGI | | 1.94E-08 | 2.28E-08 | 1.94E-08 | 1.94E-08 |
| $LC_{50}$ | | 2.39E-08 | >1.14E-07 | 4.33E-08 | 3.76E-08 |
| $GI_{50}$ | 46-R | 1.51E-09 | 1.21E-09 | 1.23E-09 | 9.95E-10 |
| TGI | | 2.77E-09 | 1.39E-09 | 1.39E-09 | 1.51E-09 |
| $LC_{50}$ | | >1.26E-07 | >1.26E-07 | 1.51E-09 | 2.65E-09 |
| $GI_{50}$ | 39-R | 2.67E-10 | 2.93E-10 | 2.04E-10 | 3.65E-10 |
| TGI | | 4.33E-10 | 6.24E-10 | 5.98E-10 | 5.73E-10 |
| $LC_{50}$ | | >1.27E-07 | >1.27E-07 | 2.80E-09 | 1.06E-09 |
| $GI_{50}$ | 47-R | 2.04E-09 | 8.03E-10 | 5.99E-10 | 1.40E-09 |
| TGI | | 3.82E-09 | 1.40E-09 | 1.17E-09 | 2.04E-09 |
| $LC_{50}$ | | 1.40E-08 | >1.27E-07 | 2.55E-09 | 3.31E-09 |

TABLE 7

Biological activity (Molar)
Compound

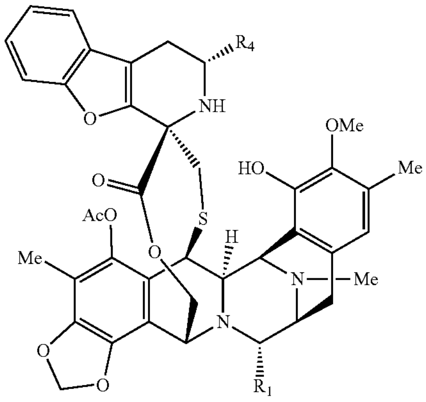

18-S $R_1$ = CN, $R_4$ = —$CH_2OH$
25-S $R_1$ = CN, $R_4$ = —$CH_2NHAlloc$
26-S $R_1$ = CN, $R_4$ = —$CH_2NH_2$
19-S $R_1$ = OH, $R_4$ = —$CH_2OH$
27-S $R_1$ = OH, $R_4$ = —$CH_2NH_2$

| | | A549 | HT29 | MDA-MB-231 | PSN1 |
|---|---|---|---|---|---|
| $GI_{50}$ | 18-S | 1.70E-09 | 1.21E-09 | 1.21E-09 | 9.59E-10 |
| TGI | | 3.03E-09 | 1.34E-09 | 1.34E-09 | 1.34E-09 |
| $LC_{50}$ | | >1.21E-07 | >1.21E-07 | 1.58E-09 | >1.21E-07 |
| $GI_{50}$ | 25-S | 7.17E-09 | 7.17E-09 | 5.84E-09 | 6.84E-09 |
| TGI | | 7.61E-09 | 7.72E-09 | 9.04E-09 | 9.26E-09 |
| $LC_{50}$ | | >1.10E-07 | >1.10E-07 | 1.54E-08 | 1.43E-08 |
| $GI_{50}$ | 26-S | 1.12E-08 | 2.79E-09 | 1.34E-09 | 3.04E-09 |
| TGI | | 2.19E-08 | 3.16E-09 | 1.94E-09 | 3.28E-09 |
| $LC_{50}$ | | >1.22E-07 | >1.22E-07 | 3.89E-09 | 3.52E-09 |
| $GI_{50}$ | 19-S | 3.07E-09 | 1.35E-09 | 1.96E-09 | 2.95E-09 |
| TGI | | 3.31E-09 | 1.60E-09 | 3.31E-09 | 3.19E-09 |
| $LC_{50}$ | | >1.23E-07 | >1.23E-07 | 1.10E-08 | >1.23E-07 |
| $GI_{50}$ | 27-S | 6.02E-09 | 1.23E-09 | 1.19E-09 | 1.97E-09 |
| TGI | | 1.12E-08 | 1.35E-09 | 1.23E-09 | 2.83E-09 |
| $LC_{50}$ | | >1.23E-07 | >1.23E-07 | 1.35E-09 | 4.55E-09 |

TABLE 8

Biological activity (Molar)
Compound

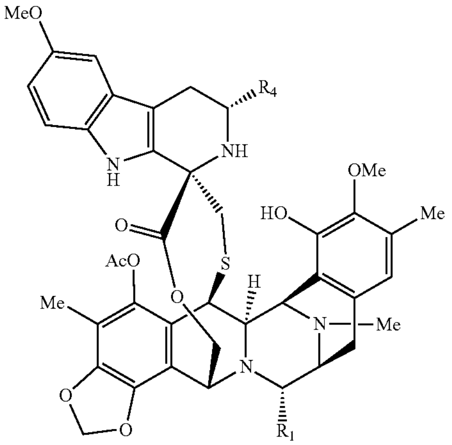

18-R $R_1$ = CN, $R_4$ = —$CH_2OH$
25-R $R_1$ = CN, $R_4$ = —$CH_2NHAlloc$
26-R $R_1$ = CN, $R_4$ = —$CH_2NH_2$ TABLE 8-continued

19-R $R_1$ = OH, $R_4$ = —$CH_2OH$
27-R $R_1$ = OH, $R_4$ = —$CH_2NH_2$

| | | A549 | HT29 | MDA-MB-231 | PSN1 |
|---|---|---|---|---|---|
| $GI_{50}$ | 18-R | 1.21E-09 | 1.21E-09 | 1.21E-09 | 5.70E-10 |
| TGI | | 1.34E-09 | 1.34E-09 | 1.34E-09 | 1.06E-09 |
| $LC_{50}$ | | >1.21E-07 | >1.21E-07 | 1.46E-09 | >1.21E-07 |
| $GI_{50}$ | 25-R | 1.32E-09 | 1.54E-09 | 1.21E-09 | 1.21E-09 |
| TGI | | 2.43E-09 | 2.76E-09 | 2.54E-09 | 2.32E-09 |
| $LC_{50}$ | | 9.92E-09 | >1.10E-07 | 8.38E-09 | 6.73E-09 |
| $GI_{50}$ | 26-R | 1.94E-09 | 7.29E-10 | 1.17E-09 | 9.72E-10 |
| TGI | | 3.40E-09 | 1.58E-09 | 1.22E-09 | 1.70E-09 |
| $LC_{50}$ | | >1.22E-07 | >1.22E-07 | 1.46E-09 | 3.52E-09 |
| $GI_{50}$ | 19-R | 1.47E-09 | 1.72E-09 | 1.23E-09 | 1.23E-09 |
| TGI | | 3.56E-09 | 1.72E-09 | 1.35E-09 | 1.35E-09 |
| $LC_{50}$ | | >1.23E-07 | >1.23E-07 | 1.23E-07 | 1.47E-09 |
| $GI_{50}$ | 27-R | 2.09E-09 | 5.04E-10 | 3.07E-10 | 6.39E-10 |
| TGI | | 3.93E-09 | 5.53E-10 | 5.41E-10 | 1.17E-09 |
| $LC_{50}$ | | 1.01E-08 | >1.23E-07 | 8.60E-10 | 2.46E-09 |

TABLE 9

Biological activity (Molar)
Compound

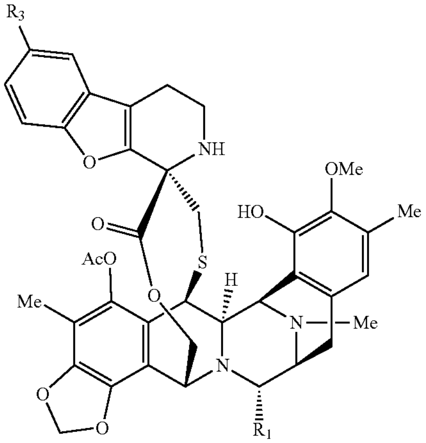

31 $R_1$ = CN, $R_3$ = H
32 $R_1$ = OH, $R_3$ = H
34 $R_1$ = CN, $R_3$ = OMe
35 $R_1$ = OH, $R_3$ = OMe

| | | A549 | HT29 | MDA-MB-231 | PSN1 |
|---|---|---|---|---|---|
| $GI_{50}$ | 31 | 1.96E-08 | 1.05E-08 | 8.89E-09 | 6.80E-09 |
| TGI | | 2.09E-08 | 1.57E-08 | 1.70E-08 | 1.57E-08 |
| $LC_{50}$ | | 2.35E-08 | >1.31E-07 | 3.53E-08 | 4.31E-08 |
| $GI_{50}$ | 32 | 6.88E-09 | 6.88E-09 | 4.76E-09 | 6.09E-09 |
| TGI | | >1.32E-08 | >1.32E-08 | 1.05E-08 | 8.34E-09 |
| $LC_{50}$ | | >1.32E-08 | >1.32E-08 | >1.32E-08 | 1.20E-08 |
| $GI_{50}$ | 34 | 5.91E-08 | 5.41E-08 | 4.53E-08 | 5.41E-08 |
| TGI | | 8.05E-08 | 8.55E-08 | 7.67E-08 | 5.91E-08 |
| $LC_{50}$ | | >1.26E-07 | 1.25E-07 | 1.12E-07 | >1.26E-07 |
| $GI_{50}$ | 35 | 8.14E-09 | 7.89E-09 | 4.58E-09 | 6.24E-09 |

TABLE 9-continued

| | | | | |
|---|---|---|---|---|
| TGI | 8.78E-09 | 8.65E-09 | 8.27E-09 | 9.03E-09 |
| $LC_{50}$ | >1.27E-07 | >1.27E-07 | 1.65E-08 | 1.40E-08 |

This data demonstrates that the payloads employed in the present invention have high potency in vitro.

Synthesis of Linkers

Preparation of LIN 1: MC-Val-Cit-PABC-PNP

Reaction Scheme

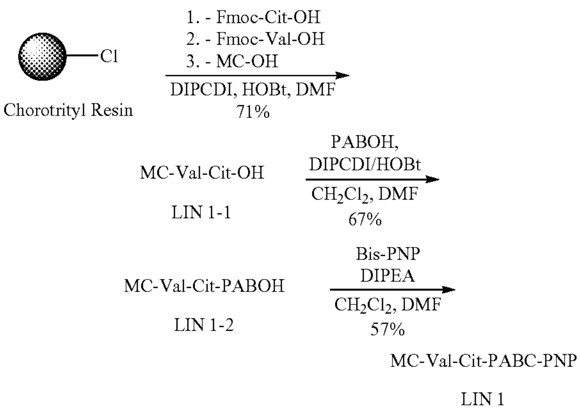

(a) Preparation of LIN 1-1: MC-Val-Cit-OH

LIN 1-1

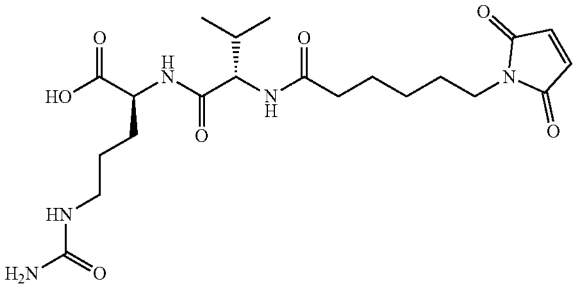

Cl-TrtCl-resin (20 g, 1.49 mmol/g) (Iris Biotech, Ref.: BR-1065, 2-Chlorotrityl chloride resin (200-400 mesh, 1% DVB, 1.0-1.6 mmol/g), CAS 42074-68-0) was placed in a filter plate. 100 mL of DCM was added to the resin and the mixture was stirred for 1 h. The solvent was eliminated by filtration under vacuum. A solution of Fmoc-Cit-OH (11.83 g, 29.78 mmol) and DIPEA (17.15 mL, 98.45 mmol) in DCM (80 mL) was added and the mixture was stirred for 10 min. After that DIPEA (34.82 mmol, 199.98 mmol) was added and the mixture was stirred for 1 h. The reaction was terminated by addition of MeOH (30 mL) after stirring for 15 minutes. The Fmoc-Cit-O-TrtCl-resin produced as a result was subjected to the following washing/treatments: DCM (5×50 mL×0.5 min), DMF (5×50 mL×0.5 min), piperidine:DMF (1:4, 1×1 min, 2×10 min), DMF (5×50 mL×0.5 min), DCM (5×50 mL×0.5 min). The final piperidine wash gave $NH_2$—Cit-O-TrtCl-resin. The loading was calculated: 1.15 mmol/g.

The $NH_2$-Cit-O-TrtCl-resin produced above was washed with DMF (5×50 mL×0.5 min) and a solution of Fmoc-Val-OH (31.22 g, 91.98 mmol), HOBt (11.23 g, 91.98 mmol) in DMF (100 mL) was added to the $NH_2$-Cit-O-TrtCl-resin, stirred and DIPCDI (14.24 mL, 91.98 mmol) was added and the mixture was stirred for 1.5 h. The reaction was terminated by washing with DMF (5×50 mL×0.5 min). The Fmoc-Val-Cit-O-TrtCl-resin thus produced was treated with piperidine:DMF (1:4, 1×1 min, 2×10 min) and washed with DMF (5×50 mL×0.5 min). The final piperidine wash gave $NH_2$—Val-Cit-O-TrtCl-resin.

A solution of 6-maleimidocaproic acid (MC-OH) (9.7 g, 45.92 mmol), HOBt (6.21 g, 45.92 mmol) in DMF (100 mL) was added to the $NH_2$-Val-Cit-O-TrtCl-resin produced above, stirred and DIPCDI (7.12 mL, 45.92 mmol) was added and the mixture was stirred for 1.5 h. The reaction was terminated by washing with DMF (5×50 mL×0.5 min) and DCM (5×50 mL×0.5 min).

The peptide was cleaved from the resin by treatments with TFA:DCM (1:99, 5×100 mL). The resin was washed with DCM (7×50 mL×0.5 min). The combined filtrates were evaporated to dryness under reduced pressure and the solid obtained was triturated with $Et_2O$ and filtrated to obtain LIN 1-1 (7.60 g, 71%) as a white solid.

$^1H$ NMR (500 MHz, DMSO-$d_6$): δ 12.47 (s, 1H), 8.13 (d, J=7.3 Hz, 1H), 7.74 (d, J=9.0 Hz, 1H), 6.99 (s, 2H), 5.93 (s, 1H), 5.35 (s, 2H), 4.20 (dd, J=9.0, 6.8 Hz, 1H), 4.15-4.07 (m, 1H), 3.36 (t, J=7.0 Hz, 2H), 3.00-2.88 (m, 2H), 2.21-2.12 (m, 1H), 2.11-2.03 (m, 1H), 1.98-1.86 (m, 1H), 1.74-1.62 (m, 1H), 1.61-1.50 (m, 1H), 1.50-1.31 (m, 6H), 1.21-1.11 (m, 2H), 0.84 (d, J=6.8 Hz, 3H), 0.80 (d, J=6.8 Hz, 3H).

ESI-MS m/z: Calcd. for $C_{21}H_{33}N_5O_7$: 467.2. Found: 468.3 $(M+H)^+$.

(b) Preparation of LIN 1-2: MC-Val-Cit-PABOH

LIN 1-2

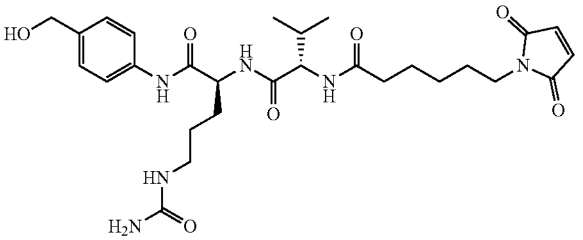

To a solution of LIN 1-1 (1.6 g, 3.42 mmol) and 4-aminobenzyl alcohol (PABOH) (0.84 g, 6.84 mmol) in DCM (60 mL) was added a solution of HOBt (0.92 g, 6.84 mmol) in DMF (5 mL). DIPCDI (1.05 mL, 6.84 mmol) was added, the reaction mixture was stirred for 2 h at 23° C., $Et_2O$ (150 mL) was added, and the solid obtained was filtrated in a filter plate under vacuum to obtain LIN 1-2 (1.31 g, 67%).

$^1H$ NMR (500 MHz, DMSO-$d_6$): δ 9.88 (s, 1H), 8.03 (d, J=7.6 Hz, 1H), 7.77 (dd, J=12.2, 8.5 Hz, 1H), 7.53 (d, J=8.2 Hz, 2H), 7.21 (d, J=8.2 Hz, 2H), 6.99 (s, 3H), 6.01-5.92 (m, 1H), 5.39 (s, 2H), 5.07 (s, 1H), 4.41 (s, 2H), 4.39-4.31 (m, 1H), 4.23-4.12 (m, 1H), 3.36 (t, J=7.0 Hz, 2H), 3.06-2.97 (m, 1H), 2.96-2.90 (m, 1H), 2.22-2.03 (m, 2H), 2.01-1.88 (m, 1H), 1.76-1.62 (m, 1H), 1.63-1.28 (m, 6H), 1.25-1.11 (m, 2H), 0.84 (d, J=6.9 Hz, 3H), 0.81 (d, J=6.8 Hz, 3H).

ESI-MS m/z: Calcd. for $C_{28}H_{40}N_6O_7$: 572.3. Found: 573.3 $(M+H)^+$.

(c) Preparation of LIN 1: MC-Val-Cit-PAB-PNP

LIN 1

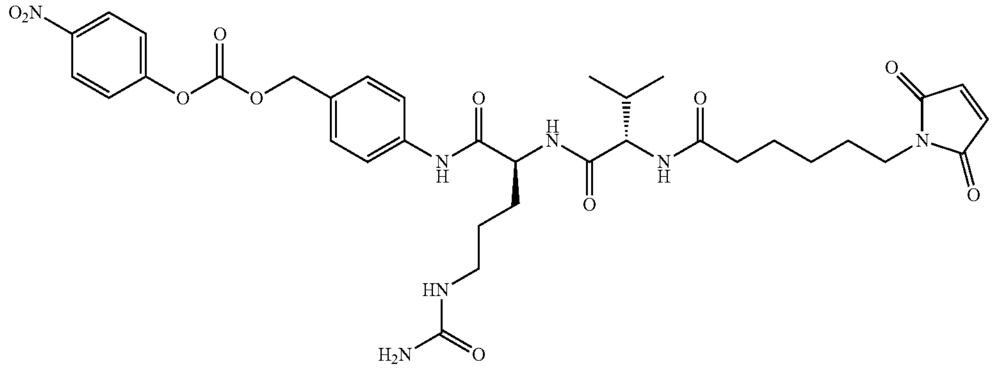

To a solution of LIN 1-2 (500 mg, 0.87 mmol) and bis(4-nitrophenyl) carbonate (bis-PNP) (2.64 g, 8.72 mmol) in DCM:DMF (8:2, 25 mL) was added DIPEA (0.45 mL, 2.61 mmol). The reaction mixture was stirred for 20 h at 23° C. and poured onto a silica gel column (DCM:$CH_3OH$, from 50:1 to 10:1) to afford pure target LIN 1 (364 mg, 57%).

$R_f$=0.40 ($CH_2Cl_2$:$CH_3OH$, 9:1).

$^1$H NMR (400 MHz, $CDCl_3$/$CD_3OD$): δ 9.45 (s, 1H), 8.23 (d, J=8.3 Hz, 2H), 7.59 (d, J=8.5 Hz, 2H), 7.35 (d, J=8.3 Hz, 2H), 7.34 (d, J=8.5 Hz, 2H), 6.65 (s, 2H), 5.20 (s, 2H), 4.56 (dt, J=10.5, 5.4 Hz, 1H), 4.15 (d, J=7.2 Hz, 1H), 3.46 (dd, J=8.0, 6.4 Hz, 2H), 3.16-2.89 (m, 2H), 2.21 (dd, J=8.3, 6.6 Hz, 2H), 2.06-1.97 (m, 1H), 1.90-1.83 (m, 1H), 1.73-1.46 (m, 7H), 1.34-1.20 (m, 2H), 0.91 (d, J=6.7 Hz, 3H), 0.90 (d, J=6.7 Hz, 3H).

$^{13}$C NMR (125 MHz, $CDCl_3$/$CD_3OD$) δ 174.4, 172.4, 171.1, 170.6, 160.5, 155.5, 152.5, 145.3, 138.7, 134.1, 129.9, 129.5, 125.2, 121.8, 120.0, 70.6, 59.0, 53.2, 37.5, 35.8, 30.6, 29.6, 29.3, 28.1, 26.2, 26.2, 25.1, 19.1, 18.1.

ESI-MS m/z: Calcd. for $C_{35}H_{43}N_7O_{11}$: 737.3. Found: 738.3 $(M+H)^+$.

Preparation of LIN-2: MC2-PEG4-Val-Cit-PABC-PNP

Rection Scheme

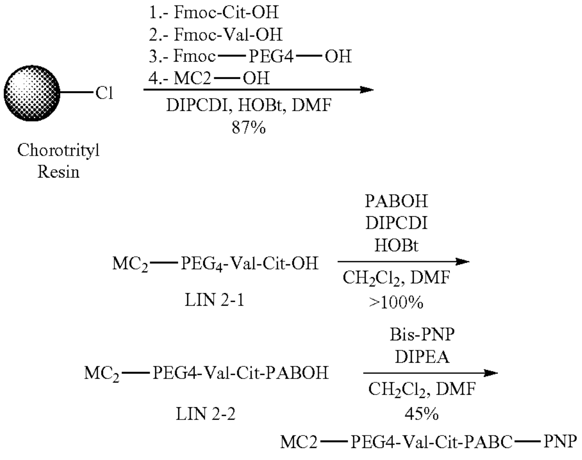

a) Preparation of LIN 2-1: MC2-PEG4-Val-Cit-OH

LIN 2-1

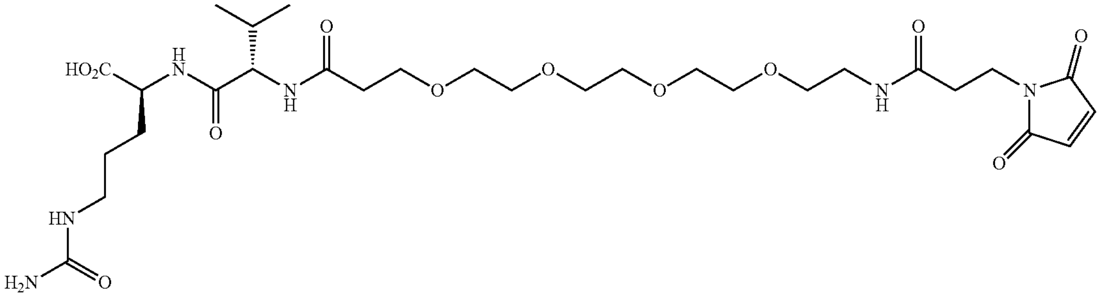

Cl-TrtCl-resin (5 g, 1.49 mmol/g) was placed in a filter plate. To the resin was added $CH_2Cl_2$ (25 mL) and the mixture was stirred for 1 h at 23° C. The solvent was eliminated by filtration over vacuum. A solution of Fmoc-Cit-OH (2.95 g, 7.44 mmol) and DIPEA (4.29 mL, 24.61 mmol) in $CH_2Cl_2$ (20 mL) was added and the mixture was stirred for 10 min at 23° C. DIPEA (8.70 mL, 49.99 mmol) was additionally added and the mixture was stirred for 1 h at 23° C. The reaction was stopped by addition of MeOH (10 mL) and stirred 15 min at 23° C. The Fmoc-Cit-O-TrtCl-resin was subjected to the following washing/treatments: $CH_2Cl_2$ (5×15 mL×0.5 min), DMF (5×15 mL×0.5 min), piperidine:DMF (1:4, 15 mL, 1×1 min, 2×10 min), DMF (5×15 mL×0.5 min), $CH_2Cl_2$ (5×15 mL×0.5 min). The loading was calculated: 1.17 mmol/g.

The $NH_2$—Cit-O-TrtCl-resin was washed with DMF (5×15 mL×0.5 min) and a solution of Fmoc-Val-OH (7.80 g, 22.99 mmol) and HOBt (2.80 g, 24.5 mmol) in DMF (25 mL) was added to the $NH_2$-Cit-O-TrtCl-resin followed by addition of DIPCDI (3.56 mL, 24.5 mmol) at 23° C. The reaction mixture was stirred for 1.5 h at 23° C. The reaction was stopped by washing with DMF (5×15 mL×0.5 min). The Fmoc-Val-Cit-O-TrtCl-resin was treated with piperidine: DMF (1:4, 15 mL, 1×1 min, 2×10 min) and washed with DMF (5×15 mL×0.5 min).

A solution of 15-(9-Fluorenylmethyloxycarbonyl)amino-4,7,10,13-tetraoxa-pentadecanoic acid (Fmoc-NH-PEG4-OH) (4.27 g, 8.75 mmol) and HOBt (1.18 g, 8.72 mmol) in DMF (30 mL) was added to the $NH_2$-Val-Cit-O-TrtCl-resin followed by addition of DIPCDI (1.35 mL, 8.72 mmol) at 23° C. The reaction mixture was stirred for 24 h at 23° C. The reaction was stopped by washing with DMF (5×15 mL×0.5 min). The Fmoc-NH-PEG4-Val-Cit-O-TrtCl-resin was treated with piperidine:DMF (1:4, 15 mL, 1×1 min, 2×10 min) and washed with DMF (5×15 mL×0.5 min).

A solution of 3-(Maleimido)propionic acid (MC2-OH) (3.95 g, 23.35 mmol) and HOBt (3.16 g, 23.37 mmol) in DMF (30 mL) was added to the $NH_2$-PEG4-Val-Cit-O-TrtCl-resin followed by addition of DIPCDI (3.62 mL, 23.37 mmol) at 23° C. The reaction mixture was stirred for 2 h at 23° C. The reaction was stopped by washing with DMF (5×15 mL×0.5 min) and $CH_2Cl_2$ (5×15 mL×0.5 min).

The peptide was cleaved from the resin by treatments with TFA:$CH_2Cl_2$ (1:99, 5×50 mL). The resin was washed with $CH_2Cl_2$ (7×50 mL×0.5 min). The combined filtrates were evaporated to dryness under reduced pressure, the solid obtained was triturated with $Et_2O$ and filtrated to obtain LIN 2-1 (4.59 g, 87% yield) as a white solid.

$^1H$ NMR (300 MHz, $CDCl_3$): δ 7.67-7.57 (m, 1H), 7.44 (d, J=8.3 Hz, 1H), 7.11 (t, J=5.4 Hz, 1H), 6.73 (s, 2H), 4.49 (d, J=7.2 Hz, 1H), 4.35 (t, J=7.7 Hz, 1H), 3.82 (t, J=7.0 Hz, 2H), 3.74 (t, J=6.2 Hz, 2H), 3.68-3.56 (m, 13H), 3.56-3.45 (m, 2H), 3.39 (q, J=5.4 Hz, 2H), 3.17 (s, 2H), 2.55 (q, J=7.0, 6.0 Hz, 4H), 2.16-1.99 (m, 1H), 1.91 (s, 1H), 1.75 (s, 1H), 1.43 (s, 2H), 0.94 (d, =9.7 Hz, 3H), 0.93 (d, =9.7 Hz, 3H).

ESI-MS m/z: 673.3 $(M+H)^+$.

(b) Preparation of LIN 2-2: MC2-PEG4-Val-Cit-PABOH

LIN 2-2

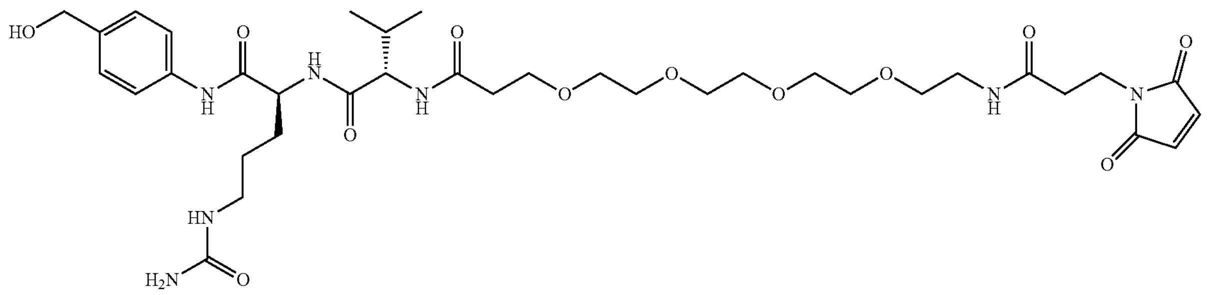

To a solution of LIN 2-1 (1.5 g, 2.22 mmol) and 4-aminobenzyl alcohol (PABOH) (0.55 g, 4.45 mmol) in $CH_2Cl_2$ (60 mL) was added a solution of HOBt (0.60 g, 4.45 mmol) in DMF (5 mL) followed by addition of DIPCDI (0.69 mL, 4.45 mmol) at 23° C. The reaction mixture was stirred for 5 h at 23° C., $Et_2O$ (150 mL) was added, and the solid obtained was filtrated under vacuum to obtain crude LIN 2-2 (2.37 g, >100% yield) which was used in the next step without further purification.

$^1H$ NMR (500 MHz, DMSO-$d_6$): δ 7.57 (d, J=8.6 Hz, 2H), 7.30 (d, J=8.6 Hz, 2H), 6.81 (s, 2H), 4.58 (s, 1H), 4.56 (s, 2H), 4.50 (dd, J=9.1, 5.1 Hz, 1H), 4.21 (d, J=7.0 Hz, 1H), 3.80-3.68 (m, 4H), 3.65-3.59 (m, 12H), 3.55-3.47 (m, 1H), 3.20 (dd, J=13.6, 6.9 Hz, 1H), 3.12 (dt, J=13.5, 6.7 Hz, 1H), 2.55 (td, J=6.1, 2.1 Hz, 2H), 2.46 (t, J=6.9 Hz, 2H), 2.15-2.07 (m, 1H), 1.95-1.88 (m, 1H), 1.79-1.70 (m, 1H), 1.67-1.50 (m, 2H), 0.99 (d, J=7.0 Hz, 3H), 0.98 (d, J=7.0 Hz, 3H).

ESI-MS m/z: 778.4 $(M+H)^+$.

(c) Preparation of LIN 2: MC2-PEG4-Val-Cit-PABC-PNP

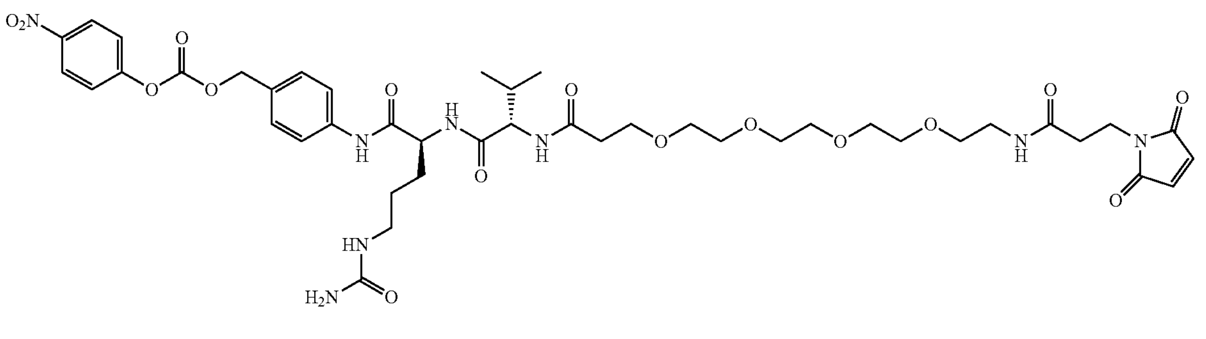 [SMILES: CC(C)[C@H](NC(=O)CCOCCOCCOCCOCCNC(=O)CCN1C(=O)C=CC1=O)C(=O)N[C@@H](CCCNC(N)=O)C(=O)Nc1ccc(COC(=O)Oc2ccc([N+](=O)[O-])cc2)cc1]

To a solution of LIN 2-2 (1.73 g, 2.22 mmol) and bis(4-nitrophenyl) carbonate (bis-PNP) (3.38 g, 11.12 mmol) in DCM:DMF (8:2, 75 mL) was added DIPEA (1.16 mL, 6.07 mmol) at 23° C. The reaction mixture was stirred for 19 h at 23° C. and poured onto silica gel column ($CH_2Cl_2$:$CH_3OH$, from 50:1 to 10:1) to afford pure LIN 2 (945 mg, 45% yield).

$^1$H NMR (500 MHz, $CD_3OD$): δ 8.22 (d, J=9.2 Hz, 2H), 7.61 (d, J=8.6 Hz, 2H), 7.34 (d, J=9.2 Hz, 2H), 7.33 (d, J=8.6 Hz, 2H), 6.67 (s, 2H), 4.57-4.47 (m, 1H), 4.23-4.12 (m, 1H), 3.78-3.76 (m, 12H), 3.63-3.50 (m, 16H), 3.49-3.41 (m, 2H), 3.34-3.25 (m, 2H), 3.18-3.03 (m, 2H), 2.51 (t, J=5.9 Hz, 2H), 2.45 (t, J=7.2 Hz, 2H), 2.13-1.99 (m, 1H), 1.92-1.84 (m, 1H), 1.73-1.62 (m, 1H), 1.55-1.45 (m, 2H), 0.92 (d, J=6.8 Hz, 3H), 0.90 (d, J=6.8 Hz, 3H).

$^{13}$C NMR (75 MHz, $CDCl_3$/$CD_3OD$): δ 174.4, 172.9, 172.4, 172.4, 171.6, 170.9, 170.8, 170.7, 163.7, 155.8, 155.7, 152.5, 145.4, 138.8, 134.1, 131.3, 130.4, 129.2, 128.7, 125.7, 124.9, 121.8, 119.8 (×2), 115.1, 70.2 (×2), 70.1 (×2), 70.0, 69.9, 69.8, 69.0, 66.9, 59.2, 53.5, 39.0, 36.0, 34.4, 34.1, 30.4, 29.0, 18.5, 17.5.

ESI-MS m/z: 943.4 $(M+H)^+$.

$R_f$=0.20 ($CH_2Cl_2$:$CH_3OH$, 9:1).

Preparation of LIN 3: MC2-PEG4-Val-Ala-PABC-PNP

Reaction Scheme

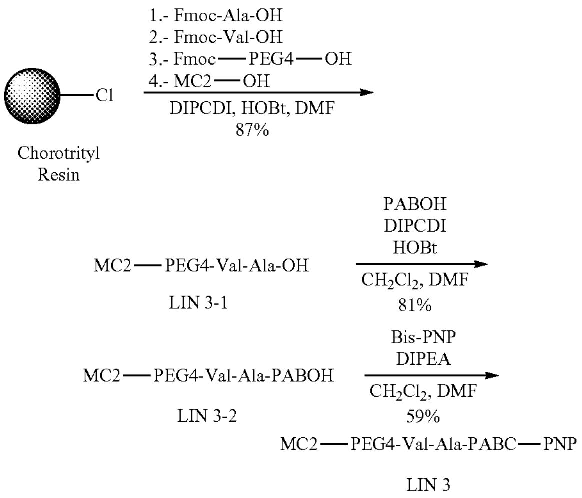

(a) Preparation of LIN 3-1: MC2-PEG4-Val-Ala-OH

LIN 3-1

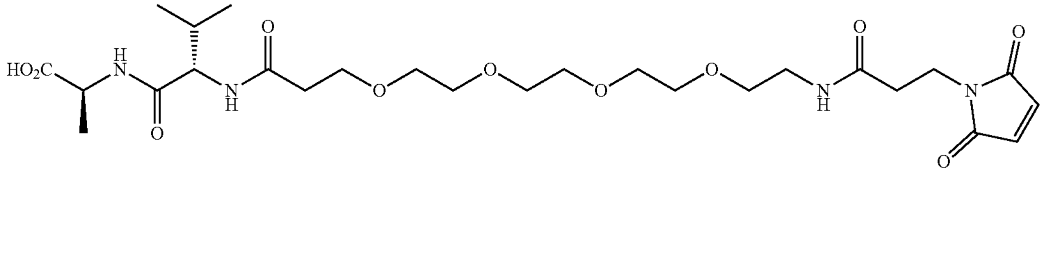

Cl-TrtCl-resin (5 g, 1.49 mmol/g) was placed in a filter plate. To the resin was added $CH_2Cl_2$ (25 mL) and the mixture was stirred for 1 h at 23° C. The solvent was eliminated by filtration over vacuum. A solution of Fmoc-Ala-OH (2.31 g, 7.41 mmol) and DIPEA (4.28 mL, 24.61 mmol) in $CH_2Cl_2$ (20 mL) was added and the mixture was stirred for 10 min at 23° C. DIPEA (8.60 mL, 49.37 mmol) was additionally added and the reaction mixture was stirred for 1 h at 23° C. The reaction was stopped by addition of MeOH (10 mL) and stirred 15 min at 23° C. The Fmoc-Ala-O-TrtCl-resin was subjected to the following washing/treatments: $CH_2Cl_2$ (5×15 mL×0.5 min), DMF (5×15 mL×0.5 min), piperidine:DMF (1:4, 15 mL, 1×1 min, 2×10 min), DMF (5×15 mL×0.5 min), $CH_2Cl_2$ (5×15 mL×0.5 min). The loading was calculated: 1.34 mmol/g.

The $NH_2$-Ala-O-TrtCl-resin was washed with DMF (5×15 mL×0.5 min) and a solution of Fmoc-Val-OH (9.09 g, 26.79 mmol) and HOBt (3.62 g, 26.79 mmol) in DMF (25 mL) was added to the $NH_2$-Ala-O-TrtCl-resin followed by addition DIPCDI (4.14 mL, 26.79 mmol) at 23° C. The mixture was stirred for 1.5 h at 23° C. The reaction was stopped by washing with DMF (5×15 mL×0.5 min). The Fmoc-Val-Ala-O-TrtCl-resin was treated with piperidine: DMF (1:4, 15 mL, 1×1 min, 2×10 min) and washed with DMF (5×15 mL×0.5 min).

A solution of 15-(9-Fluorenylmethyloxycarbonyl)amino-4,7,10,13-tetraoxa-pentadecanoic acid (Fmoc-NH-PEG4-OH) (4.90 g, 8.75 mmol) and HOBt (1.35 g, 9.98 mmol) in DMF (30 mL) was added to the $NH_2$-Val-Ala-O-TrtCl-resin followed by addition DIPCDI (1.55 mL, 10.0 mmol) at 23° C. The reaction mixture was stirred for 22 h at 23° C. The reaction was stopped by washing with DMF (5×15 mL×0.5 min). The Fmoc-NH-PEG4-Val-Ala-O-TrtCl-resin was treated with piperidine:DMF (1:4, 15 mL, 1×1 min, 2×10 min) and washed with DMF (5×15 mL×0.5 min).

A solution of 3-(Maleimido)propionic acid (MC2-OH) (4.53 g, 26.78 mmol) and HOBt (3.62 g, 26.77 mmol) in DMF (30 mL) was added to the $NH_2$-PEG4-Val-Ala-O-TrtCl-resin followed by addition of DIPCDI (4.15 mL, 26.80 mmol) at 23° C. The reaction mixture was stirred for 2 h at 23° C. The reaction was stopped by washing with DMF (5×15 mL×0.5 min) and $CH_2Cl_2$ (5×15 mL×0.5 min).

The peptide was cleaved from the resin by treatments with TFA:$CH_2Cl_2$ (1:99, 5×50 mL). The resin was washed with $CH_2Cl_2$ (7×50 mL×0.5 min). The combined filtrates were evaporated to dryness under reduced pressure, the solid obtained was triturated with $Et_2O$ and filtrated to obtain L 3-1 (4.73 g, 87% yield) as a white solid.

$^1H$ NMR (500 MHz, $CDCl_3$): δ 7.67 (bs, 1H), 7.31 (d, J=8.9 Hz, 1H), 7.17 (d, J=7.0 Hz, 1H), 6.85 (t, J=5.6 Hz, 1H), 6.72 (s, 2H), 4.51 (q, J=7.1 Hz, 1H), 4.38 (dd, J=8.9, 6.9 Hz, 1H), 3.84 (t, J=7.1 Hz, 2H), 3.75 (t, J=5.9 Hz, 2H), 3.69-3.59 (m, 12H), 3.55 (t, J=5.1 Hz, 2H), 3.41 (qd, J=5.0, 1.7 Hz, 2H), 2.62-2.49 (m, 4H), 2.19-2.01 (m, 1H), 1.44 (d, J=7.2 Hz, 3H), 0.95 (d, J=11.9 Hz, 1H), 0.94 (d, J=11.9 Hz, 1H).

(b) Preparation of LIN 3-2: MC2-PEG4-Val-Ala-PABOH

LIN 3-2

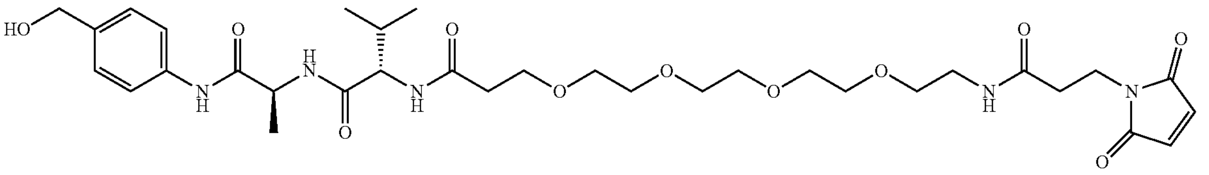

To a solution of LIN 3-1 (1.84 g, 3.13 mmol) and 4-aminobenzyl alcohol (PABOH) (0.77 g, 6.27 mmol) in $CH_2Cl_2$ (70 mL) was added a solution of HOBt (0.84 g, 6.27 mmol) in DMF (5 mL) followed by addition of DIPCDI (0.97 mL, 6.27 mmol) at 23° C. The reaction mixture was stirred for 5 h at 23° C., $Et_2O$ (150 mL) was added, and the solid obtained was filtrated under vacuum to obtain crude LIN 3-2 (1.74 g, 81% yield) which was used in the next step without further purification.

$^1H$ NMR (500 MHz, DMSO-$d_6$): δ 7.58 (d, J=8.5 Hz, 2H), 7.30 (d, J=8.5 Hz, 2H), 6.81 (s, 2H), 4.56 (s, 2H), 4.52-4.41 (m, 1H), 4.21 (d, J=6.7 Hz, 1H), 3.91 (p, J=6.5 Hz, 1H), 3.81-3.67 (m, 4H), 3.65-3.54 (m, 12H), 3.49 (t, J=5.5 Hz, 2H), 2.56 (dd, J=6.6, 5.5 Hz, 2H), 2.46 (t, J=6.9 Hz, 2H), 2.12 (h, J=6.8 Hz, 1H), 1.45 (d, J=7.2 Hz, 3H), 1.00 (d, J=12.1 Hz, 3H), 0.98 (d, J=12.1 Hz, 3H).

(c) Preparation of LIN 3: MC2-PEG4-Val-Ala-PABC-PNP

LIN 3

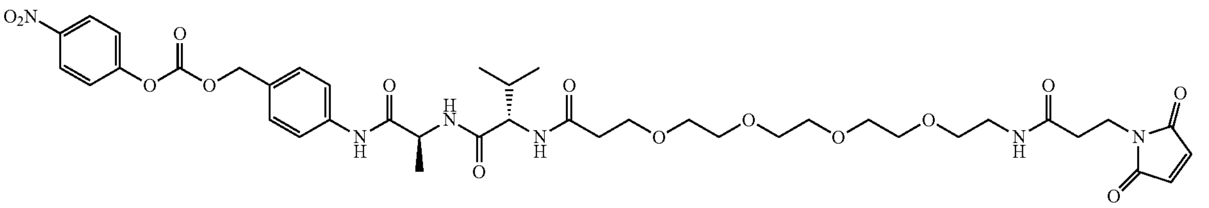

To a solution of LIN 3-2 (1.74 g, 2.51 mmol) and bis(4-nitrophenyl) carbonate (bis-PNP) (3.82 g, 12.57 mmol) in $CH_2Cl_2$:DMF (8:1, 70 mL) was added DIPEA (1.31 mL, 7.54 mmol) at 23° C. The reaction mixture was stirred for 20 h at 23° C. and poured onto silica gel column ($CH_2Cl_2$:$CH_3OH$, from 50:1 to 10:1) to afford pure LIN 3 (1.26 g, 59% yield).

$^1H$ NMR (500 MHz, $CDCl_3$): δ 8.82 (s, 1H), 8.27 (d, J=9.2 Hz, 2H), 7.73 (d, J=8.6 Hz, 2H), 7.38 (d, J=9.1 Hz, 4H), 7.15 (dd, J=21.8, 7.2 Hz, 2H), 6.69 (s, 2H), 6.62 (t, J=5.7 Hz, 1H), 5.24 (s, 2H), 4.67 (p, J=7.2 Hz, 1H), 4.24 (dd, J=6.8, 5.7 Hz, 1H), 3.91-3.76 (m, 2H), 3.71 (ddd, J=10.1, 6.1, 4.3 Hz, 1H), 3.66-3.54 (m, 14H), 3.53 (t, J=5.1 Hz, 1H), 3.46-3.33 (m, 2H), 2.76-2.57 (m, 1H), 2.57-2.42 (m, 2H), 2.33-2.19 (m, 1H), 1.46 (d, J=7.1 Hz, 3H), 1.01 (d, J=12.1 Hz, 3H), 1.00 (d, J=12.1 Hz, 3H).

$^{13}C$ NMR (75 MHz, $CD_3OD$): δ 173.0, 172.1, 171.6 (×2), 170.7, 163.8, 155.7, 152.5, 145.4, 140.3, 138.9, 134.1, 130.4, 129.1, 125.6, 124.8, 121.9, 119.7, 115.1, 70.2, 70.1 (×3), 70.0, 69.9, 69.8, 69.0, 66.9, 59.1, 53.4, 49.7, 39.0, 36.0, 34.3, 34.1, 30.4, 18.3, 17.3, 16.6.

ESI-MS m/z: 857.3 $(M+H)^+$.

$R_f$=0.45 ($CH_2Cl_2$:$CH_3OH$, 9:1).

Example 1: Synthesis of a Compounds of Formula D-X-$(AA)_w$-$(T)_g$-$L_1$

Preparation of Compound DL-1

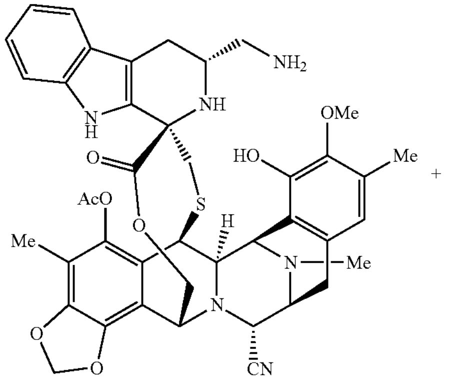

11-R

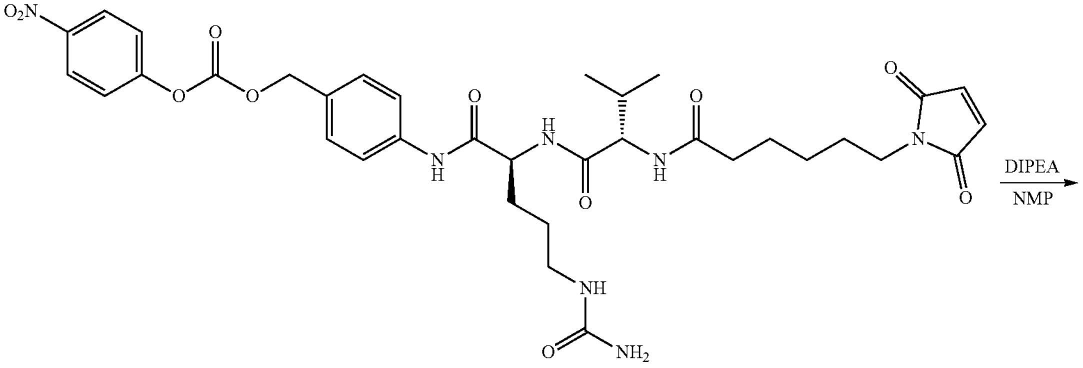

LIN 1

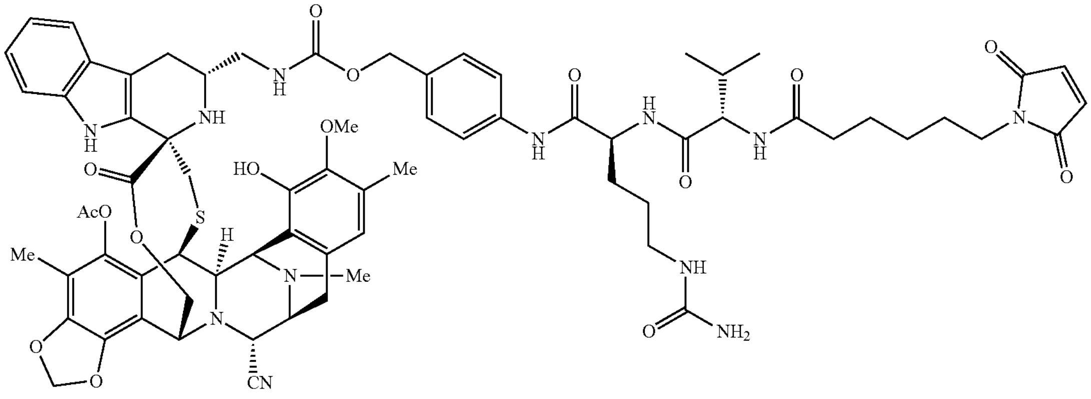

DL 1

To a solution of 11-R (100 mg, 0.12 mmol) and LIN 1 (465 mg, 0.63 mmol) in N-Methyl-2-pyrrolidone (NMP) (15 mL) was added N,N-diisopropylethylamine (DIPEA) (111 μL, 0.63 mmol) at 23° C. The reaction mixture was stirred for 3 days at 23° C., diluted with EtOAc (50 mL) and washed with $H_2O$ (4×30 mL) and a saturated aqueous solution of NaCl (30 mL). The combined organic layers were dried over anhydrous $Na_2SO_4$, filtered, and concentrated under vacuum. The residue was purified by flash chromatography on silica gel ($CH_2Cl_2$:$CH_3OH$, from 99:1 to 90:10) to obtain DL 1 which was purified by HPLC preparative to yield pure DL 1 (69 mg, 40% yield).

$^1H$ NMR (400 MHz, $CD_3OD/CDCl_3$): δ 7.85 (d, J=7.9 Hz, 1H), 7.59 (d, J=8.1 Hz, 2H), 7.36 (d, J=8.2 Hz, 2H), 7.30 (d, J=7.9 Hz, 1H), 7.22 (d, J=8.2 Hz, 1H), 7.01 (t, J=7.6 Hz, 1H), 6.91 (t, J=7.5 Hz, 1H), 6.72 (s, 2H), 6.58 (s, 1H), 6.26 (s, 1H), 6.07 (s, 1H), 5.25-5.14 (m, 2H), 5.14-5.01 (m, 2H), 4.67 (bs, 1H), 4.51 (d, J=6.7 Hz, 2H), 4.28 (dd, J=16.2, 7.1 Hz, 4H), 4.21-4.05 (m, 3H), 3.71 (s, 3H), 3.51-3.40 (m, 2H), 3.36-3.32 (m, 2H), 3.23-2.99 (m, 2H), 2.99-2.72 (m, 2H), 2.65 (d, J=14.9 Hz, 2H), 2.28 (s, •3H), 2.25 (s, •3H), 2.10 (s, •3H), 2.04 (s, •3H), 1.96-1.83 (m, 1H), 1.80-1.68 (m, 2H), 1.65-1.50 (m, 10H), 1.35-1.23 (m, 2H), 0.95 (d, J=6.8 Hz, 3H), 0.94 (d, J=6.8 Hz, 3H).

$^{13}C$ NMR (75 MHz, $CD_3OH/CDCl_3$): δ 174.9, 172.5, 171.5, 171.1, 170.7, 169.5, 160.8, 157.4, 148.6, 146.1, 143.6, 141.1, 140.9, 138.0, 136.8, 133.9, 132.6, 130.5, 129.8, 129.6, 128.6, 126.0, 121.6, 120.4, 119.8, 119.0, 118.6, 118.0, 117.8, 116.7, 113.5, 112.8, 110.9, 109.1, 102.3, 66.0, 63.1, 62.9, 61.6, 60.2, 59.9, 59.2, 59.1, 58.9, 54.6, 54.6, 53.5, 50.7, 45.3, 42.1, 40.5, 37.1, 35.3, 30.3, 29.1, 27.9, 26.3, 26.0, 25.0, 24.5, 23.6, 19.4, 18.6, 17.7, 15.1, 8.6.

ESI-MS m/z: 1391.4 $(M+H)^+$.

$R_f$=0.40 ($CH_2Cl_2$:$CH_3OH$, 9:1).

Preparation of Compound DL 2

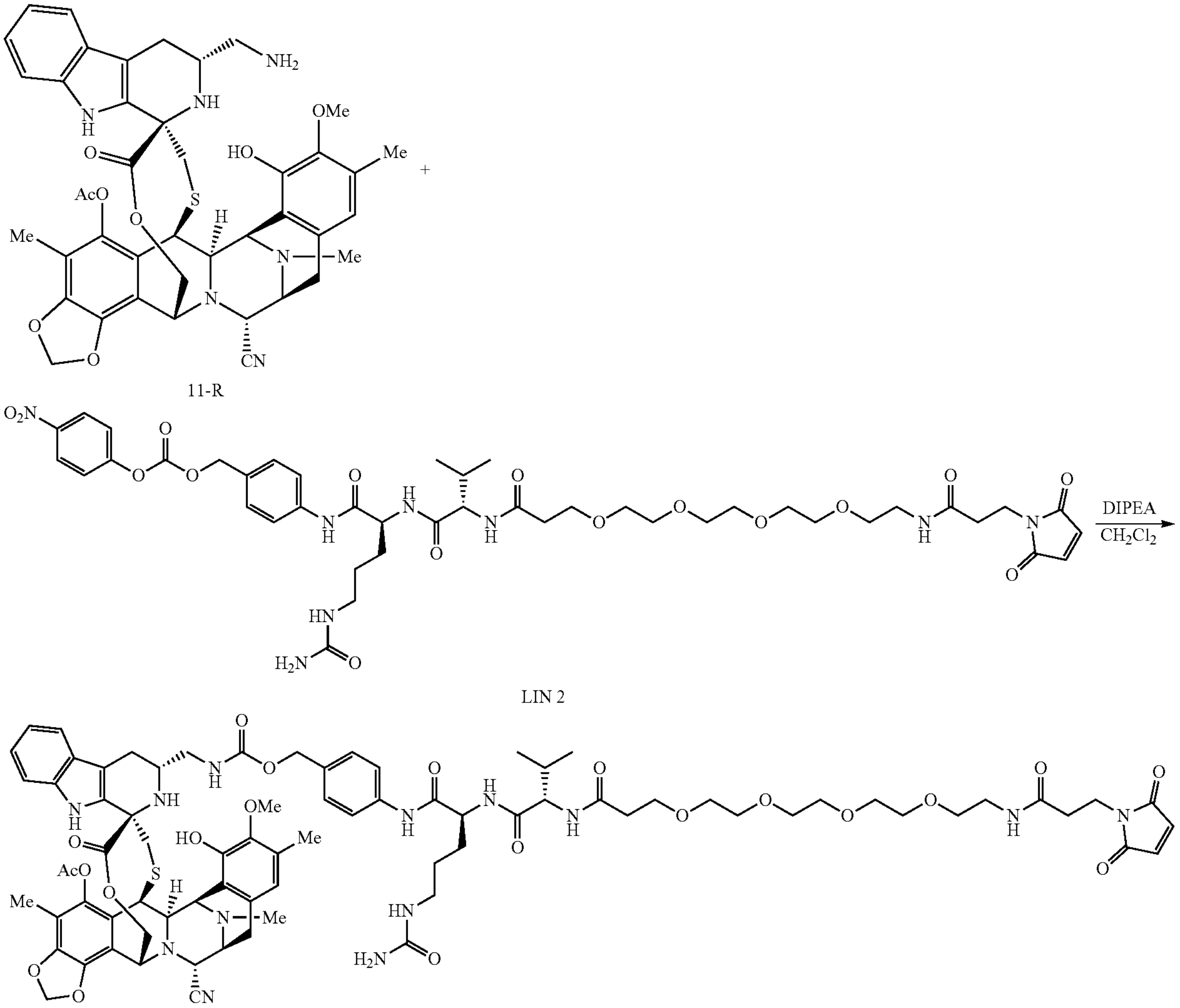

11-R

LIN 2

DL 2

To a solution of 11-R (50 mg, 0.063 mmol) and LIN 2 (118 mg, 0.12 mmol) in $CH_2Cl_2$ (2 mL) was added N,N-diisopropylethylamine (DIPEA) (22 μL, 0.12 mmol) at 23° C. The reaction mixture was stirred for 18 h at 23° C. and poured onto silica gel column ($CH_2Cl_2$:$CH_3OH$, from 99:1 to 90:10) to yield DL 2 which was purified by HPLC preparative to afford pure DL 2 (30 mg, 30% yield).

$^1H$ NMR (400 MHz, $CDCl_3$): δ 7.63 (d, J=7.9 Hz, 1H), 7.59 (d, J=8.1 Hz, 2H), 7.39 (d, J=8.2 Hz, 2H), 7.30 (d, J=7.9

Hz, 1H), 7.23 (d, J=8.2 Hz, 1H), 7.01 (t, J=7.6 Hz, 1H), 6.92 (t, J=7.5 Hz, 1H), 6.76 (s, 2H), 6.58 (s, 1H), 6.28 (s, 1H), 6.09 (s, 1H), 5.25-5.14 (m, 2H), 5.14-5.01 (m, 2H), 4.67 (bs, 1H), 4.51 (d, J=6.7 Hz, 2H), 4.36-4.24 (m, 4H), 4.23-4.15 (m, 3H), 3.73 (s, 3H), 3.75-3.69 (m 3H), 3.58-3.50 (m, 14H), 3.51-3.40 (m, 2H), 3.36-3.32 (m, 2H), 3.23-3.05 (m, 2H), 2.99-2.88 (m, 2H), 2.68 (d, J=14.9 Hz, 2H), 2.56-2.41 (m, 2H), 2.29 (s, •3H), 2.27 (s, •3H), 2.10 (s, •3H), 2.05 (s, •3H), 1.96-1.83 (m, 1H), 1.80-1.68 (m, 2H), 1.65-1.50 (m, 10H), 1.35-1.23 (m, 2H), 0.96 (d, J=6.8 Hz, 3H), 0.95 (d, J=6.8 Hz, 3H).

$^{13}C$ NMR (75 MHz, $CD_3OD$): δ 173.0, 172.34, 171.6, 171.5 (×2), 170.8 (×2), 170.7, 169.4, 160.8, 157.4, 155.8, 148.7, 148.5, 146.2, 146.1, 143.7, 141.2, 141.1, 140.9, 138.4, 136.9, 134.0, 131.3, 129.8, 128.7, 128.5, 126.0, 121.5, 120.5, 119.9, 119.7, 118.5, 117.7, 112.7, 102.4, 70.1 (×5), 70.0 (×2), 69.9, 69.8, 69.7, 69.0, 68.9, 66.8, 61.6, 59.9, 59.2, 54.6, 54.0, 53.5, 40.4, 40.0, 39.0, 36.0, 35.1, 34.4, 34.1, 30.4, 29.0, 26.4, 24.6, 23.6, 19.3, 18.5, 17.4, 15.1, 8.4.

ESI-MS m/z: 1596.6 $(M+H)^+$.

$R_f$=0.48 ($CH_2Cl_2$:$CH_3OH$, 9:1).

Preparation of Compound DL 3

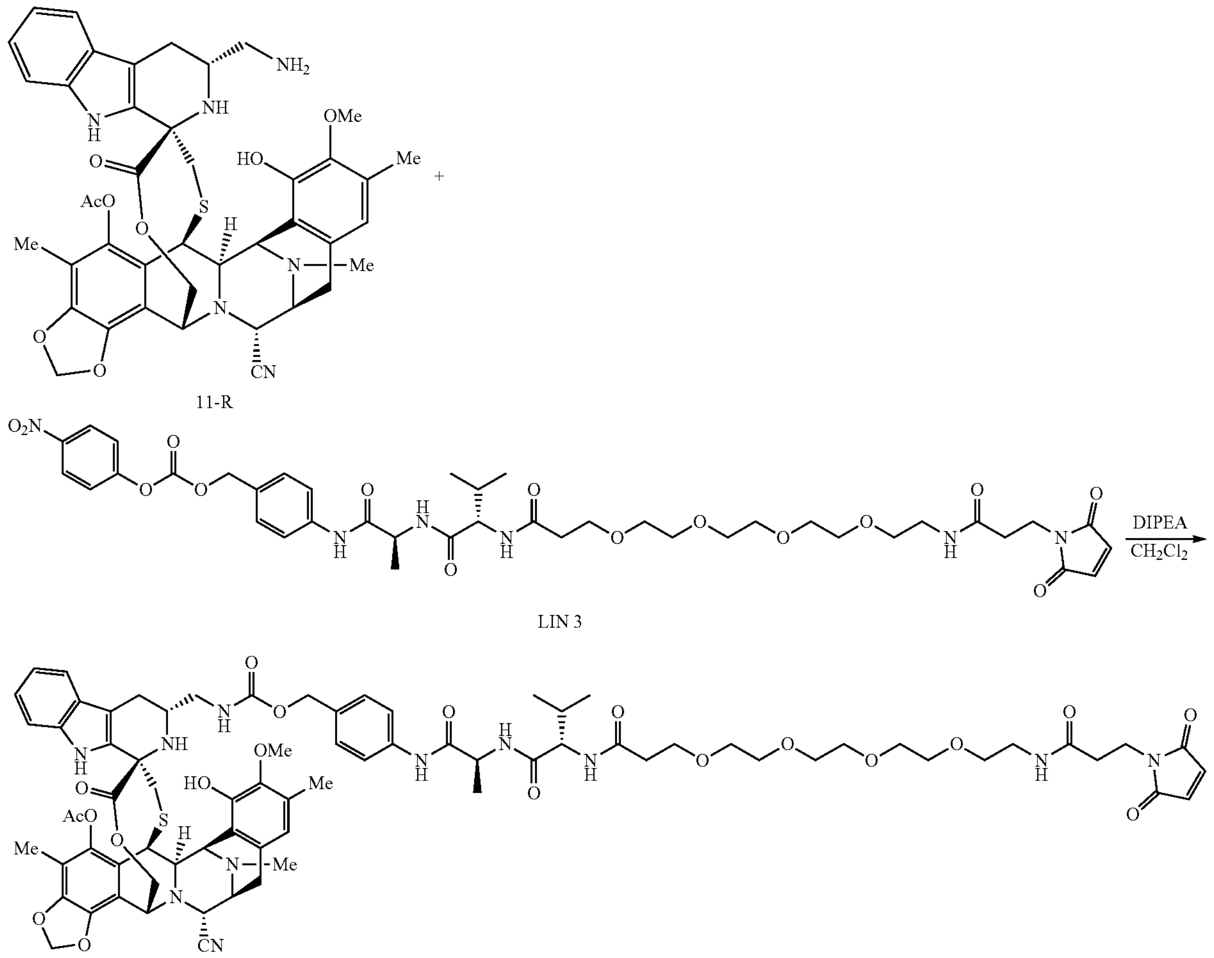

11-R

LIN 3

DL 3

To a solution of 11-R (50 mg, 0.063 mmol) and LIN 3 (108 mg, 0.12 mmol) in $CH_2Cl_2$ (2 mL) was added N,N-diisopropylethylamine (DIPEA) (22 μL, 0.12 mmol) at 23° C. The reaction mixture was stirred for 18 h at 23° C. and poured onto silica gel column ($CH_2Cl_2$:$CH_3OH$, from 99:1 to 90:10) to yield DL 3 which was purified by HPLC preparative to afford pure DL 3 (25 mg, 26% yield).

$^1H$ NMR (400 MHz, $CD_3OD$): δ 7.64 (d, J=8.2 Hz, 2H), 7.39 (d, J=8.4 Hz, 2H), 7.30 (dt, J=7.8, 1.0 Hz, 1H), 7.23 (dt, J=8.4, 0.9 Hz, 1H), 7.01 (ddd, J=8.2, 7.0, 1.2 Hz, 1H), 6.91 (ddd, J=7.9, 7.0, 1.0 Hz, 1H), 6.76 (s, 2H), 6.61 (s, 1H), 6.28 (s, 1H), 6.10 (s, 1H), 5.26-5.15 (m, 1H), 5.07 (dd, J=12.1, 4.7 Hz, 2H), 4.66 (s, 1H), 4.57 (s, 1H), 4.47 (t, J=7.1 Hz, 1H), 4.36 (s, 1H), 4.32-4.22 (m, 2H), 4.18 (d, J=6.5 Hz, 2H), 3.75-3.68 (m, 6H), 3.72 (s, 3H), 3.59-3.46 (m, 8H), 3.44 (t, J=5.3 Hz, 2H), 3.33-3.25 (m, 10H), 3.15 (dd, J=9.7, 5.0 Hz, 1H), 2.95 (d, J=17.9 Hz, 1H), 2.81 (dd, J=18.0, 9.9 Hz, 2H), 2.73-2.59 (m, 2H), 2.52 (t, J=6.1 Hz, 2H), 2.43 (t, J=6.9 Hz, 2H), 2.29 (s, 3H), 2.27 (s, 3H), 2.11 (s, 3H), 2.05 (s, 3H), 1.45 (t, J=8.7 Hz, 2H), 0.99 (d, J=9.9 Hz, 3H), 0.97 (d, J=9.9 Hz, 3H).

$^{13}C$ NMR (75 MHz, $CD_3OD$): δ 173.1, 172.1, 172.1, 171.6, 171.5, 170.7, 169.4, 148.7, 146.1, 143.6, 140.9, 138.1, 136.9, 135.7, 134.0, 134.0, 132.7, 127.1, 126.0, 121.5, 120.5, 119.8, 119.7, 119.1, 118.5, 117.6, 113.4, 110.8, 105.8, 102.4, 99.9, 86.9, 70.1, 70.1, 70.1, 70.0, 70.0, 69.9, 69.8, 69.0, 67.7, 66.8, 65.9, 63.0, 62.0, 61.6, 60.1, 59.9, 59.2, 59.1, 54.7, 54.6, 50.8, 49.6, 42.1, 40.3, 40.0, 39.0, 36.0, 34.3, 34.1, 30.4, 28.8, 23.6, 19.2, 18.4, 17.3, 16.6, 14.9, 8.4.

ESI-MS m/z: 1511.2 $(M+H)^+$.

$R_f$=0.50 ($CH_2Cl_2$:$CH_3OH$, 9:1).

Preparation of Compound DL 4

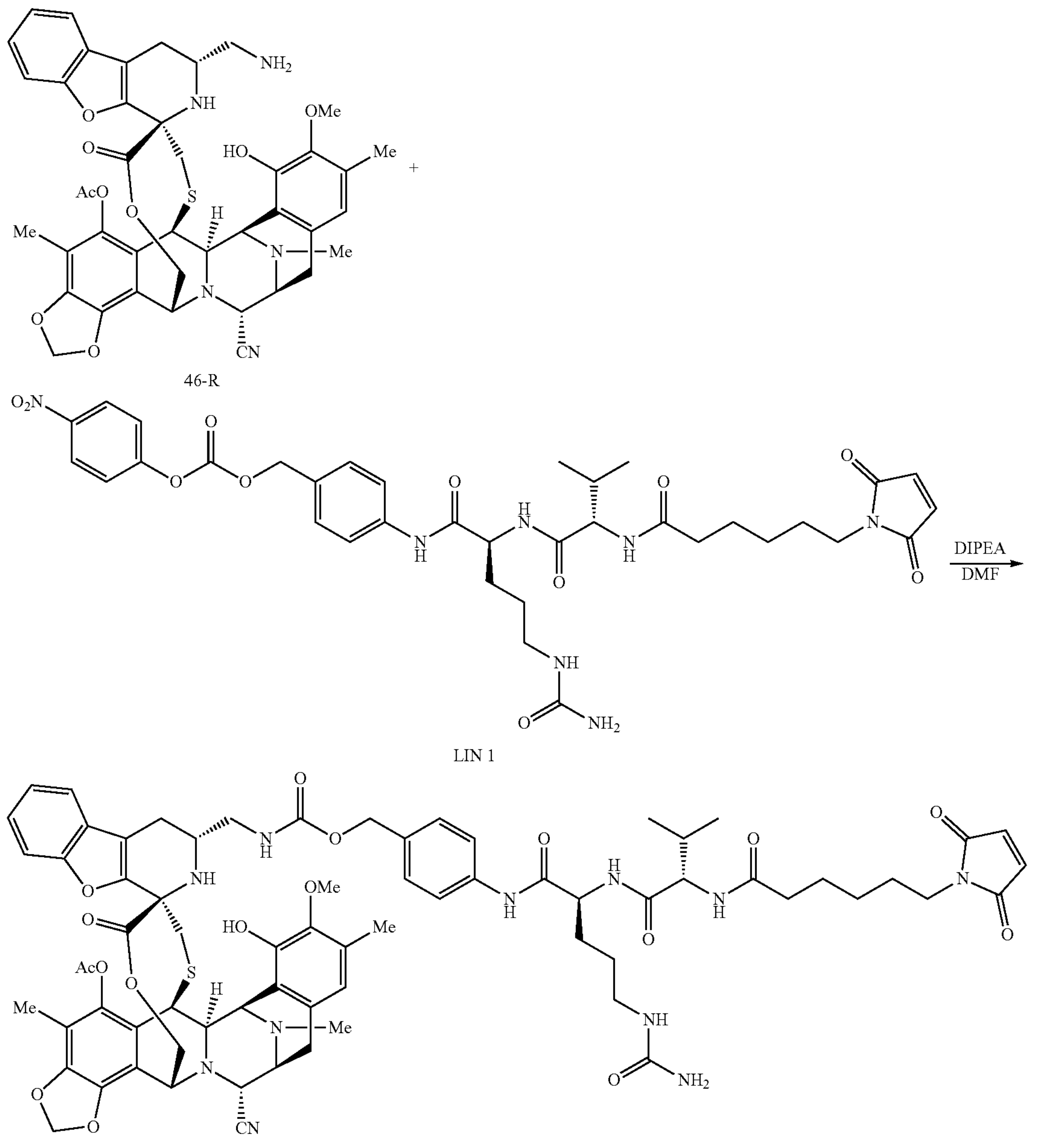

46-R

LIN 1

DL 4

To a solution of 46-R (26 mg, 0.032 mmol) and LIN 1 (48 mg, 0.64 mmol) in DMF (2 mL) was added N,N-diisopropylethylamine (DIPEA) (12 μL, 0.64 mmol) at 23° C. The reaction mixture was stirred for 18 hours at 23° C., diluted with EtOAc (50 mL) and washed with $H_2O$ (4×30 mL) and a saturated aqueous solution of NaCl (30 mL). The combined organic layers were dried over anhydrous $Na_2SO_4$, filtered, and concentrated under vacuum. The residue was purified by HPLC preparative to yield pure DL 4 (14 mg, 31% yield).

$^1H$ NMR (400 MHz, $CD_3OD$): δ 7.88 (d, J=7.9 Hz, 1H), 7.60 (d, J=8.2 Hz, 2H), 7.39-7.36 (m, 3H), 7.20-7.11 (m, 3H), 6.74 (s, 2H), 6.57 (s, 1H), 6.24 (s, 1H), 6.08 (s, 1H), 5.30-5.05 (m, 2H), 4.64 (s, 1H), 4.50 (d, J=6.1 Hz, 2H), 4.34-4.27 (m, 4H), 4.21-4.13 (m, 3H), 3.70 (s, 3H), 3.45 (t, J=7.2 Hz, 2H), 3.19-3.06 (m, 4H), 2.93-2.76 (m, 2H), 2.70-2.56 (m, 2H), 2.29-2.19 (m, 4H), 2.25 (s, 3H), 2.29-2.11 (m, 2H), 2.11 (s, 3H), 2.06 (s, 3H), 1.93-1.72 (m, 2H), 1.64-1.52 (m, 9H), 1.32-1.26 (m, 3H), 0.96-0.93 (m, 8H).

$^{13}C$ NMR (100 MHz, $CD_3OD$): δ 173.4, 171.1, 169.7, 169.3, 169.1, 167.7, 159.3, 155.9, 153.5, 147.2, 147.1, 144.3, 142.1, 139.6, 139.2, 136.6, 132.5, 131.1, 129.1, 128.3, 127.2, 125.6, 122.7, 121.0, 119.2 (×2), 118.3, 117.5, 117.4, 112.2, 112.1, 111.7, 109.7, 100.8, 97.0, 64.6, 61.7, 60.0, 58.9, 58.4, 57.7 (×2), 57.4, 53.2, 53.1, 52.0, 48.9, 43.6, 40.5, 39.0, 35.6, 33.8, 28.8, 28.1, 27.6, 26.5, 24.6, 23.6, 22.6, 22.2, 21.5, 17.9, 17.1, 16.2, 13.6, 7.1.

ESI-MS m/z: 1392.4 $(M+H)^+$.

Preparation of Compound DL 5

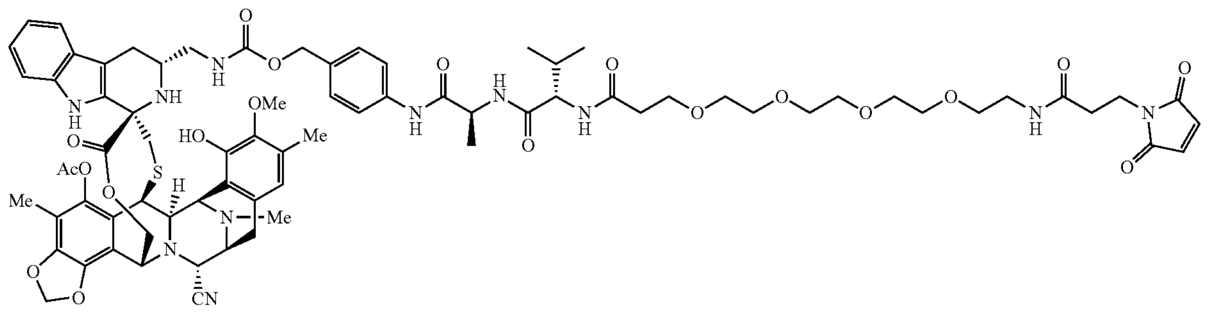

DL 3

AgNO3

CH3CN:H2O

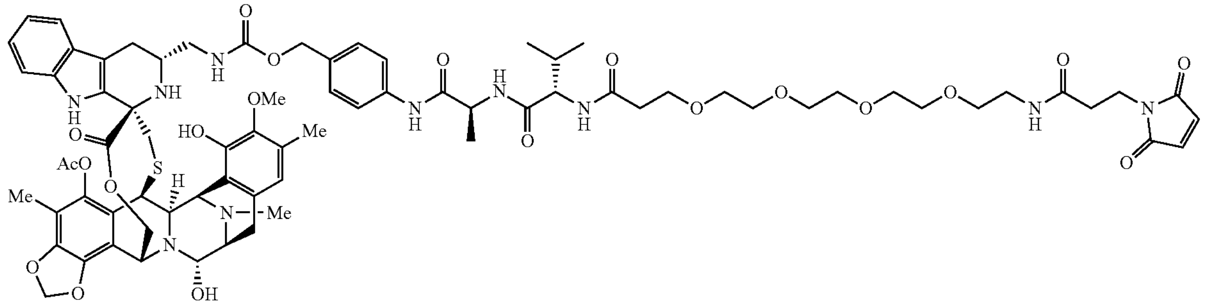

DL 5

To a solution of DL 3 (30 mg, 0.026 mmol) in $CH_3CN$:$H_2O$ (1.39:1, 6 mL, 0.015 M) was added $AgNO_3$ (132 mg, 0.79 mmol). After 18 h at 23° C., the reaction mixture was quenched with an aqueous solution of $NaHCO_3$ and extracted with $CH_2Cl_2$ (×3). The combined organic layers were dried over anhydrous $Na_2SO_4$, filtered, and concentrated under vacuum. The residue obtained was purified in an automatic system for flash chromatography ($SiO_2$, $CH_2Cl_2$:$CH_3OH$, from 95:5 to 50:50) to obtain pure DL 5 (34 mg, 87%).

$^1$H NMR (400 MHz, $CD_3OD$): 7.64 (d, J=8.4 Hz, 2H), 7.38 (d, J=8.3 Hz, 2H), 7.29 (d, J=7.8 Hz, 1H), 7.22 (d, J=8.1 Hz, 1H), 7.00 (ddd, J=8.2, 7.0, 1.2 Hz, 1H), 6.91 (ddd, J=8.0, 7.0, 1.1 Hz, 1H), 6.75 (s, 2H), 6.64 (s, 1H), 6.25 (d, J=1.4 Hz, 1H), 6.06 (d, J=1.4 Hz, 1H), 5.23-5.06 (m, 3H), 4.60 (s, 1H), 4.47 (q, J=7.1 Hz, 1H), 4.31 (dd, J=16.3, 4.1 Hz, 2H), 4.18 (d, J=6.6 Hz, 1H), 4.12 (d, J=11.6 Hz, 1H), 3.76-3.66 (m, 2H), 3.61 (d, J=5.3 Hz, 1H), 3.57-3.48 (m, 16H), 3.44 (t, J=7.2 Hz, 4H), 3.27 (t, J=5.3 Hz, 3H), 3.13 (dd, J=13.4, 6.7 Hz, 1H), 2.96 (d, J=18.0 Hz, 1H), 2.85 (dd, J=18.1, 9.3 Hz, 1H), 2.75-2.61 (m, 2H), 2.56-2.48 (m, 2H), 2.43 (t, J=6.9 Hz, 2H), 2.28 (s, 6H), 2.24 (s, 1H), 2.14 (s, 3H), 2.12-2.05 (m, 2H), 2.04 (s, 3H), 1.43 (d, J=7.2 Hz, 3H), 0.99 (d, J=6.8 Hz, 3H), 0.96 (d, J=6.8 Hz, 3H).

$^{13}$C NMR (100 MHz, $CD_3OD$): δ 173.1, 172.1, 171.7, 171.6, 171.5, 170.7, 169.3, 162.5, 157.5, 148.9, 146.1, 144.1, 141.4, 140.9, 138.2, 136.9, 134.0, 132.7, 131.2, 129.7, 128.4, 126.0, 121.4, 120.1, 119.8, 119.7, 118.5, 117.6, 114.3, 112.5, 110.8, 102.3, 90.5, 70.1 (×2), 70.0 (×2), 69.9, 69.8, 69.0, 66.8, 65.9, 63.1, 60.2, 59.2, 59.1, 57.9, 55.6, 55.1, 53.6, 50.8, 49.6, 45.4, 42.1, 40.3, 39.5, 39.0, 35.9, 34.3, 34.0 (×2), 29.3, 24.7, 23.2, 19.1, 18.3, 17.3, 16.5, 15.0, 8.2.

ESI-MS m/z: 1483.4 $(M-H_2O+H)^+$.

Preparation of Compound DL 6

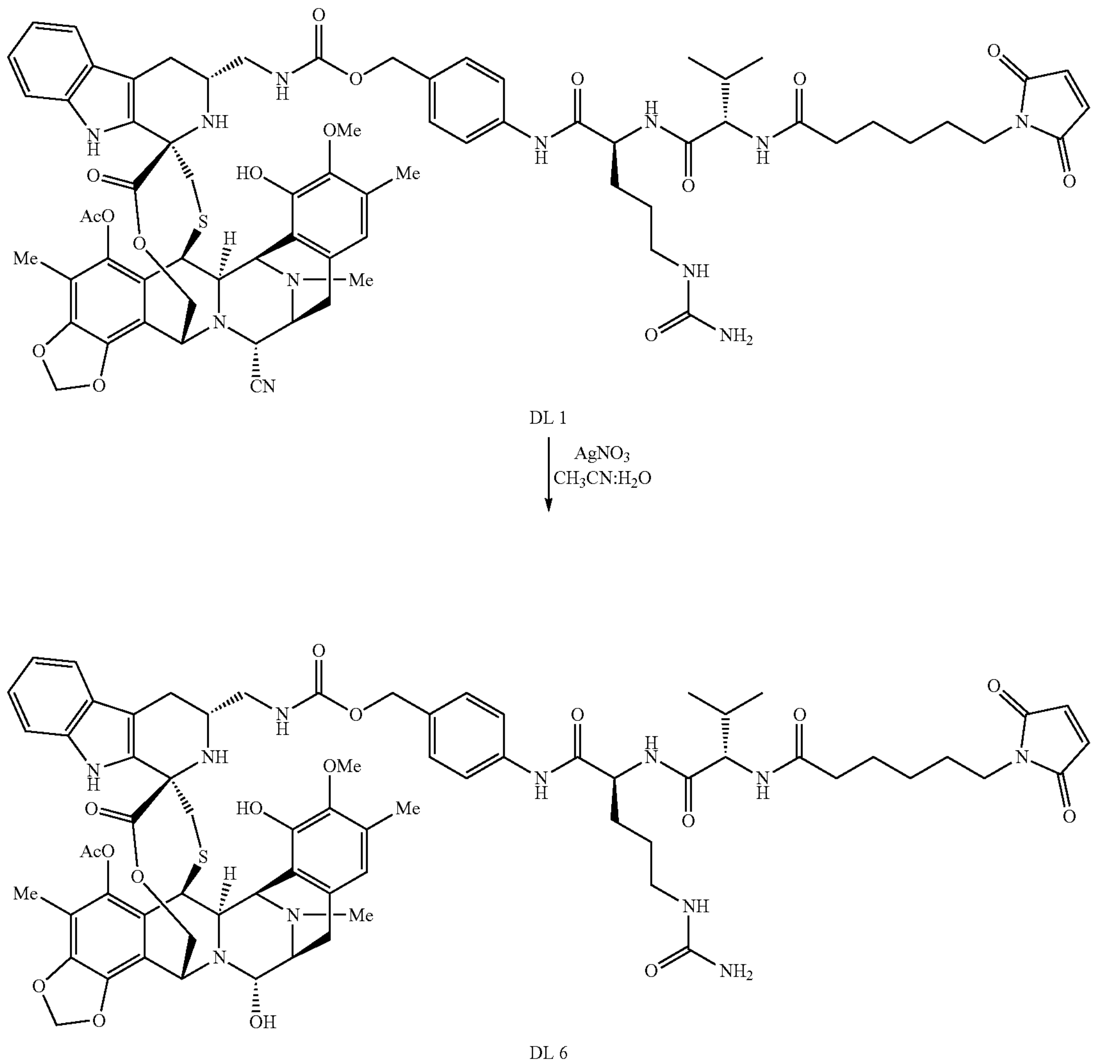

DL 1

DL 6

To a solution of DL 1 (50 mg, 0.035 mmol) in $CH_3CN$:$H_2O$ (1.39:1, 2.39 mL, 0.015 M) was added $AgNO_3$ (181 mg, 1.07 mmol). After 18 h at 23° C., the reaction mixture was quenched with an aqueous solution of $NaHCO_3$:NaCl (1:1) and extracted with $CH_2Cl_2$ (×3). The combined organic layers were dried over anhydrous $Na_2SO_4$, filtered, and concentrated under vacuum. The residue obtained was purified by HPLC preparative to obtain pure DL 6 (23 mg, 47% yield).

$^1$H NMR (400 MHz, $CD_3OD$): δ 7.62 (d, J=8.1 Hz, 2H), 7.41 (d, J=8.1 Hz, 2H), 7.39 (d, J=8.2 Hz, 1H), 7.29 (d, J=8.2 Hz, 1H), 7.12 (ddd, J=8.0, 7.0, 0.9 Hz, 1H), 7.01 (ddd, J=8.0, 7.0, 0.9 Hz, 1H), 6.82 (s, 1H), 6.75 (s, 2H), 6.32 (d, J=1.3 Hz, 1H), 6.12 (d, J=1.3 Hz, 1H), 5.32 (d, J=11.8 Hz, 1H), 5.24-5.12 (m, 3H), 4.81 (m, 2H), 4.65 (s, 1H), 4.47 (s, 1H), 4.31 (d, J=11.6 Hz, 1H), 4.18 (d, J=9.0 Hz, 1H), 4.12 (d, J=7.4 Hz, 1H), 3.93-3.83 (m, 2H), 3.76 (s, 3H), 3.65 (d, J=12.3 Hz, 1H), 3.44 (t, J=7.1 Hz, 2H), 3.23-2.99 (m, 2H), 2.92 (d, J=15.9 Hz, 1H), 2.62 (s, 3H), 2.45 (d, J=15.5 Hz, 1H), 2.35 (s, 3H), 2.30 (s, 3H), 2.28 (d, J=13.3 Hz, 6H), 2.07 (s, 3H), 2.13-2.00 (m, 2H), 1.90 (m, 1H), 1.80-1.70 (m, 2H), 1.65-1.50 (m, 4H), 1.34-1.22 (m, 2H), 0.96 (d, J=6.8 Hz, 3H), 0.95 (d, J=6.8 Hz, 3H).

$^{13}$C NMR (100 MHz, $CD_3OD$): δ 175.0, 172.6, 171.1, 170.9, 169.2, 169.1, 160.9, 157.7, 149.5, 147.0, 146.0, 144.8, 141.7, 141.2, 137.3, 136.8, 133.9, 132.5, 130.5, 129.8, 129.6, 128.5, 127.9, 122.6, 120.3, 119.8, 119.2, 118.4, 117.9, 116.7, 113.1, 112.8, 111.1, 108.4, 102.7, 101.5, 89.1, 66.2, 63.1, 62.9, 61.6, 59.3, 56.9, 56.1, 55.5, 54.7, 53.6, 50.7, 45.3, 42.2, 39.0, 38.9, 37.0, 35.1, 30.1, 29.3, 27.9, 26.5, 26.3, 26.0, 25.0, 23.1, 19.1, 18.4, 17.6, 15.2, 8.3.

ESI-MS m/z: 1364.4 $(M-H_2O+H)^+$.

Preparation of Compound DL 7

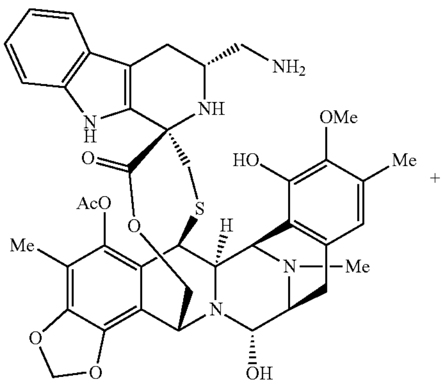

12-R

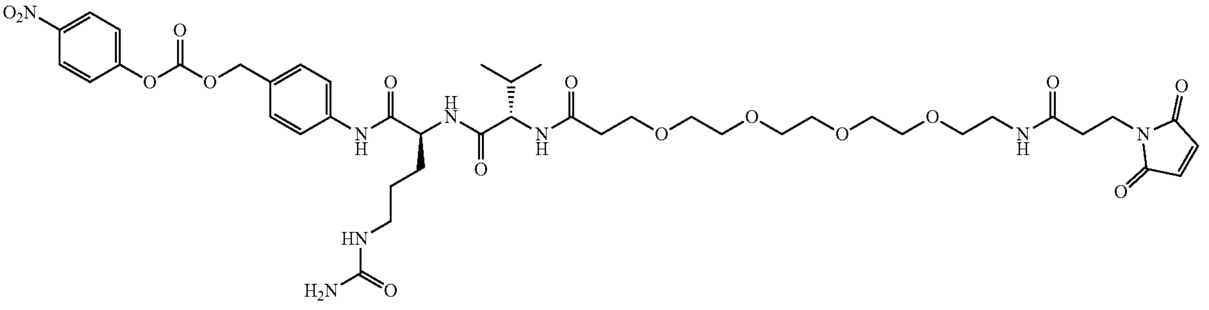

LIN 2

DIPEA
DMF

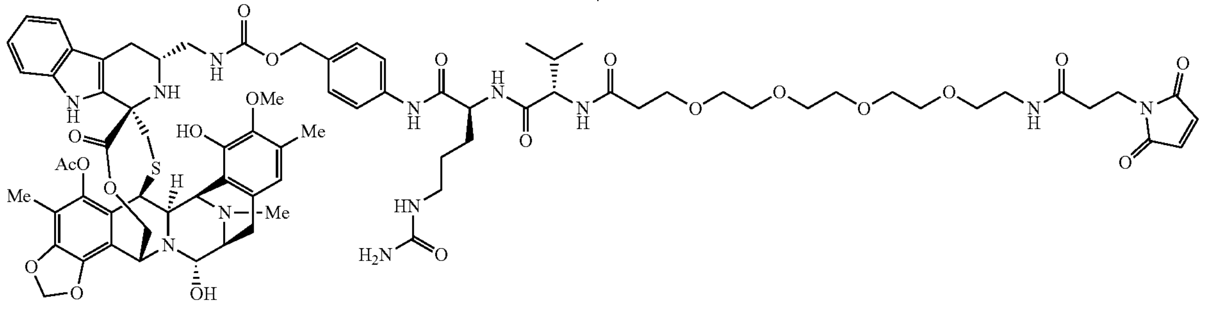

DL 7

To a solution of 12-R (100 mg, 0.12 mmol) and LIN 2 (180 mg, 0.19 mmol) in Dimethylformamide (DMF) (2 mL, 0.06 M) was added N,N-Diisopropylethylamine (DIPEA) (90 μL, 0.51 mmol) at 23° C. After 18 hours the reaction mixture was purified by HPLC preparative to yield pure DL 7 (125 mg, 62% yield).

$^{1}$H NMR (400 MHz, $CD_3OD$): δ 7.65 (d, J=8.1 Hz, 2H), 7.41 (d, J=8.1 Hz, 2H), 7.39 (d, J=8.2 Hz, 1H), 7.29 (d, J=8.2 Hz, 1H), 7.13 (ddd, J=8.2, 7.0, 1.1 Hz, 1H), 7.01 (ddd, J=8.2, 7.0, 1.1 Hz, 1H), 6.82 (s, 1H), 6.76 (s, 2H), 6.32 (d, J=1.3 Hz, 1H), 6.12 (d, J=1.3 Hz, 1H), 5.32 (d, J=11.8 Hz, 1H), 5.18 (d, J=5.7 Hz, 2H), 4.82 (m, 2H), 4.64 (d, J=2.8 Hz, 1H), 4.47 (s, 1H), 4.33 (dd, J=12.0, 2.1 Hz, 1H), 4.22-4.12 (m, 2H), 3.96 (bs, 1H), 3.88 (d, J=5.0 Hz, 1H), 3.78-3.67 (m, 8H), 3.60-3.52 (m, 14H), 3.56-3.41 (m, 3H), 3.27 (t, J=5.4 Hz, 2H), 3.22-3.04 (m, 4H), 2.93 (d, J=16.0 Hz, 1H), 2.70-2.58 (m, 3H), 2.55 (t, J=6.9 Hz, 2H), 2.43 (t, J=6.9 Hz, 2H), 2.36 (s, 3H), 2.30 (s, 3H), 2.15-2.07 (m, 1H), 2.06 (s, 3H), 2.02 (s, 2H), 1.95-1.87 (m, 1H), 1.80-1.70 (m, 1H), 1.65-1.50 (m, 2H), 0.97 (d, J=6.8 Hz, 3H), 0.96 (d, J=6.8 Hz, 3H).

$^{13}$C NMR (125 MHz, $CD_3OD$): δ 173.1, 172.5, 171.6, 171.0, 170.7 (×2), 169.3, 168.5, 160.9, 160.0, 149.6, 147.1, 144.9, 141.8, 141.3, 138.2, 137.4, 134.1, 132.4, 128.6, 127.9, 125.2, 122.9, 120.2, 119.9, 119.4, 118.1 (×2), 117.1, 114.8, 113.2, 112.7, 111.3, 108.3, 102.7, 89.0, 70.2, 70.1 (×2), 70.0, 69.9, 69.8, 69.0, 66.9, 66.3, 65.5, 65.4, 61.9, 59.4, 56.9, 56.1, 55.4 (×2), 54.6, 53.7, 43.7, 42.4, 39.1, 39.0, 36.0, 34.4, 34.1, 31.4, 30.3, 28.9, 26.5, 23.1, 22.3, 19.2, 18.5, 17.5, 15.3, 13.2, 8.5.

ESI-MS m/z: 1570.4 $(M-H_2O+H)^+$.

Preparation of Compound DL 8

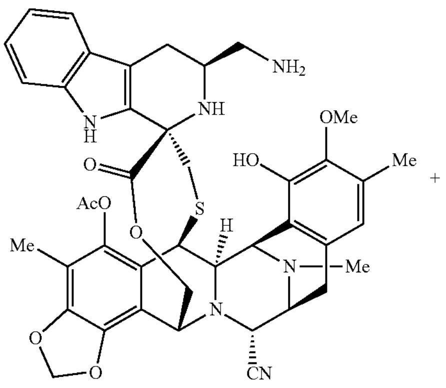

11-S

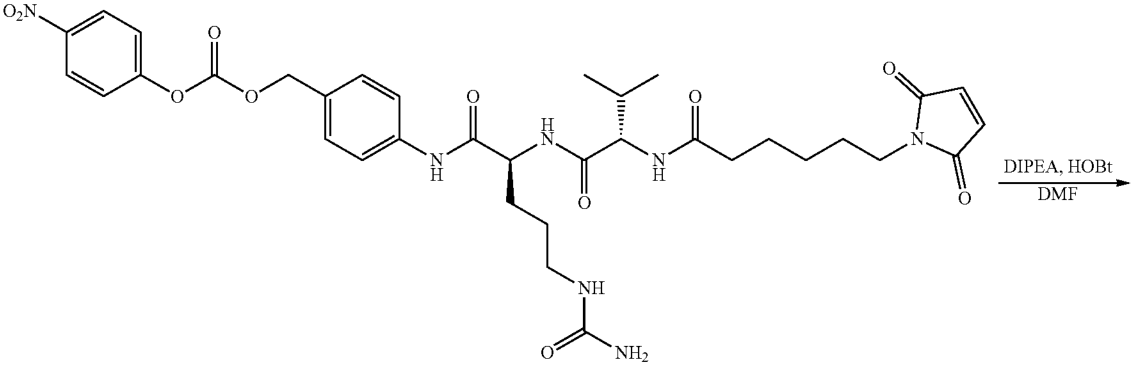

LIN 1

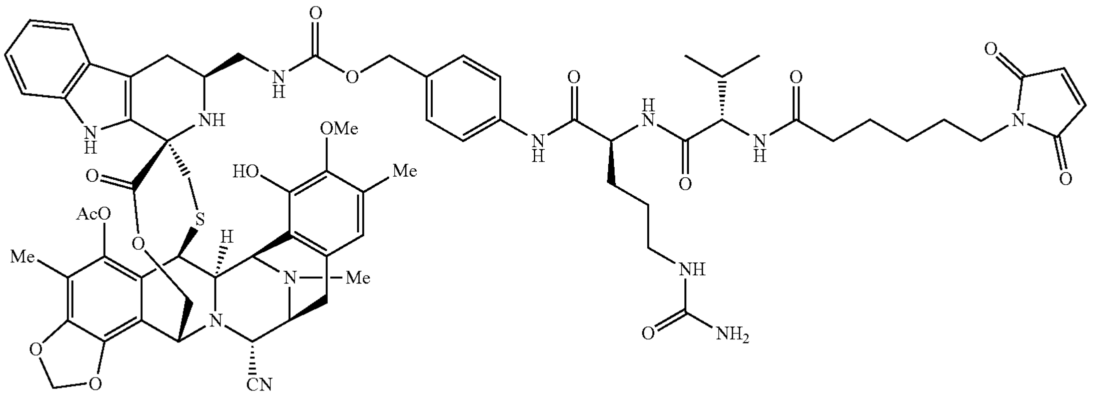

DL 8

To a solution of 11-S (30 mg, 0.037 mmol) and LIN 1 (56 mg, 0.075 mmol) in Dimethylformamide (DMF) (2 mL, 0.018 M) was added N,N-Diisopropylethylamine (DIPEA) (26 μL, 0.15 mmol) and 1-Hydroxybenzotriazole (HOBt, 10 mg, 0.075 mmol) at 23° C. After 18 hours the reaction mixture was purified by HPLC preparative to yield pure DL 8 (30 mg, 58% yield).

$^1$H NMR (400 MHz, $CD_3OD$): δ 7.59 (d, J=8.1 Hz, 2H), 7.36 (d, J=8.2 Hz, 2H), 7.28 (d, J=7.9 Hz, 1H), 7.23 (d, J=8.2 Hz, 1H), 7.00 (t, J=7.6 Hz, 1H), 6.91 (t, J=7.5 Hz, 1H), 6.74 (s, 2H), 6.50 (s, 1H), 6.27 (s, 1H), 6.09 (s, 1H), 5.20-5.03 (m, 2H), 4.65 (bs, 1H), 4.54-4.46 (m, 1H), 4.43-4.37 (m, 1H), 4.34-4.30 (m, 1H), 4.17-4.12 (m, 1H), 3.75 (s, 3H), 3.45 (t, J=7.0 Hz, 4H), 3.32-3.23 (m, 2H), 3.38 (d, J=7.6 Hz, 2H), 3.23-2.99 (m, 2H), 3.21-2.97 (m, 3H), 2.94-2.83 (m, 3H), 2.61-2.53 (m, 2H), 2.48-2.34 (m, 2H), 2.28 (s, •3H), 2.27-2.22 (m, 1H), 2.21 (s, •3H), 2.11 (s, •3H), 2.08-2.02 (m, 1H), 1.99 (s, •3H), 1.91-1.82 (m, 1H), 1.77-1.68 (m, 1H), 1.65-1.50 (m, 6H), 1.31-1.24 (m, 2H), 0.94 (d, J=6.8 Hz, 3H), 0.93 (d, J=6.8 Hz, 3H).

$^{13}$C NMR (100 MHz, $CD_3OD$): δ 174.9, 174.8, 172.5, 172.0, 171.2, 170.8, 169.4, 160.8, 157.5, 148.6, 146.0, 143.6, 140.9, 140.8, 138.0, 136.6, 136.5, 134.0, 132.7, 130.2, 129.9, 129.7, 128.7, 128.4, 126.3, 121.6, 120.5, 120.0, 119.8, 119.3, 118.7, 118.0, 117.7, 113.5, 112.9, 111.0, 107.8, 102.4, 65.9, 63.5, 61.4, 60.6, 59.7, 59.3, 59.2, 59.1, 58.8, 54.6, 54.6, 53.4, 44.8, 42.3, 40.6, 38.3, 37.1, 35.3 (×2), 30.3, 29.1, 28.0, 26.3, 26.0, 25.1, 24.0, 23.7, 19.5, 18.6, 17.7, 15.2, 8.6.

ESI-MS m/z: 1391.4 $(M+H)^+$.

Preparation of Compound DL 9

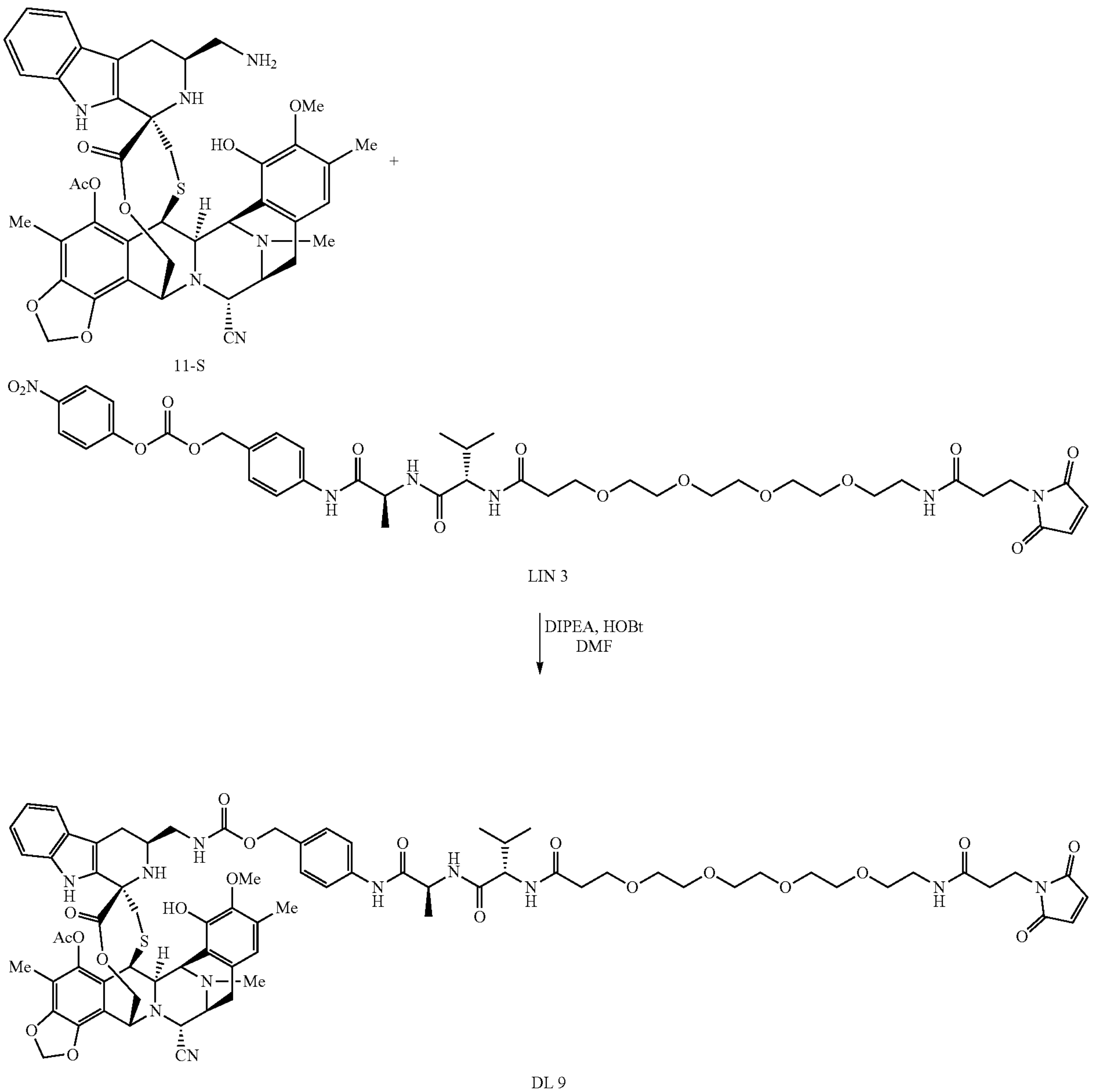

11-S

LIN 3

DL 9

To a solution of 11-S (110 mg, 0.13 mmol) and LIN-3 (119 mg, 0.13 mmol) in Dimethylformamide (DMF) (4 mL, 0.032 M) was added N,N-Diisopropylethylamine (DIPEA) (97 μL, 0.55 mmol) and 1-Hydroxybenzotriazole (HOBt, 38 mg, 0.27 mmol) at 23° C. After 18 hours the reaction mixture was purified by HPLC preparative to yield pure DL 9 (120 mg, 57% yield).

$^1$H NMR (400 MHz, $CD_3OD$): δ 7.62 (d, J=8.6 Hz, 2H), 7.36 (d, J=8.5 Hz, 2H), 7.28 (d, J=8.2 Hz, 1H), 7.23 (d, J=8.2 Hz, 1H), 7.00 (ddd, J=8.2, 7.0, 1.2 Hz, 1H), 6.91 (td, J=7.5, 7.0, 1.1 Hz, 1H), 6.75 (s, 2H), 6.50 (s, 1H), 6.26 (d, J=1.3 Hz, 1H), 6.08 (d, J=1.4 Hz, 1H), 5.19 (d, J=11.4 Hz, 1H), 5.09 (d, J=10.4 Hz, 2H), 4.65 (s, 1H), 4.48 (p, J=6.9 Hz, 1H), 4.42-4.38 (m, 2H), 4.34-4.30 (m, 2H), 4.22-4.14 (m, 1H), 3.78-3.64 (m, 5H), 3.61-3.50 (m, 8H), 3.45 (t, J=5.4 Hz, 2H), 3.38 (d, J=5.1 Hz, 1H), 3.33-3.23 (m, 3H), 3.02 (dd, J=13.5, 5.5 Hz, 1H), 2.89 (d, J=9.4 Hz, 2H), 2.62-2.33 (m, 7H), 2.27 (s, 3H), 2.22 (s, 3H), 2.12 (s, 3H), 2.15-2.05 (m, 1H), 1.99 (m, 3H), 1.42 (d, J=7.1 Hz, 3H), 0.97 (dd, J=6.8 Hz, 3H), 0.95 (dd, J=6.8 Hz, 3H).

$^{13}$C NMR (100 MHz, $CD_3OD$): δ 173.1 (×2), 172.1, 171.9, 171.6, 171.5, 171.5, 170.7, 169.3, 148.6, 146.0, 143.6, 140.9, 140.8, 138.1, 136.5, 134.1, 132.8, 130.3, 129.8, 128.4, 126.3, 121.6, 120.5, 120.0, 119.7, 119.3, 118.7, 118.0, 117.7, 113.5, 112.9, 111.0, 107.8, 102.4, 70.2, 70.1 (×2), 70.0 (×2), 69.8, 69.1, 66.9, 65.9, 63.5, 61.4, 60.6, 59.7, 59.3, 59.2, 59.1, 58.8, 54.7, 54.6, 49.6, 42.3, 40.5, 39.1, 39.0, 36.0, 34.4 (×2), 34.1, 30.4, 24.0, 23.7, 19.4, 18.5, 17.4, 16.8, 15.1, 8.5.

ESI-MS m/z: 1511.4 $(M+H)^+$.

Preparation of Compound DL 10

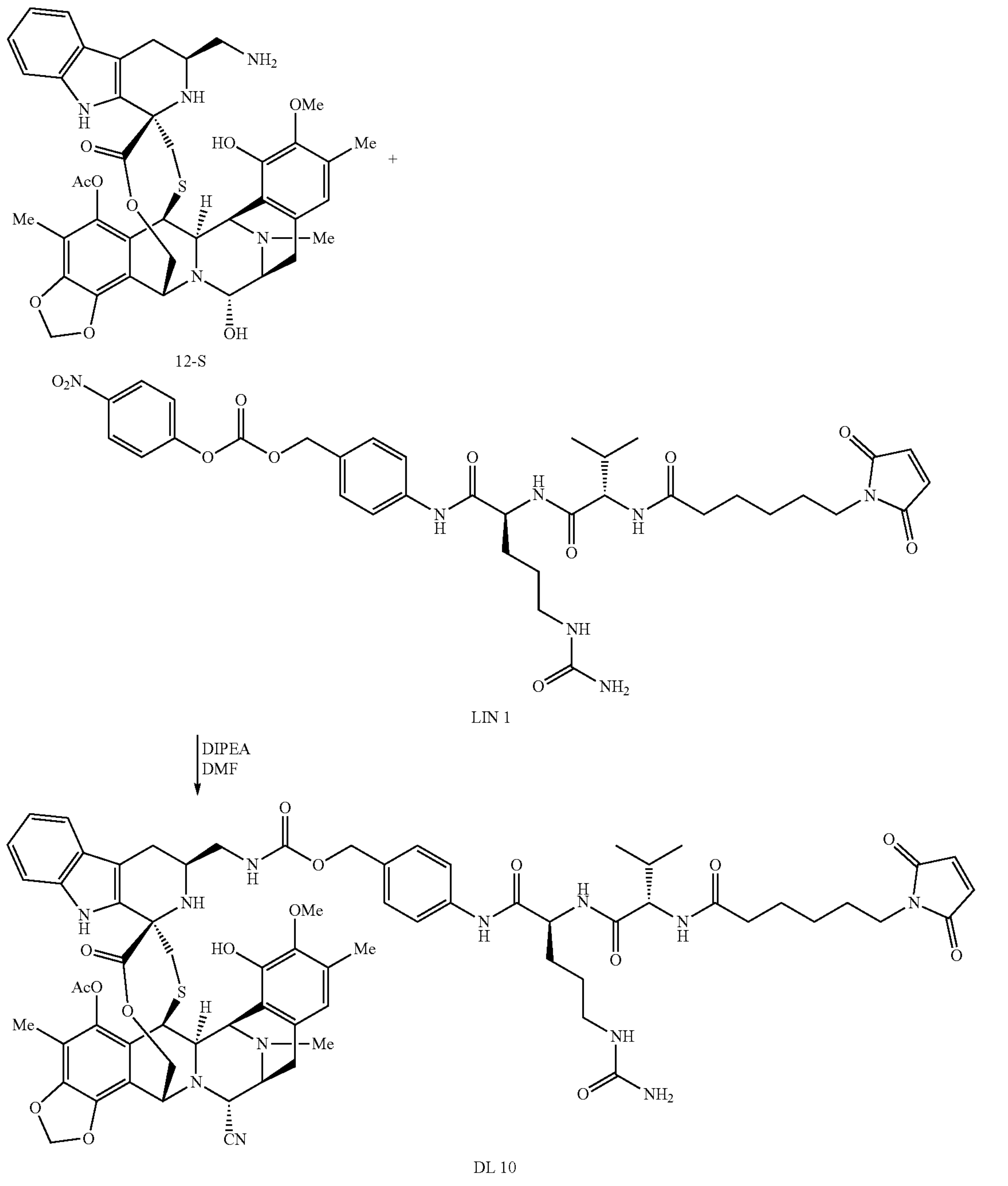

12-S

LIN 1

DL 10

To a solution of 12-S (30 mg, 0.058 mmol) and LIN 1 (98 mg, 0.13 mmol) in N-Methyl-2-pyrrolidone (NMP) (4 mL, 0.014 M) was added N,N-Diisopropylethylamine (DIPEA) (83 μL, 0.13 mmol) at 23° C. After 18 hours the reaction mixture was diluted with EtOAc (25 mL) and washed with $H_2O$ (4×25 mL) and an aqueous saturated solution of NaCl. The combined organic layers were dried over anhydrous $Na_2SO_4$, filtered, and concentrated under vacuum. The residue was purified by flash chromatography on silica gel ($CH_2Cl_2$:$CH_3OH$, from 99:1 to 90:10) and the compound obtained purified by HPLC preparative to yield pure DL 10 (11 mg, 21% yield).

$^1H$ NMR (400 MHz, $CD_3OD$): δ 7.61 (d, J=8.1 Hz, 2H), 7.39 (d, J=8.1 Hz, 2H), 7.35 (d, J=8.2 Hz, 1H), 7.29 (d, J=8.2 Hz, 1H), 7.08 (ddd, J=8.0, 7.0, 0.9 Hz, 1H), 6.98 (ddd, J=8.0, 7.0, 0.9 Hz, 1H), 6.76 (s, 2H), 6.66 (s, 1H), 6.29 (d, J=1.3 Hz, 1H), 6.14 (d, J=1.3 Hz, 1H), 5.13 (q, J=12.3 Hz, 2H), 4.93-4.81 (m, 3H), 4.69 (s, 1H), 4.48 (s, 1H), 4.23 (d, J=10.0 Hz, 1H), 4.13 (dd, J=7.5, 4.0 Hz, 1H), 3.90 (d, J=5.0, 1H), 3.76 (s, 3H), 3.49-3.41 (m, 2H), 3.40-3.27 (m, 1H), 3.28-3.24 (m, 4H), 3.22-3.05 (m, 4H), 2.80-2.65 (m, 3H), 2.63 (s, 3H), 2.29 (s, 3H), 2.28 (s, 3H), 2.13-2.00 (m, 2H), 2.03 (s, 3H), 1.93-1.83 (m, 1H), 1.79-1.69 (m, 2H), 1.65-1.51 (m, 6H), 1.34-1.22 (m, 2H), 0.96 (d, J=6.8 Hz, 3H), 0.95 (d, J=6.8 Hz, 3H).

$^{13}C$ NMR (100 MHz, $CD_3OD$): δ 174.9, 172.7, 172.6, 171.1, 170.8 (×2), 169.1, 160.9, 149.4, 146.6, 144.7, 142.3, 141.5, 141.0, 138.1, 136.8, 133.9, 133.5, 132.6, 128.5, 127.5, 125.9, 122.2, 120.9, 119.8, 117.8, 113.2, 113.0, 111.2, 107.3, 102.6, 89.2, 66.2, 61.7, 61.3, 60.2, 59.4, 59.3, 57.4, 56.9, 55.8, 55.7, 55.2, 54.8, 53.5, 42.0, 39.1, 37.1, 35.2, 31.7, 30.2, 29.4, 29.1, 29.0 (×2), 27.9, 26.4, 26.0, 25.0, 23.3, 22.4, 19.2, 18.5, 17.7, 15.2, 13.2, 8.5.

ESI-MS m/z: 1364.4 $(M-H_2O+H)^+$.

Preparation of Compound DL 11

3.34 (s, 3H), 3.27 (t, J=5.5 Hz, 3H), 3.04 (dd, J=13.4, 6.7 Hz, 1H), 2.88-2.82 (m, 3H), 2.64-2.35 (m, 7H), 2.27 (s, 3H), 2.23 (s, 3H), 2.17-2.04 (m, 1H), 2.09 (s, 3H), 2.01 (d, J=7.2 Hz, 1H), 1.98 (s, 3H), 1.42 (d, J=7.2 Hz, 3H), 0.98 (dd, J=6.8 Hz, 3H), 0.95 (dd, J=6.8 Hz, 3H).

$^{13}C$ NMR (100 MHz, $CD_3OD$): δ 173.1, 172.1, 172.0, 171.6, 171.5, 170.7, 169.4, 157.6, 148.6, 145.8, 143.7, 141.1, 140.8, 138.1, 136.5, 134.1, 132.8, 130.4, 130.0, 129.8, 128.4, 126.4, 126.2, 121.5, 120.9, 120.1, 119.8, 118.6, 117.7, 114.9, 112.4, 111.0, 107.7, 102.1, 91.0, 70.2, 70.1 (×2), 70.0 (×2), 69.8, 69.1, 66.9, 65.9, 63.5, 60.5, 59.3, 59.1, 58.2, 55.2, 54.7, 52.9, 49.6, 44.9, 42.6, 40.0, 39.0, 38.3, 36.0, 34.4, 34.1, 30.4, 29.4, 24.0, 23.3, 19.4, 18.5, 17.4, 16.8, 15.1, 8.4.

ESI-MS m/z: 1483.4 $(M-H_2O+H)^+$.

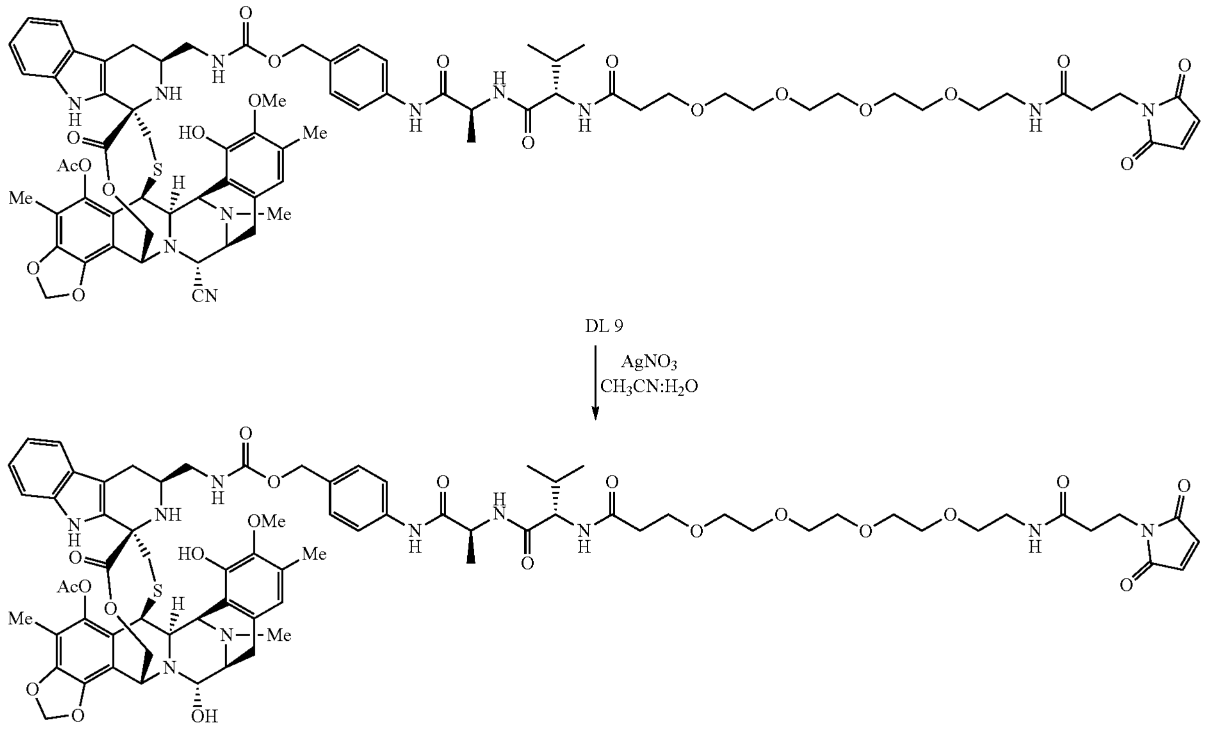

DL 9

DL 11

To a solution of DL 9 (90 mg, 0.059 mmol) in $CH_3CN$:$H_2O$ (1.39:1, 4 mL, 0.015 M) was added $AgNO_3$ (298 mg, 1.78 mmol). After 21 h at 23° C., the reaction mixture was quenched with an aqueous solution of $NaHCO_3$:NaCl (1:1) and extracted with $CH_2Cl_2$ (×3). The combined organic layers were dried over anhydrous $Na_2SO_4$, filtered, and concentrated under vacuum. The residue obtained was purified in an automatic system for flash chromatography ($SiO_2$, $CH_2Cl_2$:$CH_3OH$, from 95:5 to 50:50) to obtain pure DL 11 (65 mg, 73% yield).

$^1H$ NMR (400 MHz, $CD_3OD$): δ 7.62 (d, J=8.6 Hz, 1H), 7.37 (d, J=8.5 Hz, 2H), 7.28 (d, J=7.8 Hz, 1H), 7.23 (d, J=8.2 Hz, 1H), 6.99 (ddd, J=8.2, 7.0, 1.2 Hz, 1H), 6.90 (ddd, J=8.0, 7.0, 1.1 Hz, 1H), 6.76 (s, 2H), 6.52 (s, 1H), 6.25 (d, J=1.3 Hz, 1H), 6.06 (d, J=1.3 Hz, 1H), 5.28 (d, J=11.4 Hz, 1H), 5.09 (d, J=10.4 Hz, 1H), 4.59 (s, 1H), 4.47 (q, J=7.1 Hz, 1H), 4.33 (dd, J=11.5, 1.9 Hz, 1H), 4.33-4.25 (m, 2H), 4.19 (d, J=6.6 Hz, 1H), 3.75 (s, 3H), 3.75-3.67 m, 3H), 3.61 (d, J=5.3 Hz, 1H), 3.58-3.51 (m, 12H), 3.45 (dd, J=10.6, 5.2 Hz, 2H),

Example 2: Preparation of Antibody-Drug Conjugates (ADCs)

In this Example, syntheses of antibody-drug conjugates of the present invention are described. It should be noted that these syntheses are exemplary and that the processes described can be applied to all the compounds and antibodies described herein.

Example 2a Preparation of Anti-CD13 Monoclonal Antibody

Anti-CD13 monoclonal antibodies were obtained following well known procedures commonly used in the art. Briefly BALB/c mice were immunized with human endothelial cells isolated from umbilical cord. To that end, 1.5E7 of the cells were injected to the mice intraperitoneally on days −45 and −30 and intravenously on day −3. On day 0 spleen from these animals were removed and spleen cells were fused with SP2 mouse myeloma cells at a ratio of 4:1 according to standard techniques to produce the hybridoma and distributed on 96-well tissue culture plates (Costar Corp., Cambridge, MA). After 2 weeks hybridoma culture supernatants were harvested and their reactivity against the cell line used in the immunization step was tested by flow cytometry. Positive supernatants were assayed by immunofluorescence staining the corresponding cells used as antigens. Hybridomas showing a specific staining, immunoprecipitation pattern and cell distribution were selected and cloned and subcloned by limiting dilution.

Once the clones were selected, cells were cultured in RPMI-1640 medium supplemented with 10% (v/v) fetal calf serum, 2 mM glutamine, 100 U/mL penicillin and 100 μg/mL streptomycin at 37° C. during 3-4 days until the medium turned pale yellow. At that point, two thirds of the medium volume were removed, centrifuged at 1,000×g for 10 min to pellet the cells and the supernatant was either centrifuged again for further cleaning at 3,000×g for 10 min or filtered through 22 μm pore size membranes. The clarified supernatant was subjected to precipitation with 55% saturation ammonium sulphate and the resulting pellet was resuspended in 100 mM Tris-HCl pH 7.8 (1 mL per 100 mL of the original clarified supernatant) and dialyzed at 4° C. for 16-24 h against 5 L of 100 mM Tris-HCl pH 7.8 with 150 mM NaCl, changing the dialyzing solution at least three times. The dialyzed material was finally loaded onto a Protein A-Sepharose column and the corresponding monoclonal antibody was eluted with 100 mM sodium citrate pH 3.0 or alternatively with 1M glycine pH 3.0. Those fractions containing the antibody were neutralized with 2M Tris-HCl pH 9.0 and finally dialyzed against PBS and stored at −80° C. until its use.

Preparation of Antibody-Drug Conjugate ADC1 with Trastuzumab and DL 1

(a) Partial Reduction of Trastuzumab to Give Partially Reduced Trastuzumab.

Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (13.9 mg/mL) was determined by measuring the absorbance at 280 nm.

Trastuzumab solution (0.33 mL, 4.6 mg, 30.6 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (17.5 μL, 87.6 nmol, 3 eq.) The reduction reaction was left to stir for 90 min at 20° C. Immediately after the reduction, an Ellman assay was performed to give a Free Thiol to Antibody ratio (FTAR) of 4.0.

(b) Preparation of ADC 1.

To the solution of partially reduced Trastuzumab (140 μL, 1.4 mg, 9 nmol), N,N-Dimethylacetamide (DMA) was added (28.2 μL) followed by addition of a freshly prepared solution of DL 1 (10 mM in DMA, 6.8 μL, 67.5 nmol, 7.5 eq.) Upon addition of DL 1, the solution turned turbid. The conjugation reaction was stirred for 30 min at 20° C. and the turbidity vanished during the conjugation reaction. The excess of drug was quenched by addition of N-acetylcysteine (NAC) (10 mM, 6.8 μL, 67.5 nmol) followed by stirring the solution for 20 min. The quenched conjugation reaction was purified by desalting using Sephadex G25 NAP-5 columns into PBS buffer. The final target product ADC 1 was concentrated to a final concentration of 6.05 mg/mL as determined by UV and 232 μL (1.4 mg, 9.3 nmol, 103%) ADC solution was obtained. HIC HPLC runs were performed to determine the percentage of conjugation reaction (89%).

Preparation of Antibody-Drug Conjugate ADC 2 with Trastuzumab and DL 2

(a) Partial Reduction of Trastuzumab to Give Partially Reduced Trastuzumab.

Trastuzumab solution (0.33 mL, 4.6 mg, 30.6 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (17.5 μL, 87.6 nmol, 3 eq.) The reduction reaction was left to stir for 90 min at 20° C. Immediately after the reduction, an Ellman assay was performed to give a Free Thiol to Antibody ratio (FTAR) of 3.9.

(b) Preparation of ADC 2.

To the solution of partially reduced Trastuzumab (140 μL, 1.4 mg, 9 nmol), N,N-Dimethylacetamide (DMA) was added (28.2 μL) followed by addition of a freshly prepared solution of DL 2 (10 mM in DMA, 6.8 μL, 67.5 nmol, 7.5 eq.) Upon addition of DL 2 the solution was stirred for 30 min at 20° C. The excess of drug was quenched by addition of N-acetylcysteine (NAC) (10 mM, 6.8 μL, 67.5 nmol) followed by stirring the solution for 20 min. The quenched conjugation reaction was purified by desalting using Sephadex G25 NAP-5 columns into PBS buffer. The final target product ADC 2 was concentrated to a final concentration of 5.19 mg/mL as determined by UV and 270 μL (1.4 mg, 9.3 nmol, 103%) ADC solution was obtained. HIC HPLC runs were performed to determine the percentage of conjugation reaction (65%).

Preparation of Antibody-Drug Conjugate ADC 3 with Trastuzumab and Compound DL 3.

(a) Partial Reduction of Trastuzumab to Give Partially Reduced Trastuzumab.

Trastuzumab solution (0.33 mL, 4.6 mg, 30.6 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (17.5 μL, 87.6 nmol, 3 eq.) The reduction reaction was left to stir for 90 min at 20° C. Immediately after the reduction, an Ellman assay was performed to give a Free Thiol to Antibody ratio (FTAR) of 3.9.

(b) Preparation of ADC 3.

To the solution of partially reduced Trastuzumab (140 μL, 1.4 mg, 9 nmol), N,N-Dimethylacetamide (DMA) was added (28.2 μL) followed by addition of a freshly prepared solution of DL 3 (10 mM in DMA, 6.8 μL, 67.5 nmol, 7.5 eq.) Upon addition of DL 3 the solution was stirred for 30 min at 20° C. The excess of drug was quenched by addition of N-acetylcysteine (NAC) (10 mM, 6.8 μL, 67.5 nmol) followed by stirring the solution for 20 min. The quenched conjugation reaction was purified by desalting using Sephadex G25 NAP-5 columns into PBS buffer. The final target product ADC 3 was concentrated to a final concentration of 5.15 mg/mL as determined by UV and 280 μL (1.44 mg, 9.6 nmol, 107%) ADC solution was obtained. HIC HPLC runs were performed to determine the percentage of conjugation reaction (93%).

Preparation of Antibody-Drug Conjugate ADC 4 with Traut's-Modified Trastuzumab and Compound DL 1

(a) Reaction of Trastuzumab with 2-iminothiolane hydrochloride (Traut's reagent) to give thiol-activated Trastuzumab Trastuzumab solution (0.65 mL, 9 mg, 60 nmol) was diluted to a concentration of 10 mg/mL using phosphate buffer (50 mM phosphate, 2 mM EDTA, pH 8). Traut's reagent was added (64.4 μL, 900 nmol, 15 eq.) and the reaction stirred for 2 h at 25° C. The mixture was buffer exchanged using two Sephadex G25 NAP-5 columns into PBS buffer, and concentrated to a volume of 1.2 mL (7.5 mg/mL). Immediately after, an Ellman assay was performed to give a Free Thiol to Antibody ratio (FTAR) of 7.9.

(b) Preparation of ADC 4

To the solution of thiol-activated Trastuzumab (300 μL, 2.25 mg, 15 nmol), DMA was added (59.8 μL) followed by addition of a freshly prepared solution of DL 1 (10 mM in DMA, 22.5 μL, 225 nmol, 15 eq.). Upon addition of DL 1, the solution turned turbid. The conjugation reaction was stirred for 2 h at 25° C. and purified by desalting using a Sephadex G25 NAP-5 column into PBS buffer. The final target product ADC 4 was concentrated to a final concentration of 3.49 mg/mL as determined by UV and 252 μL (0.88 mg, 5.86 nmol, 39%) ADC solution was obtained.

Preparation of Antibody-Drug Conjugate ADC 5 with Trastuzumab and Compound DL 4.

(a) Partial Reduction of Trastuzumab to Give Partially Reduced Trastuzumab.

Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (17.1 mg/mL) was determined by measuring the absorbance at 280 nm.

Trastuzumab solution (0.5 mL, 8.55 mg, 57 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (24.5 μL, 122.4 nmol, 2.2 eq.) The reduction reaction was left to stir for 90 min at 20° C. Immediately after the reduction, an Ellman assay was performed to give a Free Thiol to Antibody ratio (FTAR) of 3.4.

(b) Preparation of ADC 5.

To the solution of partially reduced Trastuzumab (200 μL, 1.9 mg, 13.2 nmol), N,N-Dimethylacetamide (DMA) was added (42.1 μL) followed by addition of a freshly prepared solution of DL 4 (10 mM in DMA, 7.9 μL, 79.2 nmol, 6 eq.) Upon addition of DL 4, the solution turned turbid. The conjugation reaction was stirred for 30 min at 20° C. and the turbidity vanished during the conjugation reaction. The excess of drug was quenched by addition of N-acetylcysteine (NAC) (10 mM, 7.9 μL, 79.2 nmol) followed by stirring the solution for 20 min. The quenched conjugation reaction was purified by desalting using Sephadex G25 NAP-5 columns into PBS buffer. The final target product ADC 5 was concentrated to a final concentration of 5.30 mg/mL as determined by UV and 290 μL (1.54 mg, 1.0 nmol, 81%) ADC solution was obtained. HIC HPLC runs were performed to determine the percentage of conjugation reaction (91%).

Preparation of Antibody-Drug Conjugate ADC 6 with Trastuzumab and Compound DL 5.

(a) Partial Reduction of Trastuzumab to Give Partially Reduced Trastuzumab.

Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (17.6 mg/mL) was determined by measuring the absorbance at 280 nm.

Trastuzumab solution (0.55 mL, 9.7 mg, 64.6 nmol) was diluted to a concentration of 12.8 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (29.2 μL, 146 nmol, 2.2 eq.) The reduction reaction was left to stir for 90 min at 20° C. Immediately after the reduction, an Ellman assay was performed to give a Free Thiol to Antibody ratio (FTAR) of 3.4.

(b) Preparation of ADC 6.

To the solution of partially reduced Trastuzumab (140 μL, 1.8 mg, 12 nmol), N,N-Dimethylacetamide (DMA) was added (28.2 μL) followed by addition of a freshly prepared solution of DL 5 (10 mM in DMA, 6.8 μL, 67.5 nmol, 5.6 eq.) Upon addition of DL 5 the solution was stirred for 30 min at 20° C. The excess of drug was quenched by addition of N-acetylcysteine (NAC) (10 mM, 6.8 μL, 67.5 nmol) followed by stirring the solution for 20 min. The quenched conjugation reaction was purified by desalting using Sephadex G25 NAP-5 columns into PBS buffer. The final target product ADC 6 was concentrated to a final concentration of 4.29 mg/mL as determined by UV and 320 μL (1.37 mg, 9.1 nmol, 76%) ADC solution was obtained. HIC HPLC runs were performed to determine the percentage of conjugation reaction (83%).

Preparation of Antibody-Drug Conjugate ADC 7 with Anti-CD13 and Compound DL 1

(a) Partial Reduction of Anti-CD13 to Give Partially Reduced Anti-CD13.

Anti-CD13 solution (0.5 mL, 8.2 mg, 54.6 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (31.9 μL, 159 nmol, 3 eq.) The reduction reaction was left to stir for 90 min at 20° C. Immediately after the reduction, an Ellman assay was performed to give a Free Thiol to Antibody ratio (FTAR) of 4.7.

(b) Preparation of ADC 7.

To the solution of partially reduced Anti-CD13 (200 μL, 2.0 mg, 13.3 nmol), N,N-Dimethylacetamide (DMA) was added (40 μL) followed by addition of a freshly prepared solution of DL 1 (10 mM in DMA, 10 μL, 100 nmol, 7.5 eq.) Upon addition of DL 1 the solution was stirred for 30 min at 20° C. The excess of drug was quenched by addition of N-acetylcysteine (NAC) (10 mM, 10 μL, 100 nmol) followed by stirring the solution for 20 min. The quenched conjugation reaction was purified by desalting using Sephadex G25 NAP-5 columns into PBS buffer. The final target product ADC 7 was concentrated to a final concentration of 5.58 mg/mL as determined by UV and 350 μL (1.95 mg, 13 nmol, 98%) ADC solution was obtained. HIC HPLC runs were performed to determine the percentage of conjugation reaction (90%).

Preparation of Antibody-Drug Conjugate ADC 8 with Anti-CD13 and Compound DL 3

(a) Partial Reduction of Anti-CD13 to Give Partially Reduced Anti-CD13.

Anti-CD13 solution (0.5 mL, 8.2 mg, 54.6 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (31.9 μL, 159 nmol, 3 eq.) The reduction reaction was left to stir for 90 min at 20° C. Immediately after the reduction, an Ellman assay was performed to give a Free Thiol to Antibody ratio (FTAR) of 4.7.

(b) Preparation of ADC 8.

To the solution of partially reduced Anti-CD13 (200 μL, 2.0 mg, 13.3 nmol), N,N-Dimethylacetamide (DMA) was added (40 μL) followed by addition of a freshly prepared solution of DL 3 (10 mM in DMA, 10 μL, 100 nmol, 7.5 eq.) Upon addition of DL 3 the solution was stirred for 30 min at 20° C. The excess of drug was quenched by addition of N-acetylcysteine (NAC) (10 mM, 10 μL, 100 nmol) followed by stirring the solution for 20 min. The quenched conjugation reaction was purified by desalting using Sephadex G25 NAP-5 columns into PBS buffer. The final target product ADC 8 was concentrated to a final concentration of 5.83 mg/mL as determined by UV and 380 μL (2.21 mg, 14.7 nmol, 111%) ADC solution was obtained. HIC HPLC runs were performed to determine the percentage of conjugation reaction (94%).

Preparation of Antibody-Drug Conjugate ADC 9 with Anti-CD13 and Compound DL 5

(a) Partial Reduction of Anti-CD13 to Give Partially Reduced Anti-CD13.

Anti-CD13 solution (0.5 mL, 8.2 mg, 54.6 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (31.9 μL, 159 nmol, 3 eq.) The reduction reaction was left to stir for 90 min at 20° C. Immediately after the reduction, an Ellman assay was performed to give a Free Thiol to Antibody ratio (FTAR) of 4.7.

(b) Preparation of ADC 9.

To the solution of partially reduced Anti-CD13 (200 μL, 2.0 mg, 13.3 nmol), N,N-Dimethylacetamide (DMA) was added (40 μL) followed by addition of a freshly prepared solution of DL 5 (10 mM in DMA, 10 μL, 100 nmol, 7.5 eq.) Upon addition of DL 5 the solution was stirred for 30 min at 20° C. The excess of drug was quenched by addition of N-acetylcysteine (NAC) (10 mM, 10 μL, 100 nmol) followed by stirring the solution for 20 min. The quenched conjugation reaction was purified by desalting using Sephadex G25 NAP-5 columns into PBS buffer. The final target product ADC 9 was concentrated to a final concentration of 5.82 mg/mL as determined by UV and 380 μL (2.21 mg, 14.7 nmol, 111%) ADC solution was obtained. HIC HPLC runs were performed to determine the percentage of conjugation reaction (89%).

Preparation of Antibody-Drug Conjugate ADC 10 with Anti-CD13 and Compound DL 2.

(a) Partial Reduction of Anti-CD13 to Give Partially Reduced Anti-CD13.

Anti-CD13 solution (0.5 mL, 8.2 mg, 54.6 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (31.9 μL, 159.6 nmol, 3 eq.) The reduction reaction was left to stir for 90 min at 20° C. Immediately after the reduction, an Ellman assay was performed to give a Free Thiol to Antibody ratio (FTAR) of 4.7.

(b) Preparation of ADC 10.

To the solution of partially reduced Anti-CD13 (200 μL, 2 mg, 13.3 nmol), DMA was added (40 μL) followed by addition of a freshly prepared solution of DL 2 (10 mM in DMA, 10 μL, 100 nmol, 7.5 eq.). Upon addition of DL 2, the solution turned turbid. The conjugation reaction was stirred for 30 min at 20° C. The excess of drug was quenched by addition of N-acetylcysteine (NAC) (10 mM, 10 μL, 100 nmol) followed by stirring the solution for 20 min. The quenched conjugation reaction was purified by desalting using Sephadex G25 NAP-5 columns into PBS buffer. The final target product ADC 10 was concentrated to a final concentration of 6.61 mg/mL as determined by UV and 250 μL (1.65 mg, 11 nmol, 85%) ADC solution was obtained. HIC HPLC runs were performed to determine the percentage of conjugation reaction (23%).

Preparation of Antibody-Drug Conjugate ADC 11 with Trastuzumab and Compound DL 6

(a) Partial Reduction of Trastuzumab to Give Partially Reduced Trastuzumab

Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (13.9 mg/mL) was determined by measuring the absorbance at 280 nm.

Trastuzumab solution (0.33 mL, 4.6 mg, 30.6 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (17.5 μL, 87.6 nmol, 3 eq.) The reduction reaction was left to stir for 90 min at 20° C. Immediately after the reduction, an Ellman assay was performed to give a Free Thiol to Antibody ratio (FTAR) of 4.0.

(b) Preparation of ADC 11

To the solution of partially reduced Trastuzumab (140 μL, 1.4 mg, 9 nmol), DMA was added (28.2 μL) followed by addition of a freshly prepared solution of DL 6 (10 mM in DMA, 6.8 μL, 67.5 nmol, 7.5 eq.). Upon addition of DL 6, the solution turned turbid. The conjugation reaction was stirred for 30 min at 20° C. The excess of drug was quenched by addition of N-acetylcysteine (NAC) (10 mM, 6.8 μL, 67.5 nmol) followed by stirring the solution for 20 min. The quenched conjugation reaction was purified by desalting using Sephadex G25 NAP-5 columns into PBS buffer. The final target product ADC 11 was concentrated to a final concentration of 6.14 mg/mL as determined by UV and 218 μL (1.33 mg, 8.9 nmol, 99%) ADC solution was obtained. HIC HPLC runs were performed to determine the percentage of conjugation reaction (38%).

Preparation of Antibody-Drug Conjugate ADC 12 with Trastuzumab and Compound DL 7

(a) Partial Reduction of Trastuzumab to Give Partially Reduced Trastuzumab

Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (17.1 mg/mL) was determined by measuring the absorbance at 280 nm.

Trastuzumab solution (0.5 mL, 8.5 mg, 57 nmol) was diluted to a concentration of 10 mg/mL with phosphate buffer (50 mM, pH 8). Partial reduction of the disulfide bonds in the antibody was performed by the addition of a 5.0 mM tris[2-carboxyethyl]phosphine hydrochloride (TCEP) solution (24.5 μL, 122.4 nmol, 2.2 eq.) The reduction reaction was left to stir for 90 min at 20° C. Immediately after the reduction, an Ellman assay was performed to give a Free Thiol to Antibody ratio (FTAR) of 3.4.

(b) Preparation of ADC 12

To the solution of partially reduced Trastuzumab (200 μL, 2 mg, 13.2 nmol), DMA was added (42.1 μL) followed by addition of a freshly prepared solution of DL 7 (10 mM in DMA, 7.9 μL, 79 nmol, 6 eq.). Upon addition of DL 7, the solution turned turbid. The conjugation reaction was stirred for 30 min at 20° C. The excess of drug was quenched by addition of N-acetylcysteine (NAC) (10 mM, 7.9 μL, 79 nmol) followed by stirring the solution for 20 min. The quenched conjugation reaction was purified by desalting using Sephadex G25 NAP-5 columns into PBS buffer. The final target product ADC 12 was concentrated to a final concentration of 5.38 mg/mL as determined by UV and 270 μL (1.45 mg, 9.6 nmol, 72%) ADC solution was obtained. HIC HPLC runs were performed to determine the percentage of conjugation reaction (76%).

Preparation of Antibody-Drug Conjugate ADC 13 with Traut's Modified Trastuzumab and Compound DL 2

(a) Reaction of Trastuzumab with 2-iminothiolane (Traut's Reagent) to give thiol-activated Trastuzumab Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (16.1 mg/mL) was determined by measuring the absorbance at 280 nm.

Trastuzumab solution (0.5 mL, 8.0 mg, 53.7 nmol) was diluted to a concentration of 10 mg/mL using phosphate buffer (50 mM phosphate, 2 mM EDTA, pH 8). Traut's reagent was added (14 mM, 46.0 μL, 644 nmol, 12 eq.), and the reaction stirred for 2 h at 20° C. The mixture was buffer exchanged using Sephadex G25 NAP-5 columns into PBS buffer, and concentrated to a volume of 0.8 mL. Immediately after, an Ellman assay was performed to give a Free Thiol to Antibody ratio (FTAR) of 4.4.

(b) Preparation of ADC 13

To the solution of thiol-activated Trastuzumab (200 μL, 2.0 mg, 13 nmol), DMA was added (37 μL) followed by addition of a freshly prepared solution of DL 2 (10 mM in DMA, 13 μL, 130 nmol, 10 eq.). Upon addition of DL 2, the solution turned turbid. The conjugation reaction was stirred for 2 h at 25° C. and purified by desalting using a Sephadex G25 NAP-5 column into PBS buffer. The final target product ADC 13 was concentrated to a final concentration of 2.83 mg/mL as determined by UV and 340 μL (0.96 mg, 6.4 nmol, 49%) ADC solution was obtained.

Preparation of Antibody-Drug Conjugate ADC 14 with Traut's modified Trastuzumab and Compound DL 3

(a) Reaction of Trastuzumab with 2-iminothiolane (Trauct's Reagent) to give thiol-activated Trastuzumab Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (16.1 mg/mL) was determined by measuring the absorbance at 280 nm.

Trastuzumab solution (0.5 mL, 8.0 mg, 53.7 nmol) was diluted to a concentration of 10 mg/mL using phosphate buffer (50 mM phosphate, 2 mM EDTA, pH 8). Traut's reagent was added (14 mM, 46.0 μL, 644 nmol, 12 eq.), and the reaction stirred for 2 h at 20° C. The mixture was buffer exchanged using Sephadex G25 NAP-5 columns into PBS buffer, and concentrated to a volume of 0.8 mL. Immediately after, an Ellman assay was performed to give a Free Thiol to Antibody ratio (FTAR) of 4.4.

(b) Preparation of ADC 14

To the solution of thiol-activated Trastuzumab (200 μL, 2.0 mg, 13 nmol), DMA was added (37 μL) followed by addition of a freshly prepared solution of DL 3 (10 mM in DMA, 13 μL, 130 nmol, 10 eq.). Upon addition of DL 3, the solution turned turbid. The conjugation reaction was stirred for 2 h at 25° C. and purified by desalting using a Sephadex G25 NAP-5 column into PBS buffer. The final target product ADC 14 was concentrated to a final concentration of 0.75 mg/mL as determined by UV and 380 μL (0.28 mg, 1.9 nmol, 15%) ADC solution was obtained.

Preparation of Antibody-Drug Conjugate ADC 15 with Traut's modified Trastuzumab and Compound DL 5

(a) Reaction of Trastuzumab with 2-Iminothiolane (Traut's Reagent) to Give Thiol-Activated Trastuzumab Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (16.1 mg/mL) was determined by measuring the absorbance at 280 nm.

Trastuzumab solution (0.5 mL, 8.0 mg, 53.7 nmol) was diluted to a concentration of 10 mg/mL using phosphate buffer (50 mM phosphate, 2 mM EDTA, pH 8). Traut's reagent was added (14 mM, 46.0 μL, 644 nmol, 12 eq.), and the reaction stirred for 2 h at 20° C. The mixture was buffer exchanged using Sephadex G25 NAP-5 columns into PBS buffer, and concentrated to a volume of 0.8 mL. Immediately after, an Ellman assay was performed to give a Free Thiol to Antibody ratio (FTAR) of 4.4.

(b) Preparation of ADC 15

To the solution of thiol-activated Trastuzumab (200 μL, 2.0 mg, 13 nmol), DMA was added (37 μL) followed by addition of a freshly prepared solution of DL 5 (10 mM in DMA, 13 μL, 130 nmol, 10 eq.). Upon addition of DL 5, the solution turned turbid. The conjugation reaction was stirred for 2 h at 25° C. and purified by desalting using a Sephadex G25 NAP-5 column into PBS buffer. The final target product ADC 15 was concentrated to a final concentration of 1.79 mg/mL as determined by UV and 440 μL (0.79 mg, 5.2 nmol, 40%) ADC solution was obtained.

Preparation of Antibody-Drug Conjugate ADC 16 with Traut's modified Trastuzumab and Compound DL 6

(a) Reaction of Trastuzumab with 2-iminothiolane hydrochloride (Traut's reagent) to give thiol-activated Trastuzumab Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (17.1 mg/mL) was determined by measuring the absorbance at 280 nm.

Trastuzumab solution (0.25 mL, 4.3 mg, 28.5 nmol) was diluted to a concentration of 10 mg/mL using phosphate buffer (50 mM phosphate, 2 mM EDTA, pH 8). Traut's reagent was added (14 mM, 24.4 μL, 342 nmol, 12 eq.), and the reaction stirred for 2 h at 20° C. The mixture was buffer exchanged using Sephadex G25 NAP-5 columns into PBS buffer, and concentrated to a volume of 0.43 mL. Immediately after, an Ellman assay was performed to give a Free Thiol to Antibody ratio (FTAR) of 4.6.

(b) Preparation of ADC 16

To the solution of thiol-activated Trastuzumab (200 μL, 2.0 mg, 13 nmol), DMA was added (37 μL) followed by addition of a freshly prepared solution of DL 6 (10 mM in DMA, 13 μL, 130 nmol, 10 eq.). Upon addition of DL 6, the solution turned turbid. The conjugation reaction was stirred for 2 h at 25° C. and purified by desalting using a Sephadex G25 NAP-5 column into PBS buffer. The final target product ADC 16 was concentrated to a final concentration of 5.63 mg/mL as determined by UV and 230 μL (1.29 mg, 8.6 nmol, 66%) ADC solution was obtained.

Preparation of Antibody-Drug Conjugate ADC 17 with Traut's modified Trastuzumab and Compound DL 8

(a) Reaction of Trastuzumab with 2-iminothiolane (Traut's reagent) to give thiol-activated Trastuzumab Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (17.7 mg/mL) was determined by measuring the absorbance at 280 nm.

Trastuzumab solution (1.5 mL, 26.5 mg, 177 nmol) was diluted to a concentration of 10 mg/mL using phosphate buffer (50 mM phosphate, 2 mM EDTA, pH 8) and fractionated in two vials (1.3 mL each). Traut's reagent was added (14 mM, 61.8 μL, 866 nmol, 10 eq.) in each vial, and the reactions stirred for 2 h at 20° C. The reactions were mixed and buffer exchanged using Sephadex G25 NAP-10 columns into PBS buffer, and concentrated to a volume of 2.6 mL. Immediately after, an Ellman assay was performed to give a Free Thiol to Antibody ratio (FTAR) of 5.6.

(b) Preparation of ADC 17

To the solution of thiol-activated Trastuzumab (500 μL, 5.0 mg, 33 nmol), DMA was added (98.6 μL) followed by addition of a freshly prepared solution of DL 8 (10 mM in DMA, 26.4 μL, 264 nmol, 8 eq.). Upon addition of DL 8, the solution turned turbid. The conjugation reaction was stirred for 2 h at 25° C. and purified by desalting using a Sephadex G25 NAP-5 column into PBS buffer. The final target product ADC 17 was concentrated to a final concentration of 3.21 mg/mL as determined by UV and 390 μL (1.25 mg, 8.3 nmol, 25%) ADC solution was obtained.

Preparation of Antibody-Drug Conjugate ADC 18 with Traut's modified Trastuzumab and Compound DL 9

(a) Reaction of Trastuzumab with 2-iminothiolane (Traut's reagent) to give thiol-activated Trastuzumab Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (17.7 mg/mL) was determined by measuring the absorbance at 280 nm.

Trastuzumab solution (1.5 mL, 26.5 mg, 177 nmol) was diluted to a concentration of 10 mg/mL using phosphate buffer (50 mM phosphate, 2 mM EDTA, pH 8) and fractionated in two vials (1.3 mL each). Traut's reagent was added (14 mM, 61.8 μL, 866 nmol, 10 eq.) in each vial, and the reactions stirred for 2 h at 20° C. The reactions were mixed and buffer exchanged using Sephadex G25 NAP-10 columns into PBS buffer, and concentrated to a volume of 2.6 mL. Immediately after, an Ellman assay was performed to give a Free Thiol to Antibody ratio (FTAR) of 5.6.

(b) Preparation of ADC 18

To the solution of thiol-activated Trastuzumab (500 μL, 5.0 mg, 33 nmol), DMA was added (98.6 μL) followed by addition of a freshly prepared solution of DL 9 (10 mM in DMA, 26.4 μL, 264 nmol, 8 eq.). Upon addition of DL 9, the solution turned turbid. The conjugation reaction was stirred for 2 h at 25° C. and purified by desalting using a Sephadex G25 NAP-5 column into PBS buffer. The final target product ADC 18 was concentrated to a final concentration of 3.16 mg/mL as determined by UV and 390 μL (1.23 mg, 8.2 nmol, 25%) ADC solution was obtained.

Preparation of Antibody-Drug Conjugate ADC 19 with Traut's modified Trastuzumab and Compound DL 10

(a) Reaction of Trastuzumab with 2-iminothiolane (Traut's reagent) to give thiol-activated Trastuzumab Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (17.7 mg/mL) was determined by measuring the absorbance at 280 nm.

Trastuzumab solution (1.5 mL, 26.5 mg, 177 nmol) was diluted to a concentration of 10 mg/mL using phosphate buffer (50 mM phosphate, 2 mM EDTA, pH 8) and fractionated in two vials (1.3 mL each). Traut's reagent was added (14 mM, 61.8 μL, 866 nmol, 10 eq.) in each vial, and the reactions stirred for 2 h at 20° C. The reactions were mixed and buffer exchanged using Sephadex G25 NAP-10 columns into PBS buffer, and concentrated to a volume of 2.6 mL. Immediately after, an Ellman assay was performed to give a Free Thiol to Antibody ratio (FTAR) of 5.6.

(b) Preparation of ADC 19

To the solution of thiol-activated Trastuzumab (500 μL, 5.0 mg, 33 nmol), DMA was added (98.6 μL) followed by addition of a freshly prepared solution of DL 10 (10 mM in DMA, 26.4 μL, 264 nmol, 8 eq.). Upon addition of DL 10, the solution turned turbid. The conjugation reaction was stirred for 2 h at 25° C. and purified by desalting using a Sephadex G25 NAP-5 column into PBS buffer. The final target product ADC 19 was concentrated to a final concentration of 11.3 mg/mL as determined by UV and 290 μL (3.2 mg, 21.3 nmol, 64%) ADC solution was obtained.

Preparation of Antibody-Drug Conjugate ADC 20 with Traut's modified Trastuzumab and Compound DL 11

(a) Reaction of Trastuzumab with 2-iminothiolane (Traut's reagent) to give thiol-activated Trastuzumab Trastuzumab (Trastuzumab purchased from Roche as a white lyophilised powder for the preparation of a concentrated solution for infusion) was dissolved in 5 mL of phosphate buffer (50 mM, pH 8.0) and purified by desalting using Sephadex G25 PD-10 columns into phosphate buffer (50 mM, pH 8.0). Concentration of Trastuzumab (17.7 mg/mL) was determined by measuring the absorbance at 280 nm.

Trastuzumab solution (1.5 mL, 26.5 mg, 177 nmol) was diluted to a concentration of 10 mg/mL using phosphate buffer (50 mM phosphate, 2 mM EDTA, pH 8) and fractionated in two vials (1.3 mL each). Traut's reagent was added (14 mM, 61.8 μL, 866 nmol, 10 eq.) in each vial, and the reactions stirred for 2 h at 20° C. The reactions were mixed and buffer exchanged using Sephadex G25 NAP-10 columns into PBS buffer, and concentrated to a volume of 2.6 mL. Immediately after, an Ellman assay was performed to give a Free Thiol to Antibody ratio (FTAR) of 5.6.

(b) Preparation of ADC 20

To the solution of thiol-activated Trastuzumab (500 μL, 5.0 mg, 33 nmol), DMA was added (98.6 μL) followed by addition of a freshly prepared solution of DL 11 (10 mM in DMA, 26.4 μL, 264 nmol, 8 eq.). Upon addition of DL 11, the solution turned turbid. The conjugation reaction was stirred for 2 h at 25° C. and purified by desalting using a Sephadex G25 NAP-5 column into PBS buffer. The final target product ADC 20 was concentrated to a final concentration of 3.73 mg/mL as determined by UV and 440 μL (1.6 mg, 10.6 nmol, 32%) ADC solution was obtained. Example 3: Demonstrating the Cytotoxicity of the Antibody-Drug Conjugates of the Present Invention Bioassays for the Detection of Antitumor Activity The aim of the assay was to evaluate the in vitro cytostatic (ability to delay or arrest tumor cell growth) or cytotoxic (ability to kill tumor cells) activity of the samples being tested.

Cell Lines and Cell Culture

The following human cell lines were obtained from the American Type Culture Collection (ATCC): SK-BR-3 (ATCC HB-30), HCC-1954 (ATCC CRL-2338) (Breast cancer, HER2+); MDA-MB-231 (ATCC HTB-26) and MCF-7 (ATCC HTB-22) (Breast cancer, HER2−), HT-1080 (ATCC CCL-121, fibrosarcoma, CD13+), Raji (ATCC CCL-86, Burkitt's lymphoma, CD13−) and RPMI 8226 (ATCC CRM-CCL-155, myeloma, CD13−). The human acute promyelocytic leukemia cell line NB 4 (ACC 207, CD13+) was obtained from the Leibniz-Institut DSMZ (Braunschweig, Germany). Cells were maintained at 37° C., 5% $CO_2$ and 95% humidity in Dulbecco's Modified Eagle's Medium (DMEM) (for SK-BR-3, MDA-MB-231 and MCF-7 cells), Eagle's Minimum Essential Medium (EMEM) (for HT-1080 cells) or RPMI-1640 (for the rest of the cell lines), all media supplemented with 10% Fetal Calf Serum (FCS), 2 mM L-glutamine and 100 units/mL penicillin and streptomycin.

Cytotoxicity Assay

For SK-BR-3, HCC-1954, MDA-MB-231 and MCF-7 cells, a colorimetric assay using Sulforhodamine B (SRB) was adapted for quantitative measurement of cell growth and cytotoxicity, as described in V. Vichai and K. Kirtikara. Sulforhodamine B colorimetric assay for cytotoxicity screening. *Nature Protocols,* 2006, 1, 1112-1116. Briefly, cells were seeded in 96-well microtiter plates and allowed to stand for 24 hours in drug-free medium before treatment with vehicle alone or with the tested substances for 72 hours. For quantification, cells were washed twice with phosphate buffered saline (PBS), fixed for 15 min in 1% glutaraldehyde solution, rinsed twice with PBS, stained in 0.4% (w/v) SRB with 1% (v/v) acetic acid solution for 30 min, rinsed several times with 1% acetic acid solution and air-dried. SRB was then extracted in 10 mM Trizma base solution and the optical density measured at 490 nm in a microplate spectrophotometer.

For HT-1080, NB 4, Raji and RPMI-8226 cells, an alternative colorimetric assay based on the reduction of 3-(4,5-dimethylthiazol-2-yl)-2,5-diphenyltetrazolium bromide (MTT) was used for quantitative measurement of cell viability as described by T. Mosmann in "Rapid colorimetric assay for cellular growth and survival: application to proliferation and cytotoxicity assays", J Immunol Methods, 1983, 65: 55-63. Briefly, cells were seeded in 96-well trays and treated as above and after 72 hours of exposure to the tested substances cellular viability was estimated from conversion of MTT (Sigma, St Louis, MO, USA) to its coloured reaction product, MTT-formazan, which was dissolved in DMSO to measure its absorbance at 540 nm in a microplate spectrophotometer.

Cell survival was expressed as percentage of control, untreated cell survival. All evaluations were performed in triplicate and the resulting data were fitted by nonlinear regression to a four-parameters logistic curve from which the $IC_{50}$ value (the concentration of compound causing 50% cell death as compared to the control cell survival) was calculated.

Bioactivity Example 1—Cytotoxicity of the Conjugate ADC 1 and Related Reagents Against HER2 Positive and Negative Breast Cancer Cells The in vitro cytotoxicity of the ADC 1 along with the parent cytotoxic compounds DL 1 and 11-R and Trastuzumab were evaluated against four different human breast cancer cell lines over-expressing or not the HER2 receptor, including SK-BR-3, HCC-1954 (HER2-positive cells) as well as MDA-MB-231 and MCF-7 (HER2-negative cells). Standard dose-response (DR) curves for 72 hours incubation with the tested substances were performed.

Cytotoxicity of Trastuzumab

The in vitro cytotoxicty of Trastuzumab was evaluated against the different tumor cell lines by performing triplicate 10-points, 2.5-fold dilution DR curves ranging from 50 to 0.01 μg/mL (3.33E-07-8.74E-11 M). Trastuzumab was completely inactive, not reaching the $IC_{50}$ in any of the cell lines tested, independently of their HER2 status as shown in Table 10 where results corresponding to the geometric mean of the $IC_{50}$ values obtained in three independent experiments are presented.

TABLE 10

Summary of the in vitro cytotoxicity of Trastuzumab.

| | HER2 positive | | HER2 negative | |
|---|---|---|---|---|
| | SK-BR-3 | HCC-1954 | MDA-MB-231 | MCF-7 |
| $IC_{50}$, μg/mL | >50 | >50 | >50 | >50 |
| $IC_{50}$, M | >3.4E−07 | >3.4E−07 | >3.4E−07 | >3.4E−07 |

Cytotoxicity of 11-R

The cytotoxicity of the intermediate compound 11-R was evaluated against the different tumor cell lines by performing triplicate 10-points, 2.5-fold dilution DR curves ranging from 100 to 0.03 ng/mL (1.26E-07-3.3E-11 M).

As shown in Table 11, where results corresponding to the geometric mean of the $IC_{50}$ values obtained in three independent experiments are presented, the cytotoxicity of this compound was similar in all the tumor cell lines regardless of their HER2 expression, with $IC_{50}$ values in the low nanomolar range, from 0.4 to 1.4 ng/mL (5.04E-10 to 1.70E-09 M). The geometric mean $IC_{50}$ value across the whole cell panel was 0.79 ng/mL (9.94E-10 M), with the standard geometric deviation being 1.8 in agreement with the homogeneity of results across the four cell lines.

TABLE 11

Summary of the in vitro cytotoxicity of 11-R

| | HER2 positive | | HER2 negative | |
|---|---|---|---|---|
| | SK-BR-3 | HCC-1954 | MDA-MB-231 | MCF-7 |
| $IC_{50}$, μg/mL | 5.76E−04 | 1.35E−03 | 3.99E−04 | 1.24E−03 |
| $IC_{50}$, M | 7.27E−10 | 1.70E−09 | 5.04E−10 | 1.57E−09 |

experiments and Table 13 summarizes the results corresponding to the geometric mean of the $IC_{50}$ values obtained in the three independent experiments.

As observed in Table 13, ADC 1 showed a cytotoxicity which is similar to that shown by the parent drug 11-R only in HER2-positive cells. However, in HER2-negative cells such toxicity is significantly lower: nearly 40-fold lower according to the selectivity ratio obtained by dividing the mean $IC_{50}$ value in HER2-negative cells between that in HER2-positive cells. This selectivity leads us to conclude that the conjugate is acting through the interaction of the antibody with the membrane associated HER2 receptor on the tumor cells, followed by intracellular delivery of the cytotoxic drug.

TABLE 13

Summary of the in vitro cytotoxicity of ADC 1

| | HER2 positive | | HER2 negative | | IC50 in HER2+ (geom. | IC50 in HER2− (geom. | Selec. |
|---|---|---|---|---|---|---|---|
| | SK-BR-3 | HCC-1954 | MDA-MB-231 | MCF-7 | mean) | mean | ratio |
| $IC_{50}$ (μg/mL) | 3.20E−01 | 1.38E+00 | 1.36E+01 | 4.90E+01 | 6.64E−01 | 2.58E01 | 38.8 |
| $IC_{50}$ (M) | 2.14E−09 | 9.20E−09 | 9.04E−08 | 3.27E−07 | 4.44E−09 | 1.72E−07 | |

Cytotoxicity of DL 1

The cytotoxicity of the intermediate compound DL 1 was evaluated against the different tumor cell lines by performing triplicate 10-points, 2.5-fold dilution DR curves ranging from 10 μg/mL to 2.6 ng/mL (7.58E-06-1.99E-09 M).

As shown in Table 12, where results corresponding to the geometric mean of the $IC_{50}$ values obtained in three independent experiments are presented, the cytotoxicity of this compound was similar in all the tumor cell lines regardless of their HER2 expression, with $IC_{50}$ values in the high nanomolar range, from 0.07 to 0.43 μg/mL (5.23E-08 to 3.11 E-07 M). The geometric mean $IC_{50}$ value across the whole cell panel was 0.16 μg/mL (1.15E-07 M), with the standard geometric deviation being 2.1 in agreement with the homogeneity of results across the four cell lines.

TABLE 12

Summary of the in vitro cytotoxicity of DL 1

| | HER2 positive | | HER2 negative | |
|---|---|---|---|---|
| | SK-BR-3 | HCC-1954 | MDA-MB-231 | MCF-7 |
| $IC_{50}$, μg/mL | 1.16E−01 | 1.80E−01 | 7.28E−02 | 4.33E−01 |
| $IC_{50}$, M | 8.31E−08 | 1.29E−07 | 5.23E−08 | 3.11E−07 |

Cytotoxicity of ADC 1

Figure 3:
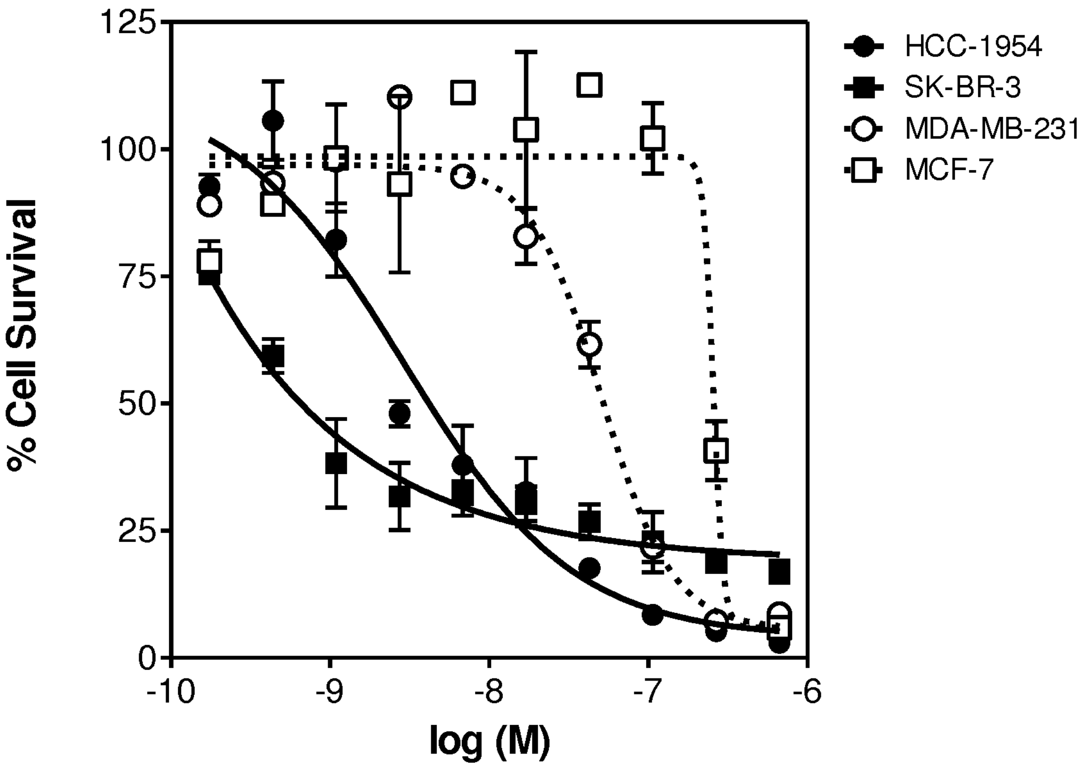
FIG. 3. Dose-response curves corresponding to one representative experiment conducted to evaluate the antiproliferative potential of the ADC 1 in HER2-positive (black symbols) or HER2-negative (hollow symbols) cell lines. Dots correspond to the average of triplicates with error bars denoting SD, drawing lines correspond to the best fitting by nonlinear regression of the experimental points to a four-parameters logistic curve used to obtain the $IC_{50}$ values reported in Table 13.
Figure 4:
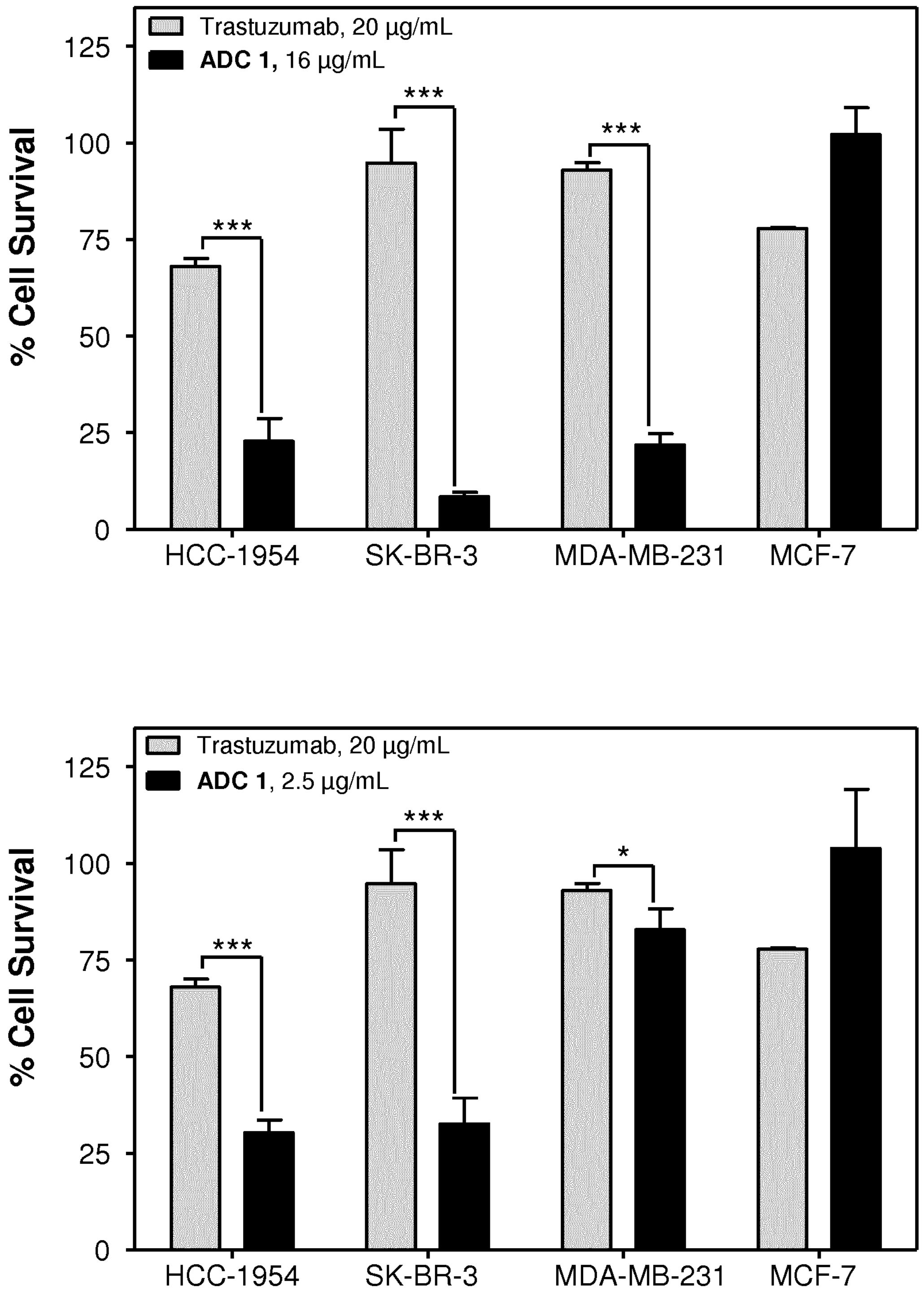
FIG. 4. Histograms showing the effect on cell survival of either Trastuzumab at 20 μg/mL or the ADC 1 at 16 or 2.5 μg/mL in several cell lines, either HER2-positive (SK-BR-3 and HCC-1954) or HER2-negative (MDA-MB-231 and MCF-7). Bars correspond to the average of three determinations with error bars denoting SD. Statistical significance was measured using an unpaired two-tailed t-test, p values are summarized as follows:***, p<0.001; *, p<0.01; *, p<0.05.

The cytotoxicity of the ADC 1 was evaluated against the different tumor cell lines by performing triplicate 10-points, 2.5-fold dilution DR curves ranging from 100 μg/mL to 26 ng/mL (6.67E-07-1.75E-10 M). The evaluation was performed in three independent experiments, FIG. 3 shows a representative DR curve corresponding to one of these experiments To graphically compare the cytotoxicity of the monoclonal antibody Trastuzumab alone with that of the conjugate ADC 1, histograms showing the percentages of cell survival after treatment of the different cell lines with the monoclonal antibody alone (20 μg/mL) or ADC 1 at 16 or 2.5 μg/mL, are shown in FIG. 4. As observed, at similar concentrations (20 versus 16 μg/mL) Trastuzumab showed negligible cytotoxicity regardless the HER2 expression levels of the cell lines (cell survival between 68% and 100%), whilst the ADC 1 showed a potent antiproliferative effect against the HER2-expressing cells HCC-1954 and SK-BR-3 (cell survival 23% and 8% respectively) and negligible against the HER2-negative cell line MCF-7 (100% cell survival). The effect of the ADC on MDA-MB-231 is noticeable at this concentration (22% cell survival) but it is very modest at lower concentrations (83% cell survival at 2.5 μg/mL) whereas it is still remarkable in the HER2-expressing cells (30% cell survival for both SK-BR-3 and HCC-1954).

These results clearly demonstrated the remarkable cytotoxicity and specificity of the ADC 1 against HER2 expressing human tumor cells in vitro.

Bioactivity Example 2—Cytotoxicity of the Conjugate ADC 2 and Related Reagents Against HER2 Positive and Negative Breast Cancer Cells The in vitro cytotoxicity of the ADC 2 along with the parent cytotoxic compound DL 2 was evaluated against four different human breast cancer cell lines over-expressing or not the HER2 receptor, including SK-BR-3, HCC-1954 (HER2 positive cells) as well as MDA-MB-231 and MCF-7 (HER2 negative cells). Standard dose-response (DR) curves for 72 hours incubation with the tested substances were performed. The results are also compared with the parent cytotoxic compound 11-R and the monoclonal antibody Trastuzumab described above.

Cytotoxicity of DL 2

The cytotoxicity of the intermediate compound DL 2 was evaluated against the different tumor cell lines by performing triplicate 10-points, 2.5-fold dilution DR curves ranging from 10 μg/mL to 2.6 ng/mL (6.26E-06-1.64E-09 M).

As shown in Table 14, the cytotoxicity of this compound was similar in all the tumor cell lines regardless of their HER2 expression, with $IC_{50}$ values in the sub-micromolar range, from 0.2 to 0.47 μg/mL (1.25E-07 to 2.94E-07 M). The geometric mean $IC_{50}$ value across the whole cell panel was 0.28 μg/mL (1.73E-07 M), with the standard geometric deviation being 1.5 in agreement with the homogeneity of results across the four cell lines.

TABLE 14

Summary of the in vitro cytotoxicity of DL 2

| | HER2 positive | | HER2 negative | |
|---|---|---|---|---|
| | SK-BR-3 | HCC-1954 | MDA-MB-231 | MCF-7 |
| $IC_{50}$, μg/mL | 2.00E−01 | 3.10E−01 | 2.00E−01 | 4.69E−01 |
| $IC_{50}$, M | 1.25E−07 | 1.94E−07 | 1.25E−07 | 2.94E−07 |

Cytotoxicity of ADC 2

Figure 5:
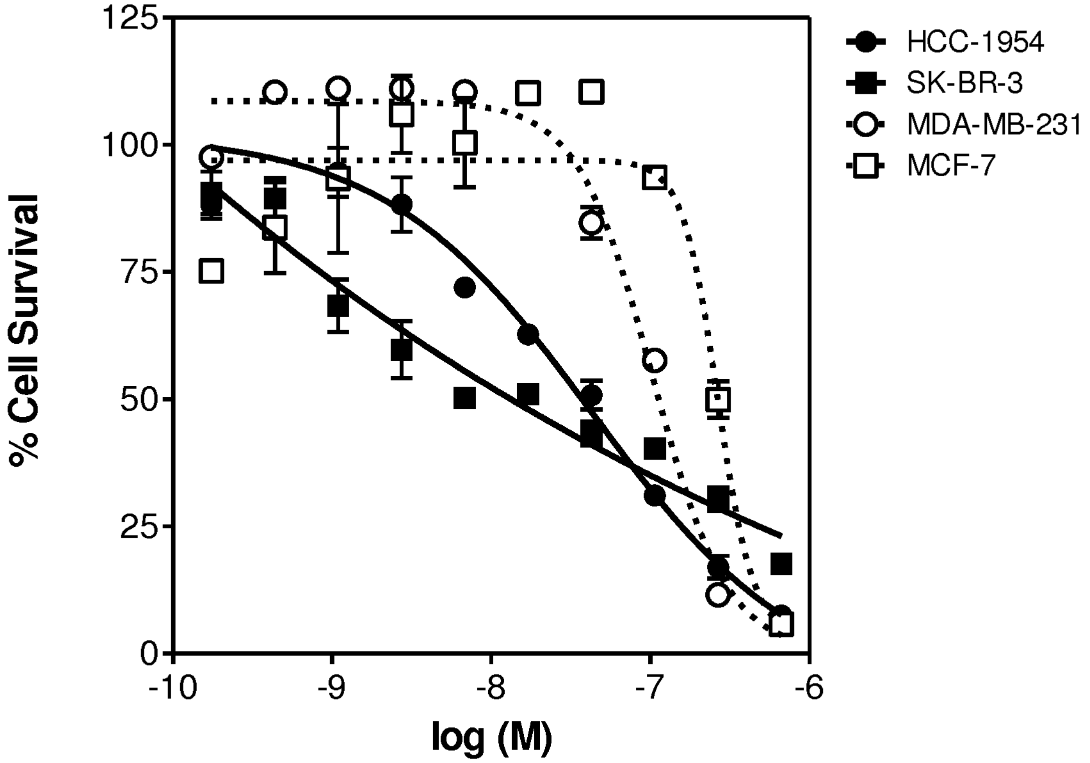
FIG. 5. Dose-response curves showing the antiproliferative potential of the ADC 2 in HER2-positive (black symbols) or HER2-negative (hollow symbols) cell lines. Dots correspond to the average of triplicates with error bars denoting SD, drawing lines correspond to the best fitting by nonlinear regression of the experimental points to a four-parameters logistic curve used to obtain the $IC_{50}$ values reported in Table 15.

The cytotoxicity of the ADC 2 was evaluated against the different tumor cell lines by performing triplicate 10-points, 2.5-fold dilution DR curves ranging from 100 μg/mL to 26 ng/mL (6.67E-07-1.75E-10 M). FIG. 5 shows the DR curve corresponding to this experiment and Table 15 summarizes the $IC_{50}$ values obtained.

As observed in Table 15, ADC 2 showed higher cytotoxicity in HER2-positive cells than in HER2-negative cells: the ADC is nearly 10-fold more potent in the former according to the selectivity ratio obtained by dividing the mean $IC_{50}$ value in HER2-negative cells between that in HER2-positive cells. Although this selectivity is rather modest, it still leads us to conclude that the conjugate is acting through the interaction of the antibody with the membrane associated HER2 receptor on the tumor cells, followed by intracellular delivery of the cytotoxic drug.

TABLE 15

Summary of the in vitro cytotoxicity of ADC 2

| | HER2 positive | | HER2 negative | | IC50 in HER2+ (geom. | IC50 in HER2− (geom. | Selec. |
|---|---|---|---|---|---|---|---|
| | SK-BR-3 | HCC-1954 | MDA-MB-231 | MCF-7 | mean) | mean | ratio |
| $IC_{50}$ (μg/mL) | 2.00E+00 | 5.60E+00 | 1.70E+01 | 4.01E+01 | 3.34E+00 | 2.61E+01 | 7.8 |
| $IC_{50}$ (M) | 1.33E−08 | 3.73E−08 | 1.13E−07 | 2.67E−07 | 2.23E−08 | 1.74E−07 | |

Figure 6:
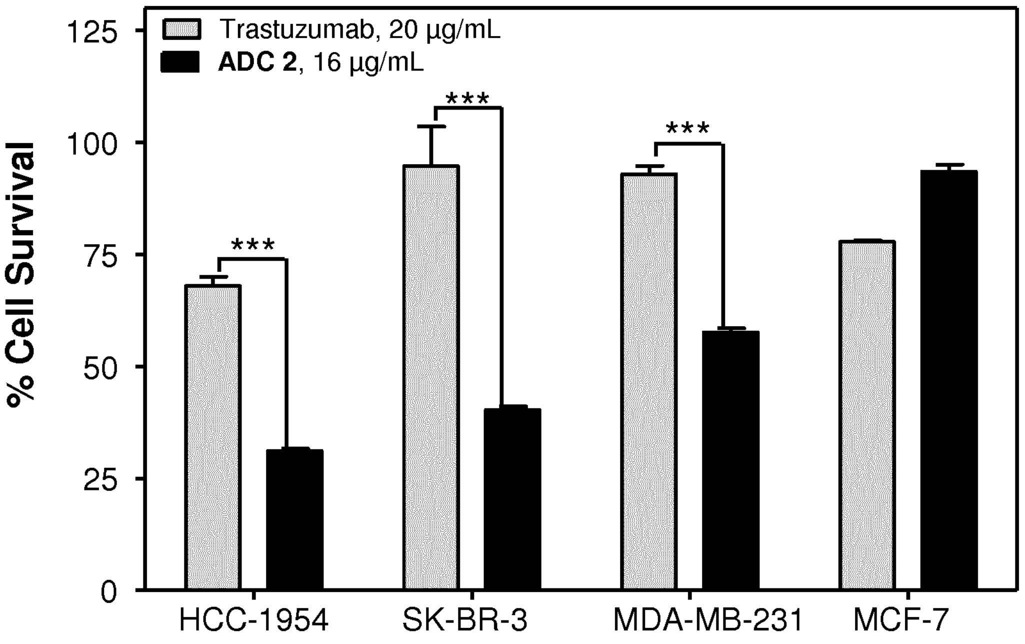
FIG. 6. Histograms showing the effect on cell survival of either Trastuzumab at 20 μg/mL or the ADC 2 at 16 or 2.5 μg/mL in several cell lines, either HER2-positive (SK-BR-3 and HCC-1954) or HER2-negative (MDA-MB-231 and MCF-7). Bars correspond to the average of three determinations with error bars denoting SD. Statistical significance was measured using an unpaired two-tailed t-test, p values are summarized as follows: ***, p<0.001; *, p<0.01; *, p<0.05.
Figure 6:
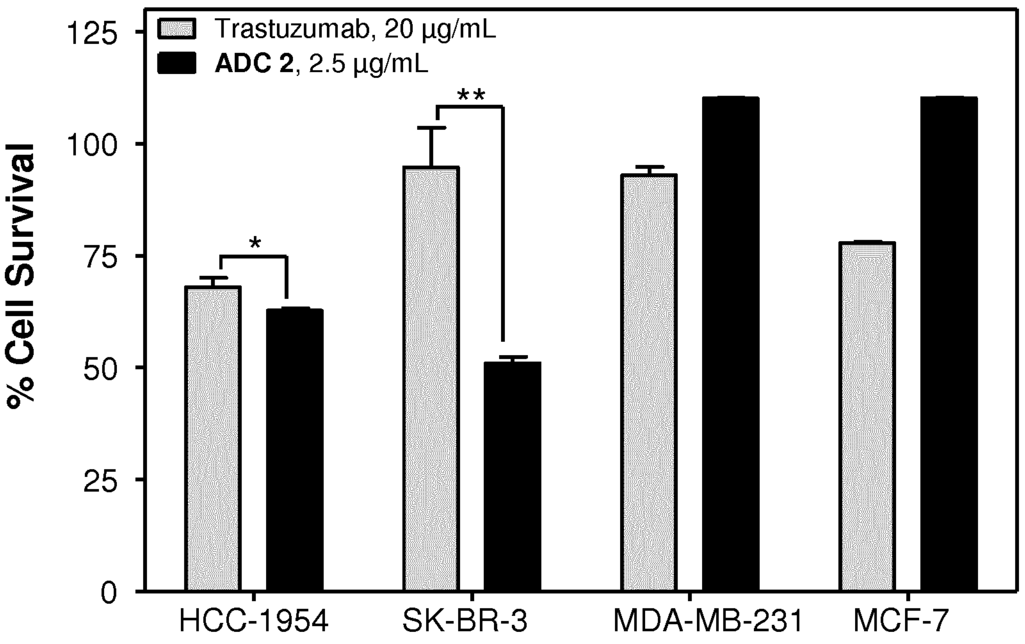

To graphically compare the cytotoxicity of the monoclonal antibody Trastuzumab alone with that of the conjugate ADC 2, histograms showing the percentages of cell survival after treatment of the different cell lines with the monoclonal antibody alone (20 μg/mL) or ADC 2 at 16 or 2.5 μg/mL, are shown in FIG. 6. As observed, at similar concentrations (20 versus 16 μg/mL) Trastuzumab showed negligible cytotoxicity disregarding the HER2 expression levels of the cell lines (cell survival between 68% and 100%), whilst the ADC 2 showed a significant antiproliferative effect against the HER2-expressing cells HCC-1954 and SK-BR-3 (cell survival 31% and 40% respectively), such effect being negligible against the HER2-negative cell line MCF-7 (94% cell survival). The effect of the ADC on the HER2-negative cell line MDA-MB-231 is also significant at this concentration, (58% cell survival) but it is null at lower concentrations (100% cell survival at 2.5 μg/mL) whereas it is still remarkable in the HER2-expressing cells (63% cell survival for HCC-1954 and 51% for SK-BR-3).

Bioactivity Example 3—Cytotoxicity of the Conjugate ADC 3 and Related Reagents Against HER2 Positive and Negative Breast Cancer Cells The in vitro cytotoxicity of the ADC 3 along with the parent cytotoxic compound DL 3 was evaluated against four different human breast cancer cell lines over-expressing or not the HER2 receptor, including SK-BR-3, HCC-1954 (HER2 positive cells) as well as MDA-MB-231 and MCF-7 (HER2 negative cells). Standard dose-response (DR) curves for 72 hours incubation with the tested substances were performed. The results are also compared with the parent cytotoxic compound 11-R and the monoclonal antibody Trastuzumab described above.

Cytotoxicity of DL 3

The cytotoxicity of the intermediate compound DL 3 was evaluated against the different tumor cell lines by performing triplicate 10-points, 2.5-fold dilution DR curves ranging from 10 μg/mL to 2.6 ng/mL (6.62E-06-1.74E-09 M).

As shown in Table 16, the cytotoxicity of this compound was similar in all the tumor cell lines regardless of their HER2 expression, with $IC_{50}$ values in the sub-micromolar range, from 0.15 to 0.28 μg/mL (9.93E-08 to 1.85E-07 M). The geometric mean $IC_{50}$ value across the whole cell panel was 0.2 μg/mL (1.33E-07 M), with the standard geometric deviation being 1.4 in agreement with the homogeneity of results across the four cell lines.

TABLE 16

Summary of the in vitro cytotoxicity of DL 3

| | HER2 positive | | HER2 negative | |
|---|---|---|---|---|
| | SK-BR-3 | HCC-1954 | MDA-MB-231 | MCF-7 |
| $IC_{50}$, μg/mL | 1.60E−01 | 2.40E−01 | 1.50E−01 | 2.79E−01 |
| $IC_{50}$, M | 1.06E−07 | 1.59E−07 | 9.93E−08 | 1.85E−07 |

Cytotoxicity of ADC 3

Figure 7:
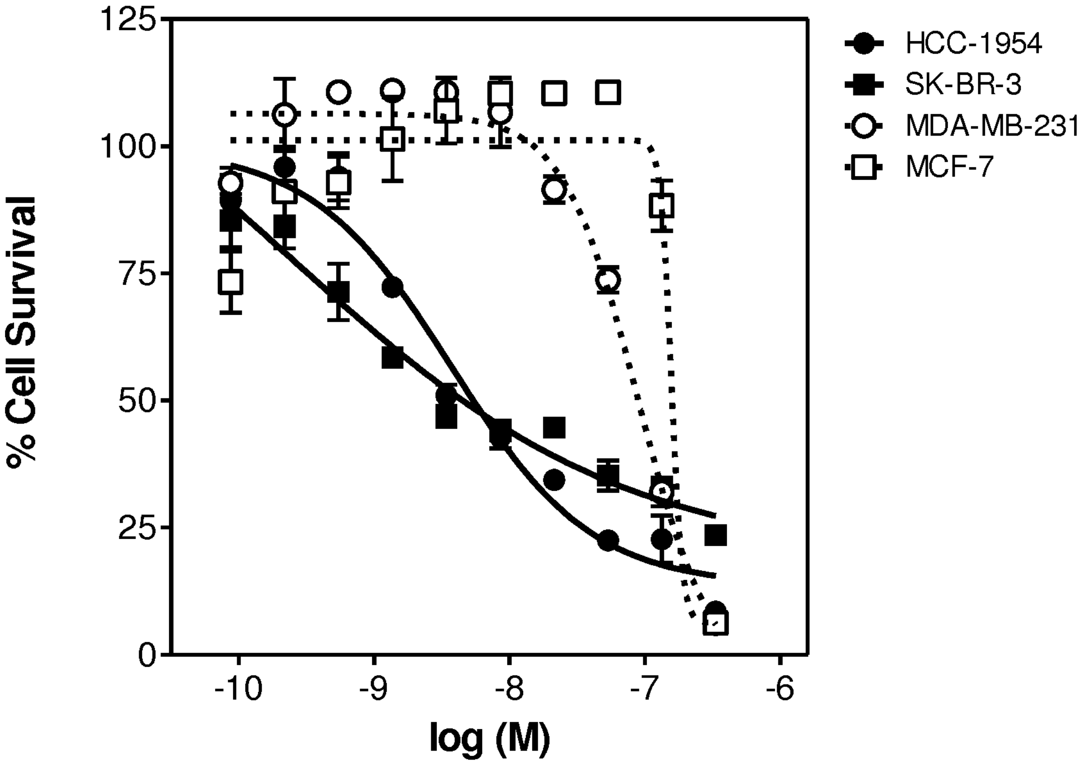
FIG. 7. Dose-response curves showing the antiproliferative potential of the ADC 3 in HER2-positive (black symbols) or HER2-negative (hollow symbols) cell lines. Dots correspond to the average of triplicates with error bars denoting SD, drawing lines correspond to the best fitting by nonlinear regression of the experimental points to a four-parameters logistic curve used to obtain the $IC_{50}$ values reported in Table 17.

The cytotoxicity of the ADC 3 was evaluated against the different tumor cell lines by performing triplicate 10-points, 2.5-fold dilution DR curves ranging from 50 μg/mL to 13 ng/mL (3.33E-07-8.74E-11 M). FIG. 7 shows the DR curve corresponding to this experiment and Table 17 summarizes the $IC_{50}$ values obtained.

As observed in Table 17, ADC 3 showed a cytotoxicity which only in HER2-positive cells is similar to that shown by the parent drug 11-R. However, in HER2-negative cells such toxicity is significantly lower: 23-fold lower according to the selectivity ratio obtained by dividing the mean $IC_{50}$ value in HER2-negative cells between that in HER2-positive cells. This selectivity leads us to conclude that the conjugate is acting through the interaction of the antibody with the membrane associated HER2 receptor on the tumor cells, followed by intracellular delivery of the cytotoxic drug as previously stated for ADC 1 and ADC 2.

TABLE 17

Summary of the in vitro cytotoxicity of ADC 3

| | HER2 positive | | HER2 negative | | IC50 in HER2+ (geom. | IC50 in HER2− (geom. | Selec. |
|---|---|---|---|---|---|---|---|
| | SK-BR-3 | HCC-1954 | MDA-MB-231 | MCF-7 | mean) | mean | ratio |
| $IC_{50}$ (µg/mL) | 6.71E−01 | 8.10E−01 | 1.30E+01 | 2.21E+01 | 7.37E−01 | 1.70E+01 | 23.0 |
| $IC_{50}$ (M) | 4.47E−09 | 5.40E−09 | 8.67E−08 | 1.47E−07 | 4.91E−09 | 1.13E−07 | |

Figure 8:
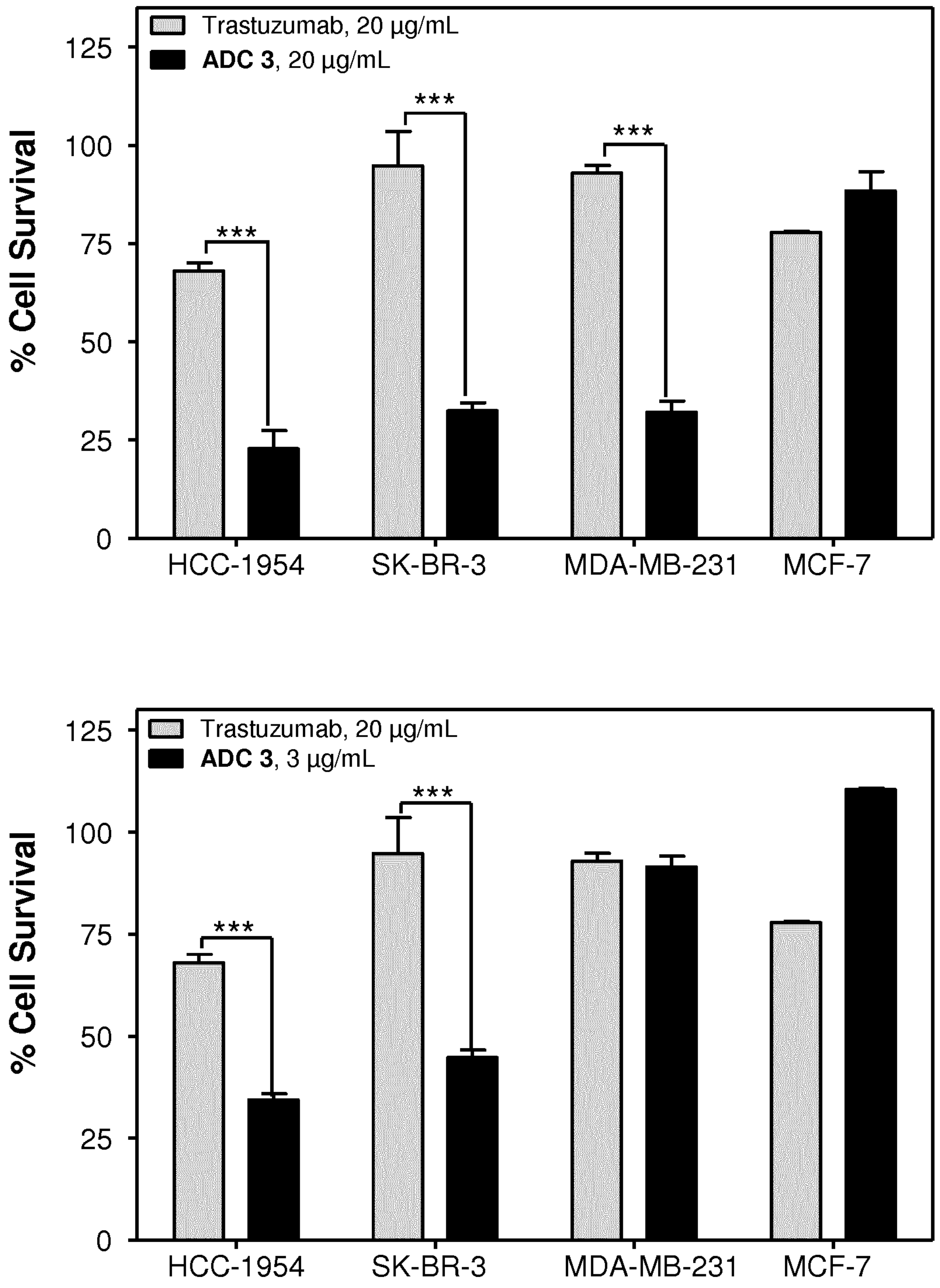
FIG. 8. Histograms showing the effect on cell survival of either Trastuzumab at 20 μg/mL or the ADC 3 at 20 or 3 μg/mL in several cell lines, either HER2-positive (SK-BR-3 and HCC-1954) or HER2-negative (MDA-MB-231 and MCF-7). Bars correspond to the average of three determinations with error bars denoting SD. Statistical significance was measured using an unpaired two-tailed t-test, p values are summarized as follows: ***, p<0.001; *, p<0.01; *, p<0.05.

To graphically compare the cytotoxicity of the monoclonal antibody Trastuzumab alone with that of the conjugate ADC 3, histograms showing the percentages of cell survival after treatment of the different cell lines with the monoclonal antibody alone (20 µg/mL) or ADC 3 at 20 or 3 µg/mL, are shown in FIG. 8. As observed, at 20 µg/mL Trastuzumab showed negligible cytotoxicity regardless the HER2 expression levels of the cell lines (cell survival between 68% and 100%), whilst the ADC 3 showed a potent antiproliferative effect against the HER2-expressing cells HCC-1954 and SK-BR-3 (cell survival 23% and 32% respectively) and only marginal against the HER2-negative cell line MCF-7 (88% cell survival). The effect of the ADC on MDA-MB-231 is noticeable at this concentration (32% cell survival) but it is negligible at lower concentrations (91% cell survival at 3 µg/mL) whereas it is still remarkable in the HER2-expressing cells (34% cell survival for HCC-1954 and 45% for SK-BR-3).

Bioactivity Example 4—Cytotoxicity of the Conjugate ADC 4 Against HER2 Positive and Negative Breast Cancer Cells The in vitro cytotoxicity of the ADC ADC 4 was evaluated against four different human breast cancer cell lines over-expressing or not the HER2 receptor, including SK-BR-3, HCC-1954 (HER2 positive cells) as well as MDA-MB-231 and MCF-7 (HER2 negative cells). Standard dose-response (DR) curves for 72 hours incubation with the ADC were performed. The results are also compared with the parent cytotoxic compounds 11-R and DL 1 as well as the monoclonal antibody Trastuzumab described above.

Cytotoxicity of ADC 4

Figure 9:
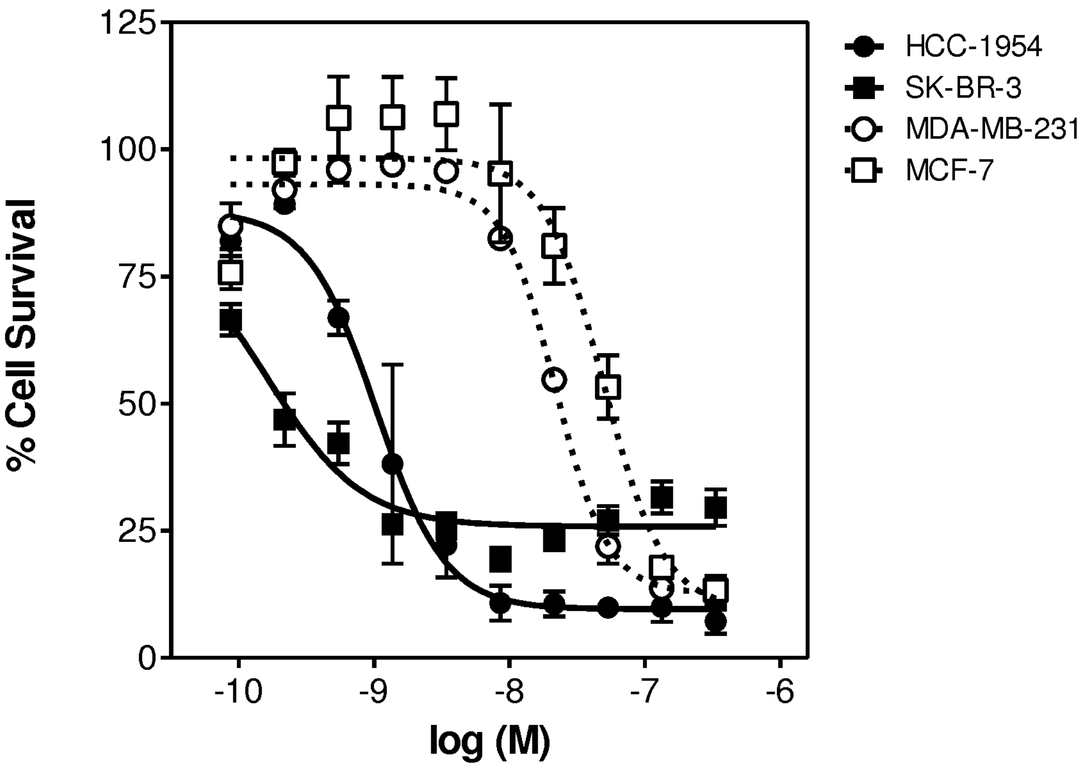
FIG. 9. Dose-response curves showing the antiproliferative potential of the ADC 4 in HER2-positive (black symbols) or HER2-negative (hollow symbols) cell lines. Dots correspond to the average of triplicates with error bars denoting SD, drawing lines correspond to the best fitting by nonlinear regression of the experimental points to a four-parameters logistic curve used to obtain the $IC_{50}$ values reported in Table 18.

The cytotoxicity of the ADC 4 was evaluated against the different tumor cell lines by performing triplicate 10-points, 2.5-fold dilution DR curves ranging from 50 µg/mL to 13 ng/mL (3.33E-07-8.74E-11 M). FIG. 9 shows the DR curve corresponding to this experiment and Table 18 summarizes the $IC_{50}$ values obtained.

As observed in Table 18, ADC 4 showed a cytotoxicity which only in HER2-positive cells is similar to that shown by the parent drug 11-R. However, in HER2-negative cells such cytotoxicity is nearly 100-fold lower according to the selectivity ratio obtained by dividing the mean $IC_{50}$ value in HER2-negative cells between that in HER2-positive cells. As already stated for ADC 1, such selectivity leads us to conclude that the conjugate is acting through the interaction of the antibody with the membrane associated HER2 receptor on the tumor cells, followed by intracellular delivery of the cytotoxic drug. Moreover, these results obtained with ADC 4 demonstrate that the antitumoral potential endowed by the payload is similar regardless of the antibody residue involved in the covalent bond, either Cys or Lys.

TABLE 18

Summary of the in vitro cytotoxicity of ADC 4

| | HER2 positive | | HER2 negative | | IC50 in HER2+ (geom. | IC50 in HER2− (geom. | Selec. |
|---|---|---|---|---|---|---|---|
| | SK-BR-3 | HCC-1954 | MDA-MB-231 | MCF-7 | mean) | mean | ratio |
| $IC_{50}$ (µg/mL) | 3.20E−02 | 1.50E−01 | 3.50E+00 | 8.10E+00 | 6.92E−02 | 5.32E+00 | 76.86 |
| $IC_{50}$ (M) | 2.13E−10 | 1.00E−09 | 2.33E−08 | 5.40E−08 | 4.62E−10 | 3.55E−08 | |

Figure 10:
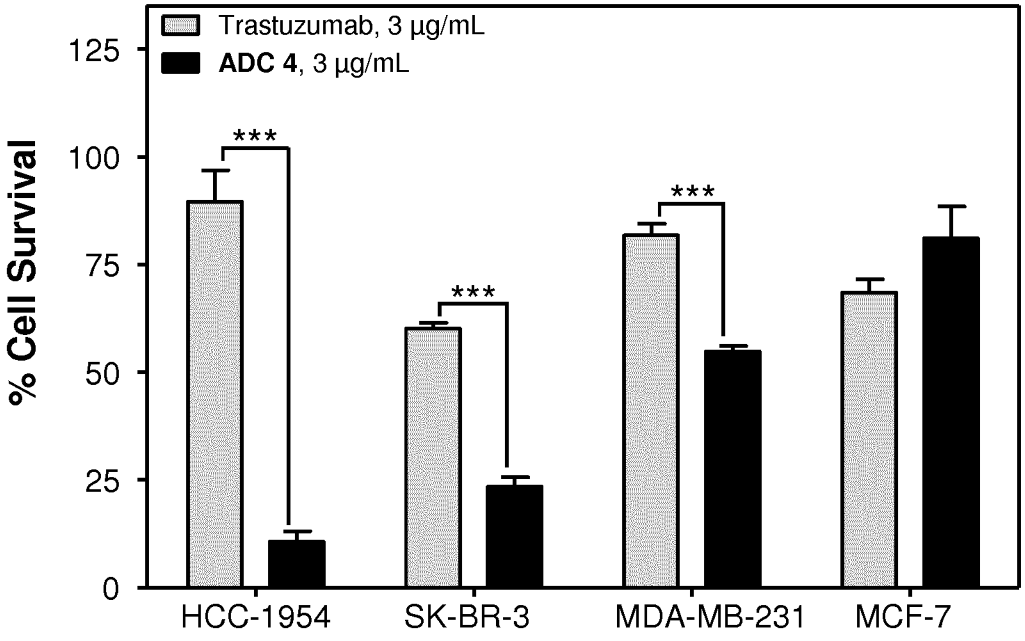
FIG. 10. Histograms showing the effect on cell survival of either Trastuzumab at 3 μg/mL or the ADC 4 at 3 or 0.2 μg/mL in several cell lines, either HER2-positive (SK-BR-3 and HCC-1954) or HER2-negative (MDA-MB-231 and MCF-7). Bars correspond to the average of three determinations with error bars denoting SD. Statistical significance was measured using an unpaired two-tailed t-test, p values are summarized as follows: ***, $p<0.001$; *, $p<0.01$; *, $p<0.05$.
Figure 10:
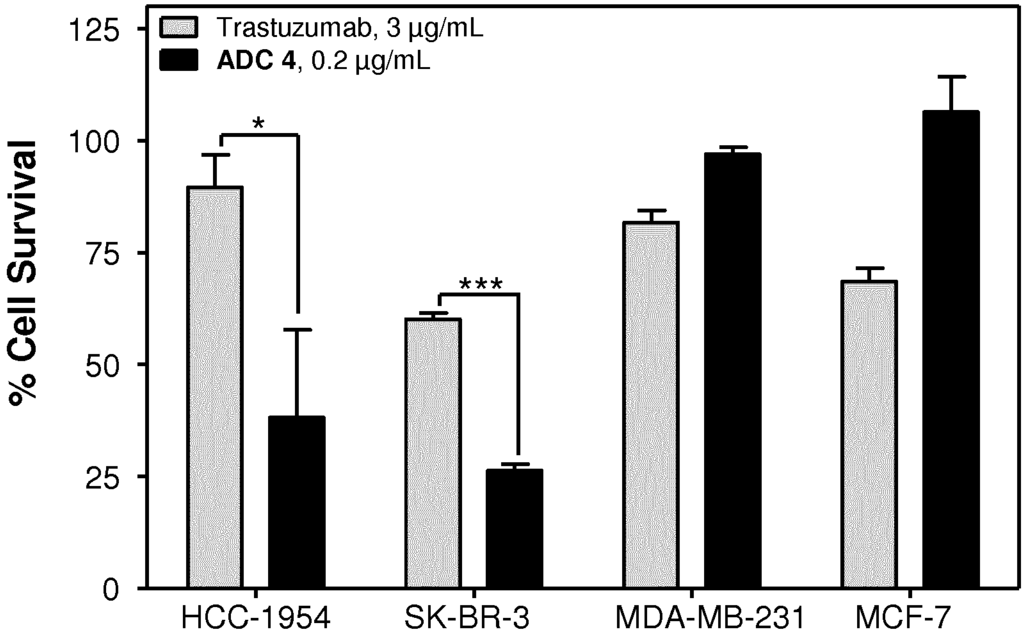

To graphically compare the cytotoxicity of the monoclonal antibody Trastuzumab alone with that of the conjugate ADC 4, histograms showing the percentages of cell survival after treatment of the different cell lines with the monoclonal antibody alone at 3 µg/mL or with the ADC at 3 or 0.2 µg/mL, are shown in FIG. 10. As observed, at 3 µg/mL Trastuzumab showed scarce cytotoxicity irrespective of the HER2 expression levels of the cell lines (cell survival between 60% and 90%), whilst the ADC 4 showed a potent antiproliferative effect against the HER2-expressing cells HCC-1954 and SK-BR-3 (cell survival 11% and 23% respectively) and nearly no effect on the HER2-negative cell line MCF-7. The effect of the ADC on the cell line MDA-MB-231 is noticeable at this concentration (55% cell survival) but it is negligible at lower concentrations (97-100% cell survival at 0.2 µg/mL) whereas it is clearly remarkable in the HER2-expressing cells (38% cell survival for HCC-1954 and 26% for SK-BR-3).

Bioactivity Example 5—Cytotoxicity of the Conjugate ADC 6 and Related Reagents Against HER2 Positive and Negative Breast Cancer Cells The in vitro cytotoxicity of the ADC 6 along with the parent cytotoxic compounds DL 5 and 12 R and were evaluated against four different human breast cancer cell lines over-expressing or not the HER2 receptor, including SK-BR-3, HCC-1954 (HER2-positive cells) as well as MDA-MB-231 and MCF-7 (HER2-negative cells). Standard dose-response (DR) curves for 72 hours incubation with the tested substances were performed.

Cytotoxicity of 12-R

The cytotoxicity of the intermediate compound 12-R was evaluated against the different tumor cell lines by performing triplicate 10-points, 2.5-fold dilution DR curves ranging from 100 to 0.03 ng/mL (1.28E-07-3.83E-11 M).

As shown in Table 19, where results corresponding to the geometric mean of the $IC_{50}$ values obtained in three independent experiments are presented, the cytotoxicity of this compound was similar in all the tumor cell lines regardless of their HER2 expression, with $IC_{50}$ values in the low nanomolar range, from 0.4 to 1.3 ng/mL (5.62E-10 to 1.62E-09 M). The geometric mean $IC_{50}$ value across the whole cell panel was 0.71 ng/mL (9.06E-10 M), with the standard geometric deviation being 1.7 in agreement with the homogeneity of results across the four cell lines.

TABLE 19

Summary of the in vitro cytotoxicity of 12-R

| | HER2 positive | | HER2 negative | |
|---|---|---|---|---|
| | SK-BR-3 | HCC-1954 | MDA-MB-231 | MCF-7 |
| $IC_{50}$, μg/mL | 4.41E−04 | 1.27E−03 | 4.93E−04 | 9.24E−04 |
| $IC_{50}$, M | 5.62E−10 | 1.62E−09 | 6.29E−10 | 1.18E−09 |

Cytotoxicity of DL 5

The cytotoxicity of the intermediate compound DL 5 was evaluated against the different tumor cell lines by performing triplicate 10-points, 2.5-fold dilution DR curves ranging from 10 μg/mL to 2.6 ng/mL (6.66E-06-1.73E-09 M).

As shown in Table 20, the cytotoxicity of this compound was similar in all the tumor cell lines regardless of their HER2 expression, with $IC_{50}$ values in the high nanomolar range, from 0.10 to 0.19 μg/mL (6.53E-08 to 1.27E-07 M). The geometric mean $IC_{50}$ value across the whole cell panel was 0.13 μg/mL (8.84E-08 M), with the standard geometric deviation being 1.4 in agreement with the homogeneity of results across the four cell lines.

TABLE 20

Summary of the in vitro cytotoxicity of DL 5

| | HER2 positive | | HER2 negative | |
|---|---|---|---|---|
| | SK-BR-3 | HCC-1954 | MDA-MB-231 | MCF-7 |
| $IC_{50}$, μg/mL | 9.81E−02 | 1.91E−01 | 9.81E−02 | 1.70E−01 |
| $IC_{50}$, M | 6.53E−08 | 1.27E−07 | 6.53E−08 | 1.13E−07 |

Cytotoxicity of ADC 6

Figure 11:
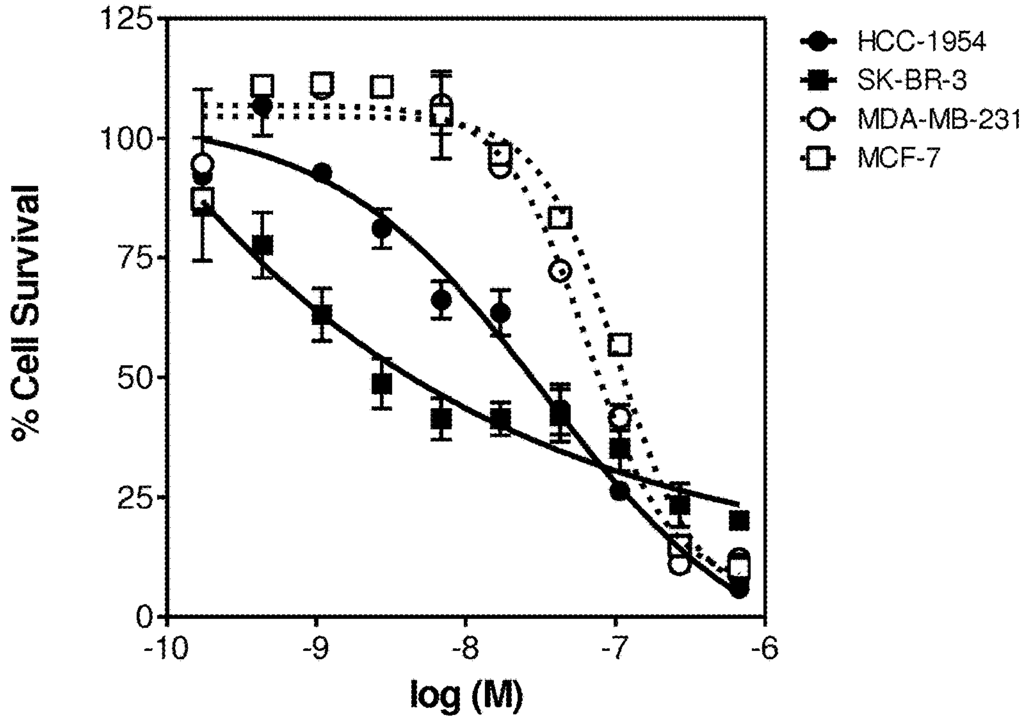
FIG. 11. Dose-response curves showing the antiproliferative potential of the ADC 6 in HER2-positive (black symbols) or HER2 negative (hollow symbols) cell lines. Dots correspond to the average of triplicates with error bars denoting SD, drawing lines correspond to the best fitting by nonlinear regression of the experimental points to a four-parameters logistic curve used to obtain the $IC_{50}$ values reported in Table 21.

The cytotoxicity of the ADC 6 was evaluated against the different tumor cell lines by performing triplicate 10-points, 2.5-fold dilution DR curves ranging from 100 μg/mL to 26 ng/mL (6.67E-07-1.75E-10 M). FIG. 11 shows the DR curve obtained and Table 21 summarizes the deduced $IC_{50}$ values.

As observed in Table 21, the cytotoxicity of ADC 6 is comparable to that shown by the parent drug 12-R only in HER2-positive cells. However, in HER2-negative cells such toxicity is lower: nearly 10-fold lower according to the selectivity ratio obtained by dividing the mean $IC_{50}$ value in HER2-negative cells between that in HER2-positive cells. These data lead us to conclude that the conjugate is acting through the interaction of the antibody with the membrane associated HER2 receptor on the tumor cells, followed by intracellular delivery of the cytotoxic drug.

TABLE 21

Summary of the in vitro cytotoxicity of ADC 6

| | HER2 positive | | HER2 negative | | IC50 in HER2+ (geom. | IC50 in HER2− (geom. | Selec. |
|---|---|---|---|---|---|---|---|
| | SK-BR-3 | HCC-1954 | MDA-MB-231 | MCF-7 | mean) | mean | ratio |
| $IC_{50}$ (μg/mL) | 6.50E−01 | 4.10E+00 | 1.20E+01 | 1.70E+01 | 1.63E00 | 1.43E01 | 8.8 |
| $IC_{50}$ (M) | 4.33E−09 | 2.73E−08 | 8.00E−08 | 1.13E−07 | 1.08E−08 | 9.51E−08 | |

Bioactivity Example 6—Cytotoxicity of the Conjugate ADC 11 and Related Reagents Against HER2 Positive and Negative Breast Cancer Cells The in vitro cytotoxicity of the ADC 11 along with the parent cytotoxic compounds DL 6 and 12 R and were evaluated against four different human breast cancer cell lines over-expressing or not the HER2 receptor, including SK-BR-3, HCC-1954 (HER2-positive cells) as well as MDA-MB-231 and MCF-7 (HER2-negative cells). Standard dose-response (DR) curves for 72 hours incubation with the tested substances were performed.

Cytotoxicity of DL 6

The cytotoxicity of the intermediate compound DL 6 was evaluated against the different tumor cell lines by performing triplicated 10-points, 2.5-fold dilution DR curves ranging from 1 μg/mL to 0.26 ng/mL (7.23E-07-1.88E-10 M).

As shown in Table 22, the cytotoxicity of this compound was similar in all the tumor cell lines regardless of their HER2 expression, with $IC_{50}$ values in the high nanomolar range, from 0.04 to 0.3 μg/mL (3.1 E-08 to 1.97E-07 M). The geometric mean $IC_{50}$ value across the whole cell panel was 0.11 μg/mL (7.89E-08 M), with the standard geometric deviation being 2.31 in agreement with the homogeneity of results across the four cell lines.

TABLE 22

| Summary of the in vitro cytotoxicity of DL 6 | | | | |
|---|---|---|---|---|
| | HER2 positive | | HER2 negative | |
| | SK-BR-3 | HCC-1954 | MDA-MB-231 | MCF-7 |
| $IC_{50}$, μg/mL | 7.09E−02 | 1.71E−01 | 4.29E−02 | 2.73E−01 |
| $IC_{50}$, M | 5.13E−08 | 1.24E−07 | 3.10E−08 | 1.97E−07 |

Cytotoxicity of ADC 11

The cytotoxicity of the ADC 11 was evaluated against the different tumor cell lines by performing triplicate 10-points, 2.5-fold dilution DR curves ranging from 50 μg/mL to 13 ng/mL (3.33E-07-8.74E-11 M). Table 23 summarizes the deduced $IC_{50}$ values.

TABLE 23

| Summary of the in vitro cytotoxicity of ADC 11 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 1.10E+01 | 3.60E+01 | >5.00E+01 | >5.00E+01 | 1.99E+01 | >5.00E+01 | >2.5 |
| $IC_{50}$ (M) | 7.33E−08 | 2.40E−07 | >3.33E−07 | >3.33E−07 | 1.33E−07 | >3.33E−07 | |

Bioactivity Example 7—Cytotoxicity of the Conjugate ADC 12 Against HER2 Positive and Negative Breast Cancer Cells The in vitro cytotoxicity of the ADC 12 was evaluated against four different human breast cancer cell lines over-expressing or not the HER2 receptor, including SK-BR-3, HCC-1954 (HER2-positive cells) as well as MDA-MB-231 and MCF-7 (HER2-negative cells). Standard dose-response (DR) curves for 72 hours incubation with the tested substances were performed.

The cytotoxicity of the ADC 12 was evaluated against the different tumor cell lines by performing triplicate 10-points, 2.5-fold dilution DR curves ranging from 100 μg/mL to 26 ng/mL (6.67E-07-1.75E-10 M). Table 24 summarizes the deduced $IC_{50}$ values. As observed, ADC 12 is significantly more active in in HER2-positive cells, yielding a noticeable selectivity ratio higher than 20.

TABLE 24

| Summary of the in vitro cytotoxicity of ADC 12 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 1.80E−01 | 2.90E−01 | 1.91E+00 | 1.30E+01 | 2.28E−01 | 4.98E+00 | 21.8 |
| $IC_{50}$ (M) | 1.20E−09 | 1.93E−09 | 1.27E−08 | 8.67E−08 | 1.52E−09 | 3.32E−08 | |

Bioactivity Example 8—Cytotoxicity of the Conjugate ADC 13 Against HER2 Positive and Negative Breast Cancer Cells The cytotoxicity of the ADC 13 was evaluated against the different tumor cell lines by performing triplicate 10-points, 2.5-fold dilution DR curves ranging from 100 μg/mL to 26 ng/mL (6.67E-07-1.75E-10 M). Table 25 summarizes the deduced $IC_{50}$ values. As observed, ADC 13 is significantly more active in HER2-positive cells, yielding an outstanding selectivity ratio close to 100.

TABLE 25

| Summary of the in vitro cytotoxicity of ADC 13 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 1.50E−01 | 2.60E−01 | 1.10E+01 | 2.90E+01 | 1.97E−01 | 1.78E+01 | 90.43 |
| $IC_{50}$ (M) | 1.00E−09 | 1.73E−09 | 7.33E−08 | 1.93E−07 | 1.32E−09 | 1.19E−07 | |

Bioactivity Example 9—Cytotoxicity of the Conjugate ADC 14 Against HER2 Positive and Negative Breast Cancer Cells The cytotoxicity of the ADC 14 was evaluated against the different tumor cell lines by performing triplicate 10-points, 2.5-fold dilution DR curves ranging from 100 μg/mL to 26 ng/mL (6.67E-07-1.75E-10 M). Table 26 summarizes the deduced $IC_{50}$ values. Remarkably, ADC 14 has shown a cytotoxic activity in the low nM range comparable to that of the parental drug 11R but only in HER2-expressing cells, whilst it has failed to show any activity in HER2-negative cells within the range of concentrations tested, thus confirming an outstanding selectivity.

TABLE 26

| Summary of the in vitro cytotoxicity of ADC 14 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 1.10E−01 | 1.80E−01 | >2.51E+01 | >2.51E+01 | 1.41E−01 | >2.51E+01 | >178 |
| $IC_{50}$ (M) | 7.33E−10 | 1.20E−09 | >1.67E−07 | >1.67E−07 | 9.38E−10 | >1.67E−07 | |

Bioactivity Example 10—Cytotoxicity of the Conjugate ADC 15 Against HER2 Positive and Negative Breast Cancer Cells The cytotoxicity of the ADC 15 was evaluated against the different tumor cell lines by performing triplicate 10-points, 2.5-fold dilution DR curves ranging from 50 μg/mL to 13 ng/mL (3.33E-07-8.74E-11 M). Table 27 summarizes the deduced $IC_{50}$ values. As observed, ADC 15 is significantly more active in in HER2-positive cells, yielding an outstanding selectivity ratio close to 200.

TABLE 27

| Summary of the in vitro cytotoxicity of ADC 15 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 8.00E−02 | 1.80E−01 | 2.10E+01 | 2.21E+01 | 1.20E−01 | 2.15E+01 | 179.4 |
| $IC_{50}$ (M) | 5.33E−10 | 1.20E−09 | 1.40E−07 | 1.47E−07 | 8.00E−10 | 1.43E−07 | |

Bioactivity Example 11—Cytotoxicity of the Conjugate ADC 16 Against HER2 Positive and Negative Breast Cancer Cells The cytotoxicity of the ADC 16 was evaluated against the different tumor cell lines by performing triplicate 10-points, 2.5-fold dilution DR curves ranging from 100 μg/mL to 26 ng/mL (6.67E-07-1.75E-10 M). Table 28 summarizes the deduced $IC_{50}$ values. As observed, ADC 16 is significantly more active in in HER2-positive cells, yielding an outstanding selectivity ratio above 100.

TABLE 28

| Summary of the in vitro cytotoxicity of ADC 16 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 4.01E−02 | 8.00E−01 | 1.30E+01 | 2.70E+01 | 1.79E−01 | 1.87E+01 | 104.7 |
| $IC_{50}$ (M) | 2.67E−10 | 5.33E−09 | 8.67E−08 | 1.80E−07 | 1.19E−09 | 1.25E−07 | |

Bioactivity Example 12—Cytotoxicity of the Conjugate ADC 17 Against HER2 Positive and Negative Breast Cancer Cells The cytotoxicity of the ADC 17 was evaluated against the different tumor cell lines by performing triplicate 10-points, 2.5-fold dilution DR curves ranging from 100 μg/mL to 26 ng/mL (6.67E-07-1.75E-10 M). Table 29 summarizes the deduced $IC_{50}$ values.

TABLE 29

| Summary of the in vitro cytotoxicity of ADC 17 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 7.40E+00 | 1.40E+01 | 4.40E+01 | 4.20E+01 | 1.02E+01 | 4.30E+01 | 4.22 |
| $IC_{50}$ (M) | 4.93E−08 | 9.33E−08 | 2.93E−07 | 2.80E−07 | 6.78E−08 | 2.86E−07 | |

Bioactivity Example 13—Cytotoxicity of the Conjugate ADC 18 Against HER2 Positive and Negative Breast Cancer Cells The cytotoxicity of the ADC 18 was evaluated against the different tumor cell lines by performing triplicate 10-points, 2.5-fold dilution DR curves ranging from 100 μg/mL to 26 ng/mL (6.67E-07-1.75E-10 M). Table 30 summarizes the deduced $IC_{50}$ values.

TABLE 30

| Summary of the in vitro cytotoxicity of ADC 18 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 4.40E+00 | 2.21E+01 | 4.31E+01 | 9.71E+01 | 9.84E+00 | 6.46E+01 | 6.57 |
| $IC_{50}$ (M) | 2.93E−08 | 1.47E−07 | 2.87E−07 | 6.47E−07 | 6.56E−08 | 4.31E−07 | |

Bioactivity Example 14—Cytotoxicity of the Conjugate ADC 19 Against HER2 Positive and Negative Breast Cancer Cells The cytotoxicity of the ADC 19 was evaluated against the different tumor cell lines by performing triplicate 10-points, 2.5-fold dilution DR curves ranging from 100 μg/mL to 26 ng/mL (6.67E-07-1.75E-10 M). Table 31 summarizes the deduced $IC_{50}$ values.

TABLE 31

| Summary of the in vitro cytotoxicity of ADC 19 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 8.30E+00 | 3.41E+01 | >1.00E+02 | >1.00E+02 | 1.68E+01 | >1.00E+02 | >5.95 |
| $IC_{50}$ (M) | 5.53E−08 | 2.27E−07 | >6.67E−07 | >6.67E−07 | 1.12E−07 | >6.67E−07 | |

Bioactivity Example 15—Cytotoxicity of the Conjugate ADC 20 Against HER2 Positive and Negative Breast Cancer Cells The cytotoxicity of the ADC 20 was evaluated against the different tumor cell lines by performing triplicate 10-points, 2.5-fold dilution DR curves ranging from 100 μg/mL to 26 ng/mL (6.67E-07-1.75E-10 M). Table 32 summarizes the deduced $IC_{50}$ values.

TABLE 32

| Summary of the in vitro cytotoxicity of ADC 20 | | | | | | | |
|---|---|---|---|---|---|---|---|
| | HER2 positive | | HER2 negative | | IC50 in HER2+ (geom. | IC50 in HER2− (geom. | Selec. |
| | SK-BR-3 | HCC-1954 | MDA-MB-231 | MCF-7 | mean) | mean | ratio |
| $IC_{50}$ (μg/mL) | 2.21E+00 | 1.61E+01 | 5.40E+01 | 4.01E+01 | 5.95E+00 | 4.65E+01 | 7.82 |
| $IC_{50}$ (M) | 1.47E−08 | 1.07E−07 | 3.60E−07 | 2.67E−07 | 3.97E−08 | 3.10E−07 | |

Bioactivity Example 16—Cytotoxicity of the Conjugate ADC 7 and Related Reagents Against CD13 Positive and Negative Cancer Cells

Cytotoxicity of 11-R

The cytotoxicity of the intermediate compound 11-R was evaluated against the different tumor cell lines by performing triplicate 10-points, 2.5-fold dilution DR curves ranging from 100 μg/mL to 0.03 ng/mL (1.26E-07-3.3E-11 M).

As shown in Table 33, where results corresponding to the geometric mean of the $IC_{50}$ values obtained in three different experiments are presented, the cytotoxicity of this compound was similar in all the tumor cell lines regardless of their CD13 expression, with $IC_{50}$ values in the low nanomolar range, from 0.5 to 1.2 ng/mL (5.8E-10 to 1.51 E-09 M). The geometric mean $IC_{50}$ value across the whole cell panel was 0.84 ng/mL (1.06E-09 M) with the standard geometric deviation being 1.5 in agreement with the homogeneity of results across the four cell lines.

TABLE 33

| Summary of the in vitro cytotoxicity of 11-R | | | | |
|---|---|---|---|---|
| | CD13 positive | | CD13 negative | |
| | HT-1080 | NB-4 | Raji | RPMI8226 |
| $IC_{50}$, μg/mL | 1.20E−03 | 4.60E−04 | 9.67E−04 | 9.28E−04 |
| $IC_{50}$, M | 1.51E−09 | 5.80E−10 | 1.22E−09 | 1.17E−09 |

Cytotoxicity of ADC 7

The cytotoxicity of the ADC 7 was evaluated against the different tumor cell lines by performing triplicate 10-points, 2.5-fold dilution DR curves ranging from 100 μg/mL to 26 ng/mL (6.67E-07-1.75E-10 M). Table 34 summarizes the deduced $IC_{50}$ values. Remarkably, ADC 7 has shown a cytotoxic activity in the low nM range comparable to that of the parental drug 11-R but only in CD13-expressing cells, whereas its activity in CD13-negative cells is rather modest. Consequently, an outstanding selectivity fair above 100 can be observed as a function of CD13 expression.

TABLE 34

| Summary of the in vitro cytotoxicity of ADC 7 | | | | | | | |
|---|---|---|---|---|---|---|---|
| | CD13 positive | | CD13 negative | | IC50 in CD13+ (geom. | IC50 in CD13− (geom. | Selec. |
| | HT-1080 | NB-4 | Raji | RPMI8226 | mean) | mean | ratio |
| $IC_{50}$ (μg/mL) | 1.30E−01 | 2.70E−01 | 2.21E+01 | 4.10E+01 | 1.87E−01 | 3.00E+01 | 160.4 |
| $IC_{50}$ (M) | 8.67E−10 | 1.80E−09 | 1.47E−07 | 2.73E−07 | 1.25E−09 | 2.00E−07 | |

Bioactivity Example 17—Cytotoxicity of the Conjugate ADC 8 Against CD13 Positive and Negative Cancer Cells The cytotoxicity of the ADC 8 was evaluated against the different tumor cell lines by performing triplicate 10-points, 2.5-fold dilution DR curves ranging from 100 μg/mL to 26 ng/mL (6.67E-07-1.75E-10 M). Table 35 summarizes the deduced $IC_{50}$ values. ADC 8 has shown a cytotoxic activity in the low nM range comparable to that of the parental drug 11-R but only in CD13-expressing cells, whereas its activity in CD13-negative cells is rather modest. Consequently, an outstanding selectivity close to 200 was obtained as a function of CD13 expression.

TABLE 35

Summary of the in vitro cytotoxicity of ADC 8

| | CD13 positive | | CD13 negative | | IC50 in CD13+ (geom. | IC50 in CD13− (geom. | Selec. |
|---|---|---|---|---|---|---|---|
| | HT-1080 | NB-4 | Raji | RPMI8226 | mean) | Mean) | ratio |
| $IC_{50}$ (μg/mL) | 1.61E−01 | 2.51E−01 | 4.31E+01 | 3.30E+01 | 2.01E−01 | 3.77E+01 | 188 |
| $IC_{50}$ (M) | 1.07E−09 | 1.67E−09 | 2.87E−07 | 2.20E−07 | 1.34E−09 | 2.51E−07 | |

Bioactivity Example 18—Cytotoxicity of the Conjugate ADC 9 and Related Reagents Against CD13 Positive and Negative Cancer Cells

Cytotoxicity of 12-R

The cytotoxicity of the intermediate compound 12-R was evaluated against the different tumor cell lines by performing triplicate 10-points, 2.5-fold dilution DR curves ranging from 100 to 0.03 ng/mL (1.28E-07-3.83E-11 M).

As shown in Table 36, where results corresponding to the geometric mean of the $IC_{50}$ values obtained in three independent experiments are presented, the cytotoxicity of this compound was similar in all the tumor cell lines regardless of their CD13 expression, with $IC_{50}$ values in the low nanomolar range, from 0.3 to 1.1 ng/mL (4.21E-10 to 1.40E-09 M). The geometric mean $IC_{50}$ value across the whole cell panel was 0.6 ng/mL (7.8E-10 M), with the standard geometric deviation being 1.7 in agreement with the homogeneity of results across the four cell lines.

TABLE 36

Summary of the in vitro cytotoxicity of 12-R.

| | CD13 positive | | CD13 negative | |
|---|---|---|---|---|
| | HT-1080 | NB-4 | Raji | RPMI8226 |
| $IC_{50}$, μg/mL | 1.10E−03 | 3.30E−04 | 4.70E−04 | 8.30E−04 |
| $IC_{50}$, M | 1.40E−09 | 4.21E−10 | 6.00E−10 | 1.06E−09 |

Cytotoxicity of ADC-9

The cytotoxicity of the ADC 9 was evaluated against the different tumor cell lines by performing triplicate 10-points, 2.5-fold dilution DR curves ranging from 100 μg/mL to 26 ng/mL (6.67E-07-1.75E-10 M). Table 37 summarizes the deduced $IC_{50}$ values. ADC 9 has shown a cytotoxic activity in the low nM range comparable to that of the parental drug 12-R but only in CD13-expressing cells, whereas its activity in CD13-negative cells is rather modest. Consequently, an outstanding selectivity ratio above 200 was yielded as a function of CD13 expression.

TABLE 37

Summary of the in vitro cytotoxicity of ADC 9

| | CD13 positive | | CD13 negative | | IC50 in CD13+ (geom. | IC50 in CD13− (geom. | Selec. |
|---|---|---|---|---|---|---|---|
| | HT-1080 | NB-4 | Raji | RPMI8226 | mean) | Mean) | ratio |
| $IC_{50}$ (μg/mL) | 1.20E−01 | 5.21E−02 | 1.70E+01 | 1.70E+01 | 7.90E−02 | 1.70E+01 | 214 |
| $IC_{50}$ (M) | 8.00E−10 | 3.47E−10 | 1.13E−07 | 1.13E−07 | 5.27E−10 | 1.13E−07 | |

Bioactivity Example 19—Cytotoxicity of the Conjugate ADC 10 Against CD13 Positive and Negative Cancer Cells The cytotoxicity of the ADC 10 was evaluated against the different tumor cell lines by performing triplicate 10-points, 2.5-fold dilution DR curves ranging from 100 μg/mL to 26 ng/mL (6.67E-07-1.75E-10 M). Table 38 summarizes the deduced $IC_{50}$ values. ADC 10 has shown a cytotoxic activity in the low nM range comparable to that of the parental drug 11-R but only in CD13-expressing cells, whereas its activity in CD13-negative cells is rather modest. Consequently, a remarkable selectivity close to 100 was obtained as a function of CD13 expression.

TABLE 38

Summary of the in vitro cytotoxicity of ADC 10

| | CD13 positive | | CD13 negative | | IC50 in CD13+ (geom. | IC50 in CD13− (geom. | Selec. |
|---|---|---|---|---|---|---|---|
| | HT1080 | NB-4 | Raji | RPMI 8226 | mean) | mean | ratio |
| $IC_{50}$ (μg/mL) | 9.71E−02 | 9.71E−01 | 3.30E+01 | 2.81E+01 | 3.07E−01 | 3.04E+01 | 99.14 |
| $IC_{50}$ (M) | 6.47E−10 | 6.47E−09 | 2.20E−07 | 1.87E−07 | 2.05E−09 | 2.03E−07 | |

Example 4: Demonstrating the In Vivo Efficacy of the Antibody-Drug Conjugates of the Present Invention Trastuzumab-based antibody drug conjugate ADC 1 was tested in several in vivo models. ADC-1 batches used in these studies were prepared using 2.2 eq of TCEP (ADC 1 2.2 TCEP) or 3 eq of TCEP (ADC-1), These batches were manufactured using the procedures described above with the exception that the final purification by size exclusion chromatography (SEC) was carried out using a Hi Load 26/600 Superdex™ 200 μg column and PBS (pH 7.4) as eluent.

Figure 12:
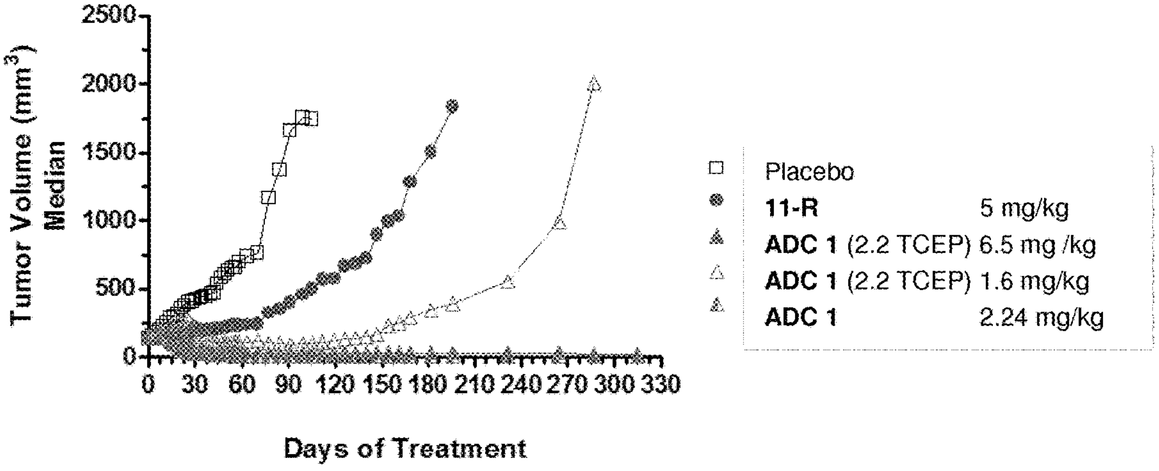
FIG. 12. Tumor volume evaluation of BT-474 tumors in mice treated with placebo, 11-R (at 5 mg/kg), ADC 1 (2.2 TCEP) (at 1.6 and 6.5 mg/kg) and ADC 1 (at 2.24 mg/kg).
Figure 13:
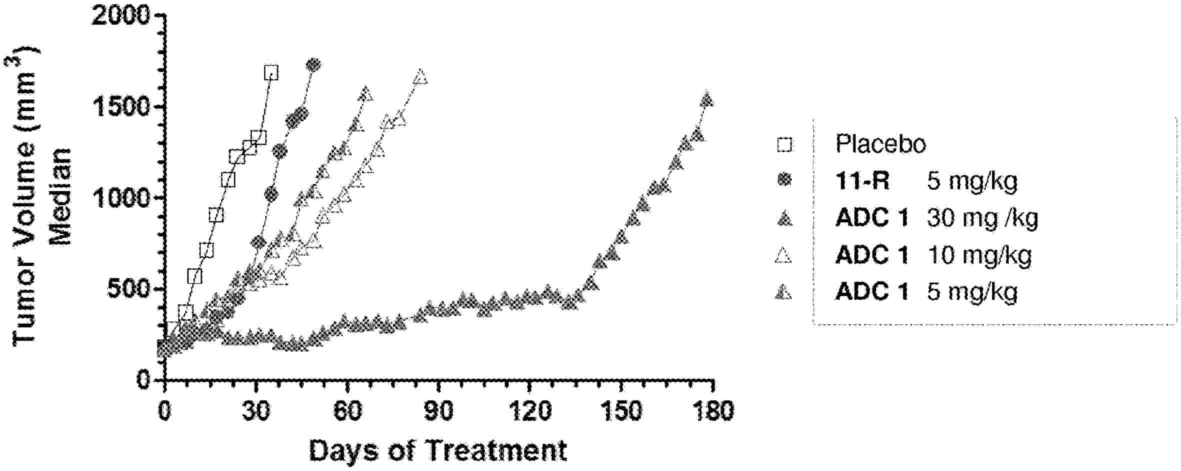
FIG. 13. Tumor volume evaluation of JIMT-1 tumors in mice treated with placebo, 11-R (at 5.0 mg/kg) and ADC 1 (at 5, 10 and 30 mg/kg).
Figure 14:
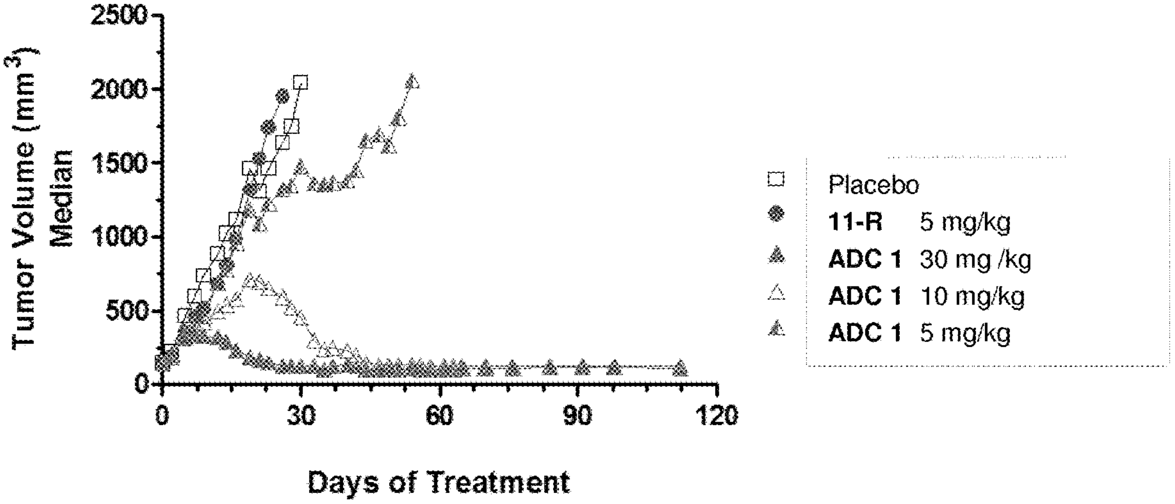
FIG. 14. Tumor volume evaluation of SKOV3 tumors in mice treated with placebo, 11-R (at 5.0 mg/kg) and ADC 1 (at 5, 10 and 30 mg/kg).
Figure 15:
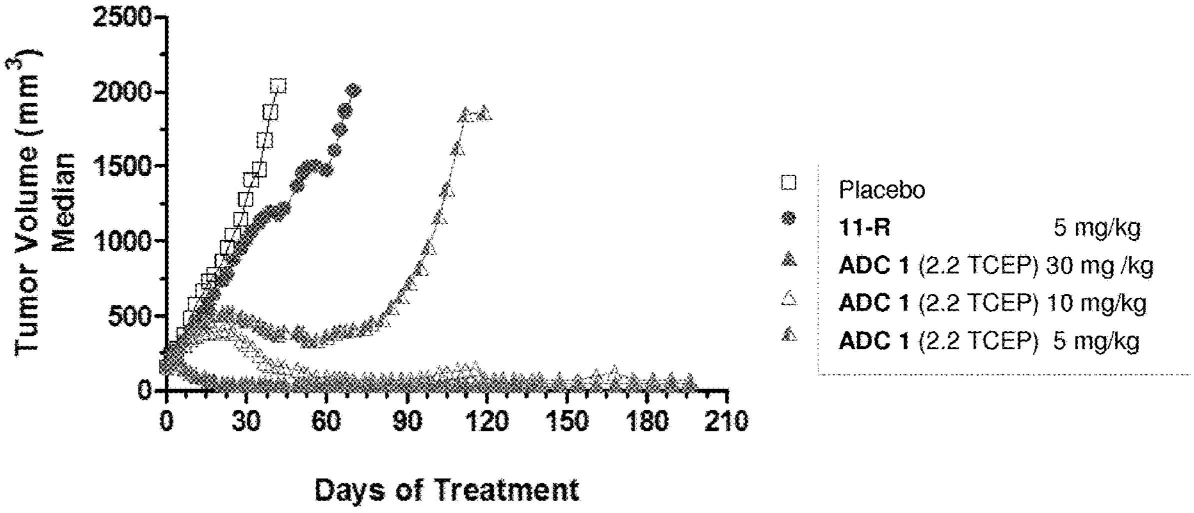
FIG. 15. Tumor volume evaluation of N87 tumors in mice treated with placebo, 11-R (at 5 mg/kg) and ADC 1 (2.2 TCEP) (at 5, 10 and 30 mg/kg).
Figure 16:
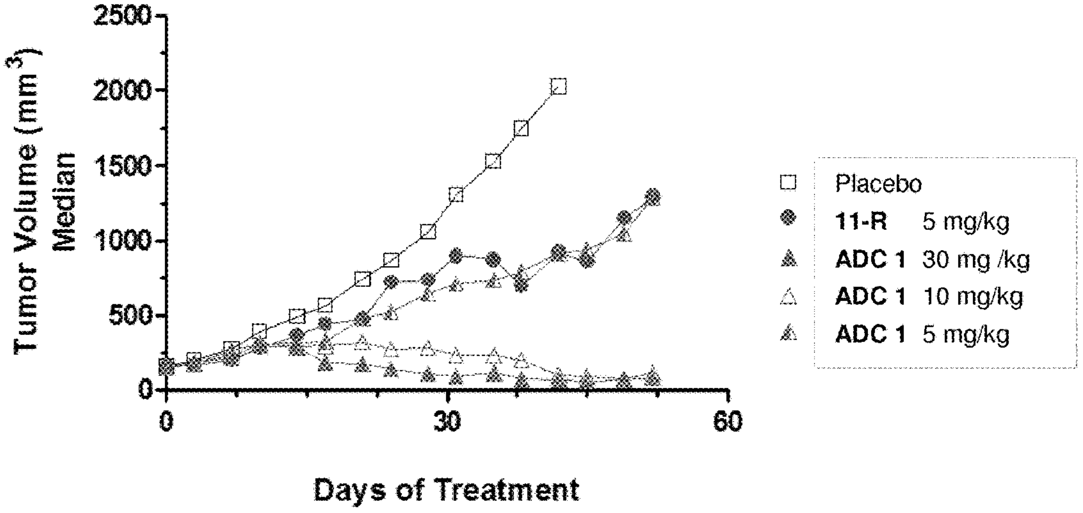
FIG. 16 Tumor volume evaluation of Gastric-008 (PDX) tumors in mice treated with placebo, 11-R (at 5 mg/kg) and ADC-1 (at 5, 10 and 30 mg/kg).

ADC-1 and ADC 1 2.2 TCEP were evaluated in a breast HER2 positive model, BT-474 together with their payload, compound 11-R. Of note, in spite of the low dose (suboptimal) administered to mice bearing tumors in this experiment, encouraging positive result was obtained (See FIG. 12). Therefore, a set of new experiments, aimed at evaluating the antitumor activity in breast and non-breast HER2 positive models were performed. ADC-1 was evaluated at a higher dose level in the breast tumor model, JIMT-1 (See FIG. 13), in one ovarian tumor model, SK-OV-3 (FIG. 14) and in a gastric model, Gastric-008, a patient derived xenograft (PDX), (FIG. 16). Additionally ADC-1 2.2 TCEP) was evaluated in another gastric model, N87 (FIG. 15).

Briefly, 4 to 6 week-old athymic nu/nu (N87, Gastric-008 or SK-OV-3) or SCID (BT-474 or JIMT-1) mice were subcutaneously implanted with either tumor cell suspension (JIMT-1 or N87) or tumor fragments (BT-474, Gastric-008 or SK-OV3) previously generated in donor mice.

Tumor dimension and body weight was recorded 3 times per week starting from the first day of treatment (Day 0). Treatments producing >20% lethality and/or 20% net body weight loss were considered toxic. Tumor volume was calculated using the equation $(a \cdot b^2)/2$, where a and b were the longest and shortest diameters, respectively. Animals were euthanized when their tumors reached ca. 2,000 $mm^3$ and/or severe necrosis was seen. Median was calculated for tumor volume on each measurement day. Complete tumor regression (CR) was defined when tumor volume <63 $mm^3$ for 2 or more consecutive measurements.

The animals were implanted as above described and when tumors reached ca. 150-200 $mm^3$, tumor bearing animals (N=8-10/group) were randomly allocated into treatment groups according to the following experimental design:

| Tumor | Group | Dose (mg/kg) |
|---|---|---|
| JIMT-1 | Control | 0.0 |
| | 11-R | 5.0 |
| | ADC-1 | 30.0 |
| | ADC-1 | 10.0 |
| | ADC-1 | 5.0 |
| N87 | Control | 0.0 |
| | 11-R | 5.0 |
| | ADC-1 (2.2 TCEP) | 30.0 |
| | ADC-1 (2.2 TCEP) | 10.0 |
| | ADC-1 (2.2 TCEP) | 5.0 |
| SK-OV-3 | Control | 0.0 |
| | 11-R | 5.0 |
| | ADC-1 | 30.0 |
| | ADC-1 | 10.0 |
| | ADC-1 | 5.0 |
| Gastric-008 | Control | 0.0 |
| | 11-R | 5.0 |
| | ADC-1 | 30.0 |
| | ADC-1 | 10.0 |
| | ADC-1 | 5.0 |
| BT-474 | Control | 0.0 |
| | 11-R | 5.0 |
| | ADC-1 (2.2 TCEP) | 6.5 |
| | ADC-1 | 2.24 |
| | ADC-1 (2.2 TCEP) | 1.6 |

The invention claimed is:

1. A drug conjugate comprising a drug moiety covalently attached to the rest of the drug conjugate, the drug conjugate having formula $[D-(X)_b-(AA)_w-(T)_g-(L)-]_n$-Ab wherein:

D is a drug moiety having the following formula (I) or a pharmaceutically acceptable salt, ester, solvate, tautomer or stereoisomer thereof, (I)

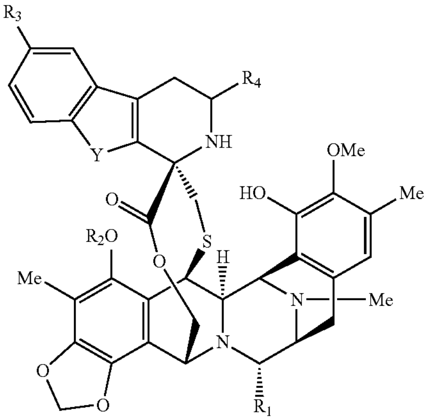

wherein:

D is covalently attached via a hydroxy or amine group to $(X)_b$ if any, or $(AA)_w$ if any, or to $(T)_g$ if any, or (L);

Y is —NH— or —O—;

$R_1$ is —OH or —CN;

$R_2$ is a —C(═O)$R_a$ group;

$R_3$ is hydrogen or a —O$R_b$ group;

$R_4$ is selected from —$CH_2$O— and —$CH_2$NH—;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

X is an extending group selected from:

where D is covalently attached via an amine group:

COO—($C_1$-$C_6$ alkylene)NH—;

COO—$CH_2$-(phenylene which may optionally be substituted with one or more substituents Rx)-NH—;

COO—($C_1$-$C_6$ alkylene)NH—COO—$CH_2$-(phenylene which may optionally be substituted with one or more substituents $R_x$)—NH—;

—$COCH_2$NH—$COCH_2$—NH—;

—$COCH_2$NH—;

—COO—($C_1$-$C_6$ alkylene)S—;

—COO—($C_1$-$C_6$ alkylene)NHCO($C_1$-$C_6$ alkylene)S—; and where D is covalently attached via an hydroxy group CONH—($C_1$-$C_6$ alkylene)NH—;

COO—$CH_2$-(phenylene which may optionally be substituted with one or more substituents $R_x$)—NH—;

—CONH—($C_1$-$C_6$ alkylene)NH—COO—$CH_2$-(phenylene which may optionally be substituted with one or more substituents Rx)-NH—;

—$COCH_2$NH—$COCH_2$—NH—;

—$COCH_2$NH—;

—CONH—($C_1$-$C_6$ alkylene)S—;

—CONH—($C_1$-$C_6$ alkylene)NHCO($C_1$-$C_6$ alkylene)S—; and b is 0 or 1;

T is an extending group selected from the group consisting of —CO—($C_1$-$C_6$ alkylene)-NH—, —CO—($C_1$-$C_6$ alkylene)-[O—($C_2$-$C_6$ alkylene)]$_j$-NH—, —COO—($C_1$-$C_6$ alkylene)-[O—($C_2$-$C_6$ alkylene)]$_j$-NH—;

where j is an integer from 1 to 25, and g is 0 or 1;

each AA is independently an amino acid unit;

L is a linker group selected from the group consisting of

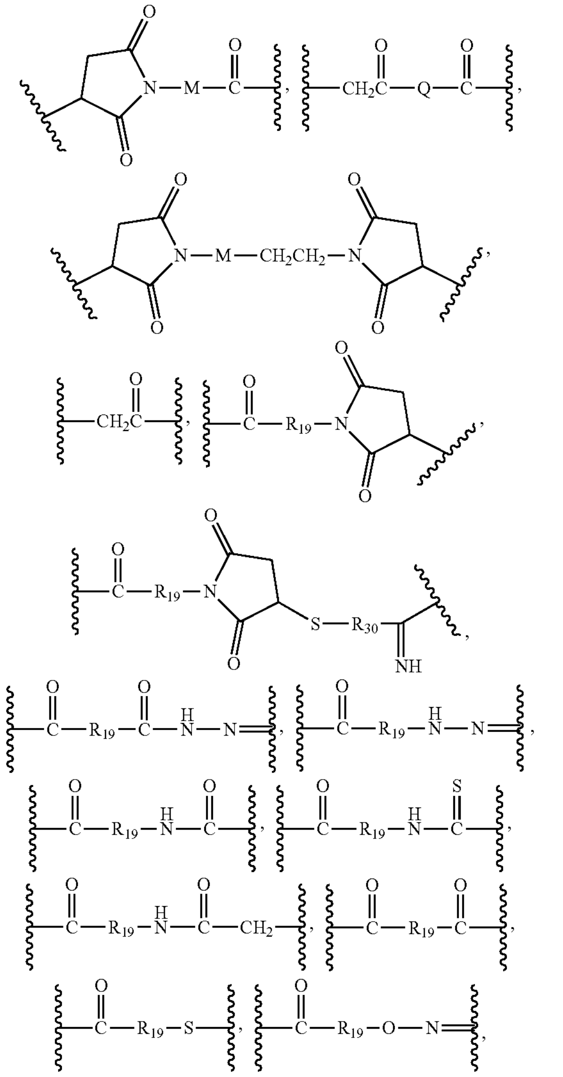

wherein the wavy lines indicate the point of covalent attachments to an Ab (the wavy line to the right) and to $(T)_g$ if any, or $(AA)_w$ if any, or $(X)_b$ if any, or D (the wavy line to the left);

$R_{19}$ is selected from —$C_1$-$C_{12}$ alkylene-, —$C_3$-$C_8$ carbocyclo, —O—($C_1$-$C_{12}$ alkylene), —$C_6$-$C_{18}$ arylene in one or more rings which may optionally be substituted with one or more substituents $R_x$, —$C_1$-$C_{12}$ alkylene-$C_6$-$C_{18}$ arylene- wherein the arylene group is in one or more rings which may optionally be substituted with one or more substituents $R_x$, —$C_6$-$C_{18}$ arylene-$C_1$-$C_{12}$ alkylene- wherein the arylene group is in one or more rings which may optionally be substituted with one or more substituents $R_x$, —$C_1$-$C_{12}$ alkylene-($C_3$-$C_8$ carbocyclo)-, —($C_3$-$C_8$ carbocyclo)-$C_1$-$C_{12}$ alkylene-, —$C_5$-$C_{14}$ heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, —$C_1$-$C_{12}$ alkylene-($C_5$-$C_{14}$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, —($C_5$-$C_{14}$ heterocyclo)-$C_1$-$C_{12}$ alkylene- wherein said heterocyclo group may be a saturated or unsaturated group having one or more rings and comprising at least one oxygen, nitrogen or sulphur atom in said ring(s), said group optionally being substituted with one or more substituents $R_x$, —$(OCH_2CH_2)_r$— and —$CH_2$—$(OCH_2CH_2)_r$—, wherein each of the above alkylene substituents whether alone or attached to another moiety the carbon chain may optionally be substituted by one or more substituents $R_x$;

$R_{30}$ is a —$C_1$-$C_6$ alkylene-group;

M is selected from the group consisting of —$C_1$-$C_6$ alkylene-, —$C_1$-$C_6$ alkylene-($C_3$-$C_8$ carbocyclo)-, $(CH_2CH_2O)_s$—, —$C_1$-$C_6$ alkylene-($C_3$-$C_8$ carbocyclo)-CON(H or $C_1$-$C_6$ alkyl)-$C_1$-$C_6$ alkylene-, phenylene which may optionally be substituted with one or more substituents $R_x$, phenylene-$C_1$-$C_6$ alkylene- wherein the phenylene moiety may optionally be substituted with one or more substituents $R_x$ and —$C_1$-$C_6$ alkylene-CON(H or $C_1$-$C_6$ alkyl) $C_1$-$C_6$ alkylene-;

Q is selected from the group consisting of —N(H or $C_1$-$C_6$ alkyl)phenylene- and —N(H or $C_1$-$C_6$ alkyl)-$(CH_2)_s$;

r is an integer ranging from 1 to 10;

s is an integer ranging from 1 to 10;

w is an integer ranging from 0 to 12;

Ab is a moiety comprising at least one antigen binding site; and n is the ratio of the group [D-$(X)_b$-$(AA)_w$-$(T)_g$-(L)-] to the moiety comprising at least one antigen binding site and is in the range from 1 to 20;

wherein the drug moiety D is conjugated via the $R_4$ position.

2. The drug conjugate according to claim 1, wherein D is selected from formula Ia or Ib, or a pharmaceutically acceptable salt or ester thereof:

Ia

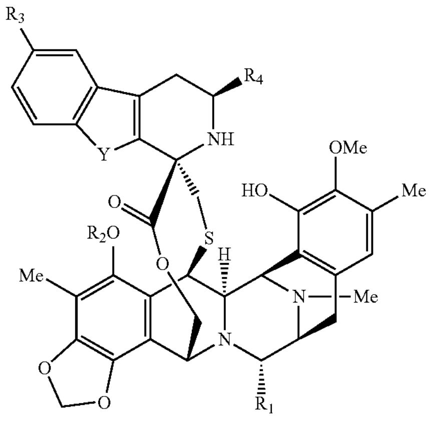

-continued

Ib

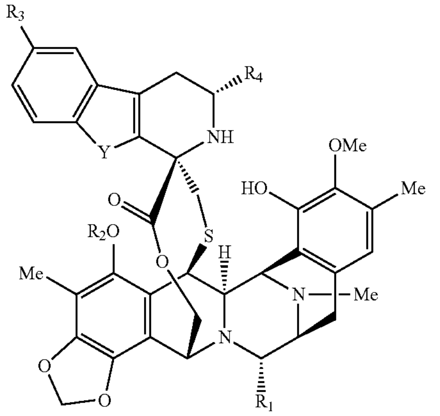

wherein:

Y is —NH— or —O—;

$R_1$ is —OH or —CN;

$R_2$ is a —C(=O) $R_a$ group;

$R_3$ is hydrogen or a —$OR_b$ group;

$R_4$ is selected from —$CH_2O$— and —$CH_2NH$—;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and $R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl.

3. The drug conjugate according to claim 1, wherein D is a compound of formula:

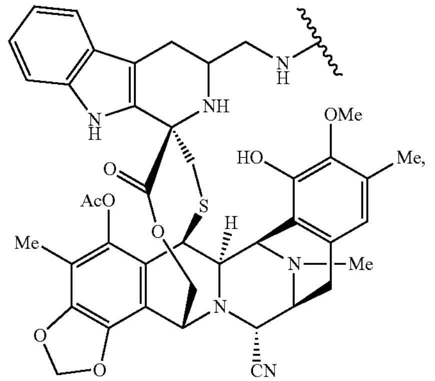

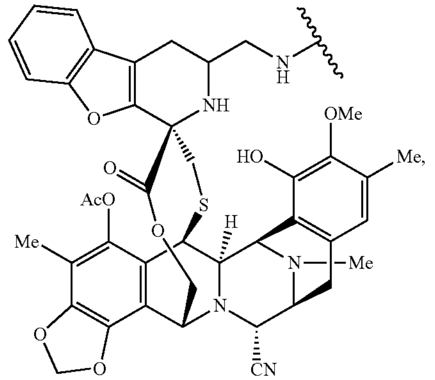

-continued

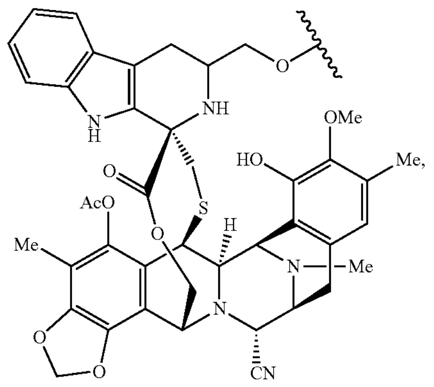

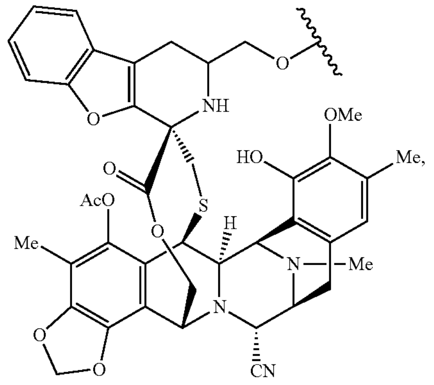

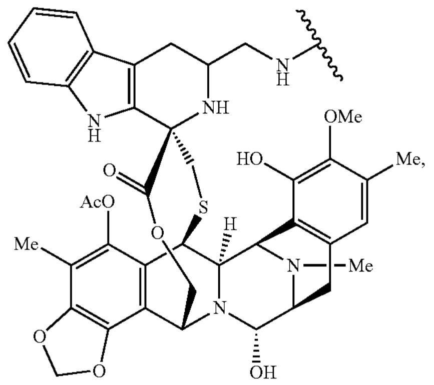

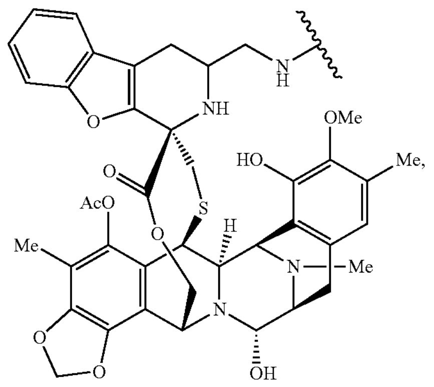

-continued
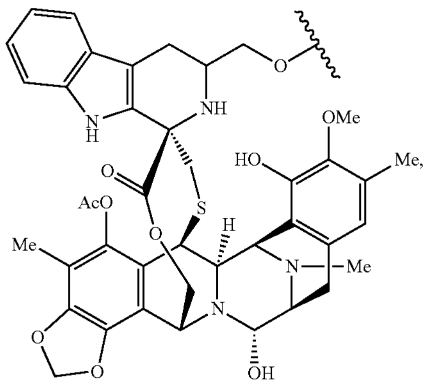
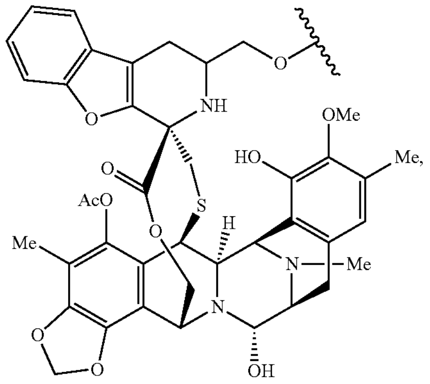
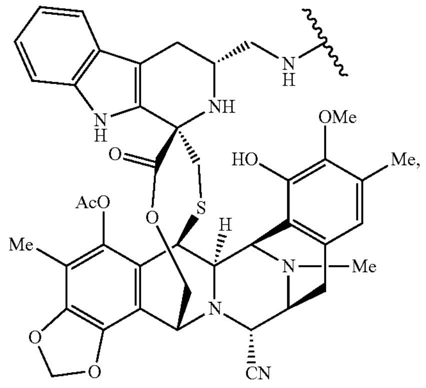
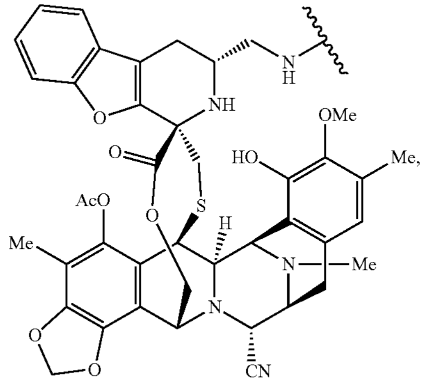
-continued
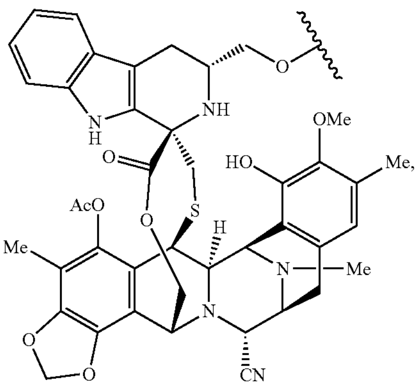
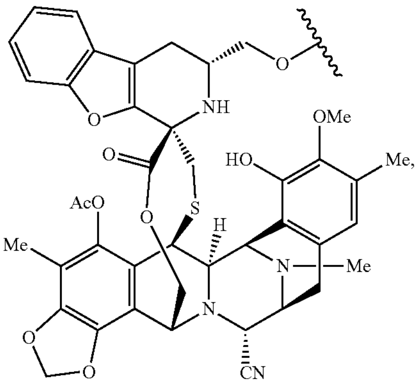
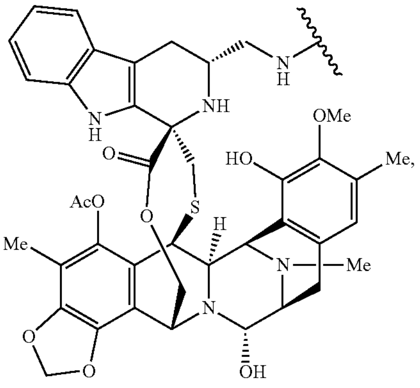
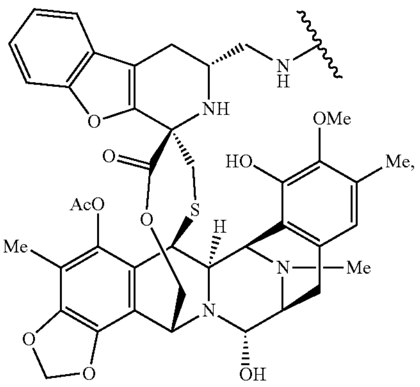

-continued
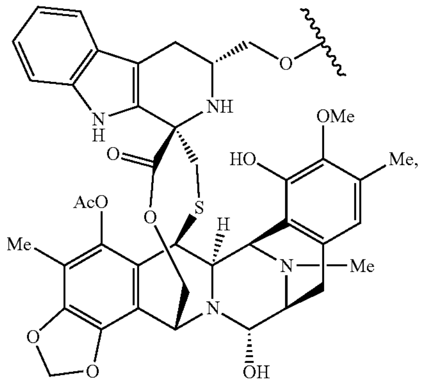
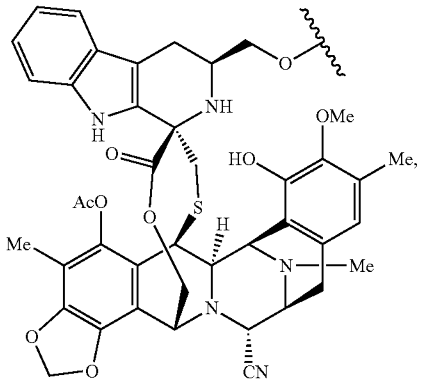
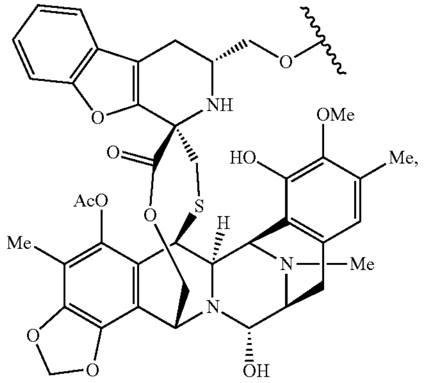
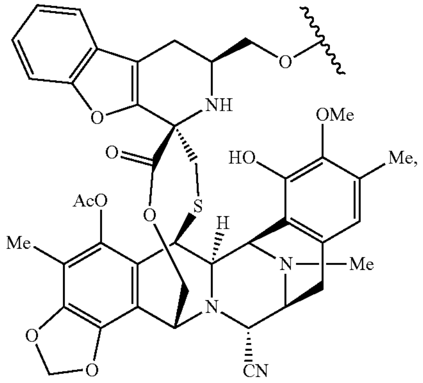
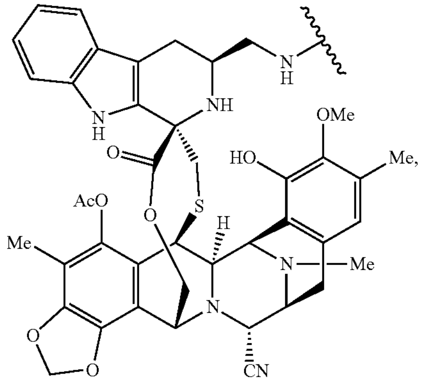
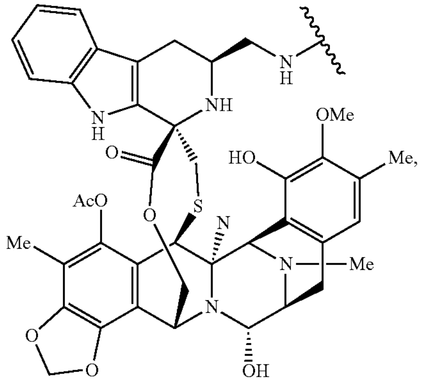
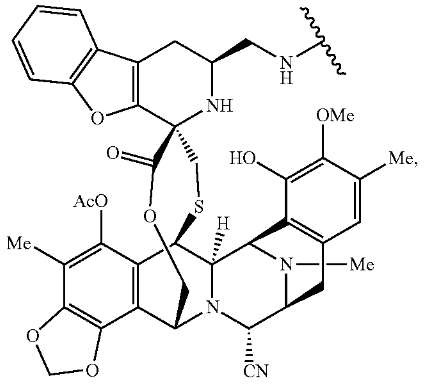
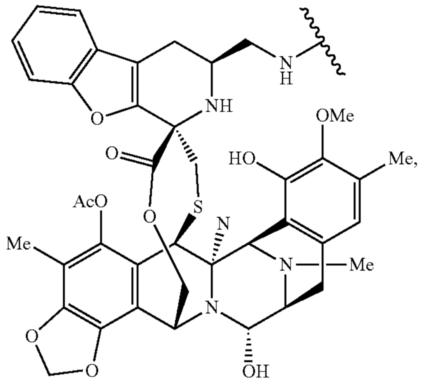

-continued

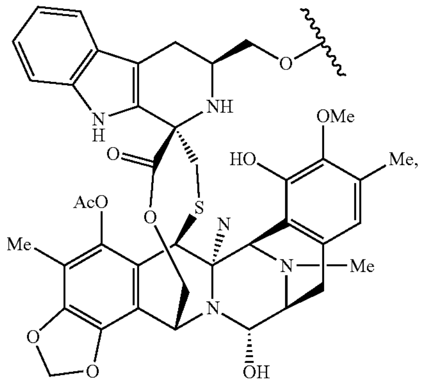

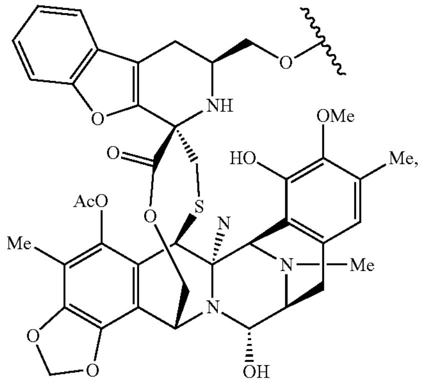

or a pharmaceutically acceptable salt or ester thereof;

wherein the wavy line indicates the point of covalent attachment to $(X)_b$ if any, or $(AA)_w$ if any, or to $(T)_g$ if any, or (L).

4. The drug conjugate according to claim 1, wherein D is a compound of formula:

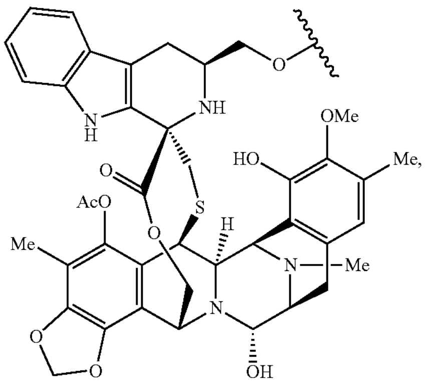 [SMILES: *OC[C@@H]1Cc2c([nH]c3ccccc23)[C@@]2(CS[C@@H]3c4c(OC(C)=O)c(C)c5c(c4[C@H](COC2=O)N2[C@@H]3[C@H]3c4c(cc(C)c(OC)c4O)C[C@@H]([C@@H]2O)N3C)OCO5)N1]

or a pharmaceutically acceptable salt or ester thereof;

wherein the wavy line indicates the point of covalent attachment to $(X)_b$ if any, or $(AA)_w$ if any, or to $(T)_g$ if any, or (L); or wherein D is a compound of formula:

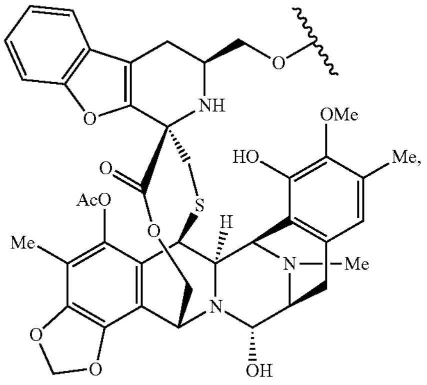 [SMILES: *OC[C@@H]1Cc2c(oc3ccccc23)[C@@]2(CS[C@@H]3c4c(OC(C)=O)c(C)c5c(c4[C@H](COC2=O)N2[C@@H]3[C@H]3c4c(cc(C)c(OC)c4O)C[C@@H]([C@@H]2O)N3C)OCO5)N1]

or a pharmaceutically acceptable salt or ester thereof;

wherein the wavy line indicates the point of covalent attachment to $(X)_b$ if any, or $(AA)_w$ if any, or to $(T)_g$ if any, or (L); or wherein D is a compound of formula:

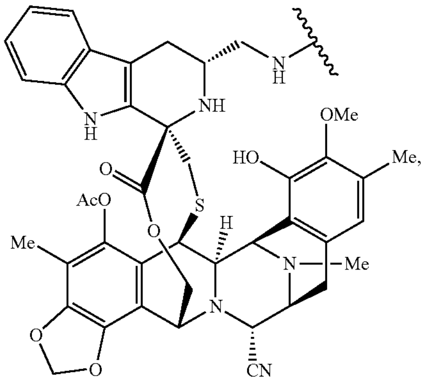 [SMILES: *NC[C@H]1Cc2c([nH]c3ccccc23)[C@@]2(CS[C@@H]3c4c(OC(C)=O)c(C)c5c(c4[C@H](COC2=O)N2[C@@H]3[C@H]3c4c(cc(C)c(OC)c4O)C[C@@H]([C@@H]2C#N)N3C)OCO5)N1]

or a pharmaceutically acceptable salt or ester thereof;

wherein the wavy line indicates the point of covalent attachment to $(X)_b$ if any, or $(AA)_w$ if any, or to $(T)_g$ if any, or (L); or wherein D is a compound of formula:

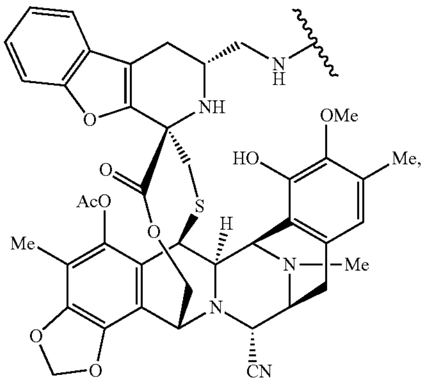 [SMILES: *NC[C@H]1Cc2c(oc3ccccc23)[C@@]2(CS[C@@H]3c4c(OC(C)=O)c(C)c5c(c4[C@H](COC2=O)N2[C@@H]3[C@H]3c4c(cc(C)c(OC)c4O)C[C@@H]([C@@H]2C#N)N3C)OCO5)N1]

or a pharmaceutically acceptable salt or ester thereof;

wherein the wavy line indicates the point of covalent attachment to $(X)_b$ if any, or $(AA)_w$ if any, or to $(T)_g$ if any, or (L); or wherein D is a compound of formula:

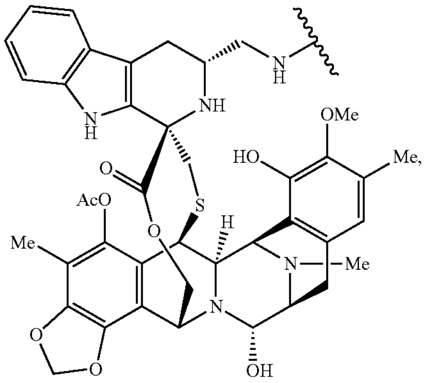 [SMILES: *NC[C@H]1Cc2c([nH]c3ccccc23)[C@@]2(CS[C@@H]3c4c(OC(C)=O)c(C)c5c(c4[C@H](COC2=O)N2[C@@H]3[C@H]3c4c(cc(C)c(OC)c4O)C[C@@H]([C@@H]2O)N3C)OCO5)N1]

or a pharmaceutically acceptable salt or ester thereof; wherein the wavy line indicates the point of covalent attachment to $(X)_b$ if any, or $(AA)_w$ if any, or to $(T)_g$ if any, or (L).

5. The drug conjugate according to claim 1 wherein:

D is a drug moiety having the following formula (IH) or a pharmaceutically acceptable salt, ester, solvate, tautomer or stereoisomer thereof:

(IH)

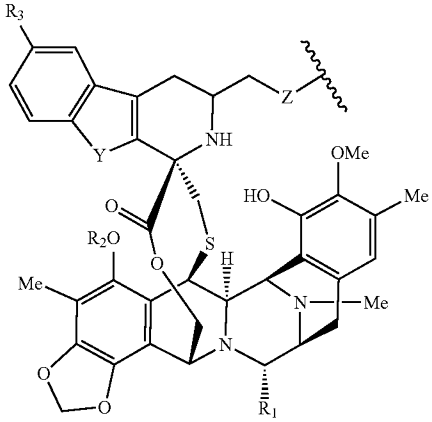

wherein:

the wavy line indicates the point of covalent attachment to $(X)_b$ if any, or $(AA)_w$ if any, or to $(T)_g$ if any, or (L);

each Y and Z is independently selected from —NH— and —O—;

$R_1$ is —OH or —CN;

$R_2$ is a —C(—O) $R_a$ group;

$R_3$ is hydrogen or a —$OR_b$ group;

$R_a$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; and $R_b$ is selected from substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $S(O)R_y$, $SO_2R_y$, $P(O)(R_y)OR_z$, $NR_yR_z$, $NR_yCOR_z$, $NR_yC({=}O)NR_yR_z$, $NR_yC({=}NR_y)NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC({=}NR_y)NR_yR_z$, aralkyl groups comprising an alkyl group having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different;

each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl groups comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s).

6. The drug conjugate according to claim 5, wherein D is a drug moiety or a pharmaceutically acceptable salt, ester, solvate, tautomer or stereoisomer thereof, selected from formulas (IHa) and (IHb):

(IHa)

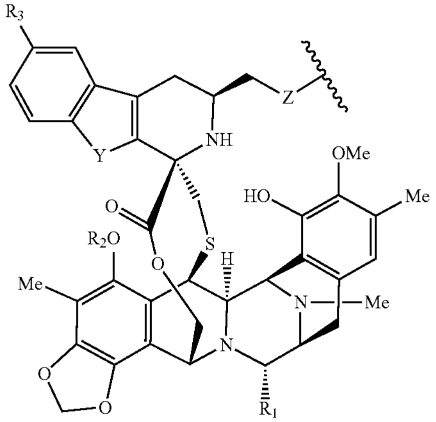

-continued (IHb)

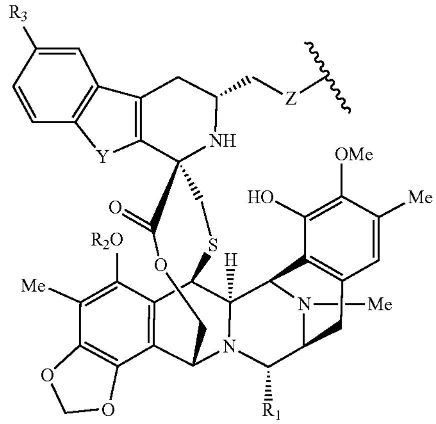

where the wavy lines, $R_1$, $R_2$, $R_3$, Y, and Z are as defined for formula (IH).

7. The drug conjugate according to claim 1, wherein the salt is selected from hydrochloride, hydrobromide, hydroiodide, sulfate, nitrate, phosphate, acetate, trifluoroacetate, maleate, fumarate, citrate, oxalate, succinate, tartrate, malate, mandelate, methanesulfonate, p-toluenesulfonate, sodium, potassium, calcium, ammonium, ethylenediamine, ethanolamine, N,N-dialkylenethanolamine, triethanolamine and basic aminoacids.

8. The drug conjugate according to claim 1, wherein L is a linker group selected from the group consisting of:

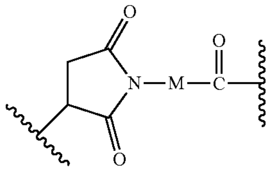
,

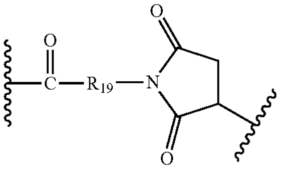

and

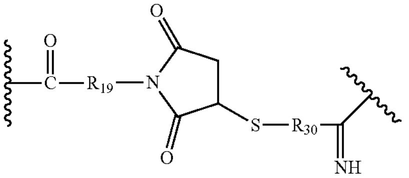

wherein:

the wavy lines indicate the point of covalent attachments to an Ab (the wavy line to the right) and to $(T)_g$ if any, or $(AA)_w$ if any, or to $(X)_b$ (the wavy line to the left);

$R_{19}$ is selected from —$C_1$-$C_{12}$ alkylene-, —O—($C_1$-$C_{12}$ alkylene), —$C_6$-$C_{12}$ arylene in one or more rings which may optionally be substituted with one or more substituents $R_x$, —$C_1$-$C_{12}$ alkylene-$C_6$-$C_{12}$ arylene- wherein the arylene group is in one or more rings which may optionally be substituted with one or more substituents $R_x$, —$C_6$-$C_{12}$ arylene-$C_1$-$C_{12}$ alkylene- wherein the arylene group is in one or more rings which may optionally be substituted with one or more substituents $R_x$, —$C_5$-$C_{12}$ heterocyclo- wherein said heterocyclo group may be a saturated or unsaturated group having one or more rings and comprising at least one oxygen, nitrogen or sulphur atom in said ring(s), said group optionally being substituted with one or more substituents $R_x$, —$C_1$-$C_{12}$ alkylene-($C_5$-$C_{12}$ heterocyclo)- wherein said heterocyclo group may be a saturated or unsaturated group having one or more rings and comprising at least one oxygen, nitrogen or sulphur atom in said ring(s), said group optionally being substituted with one or more substituents $R_x$, —($C_5$-$C_{12}$ heterocyclo)-$C_1$-$C_{12}$ alkylene- wherein said heterocyclo group may be a saturated or unsaturated group having one or more rings and comprising at least one oxygen, nitrogen or sulphur atom in said ring(s), said group optionally being substituted with one or more substituents $R_x$, —$(OCH_2CH_2)_r$— and —$CH_2$—$(OCH_2CH_2)_r$—, wherein each of the above alkylene substituents whether alone or attached to another moiety the carbon chain may optionally be substituted by one or more substituents $R_x$;

$R_{30}$ is a —$C_1$-$C_6$ alkylene-group;

M is selected from the group consisting of —$C_1$-$C_6$ alkylene-, —$C_1$-$C_6$ alkylene-($C_3$-$C_8$ carbocyclo)- and phenylene which may optionally be substituted with one or more substituents $R_x$; and r is an integer ranging from 1-6.

9. The drug conjugate according to claim 1, selected from the formulas (IV), (V) and (VI):

(IV)

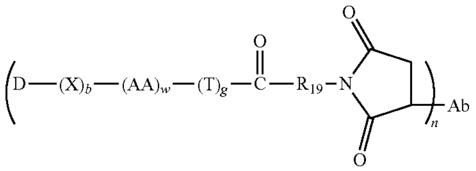

(V)

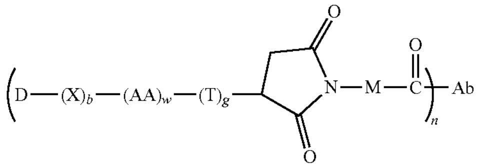

(VI)

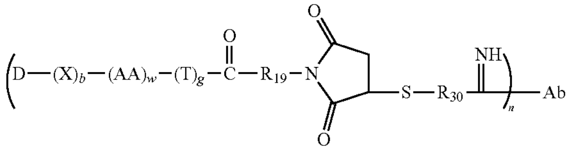

wherein:

$R_{19}$ is selected from —$C_1$-$C_8$ alkylene-, —O—($C_1$-$C_8$ alkylene), —$C_1$-$C_8$ alkylene-$C_6$-$C_{12}$ arylene- wherein the arylene group is in one or more rings which may optionally be substituted with one or more substituents $R_x$, and —$C_6$-$C_{12}$ arylene-$C_1$-$C_8$alkylene- wherein the arylene group is in one or more rings which may optionally be substituted with one or more substituents $R_x$, wherein each of the above alkylene substituents whether alone or attached to another moiety the carbon chain may optionally be substituted by one or more substituents $R_x$;

$R_{30}$ is a —$C_2$-$C_4$ alkylene-group; and

M is selected from the group consisting of —$C_1$-$C_3$ alkylene- and —$C_1$-$C_3$ alkylene-($C_5$-$C_7$ carbocyclo)-; or selected from the formulas (IV), (V) and (VI):

(IV)

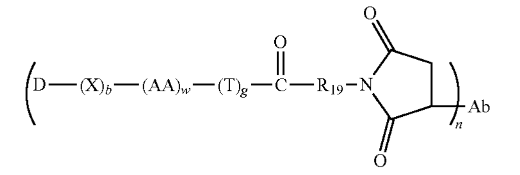

(V)

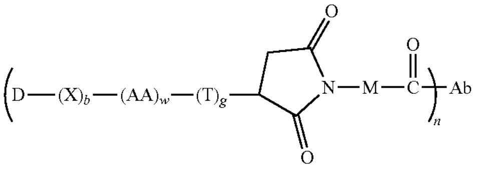

(VI)

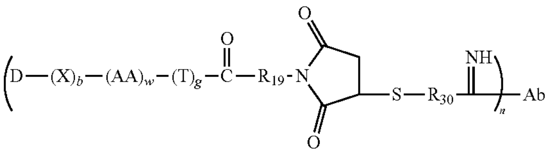

wherein:

$R_{19}$ is selected from —$C_1$-$C_6$ alkylene-, phenylene-$C_1$-$C_6$ alkylene- wherein the phenylene group may optionally be substituted with one or more substituents $R_x$ selected from the group consisting of alkyl groups having from 1 to 6 carbon atoms, alkoxy groups having from 1 to 6 carbon atoms, halogen atoms, nitro groups and cyano groups, wherein each of the above alkylene substituents whether alone or attached to another moiety in the carbon chain may optionally be substituted by one or more substituents $R_x$ selected from the group consisting of alkyl groups having from 1 to 6 carbon atoms, alkoxy groups having from 1 to 6 carbon atoms, aryl groups having from 6 to 12 carbon atoms, halogen atoms, nitro groups and cyano groups, and optionally $R_{19}$ is a —$C_1$-$C_6$ alkylene group;

$R_{30}$ is a —$C_2$-$C_4$ alkylene-group; and

M is —$C_1$-$C_3$ alkylene-($C_5$-$C_7$ carbocyclo)-.

10. The drug conjugate according to claim 1, wherein $(AA)_w$ is of formula (II):

(II)

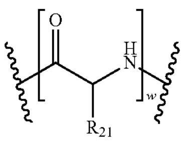

wherein the wavy lines indicate the point of covalent attachments to $(X)_b$ if any, or to the drug moiety (the wavy line to the left) and to $(T)_g$ if any, or to the linker (the wavy line to the right); and $R_{21}$ is, at each occurrence, selected from the group consisting of hydrogen, methyl, isopropyl, isobutyl, sec-butyl, benzyl, p-hydroxybenzyl, —$CH_2OH$, —CH(OH)$CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

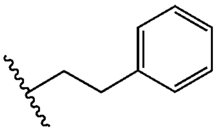,

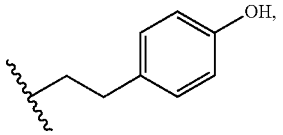

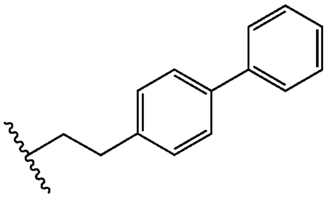,

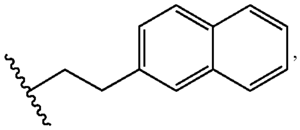,

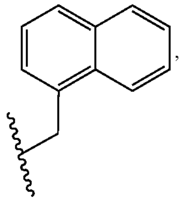,

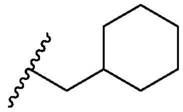,

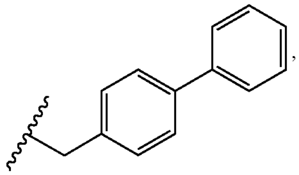,

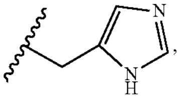, and

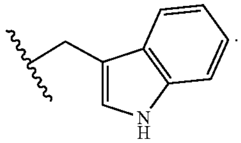.

and w is an integer ranging from 0 to 12; or wherein $(AA)_w$ is of formula (II) wherein:

$R_{21}$ is selected, at each occurrence, from the group consisting of hydrogen, methyl, isopropyl, sec-butyl, benzyl, indolylmethyl, —$(CH_2)_3NHCONH_2$, —$(CH_2)_4NH_2$, —$(CH_2)_3NHC(=NH)NH_2$ and —$(CH_2)_4NHC(=NH)NH_2$; and w is an integer ranging from 0 to 6; or wherein w is 0 or 2, and where w is 2, then $(AA)_w$ is of formula (III):

(III)

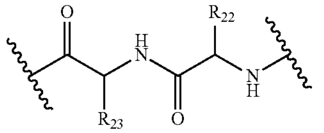

wherein:

the wavy lines indicate the point of covalent attachments to $(X)_b$ if any, or to the drug moiety (the wavy line to the left) and to $(T)_g$ if any, or to the linker (the wavy line to the right);

$R_{22}$ is selected from methyl, benzyl, isopropyl, sec-butyl and indolylmethyl; and $R_{23}$ is selected from methyl, —$(CH_2)_4NH_2$, —$(CH_2)_3NHCONH_2$ and —$(CH_2)_3NHC(=NH)NH_2$.

11. The drug conjugate according to claim 1, wherein X is an extending group selected from the group consisting of:

where D is covalently attached via an amine group:

—COO—($C_2$-$C_4$ alkylene)NH—;

COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups;

—COO—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—;

—$COCH_2NH$—$COCH_2$—NH—;

—COO—($C_2$-$C_4$ alkylene)S—; and

—COO—($C_2$-$C_4$ alkylene)NHCO($C_1$-$C_3$ alkylene)S—; or where D is covalently attached via an hydroxy group:

—CONH—($C_2$-$C_4$ alkylene)NH—;

—COO—$CH_2$-phenylene-NH—, wherein said phenylene group may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups;

—CONH—($C_2$-$C_4$ alkylene)NH—COO—$CH_2$-(phenylene which may optionally be substituted with from one to four substituents $R_x$ selected from the group consisting of alkyl groups having from 1 to 6 carbon atoms, alkoxy groups having from 1 to 6 carbon atoms, halogen atoms, nitro groups and cyano groups)-NH—;

—$COCH_2NH$—$COCH_2$—NH—;

—CONH—($C_2$-$C_4$ alkylene)S—; and

—CONH—($C_2$-$C_4$ alkylene)NHCO($C_1$-$C_3$ alkylene)S—;

wherein b is 0 or 1.

12. The drug conjugate according to claim 1, wherein Tis an extending group selected from the group consisting of —CO—($C_1$-$C_4$ alkylene)NH—, —CO—($C_1$-$C_4$ alkylene)-[O—($C_2$-$C_4$ alkylene)]$_j$-NH—, —COO—($C_1$-$C_4$ alkylene)-[O—($C_2$-$C_4$ alkylene)]$_j$-NH—, where j is an integer from 1 to 10; and g is 0 or 1; or wherein T is an extending group selected from the group consisting of —CO—($C_1$-$C_4$ alkylene)NH—, —CO—($C_1$-$C_4$ alkylene)-[O—($C_2$-$C_4$ alkylene)]$_j$-NH—, —COO—($C_1$-$C_4$ alkylene)-[O—($C_2$-$C_4$ alkylene)]$_j$—NH—; where j is an integer from 1 to 5; and g is 0 or 1.

13. The drug conjugate according to claim 5, wherein D is a drug moiety of formula (IHa) or formula (IHb) or a pharmaceutically acceptable salt, ester, solvate, tautomer or stereoisomer thereof, wherein:

$R_1$ is CN or OH;

$R_2$ is C(=O)$R_a$, wherein $R_a$ is selected from hydrogen and substituted or unsubstituted $C_1$-$C_6$ alkyl, wherein the optional substituents are one or more substituents $R_x$;

$R_3$ is hydrogen or a —$OR_b$ group wherein $R_b$ is a substituted or unsubstituted $C_1$-$C_6$ alkyl group, wherein the optional substituents are one or more substituents $R_x$, Y is —NH— or —O—; and Z is —NH— or —O; or wherein D is a drug moiety of formula (IHa) or formula (IHb) or a pharmaceutically acceptable salt, ester, solvate, tautomer or stereoisomer thereof, wherein:

$R_1$ is CN or OH;

$R_2$ is acetyl;

$R_3$ is hydrogen or methoxy;

Y is —NH— or —O—; and

Z is —NH— or —O; or wherein D is a drug moiety of formula (IHa) or formula (IHb), or a pharmaceutically acceptable salt, ester, solvate, tautomer or stereoisomer thereof wherein:

$R_1$ is CN;

$R_2$ is acetyl:

$R_3$ is hydrogen;

Y is —NH— or —O—; and

Z is —NH—.

14. The drug conjugate according to claim 1, wherein D is selected from:

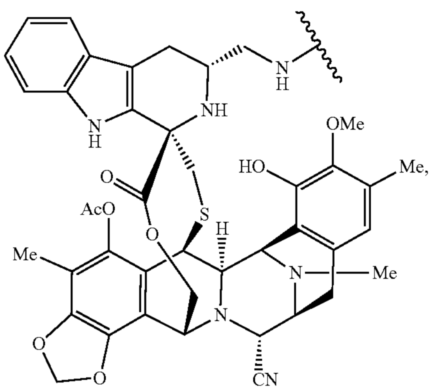

,

-continued

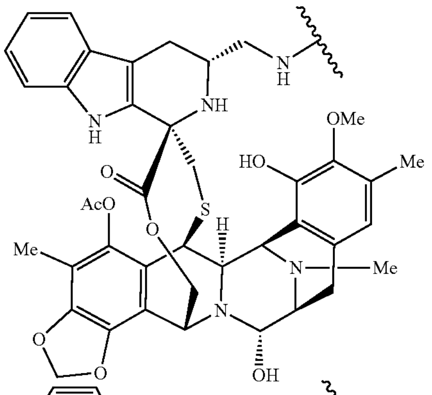

and

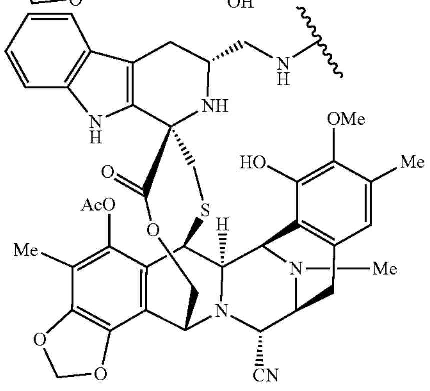

or a pharmaceutically acceptable salt, ester, solvate, tautomer or stereoisomer thereof, wherein the wavy line indicates the point of covalent attachment to $(X)_b$ if any, or $(AA)_w$ if any, or to $(T)_g$ if any, or to (L); or wherein D is

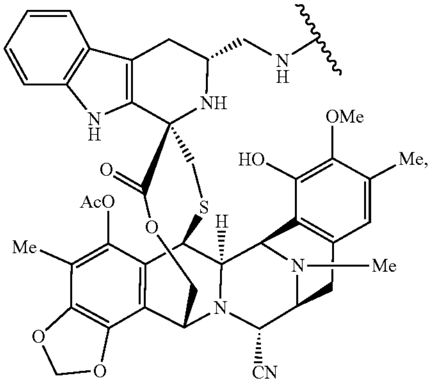

-continued

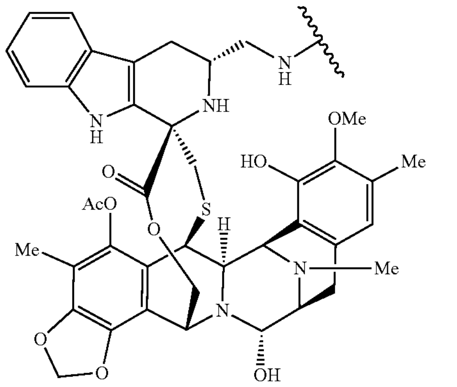

and

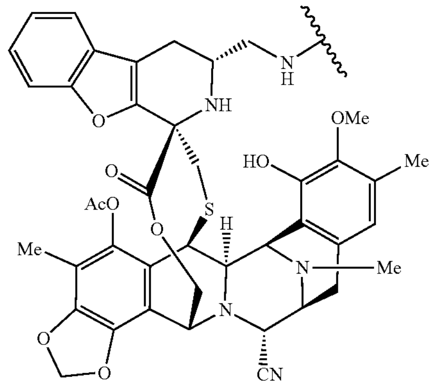

or a pharmaceutically acceptable salt, ester, solvate, tautomer or stereoisomer thereof, wherein the wavy line indicates the point of covalent attachment to $(X)_b$ if any, or $(AA)_w$ if any, or to $(T)_g$ if any, or to (L).

15. The drug conjugate according to claim 1, wherein the moiety Ab comprising at least one antigen binding site is an antigen-binding peptide.

16. The drug conjugate according to claim 1, that is an antibody drug conjugate, selected from the group consisting of:

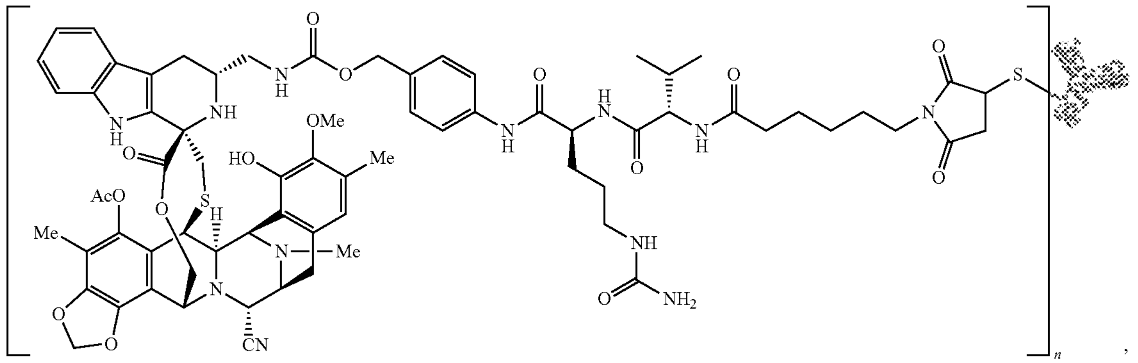

,

-continued
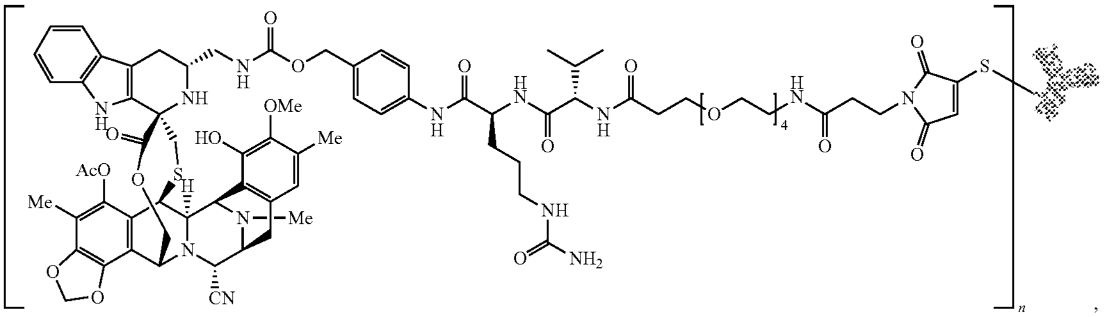
,
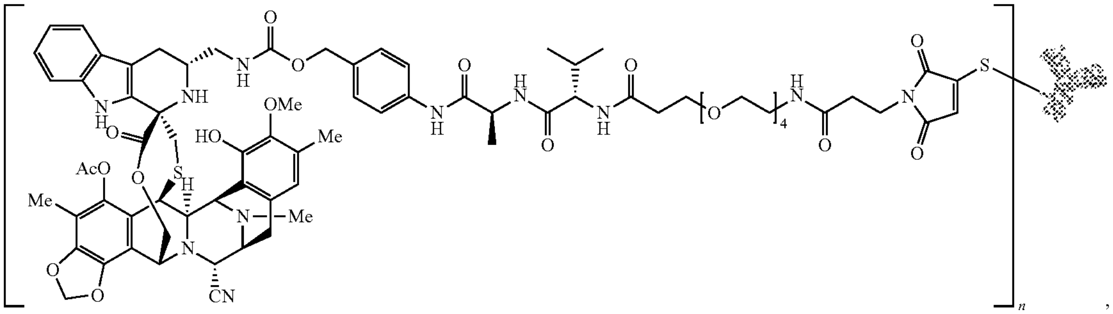
,
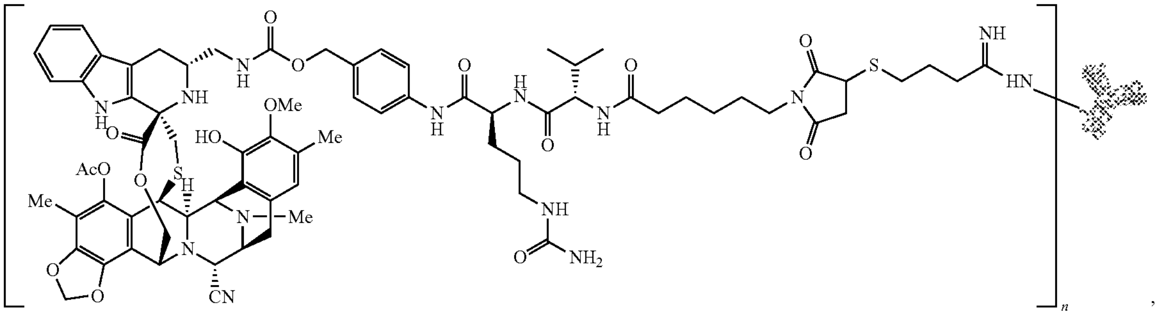
,
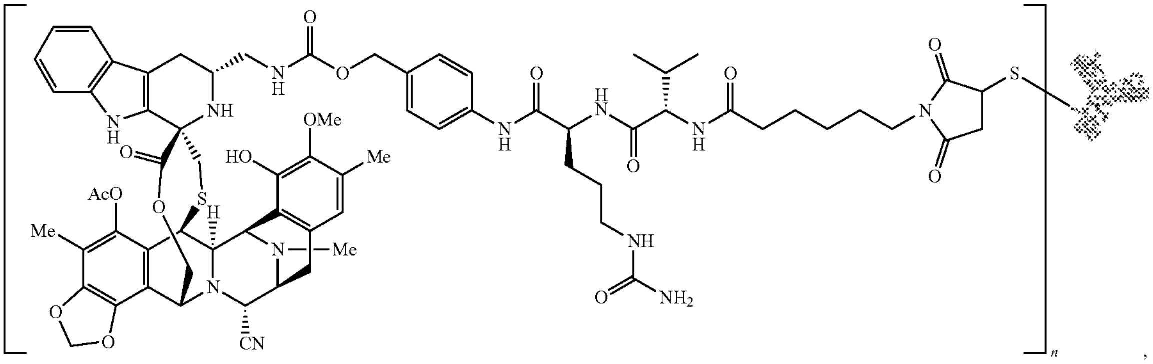
, and
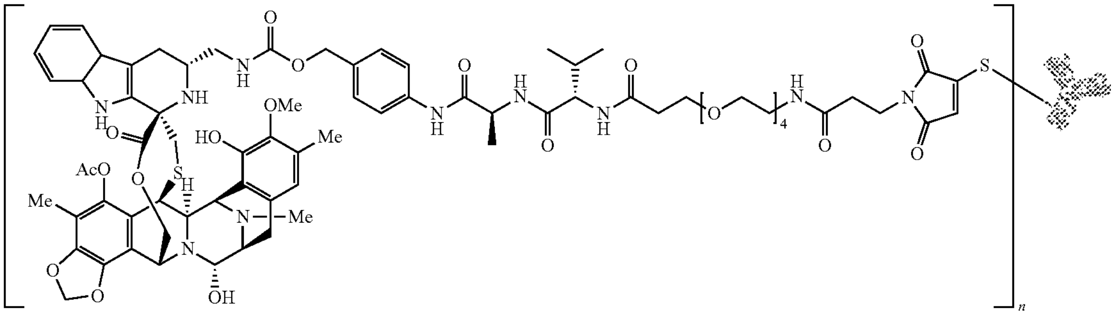
, wherein n is from 2 to 6, and each 900 and 901 is independently selected from Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologically active portion thereof.

17. The drug conjugate according to claim 16, wherein each 900 and 901 is selected from Trastuzumab and anti-CD13 antibody or an antigen-binding fragment or an immunologically active portion thereof.

18. The drug conjugate according to claim 16, wherein each 900 and 901 is selected from Trastuzumab or an antigen-binding fragment or an immunologically active portion thereof.

19. The drug conjugate according to claim 1, selected from the group consisting of:

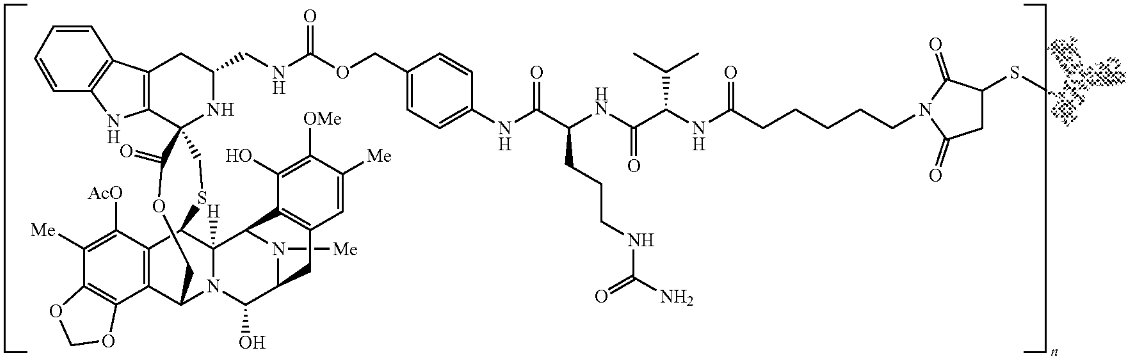
,

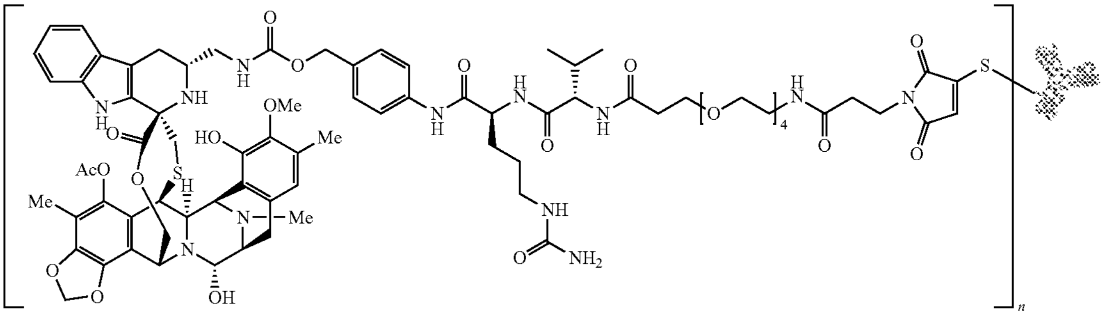
,

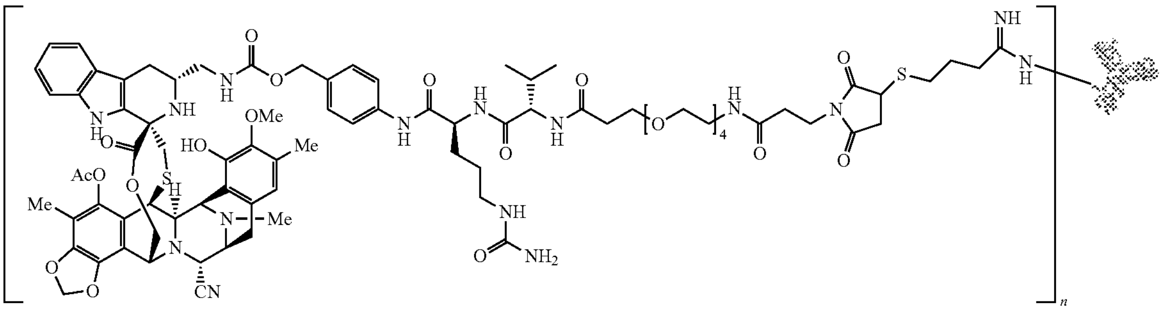
,

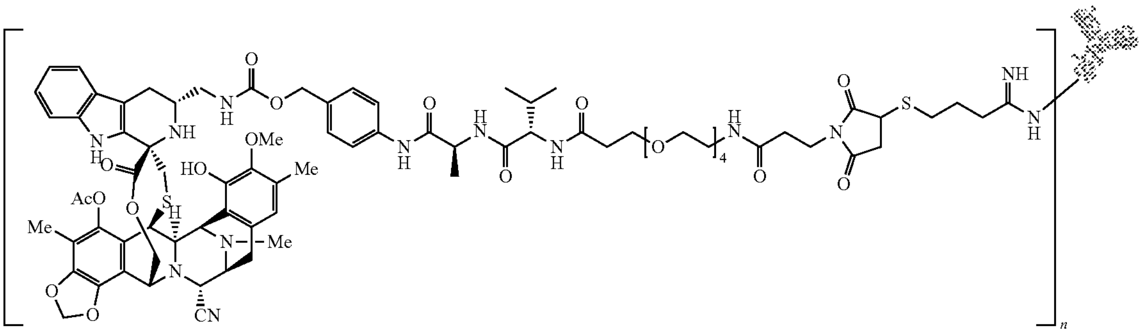
,

-continued
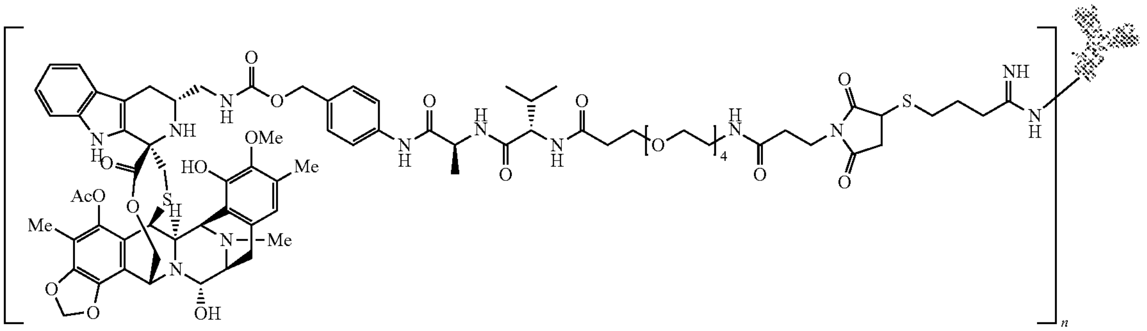
,
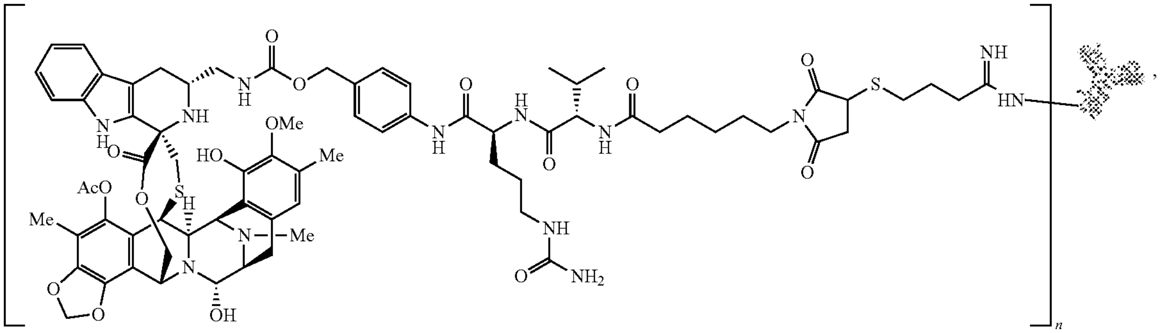
,
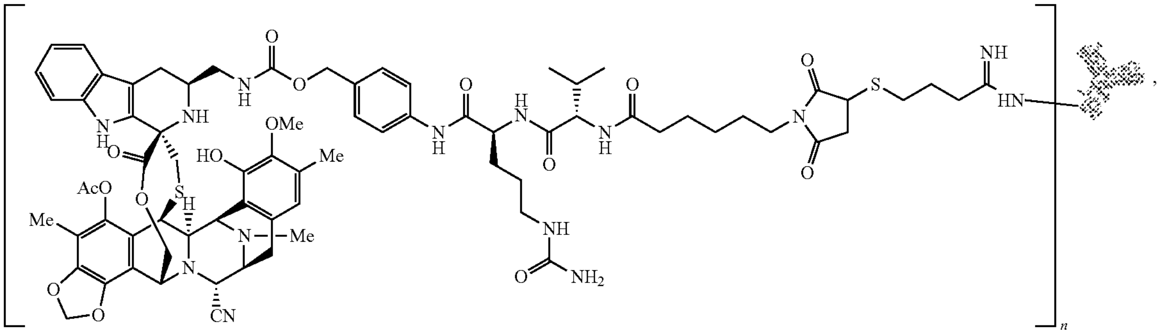
,
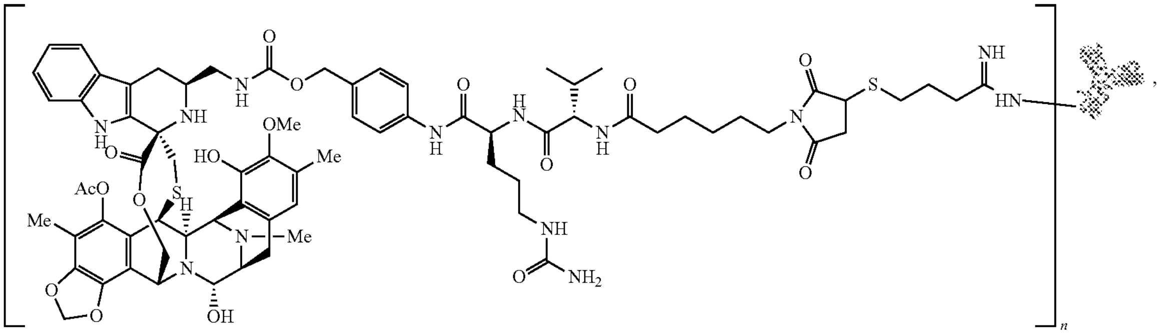
,
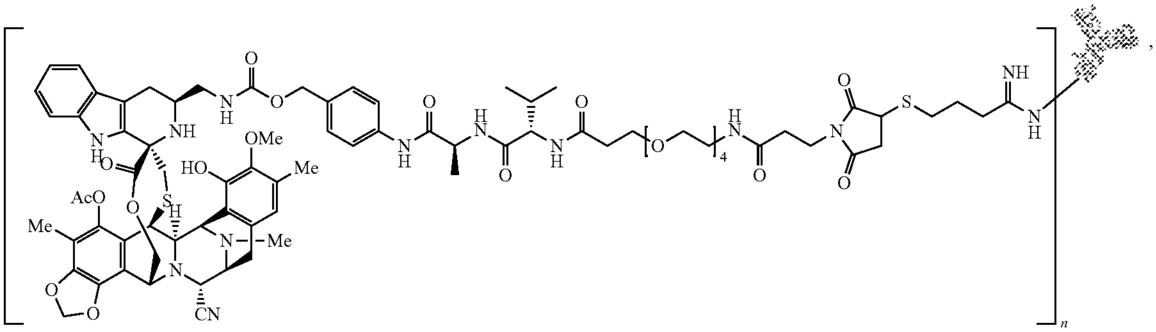
, -continued and

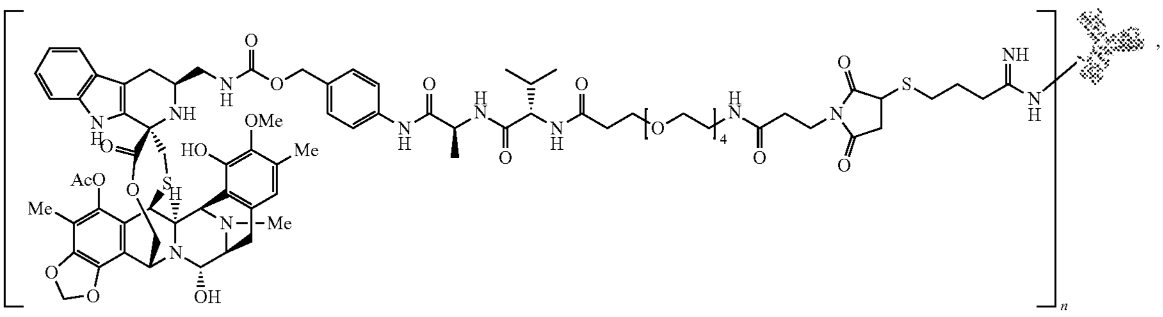

wherein n is from 2 to 6, and each 900 and 901 is independently selected from Brentuximab, Gemtuzumab, Inozutumab, Rovalpituzumab, Trastuzumab, an anti-CD4 antibody, an anti-CD5 antibody, an anti-CD13 antibody and an anti-CD 30 antibody, or an antigen-binding fragment or an immunologically active portion thereof, or a drug conjugate of formula

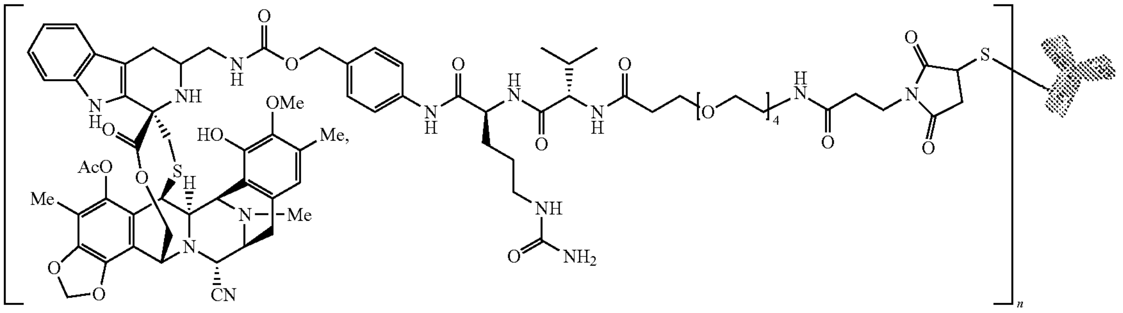

wherein n is from 2 to 6, 900 and is an anti-CD13 antibody or an antigen-binding fragment or an immunologically active portion thereof.

20. The drug conjugate according to claim 19, wherein each 900 and 901 is selected from Trastuzumab and anti-CD13 antibody or an antigen-binding fragment or an immunologically active portion thereof.

21. The drug conjugate according to claim 19, wherein each 900 and 901 is selected from Trastuzumab or an antigen-binding fragment or an immunologically active portion thereof.

22. The drug conjugate according to claim 1 that is an antibody drug conjugate in isolated or purified form.

23. A drug conjugate according to claim 1, wherein b+g+w is not 0; or wherein b+w is not 0; or wherein when w is not 0, then b is 1.

24. A pharmaceutical composition comprising a drug conjugate according to claim 1 and a pharmaceutically acceptable carrier.

25. A method of treating cancer comprising administering an effective amount of a drug conjugate according to claim 1 to a patient in need thereof.

26. The method according to claim 25, wherein the cancer is selected from lung cancer, colorectal cancer, breast cancer, pancreas carcinoma, kidney cancer, leukaemia, multiple myeloma, lymphoma, gastric and ovarian cancer.

27. A kit comprising a therapeutically effective amount of a drug conjugate according to claim 1 and a pharmaceutically acceptable carrier.

28. The drug conjugate according to claim 1, wherein n is in the range of from 1-12.

29. A process for the preparation of a drug antibody conjugate according to claim 1 comprising conjugating a moiety Ab comprising at least one antigen binding site and a drug D, Ab and D being as defined in claim 1, wherein the process comprises the preparation of a drug antibody conjugate of formula (G) or (G'):

(G)
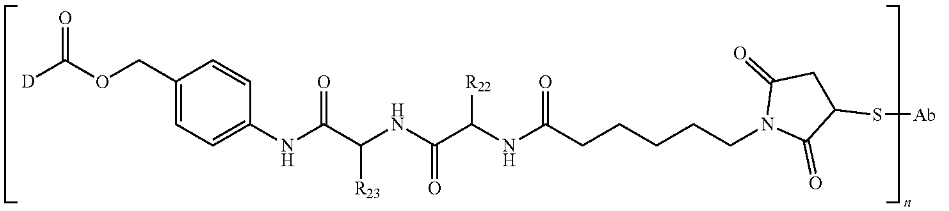
(G')
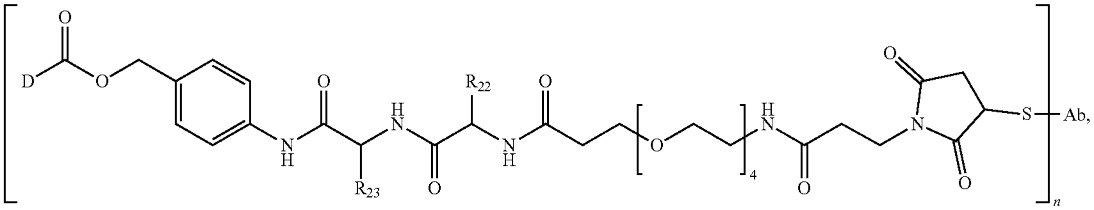
the preparation of (G) or (G') comprising the following steps:
(i) reacting a drug D-H of formula (IH)-H:
((IH)-H)
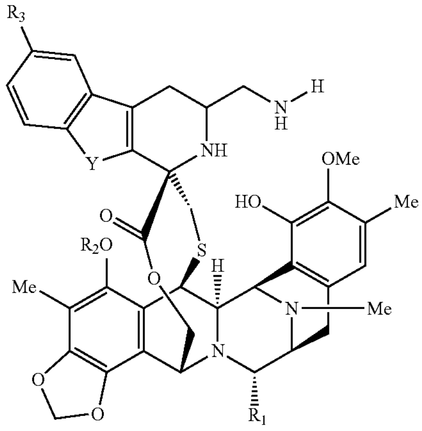
wherein the substituents in the definitions of (IH)-H are as defined in claim 3, with a compound of formula (D') or (E):
(D')
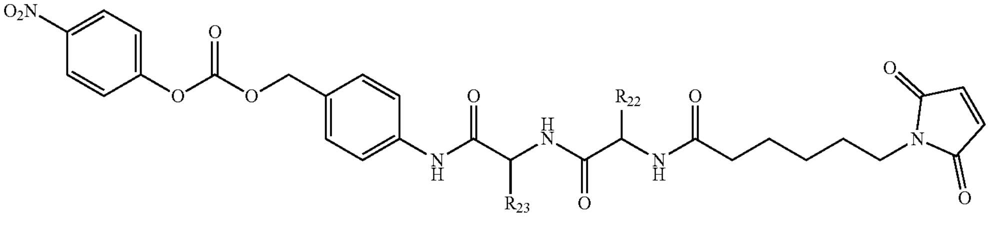

-continued (E)

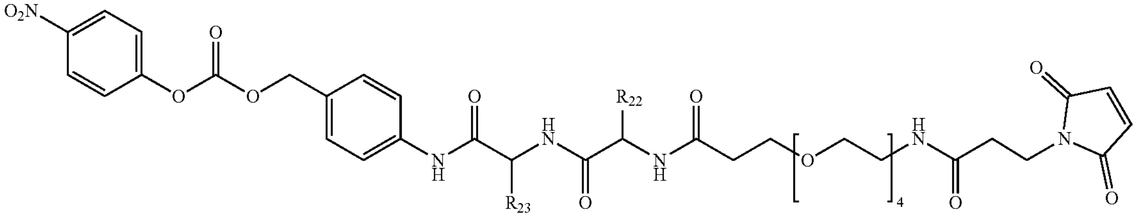

to give a compound of formula (F) or (F'), respectively:

(F)

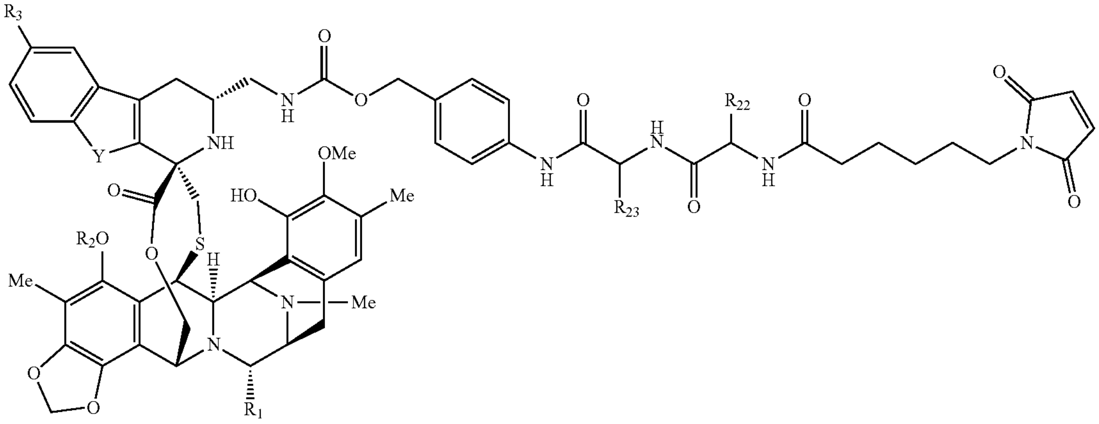

(F')

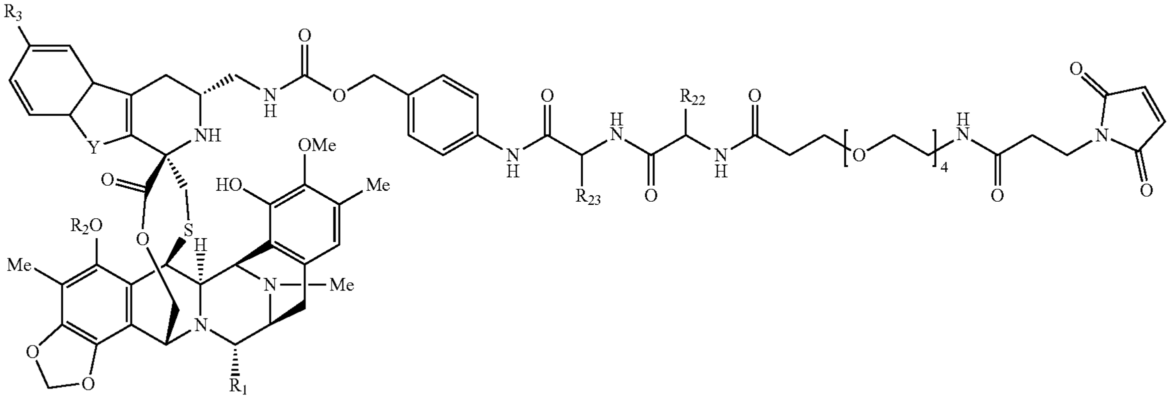

(ii) partial reduction of one or more disulfide bonds in the antibody to be conjugated to give a reduced antibody Ab-SH having free thiol groups:

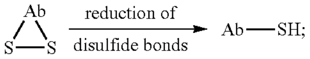

and (iii) reaction of the partially reduced antibody Ab-SH having free thiol groups with the compound of formula (F) or (F') produced in step (i) to give the desired drug antibody conjugate of formula (G) or (G') respectively:

(G)

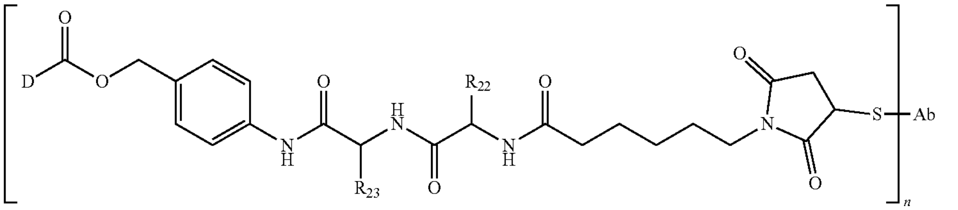

(G')

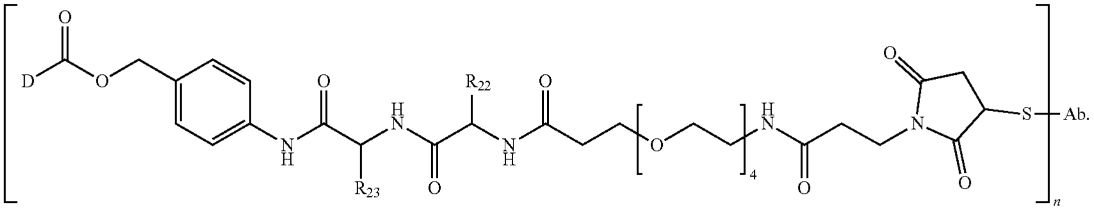

30. The drug conjugate according to claim 1, wherein the moiety Ab comprising at least one antigen binding site is an antibody, a single domain antibody or an antigen-binding fragment thereof.

31. The drug conjugate according to claim 1, wherein the moiety Ab comprising at least one antigen binding site is a monoclonal antibody, polyclonal antibody or bispecific antibody and wherein the antibody or an antigen-binding fragment thereof is derived from any species.

32. The drug conjugate according to claim 31, wherein the antibody or antigen-binding fragment thereof is selected from the group consisting of a human antibody, an antigen-binding fragment of a human antibody, a humanized antibody, an antigen-binding fragment of a humanized antibody, a chimeric antibody, an antigen-binding fragment of a chimeric antibody, a glycosylated antibody and a glycosylated antigen binding fragment.

33. The drug conjugate according to claim 31, wherein the antibody or antigen-binding fragment thereof is an antigen-binding fragment selected from the group consisting of an Fab fragment, an Fab' fragment, an F(ab')2 fragment and an Fv fragment.

34. The drug conjugate according to claim 31, wherein the antibody or antigen-binding fragment thereof is a monoclonal antibody which immunospecifically binds to an antigen selected from the group consisting of cancer cell antigens, viral antigens, antigens of cells that produce autoimmune antibodies associated with autoimmune disease, and microbial antigens.

35. The drug conjugate according to claim 34, wherein the antibody or antigen binding fragment thereof is a monoclonal antibody which immunospecifically binds to cancer cell antigens.

36. The drug conjugate according to claim 1, wherein the moiety Ab comprising at least one antigen binding site is an antibody selected from the group consisting of Abciximab, Alemtuzumab, Anetumab, Atezolizumab, Avelumab, Basiliximab, Bevacizumab, Blinatomumab, Brentuximab, Catumaxomab, Cetuximab, Coltuximab, Daclizumab, Daratumumab, Denintuzumab, Denosumab, Depatuxizumab, Dinutuximab, Durvalumab, Elotuzumab, Enfortumab, Glembatumumab, Gemtuzumab, Ibritumomab, Indatuximab, Indusatumab, Inotuzumab, Ipilimumab, Labetuzumab, Ladiratuzumab, Laprituximab, Lifastuzumab, Lorvotuzumab, Milatuzumab, Mirvetuximab, Naratuximab, Necitumumab, Nimotuzumab, Nivolumab, Obinutuzumab, Ofatumumab, Olaratumab, Omalizumab, Palivizumab, Panitumumab, Pembrolizumab, Pertuzumab, Pinatuzumab, Polatuzumab, Ramucirumab, Rovalpituzumab, Sacituzumab, Siltuximab, Sirtratumab, Sofituzumab, Vadastuximab, Vorsetuzumab, Trastuzumab, an anti-CD4 antibody, an anti-CD5 antibody, an anti-CD13 antibody and an anti-CD 30 antibody, or an antigen-binding fragment or an immunologically active portion thereof.

37. The drug conjugate according to claim 1, wherein the moiety Ab comprising at least one antigen binding site is an antibody selected from the group consisting of Abciximab, Alemtuzumab, Anetumab, Atezolizumab, Avelumab, Basiliximab, Bevacizumab, Blinatomumab, Brentuximab, Catumaxomab, Cetuximab, Daclizumab, Daratumumab, Denintuzumab, Denosumab, Depatuxizumab, Dinutuximab, Durvalumab, Elotuzumab, Enfortumab, Glembatumumab, Gemtuzumab, Ibritumomab, Indatuximab, Indusatumab, Inotuzumab, Ipilimumab, Labetuzumab, Ladiratuzumab, Laprituximab, Mirvetuximab, Naratuximab, Necitumumab, Nimotuzumab, Nivolumab, Obinutuzumab, Ofatumumab, Olaratumab, Omalizumab, Palivizumab, Panitumumab, Pembrolizumab, Pertuzumab, Polatuzumab, Ramucirumab, Rovalpituzumab, Sacituzumab, Siltuximab, Sirtratumab, Vadastuximab, Vorsetuzumab, Trastuzumab, an anti-CD4 antibody, an anti-CD5 antibody, an anti-CD13 antibody and an anti-CD 30 antibody, or an antigen-binding fragment or an immunologically active portion thereof.

38. The drug conjugate according to claim 1, wherein the moiety Ab comprising at least one antigen binding site is an antibody selected from the group consisting of Abciximab, Alemtuzumab, Atezolizumab, Avelumab, Basiliximab, Bevacizumab, Blinatomumab, Brentuximab, Catumaxomab, Cetuximab, Daclizumab, Daratumumab, Denosumab, Dinutuximab, Durvalumab, Elotuzumab, Gemtuzumab, Ibritumomab, Inotuzumab, Ipilimumab, Labetuzumab, Necitumumab, Nimotuzumab, Nivolumab, Obinutuzumab, Ofatumumab, Olaratumab, Omalizumab, Palivizumab, Panitumumab, Pembrolizumab, Pertuzumab, Ramucirumab, Rovalpituzumab, Siltuximab, Trastuzumab, an anti-CD4 antibody, an anti-CD5 antibody, an anti-CD13 antibody and an anti-CD 30 antibody, or an antigen-binding fragment or an immunologically active portion thereof.

39. The drug conjugate according to claim 1, wherein the moiety Ab comprising at least one antigen binding site is an antibody selected from the group consisting of Abciximab, Alemtuzumab, Anetumab, Atezolizumab, Avelumab, Basiliximab, Bevacizumab, Blinatomumab, Brentuximab, Catumaxomab, Cetuximab, Coltuximab, Daclizumab, Daratumumab, Denintuzumab, Denosumab, Depatuxizumab, Dinutuximab, Durvalumab, Elotuzumab, Enfortumab, Glembatumumab, Gemtuzumab, Ibritumomab, Indatuximab, Indusatumab, Inotuzumab, Ipilimumab, Labetuzumab, Ladiratuzumab, Laprituximab, Lifastuzumab, Lorvotuzumab, Milatuzumab, Mirvetuximab, Naratuximab, Necitumumab, Nimotuzumab, Nivolumab, Obinutuzumab, Ofatumumab, Olaratumab, Omalizumab, Palivizumab, Panitumumab, Pembrolizumab, Pertuzumab, Pinatuzumab, Polatuzumab, Ramucirumab, Rovalpituzumab, Sacituzumab, Siltuximab, Sirtratumab, Sofituzumab, Vadastuximab, Vorsetuzumab, and Trastuzumab or an antigen-binding fragment of any of the foregoing antibodies.

* * * * *